(12) United States Patent
Matsumoto et al.

(10) Patent No.: US 8,772,277 B2
(45) Date of Patent: Jul. 8, 2014

(54) NITROGEN-CONTAINING HETEROCYCLIC COMPOUND

(75) Inventors: Shigemitsu Matsumoto, Kanagawa (JP); Koji Ono, Kanagawa (JP); Yusuke Tominari, Kanagawa (JP); Taisuke Katoh, Kanagawa (JP); Kazuhiro Miwa, Osaka (JP); Atsushi Hasuoka, Kanagawa (JP); Shinichi Imamura, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/566,091

(22) Filed: Aug. 3, 2012

(65) Prior Publication Data
US 2013/0072467 A1     Mar. 21, 2013

(30) Foreign Application Priority Data
Aug. 4, 2011   (JP) .................................. 2011-171387

(51) Int. Cl.
*A61K 31/00* (2006.01)
*C07D 401/00* (2006.01)

(52) U.S. Cl.
USPC ......... 514/210.2; 514/326; 546/209; 546/125

(58) Field of Classification Search
USPC ........................ 514/210.2, 326; 546/209, 125
See application file for complete search history.

(56) References Cited

U.S. PATENT DOCUMENTS

| | | | |
|---|---|---|---|
| 6,641,889 B2 | 11/2003 | Berneth et al. | |
| 7,799,782 B2 * | 9/2010 | Munson et al. | 514/234.5 |
| 2002/0187953 A1 | 12/2002 | Aubin et al. | |
| 2002/0197439 A1 | 12/2002 | Berneth et al. | |
| 2003/0013041 A1 | 1/2003 | Berneth et al. | |
| 2003/0152959 A1 | 8/2003 | Mertz et al. | |
| 2006/0014812 A1 | 1/2006 | Player et al. | |
| 2008/0221179 A1 | 9/2008 | Gaul et al. | |
| 2012/0196864 A1 | 8/2012 | Hasuoka et al. | |

FOREIGN PATENT DOCUMENTS

| | | |
|---|---|---|
| JP | 09-003067 A | 1/1997 |
| WO | WO 98/33797 A1 | 8/1998 |
| WO | WO 02/24695 A2 | 3/2002 |
| WO | WO 02/080160 A1 | 10/2002 |
| WO | WO 2005/072731 A1 | 8/2005 |
| WO | WO 2006/019741 A1 | 2/2006 |
| WO | WO 2006/047269 A2 | 5/2006 |
| WO | WO 2008/109727 A1 | 9/2008 |
| WO | WO 2008/109731 A2 | 9/2008 |
| WO | WO 2008/109737 A1 | 9/2008 |
| WO | WO 2009/005729 A1 | 1/2009 |
| WO | WO 2011/016501 A1 | 2/2011 |

OTHER PUBLICATIONS

Bonnelye et al., "Review: Estrogen Receptor-Related Receptor α: A Mediator of Estrogen Response in Bone," Journal of Clinical Endocrinology & Metabolism, 2005, 90(5):3115-3121.
Chemical Abstracts Service, Registry Nos. 712310-91-3 and 712310-92-4, Jul. 19, 2004, 1 page.
Chisamore et al,. "Estrogen-related receptor-α antagonist inhibits both estrogen receptor-positive and estrogen receptor-negative breast tumor growth in mouse xenografts," Mol. Cancer Ther., Mar. 2009, 8(3):672-681.
Fujisaki et al., "Antibacterial Activity of 5-Dialkylaminomethylhydantoins and Related Compounds," Chem. Pharm. Bull., Aug. 2010, 58(8):1123-1126.
Fujisaki et al., "Preparation and Chemical Properties of 5-Dialkylaminomethylhydantoins and 2-Thio-Analogues," Chem. Pharm. Bull., Dec. 2009, 57(12):1415-1420.
Grundy et al., "Definition of Metabolic Syndrome, Report of the National Heart, Lung and Blood Institute/American Heart Association Conference on Scientific Issues Related to Definition," Circulation, 2004, 109:433-438.
Stein et al., "Estrogen-Related Receptor α Is Critical for the Growth of Estrogen Receptor-Negative Breast Cancer," Cancer Research, Nov. 2008 [online Oct. 30, 2008], 68(21):8805-8812.
Vanacker et al., "Transcriptional targets shared by estrogen receptor-related receptors (ERRs) and estrogen receptor (ER)α, but not by ERβ," The EMBO Journal, 1999, 18(15):4270-4279.
Yang et al., "Estrogen-related Receptor, hERR1, Modulates Estrogen Receptor-mediated Response of Human Lactoferrin Gene Promoter," Journal of Biological Chemistry, Mar. 8, 1996, 271(10):5795-5804.
Zhang et al., "Estrogen receptor α and estrogen receptor-related receptor aI compete for binding and coactivator," Molecular and Cellular Endocrinology, 2001, 172:223-233.

* cited by examiner

*Primary Examiner* — Rei-tsang Shiao
(74) *Attorney, Agent, or Firm* — Foley & Lardner LLP

(57) ABSTRACT

The present invention provides a novel compound having a superior activity as an ERR-α modulator and useful as an agent for the prophylaxis or treatment of ERR-α associated diseases.
The present invention relates to a compound represented by the formula

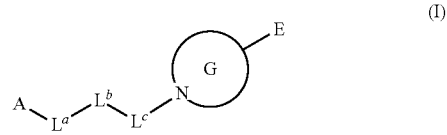

wherein each symbol is as defined in the specification, or a salt thereof.

23 Claims, No Drawings

NITROGEN-CONTAINING HETEROCYCLIC COMPOUND

TECHNICAL FIELD OF THE INVENTION

The present invention relates to a novel compound having a superior activity as an estrogen-related receptor-α (in the present specification, sometimes to be abbreviated as ERR-α) modulator and useful as an agent for the prophylaxis or treatment of ERR-α associated diseases such as malignant tumor (e.g., breast cancer, malignant lymphoma, multiple myeloma, prostate cancer, colorectal cancer, lung cancer, ovarian cancer, endometrial carcinoma) and the like.

BACKGROUND OF THE INVENTION

Nuclear receptors are transcription regulators that respond to various stimuli such as physiological factors (e.g., development and differentiation), environmental factors and the like, and regulate gene expression in a ligand dependent manner. They form a gene superfamily based on their structural characteristics. Among them are included classic nuclear receptors such as estrogen receptor (ER) with estrogen as a ligand, and the like, and orphan nuclear receptors whose ligands and physiological functions are unknown.

Estrogen-related receptor-α (ERR-α, NR3B1) belongs to the estrogen-related receptor subfamily (ERR subfamily) (orphan nuclear receptor closely related to ER). ERR-β and ERR-γ have additionally been identified as the members of the ERR subfamily, and all the members show high homology with ER in the DNA-binding domain. ER and the ERR subfamily are known to have common target genes such as estrogen-responsive genes and the like.

Crosstalks occur between the signal transduction pathways of ER and the ERR subfamily (non-patent documents 1 to 4). Therefore, a compound capable of modulating the activity of ERR-α (ERR-α modulator) could provide a therapeutic effect for both the diseases related to ERR-α and the diseases related to ER, through a direct modulation of the ERR-α transcriptional effect or an indirect effect on the ER signal transduction pathway.

In consideration of the wide activity of ERR-α, an ERR-α modulator is expected to be useful for the prophylaxis or treatment of various disease conditions (e.g., cancers such as to breast cancer and the like, diabetes, hyperlipidemia, obesity, metabolic syndrome, arthritis, atherosclerosis, rheumatoid arthritis, atopic dermatitis, osteoporosis, anxiety, depression, Parkinson's disease, Alzheimer's disease etc.) (patent documents 1 and 2, non-patent document 5).

In recent years, it has been reported that siRNA and a low-molecular-weight compound having an ERR-α inhibitory activity can provide a good antitumor effect against estrogen receptor-positive and -negative breast cancers in mouse models (non-patent documents 6 and 7).

As an ERR-α inverse agonist, patent document 3 (WO 2011/016501) discloses a compound represented by the formula:

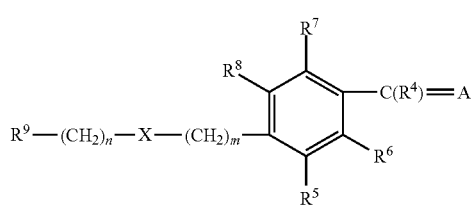

(I)

wherein
A is a group represented by the formula

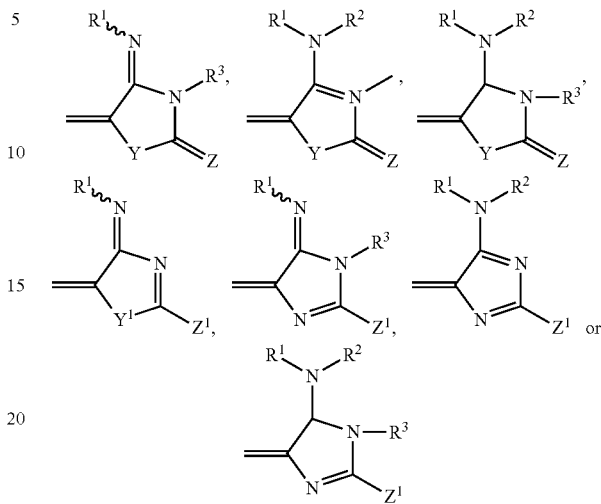

wherein
$R^1$, $R^2$ and $R^3$ are each independently a hydrogen atom, a hydrocarbon group optionally having substituent(s), a heterocyclic group optionally having substituent(s), an acyl group, or a hydroxyl group optionally substituted by an alkyl group optionally having substituent(s);
Y is —O—, —S— or —NR$^a$— wherein R$^a$ is a hydrogen atom, a hydrocarbon group optionally having substituent(s), a heterocyclic group optionally having substituent(s), an acyl group, or a hydroxyl group optionally substituted by an alkyl group optionally having substituent(s);
Z is =O, =S or =NR$^b$ wherein R$^b$ is a hydrogen atom, a hydrocarbon group optionally having substituent(s), a heterocyclic group optionally having substituent(s), an acyl group, or a hydroxyl group optionally substituted by an alkyl group optionally having substituent(s);
$Y^1$ is —O—, —S— or —NR$^c$— wherein R$^c$ is a hydrogen atom, a hydrocarbon group optionally having substituent(s), a heterocyclic group optionally having substituent(s), or an acyl group;
$Z^1$ is —OR$^d$, —SR$^d$ or —NHR$^d$ wherein R$^d$ are each independently a hydrogen atom, a hydrocarbon group optionally having substituent(s), a heterocyclic group optionally having substituent(s), or an acyl group;
$R^4$ is a hydrogen atom or an alkyl group optionally having substituent(s);
$R^5$, $R^6$, $R^7$ and $R^8$ are each independently a hydrogen atom, a hydrocarbon group optionally having substituent(s), an amino group optionally having substituent(s), a hydroxyl group optionally having a substituent, a thiol group optionally having a substituent, a carbamoyl group optionally having substituent(s), an alkyloxycarbonyl group optionally having substituent(s), a halogen atom, a cyano group or a nitro group;
m and n are each independently an integer of 0 to 3;
X is —O—, —CO—, —O—CO—, —CO—O—, —SO$_2$—, —SO—, —S—, —SO$_2$—O—, —NR$^{c1}$—, —CO—NR$^{c1}$—, —NR$^{c1}$—CO—, —NR$^{c1}$—CO—NR$^{c2}$—, —O—CO—NR$^{c1}$—, —NR$^{c1}$—CO—O—, —SO$_2$—NR$^{c1}$—, —NR$^{c1}$—SO$_2$— or —NR$^{c1}$—SO$_2$—NR$^{c2}$—
wherein $R^{c1}$ and $R^{c2}$ are each independently a hydrogen atom, a hydrocarbon group optionally having substituent(s), a heterocyclic group optionally having substituent(s), an acyl group, or a hydroxyl group optionally substituted by an alkyl group optionally having substituent(s); and $R^9$ is an aromatic ring group optionally having substituent(s), provided that the following two compound:

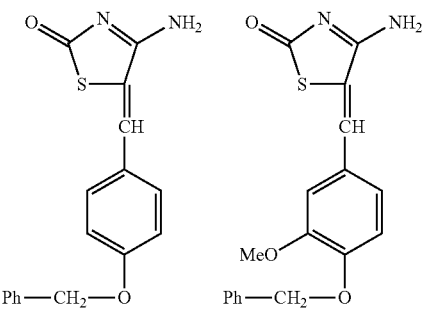 [SMILES: NC1=NC(=O)SC1=Cc1ccc(OCc2ccccc2)cc1 ; COc1cc(C=C2SC(=O)N=C2N)ccc1OCc1ccccc1]

are excluded.

As an antiallergic agent and antihistamine agent, patent document 4 (JP-A-9-3067) discloses a compound represented by the formula:

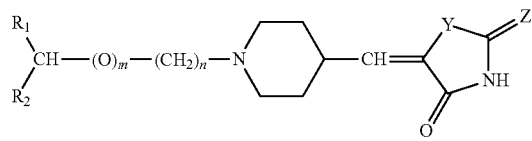

wherein $R_1$ is a hydrogen atom, a lower alkyl group, or an unsubstituted or substituted phenyl group, $R_2$ is an unsubstituted or substituted phenyl group, a pyridyl group, or a 2-benzimidazolyl group having a lower alkyl group, a lower alkoxyalkyl group or an unsubstituted or substituted aralkyl group at N-position, m is an integer of 0 or 1, n is an integer of 0 to 3, Y is >S, >NH or >N—$CH_3$, and Z is =S, =NH, =O, =NC(=NH)$NH_2$, =NCO—$R_3$ or =$NSO_2$—$R_3$ wherein $R_3$ is a straight chain or branched lower alkyl group, a trifluoromethyl group or an aryl group.

As a phospholipase $A_2$ inhibitory activating agent, patent document 5 (WO 1998/033797) discloses a compound represented by the formula:

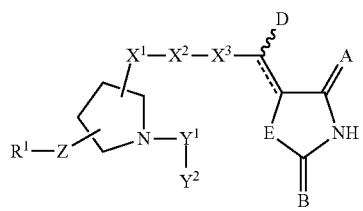

wherein $R^1$ is a hydrogen atom, lower alkyl, optionally substituted aryl, aryl fused to a non-aromatic hydrocarbon ring or a non-aromatic heterocycle, optionally substituted aralkyl, optionally substituted arylcarbonyl, or optionally substituted heteroaryl;

Z is —S—, —SO—, —O—, —$OCH_2$—, —CONH—, —$CONHCH_2$—, —N($R^{16}$)— wherein $R^{16}$ is a hydrogen atom, alkyl or aralkyl, or a single bond;

$X^1$ is —$(CH_2)_q$—CO— wherein q is an integer of 0 to 3, —$(CH_2)_r$-CO—N($R^{17}$)— wherein $R^{17}$ is a hydrogen atom or lower alkyl and r is an integer of 0 to 3, —$CH_2NHSO_2$—, —$(CH_2)_s$—N($R^{18}$)—CO— wherein $R^{18}$ is a hydrogen atom or lower alkyl and s is an integer of 0 to 3, —$CH_2NHCOCH_2O$—, —$CH_2N(R^{19})COCH=CH$— wherein $R^{19}$ is a hydrogen atom or lower alkyl, —$CH_2NHCS$—, —$CH_2O$—, —$OCH_2$—, —$CH_2OCH_2$—, —$CH_2$—N($R^{20}$)—$CH_2$— wherein $R^{20}$ is a hydrogen atom, lower alkyl or acyl, alkylene, alkenylene or a single bond;

$X^2$ is optionally substituted arylene, optionally substituted heteroarylene, heterocyclediyl, —C≡C— or a single bond;

$X^3$ is alkylene, alkenylene or a single bond;

A, B, and E are each independently an oxygen atom or a sulfur atom;

D is a hydrogen atom or hydroxy lower alkyl;

Y is —$(CH_2)_mCO$—, —$(CH_2)_mCONH$—, —$(CH_2)_mC-SNH$—, —$(CH_2)_mSO_2$, —$(CH_2)_mCOO$—, —$(CH_2)_nNHCO$—, —$(CH_2)_nNHSO_2$— or a single bond;

m is an integer of 0 to 3;

n is an integer of 1 to 3; and $Y^2$ is a group represented by the formula:

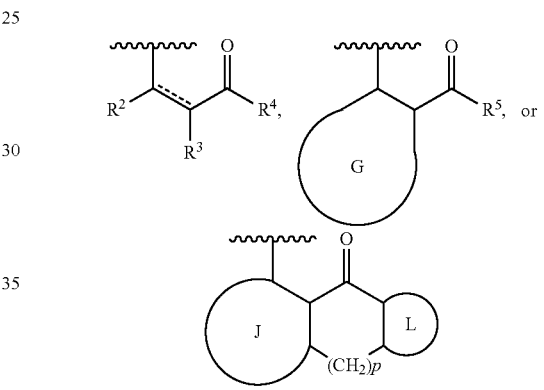

wherein $R^2$ and $R^3$ are both hydrogen atoms, or the one is optionally substituted aryl, optionally substituted heteroaryl, or optionally substituted 39 cycloalkyl, and the other is a hydrogen atom or a lower alkyl;

$R^4$, $R^5$, G ring, J ring and L ring are each independently optionally substituted aryl, optionally substituted heteroaryl, optionally substituted cycloalkyl, or cycloalkenyl;

broken line (---) shows presence or absence of a bond; and p is an integer of 0 to 2, broken line (---) shows presence or absence of a bond; and a wavy line (~) means that the bond of D is cis or trans relation to E, provided that when the bond between the carbon atom adjacent to D and the carbon atom of the ring is a single bond, then $X^1$ is alkylene and $X^2$ and $X^3$ are single bonds, and when $X^1$ is —$CH_2O$—, then $Y^1$ is not a single bond, which is useful for the prophylaxis or treatment of inflammatory disease and the like.

Non-patent document 8 (Chemical & Pharmaceutical Bulletin, 2009, vol. 57 (12), p. 1415-1420) discloses synthetic route for a compound having the following formula, and non-patent document 9 (Chemical & Pharmaceutical Bulletin, 2010, vol. 58 (8), p. 1123-1126) discloses antibacterial activity of the compound.

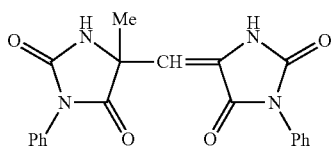 [SMILES: CC1(C=C2NC(=O)N(c3ccccc3)C2=O)NC(=O)N(c2ccccc2)C1=O]

DOCUMENT LIST

Patent Document patent document 1: US 2003/0152959
patent document 2: US 2002/0187953
patent document 3: WO 2011/016501
patent document 4: JP-A-9-3067
patent document 5: WO 1998/033797

Non-Patent Document non-patent document 1: J. Clin. Endocrinol. Metab., 2005, vol. 90, p. 3115-21
non-patent document 2: EMBO J., 1999, vol. 18, p. 4270-9
non-patent document 3: Mol. Cell. Endocrinol., 2001, vol. 172, p. 223-33
non-patent document 4: J. Biol. Chem., 1996, vol. 271, p. 5795-804
non-patent document 5: Circulation, 2004, vol. 109, p. 433-8
non-patent document 6: Cancer Research, 2008, vol. 68, p. 8805-12
non-patent document 7: Mol. Cancer. Ther., 2009, vol. 8, p. 672-81
non-patent document 8: Chemical & Pharmaceutical Bulletin, 2009, vol. 57 (12), p. 1415-1420
non-patent document 9: Chemical & Pharmaceutical Bulletin, 2010, vol. 58 (8), p. 1123-1126

SUMMARY OF THE INVENTION

Problems to be Solved by the Invention

There is a demand for the development of a novel compound having a superior activity as an ERR-α modulator and useful as an agent for the prophylaxis or treatment of ERR-α associated diseases such as malignant tumor (e.g., breast cancer, malignant lymphoma, multiple myeloma, prostate cancer, colorectal cancer, lung cancer, ovarian cancer, endometrial carcinoma) and the like, and the like.

Means of Solving the Problems

The present inventors have conducted intensive studies in an attempt to solve the above-mentioned problem and found that the following compound represented by the formula (I) or a salt thereof has a superior activity as an ERR-(modulator, and conducted further studies, which resulted in the completion of the present invention.

Accordingly, the present invention is as follows;

[1] A compound represented by the formula

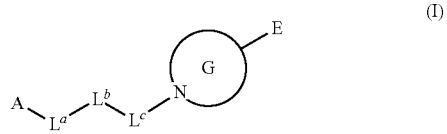

wherein

A is a cyclic group optionally having substituent(s);

$L^a$ is a bond, —O—, —CO—, —S—, —SO—, —SO$_2$—, —NR$^{L1}$— or —NR$^{L1}$—CO—;

$L^b$ is a bond or a $C_{1-3}$ alkylene group optionally having substituent(s);

$L^c$ is a bond, —CO—, —O—CO—, —NR$^{L2}$—CO—, —SO$_2$— or —NR$^{L2}$—SO$_2$—;

$R^{L1}$ and $R^{L2}$ are each independently a hydrogen atom, a hydrocarbon group optionally having substituent(s), a heterocyclic group optionally having substituent(s), a hydroxy group optionally having a substituent, an amino group optionally having substituent(s), or an acyl group;

ring G is a 4- to 10-membered saturated heterocycle containing one nitrogen atom as a ring-constituting hetero atom, which is optionally bridged and optionally has substituent(s); and E is a group represented by the formula

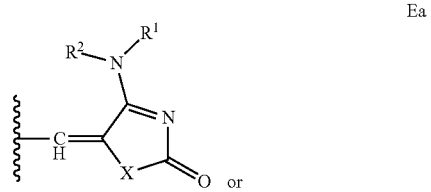

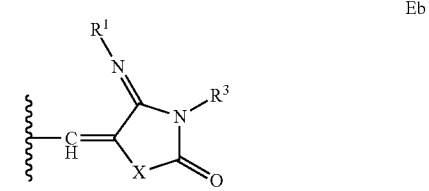

wherein

X is —S—, —O— or —NR$^X$—; and $R^1$, $R^2$, $R^3$ and $R^X$ are each independently a hydrogen atom, a hydrocarbon group optionally having substituent(s), a heterocyclic group optionally having substituent(s), a hydroxy group optionally having a substituent, an amino group optionally having substituent(s), or an acyl group, or $R^1$ and $R^2$ in combination optionally form, together with the adjacent nitrogen atom, a nitrogen-containing heterocycle optionally having substituent(s), or $R^1$ and $R^3$ in combination optionally form, together with the adjacent nitrogen atoms, a 5- to 7-membered nitrogen-containing heterocycle optionally having substituent(s), or a salt thereof.

[2] A compound represented by the formula

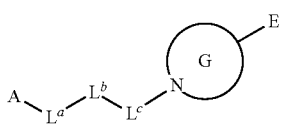

wherein

A is a cyclic group optionally having substituent(s);

$L^a$ is a bond, —O—, —CO—, —S—, —SO—, —SO$_2$—, —NR$^{L1}$ or —NR$^{L1}$—CO—;

$L^b$ is a bond or a $C_{1-3}$ alkylene group optionally having substituent(s);

$L^c$ is a bond, —CO—, —O—CO—, —NR$^{L2}$—CO—, —SO$_2$— or —NR$^{L2}$—SO$_2$—;

$R^{L1}$ and $R^{L2}$ are each independently a hydrogen atom, a hydrocarbon group optionally having substituent(s), a heterocyclic group optionally having substituent(s), a hydroxy group optionally having a substituent, an amino group optionally having substituent(s), or an acyl group;

ring G is a 4- to 10-membered saturated heterocycle containing one nitrogen atom as a ring-constituting hetero atom, which is optionally bridged and optionally has substituent(s); and E is a group represented by the formula

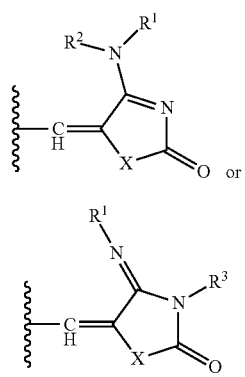

wherein

X is —S—, —O— or —NR$^X$—; and $R^1$, $R^2$, $R^3$ and $R^X$ are each independently a hydrogen atom, a hydrocarbon group optionally having substituent(s), a heterocyclic group optionally having substituent(s), a hydroxy group optionally having a substituent, an amino group optionally having substituent(s), or an acyl group, or $R^1$ and $R^2$ in combination optionally form, together with the adjacent nitrogen atom, a nitrogen-containing heterocycle optionally having substituent(s), or a salt thereof.

[3] The compound or salt of the above-mentioned [1] or [2], wherein A is a $C_{6-10}$ aryl group, an aromatic heterocyclic group or a $C_{3-10}$ cycloalkyl group, each optionally having substituent (s).

[3A] The compound or salt of the above-mentioned [1] or [2], wherein the cyclic group of the cyclic group optionally having substituent(s) for A is a phenyl group, a naphthyl group, a benzofuryl group, an indolyl group, a benzimidazolyl group or a $C_{3-10}$ cycloalkyl group.

[4] The compound or salt of any one of the above-mentioned [1]-[3A], wherein the substituent of the cyclic group optionally having substituent(s) for A is selected from
(a) a halogen atom,
(b) a cyano group,
(c) a $C_{1-6}$ alkyl group optionally substituted by 1 to 3 halogen atoms,
(d) a $C_{1-6}$ alkoxy group optionally substituted by 1 to 3 halogen atoms,
(e) a hydroxy group, and
(f) a pentafluorosulfanyl group.

[4A] The compound or salt of any one of the above-mentioned [1]-[3A], wherein A is a phenyl group, a naphthyl group, a benzofuryl group, an indolyl group, a benzimidazolyl group or a $C_{3-10}$ cycloalkyl group, each optionally substituted by 1 to 3 substituents selected from
(a) a halogen atom,
(b) a cyano group,
(c) a $C_{1-6}$ alkyl group optionally substituted by 1 to 3 halogen atoms,
(d) a $C_{1-6}$ alkoxy group optionally substituted by 1 to 3 halogen atoms,
(e) a hydroxy group, and
(f) a pentafluorosulfanyl group.

[4B] The compound or salt of any one of the above-mentioned [1]-[3A], wherein A is a phenyl group optionally substituted by 1 to 3 substituents selected from
(a) a halogen atom,
(b) a cyano group,
(c) a $C_{1-6}$ alkyl group optionally substituted by 1 to 3 halogen atoms,
(d) a $C_{1-6}$ alkoxy group optionally substituted by 1 to 3 halogen atoms,
(e) a hydroxy group, and
(f) a pentafluorosulfanyl group.

[5] The compound or salt of any one of the above-mentioned [1]-[4B], wherein
$L^a$ is a bond;
$L^b$ is a bond or a $C_{1-3}$ alkylene group optionally substituted by 1 to 3 $C_{1-6}$ alkyl groups; and
$L^c$ is a bond or —CO—.

[5A] The compound or salt of any one of the above-mentioned [1]-[4B], wherein
$L^a$ is a bond;
$L^b$ is a $C_{1-3}$ alkylene group optionally substituted by 1 to 3 $C_{1-6}$ alkyl groups; and
$L^c$ is a bond.

[5B] The compound or salt of any one of the above-mentioned [1]-[4B], wherein
$L^a$ is a bond;
$L^b$ is methylene group; and
$L^c$ is a bond.

[6] The compound or salt of any one of the above-mentioned [1]-[5B], wherein ring G is an azetidine ring, a pyrrolidine ring, a piperidine ring, an azepane ring, a 3-azabicyclo[3.1.0]hexane ring, a 8-azabicyclo[3.2.1]octane ring, a 3-azabicyclo[3.3.1]nonane ring or a 3-azabicyclo[3.3.0]octane ring, each optionally having substituent(s).

[6A] The compound or salt of any one of the above-mentioned [1]-[5B], wherein ring G is a piperidine ring optionally substituted by 1 to 3 substituents selected from a $C_{1-6}$ alkyl group and an oxo group.

[6B] The compound or salt of any one of the above-mentioned [1]-[5B], wherein the substituent of the 4- to 10-membered saturated heterocycle containing one nitrogen atom as a ring-constituting hetero atom, which is optionally bridged and optionally has substituent(s) for ring G is selected from a $C_{1-6}$ alkyl group and an oxo group.

[6C] The compound or salt of any one of the above-mentioned [1]-[5B], wherein ring G is an azetidine ring, a pyrrolidine ring, a piperidine ring, an azepane ring, a 3-azabicyclo[3.1.0]hexane ring, a 8-azabicyclo[3.2.1]octane ring, a 3-azabicyclo[3.3.1]nonane ring or a 3-azabicyclo[3.3.0]octane ring, each optionally substituted by 1 to 3 $C_{1-6}$ alkyl groups or one oxo group.

[7] The compound or salt of any one of the above-mentioned [1]-[6C], wherein E is a group represented by the formula

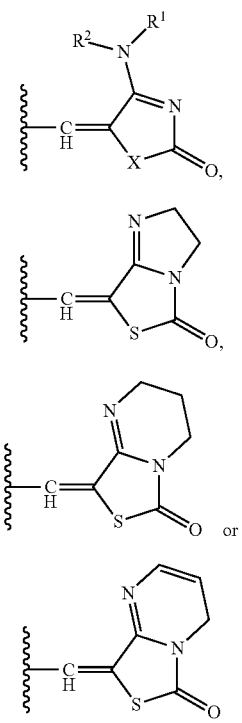

wherein
X is —S—, —O— or —NR$^X$—;
R$^X$ is a $C_{1-6}$ alkyl group;
R$^1$ is
(1) a hydrogen atom;
(2) a $C_{1-6}$ alkyl group optionally substituted by 1 to 5 substituents selected from
  (a) an amino group optionally mono- or di-substituted by $C_{1-6}$ alkyl group(s) optionally substituted by 1 to 3 hydroxy groups,
  (b) a hydroxy group,
  (c) a $C_{1-6}$ alkoxy group optionally substituted by 1 to 3 substituents selected from a hydroxy group, a $C_{1-6}$ alkoxy group and a mono- or di-$C_{1-6}$ alkylamino group,
  (d) a carboxy group,
  (e) a halogen atom,
  (f) a $C_{1-6}$ alkoxy-carbonyl group,
  (g) a carbamoyl group optionally mono- or di-substituted by substituent(s) selected from
    (i) a $C_{1-6}$ alkyl group optionally substituted by 1 to 3 substituents selected from a hydroxy group and a $C_{1-6}$ alkoxy group,
    (ii) a $C_{3-10}$ cycloalkyl group, and
    (iii) a 4- to 6-membered non-aromatic heterocyclic group,
  (h) a $C_{1-6}$ alkylsulfonyl group,
  (i) a $C_{6-14}$ aryl group,
  (j) a 5- or 6-membered aromatic heterocyclic group,
  (k) a 4- to 6-membered non-aromatic heterocyclic group optionally substituted by 1 to 3 substituents selected from
    (i) an oxo group, and
    (ii) a $C_{1-6}$ alkyl group optionally substituted by 1 to 3 hydroxy groups, and
  (l) a 4- to 6-membered non-aromatic heterocyclylcarbonyl group optionally substituted by 1 to 3 substituents selected from
    (i) a hydroxy group, and
    (ii) a $C_{1-6}$ alkyl group;
(3) a $C_{2-6}$ alkenyl group optionally substituted by 1 to 3 mono- or di-$C_{1-6}$ alkylamino groups;
(4) a $C_{2-6}$ alkynyl group optionally substituted by 1 to 3 substituents selected from
  (a) a mono- or di-$C_{1-6}$ alkylamino group,
  (b) a $C_{3-10}$ cycloalkyl group, and
  (c) a hydroxy group;
(5) a $C_{3-10}$ cycloalkyl group optionally substituted by 1 to 3 substituents selected from
  (a) a halogen atom, and
  (b) a hydroxy group;
(6) a $C_{3-10}$ cycloalkyl-$C_{1-6}$ alkyl group optionally substituted by 1 to 3 substituents selected from
  (a) a hydroxy group,
  (b) a $C_{1-6}$ alkyl group optionally substituted by 1 to 3 hydroxy groups, and
  (c) a carbamoyl group optionally mono- or di-substituted by $C_{1-6}$ alkyl group(s); or
(7) a 4- to 6-membered non-aromatic heterocyclic group optionally substituted by 1 to 3 substituents selected from
  (a) a $C_{1-6}$ alkyl group,
  (b) a hydroxy group, and
  (c) an oxo group; and
R$^2$ is a hydrogen atom; or
R$^1$ and R$^2$ in combination form, together with the adjacent nitrogen atom, a 4- to 7-membered nitrogen-containing heterocycle optionally substituted by 1 to 3 substituents selected from
  (1) a hydroxy group, and
  (2) a carbamoyl group optionally mono- or di-substituted by $C_{1-6}$ alkyl group(s).

[7A] The compound or salt of any one of the above-mentioned [1]-[6C], wherein E is a group represented by the formula

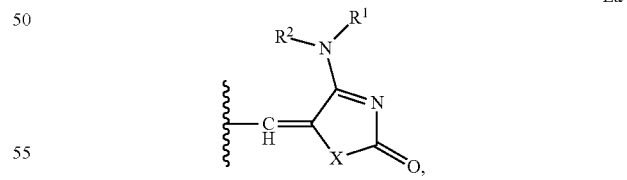

wherein each symbol is as defined in the above-mentioned [7].

[8] The compound or salt of any one of the above-mentioned [1]-[7A], wherein
A is a phenyl group, a naphthyl group, a benzofuryl group, an indolyl group, a benzimidazolyl group or a $C_{3-10}$ cycloalkyl group, each optionally substituted by 1 to 3 substituents selected from
  (a) a halogen atom,
  (b) a cyano group, (c) a $C_{1-6}$ alkyl group optionally substituted by 1 to 3 halogen atoms,
(d) a $C_{1-6}$ alkoxy group optionally substituted by 1 to 3 halogen atoms,
(e) a hydroxy group, and
(f) a pentafluorosulfanyl group;
$L^a$ is a bond;
$L^b$ is a bond or a $C_{1-3}$ alkylene group optionally substituted by 1 to 3 $C_{1-6}$ alkyl groups;
$L^c$ is a bond or —CO—;
ring G is an azetidine ring, a pyrrolidine ring, a piperidine ring, an azepane ring, a 3-azabicyclo[3.1.0]hexane ring, a 8-azabicyclo[3.2.1]octane ring, a 3-azabicyclo[3.3.1]nonane ring or a 3-azabicyclo[3.3.0]octane ring, each optionally substituted by 1 to 3 $C_{1-6}$ alkyl groups or one oxo group; and
E is a group represented by the formula

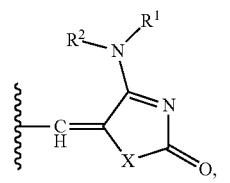
Ea

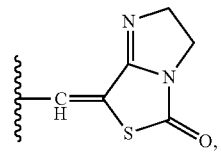
Ec

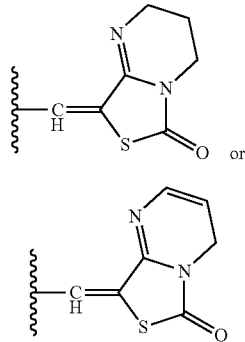
Ed or

Ee wherein
X is —S—, —O— or —NR$^x$—;
R$^x$ is a $C_{1-6}$ alkyl group;
R$^1$ is
(1) a hydrogen atom;
(2) a $C_{1-6}$ alkyl group optionally substituted by 1 to 5 substituents selected from
(a) a halogen atom,
(b) an amino group optionally mono- or di-substituted by $C_{1-6}$ alkyl group(s) optionally substituted by 1 to 3 hydroxy groups,
(c) a hydroxy group,
(d) a $C_{1-6}$ alkoxy group optionally substituted by 1 to 3 substituents selected from a hydroxy group, a $C_{1-6}$ alkoxy group and a di-$C_{1-6}$ alkylamino group,
(e) a carbamoyl group optionally mono- or di-substituted by substituent(s) selected from
(i) a $C_{1-6}$ alkyl group optionally substituted by 1 to 3 substituents selected from a hydroxy group and a $C_{1-6}$ alkoxy group,
(ii) a $C_{3-10}$ cycloalkyl group, and
(iii) an oxetanyl group,
(f) a carboxy group,
(g) a $C_{1-6}$ alkoxy-carbonyl group,
(h) a pyrrolidylcarbonyl group optionally substituted by hydroxy group(s),
(i) a morpholinylcarbonyl group,
(j) a piperazinylcarbonyl group substituted by $C_{1-6}$ alkyl group(s),
(k) a dioxanyl group,
(l) a tetrahydropyranyl group substituted by $C_{1-6}$ alkyl group(s) substituted by hydroxy group(s),
(m) an oxopyrrolidinyl group,
(n) an oxazolyl group,
(o) an isoxazolyl group,
(p) a phenyl group, and
(q) a $C_{1-6}$ alkylsulfonyl group;
(3) a $C_{2-6}$ alkenyl group optionally substituted by 1 to 3 di-$C_{1-6}$ alkylamino groups;
(4) a $C_{2-6}$ alkynyl group optionally substituted by 1 to 3 substituents selected from
(a) a di-$C_{1-6}$ alkylamino group,
(b) a $C_{3-10}$ cycloalkyl group, and
(c) a hydroxy group;
(5) a $C_{3-10}$ cycloalkyl group optionally substituted by 1 to 3 substituents selected from
(a) a halogen atom, and
(b) a hydroxy group;
(6) a $C_{3-10}$ cycloalkyl-$C_{1-6}$ alkyl group optionally substituted by 1 to 3 substituents selected from
(a) a hydroxy group,
(b) a $C_{1-6}$ alkyl group substituted by hydroxy group(s), and
(c) a di-$C_{1-6}$ alkyl-carbamoyl group;
(7) an oxetanyl group;
(8) a tetrahydrofuryl group optionally substituted by hydroxy group(s);
(9) a tetrahydropyranyl group optionally substituted by hydroxy group(s);
(10) a pyrrolidinyl group optionally substituted by 1 to 3 substituents selected from a $C_{1-6}$ alkyl group and an oxo group; or
(11) a piperidyl group optionally substituted by 1 to 3 substituents selected from a $C_{1-6}$ alkyl group and an oxo group; and
R$^2$ is a hydrogen atom; or
R$^1$ and R$^2$ in combination form, together with the adjacent nitrogen atom,
(1) a pyrrolidine ring optionally substituted by 1 to 3 hydroxy groups or carbamoyl group(s) di-substituted by $C_{1-6}$ alkyl groups; or
(2) an azetidine ring substituted by carbamoyl group(s) di-substituted by $C_{1-6}$ alkyl groups.
[8A] The compound or salt of any one of the above-mentioned [1]-[7A], wherein
A is a phenyl group optionally substituted by 1 to 3 substituents selected from
(a) a halogen atom, and
(b) a $C_{1-6}$ alkyl group optionally substituted by 1 to 3 halogen atoms;
$L^a$ is a bond;
$L^b$ is a $C_{1-3}$ alkylene group optionally substituted by 1 to 3 $C_{1-6}$ alkyl groups;
$L^c$ is a bond;
ring G is a piperidine ring; and E is a group represented by the formula

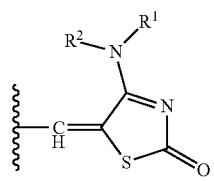

wherein
R¹ is
(1) a $C_{1-6}$ alkyl group optionally substituted by 1 to 5 substituents selected from
   (a) a halogen atom,
   (b) an amino group di-substituted by $C_{1-6}$ alkyl groups optionally substituted by 1 to 3 hydroxy groups,
   (c) a hydroxy group,
   (d) a $C_{1-6}$ alkoxy group optionally substituted by 1 to 3 substituents selected from a hydroxy group, a $C_{1-6}$ alkoxy group and a di-$C_{1-6}$ alkylamino group,
   (e) a carbamoyl group optionally mono- or di-substituted by substituent(s) selected from
      (i) a $C_{1-6}$ alkyl group optionally substituted by 1 to 3 hydroxy groups,
      (ii) a $C_{1-6}$ alkyl group substituted by $C_{1-6}$ alkoxy group(s),
      (iii) a $C_{3-10}$ cycloalkyl group, and
      (iv) an oxetanyl group,
   (f) a carboxy group,
   (g) a $C_{1-6}$ alkoxy-carbonyl group,
   (h) a pyrrolidylcarbonyl group optionally substituted by hydroxy group(s),
   (i) a morpholinylcarbonyl group,
   (j) a piperazinylcarbonyl group substituted by $C_{1-6}$ alkyl group(s),
   (k) a dioxanyl group,
   (l) a tetrahydropyranyl group substituted by $C_{1-6}$ alkyl group(s) substituted by hydroxy group(s),
   (m) an oxopyrrolidinyl group,
   (n) an oxazolyl group,
   (o) an isoxazolyl group,
   (p) a phenyl group, and
   (q) a $C_{1-6}$ alkylsulfonyl group;
(2) a $C_{2-6}$ alkenyl group optionally substituted by 1 to 3 di-$C_{1-6}$ alkylamino groups;
(3) a $C_{2-6}$ alkynyl group optionally substituted by 1 to 3 substituents selected from
   (a) a di-$C_{1-6}$ alkylamino group,
   (b) a $C_{3-10}$ cycloalkyl group, and
   (c) a hydroxy group;
(4) a $C_{3-10}$ cycloalkyl group optionally substituted by 1 to 3 substituents selected from
   (a) a halogen atom, and
   (b) a hydroxy group;
(5) a $C_{3-10}$ cycloalkyl-$C_{1-6}$ alkyl group optionally substituted by 1 to 3 substituents selected from
   (a) a hydroxy group,
   (b) a $C_{1-6}$ alkyl group substituted by hydroxy group(s), and
   (c) a di-$C_{1-6}$ alkyl-carbamoyl group;
(6) an oxetanyl group;
(7) a tetrahydrofuryl group optionally substituted by hydroxy group(s);
(8) a tetrahydropyranyl group substituted by hydroxy group(s);
(9) a pyrrolidinyl group optionally substituted by 1 to 3 substituents selected from a $C_{1-6}$ alkyl group and an oxo group; or
(10) a piperidyl group optionally substituted by 1 to 3 substituents selected from a $C_{1-6}$ alkyl group and an oxo group; and
R² is a hydrogen atom; or
R¹ and R² in combination form, together with the adjacent nitrogen atom,
(1) a pyrrolidine ring optionally substituted by 1 to 3 hydroxy groups or carbamoyl group(s) di-substituted by $C_{1-6}$ alkyl groups; or
(2) an azetidine ring substituted by carbamoyl group(s) di-substituted by $C_{1-6}$ alkyl groups.

[9] The compound or salt of any one of the above-mentioned [1]-[8A], wherein
A is a phenyl group optionally substituted by 1 to 3 substituents selected from
   (a) a halogen atom,
   (b) a cyano group, and
   (c) a $C_{1-6}$ alkyl group optionally substituted by 1 to 3 halogen atoms;
$L^a$ is a bond;
$L^b$ is a $C_{1-3}$ alkylene group;
$L^c$ is a bond;
ring G is pyrrolidine ring, a piperidine ring or a 8-azabicyclo[3.2.1]octane ring; and
E is a group represented by the formula

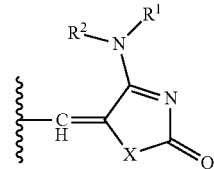

wherein
X is —S— or —NR$^X$—;
R$^X$ is a $C_{1-6}$ alkyl group;
R¹ is
(1) a $C_{1-6}$ alkyl group optionally substituted by 1 to 3 substituents selected from
   (a) an amino group di-substituted by $C_{1-6}$ alkyl groups optionally substituted by 1 to 3 hydroxy groups,
   (b) a hydroxy group,
   (c) a $C_{1-6}$ alkoxy group substituted by 1 to 3 substituents selected from a hydroxy group, a $C_{1-6}$ alkoxy group and a di-$C_{1-6}$ alkylamino group, and
   (d) a carbamoyl group di-substituted by $C_{1-6}$ alkyl groups;
(2) a $C_{2-6}$ alkynyl group;
(3) a $C_{3-10}$ cycloalkyl-$C_{1-6}$ alkyl group;
(4) an oxetanyl group; or
(5) a tetrahydrofuryl group; and
R² is a hydrogen atom.

[9A] The compound or salt of any one of the above-mentioned [1]-[8A], wherein
A is a phenyl group optionally substituted by 1 to 3 substituents selected from
   (a) a halogen atom,
   (b) a cyano group, and
   (c) a $C_{1-6}$ alkyl group optionally substituted by 1 to 3 halogen atoms;

$L^a$ is a bond;
$L^b$ is a $C_{1-3}$ alkylene group;
$L^c$ is a bond;
ring G is pyrrolidine ring or a piperidine ring; and
E is a group represented by the formula

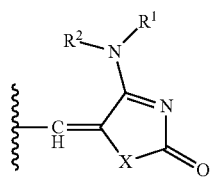

Ea wherein
X is —S— or —$NR^X$—;
$R^X$ is a $C_{1-6}$ alkyl group;
$R^1$ is
(1) a $C_{1-6}$ alkyl group optionally substituted by 1 to 3 substituents selected from
 (a) an amino group di-substituted by $C_{1-6}$ alkyl groups optionally substituted by 1 to 3 hydroxy groups,
 (b) a hydroxy group,
 (c) a $C_{1-6}$ alkoxy group substituted by 1 to 3 substituents selected from a hydroxy group, a $C_{1-6}$ alkoxy group and a di-$C_{1-6}$ alkylamino group, and
 (d) a carbamoyl group di-substituted by $C_{1-6}$ alkyl groups;
(2) a $C_{2-6}$ alkynyl group;
(3) a $C_{3-10}$ cycloalkyl-$C_{1-6}$ alkyl group;
(4) an oxetanyl group; or
(5) a tetrahydrofuryl group; and
$R^2$ is a hydrogen atom.

[10] The compound or salt of any one of the above-mentioned [1]-[9A], wherein
A is a phenyl group substituted by 1 to 3 substituents selected from a $C_{1-6}$ alkyl group optionally substituted by 1 to 3 halogen atoms;
$L^a$ is a bond;
$L^b$ is a $C_{1-3}$ alkylene group;
$L^c$ is a bond;
ring G is a piperidine ring; and
E is a group represented by the formula

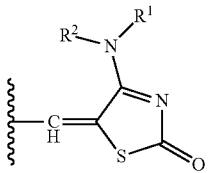

Eaa wherein
$R^1$ is
(1) a $C_{1-6}$ alkyl group optionally substituted by 1 to 3 substituents selected from
 (a) a hydroxy group,
 (b) a $C_{1-6}$ alkoxy group substituted by 1 to 3 hydroxy groups, and
 (c) a carbamoyl group di-substituted by $C_{1-6}$ alkyl groups; or (2) a $C_{2-6}$ alkynyl group; and
$R^2$ is a hydrogen atom.

[10A] The compound or salt of any one of the above-mentioned [1]-[9A], wherein
A is a phenyl group substituted by 1 to 3 substituents selected from a $C_{1-6}$ alkyl group optionally substituted by 1 to 3 halogen atoms;
$L^a$ is a bond;
$L^b$ is a $C_{1-3}$ alkylene group;
$L^c$ is a bond;
ring G is a piperidine ring; and
E is a group represented by the formula

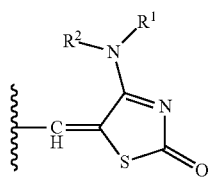

Eaa wherein
$R^1$ is
(1) a $C_{1-6}$ alkyl group substituted by 1 to 3 substituents selected from a $C_{1-6}$ alkoxy group substituted by 1 to 3 hydroxy groups; or
(2) a $C_{2-6}$ alkynyl group; and
$R^2$ is a hydrogen atom.

[10B]
(5Z)-5-({1-[2,4-bis(trifluoromethyl)benzyl]piperidin-4-yl}methylidene)-4-(methylamino)-1,3-thiazol-2(5H)-one,
(5Z)-5-({1-[2,4-bis(trifluoromethyl)benzyl]piperidin-4-yl}methylidene)-4-(prop-2-yn-1-ylamino)-1,3-thiazol-2(5H)-one
(5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one,
(5Z)-5-({1-[2,4-bis(trifluoromethyl)benzyl]piperidin-4-yl}methylidene)-4-{[2-(diethylamino)ethyl]amino}-1,3-thiazol-2(5H)-one,
(5Z)-5-({(3-exo)-8-[2,4-bis(trifluoromethyl)benzyl]-8-azabicyclo[3.2.1]oct-3-yl}methylidene)-4-(methylamino)-1,3-thiazol-2(5H)-one,
(5Z)-5-({1-[2,4-bis(trifluoromethyl)benzyl]piperidin-4-yl}methylidene)-4-[(2-hydroxy-2-methylpropyl)amino]-1,3-thiazol-2(5H)-one,
(5Z)-5-({1-[2,4-bis(trifluoromethyl)benzyl]piperidin-4-yl}methylidene)-4-(oxetan-3-ylamino)-1,3-thiazol-2(5H)-one,
(5Z)-5-({1-[4-chloro-2-(trifluoromethyl)benzyl]piperidin-4-yl}methylidene)-4-(prop-2-yn-1-ylamino)-1,3-thiazol-2(5H)-one,
(5Z)-5-({1-[2,4-bis(trifluoromethyl)benzyl]piperidin-4-yl}methylidene)-4-{[2-(2-methoxyethoxy)ethyl]amino}-1,3-thiazol-2(5H)-one,
4-[(4-{(Z)-[2-oxo-4-(prop-2-yn-1-ylamino)-1,3-thiazol-5(2H)-ylidene]methyl}piperidin-1-yl)methyl]-3-(trifluoromethyl)benzonitrile,
(5Z)-5-({-[2,4-bis(trifluoromethyl)benzyl]piperidin-4-yl}methylidene)-4-(tetrahydrofuran-3-ylamino)-1,3-thiazol-2(5H)-one,
(5Z)-5-({1-[2,4-bis(trifluoromethyl)benzyl]piperidin-4-yl}methylidene)-4-({2-[2-(diethylamino)ethoxy]ethyl}amino)-1,3-thiazol-2(5H)-one, (5Z)-5-({1-[2,4-bis(trifluoromethyl)benzyl]piperidin-4-yl}methylidene)-4-[(2,3-dihydroxypropyl)amino]-1,3-thiazol-2(5H)-one, (5Z)-5-({1-[2,4-bis(trifluoromethyl)benzyl]piperidin-4-yl}methylidene)-4-({2-[(2-hydroxyethyl)(methyl)amino]ethyl}amino)-1,3-thiazol-2(5H)-one, (5Z)-5-({1-[2-chloro-4-(trifluoromethyl)benzyl]piperidin-4-yl}methylidene)-4-(prop-2-yn-1-ylamino)-1,3-thiazol-2(5H)-one, (5Z)-5-({1-[2,4-bis(trifluoromethyl)benzyl]piperidin-4-yl}methylidene)-4-[(cyclopropylmethyl)amino]-1,3-thiazol-2(5H)-one, (5Z)-5-({1-[2,4-bis(trifluoromethyl)benzyl]pyrrolidin-3-yl}methylidene)-4-(prop-2-yn-1-ylamino)-1,3-thiazol-2(5H)-one, (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one, (5Z)-5-({1-[2,4-bis(trifluoromethyl)benzyl]piperidin-4-yl}methylidene)-1-methyl-4-(methylamino)-1,5-dihydro-2H-imidazol-2-one, $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethylglycinamide, $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide, $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-serinamide, $N^3$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-β-alaninamide, (5Z)-5-({1-[2,4-bis(trifluoromethyl)benzyl]piperidin-4-yl}methylidene)-4-(ethylamino)-1,3-thiazol-2 (5H)-one, or (5Z)-5-({1-[2,4-bis(trifluoromethyl)benzyl]piperidin-4-yl}methylidene)-4-(propylamino)-1,3-thiazol-2(5H)-one, or a salt thereof.

[10C]
(5Z)-5-({1-[2,4-bis(trifluoromethyl)benzyl]piperidin-4-yl}methylidene)-4-(prop-2-yn-1-ylamino)-1,3-thiazol-2(5H)-one, (5Z)-5-({1-[2,4-bis(trifluoromethyl)benzyl]piperidin-4-yl}methylidene)-4-[(2-hydroxy-2-methylpropyl)amino]-1,3-thiazol-2(5H)-one, (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one, $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethylglycinamide, $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide, $N^3$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-β-alaninamide, or (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one, or a salt thereof.

[11] (5Z)-5-({1-[2,4-bis(trifluoromethyl)benzyl]piperidin-4-yl}methylidene)-4-(prop-2-yn-1-ylamino)-1,3-thiazol-2(5H)-one or a salt thereof.

[12] (5Z)-5-({1-[2,4-bis(trifluoromethyl)benzyl]piperidin-4-yl}methylidene)-4-[(2-hydroxy-2-methylpropyl)amino]-1,3-thiazol-2(5H)-one or a salt thereof.

[13] (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one or a salt thereof.

[14] $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethylglycinamide or a salt thereof.

[15] $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide or a salt thereof.

[16] (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one or a salt thereof.

[17] A medicament comprising the compound or salt of any one of the above-mentioned [1]-[16].

[18] The medicament according to the above-mentioned [17], which is an ERR-α inverse agonist.

[19] The medicament according to the above-mentioned [17], which is an agent for the prophylaxis or treatment of cancer.

[19A] The medicament according to the above-mentioned [17], which is an agent for the prophylaxis or treatment of breast cancer, malignant lymphoma, multiple myeloma, prostate cancer, colorectal cancer, lung cancer, ovarian cancer or endometrial carcinoma.

[20] A method of inversing ERR-α in a mammal, which comprises administering an effective amount of the compound or salt of any one of the above-mentioned [1]-[16] to a mammal.

[21] A method for the prophylaxis or treatment of cancer in a mammal, which comprises administering an effective amount of the compound or salt of any one of the above-mentioned [1]-[16] to a mammal.

[21A] A method for the prophylaxis or treatment of breast cancer, malignant lymphoma, multiple myeloma, prostate cancer, colorectal cancer, lung cancer, ovarian cancer or endometrial carcinoma in a mammal, which comprises administering an effective amount of the compound or salt of any one of the above-mentioned [1]-[16] to a mammal.

[22] Use of the compound or salt of any one of the above-mentioned [1]-[16] for the production of an agent for the prophylaxis or treatment of cancer.

[22A] Use of the compound or salt of any one of the above-mentioned [1]-[16] for the production of an agent for the prophylaxis or treatment of breast cancer, malignant lymphoma, multiple myeloma, prostate cancer, colorectal cancer, lung cancer, ovarian cancer or endometrial carcinoma.

[22B] Use of the compound or salt of any one of the above-mentioned [1]-[16] for the production of an ERR-α inverse agonist.

[23] The compound or salt of any one of the above-mentioned [1]-[16] for use as an agent for the prophylaxis or treatment of cancer.

[23A] The compound or salt of any one of the above-mentioned [1]-[16] for use as an agent for the prophylaxis or treatment of breast cancer, malignant lymphoma, multiple myeloma, prostate cancer, colorectal cancer, lung cancer, ovarian cancer or endometrial carcinoma.

Effect of the Invention

Since the compound of the present invention has a superior activity as an ERR-α modulator (particularly, inverse agonist) and superior properties from the aspect of in vivo kinetics and the like, it is useful as an agent for the prophylaxis or treatment of ERR-α associated diseases such as malignant tumor (e.g., breast cancer, malignant lymphoma, multiple myeloma, prostate cancer, colorectal cancer, lung cancer, ovarian cancer, endometrial carcinoma) and the like.

DETAILED DESCRIPTION OF THE INVENTION

In the present specification, unless otherwise specified, the "halogen atom" means a fluorine atom, a chlorine atom, a bromine atom or an iodine atom.

In the present specification, unless otherwise specified, the "$C_{1-6}$ alkyl group" means methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

In the present specification, unless otherwise specified, the "$C_{1-6}$ alkoxy group" means methoxy, ethoxy, propoxy, isopropoxy, butoxy, isobutoxy, sec-butoxy, tert-butoxy, pentyloxy, hexyloxy and the like.

In the present specification, unless otherwise specified, the "$C_{1-6}$ alkoxy-carbonyl group" means methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

In the present specification, unless otherwise specified, the "$C_{1-6}$ alkyl-carbonyl group" means acetyl, propanoyl, butanoyl, 2-methylpropanoyl, pentanoyl, 3-methylbutanoyl, 2-methylbutanoyl, 2,2-dimethylpropanoyl, hexanoyl, heptanoyl and the like.

The definition of each symbol in the formula (I) is described in detail in the following.

E is a group represented by the formula

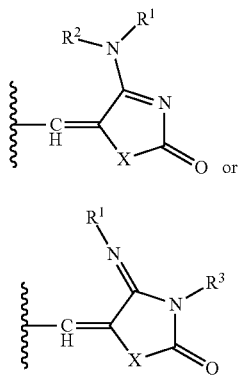

wherein each symbol is as defined above.

These groups may contain a tautomer. For example, a group represented by the formula

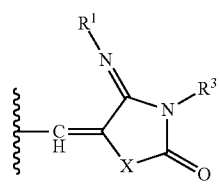

wherein $R^3$ is a hydrogen atom contains a tautomer such as

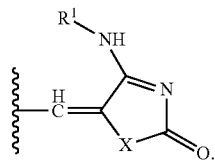

In the present specification, when E is, for example, a group represented by the formula

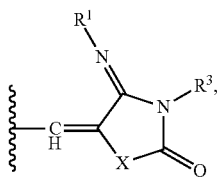

the group contains any of the above-mentioned tautomers. Similarly, Ea may contain any possible tautomer.

X is —S—, —O— or —NR$^x$—, and $R^1$, $R^2$, $R^3$ and $R^x$ are each independently a hydrogen atom, a hydrocarbon group optionally having substituent(s), a heterocyclic group optionally having substituent(s), a hydroxy group optionally having a substituent, an amino group optionally having substituent(s), or an acyl group, or $R^1$ and $R^2$ in combination optionally form, together with the adjacent nitrogen atom, a nitrogen-containing heterocycle optionally having substituent(s), or $R^1$ and $R^3$ in combination optionally form, together with the adjacent nitrogen atoms, a 5- to 7-membered nitrogen-containing heterocycle optionally having substituent(s).

Examples of the "hydrocarbon group" of the "hydrocarbon group optionally having substituent(s)" for $R^1$, $R^2$, $R^3$ or $R^x$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, a $C_{8-13}$ arylalkenyl group, a $C_{3-10}$ cycloalkyl-$C_{1-6}$ alkyl group and the like.

Here, examples of the $C_{1-10}$ alkyl group include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

Examples of the $C_{2-10}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Examples of the $C_{2-10}$ alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4-methyl-2-pentynyl, 1-heptynyl, 1-octynyl and the like.

Examples of the $C_{3-10}$ cycloalkyl group include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Examples of the $C_{3-10}$ cycloalkenyl group include 2-cyclopenten-1-yl, 3-cyclopenten-1-yl, 2-cyclohexen-1-yl, 3-cyclohexen-1-yl and the like.

Examples of the $C_{4-10}$ cycloalkadienyl group include 2,4-cyclopentadien-1-yl, 2,4-cyclohexadien-1-yl, 2,5-cyclohexadien-1-yl and the like.

The above-mentioned $C_{3-10}$ cycloalkyl group, $C_{3-10}$ cycloalkenyl group and $C_{4-10}$ cycloalkadienyl group each may be fused with a benzene ring, and examples of such fused ring group include indanyl, dihydronaphthyl, tetrahydronaphthyl, fluorenyl and the like.

Examples of the $C_{6-14}$ aryl group include phenyl, naphthyl, anthryl, phenanthryl, acenaphthylenyl, biphenylyl and the like.

Examples of the $C_{7-13}$ aralkyl group include benzyl, phenethyl, naphthylmethyl, biphenylylmethyl, phenylpropyl and the like.

Examples of the $C_{8-13}$ arylalkenyl group include styryl and the like.

Examples of the $C_{3-10}$ cycloalkyl-$C_{1-6}$ alkyl group include cyclopropylmethyl, cyclohexylmethyl, 1-cyclohexylethyl, 2-cyclohexylethyl and the like.

The $C_{1-10}$ alkyl group, $C_{2-10}$ alkenyl group and $C_{2-10}$ alkynyl group exemplified as the aforementioned "hydrocarbon group" optionally have 1 to 3 substituents at substitutable position(s).

Examples of such substituent include (1) a $C_{3-10}$ cycloalkyl group (e.g., cyclopropyl, cyclohexyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group, and
   (d) a halogen atom;

(2) a $C_{6-14}$ aryl group (e.g., phenyl, naphthyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group, and
   (d) a halogen atom;

(3) an aromatic heterocyclic group (e.g., thienyl, furyl, pyrrolyl, pyridyl, oxazolyl, thiazolyl, tetrazolyl, oxadiazolyl, pyrazinyl, quinolyl, indolyl, pyrimidinyl, imidazolyl, pyrazolyl, thiadiazolyl, isoxazolyl) optionally substituted by 1 to 3 substituents selected from
   (a) a $C_{1-6}$ alkyl group optionally substituted by 1 to 3 substituents selected from a halogen atom and a hydroxy group,
   (b) a hydroxy group,
   (c) a $C_{1-6}$ alkoxy group, and
   (d) a halogen atom;

(4) a non-aromatic heterocyclic group (e.g., tetrahydrofuryl, morpholinyl, thiomorpholinyl, piperidyl, pyrrolidinyl, piperazinyl, dioxolyl, dioxolanyl, 1,3-dihydro-2-benzofuranyl, thiazolidinyl, tetrahydropyranyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group,
   (d) a halogen atom, and
   (e) a $C_{1-6}$ alkyl-carbonyl group;

(5) an amino group optionally mono- or di-substituted by substituent(s) selected from
   (a) a $C_{1-6}$ alkyl group optionally substituted by 1 to 3 substituents selected from
     (i) a $C_{1-6}$ alkoxy group,
     (ii) a $C_{6-14}$ aryloxy group (e.g., phenoxy),
     (iii) a carboxyl group,
     (iv) a $C_{1-6}$ alkoxy-carbonyl group, and
     (v) a hydroxy group,
   (b) a $C_{7-13}$ aralkyloxy group (e.g., benzyloxy),
   (c) a $C_{1-6}$ alkyl-carbonyl group optionally substituted by 1 to 3 substituents selected from
     (i) a hydroxy group, and
     (ii) an aromatic heterocyclic group (e.g., thienyl, furyl, pyridyl, oxazolyl, thiazolyl, tetrazolyl, oxadiazolyl, pyrazinyl, quinolyl, indolyl, imidazolyl, pyrazolyl, thiadiazolyl, isoxazolyl),
   (d) a $C_{3-10}$ cycloalkyl-carbonyl group (e.g., cyclopropylcarbonyl, cyclopentylcarbonyl, cyclohexylcarbonyl),
   (e) a $C_{1-6}$ alkoxy-carbonyl group,
   (f) a $C_{6-14}$ aryl-carbonyl group (e.g., benzoyl) optionally substituted by 1 to 3 substituents selected from
     (i) a $C_{1-6}$ alkyl group optionally substituted by 1 to 3 halogen atoms (e.g., trifluoromethyl), and
     (ii) a halogen atom,
   (g) a $C_{7-13}$ aralkyl-carbonyl group (e.g., benzylcarbonyl, phenethylcarbonyl),
   (h) an aromatic heterocyclyl-carbonyl group (e.g., thienylcarbonyl, furylcarbonyl, pyridylcarbonyl, oxazolylcarbonyl, thiazolylcarbonyl, tetrazolylcarbonyl, oxadiazolylcarbonyl, pyrazinylcarbonyl, quinolylcarbonyl, indolylcarbonyl, imidazolylcarbonyl, pyrazolylcarbonyl, thiadiazolylcarbonyl, isoxazolylcarbonyl) optionally substituted by 1 to 3$C_{1-6}$ alkyl groups,
   (i) an aromatic heterocyclyl-carbamoyl group (e.g., thienylcarbamoyl, furylcarbamoyl, pyridylcarbamoyl, oxazolylcarbamoyl, thiazolylcarbamoyl, tetrazolylcarbamoyl, oxadiazolylcarbamoyl, pyrazinylcarbamoyl, quinolylcarbamoyl, indolylcarbamoyl, imidazolylcarbamoyl, pyrazolylcarbamoyl, thiadiazolylcarbamoyl, isoxazolylcarbamoyl),
   (j) a $C_{1-6}$ alkyl-carbamoyl group (e.g., methylcarbamoyl, ethylcarbamoyl),
   (k) a $C_{6-14}$ aryl-carbamoyl group (e.g., phenylcarbamoyl, 1-naphthylcarbamoyl, 2-naphthylcarbamoyl),
   (l) a $C_{7-13}$ aralkyl-carbamoyl group (e.g., benzylcarbamoyl),
   (m) a $C_{1-6}$ alkylsulfonyl group (e.g., methylsulfonyl, ethylsulfonyl, isopropylsulfonyl),
   (n) a $C_{6-14}$ arylsulfonyl group (e.g., benzenesulfonyl, toluenesulfonyl, 1-naphthalenesulfonyl, 2-naphthalenesulfonyl), and
   (o) a $C_{7-13}$ aralkylsulfonyl group (e.g., benzylsulfonyl);

(6) an amidino group;

(7) a $C_{1-6}$ alkyl-carbonyl group optionally substituted by 1 to 3 halogen atoms;

(8) a $C_{1-6}$ alkoxy-carbonyl group optionally substituted by 1 to 3 halogen atoms;

(9) a $C_{1-6}$ alkylsulfonyl group (e.g., methylsulfonyl) optionally substituted by 1 to 3 halogen atoms;

(10) a carbamoyl group optionally mono- or di-substituted by substituents selected from
   (a) a $C_{1-6}$ alkyl group optionally substituted by 1 to 3 substituents selected from
     (i) a halogen atom,
     (ii) a cyano group,
     (iii) a hydroxy group, and
     (iv) an aromatic heterocyclic group (e.g., thienyl, furyl, pyridyl, oxazolyl, thiazolyl, tetrazolyl, oxadiazolyl, pyrazinyl, quinolyl, indolyl, imidazolyl, pyrazolyl, thiadiazolyl, isoxazolyl), (b) a $C_{6-14}$ aryl group (e.g., phenyl),
(c) a $C_{7-13}$ aralkyl group (e.g., benzyl), and
(d) an aromatic heterocyclyl-$C_{1-6}$ alkyl group (e.g., furfuryl);
(11) a thiocarbamoyl group optionally mono- or di-substituted by $C_{1-6}$ alkyl groups optionally substituted by 1 to 3 halogen atoms;
(12) a sulfamoyl group optionally mono- or di-substituted by $C_{1-6}$ alkyl groups optionally substituted by 1 to 3 halogen atoms;
(13) a carboxyl group;
(14) a hydroxy group;
(15) a $C_{1-6}$ alkoxy group optionally substituted by 1 to 3 substituents selected from
  (a) a halogen atom,
  (b) a carboxyl group,
  (c) a $C_{1-6}$ alkoxy group,
  (d) a $C_{1-6}$ alkoxy-carbonyl group,
  (e) a hydroxy group, and
  (f) an amino group optionally mono- or di-substituted by $C_{1-6}$ alkyl group(s);
(16) a $C_{2-6}$ alkenyloxy group (e.g., ethenyloxy) optionally substituted by 1 to 3 halogen atoms;
(17) a $C_{3-10}$ cycloalkyloxy group (e.g., cyclohexyloxy);
(18) a $C_{7-13}$ aralkyloxy group (e.g., benzyloxy);
(19) a $C_{6-14}$ aryloxy group (e.g., phenoxy, naphthyloxy) optionally substituted by 1 to 3 halogen atoms;
(20) a $C_{1-6}$ alkyl-carbonyloxy group (e.g., acetyloxy, tert-butylcarbonyloxy);
(21) a mercapto group;
(22) a $C_{1-6}$ alkylthio group (e.g., methylthio, ethylthio) optionally substituted by 1 to 3 halogen atoms;
(23) a $C_{7-13}$ aralkylthio group (e.g., benzylthio);
(24) a $C_{6-14}$ arylthio group (e.g., phenylthio, naphthylthio);
(25) a sulfo group;
(26) a cyano group;
(27) an azido group;
(28) a nitro group;
(29) a nitroso group;
(30) a halogen atom;
(31) a $C_{1-6}$ alkylsulfinyl group (e.g., methylsulfinyl);
(32) a $C_{3-10}$ cycloalkyl-$C_{1-6}$ alkyloxy group (e.g., cyclopropylmethyloxy);
(33) a $C_{1-3}$ alkylenedioxy group;
(34) an N-hydroxycarbamoyl group;
(35) a mono or di-$C_{1-6}$ alkylphosphoryl group (e.g., diethylphosphoryl);
(36) a $C_{6-14}$ arylsulfonyl group (e.g., phenylsulfonyl);
(37) a non-aromatic heterocyclyl-carbonyl group (e.g., tetrahydrofurylcarbonyl, morpholinylcarbonyl, thiomorpholinylcarbonyl, piperidylcarbonyl, pyrrolidinylcarbonyl, piperazinylcarbonyl, dioxolylcarbonyl, dioxolanylcarbonyl, 1,3-dihydro-2-benzofuranylcarbonyl, thiazolidinylcarbonyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group, and
    (d) a halogen atom;
and the like. When the number of substituents is two or more, the substituents may be the same or different.

The $C_{6-14}$ aryl group, $C_{7-13}$ aralkyl group and $C_{8-13}$ aralkenyl group exemplified as the aforementioned "hydrocarbon group" optionally have 1 to 3 substituents at substitutable position(s).

Examples of such substituent include
(1) the aforementioned groups exemplified as the substituents that $C_{1-10}$ alkyl group and the like optionally have;
(2) a $C_{1-6}$ alkyl group optionally substituted by 1 to 3 substituents selected from
  (a) a halogen atom,
  (b) a carboxyl group,
  (c) a hydroxy group,
  (d) a non-aromatic heterocycleoxy group (e.g., piperidyloxy, tetrahydropyranyloxy),
  (e) an amino group optionally mono- or di-substituted by $C_{1-6}$ alkyl groups,
  (f) a $C_{6-14}$ aryl group (e.g., phenyl),
  (g) a $C_{1-6}$ alkoxy-carbonyl group,
  (h) a $C_{1-6}$ alkyl-carbonyloxy group (e.g., acetyloxy, tert-butylcarbonyloxy),
  (i) a carbamoyl group,
  (j) an aromatic heterocyclic group (e.g., thienyl, furyl, pyridyl, oxazolyl, thiazolyl, tetrazolyl, oxadiazolyl, pyrazinyl, quinolyl, indolyl, imidazolyl, pyrazolyl, thiadiazolyl, isoxazolyl) optionally substituted by 1 to 3$C_{1-6}$ alkyl groups optionally substituted by 1 to 3 hydroxy groups (e.g., hydroxymethyl), and
  (k) a non-aromatic heterocyclic group (e.g., piperidyl, tetrahydropyranyl);
(3) a $C_{2-6}$ alkenyl group (e.g., ethenyl, 1-propenyl) optionally substituted by 1 to 3 substituents selected from
  (a) a halogen atom,
  (b) a carboxyl group,
  (c) a $C_{1-6}$ alkoxy-carbonyl group, and
  (d) a carbamoyl group;
and the like. When the number of substituents is two or more, the substituents may be the same or different.

The $C_{3-10}$ cycloalkyl group, $C_{3-10}$ cycloalkenyl group, $C_{4-10}$ cycloalkadienyl group and $C_{3-10}$ cycloalkyl-$C_{1-6}$ alkyl group exemplified as the aforementioned "hydrocarbon group" optionally have 1 to 3 substituents at substitutable position(s).

Examples of such substituent include
(1) the groups exemplified as the substituent that the aforementioned $C_{6-14}$ aryl group and the like optionally have;
(2) an oxo group; and the like. When the number of substituents is two or more, the substituents may be the same or different.

Examples of the "heterocyclic group" of the "heterocyclic group optionally having substituent(s)" for $R^1$, $R^2$, $R^3$ or $R^X$ include an aromatic heterocyclic group and a non-aromatic heterocyclic group.

Here, examples of the aromatic heterocyclic group include a 4- to 7-membered (preferably 5- or 6-membered) monocyclic aromatic heterocyclic group containing, as a ring-constituting atom besides carbon atom, 1 to 4 hetero atoms selected from an oxygen atom, a sulfur atom and a nitrogen atom, and a fused aromatic heterocyclic group. Examples of the fused aromatic heterocyclic group include a group derived from a group wherein a group corresponding to such 4- to 7-membered monocyclic aromatic heterocyclic group is fused with one or two selected from 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene), a benzene ring and the like, and the like.

Preferable examples of the aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl, 5-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-3-yl, 1,2,4-triazin-5-yl, 1,2,4-triazin-6-yl) and the like; fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl, 4-benzofuranyl, 5-benzofuranyl, 6-benzofuranyl, 7-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), benzothiadiazolyl (e.g., 1,2,3-benzothiadiazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like.

Examples of the non-aromatic heterocyclic group include a 3- to 7-membered (preferably 4- to 6-membered) monocyclic non-aromatic heterocyclic group, containing, as a ring-constituting atom besides carbon atom, 1 to 4 hetero atoms selected from an oxygen atom, a sulfur atom and a nitrogen atom, and a fused non-aromatic heterocyclic group. Examples of the fused non-aromatic heterocyclic group include a group derived from a group wherein a group corresponding to such 4- to 7-membered monocyclic non-aromatic heterocyclic group is fused with one or two selected from a 5- or 6-membered aromatic or non-aromatic heterocycle containing 1 or 2 nitrogen atoms (e.g., pyrrole, imidazole, pyrazole, pyrazine, pyridine, pyrimidine), a 5-membered aromatic or non-aromatic heterocycle containing one sulfur atom (e.g., thiophene), a benzene ring and the like, and the like.

Preferable examples of the non-aromatic heterocyclic group include
monocyclic non-aromatic heterocyclic groups such as oxiranyl (e.g., 2-oxiranyl), oxetanyl (e.g., 2-oxetanyl, 3-oxetanyl), aziridinyl (e.g., 1-aziridinyl, 2-aziridinyl), azetidinyl (e.g., 1-azetidinyl, 2-azetidinyl, 3-azetidinyl), pyrrolidinyl (e.g., 1-pyrrolidinyl, 2-pyrrolidinyl), piperidyl (e.g., 1-piperidyl, 2-piperidyl, 3-piperidyl, 4-piperidyl), homopiperidyl (e.g., 1-homopiperidyl, 2-homopiperidyl, 3-homopiperidyl, 4-homopiperidyl), tetrahydropyridyl (e.g., 1,2,3,6-tetrahydropyridin-1-yl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), 2-thioxo-1,3-oxazolidin-5-yl, pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), oxodihydrooxadiazolyl (e.g., 5-oxo-4,5-dihydro-1,2,4-oxadiazol-3-yl) and the like;
fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuranyl (e.g., 4,5,6,7-tetrahydro-1-benzofuran-3-yl), chromenyl (e.g., 4H-chromen-2-yl, 2H-chromen-3-yl, 2H-chromen-7-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl, 1,2,3,4-tetrahydroisoquinolin-2-yl), dihydrophthalazinyl (e.g., 1,4-dihydrophthalazin-4-yl), tetrahydrobenzoazepinyl (e.g., 2,3,4,5-tetrahydro-1H-benzo[c]azepin-1-yl) and the like;
and the like.

The aforementioned aromatic heterocyclic group and non-aromatic heterocyclic group optionally have 1 to 3 substituents at substitutable position(s).

Examples of the substituent of the aromatic heterocyclic group include those exemplified as the substituents that $C_{6-14}$ aryl and the like exemplified as the "hydrocarbon group" of the aforementioned "hydrocarbon group optionally having substituent(s)" optionally have. When the number of substituents is two or more, the substituents may be the same or different.

Examples of the substituent of the non-aromatic heterocyclic group include those exemplified as the substituents that $C_{3-10}$ cycloalkyl group and the like exemplified as the "hydrocarbon group" of the aforementioned "hydrocarbon group optionally having substituent(s)" optionally have. When the number of substituents is two or more, the substituents may be the same or different.

Examples of the "hydroxy group optionally having a substituent" for $R^1$, $R^2$, $R^3$ or $R^X$ include a hydroxy group optionally substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{3-10}$ cycloalkyl-$C_{1-6}$ alkyl group, a $C_{1-6}$ alkyl-carbonyl group, a heterocyclic group and the like, each optionally having substituent(s).

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and $C_{3-10}$ cycloalkyl-$C_{1-6}$ alkyl group include those exemplified as the "hydrocarbon group" of the "hydrocarbon group optionally having substituent(s)" for $R^1$, $R^2$, $R^3$ or $R^X$.

Examples of the heterocyclic group include the aromatic heterocyclic group and non-aromatic heterocyclic group those exemplified as the "heterocyclic group" of the "heterocyclic group optionally having substituent(s)" for $R^1$, $R^2$, $R^3$ or $R^X$.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{3-10}$ cycloalkyl-$C_{1-6}$ alkyl group, $C_{1-6}$ alkyl-carbonyl group, aromatic heterocyclic group and non-aromatic heterocyclic group optionally have 1 to 3 substituents at substitutable position(s). When the number of substituents is two or more, the substituents may be the same or different.

Examples of the substituent of the $C_{1-10}$ alkyl group, $C_{2-10}$ alkenyl group and $C_{1-6}$ alkyl-carbonyl group include those exemplified as the substituents that $C_{1-10}$ alkyl group and the like exemplified as the "hydrocarbon group" of the "hydrocarbon group optionally having substituent(s)" for $R^1$, $R^2$, $R^3$ or $R^X$ optionally have.

Examples of the substituent of the $C_{3-10}$ cycloalkyl group, $C_{3-10}$ cycloalkenyl group, $C_{3-10}$ cycloalkyl-$C_{1-6}$ alkyl group and non-aromatic heterocyclic group include those exemplified as the substituents that $C_{3-10}$ cycloalkyl group and the like exemplified as the "hydrocarbon group" of the "hydrocarbon group optionally having substituent(s)" for $R^1$, $R^2$, $R^3$ or $R^X$ optionally have.

Examples of the substituent of the $C_{6-14}$ aryl group, $C_{7-13}$ aralkyl group and $C_{8-13}$ arylalkenyl group and aromatic heterocyclic group include those exemplified as the substituents that $C_{6-14}$ aryl cycloalkyl group and the like exemplified as the "hydrocarbon group" of the "hydrocarbon group optionally having substituent(s)" for $R^1$, $R^2$, $R^3$ or $R^X$ optionally have.

Examples of the "amino group optionally having substituent(s)" for $R^1$, $R^2$, $R^3$ or $R^X$ include an amino group optionally substituted by 1 or 2 substituents selected from a $C_{1-10}$ alkyl group, a $C_{2-10}$ alkenyl group, a $C_{3-10}$ cycloalkyl group, a $C_{3-10}$ cycloalkenyl group, a $C_{1-14}$ aryl group, a $C_{7-13}$ aralkyl group, a $C_{8-13}$ arylalkenyl group, a $C_{3-10}$ cycloalkyl-$C_{1-6}$ alkyl group and a heterocyclic group, each optionally having substituent(s); an acyl group and the like.

Examples of the $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group and cycloalkyl-$C_{1-6}$ alkyl group include those exemplified as the "hydrocarbon group" of the "hydrocarbon group optionally having substituent(s)" for $R^1$, $R^2$, $R^3$ or $R^X$.

Examples of the heterocyclic group include the aromatic heterocyclic group and non-aromatic heterocyclic group include those exemplified as the "heterocyclic group" of the "heterocyclic group optionally having substituent(s)" for $R^1$, $R^2$, $R^3$ or $R^X$.

The $C_{1-10}$ alkyl group, $C_{2-10}$ alkenyl group, $C_{3-10}$ cycloalkyl group, $C_{3-10}$ cycloalkenyl group, $C_{6-14}$ aryl group, $C_{7-13}$ aralkyl group, $C_{8-13}$ arylalkenyl group, $C_{3-10}$ cycloalkyl-$C_{1-6}$ alkyl group, aromatic heterocyclic group and non-aromatic heterocyclic group optionally have 1 to 3 substituents at substitutable position(s). When the number of substituents is two or more, the substituents may be the same or different.

Examples of the substituent of the $C_{1-10}$ alkyl group and $C_{2-10}$ alkenyl group include those exemplified as the substituents that $C_{1-10}$ alkyl group and the like exemplified as the "hydrocarbon group" of the "hydrocarbon group optionally having substituent(s)" for $R^1$, $R^2$, $R^3$ or $R^X$ optionally have.

Examples of the substituent of the $C_{3-10}$ cycloalkyl group, $C_{3-10}$ cycloalkenyl group, $C_{3-10}$ cycloalkyl-$C_{1-6}$ alkyl group and non-aromatic heterocyclic group include those exemplified as the substituents that $C_{3-10}$ cycloalkyl group and the like exemplified as the "hydrocarbon group" of the "hydrocarbon group optionally having substituent(s)" for $R^1$, $R^2$, $R^3$ or $R^X$ optionally have.

Examples of the substituent of the $C_{6-14}$ aryl group, $C_{7-13}$ aralkyl group, $C_{8-13}$ arylalkenyl group and aromatic heterocyclic group include those exemplified as the substituents that $C_{6-14}$ aryl cycloalkyl group and the like exemplified as the "hydrocarbon group" of the "hydrocarbon group optionally having substituent(s)" for $R^1$, $R^2$, $R^3$ or $R^X$ optionally have.

Examples of the "acyl group" for $R^1$, $R^2$, $R^3$ or $R^X$ and the "acyl group" as the substituent of the aforementioned "amino group optionally having substituent(s)" include a group represented by the formula: $-COR^A$, $-CO-OR^A$, $-SO_2R^A$, $-SOR^A$, $-CO-NR^{A'}R^{B'}$, $-SO_2-NR^{A'}R^{B'}$, $-SO_2-NR^{A'}(COR^{B'})$, $-CS-NR^{A'}R^{B'}$ wherein $R^A$ is a hydrogen atom, a hydrocarbon group optionally having substituent(s) or a heterocyclic group optionally having substituent(s); $R^{A'}$ is a hydrogen atom, a hydroxy group optionally having a substituent, a hydrocarbon group optionally having substituent(s) or a heterocyclic group optionally having substituent(s); and $R^{B'}$ is a hydrogen atom, a hydrocarbon group optionally having substituent(s) or a heterocyclic group optionally having substituent(s); or $R^{A'}$ and $R^{B'}$ in combination form, together with the adjacent nitrogen atom, a nitrogen-containing heterocycle optionally having substituent(s).

Examples of the "hydrocarbon group optionally having substituent(s)" and "heterocyclic group optionally having substituent(s)" for $R^A$, $R^{A'}$ or $R^{B'}$ include those similar to the "hydrocarbon group optionally having substituent(s)" and "heterocyclic group optionally having substituent(s)" for $R^1$, $R^2$, $R^3$ or $R^X$.

Examples of the "hydroxy group optionally having a substituent" for $R^{A'}$ include those similar to the "hydroxy group optionally having a substituent" for $R^1$, $R^2$, $R^3$ or $R^X$ Examples of the "nitrogen-containing heterocycle" of the "nitrogen-containing heterocycle optionally having substituent(s)" formed by $R^{A'}$ and $R^{B'}$ in combination together with the adjacent nitrogen atom include a 5- to 7-membered nitrogen-containing heterocycle containing, as a ring-constituting atom besides carbon atom, at least one nitrogen atom, and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, oxopiperazine and the like.

The nitrogen-containing heterocycle optionally has 1 to 3 (preferably 1 or 2) substituents at substitutable position(s). Examples of the substituent include those exemplified as the substituent that the $C_{3-10}$ cycloalkyl group and the like exemplified as the "hydrocarbon group" of the "hydrocarbon group optionally having substituent(s)" for $R^1$, $R^2$, $R^3$ or $R^X$ optionally have. When the number of substituents is two or more, the substituents may be the same or different.

Specific examples of the "acyl group" include
(1) a formyl group,
(2) a $C_{1-6}$ alkyl-carbonyl group optionally having substituent(s),
(3) a $C_{2-6}$ alkenyl-carbonyl group optionally having substituent(s),
(4) a $C_{2-6}$ alkynyl-carbonyl group optionally having substituent(s), (5) a $C_{3-6}$ cycloalkyl-carbonyl group optionally having substituent(s),
(6) a $C_{3-6}$ cycloalkenyl-carbonyl group optionally having substituent(s),
(7) a $C_{6-10}$ aryl-carbonyl group optionally having substituent(s),
(8) a heterocyclylcarbonyl group optionally having substituent(s),
(9) a carboxy group,
(10) a $C_{1-6}$ alkoxy-carbonyl group optionally having substituent(s),
(11) a $C_{2-6}$ alkenyloxy-carbonyl group optionally having substituent(s),
(12) a $C_{2-6}$ alkynyloxy-carbonyl group optionally having substituent(s),
(13) a $C_{3-6}$ cycloalkyloxy-carbonyl group optionally having substituent(s),
(14) a $C_{3-6}$ cycloalkenyloxy-carbonyl group optionally having substituent(s),
(15) a $C_{6-10}$ aryloxy-carbonyl group optionally having substituent(s),
(16) a heterocyclyloxycarbonyl group optionally having substituent(s),
(17) a carbamoyl group optionally having substituent(s),
(18) a $C_{1-6}$ alkylsulfonyl group optionally having substituent(s) and the like.

Examples of the "$C_{2-6}$ alkenyl-carbonyl group" of the "$C_{2-6}$ alkenyl-carbonyl group optionally having substituent(s)" include ethenylcarbonyl, 1-propenylcarbonyl, 2-propenylcarbonyl, 2-methyl-1-propenylcarbonyl, 1-butenylcarbonyl, 2-butenylcarbonyl, 3-butenylcarbonyl, 3-methyl-2-butenylcarbonyl, 1-pentenylcarbonyl, 2-pentenylcarbonyl, 3-pentenylcarbonyl, 4-pentenylcarbonyl, 4-methyl-3-pentenylcarbonyl, 1-hexenylcarbonyl, 2-hexenylcarbonyl, 3-hexenylcarbonyl, 4-hexenylcarbonyl, 5-hexenylcarbonyl and the like.

Examples of the "$C_{2-6}$ alkynyl-carbonyl group" of the "$C_{2-6}$ alkynyl-carbonyl group optionally having substituent(s)" include ethynylcarbonyl, 1-propynylcarbonyl, 2-propynylcarbonyl, 1-butynylcarbonyl, 2-butynylcarbonyl, 3-butynylcarbonyl, 1-pentynylcarbonyl, 2-pentynylcarbonyl, 3-pentynylcarbonyl, 4-pentynylcarbonyl, 1-hexynylcarbonyl, 2-hexynylcarbonyl, 3-hexynylcarbonyl, 4-hexynylcarbonyl, 5-hexynylcarbonyl and the like.

Examples of the "$C_{3-6}$ cycloalkyl-carbonyl group" of the "$C_{3-6}$ cycloalkyl-carbonyl group optionally having substituent(s)" include cyclopropylcarbonyl, cyclobutylcarbonyl, cyclopentylcarbonyl, cyclohexylcarbonyl and the like.

Examples of the "$C_{3-6}$ cycloalkenyl-carbonyl group" of the "$C_{3-6}$ cycloalkenyl-carbonyl group optionally having substituent(s)" include 2-cyclopropen-1-ylcarbonyl, 2-cyclobuten-1-ylcarbonyl, 2-cyclopenten-1-ylcarbonyl, 3-cyclopenten-1-ylcarbonyl, 2-cyclohexen-1-ylcarbonyl, 3-cyclohexen-1-ylcarbonyl and the like.

Examples of the "$C_{6-10}$ aryl-carbonyl group" of the "$C_{6-10}$ aryl-carbonyl group optionally having substituent(s)" include benzoyl, 1-naphthoyl, 2-naphthoyl and the like.

Examples of the "heterocyclylcarbonyl group" of the "heterocyclylcarbonyl group optionally having substituent(s)" include (1) 5- or 6-membered monocyclic aromatic heterocycle (e.g., furan, thiophene, pyrrole, oxazole, isoxazole, thiazole, isothiazole, imidazole, pyridine, pyrazole etc.)-carbonyl, (2) 8- to 12-membered fused aromatic heterocycle (e.g., benzofuran, isobenzofuran, benzothiophene, isobenzothiophene, indole, isoindole, 1H-indazole, benzimidazole, benzoxazole etc.)-carbonyl, (3) 3 to 6-membered non-aromatic heterocycle (e.g., oxirane, azetidine, oxetane, pyrrolidine, tetrahydrofuran, thioran, piperidine etc.)-carbonyl and the like.

Examples of the "$C_{2-6}$ alkenyloxy-carbonyl group" of the "$C_{2-6}$ alkenyloxy-carbonyl group optionally having substituent(s)" include ethenyloxycarbonyl, 1-propenyloxycarbonyl, 2-propenyloxycarbonyl, 1-butenyloxycarbonyl, 2-butenyloxycarbonyl, 3-butenyloxycarbonyl, 3-methyl-2-butenyloxycarbonyl, 1-pentenyloxycarbonyl, 2-pentenyloxycarbonyl, 3-pentenyloxycarbonyl, 4-pentenyloxycarbonyl, 1-hexenyloxycarbonyl, 2-hexenyloxycarbonyl, 3-hexenyloxycarbonyl, 4-hexenyloxycarbonyl, 5-hexenyloxycarbonyl and the like.

Examples of the "$C_{2-6}$ alkynyloxy-carbonyl group" of the "$C_{2-6}$ alkynyloxy-carbonyl group optionally having substituent(s)" include ethynyloxycarbonyl, 1-propynyloxycarbonyl, 2-propynyloxycarbonyl, 1-butynyloxycarbonyl, 2-butynyloxycarbonyl, 3-butynyloxycarbonyl, 1-pentynyloxycarbonyl, 2-pentynyloxycarbonyl, 3-pentynyloxycarbonyl, 4-pentynyloxycarbonyl, 1-hexynyloxycarbonyl, 2-hexynyloxycarbonyl, 3-hexynyloxycarbonyl, 4-hexynyloxycarbonyl, 5-hexynyloxycarbonyl and the like.

Examples of the "$C_{3-6}$ cycloalkyloxy-carbonyl group" of the "$C_{3-6}$ cycloalkyloxy-carbonyl group optionally having substituent(s)" include cyclopropyloxycarbonyl, cyclobutyloxycarbonyl, cyclopentyloxycarbonyl, cyclohexyloxycarbonyl and the like.

Examples of the "$C_{3-6}$ cycloalkenyloxy-carbonyl group" of the "$C_{3-5}$ cycloalkenyloxy-carbonyl group optionally having substituent(s)" include 2-cyclopropen-1-yloxycarbonyl, 2-cyclobuten-1-yloxycarbonyl, 2-cyclopenten-1-yloxycarbonyl, 3-cyclopenten-1-yloxycarbonyl, 2-cyclohexen-1-yloxycarbonyl, 3-cyclohexen-1-yloxycarbonyl and the like.

Examples of the "$C_{6-10}$ aryloxy-carbonyl group" of the "$C_{6-10}$ aryloxy-carbonyl group optionally having substituent(s)" include phenoxycarbonyl, 1-naphthyloxycarbonyl, 2-naphthyloxycarbonyl and the like.

Examples of the "heterocyclyloxycarbonyl group" of the "heterocyclyloxycarbonyl group optionally having substituent(s)" include (1) 5- or 6-membered monocyclic aromatic heterocycle (e.g., furan, thiophene, pyrrole, oxazole, isoxazole, thiazole, isothiazole, imidazole, pyridine, pyrazole etc.)-oxycarbonyl, (2) 8- to 12-membered fused aromatic heterocycle (e.g., benzofuran, isobenzofuran, so benzothiophene, isobenzothiophene, indole, isoindole, 1H-indazole, benzimidazole, benzoxazole etc.)-oxycarbonyl, (3) 3 to 6-membered non-aromatic heterocycle (e.g., oxirane, azetidine, oxetane, pyrrolidine, tetrahydrofuran, thioran, piperidine etc.)-oxycarbonyl and the like.

Examples of the "$C_{1-6}$ alkylsulfonyl group" of the "$C_{1-6}$ alkylsulfonyl group optionally having substituent(s)" include, unless otherwise specified, methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, 1-ethylpropylsulfonyl, hexylsulfonyl, isohexylsulfonyl, 1,1-dimethylbutylsulfonyl, 2,2-dimethylbutylsulfonyl, 3,3-dimethylbutylsulfonyl, 2-ethylbutylsulfonyl and the like.

The $C_{1-6}$ alkyl-carbonyl group, $C_{2-6}$ alkenyl-carbonyl group, $C_{2-6}$ alkynyl-carbonyl group, $C_{3-6}$ cycloalkyl-carbonyl group, $C_{3-6}$ cycloalkenyl-carbonyl group, $C_{6-10}$ aryl-carbonyl group, heterocyclylcarbonyl group, $C_{1-6}$ alkoxy-carbonyl group, $C_{2-6}$ alkenyloxy-carbonyl group, $C_{2-6}$ alkynyloxy-carbonyl group, $C_{3-6}$ cycloalkyloxy-carbonyl group, $C_{3-6}$ cycloalkenyloxy-carbonyl group, $C_{6-10}$ aryloxy-carbonyl group, heterocyclyloxycarbonyl group and $C_{1-6}$ alkylsulfonyl group optionally have 1 to 3 substituents at substitutable position(s). When the number of substituents is two or more, the substituents may be the same or different.

Examples of the substituent of the $C_{1-6}$ alkyl-carbonyl group, $C_{2-6}$ alkenyl-carbonyl group, $C_{2-6}$ alkynyl-carbonyl group, $C_{1-5}$ alkoxy-carbonyl group, $C_{2-6}$ alkenyloxy-carbonyl group, $C_{2-6}$ alkynyloxy-carbonyl group and $C_{1-6}$ alkylsulfonyl group include those exemplified as the substituent that the $C_{1-10}$ alkyl group and the like exemplified as the "hydrocarbon group" of the "hydrocarbon group optionally having substituent(s)" for $R^1$, $R^2$, $R^3$ or $R^X$ optionally have.

Examples of the substituent of the $C_{3-6}$ cycloalkyl-carbonyl group, $C_{3-6}$ cycloalkenyl-carbonyl group, heterocyclylcarbonyl group, $C_{3-6}$ cycloalkyloxy-carbonyl group, $C_{3-6}$ cycloalkenyloxy-carbonyl group and heterocyclyloxycarbonyl group include those exemplified as the substituent that the $C_{3-10}$ cycloalkyl group and the like exemplified as the "hydrocarbon group" of the "hydrocarbon group optionally having substituent(s)" for $R^1$, $R^2$, $R^3$ or $R^X$ optionally have, excluding oxo when the heterocycle of the heterocyclylcarbonyl group and heterocyclyloxycarbonyl group are each an aromatic heterocycle.

Examples of the substituent of the $C_{6-10}$ aryl-carbonyl group and $C_{6-10}$ aryloxy-carbonyl group include those exemplified as the substituent that the $C_{6-14}$ aryl group and the like exemplified as the "hydrocarbon group" of the "hydrocarbon group optionally having substituent(s)" for $R^1$, $R^2$, $R^3$ or $R^X$ optionally have.

Examples of the "carbamoyl optionally having substituent(s)" include a carbamoyl group optionally substituted by 1 or 2 substituents selected from a $C_{1-10}$ alkyl group, a $C_{2-10}$ alkenyl group, a $C_{3-10}$ cycloalkyl group, a $C_{3-10}$ cycloalkenyl group, a $C_{3-10}$ cycloalkyl-$C_{1-6}$ alkyl group, a $C_{6-14}$ aryl group, a $C_{7-13}$ aralkyl group, a $C_{8-13}$ arylalkenyl group and a heterocyclic group and the like, each optionally having substituent (s).

Examples of the $C_{1-10}$ alkyl group, $C_{2-10}$ alkenyl group, $C_{3-10}$ cycloalkyl group, $C_{3-10}$ cycloalkenyl group, $C_{3-10}$ cycloalkyl-$C_{1-6}$ alkyl group, $C_{6-14}$ aryl group, $C_{7-13}$ aralkyl group, and $C_{9-13}$ arylalkenyl group include those exemplified as the "hydrocarbon group" of the "hydrocarbon group optionally having substituent (s)" for $R^1$, $R^2$, $R^3$ or $R^X$.

Examples of the heterocyclic group include the aromatic heterocyclic group and non-aromatic heterocyclic group those exemplified as the "heterocyclic group" of the "heterocyclic group optionally having substituent(s)" for $R^1$, $R^2$, $R^3$ or $R^X$. The $C_{1-10}$ alkyl group, $C_{2-10}$ alkenyl group, $C_{3-10}$ cycloalkyl group, $C_{3-10}$ cycloalkenyl group, $C_{3-10}$ cycloalkyl-$C_{1-6}$ alkyl group, $C_{6-14}$ aryl group, $C_{7-13}$ aralkyl group, $C_{8-13}$ arylalkenyl group, aromatic heterocyclic group and non-aromatic heterocyclic group optionally have 1 to 3 substituents at substitutable position(s). When the number of substituents is two or more, the substituents may be the same or different.

Examples of the substituent of the $C_{1-10}$ alkyl group and $C_{2-10}$ alkenyl group include those exemplified as the substituents that $C_{1-10}$ alkyl group and the like exemplified as the "hydrocarbon group" of the "hydrocarbon group optionally having substituent(s)" for $R^1$, $R^2$, $R^3$ or $R^X$ optionally have.

Examples of the substituent of the $C_{3-10}$ cycloalkyl group, $C_{3-10}$ cycloalkenyl group, $C_{3-10}$ cycloalkyl-$C_{1-6}$ alkyl group and non-aromatic heterocyclic group include those exemplified as the substituents that $C_{3-10}$ cycloalkyl group and the like exemplified as the "hydrocarbon group" of the "hydrocarbon group optionally having substituent (s)" for $R^1$, $R^2$, $R^3$ or $R^X$ optionally have.

Examples of the substituent of the $C_{6-14}$ aryl group, $C_{7-13}$ aralkyl group, $C_{8-13}$ arylalkenyl group and aromatic heterocyclic group include those exemplified as the substituents that $C_{6-14}$ aryl cycloalkyl group and the like exemplified as the "hydrocarbon group" of the "hydrocarbon group optionally having substituent(s)" for $R^1$, $R^2$, $R^3$ or $R^X$ optionally have.

Examples of the "nitrogen-containing heterocycle optionally having substituent(s)" formed by $R^1$ and $R^2$ in combination together with the adjacent nitrogen atom include those similar to the "nitrogen-containing heterocycle optionally having substituent(s)" formed by $R^{A'}$ and $R^{B'}$ in combination together with the adjacent nitrogen atom.

Examples of the "5- to 7-membered nitrogen-containing heterocycle optionally having substituent(s)" formed by $R^1$ and $R^3$ in combination together with the adjacent nitrogen atom include a 5- to 7-membered nitrogen-containing heterocycle, from among the "nitrogen-containing heterocycle optionally having substituent(s)" formed by $R^{A'}$ and $R^{B'}$ in combination together with the adjacent nitrogen atom.

E is preferably a group represented by the formula

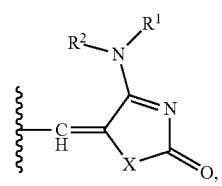

Ea

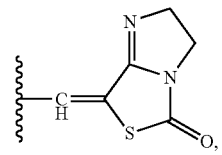

Ec

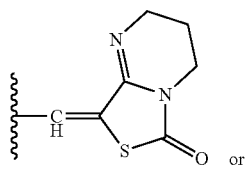

Ed or

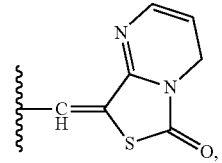

Ee particularly

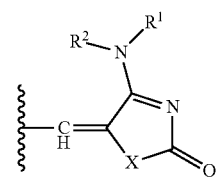

Ea wherein

X is —S—, —O— or —NR$^X$— (preferably —S—);

R$^X$ is a hydrocarbon group optionally having substituent(s) (preferably a $C_{1-6}$ alkyl group (preferably methyl));

R$^1$ is a hydrogen atom, a hydrocarbon group optionally having substituent(s) or a heterocyclic group optionally having substituent(s) (preferably a hydrogen atom, a $C_{1-6}$ alkyl group optionally having substituent(s), a $C_{2-6}$ alkenyl group optionally having substituent(s), a $C_{2-6}$ alkynyl group optionally having substituent(s), a $C_{3-10}$ cycloalkyl group optionally having substituent(s), a $C_{3-10}$ cycloalkyl-$C_{1-6}$ alkyl group optionally having substituent(s), or a non-aromatic heterocyclic group optionally having substituent(s)); and $R^2$ is a hydrogen atom; or $R^1$ and $R^2$ in combination form, together with the adjacent nitrogen atom, a 4- to 7-membered nitrogen-containing heterocycle (preferably pyrrolidine, azetidine) optionally having substituent(s).

E is more preferably a group represented by the formula

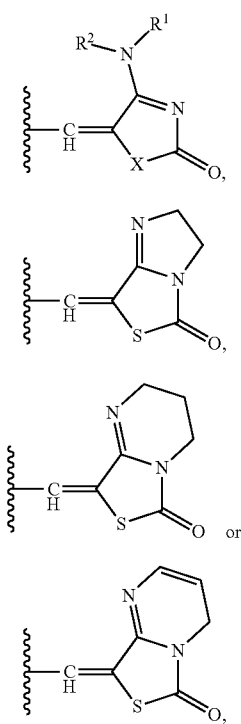

particularly

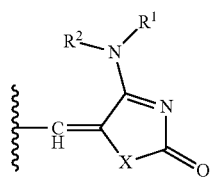

wherein

X is —S—, —O— or —NR$^X$— (preferably —S—);

$R^X$ is a $C_{1-6}$ alkyl group (preferably methyl);

$R^1$ is (1) a hydrogen atom;

(2) a $C_{1-6}$ alkyl group (preferably methyl, ethyl, propyl, isobutyl, isopentyl, neopentyl, 2-methylbutyl) optionally substituted by 1 to 5 substituents selected from
  (a) an amino group optionally mono- or di-substituted by $C_{1-6}$ alkyl group(s) (preferably methyl, ethyl) optionally substituted by 1 to 3 hydroxy groups,
  (b) a hydroxy group,
  (c) a $C_{1-6}$ alkoxy group (preferably methoxy, ethoxy) optionally substituted by 1 to 3 substituents selected from a hydroxy group, a $C_{1-6}$ alkoxy group (preferably methoxy) and a mono- or di-$C_{1-6}$ alkylamino group (preferably diethylamino),
  (d) a carboxy group,
  (e) a halogen atom (preferably a fluorine atom),
  (f) a $C_{1-6}$ alkoxy-carbonyl group (preferably ethoxycarbonyl, tert-butoxycarbonyl),
  (g) a carbamoyl group optionally mono- or di-substituted by substituent(s) selected from
    (i) a $C_{1-6}$ alkyl group (preferably methyl, ethyl, isobutyl) optionally substituted by 1 to 3 substituents selected from a hydroxy group and a $C_{1-6}$ alkoxy group (preferably methoxy),
    (ii) a $C_{3-10}$ cycloalkyl group (preferably cyclopropyl), and
    (iii) a 4- to 6-membered non-aromatic heterocyclic group (preferably oxetanyl),
  (h) a $C_{1-6}$ alkylsulfonyl group (preferably methylsulfonyl),
  (i) a $C_{6-14}$ aryl group (preferably phenyl),
  (j) a 5- or 6-membered aromatic heterocyclic group (preferably oxazolyl, isoxazolyl),
  (k) a 4- to 6-membered non-aromatic heterocyclic group (preferably pyrrolidinyl, tetrahydropyranyl, dioxanyl) optionally substituted by 1 to 3 substituents selected from
    (i) an oxo group, and
    (ii) a $C_{1-6}$ alkyl group (preferably methyl) optionally substituted by 1 to 3 hydroxy groups, and
  (l) a 4- to 6-membered non-aromatic heterocyclylcarbonyl group (preferably pyrrolidinylcarbonyl, piperazinylcarbonyl, morpholinylcarbonyl) optionally substituted by 1 to 3 substituents selected from
    (i) a hydroxy group, and
    (ii) a $C_{1-6}$ alkyl group (preferably methyl);

(3) a $C_{2-6}$ alkenyl group (preferably 2-propenyl, 2-butenyl) optionally substituted by 1 to 3 mono- or di-$C_{1-6}$ alkylamino groups (preferably diethylamino);

(4) a $C_{2-6}$ alkynyl group (preferably 2-propynyl, 2-butynyl, 3-butynyl, 1-methyl-2-propynyl, 4-methyl-2-pentynyl) optionally substituted by 1 to 3 substituents selected from
  (a) a mono- or di-$C_{1-6}$ alkylamino group (preferably diethylamino),
  (b) a $C_{3-10}$ cycloalkyl group (preferably cyclopropyl), and
  (c) a hydroxy group;

(5) a $C_{3-10}$ cycloalkyl group (preferably cyclopentyl, cyclohexyl) optionally substituted by 1 to 3 substituents selected from
  (a) a halogen atom (preferably a fluorine atom), and
  (b) a hydroxy group;

(6) a $C_{3-10}$ cycloalkyl-$C_{1-6}$ alkyl group (preferably cyclopropylmethyl, cyclobutylmethyl) optionally substituted by 1 to 3 substituents selected from
  (a) a hydroxy group,
  (b) a $C_{1-6}$ alkyl group (preferably methyl) optionally substituted by 1 to 3 hydroxy groups, and
  (c) a carbamoyl group optionally mono- or di-substituted by $C_{1-6}$ alkyl group(s) (preferably methyl); or (7) a 4- to 6-membered non-aromatic heterocyclic group (preferably oxetanyl, tetrahydrofuryl, pyrrolidinyl, piperidyl, tetrahydropyranyl) optionally substituted by 1 to 3 substituents selected from
  (a) a $C_{1-6}$ alkyl group (preferably methyl),
  (b) a hydroxy group, and
  (c) an oxo group; and $R^2$ is a hydrogen atom; or $R^1$ and $R^2$ in combination form, together with the adjacent nitrogen atom, a 4- to 7-membered nitrogen-containing heterocycle (preferably pyrrolidine, azetidine) optionally substituted by 1 to 3 substituents selected from
(1) a hydroxy group, and
(2) a carbamoyl group optionally mono- or di-substituted by
$C_{1-6}$ alkyl group(s) (preferably methyl).

As another embodiment, E is more preferably a group represented by the formula

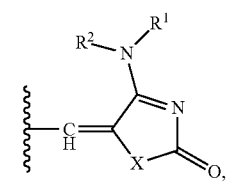
Ea

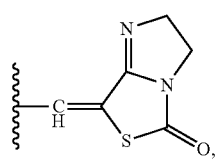
Ec

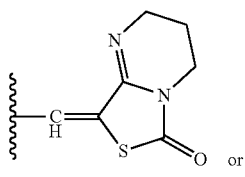
Ed or

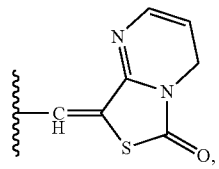
Ee particularly

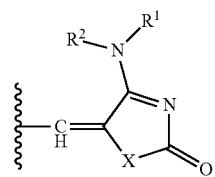
Ea wherein
X is —S—, —O— or —$NR^X$— (preferably —S—);
$R^X$ is a $C_{1-6}$ alkyl group (preferably methyl);
$R^1$ is
(1) a hydrogen atom;
(2) a $C_{1-6}$ alkyl group (preferably methyl, ethyl, propyl, isobutyl, isopentyl, neopentyl, 2-methylbutyl) optionally substituted by 1 to 5 substituents selected from
(a) a halogen atom (preferably a fluorine atom),
(b) an amino group optionally mono- or di-substituted by $C_{1-6}$ alkyl group(s) (preferably methyl, ethyl) optionally substituted by 1 to 3 hydroxy groups,
(c) a hydroxy group,
(d) a $C_{1-6}$ alkoxy group (preferably methoxy, ethoxy) optionally substituted by 1 to 3 substituents selected from a hydroxy group, a $C_{1-6}$ alkoxy group (preferably methoxy) and a di-$C_{1-6}$ alkylamino group (preferably diethylamino),
(e) a carbamoyl group optionally mono- or di-substituted by substituent(s) selected from
(i) a $C_{1-6}$ alkyl group (preferably methyl, ethyl, isobutyl) optionally substituted by 1 to 3 substituents selected from a hydroxy group and a $C_{1-6}$ alkoxy group (preferably methoxy),
(ii) a $C_{3-10}$ cycloalkyl group (preferably cyclopropyl), and
(iii) an oxetanyl group,
(f) a carboxy group,
(g) a $C_{1-6}$ alkoxy-carbonyl group (preferably ethoxycarbonyl, tert-butoxycarbonyl),
(h) a pyrrolidylcarbonyl group optionally substituted by hydroxy group(s),
(i) a morpholinylcarbonyl group,
(j) a piperazinylcarbonyl group substituted by $C_{1-6}$ alkyl group(s) (preferably methyl),
(k) a dioxanyl group,
(l) a tetrahydropyranyl group substituted by $C_{1-6}$ alkyl group(s) (preferably methyl) substituted by hydroxy group(s),
(m) an oxopyrrolidinyl group,
(n) an oxazolyl group,
(o) an isoxazolyl group,
(p) a phenyl group, and
(q) a $C_{1-6}$ alkylsulfonyl group (preferably methylsulfonyl);
(3) a $C_{2-6}$ alkenyl group (preferably 2-propenyl, 2-butenyl) optionally substituted by 1 to 3 di-$C_{1-6}$ alkylamino groups (preferably diethylamino);
(4) a $C_{2-6}$ alkynyl group (preferably 2-propynyl, 2-butynyl, 3-butynyl, 1-methyl-2-propynyl, 4-methyl-2-pentynyl) optionally substituted by 1 to 3 substituents selected from
(a) a di-$C_{1-6}$ alkylamino group (preferably diethylamino),
(b) a $C_{3-10}$ cycloalkyl group (preferably cyclopropyl), and
(c) a hydroxy group;
(5) a $C_{3-10}$ cycloalkyl group (preferably cyclopentyl, cyclohexyl) optionally substituted by 1 to 3 substituents selected from
(a) a halogen atom (preferably a fluorine atom), and
(b) a hydroxy group;
(6) a $C_{3-10}$ cycloalkyl-$C_{1-6}$ alkyl group (preferably cyclopropylmethyl, cyclobutylmethyl) optionally substituted by 1 to 3 substituents selected from
(a) a hydroxy group,
(b) a $C_{1-6}$ alkyl group (preferably methyl) substituted by hydroxy group(s), and
(c) a di-$C_{1-6}$ alkyl-carbamoyl group (preferably dimethylcarbamoyl);
(7) an oxetanyl group;
(8) a tetrahydrofuryl group optionally substituted by hydroxy group(s);
(9) a tetrahydropyranyl group optionally substituted by hydroxy group(s);
(10) a pyrrolidinyl group optionally substituted by 1 to 3 substituents selected from a $C_{1-6}$ alkyl group (preferably methyl) and an oxo group; or
(11) a piperidyl group optionally substituted by 1 to 3 substituents selected from a $C_{1-6}$ alkyl group (preferably methyl) and an oxo group; and
$R^2$ is a hydrogen atom; or
$R^1$ and $R^2$ in combination form, together with the adjacent nitrogen atom, (1) a pyrrolidine ring optionally substituted by 1 to 3 hydroxy groups or carbamoyl group(s) di-substituted by $C_{1-6}$ alkyl groups (preferably methyl); or
(2) an azetidine ring substituted by carbamoyl group(s) di-substituted by $C_{1-6}$ alkyl groups (preferably methyl).

E is further more-preferably a group represented by the formula

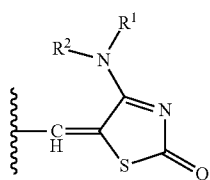

wherein
$R^1$ is
(1) a $C_{1-6}$ alkyl group (preferably methyl, ethyl, propyl, isobutyl, isopentyl, neopentyl, 2-methylbutyl) optionally substituted by 1 to 5 substituents selected from
   (a) an amino group optionally mono- or di-substituted by $C_{1-6}$ alkyl group(s) (preferably methyl, ethyl) optionally substituted by 1 to 3 hydroxy groups,
   (b) a hydroxy group,
   (c) a $C_{1-6}$ alkoxy group (preferably methoxy, ethoxy) optionally substituted by 1 to 3 substituents selected from a hydroxy group, a $C_{1-6}$ alkoxy group (preferably methoxy) and a mono- or di-$C_{1-6}$ alkylamino group (preferably diethylamino),
   (d) a carboxy group,
   (e) a halogen atom (preferably a fluorine atom),
   (f) a $C_{1-6}$ alkoxy-carbonyl group (preferably ethoxycarbonyl, tert-butoxycarbonyl),
   (g) a carbamoyl group optionally mono- or di-substituted by substituent(s) selected from
     (i) a $C_{1-6}$ alkyl group (preferably methyl, ethyl, isobutyl) optionally substituted by 1 to 3 substituents selected from a hydroxy group and a $C_{1-6}$ alkoxy group (preferably methoxy),
     (ii) a $C_{3-10}$ cycloalkyl group (preferably cyclopropyl), and
     (iii) a 4- to 6-membered non-aromatic heterocyclic group (preferably oxetanyl),
   (h) a $C_{1-6}$ alkylsulfonyl group (preferably methylsulfonyl),
   (i) a $C_{6-14}$ aryl group (preferably phenyl),
   (j) a 5- or 6-membered aromatic heterocyclic group (preferably oxazolyl, isoxazolyl),
   (k) a 4- to 6-membered non-aromatic heterocyclic group (preferably pyrrolidinyl, tetrahydropyranyl, dioxanyl) optionally substituted by 1 to 3 substituents selected from
     (i) an oxo group, and
     (ii) a $C_{1-6}$ alkyl group (preferably methyl) optionally substituted by 1 to 3 hydroxy groups, and
   (l) a 4- to 6-membered non-aromatic heterocyclylcarbonyl group (preferably pyrrolidinylcarbonyl, piperazinylcarbonyl, morpholinylcarbonyl) optionally substituted by 1 to 3 substituents selected from
     (i) a hydroxy group, and
     (ii) a $C_{1-6}$ alkyl group (preferably methyl);
(2) a $C_{2-6}$ alkenyl group (preferably 2-propenyl, 2-butenyl) optionally substituted by 1 to 3 mono- or di-$C_{1-6}$ alkylamino groups (preferably diethylamino);
(3) a $C_{2-6}$ alkynyl group (preferably 2-propynyl, 2-butynyl, 3-butynyl, 1-methyl-2-propynyl, 4-methyl-2-pentynyl) optionally substituted by 1 to 3 substituents selected from
   (a) a mono- or di-$C_{1-6}$ alkylamino group (preferably diethylamino),
   (b) a $C_{3-10}$ cycloalkyl group (preferably cyclopropyl), and
   (c) a hydroxy group;
(4) a $C_{3-10}$ cycloalkyl group (preferably cyclohexyl) optionally substituted by 1 to 3 substituents selected from
   (a) a halogen atom (preferably a fluorine atom), and
   (b) a hydroxy group;
(5) a $C_{3-10}$ cycloalkyl-$C_{1-6}$ alkyl group (preferably cyclopropylmethyl, cyclobutylmethyl) optionally substituted by 1 to 3 substituents selected from
   (a) a hydroxy group,
   (b) a $C_{1-6}$ alkyl group (preferably methyl) optionally substituted by 1 to 3 hydroxy groups, and
   (c) a carbamoyl group optionally mono- or di-substituted by $C_{1-6}$ alkyl group(s) (preferably methyl); or
(6) a 4- to 6-membered non-aromatic heterocyclic group (preferably oxetanyl, tetrahydrofuryl, pyrrolidinyl, piperidyl, tetrahydropyranyl) optionally substituted by 1 to 3 substituents selected from
   (a) a $C_{1-6}$ alkyl group (preferably methyl),
   (b) a hydroxy group, and
   (c) an oxo group; and
$R^2$ is a hydrogen atom; or
$R^1$ and $R^2$ in combination form, together with the adjacent nitrogen atom, a 4- to 7-membered nitrogen-containing heterocycle (preferably pyrrolidine, azetidine) optionally substituted by 1 to 3 substituents selected from
   (1) a hydroxy group, and
   (2) a carbamoyl group optionally mono- or di-substituted by $C_{1-6}$ alkyl group(s) (preferably methyl).

As another embodiment, E is further more preferably a group represented by the formula

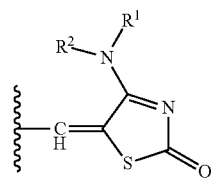

wherein
$R^1$ is
(1) a $C_{1-6}$ alkyl group (preferably methyl, ethyl, propyl, isobutyl, isopentyl, neopentyl, 2-methylbutyl) optionally substituted by 1 to 5 substituents selected from
   (a) a halogen atom (preferably a fluorine atom),
   (b) an amino group di-substituted by $C_{1-6}$ alkyl groups (preferably methyl, ethyl) optionally substituted by 1 to 3 hydroxy groups,
   (c) a hydroxy group,
   (d) a $C_{1-6}$ alkoxy group (preferably methoxy, ethoxy) optionally substituted by 1 to 3 substituents selected from a hydroxy group, a $C_{1-6}$ alkoxy group (preferably methoxy) and a di-$C_{1-6}$ alkylamino group (preferably diethylamino),
   (e) a carbamoyl group optionally mono- or di-substituted by substituent(s) selected from
     (i) a $C_{1-6}$ alkyl group (preferably methyl, ethyl, isobutyl) optionally substituted by 1 to 3 hydroxy groups, (ii) a $C_{1-6}$ alkyl group (preferably ethyl) substituted by $C_{1-6}$ alkoxy group(s) (preferably methoxy),
(iii) a $C_{3-10}$ cycloalkyl group (preferably cyclopropyl), and
(iv) an oxetanyl group,
(f) a carboxy group,
(g) a $C_{1-6}$ alkoxy-carbonyl group (preferably ethoxycarbonyl, tert-butoxycarbonyl),
(h) a pyrrolidylcarbonyl group optionally substituted by hydroxy group(s),
(i) a morpholinylcarbonyl group,
(j) a piperazinylcarbonyl group substituted by $C_{1-6}$ alkyl group(s) (preferably methyl),
(k) a dioxanyl group,
(l) a tetrahydropyranyl group substituted by $C_{1-6}$ alkyl group(s) (preferably methyl) substituted by hydroxy group(s),
(m) an oxopyrrolidinyl group,
(n) an oxazolyl group,
(o) an isoxazolyl group,
(p) a phenyl group, and
(q) a $C_{1-6}$ alkylsulfonyl group (preferably methylsulfonyl);
(2) a $C_{2-6}$ alkenyl group (preferably 2-propenyl, 2-butenyl) optionally substituted by 1 to 3 di-$C_{1-6}$ alkylamino groups (preferably diethylamino);
(3) a $C_{2-6}$ alkynyl group (preferably 2-propynyl, 2-butynyl, 3-butynyl, 1-methyl-2-propynyl, 4-methyl-2-pentynyl) optionally substituted by 1 to 3 substituents selected from
    (a) a di-$C_{1-6}$ alkylamino group (preferably diethylamino),
    (b) a $C_{3-10}$ cycloalkyl group (preferably cyclopropyl), and
    (c) a hydroxy group;
(4) a $C_{3-10}$ cycloalkyl group (preferably cyclohexyl) optionally substituted by 1 to 3 substituents selected from
    (a) a halogen atom (preferably a fluorine atom), and
    (b) a hydroxy group;
(5) a $C_{3-10}$ cycloalkyl-$C_{1-6}$ alkyl group (preferably cyclopropylmethyl, cyclobutylmethyl) optionally substituted by 1 to 3 substituents selected from
    (a) a hydroxy group,
    (b) a $C_{1-6}$ alkyl group (preferably methyl) substituted by hydroxy group(s), and
    (c) a di-$C_{1-6}$ alkyl-carbamoyl group (preferably dimethylcarbamoyl);
(6) an oxetanyl group;
(7) a tetrahydrofuryl group optionally substituted by hydroxy group(s);
(8) a tetrahydropyranyl group substituted by hydroxy group(s);
(9) a pyrrolidinyl group optionally substituted by 1 to 3 substituents selected from a $C_{1-6}$ alkyl group (preferably methyl) and an oxo group; or
(10) a piperidyl group optionally substituted by 1 to 3 substituents selected from a $C_{1-6}$ alkyl group (preferably methyl) and an oxo group; and
$R^2$ is a hydrogen atom; or
$R^1$ and $R^2$ in combination form, together with the adjacent nitrogen atom,
(1) a pyrrolidine ring optionally substituted by 1 to 3 hydroxy groups or carbamoyl group(s) di-substituted by $C_{1-6}$ alkyl groups (preferably methyl); or
(2) an azetidine ring substituted by carbamoyl group(s) di-substituted by $C_{1-6}$ alkyl groups (preferably methyl).

As another embodiment, E is further more preferably a group represented by the formula

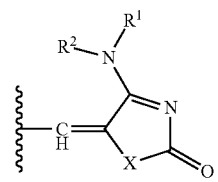

Ea wherein
X is —S— or —NR$^X$— (preferably —S—);
R$^X$ is a $C_{1-6}$ alkyl group (preferably methyl);
$R^1$ is
(1) a $C_{1-6}$ alkyl group (preferably methyl, ethyl, propyl, isobutyl, neopentyl) optionally substituted by 1 to 3 substituents selected from
    (a) an amino group di-substituted by $C_{1-6}$ alkyl groups (preferably methyl, ethyl) optionally substituted by 1 to 3 hydroxy groups,
    (b) a hydroxy group,
    (c) a $C_{1-6}$ alkoxy group (preferably ethoxy) substituted by 1 to 3 substituents selected from a hydroxy group, a $C_{1-6}$ alkoxy group (preferably methoxy) and a di-$C_{1-6}$ alkylamino group (preferably diethylamino), and (d) a carbamoyl group di-substituted by $C_{1-6}$ alkyl groups (preferably methyl);
(2) a $C_{2-6}$ alkynyl group (preferably 2-propynyl);
(3) a $C_{3-10}$ cycloalkyl-$C_{1-6}$ alkyl group (preferably cyclopropylmethyl);
(4) an oxetanyl group; or
(5) a tetrahydrofuryl group; and
$R^2$ is a hydrogen atom.

E is still more preferably a group represented by the formula

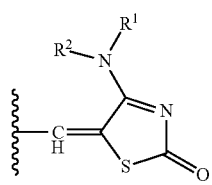

Eaa wherein
$R^1$ is
(1) a $C_{1-6}$ alkyl group (preferably methyl, ethyl, isobutyl, neopentyl) optionally substituted by 1 to 3 substituents selected from
    (a) a hydroxy group,
    (b) a $C_{1-6}$ alkoxy group (preferably ethoxy) substituted by 1 to 3 hydroxy groups, and
    (c) a carbamoyl group di-substituted by $C_{1-6}$ alkyl groups (preferably methyl); or
(2) a $C_{2-6}$ alkynyl group (preferably 2-propynyl); and
$R^2$ is a hydrogen atom.

E is particularly preferably a group represented by the formula

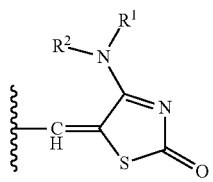

wherein
R¹ is
(1) a $C_{1-6}$ alkyl group (preferably ethyl) substituted by 1 to 3 substituents selected from a $C_{1-6}$ alkoxy group (preferably ethoxy) substituted by 1 to 3 hydroxy groups; or
(2) a $C_{2-6}$ alkynyl group (preferably 2-propynyl); and
R² is a hydrogen atom.

A is a cyclic group optionally having substituent(s).

Examples of the "cyclic group" of the "cyclic group optionally having substituent(s)" for A include an aromatic group and a non-aromatic cyclic group.

Examples of the aromatic group include an aromatic hydrocarbon group and aromatic heterocyclic group.

The aromatic hydrocarbon group is preferably a $C_{6-14}$ aryl group or the like.

Examples of the $C_{6-14}$ aryl group include those exemplified as the "hydrocarbon group" of the "hydrocarbon group optionally having substituent(s)" for R¹, R², R³ or $R^X$.

Examples of the aromatic heterocyclic group include those similar to the aromatic heterocyclic group exemplified as the "heterocyclic group" of the "heterocyclic group optionally having substituent(s)" for R¹, R², R³ or $R^X$.

The aromatic group optionally has 1 to 3 substituents at substitutable position(s). When the number of substituents is two or more, the substituents may be the same or different.

Examples of the substituent of the aromatic group include those exemplified as the substituents that $C_{6-14}$ aryl cycloalkyl group and the like exemplified as the "hydrocarbon group" of the "hydrocarbon group optionally having substituent(s)" for R¹, R², R³ or $R^X$ optionally have.

Examples of the non-aromatic cyclic group include a non-aromatic cyclic hydrocarbon group and a non-aromatic heterocyclic group.

Examples of the non-aromatic cyclic hydrocarbon group include a $C_{3-10}$ cycloalkyl group, a $C_{3-10}$ cycloalkenyl group and a $C_{4-10}$ cycloalkadienyl group, each optionally fused with a benzene ring.

Examples of the $C_{3-10}$ cycloalkyl group, $C_{3-10}$ cycloalkenyl group and $C_{4-10}$ cycloalkadienyl group include those exemplified as the "hydrocarbon group" of the "hydrocarbon group optionally having substituent(s)" for R¹, R², R³ or $R^X$.

Examples of the non-aromatic heterocyclic group include those similar to the non-aromatic heterocyclic group exemplified as the "heterocyclic group" of the "heterocyclic group optionally having substituent(s)" for R¹, R², R³ or $R^X$.

The non-aromatic cyclic group optionally has 1 to 3 substituents at substitutable position(s). When the number of substituents is two or more, the substituents may be the same or different.

Examples of the substituent of the non-aromatic cyclic group include those exemplified as the substituents that $C_{3-10}$ cycloalkyl group and the like exemplified as the "hydrocarbon group" of the "hydrocarbon group optionally having substituent(s)" for R¹, R², R³ or $R^X$ optionally have.

The "cyclic group" of the "cyclic group optionally having substituent(s)" for A is preferably a $C_{6-10}$ aryl group (preferably phenyl, naphthyl), an aromatic heterocyclic group (preferably benzofuryl, indolyl, benzimidazolyl) or a $C_{3-10}$ cycloalkyl group (preferably cyclohexyl), more preferably a phenyl group, a naphthyl group, a benzofuryl group, an indolyl group, a benzimidazolyl group or a $C_{3-10}$ cycloalkyl group (preferably cyclohexyl).

The "substituent" of the "cyclic group optionally having substituent(s)" for A is preferably selected from
(a) a halogen atom (preferably a chlorine atom, a bromine atom),
(b) a cyano group,
(c) a $C_{1-6}$ alkyl group (preferably methyl, tert-butyl) optionally substituted by 1 to 3 halogen atoms (preferably a fluorine atom) (preferably trifluoromethyl),
(d) a $C_{1-6}$ alkoxy group (preferably methoxy) optionally substituted by 1 to 3 halogen atoms (preferably a fluorine atom) (preferably trifluoromethoxy),
(e) a hydroxy group, and
(f) a pentafluorosulfanyl group.

A is preferably a $C_{6-10}$ aryl group (preferably phenyl, naphthyl), an aromatic heterocyclic group (preferably benzofuryl, indolyl, benzimidazolyl) or a $C_{3-10}$ cycloalkyl group (preferably cyclohexyl), each optionally having substituent(s)

A is more preferably
(1) a $C_{6-10}$ aryl group (preferably phenyl, naphthyl) optionally substituted by 1 to 3 substituents selected from
  (a) a $C_{1-6}$ alkyl group (preferably methyl, tert-butyl) optionally substituted by 1 to 3 halogen atoms (preferably a fluorine atom) (preferably trifluoromethyl),
  (b) a $C_{1-6}$ alkoxy group (preferably methoxy) optionally substituted by 1 to 3 halogen atoms (preferably a fluorine atom) (preferably trifluoromethoxy),
  (c) a cyano group,
  (d) a halogen atom (preferably a chlorine atom, a bromine atom),
  (e) a hydroxy group, and
  (f) a pentafluorosulfanyl group;
(2) an aromatic heterocyclic group (preferably benzofuryl, indolyl, benzimidazolyl) optionally substituted by 1 to 3 substituents selected from
  (a) a $C_{1-6}$ alkyl group (preferably methyl), and
  (b) a halogen atom (preferably a chlorine atom); or
(3) a $C_{3-10}$ cycloalkyl group (preferably cyclohexyl).

As another embodiment, A is more preferably a phenyl group, a naphthyl group, a benzofuryl group, an indolyl group, a benzimidazolyl group or a $C_{3-10}$ cycloalkyl group (preferably cyclohexyl), each optionally substituted by 1 to 3 substituents selected from
  (a) a halogen atom (preferably a chlorine atom, a bromine atom),
  (b) a cyano group,
  (c) a $C_{1-6}$ alkyl group (preferably methyl, tert-butyl) optionally substituted by 1 to 3 halogen atoms (preferably a fluorine atom) (preferably trifluoromethyl),
  (d) a $C_{1-6}$ alkoxy group (preferably methoxy) optionally substituted by 1 to 3 halogen atoms (preferably a fluorine atom) (preferably trifluoromethoxy),
  (e) a hydroxy group, and
  (f) a pentafluorosulfanyl group.

A is further more preferably a phenyl group optionally substituted by 1 to 3 substituents selected from
  (a) a halogen atom (preferably a chlorine atom, a bromine atom),
  (b) a cyano group, (c) a $C_{1-6}$ alkyl group (preferably methyl, tert-butyl) optionally substituted by 1 to 3 halogen atoms (preferably a fluorine atom) (preferably trifluoromethyl),
(d) a $C_{1-6}$ alkoxy group (preferably methoxy) optionally substituted by 1 to 3 halogen atoms (preferably a fluorine atom) (preferably trifluoromethoxy),
(e) a hydroxy group, and
(f) a pentafluorosulfanyl group.

A is still more preferably a phenyl group optionally substituted by 1 to 3 substituents selected from
(a) a halogen atom (preferably a chlorine atom),
(b) a cyano group, and
(c) a $C_{1-6}$ alkyl group (preferably methyl) optionally substituted by 1 to 3 halogen atoms (preferably a fluorine atom) (preferably trifluoromethyl).

A is particularly preferably a phenyl group optionally substituted by 1 to 3 substituents selected from
(a) a halogen atom (preferably a chlorine atom), and
(b) a $C_{1-6}$ alkyl group (preferably methyl) optionally substituted by 1 to 3 halogen atoms (preferably a fluorine atom) (preferably trifluoromethyl).

A is particularly preferably a phenyl group substituted by 1 to 3 (preferably 1 or 2) substituents selected from a $C_{1-6}$ alkyl group (preferably methyl) optionally substituted by 1 to 3 halogen atoms (preferably a fluorine atom) (preferably trifluoromethyl).

The phenyl preferably has, as a substituent, a "$C_{1-6}$ alkyl group optionally substituted by 1 to 3 halogen atoms" at both of the ortho-position and para-position, relative to the bond that A has (-$L^a$-)

$L^a$ is a bond, —O—, —CO—, —S—, —SO—, —$SO_2$—, —$NR^{L1}$— or —$NR^{L1}$— CO—;
$L^b$ is a bond or a $C_{1-3}$ alkylene group optionally having substituent (s);
$L^c$ is a bond, —CO—, —O—CO—, —$NR^{L2}$—CO—, —$SO_2$— or —$NR^{L2}$—$SO_2$—; and
$R^{L1}$ and $R^{L2}$ are each independently a hydrogen atom, a hydrocarbon group optionally having substituent(s), a heterocyclic group optionally having substituent(s), a hydroxy group optionally having a substituent, an amino group optionally having substituent(s), or an acyl group.

Examples of the "$C_{1-3}$ alkylene group" of the "$C_{1-3}$ alkylene group optionally having substituent(s)" for $L^b$ include a as methylene group, an ethylene group, a trimethylene group and the like.

The "$C_{1-3}$ alkylene group" optionally has 1 to 3 substituents at substitutable position(s). When the number of substituents is two or more, the substituents may be the same or different.

Examples of the "substituent" of the "$C_{1-3}$ alkylene group optionally having substituent(s)" include those exemplified as the substituents that $C_{6-14}$ aryl group and the like exemplified as the "hydrocarbon group" of the "hydrocarbon group to optionally having substituent(s)" for $R^1$, $R^2$, $R^3$ or $R^X$ optionally have.

Examples of the "hydrocarbon group optionally having substituent(s)", "heterocyclic group optionally having substituent(s)", "hydroxy group optionally having a substituent", "amino group optionally having substituent(s)" and "acyl group" for $R^{L1}$ or $R^{L2}$ include those similar to the "hydrocarbon group optionally having substituent(s)", "heterocyclic group optionally having substituent(s)", "hydroxy group optionally having a substituent", "amino group optionally having substituent(s)" and "acyl group" for $R^1$, $R^2$, $R^3$ or $R^X$.

$L^a$ is preferably a bond.
$L^b$ is preferably a bond or a $C_{1-3}$ alkylene group (preferably methylene) optionally substituted by 1 to $3C_{1-6}$ alkyl groups (preferably methyl).
$L^b$ is more preferably a $C_{1-3}$ alkylene group (preferably methylene) optionally substituted by 1 to $3C_{1-6}$ alkyl groups (preferably methyl).
$L^b$ is more preferably a $C_{1-3}$ alkylene group (preferably methylene).
$L^b$ is particularly preferably a methylene group.
$L^c$ is preferably a bond or —CO—.
$L^c$ is preferably a bond.
-$L^a$-$L^b$-$L^c$- is preferably a linker having 6 or less atoms, which connects A and ring G.
-$L^a$-$L^b$-$L^c$- is more preferably a bond, —CO—, —($C_{1-3}$ alkylene group (preferably methylene) optionally substituted by $C_{1-6}$ alkyl group(s) (preferably methyl))- or —($C_{1-3}$ alkylene group (preferably methylene))-CO—.
-$L^a$-$L^b$-$L^c$- is more preferably a bond, —CO— or —($C_{1-3}$ alkylene group (preferably methylene) optionally substituted by $C_{1-6}$ alkyl group(s) (preferably methyl))-.
-$L^a$-$L^b$-$L^c$- is further more preferably —($C_{1-3}$ alkylene group (preferably methylene) optionally substituted by $C_{1-6}$ alkyl group(s) (preferably methyl))-.
-$L^a$-$L^b$-$L^c$- is still more preferably —($C_{1-3}$ alkylene group (preferably methylene))-.
-$L^a$-$L^b$-$L^c$- is particularly preferably methylene group.

Ring G is a 4- to 10-membered saturated heterocycle containing one nitrogen atom as a ring-constituting hetero atom, which is optionally bridged and optionally has substituent(s).

Examples of the "4- to 10-membered saturated heterocycle containing one nitrogen atom as a ring-constituting hetero atom, which is optionally bridged" of the "4- to 10-membered saturated heterocycle containing one nitrogen atom as a ring-constituting hetero atom, which is optionally bridged and optionally has substituent(s)" for ring G include a 4- to 10-membered saturated non-bridged heterocycle containing one nitrogen atom as a ring-constituting hetero atom (e.g., azetidine, pyrrolidine, piperidine, azepane, azocane, azonane, azecane) and a 4- to 10-membered saturated bridged heterocycle containing one nitrogen atom as a ring-constituting hetero atom (e.g., 3-azabicyclo[3.1.0]hexane, 8-azabicyclo[3.2.1]octane, 3-azabicyclo[3.3.1]nonane, 3-azabicyclo[3.3.0]octane).

The "4- to 10-membered saturated heterocycle containing one nitrogen atom as a ring-constituting hetero atom, which is optionally bridged" optionally has 1 to 3 substituents at substitutable position(s). When the number of substituents is two or more, the substituents may be the same or different. Examples of the substituent thereof include those exemplified as the substituents that $C_{6-10}$ cycloalkyl group and the like exemplified as the "hydrocarbon group" of the "hydrocarbon group optionally having substituent(s)" for $R^1$, $R^2$, $R^3$ or $R^X$ optionally have. The substituent is preferably selected from a $C_{1-6}$ alkyl group (e.g., methyl) and an oxo group.

Ring G is preferably an azetidine ring, a pyrrolidine ring, a piperidine ring, an azepane ring, a 3-azabicyclo[3.1.0]hexane ring, a 8-azabicyclo[3.2.1]octane ring, a 3-azabicyclo[3.3.1]nonane ring or a 3-azabicyclo[3.3.0]octane ring, each optionally having substituent(s).

As another embodiment, ring G is preferably a 4- to 10-membered saturated heterocycle containing one nitrogen atom as a ring-constituting hetero atom (preferably azetidine, pyrrolidine, piperidine, azepane, 3-azabicyclo[3.1.0]hexane, 8-azabicyclo[3.2.1]octane, 3-azabicyclo[3.3.1]nonane, 3-azabicyclo[3.3.0]octane), which is optionally bridged and optionally substituted by 1 to 3 substituents selected from a $C_{1-6}$ alkyl group (preferably methyl) and an oxo group. Ring G is more preferably piperidine.

Ring G is more preferably an azetidine ring, a pyrrolidine ring, a piperidine ring, an azepane ring, a 3-azabicyclo[3.1.0]hexane ring, a 8-azabicyclo[3.2.1]octane ring, a 3-azabicyclo[3.3.1]nonane ring or a 3-azabicyclo[3.3.0]octane ring, each optionally substituted by 1 to 3 $C_{1-6}$ alkyl groups (preferably methyl) or one oxo group.

Ring G is further more preferably a pyrrolidine ring, a piperidine ring or a 8-azabicyclo[3.2.1]octane ring.

As another embodiment, ring G is further more preferably a piperidine ring optionally substituted by 1 to 3 substituents selected from a $C_{1-6}$ alkyl group (preferably methyl) and an oxo group.

Ring G is particularly preferably a piperidine ring.

Specific preferable examples of compound (I) include the following compound.

[Compound I-A]
Compound (I) wherein
A is
(1) a $C_{6-10}$ aryl group (preferably phenyl, naphthyl) optionally substituted by 1 to 3 substituents selected from
  (a) a $C_{1-6}$ alkyl group (preferably methyl, tert-butyl) optionally substituted by 1 to 3 halogen atoms (preferably a fluorine atom) (preferably trifluoromethyl),
  (b) a $C_{1-6}$ alkoxy group (preferably methoxy) optionally substituted by 1 to 3 halogen atoms (preferably a fluorine atom) (preferably trifluoromethoxy),
  (c) a cyano group, and
  (d) a halogen atom (preferably a chlorine atom, a bromine atom);
(2) an aromatic heterocyclic group (preferably benzofuryl) optionally substituted by 1 to 3 $C_{1-6}$ alkyl groups (preferably methyl); or
(3) a $C_{3-10}$ cycloalkyl group (preferably cyclohexyl);
$L^a$ is a bond;
$L^b$ is a bond or a $C_{1-3}$ alkylene group (preferably methylene) optionally substituted by 1 to 3 $C_{1-6}$ alkyl groups (preferably methyl);
$L^c$ is a bond or —CO—;
ring G is a 4- to 10-membered saturated heterocycle containing one nitrogen atom as a ring-constituting hetero atom (preferably azetidine, pyrrolidine, piperidine, azepane, 3-azabicyclo[3.1.0]hexane, 8-azabicyclo[3.2.1]octane, 3-azabicyclo[3.3.1]nonane), which is optionally bridged and optionally substituted by $C_{1-6}$ alkyl group(s) (preferably methyl); and
E is a group represented by the formula

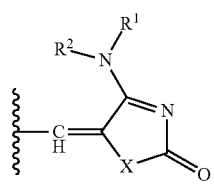

Ea wherein
X is —S— or —$NR^x$—;
$R^x$ is a $C_{1-6}$ alkyl group (preferably methyl);
$R^1$ is
(1) a hydrogen atom;
(2) a $C_{1-6}$ alkyl group (preferably methyl, ethyl, propyl, isobutyl, neopentyl) optionally substituted by 1 to 3 substituents selected from
  (a) an amino group optionally mono- or di-substituted by $C_{1-6}$ alkyl group(s) (preferably methyl, ethyl) optionally substituted by 1 to 3 hydroxy groups,
  (b) a hydroxy group, and
  (c) a $C_{1-6}$ alkoxy group (preferably ethoxy) optionally substituted by 1 to 3 substituents selected from a hydroxy group, a $C_{1-6}$ alkoxy group (preferably methoxy) and a mono- or di-$C_{1-6}$ alkylamino group (preferably diethylamino);
(3) a $C_{2-6}$ alkenyl group (preferably 2-propenyl, 2-butenyl) optionally substituted by 1 to 3 mono- or di-$C_{1-6}$ alkylamino groups (preferably diethylamino);
(4) a $C_{2-6}$ alkynyl group (preferably 2-propynyl, 2-butynyl, 4-methyl-2-pentynyl) optionally substituted by 1 to 3 substituents selected from a mono- or di-$C_{1-6}$ alkylamino group (preferably diethylamino), a $C_{3-10}$ cycloalkyl group (preferably cyclopropyl) and a hydroxy group;
(5) a $C_{3-10}$ cycloalkyl group (preferably cyclopentyl);
(6) a $C_{3-10}$ cycloalkyl-$C_{1-6}$ alkyl group (preferably cyclopropylmethyl); or
(7) a 4- to 6-membered non-aromatic heterocyclic group (preferably oxetanyl, tetrahydrofuryl); and
$R^2$ is a hydrogen atom; or
$R^1$ and $R^2$ in combination form, together with the adjacent nitrogen atom, a 5- to 7-membered nitrogen-containing heterocycle (preferably pyrrolidine) optionally substituted by 1 to 3 hydroxy groups.

[Compound I-B1]
Compound (I) wherein
A is a phenyl group, a naphthyl group, a benzofuryl group, an indolyl group, a benzimidazolyl group or a $C_{3-10}$ cycloalkyl group (preferably cyclohexyl), each optionally substituted by 1 to 3 substituents selected from
  (a) a halogen atom (preferably a chlorine atom, a bromine atom),
  (b) a cyano group,
  (c) a $C_{1-6}$ alkyl group (preferably methyl, tert-butyl) optionally substituted by 1 to 3 halogen atoms (preferably a fluorine atom) (preferably trifluoromethyl),
  (d) a $C_{1-6}$ alkoxy group (preferably methoxy) optionally substituted by 1 to 3 halogen atoms (preferably a fluorine atom) (preferably trifluoromethoxy),
  (e) a hydroxy group, and
  (f) a pentafluorosulfanyl group;
$L^a$ is a bond;
$L^b$ is a bond or a $C_{1-3}$ alkylene group (preferably methylene) optionally substituted by 1 to 3 $C_{1-6}$ alkyl groups (preferably methyl);
$L^c$ is a bond or —CO—;
ring G is an azetidine ring, a pyrrolidine ring, a piperidine ring, an azepane ring, a 3-azabicyclo[3.1.0]hexane ring, a 8-azabicyclo[3.2.1]octane ring, a 3-azabicyclo[3.3.1]nonane ring or a 3-azabicyclo[3.3.0]octane ring, each optionally substituted by 1 to 3 $C_{1-6}$ alkyl groups (preferably methyl) or one oxo group; and
E is a group represented by the formula

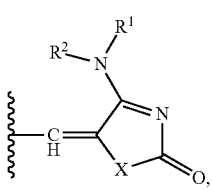

Ea

-continued

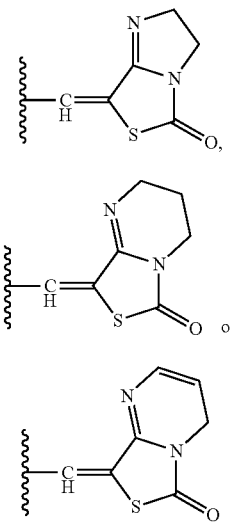

Ec

Ed

Ee wherein
X is —S—, —O— or —NR$^x$— (preferably —S—);
R$^x$ is a C$_{1-5}$ alkyl group (preferably methyl);
R$^1$ is
(1) a hydrogen atom;
(2) a C$_{1-6}$ alkyl group (preferably methyl, ethyl, propyl, isobutyl, isopentyl, neopentyl, 2-methylbutyl) optionally substituted by 1 to 5 substituents selected from
 (a) an amino group optionally mono- or di-substituted by C$_{1-6}$ alkyl group(s) (preferably methyl, ethyl) optionally substituted by 1 to 3 hydroxy groups,
 (b) a hydroxy group,
 (c) a C$_{1-6}$ alkoxy group (preferably methoxy, ethoxy) optionally substituted by 1 to 3 substituents selected from a hydroxy group, a C$_{1-6}$ alkoxy group (preferably methoxy) and a mono- or di-C$_{1-6}$ alkylamino group (preferably diethylamino),
 (d) a carboxy group,
 (e) a halogen atom (preferably a fluorine atom),
 (f) a C$_{1-6}$ alkoxy-carbonyl group (preferably ethoxycarbonyl, tert-butoxycarbonyl),
 (g) a carbamoyl group optionally mono- or di-substituted by substituent(s) selected from
  (i) a C$_{1-6}$ alkyl group (preferably methyl, ethyl, isobutyl) optionally substituted by 1 to 3 substituents selected from a hydroxy group and a C$_{1-6}$ alkoxy group (preferably methoxy),
  (ii) a C$_{3-10}$ cycloalkyl group (preferably cyclopropyl), and
  (iii) a 4- to 6-membered non-aromatic heterocyclic is group (preferably oxetanyl),
 (h) a C$_{1-6}$ alkylsulfonyl group (preferably methylsulfonyl),
 (i) a C$_{6-14}$ aryl group (preferably phenyl),
 (j) a 5- or 6-membered aromatic heterocyclic group (preferably oxazolyl, isoxazolyl),
 (k) a 4- to 6-membered non-aromatic heterocyclic group (preferably pyrrolidinyl, tetrahydropyranyl, dioxanyl) optionally substituted by 1 to 3 substituents selected from
  (i) an oxo group, and
  (ii) a C$_{1-6}$ alkyl group (preferably methyl) optionally substituted by 1 to 3 hydroxy groups, and
 (l) a 4- to 6-membered non-aromatic heterocyclylcarbonyl group (preferably pyrrolidinylcarbonyl, piperazinylcarbonyl, morpholinylcarbonyl) optionally substituted by 1 to 3 substituents selected from
  (i) a hydroxy group, and
  (ii) a C$_{1-6}$ alkyl group (preferably methyl);
(3) a C$_{2-6}$ alkenyl group (preferably 2-propenyl, 2-butenyl) optionally substituted by 1 to 3 mono- or di-C$_{1-6}$ alkylamino groups (preferably diethylamino);
(4) a C$_{2-6}$ alkynyl group (preferably 2-propynyl, 2-butynyl, 3-butynyl, 1-methyl-2-propynyl, 4-methyl-2-pentynyl) optionally substituted by 1 to 3 substituents selected from
 (a) a mono- or di-C$_{1-6}$ alkylamino group (preferably diethylamino),
 (b) a C$_{3-10}$ cycloalkyl group (preferably cyclopropyl), and
 (c) a hydroxy group;
(5) a C$_{3-10}$ cycloalkyl group (preferably cyclopentyl, cyclohexyl) optionally substituted by 1 to 3 substituents selected from
 (a) a halogen atom (preferably a fluorine atom), and
 (b) a hydroxy group;
(6) a C$_{3-10}$ cycloalkyl-C$_{1-6}$ alkyl group (preferably is cyclopropylmethyl, cyclobutylmethyl) optionally substituted by 1 to 3 substituents selected from
 (a) a hydroxy group,
 (b) a C$_{1-6}$ alkyl group (preferably methyl) optionally substituted by 1 to 3 hydroxy groups, and
 (c) a carbamoyl group optionally mono- or di-substituted by C$_{1-6}$ alkyl group(s) (preferably methyl); or
(7) a 4- to 6-membered non-aromatic heterocyclic group (preferably oxetanyl, tetrahydrofuryl, pyrrolidinyl, piperidyl, tetrahydropyranyl) optionally substituted by 1 to 3 substituents selected from
 (a) a C$_{1-6}$ alkyl group (preferably methyl),
 (b) a hydroxy group, and
 (c) an oxo group; and
R$^2$ is a hydrogen atom; or
R$^1$ and R$^2$ in combination form, together with the adjacent nitrogen atom, a 4- to 7-membered nitrogen-containing heterocycle (preferably pyrrolidine, azetidine) optionally substituted by 1 to 3 substituents selected from
 (1) a hydroxy group, and
 (2) a carbamoyl group optionally mono- or di-substituted by C$_{1-6}$ alkyl group(s) (preferably methyl).
[Compound I-B1a]
Compound (I) wherein
A is a phenyl group, a naphthyl group, a benzofuryl group, an indolyl group, a benzimidazolyl group or a C$_{3-10}$ cycloalkyl group (preferably cyclohexyl), each optionally substituted by 1 to 3 substituents selected from
 (a) a halogen atom (preferably a chlorine atom, a bromine atom),
 (b) a cyano group,
 (c) a C$_{1-6}$ alkyl group (preferably methyl, tert-butyl) optionally substituted by 1 to 3 halogen atoms (preferably a fluorine atom) (preferably trifluoromethyl),
 (d) a C$_{1-6}$ alkoxy group (preferably methoxy) optionally substituted by 1 to 3 halogen atoms (preferably a fluorine atom) (preferably trifluoromethoxy),
 (e) a hydroxy group, and
 (f) a pentafluorosulfanyl group;
L$^a$ is a bond;
L$^b$ is a bond or a C$_{1-3}$ alkylene group (preferably methylene) optionally substituted by 1 to 3 C$_{1-6}$ alkyl groups (preferably methyl);

$L^c$ is a bond or —CO—;

ring G is an azetidine ring, a pyrrolidine ring, a piperidine ring, an azepane ring, a 3-azabicyclo[3.1.0]hexane ring, a 8-azabicyclo[3.2.1]octane ring, a 3-azabicyclo[3.3.1]nonane ring or a 3-azabicyclo[3.3.0]octane ring, each optionally substituted by 1 to 3 $C_{1-6}$ alkyl groups (preferably methyl) or one oxo group; and E is a group represented by the formula

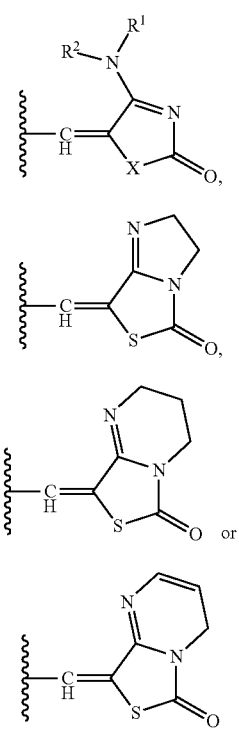

wherein

X is —S—, —O— or —NR$^X$— (preferably —S—);

R$^X$ is a $C_{1-6}$ alkyl group (preferably methyl);

R$^1$ is (1) a hydrogen atom;

(2) a $C_{1-6}$ alkyl group (preferably methyl, ethyl, propyl, isobutyl, isopentyl, neopentyl, 2-methylbutyl) optionally substituted by 1 to 5 substituents selected from
  (a) a halogen atom (preferably a fluorine atom),
  (b) an amino group optionally mono- or di-substituted by $C_{1-6}$ alkyl group(s) (preferably methyl, ethyl) optionally substituted by 1 to 3 hydroxy groups,
  (c) a hydroxy group,
  (d) a $C_{1-6}$ alkoxy group (preferably methoxy, ethoxy) optionally substituted by 1 to 3 substituents selected from a hydroxy group, a $C_{1-6}$ alkoxy group (preferably methoxy) and a di-$C_{1-6}$ alkylamino group (preferably diethylamino),
  (e) a carbamoyl group optionally mono- or di-substituted by substituent(s) selected from
    (i) a $C_{1-6}$ alkyl group (preferably methyl, ethyl, isobutyl) optionally substituted by 1 to 3 substituents selected from a hydroxy group and a $C_{1-6}$ alkoxy group (preferably methoxy),
    (ii) a $C_{3-10}$ cycloalkyl group (preferably cyclopropyl), and
    (iii) an oxetanyl group,
  (f) a carboxy group,
  (g) a $C_{1-6}$ alkoxy-carbonyl group (preferably ethoxycarbonyl, tert-butoxycarbonyl),
  (h) a pyrrolidylcarbonyl group optionally substituted by hydroxy group(s),
  (i) a morpholinylcarbonyl group,
  (j) a piperazinylcarbonyl group substituted by $C_{1-6}$ alkyl group(s) (preferably methyl),
  (k) a dioxanyl group,
  (l) a tetrahydropyranyl group substituted by $C_{1-6}$ alkyl group(s) (preferably methyl) substituted by hydroxy group(s),
  (m) an oxopyrrolidinyl group,
  (n) an oxazolyl group,
  (o) an isoxazolyl group,
  (p) a phenyl group, and
  (q) a $C_{1-6}$ alkylsulfonyl group (preferably methylsulfonyl);

(3) a $C_{2-6}$ alkenyl group (preferably 2-propenyl, 2-butenyl) optionally substituted by 1 to 3 di-$C_{1-6}$ alkylamino groups (preferably diethylamino);

(4) a $C_{2-6}$ alkynyl group (preferably 2-propynyl, 2-butynyl, 3-butynyl, 1-methyl-2-propynyl, 4-methyl-2-pentynyl) optionally substituted by 1 to 3 substituents selected from
  (a) a di-$C_{1-6}$ alkylamino group (preferably diethylamino),
  (b) a $C_{3-10}$ cycloalkyl group (preferably cyclopropyl), and
  (c) a hydroxy group;

(5) a $C_{3-10}$ cycloalkyl group (preferably cyclopentyl, cyclohexyl) optionally substituted by 1 to 3 substituents selected from
  (a) a halogen atom (preferably a fluorine atom), and
  (b) a hydroxy group;

(6) a $C_{3-10}$ cycloalkyl-$C_{1-6}$ alkyl group (preferably cyclopropylmethyl, cyclobutylmethyl) optionally substituted by 1 to 3 substituents selected from
  (a) a hydroxy group,
  (b) a $C_{1-6}$ alkyl group (preferably methyl) substituted by hydroxy group(s), and
  (c) a di-$C_{1-6}$ alkyl-carbamoyl group (preferably dimethylcarbamoyl);

(7) an oxetanyl group;

(8) a tetrahydrofuryl group optionally substituted by hydroxy group(s);

(9) a tetrahydropyranyl group optionally substituted by hydroxy group(s);

(10) a pyrrolidinyl group optionally substituted by 1 to 3 substituents selected from a $C_{1-6}$ alkyl group (preferably methyl) and an oxo group; or

(11) a piperidyl group optionally substituted by 1 to 3 substituents selected from a $C_{1-6}$ alkyl group (preferably methyl) and an oxo group; and R$^2$ is a hydrogen atom; or R$^1$ and R$^2$ in combination form, together with the adjacent nitrogen atom, (1) a pyrrolidine ring optionally substituted by 1 to 3 hydroxy groups or carbamoyl group(s) di-substituted by $C_{1-6}$ alkyl groups (preferably methyl); or (2) an azetidine ring substituted by carbamoyl group(s) di-substituted by $C_{1-6}$ alkyl groups (preferably methyl).

[Compound I-B2]
Compound (I) wherein
A is a phenyl group optionally substituted by 1 to 3 substituents selected from
  (a) a halogen atom (preferably a chlorine atom), and
  (b) a $C_{1-6}$ alkyl group (preferably methyl) optionally substituted by 1 to 3 halogen atoms (preferably a fluorine atom) (preferably trifluoromethyl);
$L^a$ is a bond;
$L^b$ is a $C_{1-3}$ alkylene group (preferably methylene) optionally substituted by 1 to 3 $C_{1-6}$ alkyl groups (preferably methyl);
$L^c$ is a bond;
ring G is a piperidine ring; and
E is a group represented by the formula

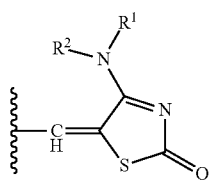

Eaa wherein
$R^1$ is
(1) a $C_{1-6}$ alkyl group (preferably methyl, ethyl, propyl, isobutyl, isopentyl, neopentyl, 2-methylbutyl) optionally substituted by 1 to 5 substituents selected from
  (a) an amino group optionally mono- or di-substituted by $C_{1-6}$ alkyl group(s) (preferably methyl, ethyl) optionally substituted by 1 to 3 hydroxy groups,
  (b) a hydroxy group,
  (c) a $C_{1-6}$ alkoxy group (preferably methoxy, ethoxy) optionally substituted by 1 to 3 substituents selected from a hydroxy group, a $C_{1-6}$ alkoxy group (preferably methoxy) and a mono- or di-$C_{1-6}$ alkylamino group (preferably diethylamino),
  (d) a carboxy group,
  (e) a halogen atom (preferably a fluorine atom),
  (f) a $C_{1-6}$ alkoxy-carbonyl group (preferably ethoxycarbonyl, tert-butoxycarbonyl),
  (g) a carbamoyl group optionally mono- or di-substituted by substituent(s) selected from
    (i) a $C_{1-6}$ alkyl group (preferably methyl, ethyl, isobutyl) optionally substituted by 1 to 3 substituents selected from a hydroxy group and a $C_{1-6}$ alkoxy group (preferably methoxy),
    (ii) a $C_{3-10}$ cycloalkyl group (preferably cyclopropyl), and
    (iii) a 4- to 6-membered non-aromatic heterocyclic group (preferably oxetanyl),
  (h) a $C_{1-6}$ alkylsulfonyl group (preferably methylsulfonyl),
  (i) a $C_{6-14}$ aryl group (preferably phenyl),
  (j) a 5- or 6-membered aromatic heterocyclic group (preferably oxazolyl, isoxazolyl),
  (k) a 4- to 6-membered non-aromatic heterocyclic group (preferably pyrrolidinyl, tetrahydropyranyl, dioxanyl) optionally substituted by 1 to 3 substituents selected from
    (i) an oxo group, and
    (ii) a $C_{1-6}$ alkyl group (preferably methyl) optionally substituted by 1 to 3 hydroxy groups, and
  (l) a 4- to 6-membered non-aromatic heterocyclylcarbonyl group (preferably pyrrolidinylcarbonyl, piperazinylcarbonyl, morpholinylcarbonyl) optionally substituted by 1 to 3 substituents selected from
    (i) a hydroxy group, and
    (ii) a $C_{1-6}$ alkyl group (preferably methyl);
(2) a $C_{2-6}$ alkenyl group (preferably 2-propenyl, 2-butenyl) optionally substituted by 1 to 3 mono- or di-$C_{1-6}$ alkylamino groups (preferably diethylamino);
(3) a $C_{2-6}$ alkynyl group (preferably 2-propynyl, 2-butynyl, 3-butynyl, 1-methyl-2-propynyl, 4-methyl-2-pentynyl) optionally substituted by 1 to 3 substituents selected from
  (a) a mono- or di-$C_{1-6}$ alkylamino group (preferably diethylamino),
  (b) a $C_{3-10}$ cycloalkyl group (preferably cyclopropyl), and
  (c) a hydroxy group;
(4) a $C_{3-10}$ cycloalkyl group (preferably cyclohexyl) optionally substituted by 1 to 3 substituents selected from
  (a) a halogen atom (preferably a fluorine atom), and
  (b) a hydroxy group;
(5) a $C_{3-10}$ cycloalkyl-$C_{1-6}$ alkyl group (preferably cyclopropylmethyl, cyclobutylmethyl) optionally substituted by 1 to 3 substituents selected from
  (a) a hydroxy group,
  (b) a $C_{1-6}$ alkyl group (preferably methyl) optionally substituted by 1 to 3 hydroxy groups, and
  (c) a carbamoyl group optionally mono- or di-substituted by $C_{1-6}$ alkyl group(s) (preferably methyl); or
(6) a 4- to 6-membered non-aromatic heterocyclic group (preferably oxetanyl, tetrahydrofuryl, pyrrolidinyl, piperidyl, tetrahydropyranyl) optionally substituted by 1 to 3 substituents selected from
  (a) a $C_{1-6}$ alkyl group (preferably methyl),
  (b) a hydroxy group, and
  (c) an oxo group; and
$R^2$ is a hydrogen atom; or
$R^1$ and $R^2$ in combination form, together with the adjacent nitrogen atom, a 4- to 7-membered nitrogen-containing heterocycle (preferably pyrrolidine, azetidine) optionally substituted by 1 to 3 substituents selected from
  (1) a hydroxy group, and
  (2) a carbamoyl group optionally mono- or di-substituted by $C_{1-6}$ alkyl group(s) (preferably methyl).

[Compound I-B2a]
Compound (I) wherein
A is a phenyl group optionally substituted by 1 to 3 substituents selected from
  (a) a halogen atom (preferably a chlorine atom), and
  (b) a $C_{1-6}$ alkyl group (preferably methyl) optionally substituted by 1 to 3 halogen atoms (preferably a fluorine atom) (preferably trifluoromethyl);
$L^a$ is a bond;
$L^b$ is a $C_{1-3}$ alkylene group (preferably methylene) optionally substituted by 1 to 3 $C_{1-6}$ alkyl groups (preferably methyl);
L is a bond;
ring G is a piperidine ring; and E is a group represented by the formula

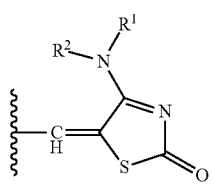

Eaa wherein
R¹ is
(1) a $C_{1-6}$ alkyl group (preferably methyl, ethyl, propyl, isobutyl, isopentyl, neopentyl, 2-methylbutyl) optionally substituted by 1 to 5 substituents selected from
   (a) a halogen atom (preferably a fluorine atom),
   (b) an amino group di-substituted by $C_{1-6}$ alkyl groups (preferably methyl, ethyl) optionally substituted by 1 to 3 hydroxy groups,
   (c) a hydroxy group,
   (d) a $C_{1-6}$ alkoxy group (preferably methoxy, ethoxy) optionally substituted by 1 to 3 substituents selected from a hydroxy group, a $C_{1-6}$ alkoxy group (preferably methoxy) and a di-$C_{1-6}$ alkylamino group (preferably diethylamino),
   (e) a carbamoyl group optionally mono- or di-substituted by substituent(s) selected from
      (i) a $C_{1-6}$ alkyl group (preferably methyl, ethyl, isobutyl) optionally substituted by 1 to 3 hydroxy groups,
      (ii) a $C_{1-6}$ alkyl group (preferably ethyl) substituted by $C_{1-6}$ alkoxy group(s) (preferably methoxy),
      (iii) a $C_{3-10}$ cycloalkyl group (preferably cyclopropyl), and
      (iv) an oxetanyl group,
   (f) a carboxy group,
   (g) a $C_{1-6}$ alkoxy-carbonyl group (preferably ethoxycarbonyl, tert-butoxycarbonyl),
   (h) a pyrrolidylcarbonyl group optionally substituted by hydroxy group(s),
   (i) a morpholinylcarbonyl group,
   (j) a piperazinylcarbonyl group substituted by $C_{1-6}$ alkyl group(s) (preferably methyl),
   (k) a dioxanyl group,
   (l) a tetrahydropyranyl group substituted by $C_{1-6}$ alkyl group(s) (preferably methyl) substituted by hydroxy group(s),
   (m) an oxopyrrolidinyl group,
   (n) an oxazolyl group,
   (o) an isoxazolyl group,
   (p) a phenyl group, and
   (q) a $C_{1-6}$ alkylsulfonyl group (preferably methylsulfonyl);
(2) a $C_{2-6}$ alkenyl group (preferably 2-propenyl, 2-butenyl) optionally substituted by 1 to 3 di-$C_{1-6}$ alkylamino groups (preferably diethylamino);
(3) a $C_{2-6}$ alkynyl group (preferably 2-propynyl, 2-butynyl, 3-butynyl, 1-methyl-2-propynyl, 4-methyl-2-pentynyl) optionally substituted by 1 to 3 substituents selected from
   (a) a di-$C_{1-6}$ alkylamino group (preferably diethylamino),
   (b) a $C_{3-10}$ cycloalkyl group (preferably cyclopropyl), and
   (c) a hydroxy group;
(4) a $C_{3-10}$ cycloalkyl group (preferably cyclohexyl) optionally substituted by 1 to 3 substituents selected from
   (a) a halogen atom (preferably a fluorine atom), and
   (b) a hydroxy group;
(5) a $C_{3-10}$ cycloalkyl-$C_{1-6}$ alkyl group (preferably cyclopropylmethyl, cyclobutylmethyl) optionally substituted by 1 to 3 substituents selected from
   (a) a hydroxy group,
   (b) a $C_{1-6}$ alkyl group (preferably methyl) substituted by hydroxy group(s), and
   (c) a di-$C_{1-6}$ alkyl-carbamoyl group (preferably dimethylcarbamoyl);
(6) an oxetanyl group;
(7) a tetrahydrofuryl group optionally substituted by hydroxy group(s);
(8) a tetrahydropyranyl group substituted by hydroxy group(s);
(9) a pyrrolidinyl group optionally substituted by 1 to 3 substituents selected from a $C_{1-6}$ alkyl group (preferably methyl) and an oxo group; or
(10) a piperidyl group optionally substituted by 1 to 3 substituents selected from a $C_{1-6}$ alkyl group (preferably methyl) and an oxo group; and
R² is a hydrogen atom; or
R¹ and R² in combination form, together with the adjacent nitrogen atom,
(1) a pyrrolidine ring optionally substituted by 1 to 3 hydroxy groups or carbamoyl group(s) di-substituted by $C_{1-6}$ alkyl groups (preferably methyl); or
(2) an azetidine ring substituted by carbamoyl group(s) di-substituted by $C_{1-6}$ alkyl groups (preferably methyl).

[Compound I-B3]
Compound (I) wherein
A is a phenyl group optionally substituted by 1 to 3 substituents selected from
   (a) a halogen atom (preferably a chlorine atom),
   (b) a cyano group, and
   (c) a $C_{1-6}$ alkyl group (preferably methyl) optionally substituted by 1 to 3 halogen atoms (preferably a fluorine atom) (preferably trifluoromethyl);
$L^a$ is a bond;
$L^b$ is a $C_{1-3}$ alkylene group (preferably methylene);
$L^c$ is a bond;
ring G is pyrrolidine ring, a piperidine ring or a 8-azabicyclo[3.2.1]octane ring; and
E is a group represented by the formula

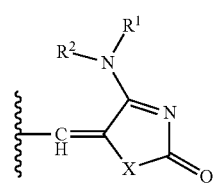

Ea wherein
X is —S— or —NR$^X$— (preferably —S—);
R$^X$ is a $C_{1-6}$ alkyl group (preferably methyl);
R¹ is
(1) a $C_{1-6}$ alkyl group (preferably methyl, ethyl, propyl, isobutyl, neopentyl) optionally substituted by 1 to 3 substituents selected from (a) an amino group di-substituted by $C_{1-6}$ alkyl groups (preferably methyl, ethyl) optionally substituted by 1 to 3 hydroxy groups,
(b) a hydroxy group,
(c) a $C_{1-6}$ alkoxy group (preferably ethoxy) substituted by 1 to 3 substituents selected from a hydroxy group, a $C_{1-6}$ alkoxy group (preferably methoxy) and a di-$C_{1-6}$ alkylamino group (preferably diethylamino), and
(d) a carbamoyl group di-substituted by $C_{1-6}$ alkyl groups (preferably methyl);
(2) a $C_{2-6}$ alkynyl group (preferably 2-propynyl);
(3) a $C_{3-10}$ cycloalkyl-$C_{1-6}$ alkyl group (preferably cyclopropylmethyl);
(4) an oxetanyl group; or
(5) a tetrahydrofuryl group; and
$R^2$ is a hydrogen atom.

[Compound I-B3a]
Compound (I) wherein
A is a phenyl group optionally substituted by 1 to 3 substituents selected from
(a) a halogen atom (preferably a chlorine atom),
(b) a cyano group, and
(c) a $C_{1-6}$ alkyl group (preferably methyl) optionally substituted by 1 to 3 halogen atoms (preferably a fluorine atom) (preferably trifluoromethyl);
$L^a$ is a bond;
$L^b$ is a $C_{1-3}$ alkylene group (preferably methylene);
$L^c$ is a bond;
ring G is pyrrolidine ring or a piperidine ring; and
E is a group represented by the formula

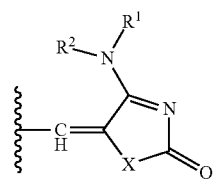

Ea wherein
X is —S— or —NR$^x$— (preferably —S—);
R$^x$ is a $C_{1-6}$ alkyl group (preferably methyl);
$R^1$ is
(1) a $C_{1-6}$ alkyl group (preferably methyl, ethyl, propyl, isobutyl, neopentyl) optionally substituted by 1 to 3 substituents selected from
(a) an amino group di-substituted by $C_{1-6}$ alkyl groups (preferably methyl, ethyl) optionally substituted by 1 to 3 hydroxy groups,
(b) a hydroxy group,
(c) a $C_{1-6}$ alkoxy group (preferably ethoxy) substituted by 1 to 3 substituents selected from a hydroxy group, a $C_{1-6}$ alkoxy group (preferably methoxy) and a di-$C_{1-6}$ alkylamino group (preferably diethylamino), and
(d) a carbamoyl group di-substituted by $C_{1-6}$ alkyl groups (preferably methyl);
(2) a $C_{2-6}$ alkynyl group (preferably 2-propynyl);
(3) a $C_{3-10}$ cycloalkyl-$C_{1-6}$ alkyl group (preferably cyclopropylmethyl);
(4) an oxetanyl group; or
(5) a tetrahydrofuryl group; and
$R^2$ is a hydrogen atom.

[Compound I-B4]
Compound (I) wherein
A is a phenyl group substituted by 1 to 3 (preferably 1 or 2) substituents selected from a $C_{1-6}$ alkyl group (preferably methyl) optionally substituted by 1 to 3 halogen atoms (preferably a fluorine atom) (preferably trifluoromethyl);
$L^a$ is a bond;
$L^b$ is a $C_{1-3}$ alkylene group (preferably methylene);
$L^c$ is a bond;
ring G is a piperidine ring; and
E is a group represented by the formula

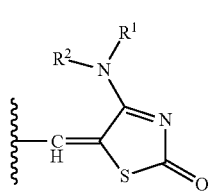

Eaa wherein
$R^1$ is
(1) a $C_{1-6}$ alkyl group (preferably methyl, ethyl, isobutyl, neopentyl) optionally substituted by 1 to 3 substituents selected from
(a) a hydroxy group,
(b) a $C_{1-6}$ alkoxy group (preferably ethoxy) substituted by 1 to 3 hydroxy groups, and
(c) a carbamoyl group di-substituted by $C_{1-6}$ alkyl groups (preferably methyl); or
(2) a $C_{2-6}$ alkynyl group (preferably 2-propynyl); and
$R^2$ is a hydrogen atom.

[Compound I-B5]
Compound (I) wherein
A is a phenyl group substituted by 1 to 3 (preferably 1 or 2) substituents selected from a $C_{1-6}$ alkyl group (preferably methyl) optionally substituted by 1 to 3 halogen atoms (preferably a fluorine atom) (preferably trifluoromethyl);
$L^a$ is a bond;
$L^b$ is a $C_{1-3}$ alkylene group (preferably methylene);
$L^c$ is a bond;
ring G is a piperidine ring; and
E is a group represented by the formula

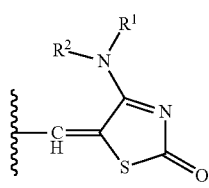

Eaa wherein
$R^1$ is
(1) a $C_{1-6}$ alkyl group (preferably ethyl) substituted by 1 to 3 substituents selected from a $C_{1-6}$ alkoxy group (preferably ethoxy) substituted by 1 to 3 hydroxy groups; or
(2) a $C_{2-6}$ alkynyl group (preferably 2-propynyl); and
$R^2$ is a hydrogen atom.

[Compound I-B6]
(5Z)-5-({1-[2,4-bis(trifluoromethyl)benzyl]piperidin-4-yl}methylidene)-4-(methylamino)-1,3-thiazol-2(5H)-one, (5Z)-5-({1-[2,4-bis(trifluoromethyl)benzyl]piperidin-4-yl}methylidene)-4-(prop-2-yn-1-ylamino)-1,3-thiazol-2(5H)-one, (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one, (5Z)-5-({1-[2,4-bis(trifluoromethyl)benzyl]piperidin-4-yl}methylidene)-4-{[2-(diethylamino)ethyl]amino}-1,3-thiazol-2(5H)-one, (5Z)-5-({(3-exo)-8-[2,4-bis(trifluoromethyl)benzyl]-8-azabicyclo[3.2.1]oct-3-yl}methylidene)-4-(methylamino)-1,3-thiazol-2(5H)-one, (5Z)-5-({1-[2,4-bis(trifluoromethyl)benzyl]piperidin-4-yl}methylidene)-4-[(2-hydroxy-2-methylpropyl)amino]-1,3-thiazol-2(5H)-one, (5Z)-5-({1-[2,4-bis(trifluoromethyl)benzyl]piperidin-4-yl}methylidene)-4-(oxetan-3-ylamino)-1,3-thiazol-2(5H)-one, (5Z)-5-({1-[4-chloro-2-(trifluoromethyl)benzyl]piperidin-4-yl}methylidene)-4-(prop-2-yn-1-ylamino)-1,3-thiazol-2(5H)-one, (5Z)-5-({1-[2,4-bis(trifluoromethyl)benzyl]piperidin-4-yl}methylidene)-4-{[2-(2-methoxyethoxy)ethyl]amino}-1,3-thiazol-2(5H)-one, 4-[(4-{(Z)-[2-oxo-4-(prop-2-yn-1-ylamino)-1,3-thiazole-5(2H)-ylidene]methyl}piperidin-1-yl)methyl]-3-(trifluoromethyl)benzonitrile, (5Z)-5-({1-[2,4-bis(trifluoromethyl)benzyl]piperidin-4-yl}methylidene)-4-(tetrahydrofuran-3-ylamino)-1,3-thiazol-2(5H)-one, (5Z)-5-({1-[2,4-bis(trifluoromethyl)benzyl]piperidin-4-yl}methylidene)-4-({2-[2-(diethylamino)ethoxy]ethyl}amino)-1,3-thiazol-2(5H)-one, (5Z)-5-({1-[2,4-bis(trifluoromethyl)benzyl]piperidin-4-yl}methylidene)-4-[(2,3-dihydroxypropyl)amino]-1,3-thiazol-2(5H)-one, (5Z)-5-({1-[2,4-bis(trifluoromethyl)benzyl]piperidin-4-yl}methylidene)-4-({2-[(2-hydroxyethyl)(methyl)amino]ethyl}amino)-1,3-thiazol-2(5H)-one, (5Z)-5-({1-[2-chloro-4-(trifluoromethyl)benzyl]piperidin-4-yl}methylidene)-4-(prop-2-yn-1-ylamino)-1,3-thiazol-2(5H)-one, (5Z)-5-({1-[2,4-bis(trifluoromethyl)benzyl]piperidin-4-yl}methylidene)-4-[(cyclopropylmethyl)amino]-1,3-thiazol-2(5H)-one, (5Z)-5-({1-[2,4-bis(trifluoromethyl)benzyl]pyrrolidin-3-yl}methylidene)-4-(prop-2-yn-1-ylamino)-1,3-thiazol-2(5H)-one, (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one, (5Z)-5-({1-[2,4-bis(trifluoromethyl)benzyl]piperidin-4-yl}methylidene)-1-methyl-4-(methylamino)-1,5-dihydro-2H-imidazol-2-one, $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethylglycinamide, $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide, $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-serinamide, $N^3$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-β-alaninamide, (5Z)-5-({1-[2,4-bis(trifluoromethyl)benzyl]piperidin-4-yl}methylidene)-4-(ethylamino)-1,3-thiazol-2(5H)-one, and (5Z)-5-({1-[2,4-bis(trifluoromethyl)benzyl]piperidin-4-yl}methylidene)-4-(propylamino)-1,3-thiazol-2(5H)-one,
and a salt thereof.

[Compound I-B7]

(5Z)-5-({1-[2,4-bis(trifluoromethyl)benzyl]piperidin-4-yl}methylidene)-4-(prop-2-yn-1-ylamino)-1,3-thiazol-2(5H)-one, (5Z)-5-({1-[2,4-bis(trifluoromethyl)benzyl]piperidin-4-yl}methylidene)-4-[(2-hydroxy-2-methylpropyl)amino]-1,3-thiazol-2(5H)-one, (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one, $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethylglycinamide, $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide, $N^3$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-β-alaninamide, and (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one,
and a salt thereof.

Compound (I) may be in a form of a salt, and the salt of compound (I) is preferably a pharmacologically acceptable salt. Examples of the salt of compound (I) include a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like, alkaline earth metal salts such as calcium salt, magnesium salt and the like, aluminum salt, ammonium salt and the like.

Preferable examples of the salt with organic base include salts with trimethylamine, triethylamine, pyridine, picoline, ethanolamine, diethanolamine, triethanolamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

The salt of compound (I) is preferably a salt with inorganic acid (preferably hydrochloric acid) or organic acid (preferably fumaric acid, maleic acid, p-toluenesulfonic acid).

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I). Examples of the prodrug for compound (I)

include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation or tert-butylation); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation); a compound obtained by subjecting a carboxyl group in compound (I) to esterification or amidation (e.g., a compound obtained by subjecting a carboxyl group in compound (I) to ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethylesterification or methylamidation) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

Compound (I) may be labeled with an isotope (e.g., $^{3}H$, $^{14}C$, $^{35}S$, $^{125}I$, $^{11}C$, $^{18}F$) and the like.

Compound (I) may be an anhydrate or a hydrate.

Compound (I) may be a solvate or a non-solvate. Furthermore, compound (I) may be a deuterium converter.

Compound (I) may be a crystal, and a single crystal form and a mixture of crystal forms are both encompassed in compound (I). The crystal can be produced by crystallizing according to a crystallization method known per se.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity and stability). The cocrystal or a salt thereof can be produced according to a cocrystallization a method known per se.

When compound (I) contains an isomer such as an optical isomer, a stereoisomer, a regicisomer, a rotamer, a geometric isomer or the like, any isomer and mixtures thereof are also encompassed in compound (I). Specifically, compound (I) contains geometric isomers based on the double bond adjacent to the bond in E to ring G, and both the geometric isomers (E form and Z form) based on the double bond and a mixture thereof are also encompassed in compound (I). When E is a group represented by the formula

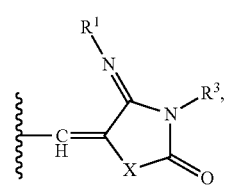

Eb geometric isomers based on the double bond of the imino group (=$NR^1$) is present, and both the geometric isomers (E form and Z form) based on the double bond and a mixture thereof are also encompassed in compound (I).

When isomers due to conformation are present, such isomers and a mixture thereof are also encompassed in compound (I). These isomers can be obtained as a single product according to synthesis methods or separation methods known per se (e.g., concentration, solvent extraction, column chromatography, recrystallization, etc.). For example, when compound (I) has optical isomers, an optical isomer resolved from this compound is also encompassed in compound (I).

The optical isomer can be produced according to a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, 2-propanol, acetonitrile, trifluoroacetic acid, diethylamine, etc.) solely or in admixture to separate the optical isomers. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when compound (I) contains a hydroxyl group, or a primary or secondary amino group in a molecule, the compound and an optically active organic acid (e.g., MTPA [α-methoxy-α-(trifluoromethyl) phenylacetic acid], (−)-menthoxyacetic acid etc.) and the like are subjected to condensation reaction to give diastereomers in the ester form or in the amide form, respectively. When compound (I) has a carboxyl group in molecule, this compound and an optically active amine or an optically active alcohol are subjected to condensation reaction to give diastereomers in the amide form or in the ester form, respectively. The separated diastereomer is converted to an optical isomer of the original compound by acid hydrolysis or base hydrolysis.

Compound (I) or a prodrug thereof (hereinafter sometimes to be simply abbreviated as the compound of the present invention) has low toxicity (e.g., acute toxicity, chronic toxicity, genetic toxicity, reproductive toxicity, heart toxicity, carcinogenicity), and can be used as it is or in the form of a pharmaceutical composition (in the present specification, sometimes to be abbreviated as "medicament of the present invention") by mixing with a pharmacologically acceptable carrier etc. to mammals (e.g., human, mouse, rat, hamster, rabbit, dog, cat, bovine, horse, swine, sheep, monkey, preferably human) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations, or solvent, solubilizing agent, suspending agent, isotonicity agent, buffer and soothing agent for liquid preparations, and the like, and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthesis aluminum silicate and magnesium alumino metasilicate.

Preferable examples of the lubricant include magnesium stearate, calcium stearate, talc and colloidal silica.

Preferable examples of the binder include gelatinated starch, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agents include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoates, chlorobutanol, benzyl alcohol, phenethyl alcohol, dehydroacetic acid and sorbic acid.

Preferable examples of the antioxidant include sulfite and ascorbate.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like food colors), water insoluble lake dyes (e.g., aluminum salt of the aforementioned aqueous food tar color) and natural dyes (e.g., β-carotene, chlorophyll, ferric oxide red).

Preferable examples of the sweetening agent include saccharin sodium, dipotassium glycyrrhizinate, aspartame and stevia.

Examples of the dosage form of the medicament of the present invention include oral preparations such as tablet (including sublingual tablet, orally disintegrating tablet), capsule (including soft capsule, microcapsule), granule, powder, troche, syrup, emulsion, suspension and the like; and parenteral agents such as injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, nasal preparation, pulmonary preparation (inhalant), eye drop and the like, which can be respectively safely administered orally or parenterally.

These preparations may be a release control preparation (e.g., sustained-release microcapsule) such as an immediate-release preparation, a sustained-release preparation and the like.

The medicament of the present invention can be produced according to a method conventionally used in the field of pharmaceutical formulation, for example, the method described in the Japanese Pharmacopoeia, and the like.

While the content of the compound of the present invention in the medicament of the present invention varies depending on the dosage form, dose of the compound of the present invention and the like, it is, for example, about 0.1 to 100 wt %.

The compound of the present invention shows a superior activity as an estrogen-related receptor-α (ERR-α) modulator (particularly, inverse agonist).

The "ERR-α modulator" means a compound having a function to control various actions of ERR-α, and includes ERR-α agonist, ERR-α antagonist, ERR-α inverse agonist and the like.

The "ERR-α inverse agonist" means a compound that inhibits the inherent function of ERR-α.

The compound of the present invention and the medicament of the present invention are effective for the prophylaxis or treatment of ERR-α associated diseases in mammals (e.g., human, mouse, rat, hamster, rabbit, dog, cat, bovine, horse, swine, sheep, monkey, preferably human).

In addition, the compound of the present invention shows high metabolic stability.

Moreover, the compound of the present invention shows high solubility and high efficacy in vivo.

Examples of the "ERR-α associated disease" include
(a) diseases or pathology relating to malignant tumor (e.g., colorectal cancer (e.g., familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer), gastric cancer (e.g., papillary adenocarcinoma, mucinous adenocarcinoma, adenosquamous carcinoma), breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), prostate cancer (e.g., hormone-dependent prostate cancer, non-hormone dependent prostate cancer), liver cancer (e.g., primary liver cancer, extrahepatic bile duct cancer), thyroid cancer (e.g., medullary thyroid carcinoma), kidney cancer (e.g., renal cell carcinoma, transitional cell carcinoma in kidney and urinary duct), uterine cancer (e.g., endometrial carcinoma), brain tumor (e.g., pineal astrocytoma, pilocytic astrocytoma, diffuse astrocytoma, anaplastic astrocytoma), melanoma (e.g., melanoma), sarcoma, urinary bladder cancer, hematologic cancer (e.g., multiple myeloma, malignant lymphoma));
(b) diseases or pathology relating to metabolic syndrome including hyperglycemia, insulin insensitivity, diabetes, obesity, hyperlipidemia, hypercholesterolemia, hyperlipoproteinemia, hypertriglyceridemia, dyslipidemia, hypertension, hyperinsulinemia, hyperuricemia or a combination thereof;
(c) diseases or pathology relating to bone or joint including arthritis, osteoarthritis and rheumatoid arthritis;
(d) inflammatory disease, condition or pathology caused by the release of inflammation-inducing cytokine, including rheumatoid arthritis, atherosclerosis and atopic dermatitis; and
(e) mental disease and neurodegenerative disorder or stress-related disorder including Parkinson's disease, Alzheimer's disease, depression, anxiety and chemical substance addiction; and the like. From among, the above-mentioned (a) is preferable.

The compound of the present invention is useful as an agent for the prophylaxis or treatment of cancer, particularly solid tumor confirmed to show enhanced expression of ERR-α (e.g., breast cancer, malignant lymphoma, multiple myeloma, prostate cancer, colorectal cancer, lung cancer, ovarian cancer, endometrial carcinoma).

As used herein, the "prophylaxis" of the above-mentioned diseases means, for example, administration of the compound of the present invention to patients before onset of a disease but having a high risk of the onset due to some factor associated with the disease or patients who developed the disease but without subjective symptoms, or administration of the compound of the present invention to patients having a risk of recurrence of disease after treatment of the disease.

The dose of the compound of the present invention to a mammal varies depending on the administration subject, route of administration, target disease, symptoms, etc. For example, when the compound of the present invention is administered orally to an adult patient with diabetes, its dose is about 0.01 to 100 mg/kg body weight per dose, preferably 0.05 to 30 mg/kg body weight per dose, more preferably 0.1 to 10 mg/kg body weight per dose and still more preferably 0.5 to 10 mg/kg body weight per dose. This amount is desirably administered in one to 3 portions daily.

Moreover, when the compound of the present invention is administered orally to an adult patient with prostate cancer, its dose is for example, about 0.01 to 100 mg/kg body weight per dose, preferably 0.1 to 30 mg/kg body weight per dose and more preferably 0.5 to 10 mg/kg body weight per dose. This amount is desirably administered in one to 3 portions daily.

The compound of the present invention can be used in combination with a medicament such as therapeutic agent for diabetes, therapeutic agents for diabetic complications, therapeutic agent for hyperlipidemia, antihypertensive agent, antiobesity agent, diuretic, chemotherapeutic agent, immunotherapeutic agent, medicament inhibiting actions of cell growth factor and receptor thereof, antithrombotic agent, therapeutic agent for osteoporosis or antidementia agent (hereinafter to be abbreviated as a concomitant drug). The time of administration of the compound of the present invention and that of the concomitant drug are not limited, and they may be administered simultaneously or in a staggered manner to the administration subject. Furthermore, the compound of the present invention and a concomitant drug may be administered as two kinds of preparations containing each active ingredient, or may be administered as a single preparation containing both active ingredients.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like. When the administration subject is human, for example, a concomitant drug can be used in 0.01 to 100 parts by weight relative to 1 part by weight of the compound of the present invention.

Examples of the therapeutic agent for diabetes include insulin preparations (e.g., animal insulin preparations extracted from pancreas of bovine and swine; human insulin preparations genetically synthesized using *Escherichia coli* or yeast; zinc insulin; protamine zinc insulin; fragments or derivatives of insulin (e.g., INS-1), oral insulin preparations), insulin sensitizers (e.g., pioglitazone or hydrochloride thereof, rosiglitazone or maleate thereof, PPARγ agonists, PPARγ antagonists, PPARγ/α dual agonists, α-glucosidase inhibitors (e.g., voglibose, acarbose, miglitol, emiglitate), biguanides (e.g., phenformin, metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide or calcium hydrate thereof], GPR40 agonists, GLP-1 receptor agonists [e.g., GLP-1, GLP-1MR agents, NN-2211, AC-2993 (exendin-4), BIM-51077, Aib(8,35)hGLP-1(7,37)NH$_2$, CJC-1131], amylin agonists (e.g., pramlintide), phosphotyrosine phosphatase inhibitors (e.g., sodium vanadate), dipeptidyl peptidase IV inhibitors (e.g., Vildagliptin (LAF-237), Sitagliptin phosphate (MK-431), Saxagliptin (BMS-477118)), 13$^3$ agonists, gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11β-HSD1 inhibitors (e.g., BVT-3498), adiponectin or agonists thereof, IKK inhibitors (e.g., AS-2868), leptin resistance improving drugs and somatostatin receptor agonists.

Examples of the therapeutic agent for diabetic complications include aldose reductase inhibitors (e.g., Tolrestat, Epalrestat, Zenarestat, Zopolrestat, minalrestat, fidarestat, CT-112), neurotrophic factors and increasing drugs thereof (e.g., NGF, NT-3, BDNF, neurotrophin production-secretion promoters described in WO 01/14372 (e.g., 4-(4-chlorophenyl)-2-(2-methyl-1-imidazolyl)-5-[3-(2-methylphenoxy)propyl]oxazole)), nerve regeneration promoters, PKC inhibitors (e.g., ruboxistaurin mesylate), AGE inhibitors (e.g., ALT946, pimagedine, N-phenacylthiazolium bromide (ALT766), ALT-711, EXO-226, Pyridorin, pyridoxamine), active oxygen scavengers (e.g., thioctic acid), cerebral vasodilators (e.g., tiapuride, mexiletine), somatostatin receptor agonists (e.g., BIM23190) and apoptosis signal regulating kinase-1 (ASK-1) inhibitors.

Examples of the therapeutic agent for hyperlipidemia include HMG-CoA reductase inhibitors (e.g., pravastatin, simvastatin, lovastatin, atorvastatin, fluvastatin, pitavastatin, rosuvastatin or a salt thereof (e.g., sodium salt, calcium salt)), squalene synthase inhibitors (e.g., fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate and plant sterols (e.g., soysterol, γ-oryzanol).

Examples of the antihypertensive agent include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121) and clonidine.

Examples of the antiobesity agent include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compound described in WO 01/82925 and WO 01/87834); neuropeptide Y antagonists (e.g., CP-422935); cannabinoid receptor antagonists (e.g., SR-141716, SR-147778); ghrelin antagonists), pancreatic lipase inhibitors (e.g., orlistat, ATL-962), β3 agonists (e.g., AJ-9677), peptide anorexiants (e.g., leptin, CNTF (Ciliary Neurotropic Factor)), cholecystokinin agonists (e.g., lintitript, FPL-15849) and anorexigenic agents (e.g., P-57).

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrcchlorothiazide, penflutizide, polythiazide, methyclothiazide), antialdosterone preparations (e.g., spironclactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide and furosemide.

Examples of the chemotherapeutic agent include alkylating agents (e.g., nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin), metabolic antagonists (e.g., mercaptopurine, 6-mercaptopurine riboside, thioinosine, methotrexate, pemetrexed, enocitabine, cytarabine, cytarabine ocfosfate, ancitabine hydrochloride, 5-FU DRUG (e.g., fluorouracil, tegafur, UFT, doxifluridine, carmofur, gallocitabine, emitefur, capecitabine), aminopterine, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, amramustine, bendamustine), antitumor antibiotics (e.g., actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride) and plant-derived antitumor agents (e.g., etoposide, etoposide phosphate, vinblastine sulfate, vincristine sulfate, vindesine sulfate, teniposide, paclitaxel, docetaxel, vinorelbine).

Examples of the immunotherapeutic agent include picibanil, krestin, schizophyllan, lentinan, ubenimex, interferon, interleukin, macrophagecolony stimulating agent, granulocyte colony stimulating factor, erythropoietin, lymphotoxin, BCG vaccine, *corynebacterium parvum*, levamisole, polysaccharide K, procodazole and anti-CTLA4 antibody.

Examples of the medicament inhibiting actions of cell growth factor and receptor thereof include anti-VEGF antibody (e.g., Bevacizumab), anti-HER2 antibody (e.g., Trastuzumab, Pertuzumab), anti-EGFR antibody (e.g., Cetuximab, Panitumumab, Matuzumab, Nimotuzumab), anti-VEGFR antibody, anti-HGF antibody, Imatinib mesylate, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorcbenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazine-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), 2-[N-[3-[4-[5-[N-(3-fluorophenyl)carbamoylmethyl]-1H-pyrazol-3-ylamino]quinazolin-7-yloxy]propyl]-N-ethylamino]ethyl phosphate (AZD-1152), 4-[9-chloro-7-(2,6-diflucrophenyl)-5H-primido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridine-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethylester (AZD-6244), N-[2(R),3-dihydroxypropoxy]-3,4-difluoro-2-(2-fluoro-4-iodophenylamino)benzamide (PD-0325901) and everolimus (RAD001)

Examples of the antithrombotic agent include heparins (e.g., heparin sodium, heparin calcium, dalteparin sodium), warfarins (e.g., warfarin potassium), anti-thrombin drugs (e.g., argatroban), thrombolytic agents (e.g., urokinase, tisokinase, alteplase, nateplase, monteplase, pamiteplase) and platelet aggregation inhibitors (e.g., ticlopidine hydrochloride, cilostazol, ethyl icosapentate, beraprost sodium and sarpogrelate hydrochloride).

Examples of the therapeutic agent for osteoporosis include alfacalcidol, calcitriol, elcatonin, calcitonin salmon, estriol, ipriflavone, risedronate disodium, pamidronate disodium, alendronate sodium hydrate and incadronate disodium.

Examples of the antidementia agent include tacrine, donepezil, rivastigmine and galanthamine.

Furthermore, drugs having a cachexia-improving action established in animal models or clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

The above-mentioned concomitant drug may be used in a combination of two or more kinds at an appropriate ratio.

When the compound of the present invention and a combination drug are used in combination, the amount of each agent can be reduced within a safe range in consideration of the opposite effect of the agents. As a result, the opposite effect caused by these agents can be prevented safely.

The compound of the present invention can also be used in combination with a non-medication therapy. Specific examples of the non-medication therapy include (1) operation; (2) hypertensive chemical therapy using angiotensin II and the like; (3) gene therapy; (4) hyperthermic therapy; (5) cryotherapy; (6) laser ablation method; (7) radiation therapy; and (8) immunotherapy.

The production method of compound (I) is explained in the following.

Compound (I) can be produced, for example, according to the method shown in the following reaction scheme or a method analogous thereto and the like.

The compounds in the reaction schemes may form a salt, and examples of such salt include those similar to the aforementioned salts of compound (I).

While the compounds obtained in each step in the reaction schemes can be directly used for the next reaction in the form of a reaction mixture or as a crude product, they can be isolated and purified from a reaction mixture according to a conventional known method such as concentration, extraction, recrystallization, distillation, chromatography and the like. Outline of each reaction scheme is shown below, wherein each symbol in the compounds is as defined above.

[Production Method 1]

Of compound (I), a compound wherein E is a group represented by

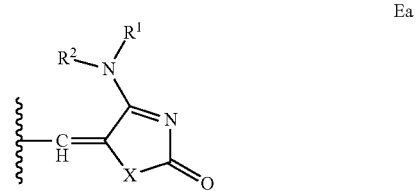

Ea wherein each symbol is as defined above,
(in the present specification, sometimes to be abbreviated as compound (Ia)), and a compound wherein E is a group represented by

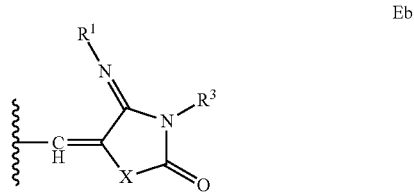

Eb wherein each symbol is as defined above,
(in the present specification, sometimes to be abbreviated as compound (Ib)) can be produced according to the following production method or a method analogous thereto.

Production Method 1
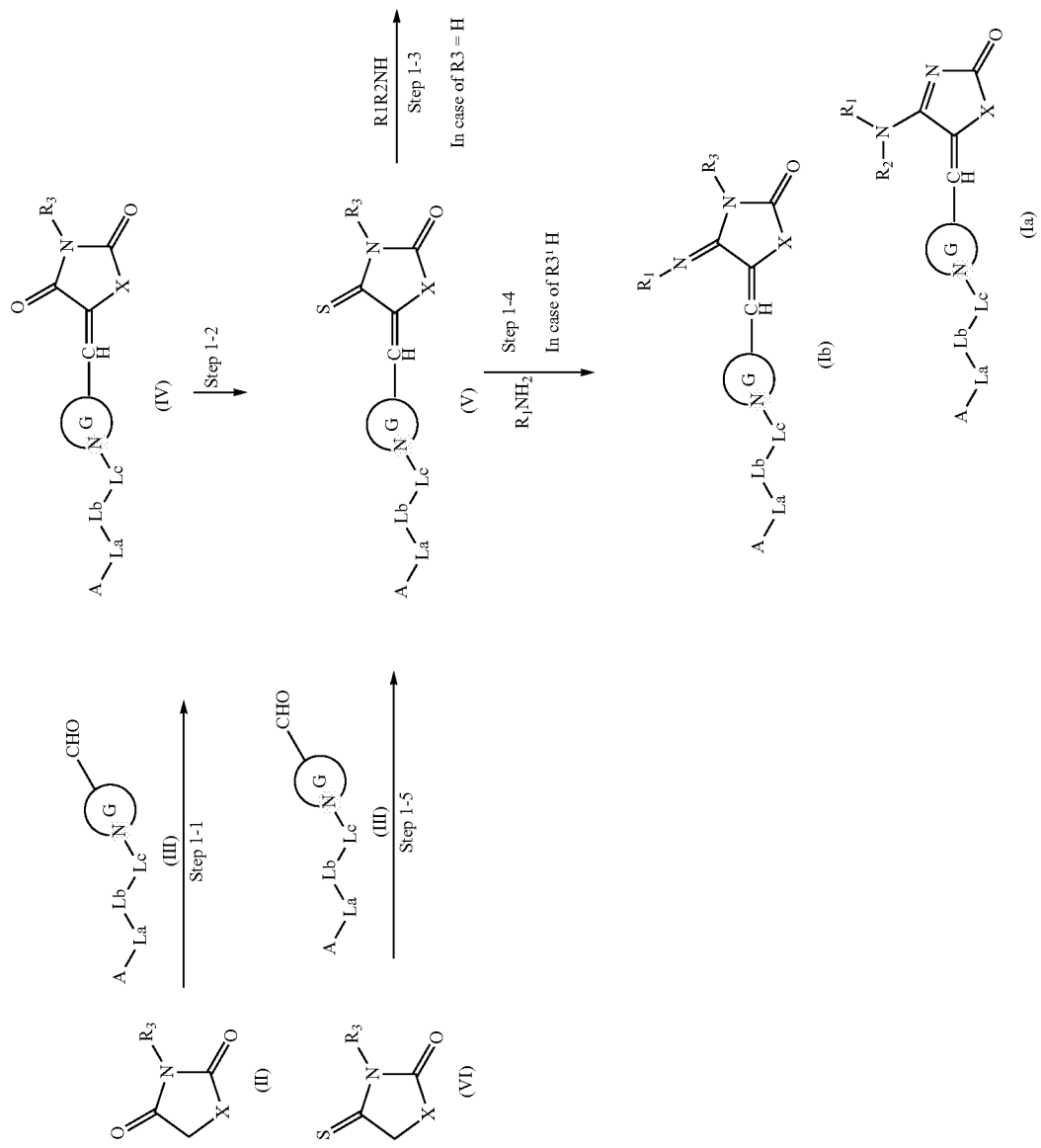

wherein each symbol is as defined above.

Step 1-1

This step is a step of producing compound (IV) by reacting compound (II) with compound (III) in the presence of a base.

The starting material compound (II) may be a commercially available product or can be produced according to a method known per se [e.g., the method described in Journal of the Chemical Society, 1644 (1956); Journal of the Chemical Society, 389 (1954); Journal of the American Chemical Society, 81, 6498 (1959); Journal of the American Chemical Society, 57, 2627 (1935) or the like] or a method analogous thereto.

The starting material compound (III) may be commercially available, or can be produced according to a method known per se [e.g., the method described in "Advanced Organic Chemistry, 4th Ed." (Jerry March) or "Comprehensive Organic Transformations, 2nd Ed." (Richard C. Larock)] or a method analogous thereto.

The amount of compound (II) to be used is generally 1 to 10 equivalents relative to compound (III).

Examples of the base include organic bases such as primary amines, secondary amines (e.g., piperidine), tertiary amines (e.g., triethylamine, N,N-diisopropylethylamine, N-methylmorpholine, 1,8-diazabicyclo[5.4.0]undec-7-ene, 1,4-diazabicyclo[2.2.2]octane) and the like, and a salt thereof (e.g., piperidinium acetate); and inorganic bases such as potassium fluoride, cesium fluoride, ammonium acetate, sodium hydride, potassium carbonate, cesium carbonate, potassium tert-butoxide and the like.

The amount of the base to be used is generally 0.1 to 10 equivalents, preferably 0.5 to 5 equivalents, relative to compound (III).

This reaction is generally carried out in an inert solvent. Examples of the inert solvent include tetrahydrofuran, diethyl ether, 1,2-dimethoxyethane, 1,4-dioxane, toluene, benzene, xylene, N,N-dimethylformamide, dimethyl sulfoxide, methanol, ethanol, 2-propanol, acetonitrile and the like. Two or more kinds of these solvents may be mixed in an appropriate ratio and used.

The reaction temperature is generally −100 to 200° C.

While the reaction time is not particularly limited, it is generally 0.1 to 100 hr, preferably 0.5 to 72 hr.

Step 1-2

This step is a step of producing compound (V) by reacting compound (IV) with the Lawesson's reagent or $P_2S_5$.

The amount of the Lawesson reagent or $P_2S_5$ to be used is generally 1 to 10 equivalents, preferably 1 to 5 equivalents, relative to compound (IV).

This reaction is generally carried out in an inert solvent. Examples of the inert solvent include tetrahydrofuran, diethyl ether, 1,2-dimethoxyethane, 1,4-dioxane, toluene, benzene, xylene, methanol, ethanol, N,N-dimethylformamide, dimethyl sulfoxide and the like. Two or more kinds of these solvents may be mixed in an appropriate ratio and used.

The reaction temperature is generally −100 to 200° C.

While the reaction time is not particularly limited, it is generally 0.1 to 100 hr, preferably 0.5 to 72 hr.

Step 1-3

When $R^3$ of compound (V) is a hydrogen atom, compound (Ia) can be produced by reacting compound (V) with an amine represented by the formula: $R^1R^2NH$ wherein each symbol is as defined above or a salt thereof.

The amount of the amine represented by the formula: $R^1R^2NH$ or a salt thereof to be used is generally 1 to 20 equivalents, preferably 1 to 10 equivalents, relative to compound (V).

This reaction is generally carried out in an inert solvent. Examples of the inert solvent include tetrahydrofuran, diethyl ether, 1,2-dimethoxyethane, 1,4-dioxane, toluene, benzene, xylene, N,N-dimethylformamide, dimethyl sulfoxide, methanol, ethanol, 2-propanol, acetonitrile, ethyl acetate and the like. Two or more kinds of these solvents may be mixed in an appropriate ratio and used.

Where necessary, this reaction is carried out with irradiation of microwave.

The reaction temperature is generally −100 to 200° C.

While the reaction time is not particularly limited, it is generally 0.1 to 100 hr, preferably 0.5 to 72 hr.

When the salt of the amine represented by the formula: $R^1R^2NH$ is used, the reaction can be accelerated by the addition of an inorganic base such as sodium hydride, potassium carbonate, cesium carbonate, potassium tert-butoxide and the like to the reaction system.

The amount of the inorganic base to be used is generally 1 equivalent or more relative to the salt of the amine represented by the formula: $R^1R^2NH$.

The amine represented by the formula: $R^1R^2NH$ or a salt thereof may be commercially available, or can be produced according to a method known per se.

Step 1-4

When $R^3$ of compound (V) is not a hydrogen atom, compound (Ib) can be produced by reacting compound (V) with an amine represented by the formula: $R^1NH_2$ wherein each symbol is as defined above or a salt thereof.

This reaction can be carried out in the same manner as in the aforementioned Step 1-3.

The amine represented by the formula: $R^1NH_2$ or a salt thereof may be commercially available, or can be produced according to a method known per se.

Step 1-5

This step is a step of producing compound (V) by reacting compound (VI) with compound (III) in the presence of a base.

The starting material compound (VI) may be commercially available, or can be produced according to a method known per se [e.g., the method described in European Journal of Medicinal Chemistry, 44, 2038 (2009); or European Journal of Medicinal Chemistry, 44, 3272 (2009)] or a method analogous thereto.

This reaction can be carried out in the same manner as in the aforementioned Step 1-1.

[Production Method 2]

Compound (Ia) and compound (Ib) can also be produced according to the following production method or a method analogous thereto.

Production Method 2

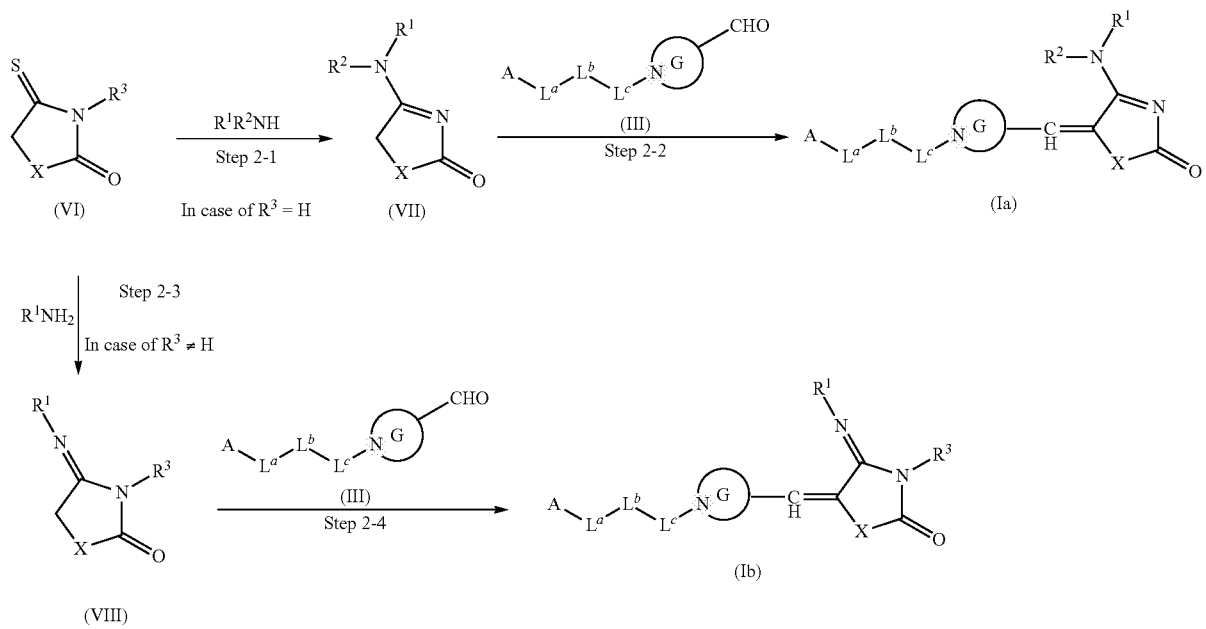

wherein each symbol is as defined above.

Step 2-1

When $R^3$ of compound (VI) is a hydrogen atom, compound (VII) can be produced by reacting compound (VI) with an amine represented by the formula: $R^1R^2NH$ or a salt thereof.

This reaction can be carried out in the same manner as in the aforementioned Step 1-3 of Production Method 1.

Step 2-2

This step is a step of producing compound (Ia) by reacting compound (VII) with compound (III) in the presence of a base.

This reaction can be carried out in the same manner as in the aforementioned Step 1-1 of Production Method 1.

Step 2-3

When $R^3$ of compound (VI) is not a hydrogen atom, compound (VIII) can be produced by reacting compound (VI) with an amine represented by the formula: $R^1R^2NH$ or a salt thereof. This reaction can be carried out in the same manner as in the aforementioned Step 1-3 of Production Method 1.

Step 2-4

This step is a step of producing compound (Ib) by reacting compound (VIII) with compound (III) in the presence of a base.

This reaction can be carried out in the same manner as in the aforementioned Step 1-1 of Production Method 1.

[Production Method 3]

Compound (Ia) can also be produced according to the following production method or a method analogous thereto.

Production Method 3

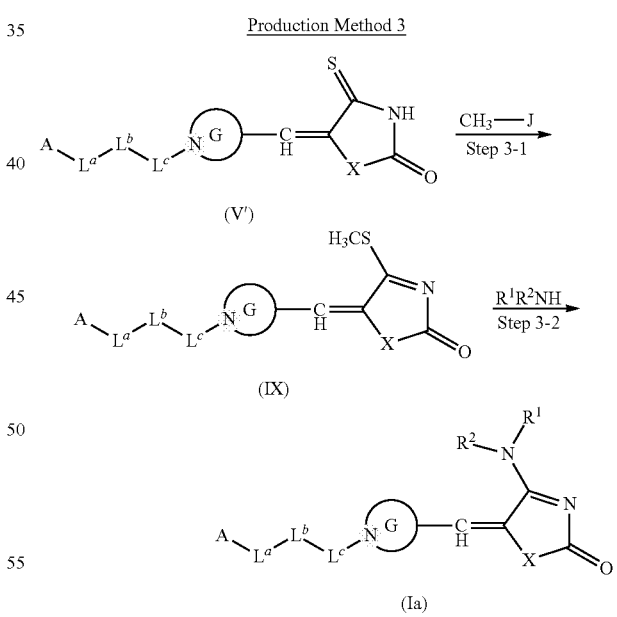

wherein J is a leaving group, and other symbols are as defined above.

Examples of the leaving group for J include a halogen atom (e.g., a fluorine atom, a chlorine atom, a bromine atom, an iodine atom), a $C_{1-6}$ alkylsulfonyloxy group (e.g., methanesulfonyloxy group), a $C_{6-14}$ arylsulfonyloxy group (e.g., toluenesulfonyloxy group) optionally substituted by $C_{1-6}$ alkyl group(s), and the like.

Step 3-1

This step is a step of producing compound (IX) by reacting compound (V') with a compound represented by the formula: CH$_3$-J.

The starting material compound (V') can be produced, for example, according to the aforementioned Production Method 1 (R$^3$=H).

The amount of the compound represented by the formula: CH$_3$-J to be used is generally 1 to 20 equivalents, preferably 1 to 10 equivalents, relative to compound (V').

This reaction is generally carried out in the presence of a base in an inert solvent.

Examples of the inert solvent include tetrahydrofuran, diethyl ether, 1,2-dimethoxyethane, 1,4-dioxane, toluene, benzene, xylene, N,N-dimethylformamide, dimethyl sulfoxide and the like. Two or more kinds of these solvents may be mixed in an appropriate ratio and used.

Examples of the base include tertiary amines (e.g., triethylamine, N,N-diisopropylethylamine, N-methylmorpholine, 1,8-diazabicyclo[5.4.0]undec-7-ene, 1,4-diazabicyclo[2.2.2]octane); and inorganic bases such as sodium hydride, potassium carbonate, cesium carbonate, potassium tert-butoxide and the like.

The amount of the base to be used is generally 1 to 10 equivalents, preferably 1 to 5 equivalents, relative to compound (V').

The reaction temperature is generally −100 to 200° C.

While the reaction time is not particularly limited, it is generally 0.1 to 100 hr, preferably 0.5 to 72 hr.

The compound represented by the formula: CH$_3$-J may be commercially available, or can be produced according to a method known per se.

Step 3-2

This step is a step of producing compound (Ia) by reacting compound (IX) with an amine represented by the formula: R$^1$R$^2$NH or a salt thereof.

This reaction can be carried out in the same manner as in the aforementioned Step 1-3 of Production Method 1.

[Production Method 4]

Compound (Ic) which is compound (Ia) wherein X=S can also be produced according to the following production method or a method analogous thereto.

The starting material compound (Id) can be produced, for example, according to the aforementioned Production Method 1 (X=S, R$^3$=H, R$^2$=H), Production Method 2 (X=S, R$^3$=H, R$^2$=H) or Production Method 3 (X=S, R$^2$=H).

Production Method 4

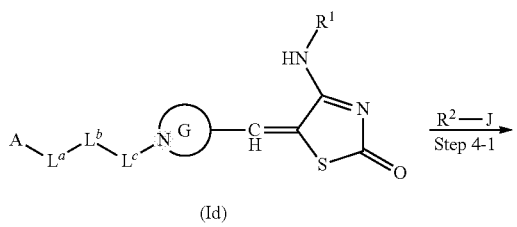

(Id)

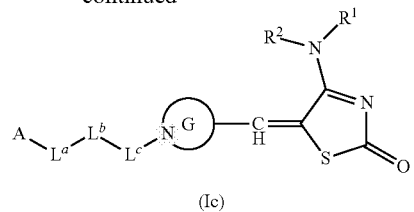

(Ic)

wherein each symbol is as defined above.

Step 4-1

This step is a step of producing compound (Ic) by reacting compound (Id) with a compound represented by the formula: R$^2$-J.

The amount of the compound represented by the formula: R$^2$-J to be used is generally 1 to 20 equivalents, preferably 1 to 10 equivalents, relative to compound (Id). This reaction is generally carried out in the presence of a base in an inert solvent.

Examples of the inert solvent include tetrahydrofuran, diethyl ether, 1,2-dimethoxyethane, 1,4-dioxane, toluene, benzene, xylene, N,N-dimethylformamide, dimethyl sulfoxide and the like. Two or more kinds of these solvents may be mixed in an appropriate ratio and used.

Examples of the base include inorganic bases such as sodium hydride, potassium carbonate, cesium carbonate, potassium tert-butoxide and the like.

The amount of the base to be used is generally 1 to 10 equivalents, preferably 1 to 5 equivalents, relative to compound (Id).

The reaction temperature is generally −100 to 200° C.

While the reaction time is not particularly limited, it is generally 0.1 to 100 hr, preferably 0.5 to 72 hr.

The compound represented by the formula: R$^2$-J may be commercially available, or can be produced according to a method known per se.

[Production Method 5]

Compound (Ie) which is compound (Ib) wherein X=S can also be produced according to the following production method or a method analogous thereto.

The starting material compound (Id) can be produced, for example, according to the aforementioned Production Method 1 (X=S, R$^3$=H, R$^2$=H), Production Method 2 (X=S, R$^3$=H, R$^2$=H) or Production Method 3 (X=S, R$^2$=H).

Production Method 5

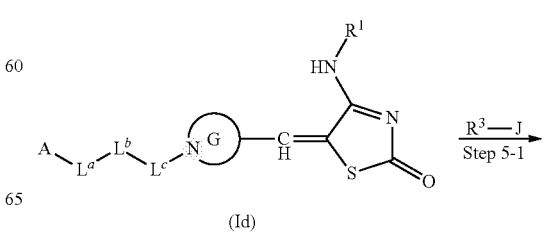

(Id)

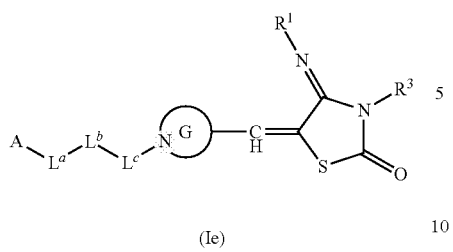

(Ie)

wherein each symbol is as defined above.

Step 5-1

This step is a step of producing compound (Ie) by reacting compound (Id) with a compound represented by the formula: $R^3$-J.

This reaction can be carried out in the same manner as in the aforementioned Step 4-1 of Production Method 4. The compound represented by the formula: $R^3$-J may be commercially available, or can be produced according to a method known per se.

[Production Method 6]

Compound (Ig) which is compound (Ib) wherein X is $—NR^X—$, and compound (If) which is compound (Ib) wherein X is $—NR^X—$ and $R^1$ is a hydrogen atom, can also be produced according to the following production method or a method analogous thereto.

Production method 6

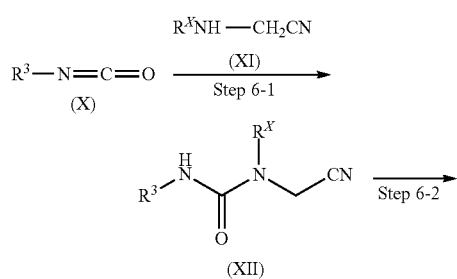

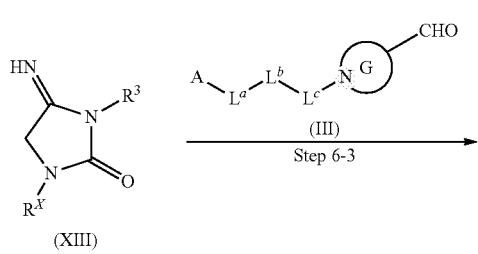

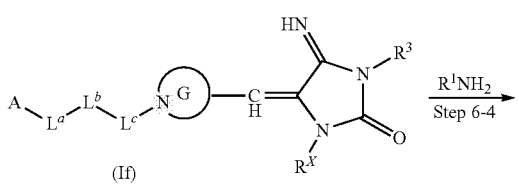

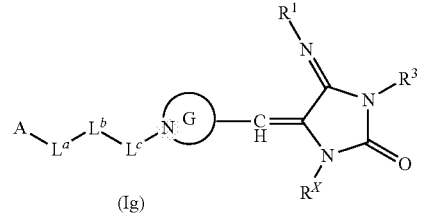

(Ig)

wherein each symbol is as defined above.

Step 6-1

This step is a step of producing compound (XII) by reacting isocyanate derivative (X) with aminoacetonitrile derivative (XI) or a salt thereof.

Isocyanate derivative (X) and aminoacetonitrile derivative (XI) may be commercially available, or can be produced according to a method known per se [e.g., the method described in "Advanced Organic Chemistry, 4th Ed." (Jerry March) or "Comprehensive Organic Transformations, 2nd Ed." (Richard C. Larock)] or a method analogous thereto.

The amount of aminoacetonitrile derivative (XI) or a salt thereof to be used is generally 1 to 10 equivalents, preferably 1 to 5 equivalents, relative to isocyanate derivative (X).

This reaction is generally carried out in an inert solvent. Examples of the inert solvent include tetrahydrofuran, diethyl ether, 1,2-dimethoxyethane, 1,4-dioxane, toluene, benzene, xylene, N,N-dimethylformamide, dimethyl sulfoxide and the like. Two or more kinds of these solvents may be mixed in an appropriate ratio and used.

The reaction temperature is generally −100 to 200° C.

While the reaction time is not particularly limited, it is generally 0.1 to 100 hr, preferably 0.5 to 72 hr.

When the salt of aminoacetonitrile derivative (XI) is used, the reaction can be accelerated by the addition of a base such as an organic base (e.g., triethylamine, N,N-diisopropylethylamine, 1,8-diazabicyclo[5.4.0]-undec-7-ene), inorganic base (e.g., potassium carbonate, cesium carbonate) and the like to the reaction system.

The amount of the base to be used is generally 0.5-10 equivalents, preferably 1 to 5 equivalents, relative to the salt of aminoacetonitrile derivative (XI).

Step 6-2

This step is a step of producing compound (XIII) by reacting compound (XII) with a base.

Examples of the base include triethylamine, 1,8-diazabicyclo[5.4.0]-undec-7-ene, potassium carbonate, cesium carbonate, sodium hydride, potassium tert-butoxide and the like. From among, sodium hydride and potassium tert-butoxide are preferable.

The amount of the base to be used is generally 1 to 20 equivalents, preferably 1 to 10 equivalents, relative to compound (XII).

This reaction is generally carried out in an inert solvent. Examples of the inert solvent include tetrahydrofuran, diethyl ether, 1,2-dimethoxyethane, 1,4-dioxane, toluene, benzene, xylene, N,N-dimethylformamide, dimethyl sulfoxide, methanol, ethanol, 2-propanol, acetonitrile and the like. Two or more kinds of these solvents may be mixed in an appropriate ratio and used.

The reaction temperature is generally −100 to 200° C.

While the reaction time is not particularly limited, it is generally 0.1 to 100 hr, preferably 0.5 to 72 hr.

Compound (XIII) can also be produced from compound (X) in a single step, without via compound (XII).

In this case, the reaction can be carried out in the same manner as in the aforementioned Step 6-1.

Step 6-3

This step is a step of producing compound (If) by reacting compound (XIII) with compound (III) in the presence of a base.

This reaction can be carried out in the same manner as in the aforementioned Step 1-1 of Production Method 1.

Step 6-4

This step is a step of producing compound (Ig) by is reacting compound (If) with an amine represented by the formula: $R^1NH_2$ or a salt thereof.

This reaction can be carried out in the same manner as in the aforementioned Step 1-3 of Production Method 1.

[Production Method 7]

Compound (Ii) which is compound (Ia) wherein X is —$NR^X$— and $R^2$ is a hydrogen atom, and compound (Ih) which is compound (Ia) wherein X is —$NR^X$— and $R^1$ and $R^2$ are hydrogen atoms, can also be produced according to the following production method or a method analogous thereto.

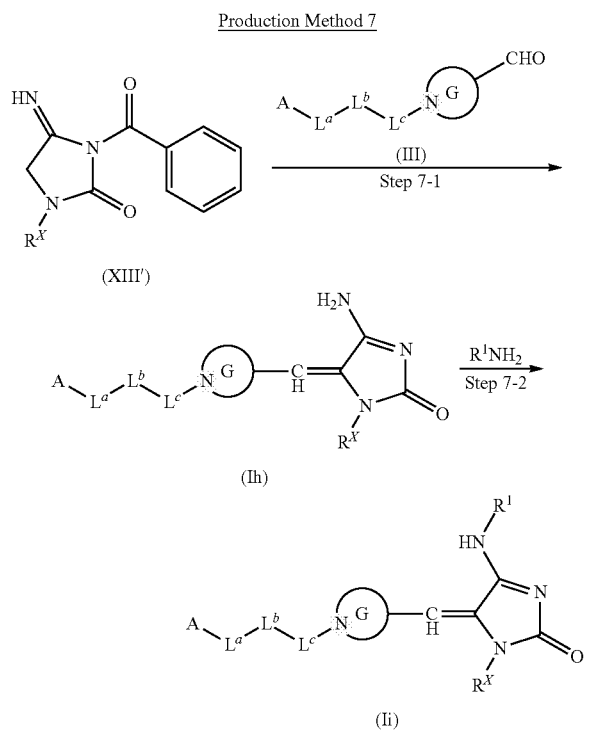

wherein each symbol is as defined above.

Step 7-1

This step is a step of producing compound (Ih) by reacting compound (XIII') with compound (III) in the presence of a base.

The starting material compound (XIII') can be produced in the same manner as in the aforementioned Step 6-1 using benzoyl isocyanate as isocyanate derivative (X) and Step 6-2 of Production Method 6.

This reaction can be carried out in the same manner as in the aforementioned Step 1-1 of Production Method 1.

Step 7-2

This step is a step of producing compound (Ii) by reacting compound (Ih) with an amine represented by the formula: $R^1NH_2$ or a salt thereof.

This reaction can be carried out in the same manner as in the aforementioned Step 1-3 of Production Method 1.

[Production Method 8]

Compound (If) described in Production Method 6 can also be produced according to the following production method or a method analogous thereto.

The starting material compound (Ij) can be produced in the same manner as in the aforementioned Step 6-1 using $H_2NCH_2CN$ as aminoacetonitrile derivative (XI), Step 6-2 and Step 6-3 of Production Method 6.

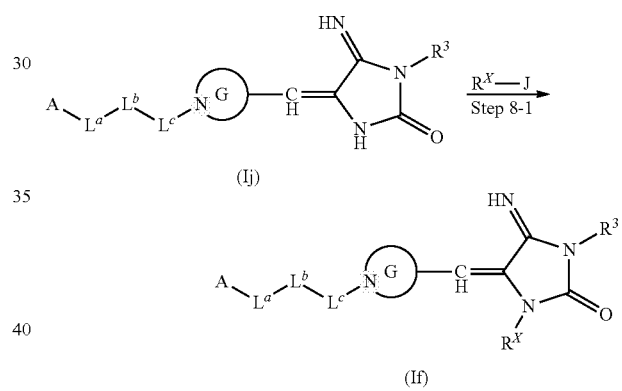

wherein each symbol is as defined above.

Step 8-1

This step is a step of producing compound (If) by reacting compound (Ij) with a compound represented by the formula: $R^X$-J.

This reaction can be carried out in the same manner as in the aforementioned Step 4-1 of Production Method 4.

The compound represented by the formula: $R^X$-J may be commercially available, or can be produced according to a method known per se.

[Production Method 9]

Compound (Ik) which is compound (Ib) wherein X is —NH—, and compound (Ig) which is compound (Ib) wherein X is —$NR^X$—, can also be produced according to the following production method or a method analogous thereto.

The starting material compound (Ij) can be produced in the same manner as in the aforementioned Step 6-1 using $H_2NCH_2CN$ as aminoacetonitrile derivative (XI), Step 6-2 and Step 6-3 of Production Method 6.

Production Method 9

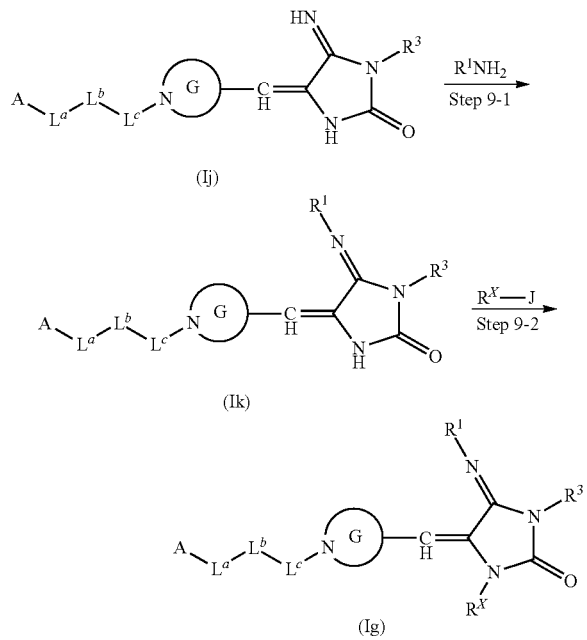

wherein each symbol is as defined above.

Step 9-1

This step is a step of producing compound (Ik) by reacting compound (Ij) with an amine represented by the formula: $R^1NH_2$ or a salt thereof.

This reaction can be carried out in the same manner as in the aforementioned Step 1-3 of Production Method 1.

Step 9-2

This step is a step of producing compound (Ig) by reacting compound (Ik) with a compound represented by the formula: $R^X$-J.

This reaction can be carried out in the same manner as in the aforementioned Step 4-1 of Production Method 4.

[Production Method 10]

Compound (III) can also be produced according to the following production method or a method analogous thereto.

Production Method 10

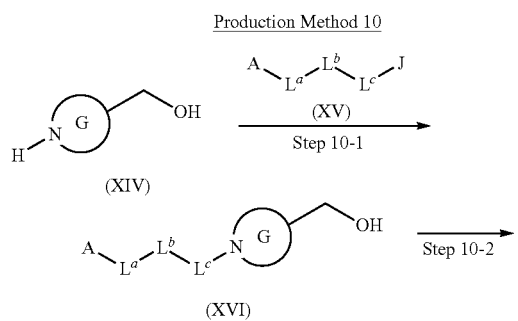

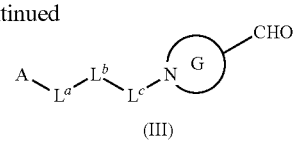

wherein each symbol is as defined above.

Step 10-1

This step is a step of producing compound (XVI) by reacting compound (XIV) with compound (XV) in the presence of a base.

Compound (XIV) and compound (XV) may be commercially available, or can be produced according to a method known per se [e.g., the method described in "Advanced Organic Chemistry, 4th Ed." (Jerry March), "Comprehensive Organic Transformations, 2nd Ed." (Richard C. Larock) or the like] or a method analogous thereto.

The amount of compound (XV) to be used is generally 0.1 to 10 equivalents relative to compound (XIV).

Examples of the base include tertiary amines (e.g., triethylamine, N,N-diisopropylethylamine, N-methylmorpholine, 1,8-diazabicyclo[5.4.0]undec-7-ene, 1,4-diazabicyclo[2.2.2]octane), and inorganic bases such as sodium hydride, potassium carbonate, cesium carbonate, potassium tert-butoxide and the like.

The amount of the base to be used is generally 0.1 to 10 equivalents relative to compound (XIV).

This reaction is generally carried out in an inert solvent. Examples of the inert solvent include tetrahydrofuran, diethyl ether, 1,2-dimethoxyethane, 1,4-dioxane, toluene, benzene, xylene, N,N-dimethylformamide, dimethyl sulfoxide, methanol, ethanol, 2-propanol, acetonitrile and the like. Two or more kinds of these solvents may be mixed in an appropriate ratio and used.

The reaction temperature is generally −100 to 200° C.

While the reaction time is not particularly limited, it is generally 0.1 to 100 hr, preferably 0.5 to 72 hr.

Step 10-2

This step is a step of producing compound (III) by subjecting compound (XVI) to an oxidation reaction.

The oxidation reaction can be carried out in the presence of dimethyl sulfoxide, an activator and a base, or can also be carried out according to a method known per se [e.g., the method described in "Advanced Organic Chemistry, 4th Ed." (Jerry March) or "Comprehensive Organic Transformations, 2nd Ed." (Richard C. Larock)] or a method analogous thereto.

Examples of the activator include sulfur trioxide pyridine complex, oxalyl chloride, trifluoroacetic anhydride and the like.

The amount of the activator to be used is generally 1 to 10 equivalents relative to compound (XVI).

Examples of the base include tertiary amines (e.g., triethylamine, N,N-diisopropylethylamine, N-methylmorpholine, 1,8-diazabicyclo[5.4.0]undec-7-ene, 1,4-diazabicyclo[2.2.2]octane) and the like. The amount of the base to be used is generally 1 to 50 equivalents relative to compound (XVI).

This reaction is carried out in dimethyl sulfoxide, or in a mixed solvent of dimethyl sulfoxide and inert solvent.

Examples of the inert solvent include tetrahydrofuran, dichloromethane and the like. Two or more kinds of these solvents may be mixed in an appropriate ratio and used.

The reaction temperature is generally −100 to 200° C.

While the reaction time is not particularly limited, it is generally 0.1 to 100 hr, preferably 0.5 to 72 hr.

[Production Method 11]
Compound (Ia) and compound (Ib) can also be produced according to the following production method or a method analogous thereto.
wherein P is a protecting group; and other symbols are as defined above.
Examples of the protecting group for P include amino-protecting groups described in Theodora W. Greene, Peter G.
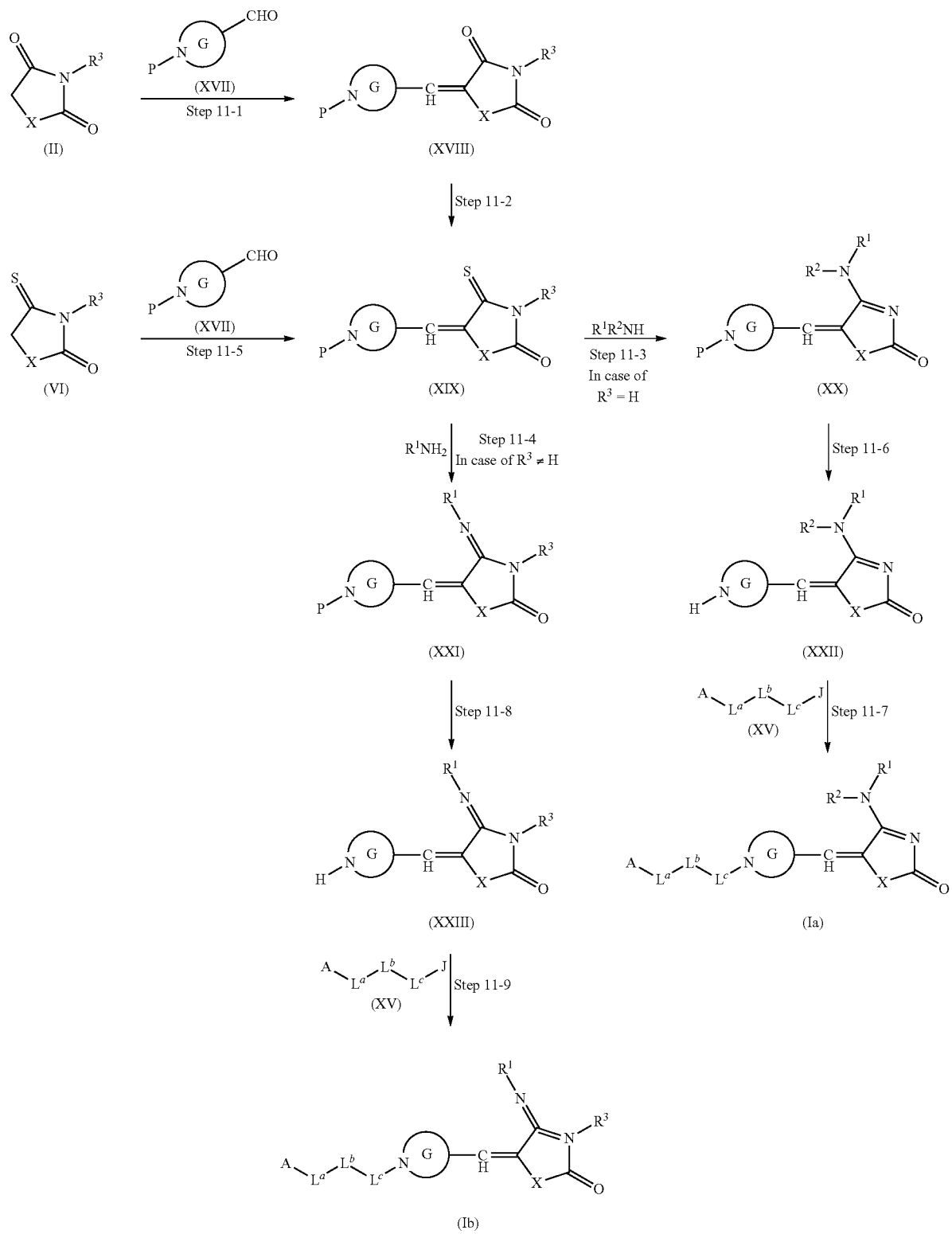

Step 11-1

This step is a step of producing compound (XVIII) by reacting compound (II) with compound (XVII) in the presence of a base.

This reaction can be carried out in the same manner as in the aforementioned Step 1-1 of Production Method 1.

Compound (XVII) may be commercially available, or can be produced according to a method known per se.

Step 11-2

This step is a step of producing compound (XIX) by reacting compound (XVIII) with the Lawesson's reagent or $P_2S_5$.

This reaction can be carried out in the same manner as in the aforementioned Step 1-2 of Production Method 1.

Step 11-3

When $R^3$ of compound (XIX) is a hydrogen atom, compound (XX) can be produced by reacting compound (XIX) with an amine represented by the formula: $R^1R^2NH$ or a salt thereof.

This reaction can be carried out in the same manner as in the aforementioned Step 1-3 of Production Method 1.

Step 11-4

When $R^3$ of compound (XIX) is not a hydrogen atom, compound (XXI) can be produced by reacting compound (XIX) with an amine represented by the formula: $R^1NH_2$ or a salt thereof.

This reaction can be carried out in the same manner as in the aforementioned Step 1-3 of Production Method 1.

Step 11-5

This step is a step of producing compound (XIX) by reacting compound (VI) with compound (XVII) in the presence of a base.

This reaction can be carried out in the same manner as in the aforementioned Step 1-1 of Production Method 1.

Step 11-6

This step is a step of producing compound (XXII) by removing the amino-protecting group P of compound (XX).

While the reaction conditions varies depending on the kind of the protecting group, this reaction can be carried out according to the method of removing an amino-protecting group described in Theodora W. Greene, Peter G. M. Wuts, Protective Groups in Organic Synthesis 3rd edition, pages 494 to 653 or a method analogous thereto.

Step 11-7

This step is a step of producing compound (Ia) by reacting compound (XXII) with compound (XV).

This reaction can be carried out in the same manner as in the aforementioned Step 10-1 of Production Method 10.

Step 11-8

This step is a step of producing compound (XXIII) by removing the amino-protecting group P of compound (XXI).

While the reaction conditions varies depending on the kind of the protecting group, this reaction can be carried out according to the method of removing an amino-protecting group described in Theodora W. Greene, Peter G. M. Wuts, Protective Groups in Organic Synthesis 3rd edition, pages 494 to 653 or a method analogous thereto.

Step 11-9

This step is a step of producing compound (Ib) by reacting compound (XXIII) with compound (XV).

This reaction can be carried out in the same manner as in the aforementioned Step 10-1 of Production Method 10.

[Production Method 12]

Compound (XX) and compound (XXI) described in Production Method 11 can also be produced according to the following production method or a method analogous thereto.

wherein each symbol is as defined above.

Step 12-1

This step is a step of producing compound (XX) by reacting compound (VII) with compound (XVII) in the presence of a base.

This reaction can be carried out in the same manner as in the aforementioned Step 1-1 of Production Method 1.

Step 12-2

This step is a step of producing compound (XXI) by reacting compound (VIII) with compound (XVII) in the presence of a base.

This reaction can be carried out in the same manner as in the aforementioned Step 1-1 of Production Method 1.

[Production Method 13]

Compound (XX) described in Production Method 11 can also be produced according to the following production method or a method analogous thereto.

Production Method 13

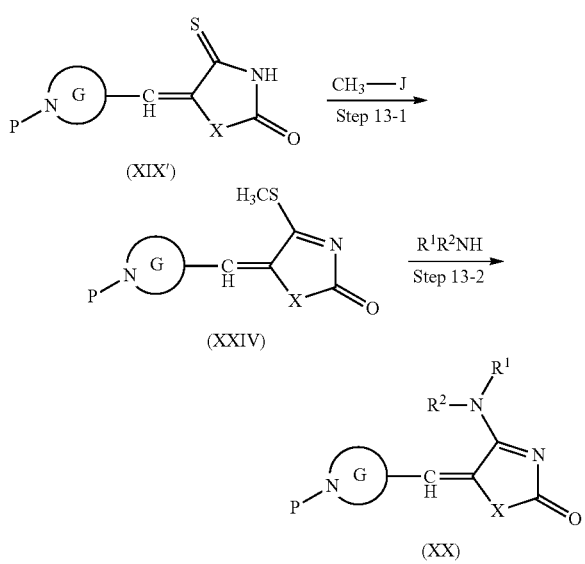

wherein each symbol is as defined above.

Step 13-1

This step is a step of producing compound (XXIV) by reacting compound (XIX') with a compound represented by the formula: $CH_3$-J.

The starting material compound (XIX') can be produced in the same manner as in the aforementioned Step 11-1 and Step 11-2 or Step 11-5 of Production Method 11 ($R^3$=H).

This reaction can be carried out in the same manner as in the aforementioned Step 3-1 of Production Method 3.

Step 13-2

This step is a step of producing compound (XX) by reacting compound (XXIV) with an amine represented by the formula: $R^1R^2NH$ or a salt thereof.

This reaction can be carried out in the same manner as in the aforementioned Step 1-3 of Production Method 1.

[Production Method 14]

Compound (IIIa) which is compound (III) wherein $L^a$ is a bond, $L^b$ is —$CHR^Y$— wherein $R^Y$ is as defined for the substituent of the "$C_{1-3}$ alkylene group optionally having substituent(s)" for $L^b$, and $L^c$ is a bond, can also be produced according to the following production method or a method analogous thereto.

Production Method 14

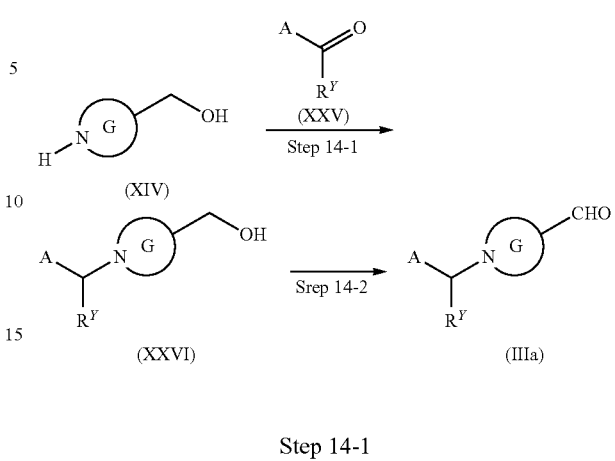

Step 14-1

This step is a step of producing compound (XXVI) by reacting compound (XIV) with compound (XXV) in the presence of a reducing agent.

Compound (XXV) may be commercially available, or can be produced according to a method known per se [e.g., the method described in "Advanced Organic Chemistry, 4th Ed." (Jerry March) or "Comprehensive Organic Transformations, 2nd Ed." (Richard C. Larock)] or a method analogous thereto.

The amount of compound (XXV) to be used is generally 0.1 to 10 equivalents relative to compound (XIV).

Examples of the reducing agent include sodium triacetoxyborohydride, sodium cyanoborohydride, sodium borohydride and the like.

The amount of the reducing agent to be used is generally 1 to 10 equivalents relative to compound (XIV).

This reaction is generally carried out in an inert solvent. Examples of the inert solvent include tetrahydrofuran, diethyl ether, 1,2-dimethoxyethane, 1,4-dioxane, toluene, benzene, xylene, N,N-dimethylformamide, dimethyl sulfoxide, methanol, ethanol, 2-propanol, acetonitrile and the like. Two or more kinds of these solvents may be mixed in an appropriate ratio and used.

When the salt of compound (XIV) is used, the reaction can be accelerated by the addition of a base to the reaction system.

Examples of the base include tertiary amines (e.g., triethylamine, N,N-diisopropylethylamine, N-methylmorpholine, 1,8-diazabicyclo[5.4.0]undec-7-ene, 1,4-diazabicyclo[2.2.2]octane) and the like.

The amount of the base to be used is generally 1 to 10 equivalents relative to compound (XIV).

The reaction temperature is generally −100 to 200° C.

While the reaction time is not particularly limited, it is generally 0.1 to 100 hr, preferably 0.5 to 72 hr. Compound (XXVI) can also be produced by reacting in advance compound (XIV) with compound (XXV) in the presence of a dehydrating agent (titanium (IV) isopropoxide etc.), and then reacting the resulting corresponding enamine with a reducing agent.

Step 14-2

This step is a step of producing compound (IIIa) by subjecting compound (XXVI) to an oxidation reaction.

This reaction can be carried out in the same manner as in the aforementioned Step 10-2 of Production Method 10.

[Production Method 15]

Compound (IIIb) which is compound (III) wherein $L^c$ is —CO— can also be produced according to the following production method or a method analogous thereto.

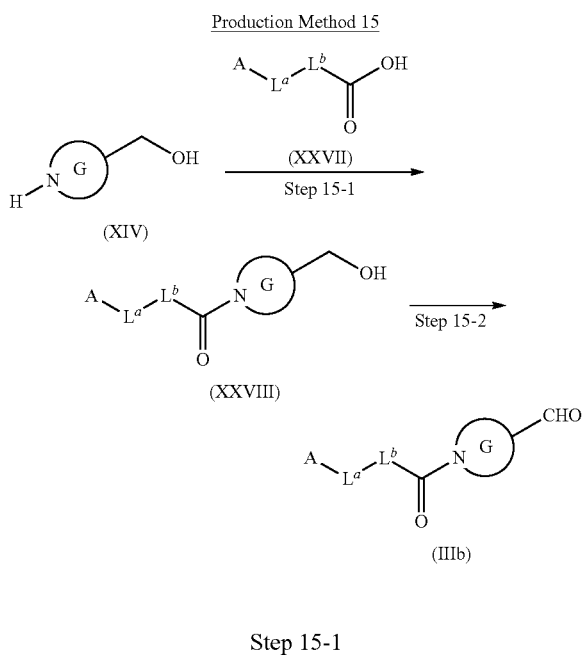

Step 15-1

This step is a step of producing compound (XVIII) by reacting compound (XIV) with compound (XXVII) in the presence of a condensing agent.

Compound (XXVII) may be commercially available, or can be produced according to a method known per se [e.g., the method described in "Advanced Organic Chemistry, 4th Ed." (Jerry March) or "Comprehensive Organic Transformations, 2nd Ed." (Richard C. Larock)] or a method analogous thereto.

The amount of compound (XXVII) to be used is generally 0.1 to 10 equivalents relative to compound (XIV).

Examples of the condensing agent include 1-ethyl-1-(3-dimethylaminopropyl)carbodiimide hydrochloride, 1,3-dicyclohexylcarbodiimide, diethyl cyanophosphate, diphenylphosphorylazide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N',N'-tetramethyluronium hexafluorophosphate, N-[(dimethylamino) (3H-[1,2,3]triazolo[4,5-b]pyridin-3-yloxy)methylidene]-N-methylmethanaminium hexafluorophosphate and the like.

The amount of the condensing agent to be used is generally 1 to 10 equivalents relative to compound (XIV).

This reaction is generally carried out in an inert solvent. Examples of the inert solvent include tetrahydrofuran, diethyl ether, 1,2-dimethoxyethane, 1,4-dioxane, toluene, benzene, xylene, N,N-dimethylformamide, dimethyl sulfoxide, methanol, ethanol, 2-propanol, acetonitrile and the like. Two or more kinds of these solvents may be mixed in an appropriate ratio and used.

Where necessary, a suitable condensation promoter (e.g., 1-hydroxybenzotriazole, N-hydroxysuccinimide etc.) can be used for this reaction.

The amount of the condensation promoter to be used is generally 0.1 to 10 equivalents relative to compound (XIV). The reaction may proceed more smoothly by the addition of a base to the reaction system.

Examples of the base include tertiary amines (e.g., triethylamine, N,N-diisopropylethylamine, N-methylmorpholine, 1,8-diazabicyclo[5.4.0]undec-7-ene, 1,4-diazabicyclo[2.2.2]octane) and the like. The amount of the base to be used is generally 0.1 to 10 equivalents relative to compound (XIV).

The reaction temperature is generally −100 to 200° C.

While the reaction time is not particularly limited, it is generally 0.1 to 100 hr, preferably 0.5 to 72 hr.

Step 15-2

This step is a step of producing compound (IIIb) by subjecting compound (XXVIII) to an oxidation reaction.

This reaction can be carried out in the same manner as in the aforementioned Step 10-2 of Production Method 10.

[Production Method 16]

Compound (IIIc) which is compound (III) wherein G is 2-piperidone can also be produced according to the following production method or a method analogous thereto.

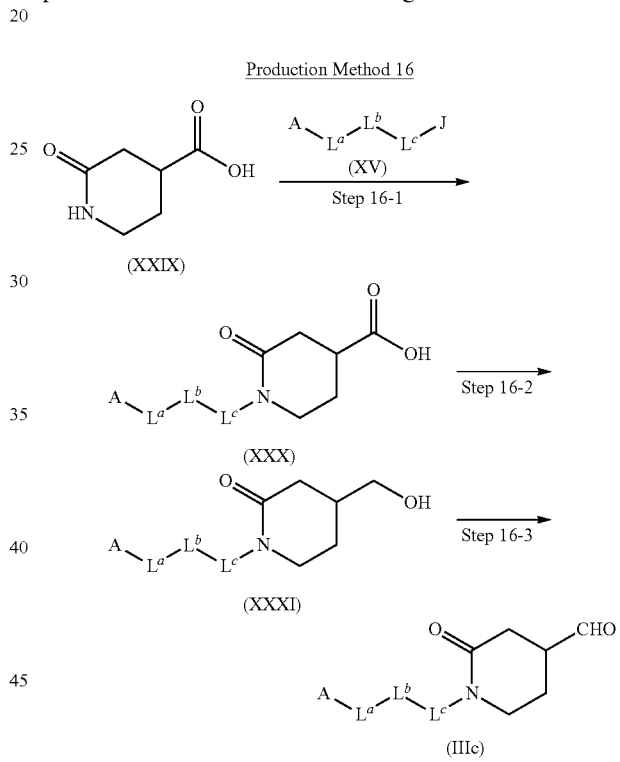

wherein each symbol is as defined above.

Step 16-1

This step is a step of producing compound (XXX) by reacting compound (XXIX) with compound (XV).

The starting material compound (XXIX) can be produced according to a method known per se [e.g., the method described in US 2007/191406 A1] or a method analogous thereto.

Compound (XV) may be commercially available, or can be produced according to a method known per se [e.g., the method described in "Advanced Organic Chemistry, 4th Ed." (Jerry March), "Comprehensive Organic Transformations, 2nd Ed." (Richard C. Larock) or the like] or a method analogous thereto.

The amount of compound (XV) to be used is generally 0.1 to 10 equivalents relative to compound (XXIX).

91

This reaction is generally carried out in the presence of a base in an inert solvent.

Examples of the inert solvent include tetrahydrofuran, diethyl ether, 1,2-dimethoxyethane, 1,4-dioxane, toluene, benzene, xylene, N,N-dimethylformamide, dimethyl sulfoxide and the like. Two or more kinds of these solvents may be mixed in an appropriate ratio and used.

Examples of the base include inorganic bases such as sodium hydride, potassium carbonate, cesium carbonate, potassium tert-butoxide and the like.

The amount of the base to be used is generally 0.1 to 10 equivalents relative to compound (XXIX).

The reaction temperature is generally −100 to 200° C.

While the reaction time is not particularly limited, it is generally 0.1 to 100 hr, preferably 0.5 to 72 hr.

Step 16-2

This step is a step of producing compound (XXXI) by subjecting compound (XXX) to a reduction reaction.

The reduction reaction can be carried out in the presence of ethyl chloroformate, sodium borohydride and a base, or can also be carried out according to a method known per se [e.g., the method described in "Advanced Organic Chemistry, 4th Ed." (Jerry March), "Comprehensive Organic Transformations, 2nd Ed." (Richard C. Larock) or the like] or a method analogous thereto.

The amount of the ethyl chloroformate to be used is generally 1 to 10 equivalents relative to compound (XXX).

Examples of the base include tertiary amines (e.g., triethylamine, N,N-diisopropylethylamine, N-methylmorpholine, 1,8-diazabicyclo[5.4.0]undec-7-ene, 1,4-diazabicyclo[2.2.2]octane) and the like.

The amount of the base to be used is generally 0.1 to 100 equivalents relative to compound (XXX).

The amount of the sodium borohydride to be used is generally 1 to 10 equivalents relative to compound (XXX).

This reaction is generally carried out in an inert solvent. Examples of the inert solvent include tetrahydrofuran, diethyl ether, 1,2-dimethoxyethane, 1,4-dioxane, toluene, benzene, xylene, N,N-dimethylformamide, dimethyl sulfoxide and the like. Two or more kinds of these solvents may be mixed in an appropriate ratio and used.

The reaction temperature is generally −100 to 200° C.

While the reaction time is not particularly limited, it is generally 0.1 to 100 hr, preferably 0.5 to 72 hr.

Step 16-3

This step is a step of producing compound (IIIc) by subjecting compound (XXXI) to an oxidation reaction.

This reaction can be carried out in the same manner as in the aforementioned Step 10-2 of Production Method 10.

[Production Method 17]

Compound (Ii) which is compound (Ia) wherein $R^1$ is —$CH_2CO_2C(CH_3)_3$, compound (Im) which $R^1$ is —$CH_2CO_2H$, and compound (In) which $R^1$ is —$CH_2CONR^{S1}R^{S2}$ can also be produced according to the following production method or a method analogous thereto.

92

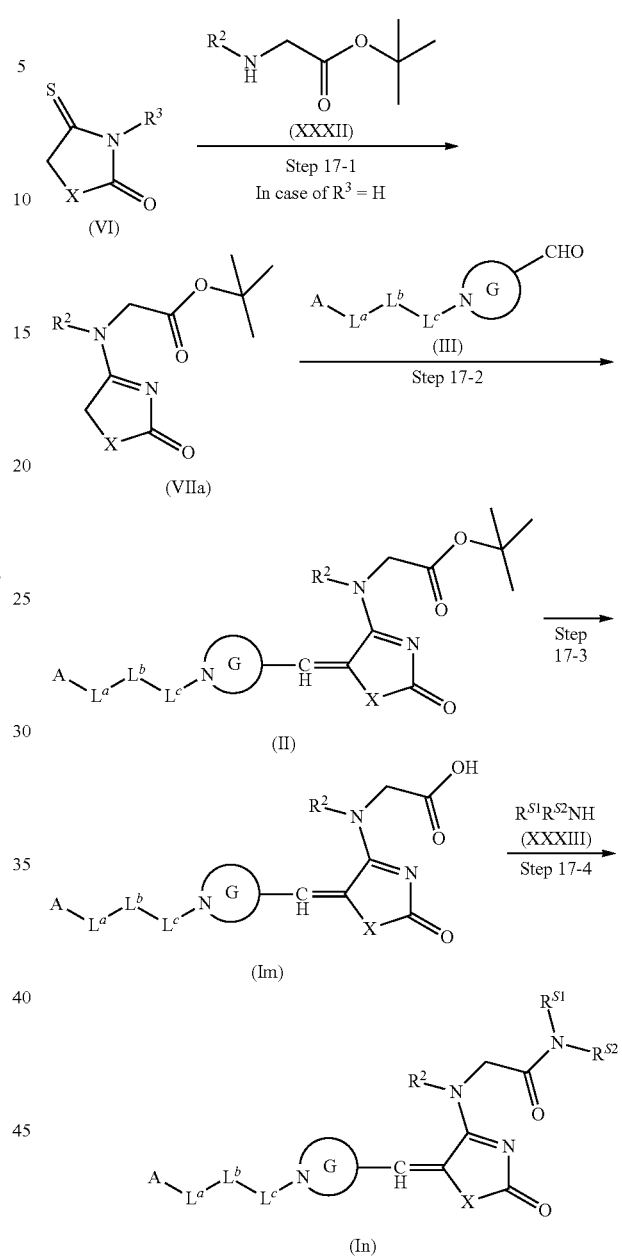

wherein $R^{S1}$ and $R^{S2}$ are each independently a hydrogen atom, a hydrocarbon group optionally having substituent(s) or a heterocyclic group optionally having substituent(s), or $R^{S1}$ and $R^{S2}$ in combination optionally form, together with the adjacent nitrogen atom, a nitrogen-containing heterocycle optionally having substituent(s), and other symbols are as defined above.

Step 17-1

This step is a step of producing compound (VIIa) by reacting compound (VI) with compound (XXXII).

This reaction can be carried out in the same manner as in the aforementioned Step 1-3 of Production Method 1.

Step 17-2

This step is a step of producing compound (Ii) by reacting compound (VIIa) with compound (III) in the presence of a base.

This reaction can be carried out in the same manner as in the aforementioned Step 1-1 of Production Method 1.

Step 17-3

This step is a step of producing compound (Im) by reacting compound (Il) with an acid.

Examples of the acid include hydrochloric acid, acetic acid, tosylic acid, sulfuric acid, trifluoroacetic acid and the like. From among, hydrochloric acid is preferable.

This reaction can be carried out according to a method known per se [e.g., the method described in Theodora W. Greene, Peter G. M. Wuts, *Protective Groups in Organic Synthesis* $3^{rd}$ edition pages 404 to 408] or a method analogous thereto.

The amount of the acid to be used is generally 1 to 100 equivalents, preferably 1 to 10 equivalents, relative to compound (II).

This reaction is generally carried out in an inert solvent. Examples of the inert solvent include ethyl acetate, tetrahydrofuran, diethyl ether, 1,2-dimethoxyethane, 1,4-dioxane, toluene, benzene, xylene, N,N-dimethylformamide, dimethyl sulfoxide, methanol, ethanol, 2-propanol, acetonitrile and the like. Two or more kinds of these solvents may be mixed in an appropriate ratio and used.

The reaction temperature is generally −100 to 200° C.

While the reaction time is not particularly limited, it is generally 0.1 to 100 hr, preferably 0.5 to 72 hr.

Step 17-4

This step is a step of producing compound (In) by reacting compound (Im) with compound (XXXIII) in the presence of a condensing agent.

This reaction can be carried out in the same manner as in the aforementioned Step 15-1 of Production Method 15.

[Production Method 18]

Compound (Io) which is compound (Ia) wherein $L^a$ is a bond, $L^b$ is —CHR$^Y$— and $L^c$ is a bond can also be produced according to the following production method or a method analogous thereto.

Production Method 18

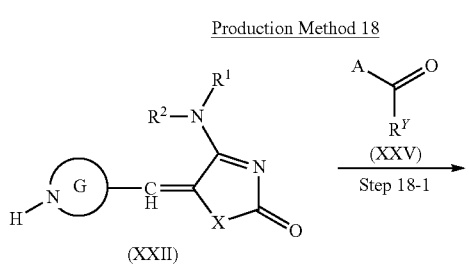

(XXII)

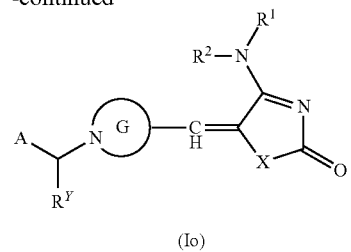

-continued

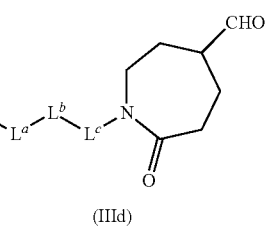

(Io)

wherein each symbol is as defined above.

Step 18-1

This step is a step of producing compound (Io) by reacting compound (XXII) with compound (XXV) in the presence of a reducing agent.

This reaction can be carried out in the same manner as in the aforementioned Step 14-1 of Production Method 14.

[Production Method 19]

Compound (IIId) which is compound (III) wherein G is azepan-2-one can also be produced according to the following production method or a method analogous thereto.

Production Method 19

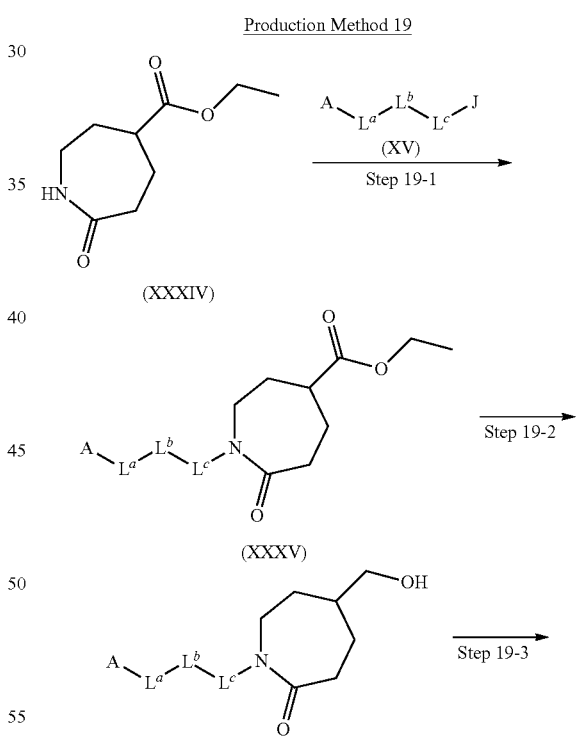

wherein each symbol is as defined above.

Step 19-1

This step is a step of producing compound (XXXV) by reacting compound (XXXIV) with compound (XV).

The starting material compound (XXXIV) can be produced according to a method known per se [e.g., the method described in EP 1602645 A1] or a method analogous thereto.

This reaction can be carried out in the same manner as in the aforementioned Step 16-1 of Production Method 16.

Step 19-2

This step is a step of producing compound (XXXVI) by subjecting compound (XXXV) to a reduction reaction. The reduction reaction can be carried out in the presence of lithium borohydride, or can also be carried out according to a method known per se [e.g., the method described in "Advanced Organic Chemistry, 4th Ed." (Jerry March) or "Comprehensive Organic Transformations, 2nd Ed." (Richard C. Larock)] or a method analogous thereto.

The amount of the reducing agent to be used is generally 0.5 to 10 equivalents, preferably 1 to 5 equivalents, relative to compound (XXXV).

This reaction is generally carried out in an inert solvent. Examples of the inert solvent include diethyl ether, tetrahydrofuran, 1,4-dioxane, 1,2-dimethoxyethane, benzene, toluene, cyclohexane, hexane and the like. Two or more kinds of these solvents may be mixed in an appropriate ratio and used.

While the reaction temperature varies depending on the kinds of the reagent and solvent to be used, it is generally −100 to 250° C., preferably −78 to 200° C.

While the reaction time varies depending on the kinds of the reagent and solvent to be used, it is generally 1 min to 200 hr, preferably 10 min to 100 hr.

Step 19-3

This step is a step of producing compound (IIId) by subjecting compound (XXXVI) to an oxidation reaction.

This reaction can be carried out in the same manner as in the aforementioned Step 10-2 of Production Method 10.

[Production Method 20]

Compound (VIIb) which is compound (VII) wherein $R^1$ is $-CR^{S3}R^{S4}CONR^{S1}R^{S2}$ can also be produced according to the following production method or a method analogous thereto.

Production Method 20

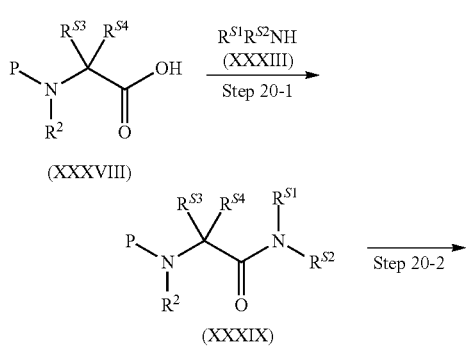

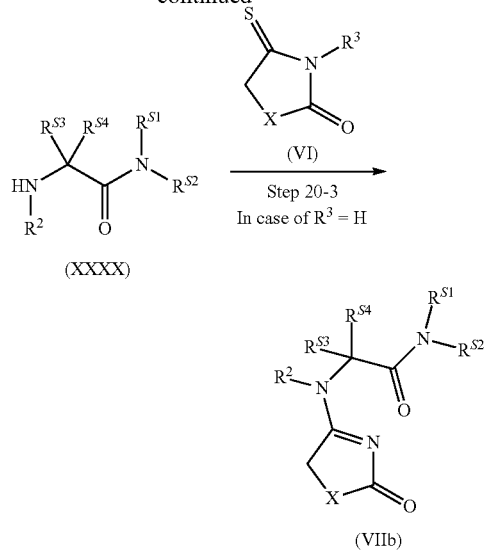

wherein $R^{S3}$ and $R^{S4}$ are each independently a hydrogen atom, a hydrocarbon group optionally having substituent(s) or a heterocyclic group optionally having substituent(s), or $R^{S3}$ and $R^{S4}$ in combination optionally form, together with the adjacent carbon atom, a hydrocarbon ring or heterocycle, each optionally having substituent(s), and the other symbols are each as defined above.

Step 20-1

This step is a step of producing compound (XXXIX) by reacting compound (XXXVIII) with compound (XXXIII) in the presence of a condensing agent.

The starting material compound (XXXVIII) may be commercially available, or can be produced according to a method known per se [e.g., the method described in "Advanced Organic Chemistry, 4th Ed." (Jerry March), "Comprehensive Organic Transformations, 2nd Ed." (Richard C. Larock) or the like] or a method analogous thereto.

This reaction can be carried out in the same manner as in the aforementioned Step 15-1 of Production Method 15.

Step 20-2

This step is a step of producing compound (XXXX) by removing the amino-protecting group P of compound (XXXIX).

While the reaction conditions varies depending on the kind of the protecting group, this reaction can be carried out according to the method of removing an amino-protecting group described Theodora W. Greene, Peter G. M. Wuts, Protective Groups in Organic Synthesis 3rd edition, pages 494 to 653 or a method analogous thereto.

Step 20-3

This step is a step of producing compound (VIIb) by reacting compound (XXXX) with compound (VI).

This reaction can be carried out in the same manner as in the aforementioned Step 1-3 of Production Method 1.

[Production Method 21]

Compound (Ip) which is compound (I) wherein E is

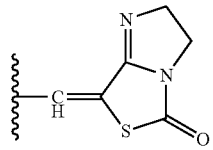

can also be produced according to the following production method or a method analogous thereto.

Production Method 21

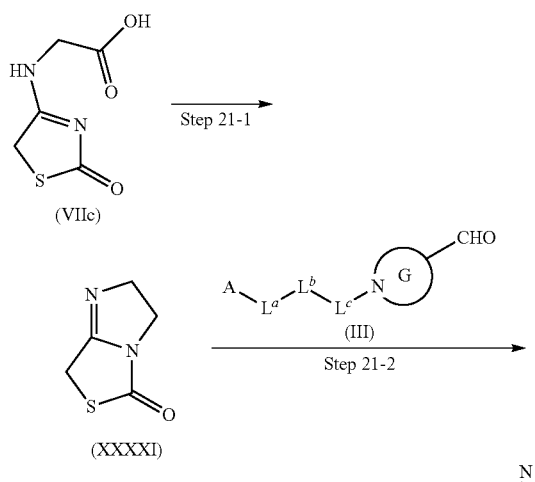

wherein each symbol is as defined above.

Step 21-1

This step is a step of producing compound (XXXXI) from compound (VIIc) in the presence of triphenylphosphine and diisopropyl azodicarboxylate.

The starting material compound (VIIc) can be produced, for example, in the same manner as in the aforementioned Step 2-1 of Production Method 2.

This reaction can be carried out in the presence of tributylphosphine and diethylazodicarboxylate, or can also be carried out according to a method known per se [e.g., the method described in "Advanced Organic Chemistry, 4th Ed." (Jerry March) or "Comprehensive Organic Transformations, 2nd Ed." (Richard C. Larock)] or a method analogous thereto.

The amount of the triphenylphosphine to be used is generally 1 to 100 equivalents, preferably 1 to 5 equivalents, relative to compound (VIIc).

The amount of the diisopropyl azodicarboxylate to be used is generally 1 to 100 equivalents, preferably 1 to 5 equivalents, relative to compound (VIIc).

This reaction is generally carried out in an inert solvent. Examples of the inert solvent include diethyl ether, tetrahydrofuran, 1,4-dioxane, 1,2-dimethoxyethane, benzene, toluene, cyclohexane, hexane, ethyl acetate, dichloromethane, chloroform, carbon tetrachloride, 1,2-dichloroethane, acetonitrile and the like. Two or more kinds of these solvents may be mixed in an appropriate ratio and used.

The reaction temperature is generally –100 to 200° C.

While the reaction time is not particularly limited, it is generally 0.1 to 100 hr, preferably 0.5 to 72 hr.

Step 21-2

This step is a step of producing compound (Ip) by reacting compound (XXXXI) with compound (III) in the presence of a base.

This reaction can be carried out in the same manner as in the aforementioned Step 1-1 of Production Method 1.

[Production Method 22]

Compound (Iq) which is compound (I) wherein E is

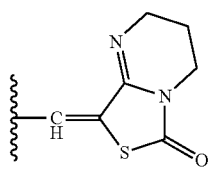

can also be produced according to the following production method or a method analogous thereto.

Production Method 22

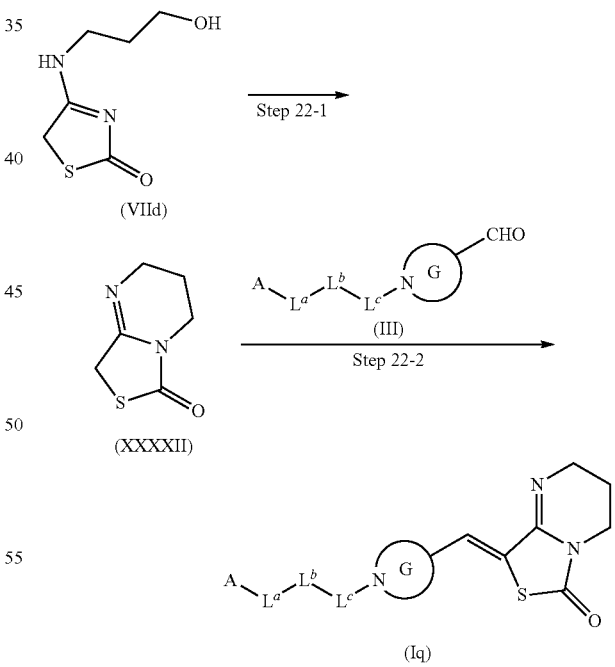

wherein each symbol is as defined above.

Step 22-1

This step is a step of producing compound (XXXXII) from compound (VIId) in the presence of triphenylphosphine and diisopropyl azodicarboxylate.

The starting material compound (VIId) can be produced, for example, in the same manner as in the aforementioned Step 2-1 of Production Method 2

This reaction can be carried out in the same manner as in the aforementioned Step 21-1 of Production Method 21.

Step 22-2

This step is a step of producing compound (Iq) by reacting compound (XXXXII) with compound (III) in the presence of a base.

This reaction can be carried out in the same manner as in the aforementioned Step 1-1 of Production Method 1.
[Production Method 23]

Compound (Ir) which is compound (I) wherein E is

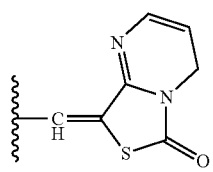

Ee can also be produced according to the following production method or a method analogous thereto.

Production Method 23

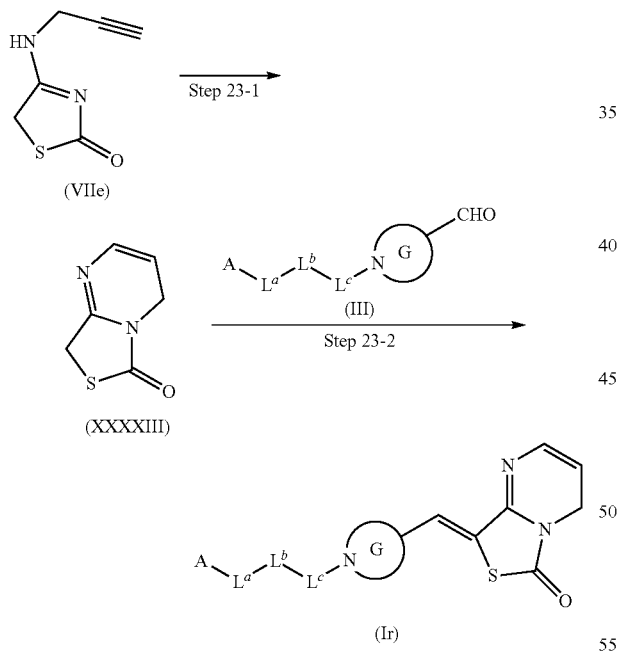

wherein each symbol is as defined above.

Step 23-1

This step is a step of producing compound (XXXXIII) from compound (VIIe).

The starting material compound (VIIe) can be produced, for example, the same manner as in the aforementioned Step 2-1 of Production Method 2.

This reaction is generally carried out in an inert solvent. Examples of the inert solvent include tetrahydrofuran, diethyl ether, 1,2-dimethoxyethane, 1,4-dioxane, toluene, benzene, xylene, N,N-dimethylformamide, dimethyl sulfoxide, methanol, ethanol, 2-propanol, acetonitrile, dichloromethane, chloroform, carbon tetrachloride, 1,2-dichloroethane and the like. Two or more kinds of these solvents may be mixed in an appropriate ratio and used.

Where necessary, this reaction is carried out with irradiation of microwave.

The reaction temperature is generally 100 to 250° C.

While the reaction time is not particularly limited, it is generally 0.1 to 100 hr, preferably 0.5 to 72 hr.

Step 23-2

This step is a step of producing compound (Ir) by reacting compound (XXXXIII) with compound (III) in the presence of a base.

This reaction can be carried out in the same manner as in the aforementioned Step 1-1 of Production Method 1.

It is also possible to produce a compound encompassed in the present invention by further applying substituent introduction or functional group conversion to compound (I) (e.g., compounds (Ia) to (Ir) obtained by the above-mentioned methods) according to a means known per se. Substituent introduction is performed according to known conventional methods such as conversion to carboxy group by ester hydrolysis, conversion to carbamoyl group by amidation of carboxy group, conversion to hydroxymethyl group by reduction of carboxy group, conversion to alcohol form by reduction or alkylation of carbonyl group, reductive amination of carbonyl group, oximation of carbonyl group, acylation, ureation, sulfonylation or alkylation of amino group, amination of activated halogen with amine, conversion to amino group by reduction of nitro group, and acylation, carbamation, sulfonylation or alkylation of hydroxy group. When a reactive substituent causing an unintended reaction during substituent introduction and functional group conversion is present, a protecting group may be introduced in advance into the reactive substituent as necessary according to a means known per se, the object reaction is performed and the protecting group is removed according to a means known per se, whereby compounds encompassed in the present invention can be produced.

In the formula (I), since a compound wherein E is a group represented by

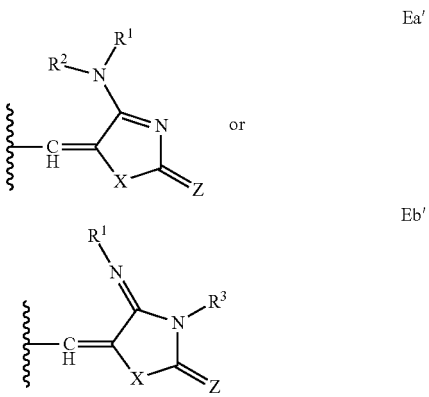

wherein Z is $=S$ or $=NR^a$ wherein $R^a$ is a hydrogen atom, a hydrocarbon group optionally having substituent(s), a heterocyclic group optionally having substituent(s), a hydroxy group optionally having a substituent, an amino group optionally having substituent(s), or an acyl group, and the other symbols are as defined above,
or a salt thereof shows a superior activity as an ERR-α modulator (particularly, inverse agonist) like the compound of the present invention, the compound is also effective for the prophylaxis or treatment of ERR-α associated diseases.

Examples of the "hydrocarbon group optionally having substituent(s)", "heterocyclic group optionally having substituent(s)", "hydroxy group optionally having a substituent", "amino group optionally having substituent(s)" and "acyl group" for $R^a$ include those similar to the "hydrocarbon group optionally having substituent(s)", "heterocyclic group optionally having substituent(s)", "hydroxy group optionally having a substituent", "amino group optionally having substituent(s)" and "acyl group" for $R^1$, $R^2$, $R^3$ or $R^X$.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

$^1$H NMR (proton nuclear magnetic resonance spectrum) was measured by Fourier-transform type NMR. For the analysis, ACD/SpecManager (trade name) and the like were used. Peaks with very mild protons such as hydroxyl group, amino group and the like are not described.

MS (mass spectrum) was measured by LC/MS (liquid chromatography mass spectrometer). As the ionization method, ESI (ElectroSpray Ionization) method, or APCI (Atmospheric Pressure Chemical Ionization) method was used. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. In the case of a compound having a hydroxyl group (—CH), a peak after elimination of $H_2O$ may be observed as a fragment ion. In the case of a salt, a molecular ion peak or fragment ion peak of free form is generally observed.

The following abbreviations are used in the following Examples.
THF: tetrahydrofuran
DMSO: dimethyl sulfoxide
DMF: N,N-dimethylformamide Example 1

(5Z)-5-[(1-{[2,4-bis(trifluoromethyl)phenyl]carbonyl}piperidin-4-yl)methylidene]-4-(methylamino)-1,3-thiazol-2(5H)-one A) 4-(methylamino)-1,3-thiazol-2(5H)-one To a solution of 4-thioxo-1,3-thiazolidin-2-one (13.8 g) in methanol (520 mL) was added 40% methylamine methanol solution (40.4 mL), and the mixture was stirred at room temperature overnight. The reaction mixture was concentrated, and the residue was recrystallized from ethyl acetate to give the title compound (11.1 g).

$^1$H NMR (300 MHz, DMSO-$d_6$) δ 2.88 (3H, s), 4.21 (2H, d, J=0.8 Hz), 8.96 (1H, brs).

B) tert-butyl 4-{(Z)-[4-(methylamino)-2-oxo-1,3-thiazol-5(2H)-ylidene]methyl}piperidine-1-carboxylate tert-Butyl 4-formylpiperidine-1-carboxylate (1.61 g) and 4-(methylamino)-1,3-thiazol-2(5H)-one (1.18 g) were suspended in ethanol (10 mL), potassium tert-butoxide (1.02 g) was added, and the mixture was stirred at 80° C. for 8 hr. The reaction mixture was concentrated, saturated aqueous ammonium chloride solution was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (NH, ethyl acetate/hexane) to give the title compound (1.27 g).

$^1$H NMR (300 MHz, CDCl$_3$) δ 1.30-1.42 (2H, m), 1.46 (9H, s), 1.77 (2H, d, J=10.8 Hz), 2.11-2.50 (1H, m), 2.70-2.90 (2H, m), 3.18 (3H, d, J=4.9 Hz), 3.85-4.31 (2H, m), 6.14 (1H, d, J=8.9 Hz), 6.73 (1H, brs).

MS (ESI+): [M+H]$^+$ 326.1.

C) (5Z)-4-(methylamino)-5-(piperidin-4-ylmethylidene)-1,3-thiazol-2(5H)-one dihydrochloride To a solution of tert-butyl 4-{(Z)-[4-(methylamino)-2-oxo-1,3-thiazol-5(2H)-ylidene]methyl}piperidine-1-carboxylate (1.27 g) in tetrahydrofuran/methanol (6 mL/6 mL) was added 4M hydrogen chloride/ethyl acetate solution (5.85 mL), and the reaction mixture was stirred at 80° C. for 2 hr. The solvent was evaporated under reduced pressure, and the residue was washed with ethyl acetate to give the title compound (1.02 g).

$^1$H NMR (300 MHz, DMSO-$d_6$) δ 1.41-1.77 (2H, m), 1.77-2.06 (2H, m), 2.15-2.47 (1H, m), 2.94-2.95 (5H, m), 3.25 (2H, d, J=12.8 Hz), 6.99 (1H, d, J=8.9 Hz), 8.90-9.20 (2H, m), 9.62 (1H, d, J=4.3 Hz).

MS (ESI+): [M+H−2HCl]$^+$ 226.1.

D) (5Z)-5-[(1-{[2,4-bis(trifluoromethyl)phenyl]carbonyl}piperidin-4-yl)methylidene]-4-(methylamino)-1,3-thiazol-2(5H)-one To a solution of 2,4-bis(trifluoromethyl)benzoic acid (83 mg) in N,N-dimethylformamide (6 mL) were added 1-hydroxybenzotriazole (123 mg) and 1-ethyl-3-(3-dimethylaminopropyl)carbodiimide hydrochloride (154 mg), and the mixture was stirred for 5 min under ice-cooling. To the reaction mixture were added triethylamine (0.2 mL) and (5Z)-4-(methylamino)-5-(piperidin-4-ylmethylidene)-1,3-thiazol-2(5H)-one dihydrochloride (200 mg) under ice-cooling, and the mixture was stirred at room temperature overnight. Water was added to the reaction mixture, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate) and recrystallized from ethyl acetate/pentane to give the title compound (85 mg).

¹H NMR (300 MHz, DMSO-d₆) δ 0.87-1.75 (3H, m), 1.75-1.90 (1H, m), 2.30-2.50 (1H, m), 2.85-3.27 (6H, m), 4.35-4.45 (1H, m), 6.73 (1H, dd, J=8.9, 3.4 Hz), 7.52-8.04 (1H, m), 8.03-8.40 (2H, m), 9.19 (1H, brs).

Example 2

4-(4-{(Z)-[4-(methylamino)-2-oxo-1,3-thiazol-5 (2H)-ylidene]methyl}piperidin-1-yl)-3-(trifluoromethyl)benzonitrile To a solution of (5Z)-4-(methylamino)-5-(piperidin-4-yl-methylidene)-1,3-thiazol-2(5H)-one dihydrochloride (100 mg) in dimethyl sulfoxide (2 mL) were added cesium carbonate (327 mg) and 4-fluoro-3-(trifluoromethyl)benzonitrile (76 mg), and the mixture was stirred at 100° C. for 3 hr. Water was added to the reaction mixture, and the mixture was extracted with ethyl acetate. The extract was washed with saturated brine, and dried over anhydrous magnesium sulfate, and the solvent was evaporated under reduced pressure. The residue was purified by silica gel column chromatography (NH, ethyl acetate/methanol) to give the title compound (14.5 mg).
¹H NMR (300 MHz, CDCl₃) δ 1.58-1.68 (2H, m), 1.96 (2H, d, J=13.6 Hz), 2.35-2.55 (1H, m), 2.93-3.15 (2H, m), 3.20 (3H, d, J=4.9 Hz), 3.93 (2H, d, J=13.2 Hz), 5.73-6.29 (2H, m), 6.97 (1H, dd, J=8.5, 2.5 Hz), 7.13 (1H, d, J=2.5 Hz), 7.62 (1H, d, J=9.3 Hz).

Example 3

(5Z)-5-({1-[2,4-bis(trifluoromethyl)benzyl]piperidin-4-yl}methylidene)-4-(methylamino)-1,3-thiazol-2(5H)-one A) 1-[2,4-bis(trifluoromethyl)benzyl]piperidine-4-carbaldehyde To a solution of 1-(bromomethyl)-2,4-bis(trifluoromethyl)benzene (89 g) in N,N-dimethylformamide (1 L) were added 4-piperidinemethanol (50 g) and potassium carbonate (60.0 g), and the mixture was stirred at room temperature for 2 hr. Water/ethyl acetate were added to the reaction mixture, and the organic layer was separated, washed with water and saturated brine, and dried over anhydrous magnesium sulfate, and the solvent was evaporated under reduced pressure. To a solution of the obtained oil and triethylamine (242 mL) in dimethyl sulfoxide (1 L) was added sulfur trioxide pyridine complex (138 g), and the mixture was stirred at room temperature for 1 hr. Water/ethyl acetate were added to the reaction mixture, and the organic layer was separated, washed with water and saturated brine, and dried over anhydrous magnesium sulfate, and the solvent was evaporated under reduced pressure. The residue was purified by silica gel column chromatography (ethyl acetate/hexane) to give the title compound (85 g).
¹H NMR (300 MHz, CDCl₃) δ 1.61-1.83 (2H, m), 1.83-2.02 (2H, m), 2.09-2.43 (3H, m), 2.80 (2H, dt, J=11.6, 3.8 Hz), 3.70 (2H, s), 7.78 (1H, d, J=8.3 Hz), 7.87 (1H, s), 8.00 (1H, d, J=8.1 Hz), 9.68 (1H, s).
MS (ESI+): [M+H]⁺ 340.1.

B) (5Z)-5-({1-[2,4-bis(trifluoromethyl)benzyl]piperidin-4-yl}methylidene)-4-(methylamino)-1,3-thiazol-2(5H)-one To a solution of 1-[2,4-bis(trifluoromethyl)benzyl]piperidine-4-carbaldehyde (1.00 g) in 2-propanol (15 mL) were added 4-(methylamino)-1,3-thiazol-2(5H)-one (0.77 g) and piperidinium acetate (0.44 g). The reaction mixture was stirred at 60° C. overnight and concentrated. Water was added to the residue, and the mixture was extracted with ethyl acetate. The extract was washed with water, dried over anhydrous magnesium sulfate, and the solvent was evaporated under reduced pressure. The residue was purified by silica gel column chromatography (ethyl acetate/hexane) and recrystallized from ethyl acetate/heptane to give the title compound (0.71 g).
¹H NMR (300 MHz, DMSO-d₆) δ 1.38-1.54 (2H, m), 1.67-1.80 (2H, m), 2.02-2.23 (3H, m), 2.70-2.81 (2H, m), 2.96 (3H, s), 3.71 (2H, s), 6.77 (1H, d, J=8.7 Hz), 7.98 (1H, s), 8.02-8.11 (2H, m), 9.17 (1H, brs).

Example 4

(5Z)-5-({1-[2,4-bis(trifluoromethyl)benzyl]piperidin-4-yl}methylidene)-4-(3-hydroxypyrrolidin-1-yl)-1,3-thiazol-2(5H)-one A) tert-butyl 4-[(Z)-(2-oxo-4-thioxo-1,3-thiazolidin-5-ylidene)methyl]piperidine-1-carboxylate tert-Butyl 4-formylpiperidine-1-carboxylate (7.6 g) and 4-thioxo-1,3-thiazolidin-2-one (4.98 g) were suspended in ethanol (200 mL), potassium tert-butoxide (4.80 g) was added, and the reaction mixture was stirred at 80° C. for 4 hr. Acetic acid/water/ethyl acetate were added to the reaction mixture, and the organic layer was separated, washed with saturated aqueous sodium hydrogen carbonate solution and saturated brine, and dried over anhydrous magnesium sulfate, and the solvent was evaporated under reduced pressure. The residue was purified by silica gel column chromatography (ethyl acetate/hexane) and washed with diethyl ether to give the title compound (7.8 g).
¹H NMR (300 MHz, DMSO-d₆) δ 1.28 (2H, qd, J=12.2, 4.3 Hz), 1.40 (9H, s), 1.56-1.73 (2H, m), 2.03-2.26 (1H, m), 2.60-2.97 (2H, m), 3.74-3.99 (2H, m), 6.65 (1H, d, J=9.2 Hz).

B) (5Z)-5-({1-[2,4-bis(trifluoromethyl)benzyl]piperidin-4-yl}methylidene)-4-(3-hydroxypyrrolidin-1-yl)-1,3-thiazol-2(5H)-one To a solution of tert-butyl 4-[(Z)-(2-oxo-4-thioxo-1,3-thiazolidin-5-ylidene)methyl]piperidine-1-carboxylate (6.75 g) in ethanol (60 mL) was added 3-pyrrolidinol (1.66 mL), and the mixture was stirred at 80° C. for 4 hr. The reaction mixture was concentrated, and the residue was purified by silica gel column chromatography (ethyl acetate/methanol) to give a mixture. To a solution of the obtained mixture in ethyl acetate (10 mL) was added 4M hydrogen chloride/ethyl acetate solution (20 mL), the mixture was stirred at room temperature for 1 hr, and the solvent was evaporated under reduced pressure. To a solution of the obtained residue in N,N-dimethylformamide (50 mL) were added triethylamine (5.55 mL) and 2,4-bis(trifluoromethyl)benzaldehyde (3.62 g). The reaction mixture was stirred at room temperature for 30 min under a nitrogen atmosphere, and sodium triacetoxyborohydride (8.44 g) was added. The mixture was stirred at room temperature for 4 hr, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/methanol) to give the title compound (2.10 g).

¹H NMR (300 MHz, CDCl₃) δ 1.46-2.33 (9H, m), 2.84 (2H, d, J=11.3 Hz), 3.56-4.06 (7H, m), 4.51-4.85 (1H, m), 6.22-6.53 (1H, m), 7.77 (1H, d, J=8.7 Hz), 7.88 (1H, s), 7.97 (1H, d, J=7.4 Hz).

Example 5

(5Z)-5-({1-[2,4-bis(trifluoromethyl)benzyl]piperidin-4-yl}methylidene)-4-(3-hydroxypyrrolidin-1-yl)-1,3-thiazol-2(5H)-one fumarate To a solution of (5Z)-5-({1-[2,4-bis(trifluoromethyl)benzyl]piperidin-4-yl}methylidene)-4-(3-hydroxypyrrolidin-1-yl)-1,3-thiazol-2(5H)-one (67.3 mg) in ethanol (2 mL) was added fumaric acid (15.4 mg). The reaction mixture was stirred at 80° C. for 1 hr, the solvent was evaporated under reduced pressure, and the residue was recrystallized from ethanol/ethyl acetate to give the title compound (35 mg).
¹H NMR (300 MHz, DMSO-d₆) δ 1.51-1.79 (4H, m), 1.81-2.22 (5H, m), 2.80 (2H, d, J=11.1 Hz), 3.59-4.00 (6H, m), 4.28-4.52 (1H, m), 5.02-5.35 (1H, m), 6.58-6.73 (3H, m), 7.98 (1H, s), 8.01-8.12 (2H, m), 13.08 (2H, brs).

Example 6

(5Z)-5-({1-[2,4-bis(trifluoromethyl)benzyl]piperidin-4-yl}methylidene)-4-{[2-(diethylamino)ethyl]amino}-1,3-thiazol-2(5H)-one A) 4-{[2-(diethylamino)ethyl]amino}-1,3-thiazol-2(5H)-one To a solution of 4-thioxo-1,3-thiazolidin-2-one (5.32 g) in methanol (200 mL) was added N,N-diethylethane-1,2-diamine (6.17 mL). The reaction mixture was stirred at room temperature overnight, and the solvent was evaporated under reduced pressure. The residue was purified by silica gel column chromatography (NH, ethyl acetate/hexane) to give the title compound (5.44 g).
¹H NMR (300 MHz, CDCl₃) δ 1.03 (6H, t, J=7.2 Hz), 2.57 (4H, q, J=7.2 Hz), 2.65 (2H, t, J=5.9 Hz), 3.55 (2H, t, J=5.9 Hz), 4.13 (2H, s), 6.76 (1H, brs).
MS (ESI+): [M+H]⁺ 216.1.

B) (5Z)-5-({1-[2,4-bis(trifluoromethyl)benzyl]piperidin-4-yl}methylidene)-4-{[2-(diethylamino)ethyl]amino}-1,3-thiazol-2(5H)-one To a solution of 1-[2,4-bis(trifluoromethyl)benzyl]piperidine-4-carbaldehyde (6.64 g) and 4-{[2-(diethylamino)ethyl]amino}-1,3-thiazol-2(5H)-one (5.48 g) in ethanol (98 mL) was added potassium tert-butoxide (2.85 g). The reaction mixture was stirred at 80° C. for 20 min, the solvent was evaporated under reduced pressure, and the residue was purified by silica gel column chromatography (NH, ethyl acetate/hexane). The solvent was evaporated under reduced pressure, the residue was dissolved in ethyl acetate, the solution was washed with water and saturated brine, and dried over anhydrous magnesium sulfate, and the solvent was evaporated under reduced pressure. The residue was purified by silica gel column chromatography (NH, methanol/ethyl acetate) and further silica gel column chromatography (methanol/ethyl acetate) to give the title compound (7.84 g).
¹H NMR (300 MHz, DMSO-d₆) δ 0.95 (6H, t, J=7.1 Hz), 1.38-1.55 (2H, m), 1.74 (2H, dd, J=13.6, 2.6 Hz), 2.03-2.30 (3H, m), 2.44-2.54 (4H, m), 2.60 (2H, t, J=6.9 Hz), 2.70-2.81 (2H, m), 3.45 (2H, t, J=6.9 Hz), 3.71 (2H, s), 6.81 (1H, d, J=8.9 Hz), 7.97-8.00 (1H, m), 8.02-8.11 (2H, m), 9.10 (1H, brs).

Example 7

(5Z)-5-({1-[2,4-bis(trifluoromethyl)benzyl]piperidin-4-yl}methylidene)-4-(prop-2-yn-1-ylamino)-1,3-thiazol-2(5H)-one A) 4-(prop-2-yn-1-ylamino)-1,3-thiazol-2(5H)-one To a suspension of 4-thioxo-1,3-thiazolidin-2-one (12.8 g) in ethanol (200 mL) was added propargylamine (9.67 mL), and the mixture was stirred at room temperature overnight. The precipitate was collected by filtration, and washed with ethanol to give the title compound (11.9 g).
¹H NMR (300 MHz, DMSO-d₆) δ 3.29-3.34 (1H, m), 4.15 (2H, brs), 4.27 (2H, s), 9.46 (1H, brs).
MS (ESI+): [M+H]⁺ 155.0.

B) (5Z)-5-({1-[2,4-bis(trifluoromethyl)benzyl]piperidin-4-yl}methylidene)-4-(prop-2-yn-1-ylamino)-1,3-thiazol-2(5H)-one To a suspension of 1-[2,4-bis(trifluoromethyl)benzyl]piperidine-4-carbaldehyde (15 g) and 4-(prop-2-yn-1-ylamino)-1,3-thiazol-2(5H)-one (8.18 g) in ethanol (150 mL) was added potassium tert-butoxide (5.95 g), and the reaction mixture was stirred at 80° C. for 30 min. The reaction mixture was concentrated, saturated aqueous ammonium chloride solution/ethyl acetate were added to the residue, and the organic layer was separated, washed with water and saturated brine, and dried over anhydrous magnesium sulfate, and the solvent was evaporated under reduced pressure. The residue was purified by silica gel column chromatography (ethyl acetate/hexane), and the residue was washed with diisopropyl ether to give the title compound (9.96 g).
¹H NMR (300 MHz, DMSO-d₆) δ 1.32-1.61 (2H, m), 1.64-1.87 (2H, m), 2.01-2.26 (3H, m), 2.64-2.87 (2H, m), 3.32-3.36 (1H, m), 3.71 (2H, s), 4.23 (2H, d, J=2.5 Hz), 6.90 (1H, d, J=8.9 Hz), 7.98 (1H, s), 8.01-8.19 (2H, m), 9.57 (1H, s).

Example 8

(5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one To a solution of 2-(2-aminoethoxy)ethanol (4.24 mL) in ethanol (30 mL) was added 4-thioxo-1,3-thiazolidin-2-one (5.65 g), and the mixture was stirred at room temperature for 4 hr. To the reaction mixture were added 1-[2,4-bis(trifluoromethyl)benzyl]piperidine-4-carbaldehyde (12 g) and potassium tert-butoxide (4.76 g), and the mixture was stirred at 80° C. for 3 hr. The reaction mixture was cooled to room temperature, saturated aqueous ammonium chloride solution/ethyl acetate were added, and the organic layer was separated, washed with water and saturated brine, and dried over anhydrous magnesium sulfate, and the solvent was evaporated under reduced pressure. The residue was purified by silica gel column chromatography (methanol/ethyl acetate) to give the title compound (4.3 g).
¹H NMR (300 MHz, DMSO-d₆) δ 1.37-1.56 (2H, m), 1.74 (2H, d, J=10.6 Hz), 2.02-2.31 (3H, m), 2.76 (2H, d, J=11.5

Hz), 3.40-3.65 (8H, m), 3.71 (2H, s), 4.62 (1H, t, J=5.3 Hz), 6.88 (1H, d, J=8.7 Hz), 7.98 (1H, s), 8.01-8.13 (2H, m), 9.18-9.27 (1H, m).

Example 9

(5Z)-5-({1-[2,4-bis(trifluoromethyl)benzyl]piperidin-4-yl}methylidene)-4-{[2-(diethylamino)ethyl]amino}-1,3-thiazol-2(5H)-one dihydrochloride To a solution of (5Z)-5-({1-[2,4-bis(trifluoromethyl)benzyl]piperidin-4-yl}methylidene)-4-{[2-(diethylamino)ethyl]amino}-1,3-thiazol-2(5H)-one (115 mg) in ethyl acetate (2 mL) was added 4M hydrogen chloride/ethyl acetate solution (0.21 mL), and the mixture was stirred at room temperature for 1 hr. The solvent was evaporated under reduced pressure, and the residue was recrystallized from ethanol/ethyl acetate to give the title compound (72 mg).
$^1$H NMR (300 MHz, DMSO-$d_5$) δ 1.22 (6H, t, J=7.2 Hz) 1.60-2.20 (4H, m) 2.31-2.47 (1H, m), 2.85-3.58 (10H, m), 3.65-3.93 (2H, m), 4.24-4.84 (2H, m) 7.02 (1H, d, J=8.7 Hz), 8.14 (1H, s), 8.21-8.39 (1H, m), 8.41-8.96 (1H, m), 9.63-9.94 (1H, m), 10.14 (1H, brs), 11.09 (1H, brs).

Example 10

(5Z)-5-({1-[2,4-bis(trifluoromethyl)benzyl]piperidin-4-yl}methylidene)-4-(prop-2-yn-1-ylamino)-1,3-thiazol-2(5H)-one fumarate To a solution of (5Z)-5-({1-[2,4-bis(trifluoromethyl)benzyl]piperidin-4-yl}methylidene)-4-(prop-2-yn-1-ylamino)-1,3-thiazol-2(5H)-one (9.95 g) in ethanol (100 mL) was added fumaric acid (2.43 g). The mixture was stirred at 80° C. for 20 min, the solvent was evaporated under reduced pressure, and the residue was recrystallized from ethanol/heptane to give the title compound (7.08 g).
$^1$H NMR (300 MHz, DMSO-$d_6$) δ 1.39-1.58 (2H, m), 1.74 (2H, d, J=10.4 Hz), 2.04-2.25 (3H, m), 2.76 (2H, d, J=11.7 Hz), 3.33 (1H, t, J=2.5 Hz), 3.71 (2H, s), 4.23 (2H, dd, J=5.3, 2.5 Hz), 6.63 (2H, s), 6.91 (1H, d, J=8.9 Hz), 7.98 (1H, s), 8.01-8.13 (2H, m), 9.57 (1H, t, J=5.4 Hz), 13.13 (2H, brs).

Example 11

(5Z)-5-({1-[2,4-bis(trifluoromethyl)benzyl]azetidin-3-yl}methylidene)-4-(methylamino)-1,3-thiazol-2(5H)-one A) methyl 1-[2,4-bis(trifluoromethyl)benzyl]azetidine-3-carboxylate To a solution of methylazetidine-3-carboxylate (5 g) and 1-(bromomethyl)-2,4-bis(trifluoromethyl)benzene (13.3 g) in DMF (100 mL) was added potassium carbonate (7.20 g) at room temperature. The reaction mixture was stirred at room temperature overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, ethyl acetate/hexane) to give the title compound (5.45 g).
$^1$H NMR (300 MHz, DMSO-$d_6$) δ 3.27-3.45 (3H, m), 3.46-3.57 (2H, m), 3.66 (3H, s), 3.83 (2H, s), 7.87-7.99 (2H, m), 8.06 (1H, d, J=8.3 Hz).
MS (ESI+): [M+H]$^+$ 342.1.

B) {1-[2,4-bis(trifluoromethyl)benzyl]azetidin-3-yl}methanol

To a solution of methyl 1-[2,4-bis(trifluoromethyl)benzyl]azetidine-3-carboxylate (341 mg) in THF (5 mL) was added a suspension of lithium aluminum hydride (38 mg) in THF (5 mL) under ice-cooling. The reaction mixture was stirred at room temperature overnight. To the reaction mixture was added 1N aqueous sodium hydroxide solution under ice-cooling. The precipitate was removed by filtration, the filtrate was concentrated, and the residue was purified by silica gel column chromatography (NH, ethyl acetate/hexane) to give the title compound (180 mg).
$^1$H NMR (300 MHz, DMSO-$d_6$) δ 2.52-2.59 (1H, m), 2.98 (2H, t, J=6.5 Hz), 3.21-3.31 (2H, m), 3.47-3.59 (2H, m), 3.79 (2H, s), 4.61 (1H, t, J=5.4 Hz), 7.86-8.00 (2H, m), 8.00-8.12 (1H, m)
MS (ESI+): [M+H]$^+$ 314.1.

C) 1-[2,4-bis(trifluoromethyl)benzyl]azetidine-3-carbaldehyde

To a solution of {1-[2,4-bis(trifluoromethyl)benzyl]azetidin-3-yl}methanol (313 mg) and triethylamine (607 mg) in DMSO (5 mL) was added sulfur trioxide pyridine complex (477 mg) at room temperature. The reaction mixture was stirred at room temperature overnight. To the reaction mixture was added saturated aqueous sodium hydrogen carbonate solution at room temperature, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (202 mg).
$^1$H NMR (300 MHz, DMSO-$d_6$) δ 3.24-3.36 (1H, m), 3.38-3.49 (4H, m), 3.84 (2H, s), 7.89-7.99 (2H, m), 8.06 (1H, d, J=8.3 Hz), 9.81 (1H, d, J=2.1 Hz).
MS (ESI+): [M+H]$^+$ 312.1.

D) (5Z)-5-({1-[2,4-bis(trifluoromethyl)benzyl]azetidin-3-yl}methylidene)-4-(methylamino)-1,3-thiazol-2(5H)-one To a solution of 1-[2,4-bis(trifluoromethyl)benzyl]azetidine-3-carbaldehyde (90 mg) and 4-(methylamino)-1,3-thiazol-2(5H)-one (38 mg) in ethanol (3 mL) was added potassium tert-butoxide (32 mg) at room temperature, and the mixture was stirred with heating under reflux for 3 hr. Water was added to the reaction mixture, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (12 mg).
$^1$H NMR (300 MHz, CDCl$_3$) δ 3.10-3.32 (6H, m), 3.60-3.70 (2H, m), 3.83 (2H, s), 6.63-6.77 (2H, m), 7.78 (1H, d, J=8.5 Hz), 7.82-7.91 (2H, m).

Example 12

(5Z)-5-({1-[2,4-bis(trifluoromethyl)benzyl]-4-methylpiperidin-4-yl}methylidene)-4-(methylamino)-1,3-thiazol-2(5H)-one To a solution of 1-[2,4-bis(trifluoromethyl)benzyl]piperidine-4-carbaldehyde (372 mg) in tetrahydrofuran (5 mL)

were added potassium tert-butoxide (123 mg) and methyl iodide (0.069 mL) under ice-cooling. The reaction mixture was stirred at room temperature for 1 hr under a nitrogen atmosphere. To the reaction mixture were added saturated aqueous ammonium chloride solution/ethyl acetate, and the organic layer was separated, washed with water and saturated brine, and dried over anhydrous magnesium sulfate, and the solvent was evaporated under reduced pressure. The residue was purified by silica gel column chromatography (ethyl acetate/hexane) to give an oil. The obtained oil and 4-(methylamino)-1,3-thiazol-2(5H)-one (143 mg) were suspended in ethanol (5 mL), and potassium tert-butoxide (123 mg) was added. The reaction mixture was stirred at 80° C. for 3 hr. To the reaction mixture were added saturated aqueous ammonium chloride solution/ethyl acetate at room temperature, and the organic layer was separated, washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (83 mg).

$^1$H NMR (300 MHz, DMSO-$d_6$) δ 1.10 (3H, s), 1.34-1.68 (2H, m), 1.85 (2H, d, J=13.4 Hz), 2.19 (2H, t, J=10.5 Hz), 2.59 (2H, d, J=11.7 Hz), 2.98 (3H, s), 3.68 (2H, s), 6.91 (1H, s), 7.97 (1H, s), 8.00-8.17 (2H, m), 9.21 (1H, s).

Example 13

(5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one ditoluenesulfonate To a solution of (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one (4.3 g) in ethyl acetate (40 ml) was added tosylic acid monohydrate (3.11 g), and the mixture was stirred at room temperature for 2 hr. The precipitate was collected by filtration, washed with ethyl acetate, and recrystallized from 2-butanone/heptane to give the title compound (4.4 g).

$^1$H NMR (300 MHz, DMSO-$d_6$) δ 1.59-1.82 (2H, m), 1.84-2.01 (2H, m), 2.29 (6H, s), 2.34-2.43 (1H, m), 3.17-3.35 (2H, m), 3.39-3.53 (6H, m), 3.54-3.66 (4H, m), 4.57 (2H, brs), 6.76 (1H, d, J=8.5 Hz), 7.12 (4H, d, J=7.7 Hz), 7.41-7.51 (4H, m), 8.12-8.22 (2H, m), 8.26-8.33 (1H, m), 9.29 (1H, brs), 9.42 (1H, brs).

Example 14

(5Z)-5-({(1R,5S,6s)-3-[2,4-bis(trifluoromethyl)benzyl]-3-azabicyclo[3.1.0]hex-6-yl}methylidene)-4-(methylamino)-1,3-thiazol-2(5H)-one A) (1R,5S,6r)-3-azabicyclo[3.1.0]hex-6-ylmethanol hydrochloride To a solution of [(1R,5S,6r)-3-benzyl-3-azabicyclo[3.1.0]hex-6-yl]methanol hydrochloride (200 mg) (Brighty, K. E.; Castaldi, M. J. Synlett 1996, 1097.) in methanol (2 mL) was added Pd—C (20 mg), and the mixture was stirred at 50° C. for 2 hr under a hydrogen atmosphere. The precipitate was separated by filtration, and the filtrate was concentrated to give the title compound (125 mg).

$^1$H NMR (300 MHz, DMSO-$d_6$) δ 0.94-1.37 (1H, m), 1.40-1.76 (2H, m), 3.09-3.31 (6H, m), 4.48-4.89 (1H, m), 9.25 (1H, brs), 9.55 (1H, brs).

B) {(1R,5S,6r)-3-[2,4-bis(trifluoromethyl)benzyl]-3-azabicyclo[3.1.0]hex-6-yl}methanol To a solution of (1R,5S,6r)-3-azabicyclo[3.1.0]hex-6-ylmethanol hydrochloride (125 mg) in N,N-dimethylformamide (3 mL) were added triethylamine (0.256 mL) and 2,4-bis(trifluoromethyl)benzaldehyde (303 mg). The reaction mixture was stirred at room temperature for 30 min under a nitrogen atmosphere, and sodium triacetoxyborohydride (531 mg) was added. The reaction mixture was stirred at room temperature for 4 hr, aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (170 mg).

$^1$H NMR (300 MHz, CDCl$_3$) δ 1.32-1.41 (2H, m), 1.56-1.65 (1H, m), 2.45 (2H, d, J=8.3 Hz), 3.03 (2H, d, J=8.5 Hz), 3.47 (2H, d, J=7.2 Hz), 3.81 (2H, s), 7.65-7.80 (1H, m), 7.80-7.96 (2H, m).

MS (ESI+): [M+H]$^+$ 340.2.

C) (1R,5S,6r)-3-[2,4-bis(trifluoromethyl)benzyl]-3-azabicyclo[3.1.0]hexane-6-carbaldehyde To a solution of {(1R,5S,6r)-3-[2,4-bis(trifluoromethyl)benzyl]-3-azabicyclo[3.1.0]hex-6-yl}methanol (170 mg) and triethylamine (0.210 mL) in dimethyl sulfoxide (2 mL) was added sulfur trioxide pyridine complex (239 mg) under ice-cooling, and the mixture was stirred at room temperature overnight. To the reaction mixture were added saturated aqueous sodium hydrogen carbonate solution/ethyl acetate, and the organic layer was separated, washed with water and saturated brine, and dried over anhydrous magnesium sulfate, and the solvent was evaporated under reduced pressure. The residue was purified by silica gel column chromatography (ethyl acetate/hexane) to give the title compound (65 mg).

$^1$H NMR (300 MHz, CDCl$_3$) δ 2.01-2.22 (2H, m), 2.35-2.47 (1H, m), 2.59 (2H, d, J=8.9 Hz), 3.10 (2H, d, J=9.1 Hz), 3.85 (2H, s), 7.69-7.84 (2H, m), 7.87 (1H, s), 9.30 (1H, d, J=4.9 Hz).

D) (5Z)-5-({(1R,5S,6s)-3-[2,4-bis(trifluoromethyl)benzyl]-3-azabicyclo[3.1.0]hex-6-yl}methylidene)-4-(methylamino)-1,3-thiazol-2(5H)-one (1R,5S,6s)-3-[2,4-Bis(trifluoromethyl)benzyl]-3-azabicyclo[3.1.0]hexane-6-carbaldehyde (65 mg) and 4-(methylamino)-1,3-thiazol-2(5H)-one (30 mg) were suspended in ethanol (2 mL), potassium tert-butoxide (26 mg) was added, and the reaction mixture was stirred at 80° C. for 3 hr. To the reaction mixture were added saturated aqueous ammonium chloride solution/ethyl acetate, and the organic layer was separated, washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/dimethyl sulfoxide/water to give the title compound (35 mg).

$^1$H NMR (300 MHz, DMSO-$d_6$) δ 1.68-1.80 (1H, m), 1.85 (2H, s), 2.45-2.50 (2H, m), 2.93 (3H, s), 3.01 (2H, d, J=9.0 Hz), 3.86 (2H, s), 6.38 (1H, d, J=10.2 Hz), 7.89 (1H, d, J=7.9 Hz), 7.99 (1H, s), 8.10 (1H, d, J=7.9 Hz), 8.98 (1H, brs).

Example 15

(5Z)-5-({(3-exo)-8-[2,4-bis(trifluoromethyl)benzyl]-8-azabicyclo[3.2.1]oct-3-yl}methylidene)-4-(methylamino)-1,3-thiazol-2(5H)-one

A) (3-exo)-8-[2,4-bis(trifluoromethyl)benzyl]-8-azabicyclo[3.2.1]octan-3-ol To a solution of (3-exo)-8-azabicyclo[3.2.1]octan-3-ol (1 g) in N,N-dimethylformamide (20 mL) was added 2,4-bis(trifluoromethyl)benzaldehyde (1.54 mL). The reaction mixture was stirred at room temperature for 30 min, and sodium triacetoxyborohydride (4.17 g) was added. The reaction mixture was stirred at room temperature for 4 hr, saturated aqueous so sodium hydrogen carbonate solution was added under ice-cooling, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (1.1 g).

$^1$H NMR (300 MHz, CDCl$_3$) δ 1.23-1.28 (1H, m), 1.71 (2H, d, J=13.4 Hz), 1.88-2.26 (6H, m), 2.98-3.24 (2H, m), 3.72 (2H, s), 4.04-4.15 (1H, m), 7.78 (1H, d, J=8.3 Hz), 7.85 (1H, s), 8.19 (1H, d, J=8.1 Hz).

MS (ESI+): [M+H]$^+$ 354.2.

B) (1R,5S)-8-[2,4-bis(trifluoromethyl)benzyl]-8-azabicyclo[3.2.1]octan-3-one To a solution of (3-exo)-8-[2,4-bis(trifluoromethyl)benzyl]-8-azabicyclo[3.2.1]octan-3-ol (1.01 g) and triethylamine (2.39 mL) in dimethyl sulfoxide (20 mL) was added sulfur trioxide pyridine complex (1.37 g), and the mixture was stirred at room temperature for 4 hr. To the so reaction mixture were added saturated aqueous sodium hydrogen carbonate solution/ethyl acetate, and the organic layer was separated, washed with water and saturated brine, and dried over anhydrous magnesium sulfate, and the solvent was evaporated under reduced pressure. The residue was purified by silica gel column chromatography (ethyl acetate/hexane) to give the title compound (840 mg).

$^1$H NMR (300 MHz, CDCl$_3$) δ 1.65-1.76 (2H, m), 2.12-2.22 (2H, m), 2.27 (2H, d, J=15.7 Hz), 2.70 (2H, dd, J=16.1, 4.3 Hz), 3.33-3.59 (2H, m), 3.95 (2H, s), 7.83 (1H, d, J=8.1 Hz), 7.90 (1H, s), 8.20 (1H, d, J=8.1 Hz).

C) (5Z)-5-({(3-exo)-8-[2,4-bis(trifluoromethyl)benzyl]-8-azabicyclo[3.2.1]oct-3-yl}methylidene)-4-(methylamino)-1,3-thiazol-2(5H)-one To a solution of potassium tert-butoxide (510 mg) in tetrahydrofuran (10 mL) was added (methoxymethyl)triphenylphosphonium chloride (1.64 g) under ice-cooling, and the mixture was stirred for 30 min under ice-cooling. To the reaction mixture was added a solution of (1R,5S)-8-[2,4-bis(trifluoromethyl)benzyl]-8-azabicyclo[3.2.1]octan-3-one (840 mg) in tetrahydrofuran (5 mL), and the mixture was stirred at room temperature for 3 hr. To the reaction mixture was added 6N hydrochloric acid (2 mL), and the mixture was further stirred at room temperature for 3 hr. To the reaction mixture were added saturated aqueous sodium hydrogen carbonate solution/diethyl ether, and the organic layer was separated, washed with water and saturated brine, and dried over anhydrous magnesium sulfate, and the solvent was evaporated under reduced pressure. The residue was purified by silica gel column chromatography (ethyl acetate/hexane) to give an oil. The obtained oil and 4-(methylamino)-1,3-thiazol-2(5H)-one (100 mg) were suspended in ethanol (2 mL), and potassium tert-butoxide (87 mg) was added. The reaction mixture was stirred at 80° C. for 3 hr, to the reaction mixture were added saturated aqueous ammonium chloride solution/ethyl acetate, and the organic layer was separated, washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (85 mg).

$^1$H NMR (300 MHz, DMSO-d$_6$) δ 1.42-1.79 (6H, m), 1.98-2.12 (2H, m), 2.29-2.45 (1H, m), 2.95 (3H, s), 3.18 (2H, brs), 3.74 (2H, s), 6.69 (1H, d, J=8.7 Hz), 7.98 (1H, s), 8.03-8.13 (1H, m), 8.13-8.26 (1H, m), 9.13 (1H, brs).

Example 16

(5Z)-5-({1-[2,4-bis(trifluoromethyl)benzyl]piperidin-4-yl}methylidene)-4-(prop-2-yn-1-ylamino)-1,3-thiazol-2(5H)-one hydrochloride To a solution of (5Z)-5-({1-[2,4-bis(trifluoromethyl)benzyl]piperidin-4-yl}methylidene)-4-(prop-2-yn-1-ylamino)-1,3-thiazol-2(5H)-one (141 mg) in ethanol (1 mL) was added 6N hydrochloric acid (0.1 mL). The reaction mixture was stirred at room temperature for 1 hr, the solvent was evaporated under reduced pressure, and the residue was recrystallized from 2-butanone/heptane to give the title compound (100 mg).

$^1$H NMR (300 MHz, DMSO-d$_6$) δ 1.61-2.09 (4H, m), 2.31-2.45 (1H, m), 3.09-3.29 (2H, m), 3.32 (1H, t, J=2.3 Hz), 3.35-3.47 (2H, m), 4.22 (2H, d, J=2.6 Hz), 4.54 (2H, brs), 6.87 (1H, d, J=9.3 Hz), 8.14 (1H, brs), 8.28 (1H, d, J=7.7 Hz), 8.60 (1H, d, J=7.6 Hz), 9.73 (1H, brs), 10.90 (1H, brs).

powder X-ray diffraction interplanar spacing (d): 15.55, 7.82, 6.01, 5.83, 5.72, 5.49, 5.16, 5.01, 4.93, 4.85, 3.86 and 3.48 Å.

Example 17

(5Z)-5-({1-[2,4-bis(trifluoromethyl)benzyl]piperidin-4-yl}methylidene)-4-[(2-hydroxy-2-methylpropyl)amino]-1,3-thiazol-2(5H)-one fumarate To a solution of (5Z)-5-({1-[2,4-bis(trifluoromethyl)benzyl]piperidin-4-yl}methylidene)-4-[(2-hydroxy-2-methylpropyl)amino]-1,3-thiazol-2(5H)-one (898 mg) in ethanol (10 mL) was added a solution of fumaric acid (205 mg) in ethanol (5 mL), and the reaction mixture was stirred at 80° C. for 30 min. The solvent was evaporated under reduced pressure, and the residue was recrystallized from ethanol/heptane to give the title compound (790 mg).

$^1$H NMR (300 MHz, DMSO-d$_6$) δ 1.12 (6H, s), 1.49 (2H, q, J=10.3 Hz), 1.75 (2H, d, J=10.8 Hz), 1.94-2.25 (3H, m), 2.77 (2H, d, J=11.7 Hz), 3.43 (2H, d, J=6.2 Hz), 3.71 (2H, s), 4.68 (1H, brs), 6.63 (2H, s), 7.03 (1H, d, J=8.9 Hz), 7.98 (1H, s), 8.01-8.15 (2H, m), 8.94 (1H, t, J=6.1 Hz), 13.13 (2H, brs).

powder X-ray diffraction interplanar spacing (d): 11.78, 8.63, 8.22, 5.75, 5.45, 4.77, 4.68, 4.46, 4.31, 3.96, 3.85 and 3.77 Å.

Example 18

(5Z)-5-({1-[2,4-bis(trifluoromethyl)benzyl]piperidin-4-yl}methylidene)-4-[(2-ethoxyethyl)amino]-1,3-thiazol-2(5H)-one A) 4-[(2-ethoxyethyl)amino]-1,3-thiazol-2(5H)-one To a solution of 2-ethoxyethanamine (4.07 g) in ethanol (100 mL) was added 4-thioxo-1,3-thiazolidin-2-one (4.05 g), and the mixture was stirred at room temperature overnight. The reaction mixture was concentrated, and the residue was purified by silica gel column chromatography (ethyl acetate/hexane) to give the title compound (4.90 g).
$^1$H NMR (300 MHz, CDCl$_3$) δ 1.11-1.32 (3H, m), 3.41-3.78 (6H, m), 4.15-4.31 (2H, m), 6.65 (1H, brs).
MS (ESI+): [M+H]$^+$ 189.0.

B) (5Z)-5-({1-[2,4-bis(trifluoromethyl)benzyl]piperidin-4-yl}methylidene)-4-[(2-ethoxyethyl)amino]-1,3-thiazol-2(5H)-one To a solution of 1-[2,4-bis(trifluoromethyl)benzyl]piperidine-4-carbaldehyde (2 g) in 2-propanol (20 mL) were added 4-[(2-ethoxyethyl)amino]-1,3-thiazol-2(5H)-one (1.67 g) and piperidinium acetate (0.856 g). The reaction mixture was stirred at 80° C. for 2 hr, and the solvent was evaporated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (2.1 g).
$^1$H NMR (300 MHz, DMSO-d$_6$) δ 1.12 (3H, t, J=6.9 Hz), 1.30-1.62 (2H, m), 1.61-1.87 (2H, m), 1.95-2.30 (3H, m), 2.63-2.94 (2H, m), 3.46 (2H, q, J=7.0 Hz), 3.56 (4H, m), 3.71 (2H, s), 6.90 (1H, d, J=8.9 Hz), 7.98 (1H, s), 8.01-8.20 (2H, m), 9.25 (1H, s).

Example 19

(5Z)-5-({1-[2,4-bis(trifluoromethyl)benzyl]piperidin-4-yl}methylidene)-4-(prop-2-en-1-ylamino)-1,3-thiazol-2(5H)-one A) 1-[2,4-bis(trifluoromethyl)benzyl]piperidine-4-carbaldehyde tosylate To a solution of 1-[2,4-bis(trifluoromethyl)benzyl]piperidine-4-carbaldehyde (170 mg) in toluene (2 mL) was added p-toluenesulfonic acid monohydrate (95 mg), and the mixture was stirred at room temperature for 2 hr. The solvent was evaporated under reduced pressure, and the residue was washed with ethyl acetate. The obtained solid was dried at 60° C. under reduced pressure to give the title compound (244 mg).
$^1$H NMR (300 MHz, DMSO-d$_6$) δ 1.50-2.35 (9H, m), 2.92-3.73 (3H, m), 4.58 (2H, brs), 7.11 (2H, d, J=7.7 Hz), 7.47 (2H, d, J=7.7 Hz), 8.05-8.37 (3H, m), 9.33 (1H, brs), 9.55-9.72 (1H, m).
MS (ESI+): [M+H]$^+$ 340.1.

B) (5Z)-5-({1-[2,4-bis(trifluoromethyl)benzyl]piperidin-4-yl}methylidene)-4-(prop-2-en-1-ylamino)-1,3-thiazol-2(5H)-one To a solution of 4-thioxo-1,3-thiazolidin-2-one (60 mg) in ethanol (2 mL) was added prop-2-en-1-amine (26 mg) at room temperature. The reaction mixture was stirred at room temperature for 2 hr. 1-[2,4-Bis(trifluoromethyl)piperidine-4-carbaldehyde tosylate (230 mg) and potassium tert-butoxide (101 mg) were added to the reaction mixture at room temperature, and the mixture was stirred at 80° C. for 3 hr. To the reaction mixture was added saturated aqueous ammonium chloride solution, and the mixture was extracted with ethyl acetate. The extract was washed with saturated brine, and dried over anhydrous magnesium sulfate, and the solvent was evaporated under reduced pressure. The residue was purified by silica gel column chromatography (NH, ethyl acetate/hexane) and recrystallized from ethyl acetate/heptane to give the title compound (95 mg).
$^1$H NMR (300 MHz, DMSO-d$_6$) δ 1.35-1.59 (2H, m), 1.66-1.81 (2H, m), 2.02-2.24 (3H, m), 2.68-2.85 (2H, m), 3.71 (2H, s), 4.05 (1H, ddd, J=5.6, 1.3, 1.3 Hz), 5.17 (1H, ddt, J=10.4, 1.3, 1.3 Hz), 5.22 (1H, ddt, J=17.2, 1.3, 1.3 Hz), 5.90 (1H, ddt, J=17.2, 10.4, 5.6 Hz), 6.89 (1H, d, J=8.7 Hz), 7.98 (1H, s), 8.01-8.11 (2H, m), 9.34 (1H, brs).

Example 20

(5Z)-5-({1-[2,4-bis(trifluoromethyl)benzyl]piperidin-4-yl}methylidene)-4-(oxetan-3-ylamino)-1,3-thiazol-2(5H)-one A) 4-(oxetan-3-ylamino)-1,3-thiazol-2(5H)-one To a solution of oxetane-3-amine (4.94 g) in ethanol (60 mL) was added 4-thioxo-1,3-thiazolidin-2-one (6 g), and the mixture was stirred at room temperature for 30 min. The precipitate was collected by filtration and washed with ethanol to give the title compound (6.39 g).
$^1$H NMR (300 MHz, DMSO-d$_6$) δ 4.29 (2H, s), 4.42-4.61 (2H, m), 4.66-4.96 (3H, m), 9.77 (1H, s).

B) (5Z)-5-({1-[2,4-bis(trifluoromethyl)benzyl]piperidin-4-yl}methylidene)-4-(oxetan-3-ylamino)-1,3-thiazol-2(5H)-one To a solution of 1-[2,4-bis(trifluoromethyl)benzyl]piperidine-4-carbaldehyde (2.5 g) in 2-propanol (20 mL) were added 4-(oxetan-3-ylamino)-1,3-thiazol-2(5H)-one (1.90 g) and piperidinium acetate (1.07 g). The reaction mixture was stirred at 80° C. for 40 min, and the solvent was evaporated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (2.7 g).
$^1$H NMR (300 MHz, DMSO-d$_5$) δ 1.41-1.58 (2H, m), 1.75 (2H, d, J=11.0 Hz), 2.04-2.25 (3H, m), 2.78 (2H, d, J=11.7 Hz), 3.72 (2H, s), 4.58-4.65 (2H, m), 4.80 (2H, t, J=6.9 Hz), 4.96 (1H, q, J=6.6 Hz), 6.97 (1H, d, J=8.7 Hz), 7.99 (1H, s), 8.02-8.14 (2H, m), 9.66 (1H, s).

Example 21

(5Z)-5-({1-[2,4-bis(trifluoromethyl)benzyl]piperidin-4-yl}methylidene)-4-[(cyclopropylmethyl)amino]-1,3-thiazol-2(5H)-one A) 4-[(cyclopropylmethyl)amino]-1,3-thiazol-2(5H)-one To a solution of 1-cyclopropylmethanamine (2.34 g) in ethanol (100 mL) was added 4-thioxo-1,3-thiazolidin-2-one (2.92 g), and the mixture was stirred at room temperature overnight. The solvent was evaporated under reduced pressure and washed with ethanol to give the title compound (1.60 g).
$^1$H NMR (300 MHz, DMSO-$d_6$) δ 0.14-0.34 (2H, m), 0.41-0.58 (2H, m), 0.85-1.18 (1H, m), 2.96-3.25 (2H, m), 4.24 (2H, s), 9.19 (1H, brs).
MS (ESI+): [M+H]$^+$ 171.1.

B) (5Z)-5-({1-[2,4-bis(trifluoromethyl)benzyl]piperidin-4-yl}methylidene)-4-[(cyclopropylmethyl)amino]-1,3-thiazol-2(5H)-one 1-[2,4-Bis(trifluoromethyl)benzyl]piperidine-4-carbaldehyde (200 mg) and 4-[(cyclopropylmethyl)amino]-1,3-thiazol-2(5H)-one (100 mg) were suspended in ethanol (3 mL), potassium tert-butoxide (66.1 mg) was added, and the reaction mixture was stirred at 80° C. for 30 min. The reaction mixture was concentrated under reduced pressure, and the residue was purified by silica gel column chromatography (ethyl acetate/hexane) and recrystallized from ethyl acetate/heptane to give the title compound (180 mg).
$^1$H NMR (300 MHz, DMSO-$d_6$) δ 0.23-0.31 (2H, m), 0.45-0.55 (2H, m), 1.02-1.16 (1H, m), 1.39-1.57 (2H, m), 1.75 (2H, d, J=10.4 Hz), 2.02-2.25 (3H, m), 2.77 (2H, d, J=11.7 Hz), 3.28 (2H, d, J=7.0 Hz), 3.71 (2H, s), 6.88 (1H, d, J=8.9 Hz), 7.98 (1H, s), 8.01-8.13 (2H, m), 9.27 (1H, s).

Example 22

(5Z)-5-{[1-(cyclohexylmethyl)piperidin-4-yl]methylidene}-4-(prop-2-yn-1-ylamino)-1,3-thiazol-2(5H)-one A) tert-butyl 4-{(Z)-[2-oxo-4-(prop-2-yn-1-ylamino)-1,3-thiazol-5(2H)-ylidene]methyl}piperidine-1-carboxylate To a solution of tert-butyl 4-formylpiperidine-1-carboxylate (11.2 g) in 2-propanol (230 mL) were added 4-(prop-2-yn-1-ylamino)-1,3-thiazol-2(5H)-one (16.3 g) and piperidinium acetate (3.90 g). The reaction mixture was stirred at 60° C. overnight, and the solvent was evaporated under reduced pressure. Ethyl acetate was added to the residue, the precipitate was removed, and the filtrate was concentrated. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (14.0 g).
$^1$H NMR (300 MHz, DMSO-$d_6$) δ 1.18-1.36 (2H, m), 1.40 (9H, s), 1.64-1.75 (2H, m), 2.18-2.34 (1H, m), 2.88 (2H, brs), 3.33-3.35 (1H, m), 3.80-3.92 (2H, m), 4.22 (2H, d, J=2.5 Hz), 6.85 (1H, d, J=9.1 Hz), 9.56 (1H, brs).
MS (ESI+): [M+H]$^+$ 350.1.

B) (5Z)-5-(piperidin-4-ylmethylidene)-4-(prop-2-yn-1-ylamino)-1,3-thiazol-2(5H)-one dihydrochloride A mixed solution of tert-butyl 4-{(Z)-[2-oxo-4-(prop-2-yn-1-ylamino)-1,3-thiazol-5(2H)-ylidene]methyl}piperidine-1-carboxylate (14.0 g) and 4M hydrogen chloride/ethyl acetate solution (80 mL) was stirred at room temperature for 1 hr, and the solvent was evaporated under reduced pressure. The residue was washed with ethyl acetate to give the title compound (12.7 g).
$^1$H NMR (300 MHz, DMSO-$d_6$) δ 1.58-1.76 (2H, m), 1.80-1.93 (2H, m), 2.32-2.47 (1H, m), 2.87-3.05 (2H, m), 3.18-3.30 (2H, m), 3.32 (1H, t, J=2.5 Hz), 4.21 (2H, dd, J=4.8, 2.5 Hz), 7.05 (1H, d, J=9.1 Hz), 8.21 (1H, brs), 8.86-9.21 (2H, m), 9.90 (1H, brs).
MS (ESI+): [M+H−2HCl]$^+$ 250.1.

C) (5Z)-5-{[1-(cyclohexylmethyl)piperidin-4-yl]methylidene}-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added triethylamine (0.35 mL) and cyclohexanecarbaldehyde (0.11 mL). The reaction mixture was stirred at room temperature for 1 hr, and sodium triacetoxyborohydride (554 mg) was added. The reaction mixture was stirred at room temperature for 3 hr, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (94 mg).
$^1$H NMR (300 MHz, DMSO-$d_6$) δ 0.74-0.89 (2H, m), 1.05-1.29 (3H, m), 1.33-1.52 (3H, m), 1.57-1.77 (7H, m), 1.85-2.09 (5H, m), 2.70-2.80 (2H, m), 3.31-3.34 (1H, m), 4.22 (2H, d, J=2.5 Hz), 6.86 (1H, d, J=8.9 Hz), 9.57 (1H, s).

Example 23

(5Z)-5-[(1-benzylpiperidin-4-yl)methylidene]-4-(prop-2-yn-1-ylamino)-1,3-thiazol-2(5H)-one fumarate To a solution of (5Z)-5-[(1-benzylpiperidin-4-yl)methylidene]-4-(prop-2-yn-1-ylamino)-1,3-thiazol-2(5H)-one (155 mg) in ethanol (4 mL) was added a solution of fumaric acid (53 mg) in ethanol (4 mL). The reaction mixture was stirred at room temperature for 1 hr, the solvent was evaporated under reduced pressure, and the residue was washed with ethyl acetate. The obtained powder was recrystallized from ethanol/diisopropyl ether to give the title compound (118 mg).
$^1$H NMR (300 MHz, DMSO-$d_6$) δ 1.38-1.54 (2H, m), 1.67-1.79 (2H, m), 2.00-2.21 (3H, m), 2.78-2.90 (2H, m), 3.32 (1H, t, J=2.5 Hz), 3.55 (2H, s), 4.18-4.26 (2H, m), 6.61 (2H, s), 6.87 (1H, d, J=8.9 Hz), 7.23-7.38 (5H, m), 9.61 (1H, brs).

Example 24

(5Z)-5-({1-[4-chloro-2-(trifluoromethyl)benzyl]piperidin-4-yl}methylidene)-4-(prop-2-yn-1-ylamino)-1,3-thiazol-2(5H)-one fumarate To a solution of (5Z)-5-({1-[4-chloro-2-(trifluoromethyl)benzyl]piperidin-4-yl}methylidene)-4-(prop-2-yn-1-ylamino)-1,3-thiazol-2(5H)-one (1.04 g) in ethyl acetate (11.8 mL) was added fumaric acid (273 mg). The reaction mixture was stirred at room temperature for 30 min, and the solvent was evaporated under reduced pressure. The residue was recrystallized from ethanol/heptane to give the title compound (1.09 g).

¹H NMR (300 MHz, DMSO-d₆) δ1.37-1.53 (2H, m), 1.68-1.79 (2H, m), 2.05-2.21 (3H, m), 2.74 (2H, d, J=11.5 Hz), 3.26-3.39 (1H, m), 3.60 (2H, s), 4.23 (2H, dd, J=5.3, 2.4 Hz), 6.63 (2H, s), 6.90 (1H, d, J=8.9 Hz), 7.72-7.83 (3H, m), 9.57 (1H, t, J=5.3 Hz), 13.11 (2H, brs).

Example 25

(5Z)-5-({1-[4-bromo-2-(trifluoromethyl)benzyl]piperidin-4-yl}methylidene)-4-(prop-2-yn-1-ylamino)-1,3-thiazol-2(5H)-one To a solution of (5Z)-5-(piperidin-4-ylmethylidene)-4-(prop-2-yn-1-ylamino)thiazol-2(5H)-one dihydrochloride (1.50 g) in DMF (23.3 mL) were added 4-bromo-2-(trifluoromethyl)benzaldehyde (1.99 g) and triethylamine (2.93 mL). The reaction mixture was stirred at room temperature for 1.5 hr, and sodium triacetoxyborohydride (3.34 g) was added. The reaction mixture was stirred at room temperature for 1 hr and poured into water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (1.71 g).
¹H NMR (300 MHz, DMSO-d₆) δ 1.38-1.54 (2H, m), 1.69-1.79 (2H, m), 2.06-2.20 (3H, m), 2.69-2.78 (2H, m), 3.33-3.35 (1H, m), 3.58 (2H, s), 4.23 (2H, d, J=2.3 Hz), 6.90 (1H, d, J=8.9 Hz), 7.73 (1H, d, J=8.1 Hz), 7.85-7.92 (2H, m), 9.57 (1H, brs).

Example 26

(5Z)-4-(prop-2-yn-1-ylamino)-5-({1-[2-(trifluoromethoxy)benzyl]piperidin-4-yl}methylidene)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added triethylamine (0.35 mL) and 2-(trifluoromethoxy)benzaldehyde (0.09 mL). The reaction mixture was stirred at room temperature for 1 hr, and sodium triacetoxyborohydride (554 mg) was added. The reaction mixture was stirred at room temperature for 3 hr, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (69 mg).
¹H NMR (300 MHz, DMSO-d₅) δ 1.33-1.51 (2H, m), 1.64-1.78 (2H, m), 1.98-2.16 (3H, m), 2.71-2.81 (2H, m), 3.32-3.34 (1H, m), 3.53 (2H, s), 4.22 (2H, d, J=2.1 Hz), 6.88 (1H, d, J=8.9 Hz), 7.30-7.45 (3H, m), 7.51-7.59 (1H, m), 9.56 (1H, brs).

Example 27

(5Z)-5-{[1-(naphthalene-1-ylmethyl)piperidin-4-yl]methylidene}-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added triethylamine (0.35 mL) and naphthalene-1-carbaldehyde (0.09 mL). The reaction mixture was stirred at room temperature for 1 hr, and sodium triacetoxyborohydride (554 mg) was added. The reaction mixture was stirred at room temperature for 3 hr, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (104 mg).
¹H NMR (300 MHz, DMSO-d₆) δ 1.31-1.48 (2H, m), 1.64-1.77 (2H, m), 2.00-2.20 (3H, m), 2.81-2.90 (2H, m), 3.30-3.32 (1H, m), 3.87 (2H, s), 4.21 (2H, d, J=2.5 Hz), 6.86 (1H, d, J=8.9 Hz), 7.41-7.59 (4H, m), 7.81-7.87 (1H, m), 7.88-7.95 (1H, m), 8.24-8.31 (1H, m), 9.55 (1H, s).

Example 28

(5Z)-4-(methylamino)-5-({1-[(3-methyl-1-benzofuran-2-yl)carbonyl]piperidin-4-yl}methylidene)-1,3-thiazol-2(5H)-one To a solution of 3-methyl-1-benzofuran-2-carboxylic acid (19.4 mg) in N,N-dimethylformamide (1 mL) were added 1-hydroxybenzotriazole (16.2 mg) and 1-ethyl-3-(3-dimethylaminopropyl)carbodiimide hydrochloride (23 mg), and the mixture was stirred at 0° C. for 5 min. To the reaction mixture were added triethylamine (0.28 mL) and (5Z)-4-(methylamino)-5-(piperidin-4-ylmethylidene)-1,3-thiazol-2(5H)-one dihydrochloride (29.8 mg), and the mixture was further stirred at room temperature for 5 hr. Water was added to the reaction mixture, and the precipitate was collected by filtration, and washed with water and diisopropyl ether to give the title compound (19.3 mg).
¹H NMR (300 MHz, DMSO-d₆) δ 1.35-1.45 (2H, m), 1.75-1.85 (2H, m), 2.30-2.35 (5H, m), 2.40-2.50 (1H, m), 2.65-2.70 (2H, m), 2.95-3.00 (3H, m), 6.76 (1H, d, J=8.9 Hz), 7.30-7.40 (1H, m), 7.40-7.50 (1H, m), 7.55-7.60 (1H, m), 7.70-7.75 (1H, m), 9.15-9.25 (1H, m).

Example 29

4-[(4-{(Z)-[2-oxo-4-(prop-2-yn-1-ylamino)-1,3-thiazol-5(2H)-ylidene]methyl}piperidin-1-yl)methyl]benzonitrile ½ fumarate To a solution of 4-[(4-{(Z)-[2-oxo-4-(prop-2-yn-1-ylamino)-1,3-thiazol-5(2H)-ylidene]methyl}piperidin-1-yl)methyl]benzonitrile (372 mg) in ethanol (5 mL) was added a solution of fumaric acid (119 mg) in ethanol (15 mL). The reaction mixture was stirred at room temperature for 1 hr, and the solvent was evaporated under reduced pressure. The residue was recrystallized from ethanol/heptane to give the title compound (356 mg).
¹H NMR (300 MHz, DMSO-d₆) δ 1.36-1.52 (2H, m), 1.66-1.77 (2H, m), 1.99-2.14 (3H, m), 2.71-2.81 (2H, m), 3.33 (1H, t, J=2.5 Hz), 3.56 (2H, s), 4.22 (2H, dd, J=5.1, 2.5 Hz), 6.62 (1H, s), 6.87 (1H, d, J=8.9 Hz), 7.51 (2H, d, J=8.1 Hz), 7.80 (2H, d, J=8.1 Hz), 9.58 (1H, t, J=5.1 Hz), 13.11 (1H, s).

Example 30

(5Z)-5-({3-[2,4-bis(trifluoromethyl)benzyl]-3-azabi-cyclo[3.3.1]non-7-yl}methylidene)-4-(prop-2-yn-1-ylamino)-1,3-thiazol-2(5H)-one

A) 3-tert-butyl 7-methyl 9-oxo-3-azabicyclo[3.3.1]nonane-3,7-dicarboxylate

To tert-butyl 4-oxopiperidine-1-carboxylate (19.0 g) in toluene (250 mL) was added pyrrolidine (19.9 mL). The reaction mixture was heated under reflux for 16 hr using Dean-Stark trap, and the solvent was evaporated under reduced pressure. The residue was dissolved in acetonitrile (250 mL), triethylamine (29.6 mL) was added, and methyl 3-bromo-2-(bromomethyl)propanoate (25.0 g) was added dropwise with heating under reflux. The reaction mixture was heated under reflux for 4 hr and cooled to room temperature. Water (250 mL) was added, and the mixture was stirred at room temperature for 16 hr. The solvent was evaporated under reduced pressure, and the residue was extracted with ethyl acetate. The extract was washed with 1M hydrochloric acid, saturated aqueous sodium hydrogen carbonate solution and saturated brine, and dried over anhydrous magnesium sulfate. The residue was purified by silica gel column chromatography (ethyl acetate/hexane) to give the title compound (22.1 g).

$^1$H NMR (300 MHz, CDCl$_3$) δ 1.51 (9H, s), 2.36-2.39 (5H, m), 2.42-2.55 (2H, m), 2.99-3.14 (2H, m), 3.69 (3H, s), 4.17-4.56 (2H, m).

MS (ESI+): [M+H−Boc]$^+$ 198.1.

B) 3-tert-butyl 7-methyl 3-azabicyclo[3.3.1]nonane-3,7-dicarboxylate

To a solution of 3-tert-butyl 7-methyl 9-oxo-3-azabicyclo[3.3.1]nonane-3,7-dicarboxylate (22.1 g) in THF (372 mL) was added p-toluenesulfonylhydrazide (16.6 g). The reaction mixture was stirred at room temperature for 2 hr, sodium cyanoborohydride was added. The mixture was stirred at 65° C. for 16 hr, and the solvent was evaporated under reduced pressure. The residue was purified by silica gel column chromatography (ethyl acetate/hexane) to give the title compound (9.50 g).

$^1$H NMR (300 MHz, CDCl$_3$) δ 1.47 (9H, s), 1.48-1.51 (1H, m), 1.61-1.69 (1H, m), 1.79-2.03 (4H, m), 2.17-2.29 (2H, m), 2.43-2.58 (1H, m), 2.81 (2H, d, J=11.9 Hz), 3.65 (3H, s), 3.76-4.00 (2H, m).

MS (ESI+): [M+H−Boc]$^+$ 184.1.

C) 3-tert-butyl 7-hydroxymethyl-3-azabicyclo[3.3.1]nonane-3-carboxylate

Lithium aluminum hydride (2.54 g) was suspended in THF (140 mL), and a solution of 3-tert-butyl 7-methyl 3-azabicyclo[3.3.1]nonane-3,7-dicarboxylate (9.49 g) in THF (27 mL) was added dropwise under ice-cooling. The reaction mixture was stirred for 30 min under ice-cooling, and water (2.54 mL) was slowly added dropwise. To the reaction mixture was added dropwise 15% aqueous sodium hydroxide solution (2.54 mL), and then water (7.5 mL) was added, and the mixture was stirred at room temperature for 3 days. The solid was removed by filtration, and the filtrate was concentrated under reduced pressure. The residue was purified by silica gel column chromatography (ethyl acetate/hexane) to give the title compound (8.02 g).

$^1$H NMR (300 MHz, CDCl$_3$) δ 0.91 (2H, t, J=11.8 Hz), 1.18-1.36 (2H, m), 1.46 (9H, s), 1.60 (2H, d, J=4.3 Hz), 1.65-1.77 (1H, m), 1.82 (1H, d, J=12.8 Hz), 1.97-2.03 (2H, m), 2.60-2.84 (2H, m), 3.40 (2H, d, J=3.8 Hz), 3.75-4.03 (2H, m).

MS (ESI+): [M+H]$^+$ 256.2.

D) 3-azabicyclo[3.3.1]non-7-ylmethanol hydrochloride

To a solution of 3-tert-butyl 7-hydroxymethyl-3-azabicyclo[3.3.1]nonane-3-carboxylate (7.78 g) in methanol (76 mL) was added 4M hydrogen chloride/ethyl acetate solution (76 mL). The reaction mixture was stirred at room temperature for 4 hr, and the solvent was evaporated under reduced pressure. The residue was dissolved in methanol (50 mL), and Amberlyst A-21 was added. The mixture was stirred at room temperature for 20 min, and the solid was removed by filtration. The solvent was evaporated under reduced pressure, and the residue was recrystallized from ethanol/ethyl acetate to give the title compound (5.22 g).

$^1$H NMR (300 MHz, DMSO-d$_6$) δ 1.09 (2H, t, J=13.2 Hz), 1.30 (1H, d, J=13.2 Hz), 1.55-1.68 (1H, m), 1.68-1.79 (1H, m), 2.01 (2H, td, J=13.1, 5.6 Hz), 2.09-2.19 (2H, m), 2.87 (2H, dd, J=12.5, 2.3 Hz), 2.93 (2H, d, J=12.5 Hz), 3.25 (2H, d, J=6.2 Hz), 4.47 (1H, brs), 8.92 (2H, brs).

MS (ESI+): [M+H−HCl]$^+$ 156.1.

E) {3-[2,4-bis(trifluoromethyl)benzyl]-3-azabicyclo[3.3.1]non-7-yl}methanol

To a solution of 3-azabicyclo[3.3.1]non-7-ylmethanol hydrochloride (2.54 g) in THF (66.2 mL) was added 2,4-bis(trifluoromethyl)benzaldehyde (2.82 mL). The reaction mixture was stirred at room temperature for 1 hr, and sodium triacetoxyborohydride (5.62 g) was added. The mixture was further stirred at room temperature for 30 min and poured into 0.1M aqueous sodium hydroxide solution, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (3.64 g).

$^1$H NMR (300 MHz, CDCl$_3$) δ 1.13 (1H, d, J=12.5 Hz), 1.26 (2H, t, J=11.2 Hz), 1.58-1.67 (1H, m), 1.68-1.85 (2H, m), 1.90-2.06 (4H, m, J=2.1 Hz), 2.14 (2H, d, J=10.8 Hz), 2.57 (2H, d, J=10.8 Hz), 3.54 (2H, d, J=5.9 Hz), 3.63 (2H, s), 7.78 (1H, d, J=8.1 Hz), 7.86 (1H, s), 8.05 (1H, d, J=8.1 Hz).

MS (ESI+): [M+H]$^+$ 382.2.

F) 3-[2,4-bis(trifluoromethyl)benzyl]-3-azabicyclo[3.3.1]nonane-7-carbaldehyde A solution of oxalyl chloride (1.19 mL) in THF (34.7 mL) was cooled to −78° C., and dimethyl sulfide (1.48 mL) was added dropwise. The reaction mixture was stirred at −78° C. for 20 min, and a solution of {3-[2,4-bis(trifluoromethyl)benzyl]-3-azabicyclo[3.3.1]non-7-yl}methanol (2.65 g) in THF (20 mL) was added dropwise. The mixture was warmed to 0° C., stirred for 30 min, cooled again to −78° C., and triethylamine (4.84 mL) was added. The reaction mixture was stirred at room temperature for 1 hr, poured into 1M aqueous sodium hydroxide solution, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (0.135 g).

¹H NMR (300 MHz, CDCl₃) δ 1.56-1.71 (5H, m), 1.92-2.04 (3H, m), 2.37 (2H, d, J=11.1 Hz), 2.89 (2H, d, J=11.1 Hz), 3.58 (2H, s), 3.81-3.96 (1H, m), 7.79-7.82 (2H, m), 7.89 (1H, s), 9.58 (1H, d, J=1.3 Hz).

G) (5Z)-5-({3-[2,4-bis(trifluoromethyl)benzyl]-3-azabicyclo[3.3.1]non-7-yl}methylidene)-4-(prop-2-yn-1-ylamino)-1,3-thiazol-2(5H)-one To a solution of 3-[2,4-bis(trifluoromethyl)benzyl]-3-azabicyclo[3.3.1]nonane-7-carbaldehyde (173.9 mg) and 4-(prop-2-yn-1-ylamino)-1,3-thiazol-2(5H)-one (141 mg) in 2-propanol (2.29 mL) was added piperidinium acetate (66.6 mg). The reaction mixture was stirred at 60° C. overnight, allowed to cool to room temperature, poured into saturated aqueous sodium hydrogen carbonate solution, and the mixture was extracted with ethyl acetate. The extract was washed with saturated brine, and dried over anhydrous magnesium sulfate, and the solvent was evaporated under reduced pressure. The residue was purified by silica gel column chromatography (NH, ethyl acetate/hexane) and recrystallized from ethyl acetate/hexane to give the title compound (36.4 mg).

¹H NMR (300 MHz, CDCl₃) δ 1.42-1.52 (2H, m), 1.55-1.68 (3H, m), 1.87-2.04 (4H, m), 2.32-2.39 (2H, m), 2.41 (1H, dd, J=2.6, 2.5 Hz), 2.85-2.93 (2H, m), 3.61 (2H, s), 4.40 (2H, dd, J=4.9, 2.6 Hz), 5.85 (1H, brs), 6.01 (1H, d, J=9.3 Hz), 7.83-7.93 (2H, m), 8.04 (1H, d, J=8.5 Hz).

Example 31

(5Z)-5-({1-[2,4-bis(trifluoromethyl)benzyl]piperidin-4-yl}methylidene)-4-[(2-hydroxy-2-methylpropyl)amino]-1,3-thiazol-2(5H)-one A) 4-[(2-hydroxy-2-methylpropyl)amino]-1,3-thiazol-2(5H)-one To a solution of 1-amino-2-methylpropan-2-ol (2.61 g) in ethanol (30 mL) was added 4-thioxo-1,3-thiazolidin-2-one (3 g), and the mixture was stirred at room temperature for 6 hr. The reaction mixture was concentrated, and the residue was washed with ethanol to give the title compound (3.90 g).

¹H NMR (300 MHz, DMSO-d₆) δ 1.12 (6H, s), 3.27-3.37 (2H, m), 4.25 (2H, s), 4.64 (1H, s), 8.95 (1H, brs).
MS (ESI+): [M+H]⁺ 189.1.

B) (5Z)-5-({1-[2,4-bis(trifluoromethyl)benzyl]piperidin-4-yl}methylidene)-4-[(2-hydroxy-2-methylpropyl)amino]-1,3-thiazol-2(5H)-one To a solution of 1-[2,4-bis(trifluoromethyl)benzyl]piperidine-4-carbaldehyde (1.11 g) in 2-propanol (10 mL) were added 4-[(2-hydroxy-2-methylpropyl)amino]-1,3-thiazol-2(5H)-one (616 mg) and piperidinium acetate (475 mg). The reaction mixture was stirred at 80° C. for 2 hr, and the solvent was evaporated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (940 mg).

¹H NMR (300 MHz, DMSO-d₆) δ 1.12 (6H, s), 1.33-1.57 (2H, m), 1.75 (2H, d, J=13.0 Hz), 2.04-2.30 (3H, m), 2.77 (2H, d, J=11.7 Hz), 3.43 (2H, d, J=5.9 Hz), 3.71 (2H, s), 4.68 (1H, s), 7.03 (1H, d, J=8.7 Hz), 7.98 (1H, s), 8.01-8.16 (2H, m), 8.54-9.10 (1H, m).

Example 32

(5Z)-5-[(1-benzylpiperidin-4-yl)methylidene]-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added triethylamine (0.35 mL) and benzaldehyde (0.10 mL). The reaction mixture was stirred at room temperature for 1 hr, and sodium triacetoxyborohydride (554 mg) was added. The reaction mixture was stirred at room temperature for 3 hr, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (163 mg).

¹H NMR (300 MHz, DMSO-d₆) δ 1.33-1.52 (2H, m), 1.64-1.76 (2H, m), 1.95-2.11 (3H, m), 2.73-2.82 (2H, m), 3.27-3.31 (1H, m), 3.46 (2H, s), 4.19-4.23 (2H, m), 6.86 (1H, d, J=8.7 Hz), 7.19-7.36 (5H, m), 9.57 (1H, brs).

Example 33

(5Z)-5-({1-[4-chloro-2-(trifluoromethyl)benzyl]piperidin-4-yl}methylidene)-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (1.00 g) in DMF (15.5 mL) were added 4-chloro-2-(trifluoromethyl)benzaldehyde (1.10 g) and triethylamine (1.95 mL). The reaction mixture was stirred at room temperature for 1.5 hr, and sodium triacetoxyborohydride (2.28 g) was added. The reaction mixture was stirred at room temperature for 1 hr, poured into water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (1.04 g).

¹H NMR (300 MHz, DMSO-d₆) δ 1.37-1.53 (2H, m), 1.66-1.80 (2H, m), 2.04-2.22 (3H, m), 2.69-2.78 (2H, m), 3.33-3.35 (1H, m), 3.60 (2H, s), 4.23 (2H, d, J=2.4 Hz), 6.90 (1H, d, J=8.9 Hz), 7.73-7.83 (3H, m), 9.57 (1H, brs).

Example 34

(5Z)-4-(prop-2-yn-1-ylamino)-5-({1-[4-(trifluoromethyl)benzyl]piperidin-4-yl}methylidene)-1,3-thiazol-2(5H)-one fumarate To a solution of (5Z)-4-(prop-2-yn-1-ylamino)-5-({1-[4-(trifluoromethyl)benzyl]piperidin-4-yl}methylidene)-1,3-thiazol-2(5H)-one (650 mg) in ethanol (5 mL) was added a solution of fumaric acid (189 mg) in ethanol (20 mL). The reaction mixture was stirred at room temperature for 1 hr, and the solvent was evaporated under reduced pressure. The residue was recrystallized from ethanol/heptane to give the title compound (631 mg).

¹H NMR (300 MHz, DMSO-d₆) δ 1.37-1.54 (2H, m), 1.67-1.78 (2H, m), 2.00-2.17 (3H, m), 2.74-2.85 (2H, m), 3.33 (1H, t, J=2.5 Hz), 3.60 (2H, s), 4.22 (2H, dd, J=5.2, 2.5

Hz), 6.62 (2H, s), 6.88 (1H, d, J=8.9 Hz), 7.54 (2H, d, J=8.1 Hz), 7.70 (2H, d, J=8.1 Hz), 9.59 (1H, t, J=5.2 Hz), 13.09 (2H, brs)

Example 35

(5Z)-5-{[1-(2-methoxybenzyl)piperidin-4-yl]methylidene}-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added triethylamine (0.35 mL) and 2-methoxybenzaldehyde (0.08 mL). The reaction mixture was stirred at room temperature for 1 hr, and sodium triacetoxyborohydride (554 mg) was added. The reaction mixture was stirred at room temperature for 3 hr, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (119 mg).
$^1$H NMR (300 MHz, DMSO-$d_E$) δ 1.36-1.52 (2H, m), 1.64-1.75 (2H, m), 1.96-2.12 (3H, m), 2.74-2.84 (2H, m), 3.32 (1H, t, J=2.5 Hz), 3.46 (2H, s), 3.77 (3H, s), 4.22 (2H, d, J=2.5 Hz), 6.84-7.00 (3H, m), 7.18-7.26 (1H, m), 7.29 (1H, dd, J=7.5, 1.6 Hz), 9.57 (1H, s).

Example 36

(5Z)-4-(prop-2-yn-1-ylamino)-5-({1-[3-(trifluoromethyl)benzyl]piperidin-4-yl}methylidene)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (300 mg) in DMF (3 mL) were added potassium carbonate (517 mg) and 1-(bromomethyl)-3-(trifluoromethyl)benzene (0.15 mL). The reaction mixture was stirred at room temperature for 4 hr, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (64 mg).
$^1$H NMR (300 MHz, DMSO-$d_6$) δ 1.35-1.52 (2H, m), 1.66-1.77 (2H, m), 1.98-2.13 (3H, m), 2.71-2.83 (2H, m), 3.30-3.34 (1H, m), 3.57 (2H, s), 4.22 (2H, d, J=2.5 Hz), 6.88 (1H, d, J=8.9 Hz), 7.53-7.66 (4H, m), 9.57 (1H, s).

Example 37

(5Z)-5-({1-[2,4-bis(trifluoromethyl)benzyl]piperidin-4-yl}methylidene)-4-(methylamino)-1,3-thiazol-2(5H)-one fumarate To a solution of (5Z)-5-({1-[2,4-bis(trifluoromethyl)benzyl]piperidin-4-yl}methylidene)-4-(methylamino)-1,3-thiazol-2(5H)-one (765 mg) in ethanol (15 mL) was added a solution of fumaric acid (197 mg) in ethanol (45 mL). The reaction mixture was stirred at room temperature for 1 hr, the solvent was evaporated under reduced pressure, and the residue was washed with ethyl acetate. The obtained powder was recrystallized from ethanol/heptane to give the title compound (662 mg).
$^1$H NMR (300 MHz, DMSO-$d_6$) δ 1.38-1.54 (2H, m), 1.68-1.79 (2H, m), 2.02-2.24 (3H, m), 2.69-2.81 (2H, m), 2.96 (3H, d, J=4.5 Hz), 3.71 (2H, s), 6.63 (2H, s), 6.77 (1H, d, J=8.9 Hz), 7.98 (1H, s), 8.02-8.11 (2H, m), 9.12-9.23 (1H, m), 13.13 (2H, brs).

Example 38

(5Z)-4-(prop-2-yn-1-ylamino)-5-({1-[4-(trifluoromethyl)benzyl]piperidin-4-yl}methylidene)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added triethylamine (0.35 mL) and 4-(trifluoromethyl)benzaldehyde (0.09 mL). The reaction mixture was stirred at room temperature for 1 hr, and sodium triacetoxyborohydride (554 mg) was added. The reaction mixture was stirred at room temperature for 3 hr, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (115 mg).
$^1$H NMR (300 MHz, DMSO-$d_6$) δ 1.36-1.52 (2H, m), 1.66-1.77 (2H, m), 1.99-2.13 (3H, m), 2.70-2.83 (2H, m), 3.30-3.35 (1H, m), 3.56 (2H, s), 4.22 (2H, d, J=2.5 Hz), 6.88 (1H, d, J=8.9 Hz), 7.53 (2H, d, J=8.1 Hz), 7.69 (2H, d, J=8.1 Hz), 9.58 (1H, s).

Example 39

(5Z)-5-({1-[2,4-bis(trifluoromethyl)benzyl]piperidin-4-yl}methylidene)-4-{[2-(2-methoxyethoxy)ethyl]amino}-1,3-thiazol-2(5H)-one A) 4-{[2-(2-methoxyethoxy)ethyl]amino}-1,3-thiazol-2(5H)-one To a solution of 4-thioxo-1,3-thiazolidin-2-one (2.24 g) in ethanol (20 mL) was added 2-(2-methoxyethoxy)ethanamine (2.5 g), and the mixture was stirred at room temperature for 5 hr. The solvent was evaporated under reduced pressure, and the residue was purified by silica gel column chromatography (ethyl acetate) to give the title compound (3.1 g).
$^1$H NMR (300 MHz, CDCl$_3$) δ 3.43 (3H, s), 3.48-3.63 (2H, m), 3.63-3.83 (6H, m), 4.13 (2H, s), 6.83 (1H, brs).
MS (ESI+): [M+H]$^+$ 219.1.

B) (5Z)-5-({1-[2,4-bis(trifluoromethyl)benzyl]piperidin-4-yl}methylidene)-4-{[2-(2-methoxyethoxy)ethyl]amino}-1,3-thiazol-2(5H)-one To a solution of 1-[2,4-bis(trifluoromethyl)benzyl]piperidine-4-carbaldehyde (1.66 g) in 2-propanol (20 mL) were added 4-{[2-(2-methoxyethoxy)ethyl]amino}-1,3-thiazol-2(5H)-one (1.60 g) and piperidinium acetate (0.710 g). The reaction mixture was stirred at 80° C. for 2 hr, and the solvent was evaporated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (1.88 g).

$^1$H NMR (300 MHz, DMSO-$d_6$) δ 1.28-1.61 (2H, m), 1.74 (2H, d, J=11.0 Hz), 2.02-2.34 (3H, m), 2.76 (2H, d, J=11.3 Hz), 3.23 (3H, s), 3.39-3.47 (2H, m), 3.47-3.63 (6H, m), 3.71 (2H, s), 6.89 (1H, d, J=8.9 Hz), 7.98 (1H, s), 8.01-8.11 (2H, m), 9.15 (1H, brs).

Example 40

4-[(4-{(Z)-[2-oxo-4-(prop-2-yn-1-ylamino)-1,3-thiazol-5(2H)-ylidene]methyl}piperidin-1-yl)methyl]-3-(trifluoromethyl)benzonitrile A) 4-formyl-3-(trifluoromethyl)benzonitrile To a solution of 4-bromo-2-(trifluoromethyl)benzaldehyde (2.0 g) in N-methylpyrrolidin-2-one (39.5 mL) was added copper(I) cyanide (1.42 g). The reaction mixture was stirred at 200° C. for 3 hr, allowed to cool to room temperature, poured into water, and diethyl ether was added. The insoluble material was removed by filtration through celite. The organic layer of the filtrate was separated, washed with water and saturated brine, and dried over anhydrous magnesium sulfate, and the solvent was evaporated under reduced pressure. The residue was purified by silica gel column chromatography (ethyl acetate/hexane) to give the title compound (0.610 g).

$^1$H NMR (300 MHz, CDCl$_3$) δ 8.02 (1H, d, J=8.1 Hz), 8.06-8.13 (1H, m), 8.25 (1H, d, J=8.1 Hz), 10.41-10.44 (1H, m).

B) 4-[(4-{(Z)-[2-oxo-4-(prop-2-yn-1-ylamino)-1,3-thiazol-5(2H)-ylidene]methyl}piperidin-1-yl)methyl]-3-(trifluoromethyl)benzonitrile To a solution of (5Z)-5-(piperidin-4-ylmethylidene)-4-(prop-2-yn-1-ylamino)-1,3-thiazol-2(5H)-one dihydrochloride (823 mg) in DMF (12.8 mL) were added 4-formyl-3-(trifluoromethyl)benzonitrile (610 mg) and triethylamine (1.42 mL). The reaction mixture was stirred at room temperature for 1.5 hr, and sodium triacetoxyborohydride (1.62 g) was added. The mixture was further stirred at room temperature for 1 hr, poured into water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (618 mg).

$^1$H NMR (300 MHz, DMSO-$d_6$) δ 1.39-1.55 (2H, m), 1.68-1.80 (2H, m), 2.08-2.30 (3H, m), 2.68-2.80 (2H, m), 3.33-3.36 (1H, m), 3.70 (2H, s), 4.23 (2H, d, J=1.4 Hz), 6.90 (1H, d, J=8.9 Hz), 8.00 (1H, d, J=8.5 Hz), 8.16 (1H, dd, J=8.5, 1.1 Hz), 8.24 (1H, d, J=1.1 Hz), 9.58 (1H, brs).

Example 41

(5Z)-4-(prop-2-yn-1-ylamino)-5-({1-[2-(trifluoromethyl)benzyl]piperidin-4-yl}methylidene)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added potassium carbonate (345 mg) and 1-(bromomethyl)-2-(trifluoromethyl)benzene (0.09 mL). The reaction mixture was stirred at room temperature overnight, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (120 mg).

$^1$H NMR (300 MHz, DMSO-$d_6$) δ 1.38-1.53 (2H, m), 1.67-1.79 (2H, m), 2.05-2.19 (3H, m), 2.70-2.80 (2H, m), 3.32-3.34 (1H, m), 3.62 (2H, s), 4.23 (2H, d, J=2.5 Hz), 6.90 (1H, d, J=8.9 Hz), 7.42-7.50 (1H, m), 7.62-7.72 (2H, m), 7.73-7.81 (1H, m), 9.56 (1H, s).

Example 42

(5Z)-5-({1-[2,4-bis(trifluoromethyl)benzyl]piperidin-4-yl}methylidene)-4-(tetrahydrofuran-3-ylamino)-1,3-thiazol-2(5H)-one A) 4-(tetrahydrofuran-3-ylamino)-1,3-thiazol-2(5H)-one To a solution of tetrahydrofuran-3-amine (2.94 g) in ethanol (20 mL) was added 4-thioxo-1,3-thiazolidin-2-one (3.0 g), and the mixture was stirred at room temperature for 1 hr. The precipitate was collected by filtration and washed with ethanol to give the title compound (2.41 g).

$^1$H NMR (300 MHz, DMSO-$d_6$) δ 1.80-1.92 (1H, m), 2.18 (1H, dq, J=13.0, 7.6 Hz), 3.60-3.88 (4H, m), 4.22 (2H, s), 4.32-4.43 (1H, m), 9.29 (1H, d, J=5.3 Hz).

MS (ESI+): [M+H]$^+$ 187.0.

B) (5Z)-5-({1-[2,4-bis(trifluoromethyl)benzyl]piperidin-4-yl}methylidene)-4-(tetrahydrofuran-3-ylamino)-1,3-thiazol-2(5H)-one To a solution of 1-[2,4-bis(trifluoromethyl)benzyl]piperidine-4-carbaldehyde (2.5 g) in 2-propanol (20 mL) were added 4-(tetrahydrofuran-3-ylamino)-1,3-thiazol-2(5H)-one (2.06 g) and piperidinium acetate (1.07 g). The reaction mixture was stirred at 80° C. for 1 hr, and the solvent was evaporated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (2.67 g).

$^1$H NMR (300 MHz, DMSO-$d_6$) δ 1.30-1.62 (2H, m), 1.74 (2H, d, J=10.6 Hz), 1.90-2.34 (5H, m), 2.77 (2H, d, J=11.5 Hz), 3.57-3.96 (6H, m), 4.50 (1H, brs), 6.99 (1H, d, J=8.9 Hz), 7.98 (1H, s), 8.00-8.15 (2H, m), 9.09 (1H, brs).

Example 43

(5Z)-5-({1-[2,4-bis(trifluoromethyl)benzyl]piperidin-4-yl}methylidene)-4-(tetrahydrofuran-3-ylamino)-1,3-thiazol-2(5H)-one 0.5 fumarate To a solution of (5Z)-5-({1-[2,4-bis(trifluoromethyl)benzyl]piperidin-4-yl}methylidene)-4-(tetrahydrofuran-3-ylamino)-1,3-thiazol-2(5H)-one (2.67 g) in ethanol (30 mL) was added a solution of fumaric acid (611 mg) in ethanol (5 mL). The reaction mixture was stirred at 80° C. for 30 min, the solvent was evaporated under reduced pressure, and the residue was recrystallized from ethanol/heptane to give the title compound (2.33 g).

¹H NMR (300 MHz, DMSO-d₆) δ 1.30-1.61 (2H, m), 1.74 (2H, d, J=10.8 Hz), 1.87-2.35 (5H, m), 2.77 (2H, d, J=11.3 Hz), 3.62-3.77 (4H, m), 3.77-3.97 (2H, m), 4.35-4.65 (1H, m), 6.63 (1H, s), 6.98 (1H, d, J=8.9 Hz), 7.98 (1H, s), 8.00-8.19 (2H, m), 9.09 (1H, d, J=6.4 Hz), 13.13 (1H, brs).

Example 44

(5Z)-5-({1-[2,4-bis(trifluoromethyl)benzyl]piperidin-4-yl}methylidene)-4-(oxetan-3-ylamino)-1,3-thiazol-2(5H)-one fumarate To a solution of (5Z)-5-({1-[2,4-bis(trifluoromethyl)benzyl]piperidin-4-yl}methylidene)-4-(oxetan-3-ylamino)-1,3-thiazol-2(5H)-one (1.5 g) in ethanol (10 mL) was added a solution of fumaric acid (353 mg) in ethanol (10 mL). The reaction mixture was stirred at 80° C. for min, the solvent was evaporated under reduced pressure, and the residue was recrystallized from ethanol/heptane to give the title compound (1.22 g).
¹H NMR (300 MHz, DMSO-d₆) δ 1.35-1.59 (2H, m), 1.60-1.89 (2H, m), 2.04-2.35 (3H, m), 2.58-2.96 (2H, m), 3.72 (2H, s), 4.36-4.69 (2H, m), 4.79 (2H, t, J=7.0 Hz), 4.85-5.08 (1H, m), 6.63 (2H, s), 6.97 (1H, d, J=8.9 Hz), 7.99 (1H, s), 8.01-8.23 (2H, m), 9.66 (1H, d, J=5.5 Hz), 13.13 (2H, brs).

Example 45

(5Z)-5-({1-[2-chloro-4-(trifluoromethyl)benzyl]piperidin-4-yl}methylidene)-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added triethylamine (0.35 mL) and 2-chloro-4-(trifluoromethyl)benzaldehyde (129 mg). The reaction mixture was stirred at room temperature for 1 hr, and sodium triacetoxyborohydride (554 mg) was added. The reaction mixture was stirred at room temperature for 3 hr, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (85 mg).
¹H NMR (300 MHz, DMSO-d₆) δ 1.38-1.55 (2H, m), 1.68-1.80 (2H, m), 2.02-2.26 (3H, m), 2.74-2.88 (2H, m), 3.32-3.34 (1H, m), 3.64 (2H, s), 4.23 (2H, d, J=2.5 Hz), 6.89 (1H, d, J=8.9 Hz), 7.73 (2H, s), 7.84 (1H, s), 9.57 (1H, brs).

Example 46

(5Z)-5-({1-[2,4-bis(trifluoromethyl)benzyl]piperidin-4-yl}methylidene)-4-({2-[2-(diethylamino)ethoxy]ethyl}amino)-1,3-thiazol-2(5H)-one A) tert-butyl{2-[2-(diethylamino)ethoxy]ethyl}carbamate To a solution of 2-{2-[(tert-butoxycarbonyl)amino]ethoxy}ethyl 4-methylbenzenesulfonate (5.00 g) in THF (40 mL) was added diethylamine (14.5 mL). The reaction mixture was stirred at room temperature overnight, and 1N aqueous sodium hydroxide solution was added. The mixture was extracted with ethyl acetate, dried over anhydrous magnesium sulfate, and the solvent was evaporated under reduced pressure to give the title compound (3.77 g).
¹H NMR (300 MHz, CDCl₃) δ 1.05 (6H, t, J=7.1 Hz), 1.44 (9H, s), 2.54-2.70 (6H, m), 3.25-3.34 (2H, m), 3.48-3.59 (4H, m), 5.39 (1H, brs).

B) 2-(2-aminoethoxy)-N,N-diethylethanamine

A mixed solution of tert-butyl {2-[2-(diethylamino)ethoxy]ethyl}carbamate (3.77 g) and 4M hydrogen chloride/ethyl acetate solution (40 mL) was stirred at room temperature for 3 hr, and the solvent was evaporated under reduced pressure. The residue was purified by silica gel column chromatography (NH, methanol/ethyl acetate) to give the title compound (2.23 g).
¹H NMR (300 MHz, DMSO-d₆) δ 1.01 (6H, t, J=7.1 Hz), 2.63 (4H, q, J=7.2 Hz), 2.71 (2H, t, J=6.0 Hz), 2.92 (2H, t, J=5.4 Hz), 3.54 (2H, t, J=6.0 Hz), 3.60 (2H, t, J=5.4 Hz), 7.11 (2H, brs).

C) 4-({2-[2-(diethylamino)ethoxy]ethyl}amino)-1,3-thiazol-2(5H)-one

To a solution of 2-(2-aminoethoxy)-N,N-diethylethanamine (2.23 g) in ethanol (50 mL) was added 4-thioxo-1,3-thiazolidin-2-one (1.76 g), and the mixture was stirred at room temperature overnight. The reaction mixture was concentrated, and the residue was purified by silica gel column chromatography (NH, methanol/ethyl acetate) to give the title compound (1.85 g).
¹H NMR (300 MHz, CDCl₃) δ 0.99-1.12 (6H, m), 2.58-2.69 (6H, m), 3.57-3.73 (6H, m), 4.11 (2H, s), 8.35 (1H, brs). MS (ESI+): [M+H]⁺ 260.1.

D) (5Z)-5-({1-[2,4-bis(trifluoromethyl)benzyl]piperidin-4-yl}methylidene)-4-({2-[2-(diethylamino)ethoxy]ethyl}amino)-1,3-thiazol-2(5H)-one To a solution of 1-[2,4-bis(trifluoromethyl)benzyl]piperidine-4-carbaldehyde (1.21 g) in 2-propanol (15 mL) was added a solution of 4-({2-[2-(diethylamino)ethoxy]ethyl}amino)-1,3-thiazol-2(5H)-one (1.85 g) in 2-propanol (5 mL), and piperidinium acetate (0.52 g) was added. The reaction mixture was stirred at 60° C. overnight and concentrated. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, methanol/ethyl acetate) to give the title compound (1.26 g).
¹H NMR (300 MHz, DMSO-d₅) δ 0.91 (6H, t, J=7.1 Hz), 1.38-1.56 (2H, m), 1.74 (2H, d, J=10.6 Hz), 2.03-2.24 (3H, m), 2.45 (4H, q, J=7.1 Hz), 2.52-2.57 (2H, m), 2.69-2.81 (2H, m), 3.47 (2H, t, J=6.1 Hz), 3.57 (4H, s), 3.71 (2H, s), 6.88 (1H, d, J=8.9 Hz), 7.98 (1H, s), 8.01-8.12 (2H, m), 9.22 (1H, brs).

Example 47

(5Z)-5-({1-[2,4-bis(trifluoromethyl)benzyl]piperidin-4-yl}methylidene)-4-({2-[2-(diethylamino)ethoxy]ethyl}amino)-1,3-thiazol-2(5H)-one ditosylate To a solution of (5Z)-5-({1-[2,4-bis(trifluoromethyl)benzyl]piperidin-4-yl}methylidene)-4-({2-[2-(diethylamino)ethoxy]ethyl}amino)-1,3-thiazol-2(5H)-one (950 mg) in ethanol (2 mL) was added a solution of tosylic acid (635 mg)

in ethanol (3 mL). The reaction mixture was stirred at room temperature for 1 hr, and the solvent was evaporated under reduced pressure. The residue was recrystallized from 2-butanone/heptane to give the title compound (992 mg).

$^1$H NMR (300 MHz, DMSO-d$_6$) δ 1.15 (6H, t, J=7.2 Hz), 1.63-2.00 (4H, m), 2.29 (6H, s), 2.41 (1H, d, J=10.4 Hz), 3.03-3.37 (8H, m), 3.38-3.51 (2H, m), 3.64 (4H, brs), 3.73 (2H, t, J=4.8 Hz), 4.58 (2H, brs), 6.79 (1H, d, J=8.9 Hz), 7.13 (4H, d, J=8.1 Hz), 7.50 (4H, d, J=7.9 Hz), 8.09-8.27 (3H, m), 8.96 (1H, brs), 9.24-9.73 (2H, m).

Example 48

(5Z)-5-{[1-(4-chlorobenzyl)piperidin-4-yl]methylidene}-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added potassium carbonate (345 mg) and 1-chloro-4-(chloromethyl)benzene (103 mg). The reaction mixture was stirred at room temperature overnight, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (110 mg).

$^1$H NMR (300 MHz, DMSO-d$_6$) δ 1.34-1.50 (2H, m), 1.64-1.76 (2H, m), 1.96-2.12 (3H, m), 2.69-2.81 (2H, m), 3.29-3.34 (1H, m), 3.45 (2H, s), 4.22 (2H, d, J=2.6 Hz), 6.87 (1H, d, J=8.9 Hz), 7.28-7.35 (2H, m), 7.35-7.41 (2H, m), 9.57 (1H, s).

Example 49

4-[(4-{(Z)-[2-oxo-4-(prop-2-yn-1-ylamino)-1,3-thiazol-5(2H)-ylidene]methyl}piperidin-1-yl)methyl]benzonitrile To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added triethylamine (0.35 mL) and 4-formylbenzonitrile (82 mg). The reaction mixture was stirred at room temperature for 1 hr, and sodium triacetoxyborohydride (554 mg) was added. The reaction mixture was stirred at room temperature for 3 hr, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (100 mg).

$^1$H NMR (300 MHz, DMSO-d$_6$) δ 1.36-1.52 (2H, m), 1.65-1.77 (2H, m), 1.99-2.13 (3H, m), 2.70-2.82 (2H, m), 3.29-3.35 (1H, m), 3.56 (2H, s), 4.22 (2H, d, J=2.5 Hz), 6.87 (1H, d, J=8.9 Hz), 7.51 (2H, d, J=8.1 Hz), 7.79 (2H, d, J=8.1 Hz), 9.57 (1H, s).

Example 50

(5Z)-5-{[1-(naphthalen-2-ylmethyl)piperidin-4-yl]methylidene}-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added triethylamine (0.35 mL) and naphthalene-2-carbaldehyde (97 mg). The reaction mixture was stirred at room temperature for 1 hr, and sodium triacetoxyborohydride (554 mg) was added. The reaction mixture was stirred at room temperature overnight, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (120 mg).

$^1$H NMR (300 MHz, DMSO-d$_6$) δ 1.37-1.53 (2H, m), 1.66-1.77 (2H, m), 2.01-2.14 (3H, m), 2.77-2.89 (2H, m), 3.29-3.34 (1H, m), 3.63 (2H, s), 4.22 (2H, d, J=2.5 Hz), 6.88 (1H, d, J=8.9 Hz), 7.44-7.54 (3H, m), 7.78 (1H, s), 7.84-7.92 (3H, m), 9.57 (1H, s).

Example 51

(5Z)-5-({1-[2-chloro-4-(trifluoromethyl)benzyl]piperidin-4-yl}methylidene)-4-[(2-hydroxy-2-methylpropyl)amino]-1,3-thiazol-2(5H)-one A) tert-butyl 4-[(Z)-{4-[(2-hydroxy-2-methylpropyl)amino]-2-oxo-1,3-thiazol-5(2H)-ylidene}methyl]piperidine-1-carboxylate To a solution of tert-butyl 4-formylpiperidine-1-carboxylate (1.70 g) in 2-propanol (30 mL) were added 4-[(2-hydroxy-2-methylpropyl)amino]-1,3-thiazol-2(5H)-one (3.00 g), and piperidinium acetate (1.18 g). The reaction mixture was stirred at 60° C. overnight and concentrated. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (1.72 g).

$^1$H NMR (300 MHz, DMSO-d$_6$) δ 1.11 (6H, s), 1.21-1.37 (2H, m), 1.40 (9H, s), 1.64-1.76 (2H, m), 2.18-2.34 (1H, m), 2.88 (2H, brs), 3.42 (2H, d, J=4.9 Hz), 3.86 (2H, d, J=13.2 Hz), 4.67 (1H, s), 6.98 (1H, d, J=8.9 Hz), 8.91 (1H, brs).

MS (ESI+): [M+H]$^+$ 384.2.

B) (5Z)-4-[(2-hydroxy-2-methylpropyl)amino]-5-(piperidin-4-ylmethylidene)-1,3-thiazol-2(5H)-one dihydrochloride A mixed solution of tert-butyl 4-[(Z)-{4-[(2-hydroxy-2-methylpropyl)amino]-2-oxo-1,3-thiazol-5(2H)-ylidene}methyl]piperidine-1-carboxylate (1.93 g) and 4M hydrogen chloride/ethyl acetate solution (20 mL) was stirred at room temperature for 1 hr, and the solvent was evaporated under reduced pressure to give the title compound (1.70 g).

$^1$H NMR (300 MHz, DMSO-d$_6$) δ 1.12 (6H, s), 1.62-1.78 (2H, m), 1.80-1.93 (2H, m), 2.32-2.47 (1H, m), 2.88-3.05 (2H, m), 3.20-3.32 (2H, m), 3.43 (2H, d, J=5.5 Hz), 7.25 (1H, d, J=8.9 Hz), 8.91-9.23 (2H, m), 9.31 (1H, brs).

MS (ESI+): [M+H−2HCl]$^+$ 284.2.

C) (5Z)-5-({1-[2-chloro-4-(trifluoromethyl)benzyl]piperidin-4-yl}methylidene)-4-[(2-hydroxy-2-methylpropyl)amino]-1,3-thiazol-2(5H)-one To a solution of (5Z)-4-[(2-hydroxy-2-methylpropyl)amino]-5-(piperidin-4-ylmethylidene)-1,3-thiazol-2(5H)-one dihydrochloride (200 mg) in DMF (2 mL) was added a solution of triethylamine (0.32 mL) and 2-chloro-4-(trifluoromethyl)benzaldehyde (117 mg) in DMF (1 mL). The reaction mixture was stirred at room temperature for 1 hr, and sodium triacetoxyborohydride (501 mg) was added. The reaction mixture was stirred at room temperature overnight, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (73 mg).

$^1$H NMR (300 MHz, DMSO-$d_6$) δ 1.12 (6H, s), 1.40-1.56 (2H, m), 1.67-1.80 (2H, m), 2.01-2.25 (3H, m), 2.77-2.87 (2H, m), 3.42 (2H, s), 3.64 (2H, s), 4.68 (1H, s), 7.01 (1H, d, J=8.7 Hz), 7.73 (2H, s), 7.84 (1H, s), 8.94 (1H, brs).

Example 52

(5Z)-5-({1-[4-chloro-2-(trifluoromethyl)benzyl]piperidin-4-yl}methylidene)-4-[(2-hydroxy-2-methylpropyl)amino]-1,3-thiazol-2(5H)-one To a solution of (5Z)-4-[(2-hydroxy-2-methylpropyl)amino]-5-(piperidin-4-ylmethylidene)-1,3-thiazol-2(5H)-one dihydrochloride (200 mg) in DMF (2 mL) was added a solution of triethylamine (0.32 mL) and 4-chloro-2-(trifluoromethyl)benzaldehyde (117 mg) in DMF (1 mL). The reaction mixture was stirred at room temperature for 1 hr, and sodium triacetoxyborohydride (501 mg) was added. The reaction mixture was stirred at room temperature overnight, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (82 mg).

$^1$H NMR (300 MHz, DMSO-$d_6$) δ 1.12 (6H, s), 1.36-1.56 (2H, m), 1.66-1.79 (2H, m), 2.02-2.19 (3H, m), 2.70-2.80 (2H, m), 3.42 (2H, s), 3.60 (2H, s), 4.67 (1H, s), 7.02 (1H, d, J=8.7 Hz), 7.72-7.84 (3H, m), 8.93 (1H, brs).

Example 53

4-({4-[(Z)-{4-[(2-hydroxy-2-methylpropyl)amino]-2-oxo-1,3-thiazol-5(2H)-ylidene}methyl]piperidin-1-yl}methyl)-3-(trifluoromethyl)benzonitrile To a solution of (5Z)-5-(piperidin-4-ylmethylidene)-4-(prop-2-yn-1-ylamino)-1,3-thiazol-2(5H)-one dihydrochloride (200 mg) in DMF (2 mL) was added a solution of potassium carbonate (312 mg) and 4-(bromomethyl)-3-(trifluoromethyl)benzonitrile (148 mg) in DMF (1 mL). The reaction mixture was stirred at room temperature overnight, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (133 mg).

$^1$H NMR (300 MHz, DMSO-$d_6$) δ 1.12 (6H, s), 1.40-1.56 (2H, m), 1.68-1.80 (2H, m), 2.03-2.23 (3H, m), 2.69-2.81 (2H, m), 3.42 (2H, s), 3.70 (2H, s), 4.67 (1H, s), 7.02 (1H, d, J=8.7 Hz), 7.99 (1H, d, J=8.1 Hz), 8.15 (1H, d, J=8.1 Hz), 8.24 (1H, s), 8.94 (1H, brs).

Example 54

(5Z)-5-({1-[2,4-bis(trifluoromethyl)benzyl]piperidin-4-yl}methylidene)-4-{[4-(diethylamino)but-2-yn-1-yl]amino}-1,3-thiazol-2(5H)-one A) 2-(4-chlorobut-2-yn-1-yl)-1H-isoindole-1,3(2H)-dione To a solution of 1H-isoindole-1,3(2H)-dione (441 mg) in DMF (5 mL) were added potassium carbonate (829 mg) and 1,4-dichlorobut-2-yne (2.21 g) at room temperature. The reaction mixture was stirred at 80° C. for 5 hr. The reaction mixture was added to water at room temperature, and the mixture was extracted with ethyl acetate. The extract was washed with water and saturated brine, dried over anhydrous magnesium sulfate, and filtered. The solvent was evaporated under reduced pressure, and the residue was purified by silica gel column chromatography (NH, ethyl acetate/hexane) to give the title compound (202 mg).

$^1$H NMR (300 MHz, CDCl$_3$) δ 4.10 (2H, t, J=2.1 Hz), 4.51 (2H, t, J=2.1 Hz), 7.75 (2H, dd, J=5.5, 3.1 Hz), 7.89 (2H, dd, J=5.5, 3.1 Hz).

B) 2-[4-(diethylamino)but-2-yn-1-yl]-1H-isoindole-1,3(2H)-dione

To a solution of 2-(4-chlorobut-2-yn-1-yl)-1H-isoindole-1,3(2H)-dione (200 mg) in acetonitrile (3 mL) was added diethylamine (188 mg) at room temperature. The reaction mixture was stirred at room temperature for 4 hr, and added to water at room temperature, and the mixture was extracted with ethyl acetate. The extract was washed with saturated brine, dried over anhydrous magnesium sulfate, and filtered. The solvent was evaporated under reduced pressure, and the residue was purified by silica gel column chromatography (ethyl acetate/hexane) to give the title compound (112 mg).

$^1$H NMR (300 MHz, CDCl$_3$) δ 1.03 (6H, t, J=7.2 Hz), 2.51 (4H, q, J=7.2 Hz), 3.38 (2H, t, J=2.0 Hz), 4.47 (2H, t, J=2.0 Hz), 7.74 (2H, dd, J=5.6, 3.1 Hz), 7.88 (2H, dd, J=5.4, 3.1 Hz).

MS (ESI+): [M+H]$^+$ 271.1.

C) 4-{[4-(diethylamino)but-2-yn-1-yl]amino}-1,3-thiazol-2(5H)-one

D) 4-{[(2Z)-4-(diethylamino)but-2-en-1-yl]amino}-1,3-thiazol-2(5H)-one

To a solution of 2-[4-(diethylamino)but-2-yn-1-yl]-1H-isoindole-1,3(2H)-dione (811 mg) in ethanol (5 mL) was added hydrazine monohydrate (0.306 mL) at room temperature, and the mixture was stirred at 80° C. overnight. The reaction mixture was ice-cooled, and the precipitate was removed by filtration. The filtrate was purified by silica gel column chromatography (NH, ethyl acetate), and the obtained compound was added to a solution of 4-thioxo-1,3-thiazolidin-2-one (360 mg) in ethanol (3 mL) at room temperature. The reaction mixture was stirred at room temperature for 1 hr, the solvent was evaporated under reduced pressure, and the residue was purified by silica gel column chromatography (NH, methanol/ethyl acetate) to give 4-{[4-(diethylamino)but-2-yn-1-yl]amino}-1,3-thiazol-2(5H)-one (550 mg) and 4-{[(2Z)-4-(diethylamino)but-2-en-1-yl]amino}-1,3-thiazol-2(5H)-one (30 mg).

C) $^1$H NMR (300 MHz, CDCl$_3$) δ 1.06 (6H, t, J=7.2 Hz), 2.54 (4H, q, J=7.2 Hz), 3.40 (2H, t, J=2.0 Hz), 4.20 (2H, s), 4.29-4.35 (2H, m), 7.08 (1H, brs).

D) $^1$H NMR (300 MHz, CDCl$_3$) δ 1.07 (6H, t, J=7.2 Hz), 2.62 (4H, q, J=7.1 Hz), 3.07 (2H, d, J=6.0 Hz), 4.06 (2H, s), 4.15 (2H, d, J=5.5 Hz), 5.54-6.17 (2H, m), 9.63 (1H, brs). MS (ESI+): [M+H]$^+$ 242.1.

E) (5Z)-5-({1-[2,4-bis(trifluoromethyl)benzyl]piperidin-4-yl}methylidene)-4-{[4-(diethylamino)but-2-yn-1-yl]amino}-1,3-thiazol-2(5H)-one To a solution of 1-[2,4-bis(trifluoromethyl)benzyl]piperidine-4-carbaldehyde (780 mg) in 2-propanol (5 mL) were added 4-{[4-(diethylamino)but-2-yn-1-yl]amino}-1,3-thiazol-2(5H)-one (550 mg) and piperidinium acetate (334 mg) at room temperature. The reaction mixture was stirred at 60° C. for 3 hr. The solvent was evaporated under reduced pressure, and the residue was purified by silica gel column chromatography (NH, ethyl acetate/hexane) to give the title compound (640 mg).

$^1$H NMR (300 MHz, DMSO-d$_6$) δ 0.96 (6H, t, J=7.2 Hz), 1.37-1.60 (2H, m), 1.65-1.84 (2H, m), 2.03-2.29 (3H, m), 2.45 (4H, q, J=7.2 Hz), 2.63-2.89 (2H, m), 3.37 (2H, s), 3.71 (2H, s), 4.28 (2H, s), 6.91 (1H, d, J=8.9 Hz), 7.97 (1H, s), 8.07 (2H, s), 9.55 (1H, brs).

Example 55

(5Z)-5-({1-[2,4-bis(trifluoromethyl)benzyl]piperidin-4-yl}methylidene)-4-{[4-(diethylamino)but-2-yn-1-yl]amino}-1,3-thiazol-2(5H)-one tosylate To a solution of (5Z)-5-({1-[2,4-bis(trifluoromethyl)benzyl]piperidin-4-yl}methylidene)-4-{[4-(diethylamino)but-2-yn-1-yl]amino}-1,3-thiazol-2(5H)-one (540 mg) in ethyl acetate (3 mL) was added tosylic acid monohydrate (183 mg) at room temperature. The reaction mixture was stirred at 60° C. for 5 min. The solvent was evaporated under reduced pressure, and the obtained solid was recrystallized from ethanol/heptane to give the title compound (380 mg).

$^1$H NMR (300 MHz, DMSO-d$_6$) δ 1.18 (6H, t, J=7.3 Hz), 1.33-1.57 (2H, m), 1.65-1.81 (2H, m), 2.00-2.23 (3H, m), 2.29 (3H, s), 2.67-2.85 (2H, m), 3.03-3.25 (4H, m), 3.71 (2H, brs), 4.13 (2H, brs), 4.34 (2H, d, J=4.7 Hz), 6.88 (1H, d, J=8.7 Hz), 7.12 (2H, d, J=7.9 Hz), 7.49 (2H, d, J=7.9 Hz), 7.93-8.15 (3H, m), 9.53-9.75 (2H, m).

Example 56

(5Z)-5-({1-[2,4-bis(trifluoromethyl)benzyl]piperidin-4-yl}methylidene)-4-[(2,3-dihydroxypropyl)amino]-1,3-thiazol-2(5H)-one A) 4-[(2,3-dihydroxypropyl)amino]-1,3-thiazol-2(5H)-one To a solution of 4-thioxo-1,3-thiazolidin-2-one (2.0 g) in ethanol (20 mL) was added 3-aminopropane-1,2-diol (1.00 g), and the mixture was stirred at room temperature for 3 hr. The precipitate was collected by filtration and washed with ethanol to give the title compound (1.56 g).

$^1$H NMR (300 MHz, DMSO-d$_6$) δ 3.17-3.41 (3H, m), 3.49 (1H, dt, J=13.3, 5.0 Hz), 3.56-3.72 (1H, m), 4.22 (2H, s), 4.67 (1H, brs), 4.93 (1H, brs), 9.07 (1H, brs).

B) (5Z)-5-({1-[2,4-bis(trifluoromethyl)benzyl]piperidin-4-yl}methylidene)-4-[(2,3-dihydroxypropyl)amino]-1,3-thiazol-2(5H)-one To a solution of 1-[2,4-bis(trifluoromethyl)benzyl]piperidine-4-carbaldehyde (1.86 g) in 2-propanol (20 mL) were added 4-[(2,3-dihydroxypropyl)amino]-1,3-thiazol-2(5H)-one (1.56 g) and piperidinium acetate (0.794 g). The reaction mixture was stirred at 80° C. for 1 hr, and the solvent was evaporated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (methanol/ethyl acetate) and recrystallized from ethyl acetate/heptane to give the title compound (1.22 g).

$^1$H NMR (300 MHz, DMSO-d$_5$) δ 1.47 (2H, q, J=10.5 Hz), 1.74 (2H, d, J=10.8 Hz), 2.04-2.23 (3H, m), 2.76 (2H, d, J=11.3 Hz), 3.23-3.43 (3H, m), 3.55 (1H, dd, J=13.3, 3.9 Hz), 3.71-3.76 (3H, m), 4.68 (1H, brs), 4.98 (1H, d, J=5.1 Hz), 6.93 (1H, d, J=8.9 Hz), 7.98 (1H, s), 8.02-8.11 (2H, m), 9.17 (1H, brs).

Example 57

(5Z)-5-({1-[2,4-bis(trifluoromethyl)benzyl]piperidin-4-yl}methylidene)-4-({2-[(2-hydroxyethyl)(methyl)amino]ethyl}amino)-1,3-thiazol-2(5H)-one A) 4-({2-[(2-hydroxyethyl)(methyl)amino]ethyl}amino)-1,3-thiazol-2(5H)-one To a solution of 2-[(2-aminoethyl)(methyl)amino]ethanol (1.00 g) in ethanol (30 mL) was added 4-thioxo-1,3-thiazolidin-2-one (1.07 g). The reaction mixture was stirred at room temperature for 3 days, and the solvent was evaporated under reduced pressure. The residue was purified by silica gel column chromatography (NH, methanol/ethyl acetate) to give the title compound (1.71 g).

$^1$H NMR (300 MHz, DMSO-d$_6$) δ 2.22 (3H, s), 2.45 (2H, t, J=6.2 Hz), 2.48-2.58 (3H, m), 3.36-3.51 (4H, m), 4.22 (2H, s), 8.95 (1H, brs).
MS (ESI+): [M+H]$^+$ 218.1.

B) (5Z)-5-({1-[2,4-bis(trifluoromethyl)benzyl]piperidin-4-yl}methylidene)-4-({2-[(2-hydroxyethyl)(methyl)amino]ethyl}amino)-1,3-thiazol-2(5H)-one To a solution of 1-[2,4-bis(trifluoromethyl)benzyl]piperidine-4-carbaldehyde (1.34 g) in 2-propanol (20 mL) were added 4-({2-[(2-hydroxyethyl)(methyl)amino]ethyl}amino)-1,3-thiazol-2(5H)-one (1.71 g) and piperidinium acetate (0.57 g). The reaction mixture was stirred at 60° C. overnight and concentrated. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, methanol/ethyl acetate) to give the title compound (0.98 g).

$^1$H NMR (300 MHz, DMSO-d$_6$) δ 1.40-1.55 (2H, m), 1.68-1.80 (2H, m), 2.06-2.22 (3H, m), 2.24 (3H, s), 2.46 (2H, t, J=6.2 Hz), 2.59 (2H, t, J=6.6 Hz), 2.70-2.83 (2H, m), 3.41-3.54 (4H, m), 3.71 (2H, s), 4.42 (1H, brs), 6.81 (1H, d, J=8.7 Hz), 7.98 (1H, s), 8.02-8.11 (2H, m), 9.06 (1H, brs).

Example 58

(5Z)-5-({1-[2,4-bis(trifluoromethyl)benzyl]piperidin-4-yl}methylidene)-4-({2-[(2-hydroxyethyl)(methyl)amino]ethyl}amino)-1,3-thiazol-2(5H)-one ½fumarate To a solution of (5Z)-5-({1-[2,4-bis(trifluoromethyl)benzyl]piperidin-4-yl}methylidene)-4-({2-[(2-hydroxyethyl)(methyl)amino]ethyl}amino)-1,3-thiazol-2(5H)-one (630 mg) in ethanol (5 mL) was added a solution of fumaric acid (69 mg) in ethanol (15 mL). The reaction mixture was stirred at room temperature for 1 hr, and the solvent was evaporated under reduced pressure. The residue was recrystallized from ethanol/heptane to give the title compound (542 mg).

$^1$H NMR (300 MHz, DMSO-$d_6$) δ 1.39-1.55 (2H, m), 1.67-1.80 (2H, m), 2.02-2.22 (3H, m), 2.28 (3H, s), 2.47-2.56 (2H, m), 2.65 (2H, t, J=6.5 Hz), 2.71-2.81 (2H, m), 3.44-3.56 (4H, m), 3.71 (2H, s), 6.60 (1H, s), 6.81 (1H, d, J=8.9 Hz), 7.98 (1H, s), 8.01-8.12 (2H, m), 9.11 (1H, brs).

Example 59

(5Z)-5-({1-[2-chloro-4-(trifluoromethyl)benzyl]piperidin-4-yl}methylidene)-4-(prop-2-yn-1-ylamino)-1,3-thiazol-2(5H)-one fumarate To a solution of (5Z)-5-({1-[2-chloro-4-(trifluoromethyl)benzyl]piperidin-4-yl}methylidene)-4-(prop-2-yn-1-ylamino)-1,3-thiazol-2(5H)-one (1.05 g) in ethanol (5 mL) was added a solution of fumaric acid (281 mg) in ethanol (15 mL). The reaction mixture was stirred at room temperature for 1 hr, and the solvent was evaporated under reduced pressure. The residue was recrystallized from ethanol/heptane to give the title compound (1.10 g).

$^1$H NMR (300 MHz, DMSO-$d_6$) δ 1.39-1.56 (2H, m), 1.67-1.81 (2H, m), 2.02-2.28 (3H, m), 2.75-2.88 (2H, m), 3.33 (1H, t, J=2.5 Hz), 3.65 (2H, s), 4.23 (2H, dd, J=5.2, 2.5 Hz), 6.63 (2H, s), 6.90 (1H, d, J=8.9 Hz), 7.69-7.77 (2H, m), 7.84 (1H, s), 9.59 (1H, t, J=5.2 Hz), 13.14 (2H, brs).

Example 60

(5Z)-5-[(1-{1-[2,4-bis(trifluoromethyl)phenyl]ethyl}piperidin-4-yl)methylidene]-4-(prop-2-yn-1-ylamino)-1,3-thiazol-2(5H)-one

A) (1-{1-[2,4-bis(trifluoromethyl)phenyl]ethenyl}piperidin-4-yl)methanol

To a solution of 1-[2,4-bis(trifluoromethyl)phenyl]ethanone (10.0 g) and piperidin-4-ylmethanol (5.40 g) in THF (368 mL) was added titanium (IV) isopropoxide (34.6 mL). The reaction mixture was stirred at 70° C. overnight, and poured into ice-cooled saturated aqueous sodium hydrogen carbonate solution and the insoluble material was filtered through celite. The organic layer of the filtrate was separated, and the aqueous layer was extracted with ethyl acetate. The organic layer was washed with saturated brine, dried over anhydrous magnesium sulfate, and the solvent was evaporated under reduced pressure to give the title compound so (12.6 g).

MS (ESI+): [M+H]$^+$ 354.2.

B) (1-{1-[2,4-bis(trifluoromethyl)phenyl]ethyl}piperidin-4-yl)methanol

To a solution of (1-{1-[2,4-bis(trifluoromethyl)phenyl]ethenyl}piperidin-4-yl)methanol (12.6 g) in methanol (178 mL) was added sodium borohydride (2.02 g). The reaction mixture was stirred at room temperature for 20 min, saturated aqueous sodium hydrogen carbonate solution was added, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (10.9 g).

$^1$H NMR (300 MHz, CDCl$_3$) δ 1.07-1.19 (1H, m), 1.28 (3H, d, J=6.4 Hz), 1.30-1.42 (1H, m), 1.47-1.62 (2H, m), 1.78-1.92 (2H, m), 1.99 (1H, dd, J=11.1, 2.6 Hz), 2.47-2.55 (1H, m), 3.26-3.36 (1H, m), 3.49 (2H, d, J=5.7 Hz), 3.64-3.74 (1H, m), 7.77 (1H, d, J=8.3 Hz), 7.85 (1H, s), 8.05 (1H, d, J=8.3 Hz).

MS (ESI+): [M+H]$^+$ 356.2.

C) 1-{1-[2,4-bis(trifluoromethyl)phenyl]ethyl}piperidine-4-carbaldehyde

To a solution of (1-{1-[2,4-bis(trifluoromethyl)phenyl]ethyl}piperidin-4-yl)methanol (2.0 g) and triethylamine (2.35 mL) in DMSO (22.5 mL) was added sulfur trioxide pyridine complex (2.69 g). The reaction mixture was stirred at room temperature for 1.5 hr, water was added, and the mixture was extracted with ethyl acetate. The extract was washed with water and saturated brine, and dried over anhydrous magnesium sulfate, and the solvent was evaporated under reduced pressure. The residue was purified by so silica gel column chromatography (ethyl acetate/hexane) to give the title compound (1.15 g).

$^1$H NMR (300 MHz, CDCl$_3$) δ 1.30 (3H, d, J=6.4 Hz), 1.49-1.67 (1H, m), 1.67-1.86 (2H, m), 1.93-2.04 (1H, m), 2.04-2.17 (2H, m), 2.21-2.36 (1H, m), 2.46-2.59 (1H, m), 3.08-3.26 (1H, m), 3.66-3.81 (1H, m), 7.80 (1H, d, J=8.3 Hz), 7.87 (1H, s), 8.05 (1H, d, J=8.3 Hz), 9.67 (1H, d, J=0.9 Hz).

MS (ESI+): [M+H]$^+$ 354.1.

D) (5Z)-5-[(1-{1-[2,4-bis(trifluoromethyl)phenyl]ethyl}piperidin-4-yl)methylidene]-4-(prop-2-yn-1-ylamino)-1,3-thiazol-2(5H)-one To a solution of 1-{1-[2,4-bis(trifluoromethyl)phenyl]ethyl}piperidine-4-carbaldehyde (1.15 g) and 4-(prop-2-yn-1-ylamino)-1,3-thiazol-2(5H)-one (1.00 g) in 2-propanol (16.3 mL) was added piperidinium acetate (0.473 g). The reaction mixture was stirred at 60° C. overnight, allowed to cool to room temperature, and diluted with ethyl acetate. The mixture was washed with water and saturated brine, and dried over anhydrous magnesium sulfate, and the solvent was evaporated under reduced pressure. The residue was purified by silica gel column chromatography (NH, ethyl acetate/hexane), further purified by silica gel column chromatography (ethyl acetate/hexane), and recrystallized from ethyl acetate/hexane to give the title compound (1.13 g).

$^1$H NMR (300 MHz, DMSO-$d_6$) δ 1.27 (3H, d, J=6.2 Hz), 1.30-1.55 (2H, m), 1.63 (1H, d, J=12.4 Hz), 1.80 (1H, d, J=14.7 Hz), 1.96-2.17 (3H, m), 2.39-2.47 (1H, m), 3.12 (1H, d, J=10.4 Hz), 3.32-3.34 (1H, m), 3.66 (1H, d, J=6.2 Hz), 4.22 (2H, d, J=2.3 Hz), 6.88 (1H, d, J=8.9 Hz), 7.96 (1H, s), 8.06-8.14 (2H, m), 9.57 (1H, brs).

Example 61

(5Z)-5-({1-[2,4-bis(trifluoromethyl)benzyl]piperidin-4-yl}methylidene)-4-[(cyclopropylmethyl)amino]-1,3-thiazol-2(5H)-one fumarate To a solution of (5Z)-5-({1-[2,4-bis(trifluoromethyl)benzyl]piperidin-4-yl}methylidene)-4-[(cyclopropylmethyl)amino]-1,3-thiazol-2(5H)-one (1.94 g) in ethanol (15 mL) was added fumaric acid (458 mg). The reaction mixture was stirred at 80° C. for 20 min, the solvent was evaporated under reduced pressure, and the residue was recrystallized from ethanol/heptane to give the title compound (1.52 g).
$^1$H NMR (300 MHz, DMSO-$d_6$) δ 0.23-0.32 (2H, m), 0.45-0.56 (2H, m), 1.00-1.17 (1H, m), 1.40-1.56 (2H, m), 1.75 (2H, d, J=10.8 Hz), 2.01-2.25 (3H, m), 2.77 (2H, d, J=11.7 Hz), 3.23-3.30 (2H, m), 3.71 (2H, s), 6.63 (2H, s), 6.88 (1H, d, J=8.7 Hz), 7.99 (1H, s), 8.01-8.13 (2H, m), 9.27 (1H, t, J=5.3 Hz), 13.13 (2H, brs)

Example 62

(5Z)-5-({1-[2,4-bis(trifluoromethyl)benzyl]azepan-4-yl}methylidene)-4-(prop-2-yn-1-ylamino)-1,3-thiazol-2(5H)-one A) ethyl 4-(hydroxyimino)cyclohexanecarboxylate To a solution of hydroxyamine hydrochloride (15.3 g) and sodium acetate (24.1 g) in water (58.8 mL) was added dropwise ethyl 4-oxocyclohexanecarboxylate (25.0 g) over 20 min. The reaction mixture was stirred at room temperature overnight, and extracted with tert-butyl methyl ether. The extract was washed with saturated brine, dried over anhydrous magnesium sulfate, and the solvent was evaporated under reduced pressure to give the title compound (27.2 g).
$^1$H NMR (300 MHz, CDCl$_3$) δ 1.26 (3H, t, J=7.2 Hz), 1.62-1.86 (2H, m), 1.98-2.23 (5H, m), 2.37-2.48 (1H, m), 2.50-2.62 (1H, m), 3.08-3.22 (1H, m), 4.15 (2H, q, J=7.2 Hz).

B) azepan-4-ylmethanol

To a solution of 2,4,6-trichloro-1,3,5-triazine (21.7 g) in DMF (25 mL) was added dropwise ethyl 4-(hydroxyimino) cyclohexanecarboxylate (27.2 g) in DMF (220 mL) over 30 min. The mixture was stirred at room temperature overnight, poured into water, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give ethyl 7-oxoazepane-4-carboxylate (2.40 g).
A solution of the obtained 7-oxoazepane-4-carboxylate (2.02 g) in THF (29 mL) was added dropwise to a suspension of lithium aluminum hydride (2.07 g) in THF (80 mL) under ice-cooling. The reaction mixture was stirred at room temperature for 3 hr and at 60° C. overnight. The reaction mixture was ice-cooled, diluted with THF (200 mL), and water (2.02 mL) was slowly added dropwise. Furthermore, 15% aqueous sodium hydroxide solution (2.02 mL) was added dropwise, then water (4.04 mL) was added, and the mixture was stirred at room temperature for 3 hr. The solid was separated by filtration, and the filtrate was concentrated under reduced pressure to give the title compound (1.41 g).
$^1$H NMR (300 MHz, CDCl$_3$) δ 0.84-1.24 (1H, m), 1.28-2.07 (8H, m), 2.66-3.12 (2H, m), 3.39-3.62 (2H, m).
MS (ESI+): [M+H]$^+$ 130.2.

C) {1-[2,4-bis(trifluoromethyl)benzyl]azepan-4-yl}methanol

To a solution of azepan-4-ylmethanol (1.40 g) and potassium carbonate (3.00 g) in DMF (54.2 mL) was added 1-(bromomethyl)-2,4-bis(trifluoromethyl)benzene (2.03 mL). The reaction mixture was stirred at room temperature overnight, poured into water, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (0.901 g).
$^1$H NMR (300 MHz, CDCl$_3$) δ 1.34-1.51 (2H, m), 1.52-1.71 (3H, m), 1.77-1.87 (3H, m), 2.55-2.68 (3H, m), 2.68-2.80 (1H, m), 3.50 (2H, d, J=6.2 Hz), 3.83 (2H, s), 7.78 (1H, d, J=8.1 Hz), 7.86 (1H, s), 8.07 (1H, d, J=8.1 Hz).
MS (ESI+): [M+H]$^+$ 356.2.

D) 1-[2,4-bis(trifluoromethyl)benzyl]azepane-4-carbaldehyde

To a solution of {1-[2,4-bis(trifluoromethyl)benzyl] azepan-4-yl}methanol (901.4 mg) and triethylamine (1.06 mL) in DMSO (1.01 mL) was added sulfur trioxide pyridine complex (1.21 g). The reaction mixture was stirred at room temperature for 1.5 hr, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (289.8 mg).
$^1$H NMR (300 MHz, CDCl$_3$) δ 1.67-1.91 (4H, m), 1.97-2.10 (2H, m), 2.53-2.79 (5H, m), 3.83 (2H, s), 7.79 (1H, d, J=8.1 Hz), 7.87 (1H, s), 8.02 (1H, d, J=8.1 Hz), 9.69 (1H, s).
MS (ESI+): [M+H]$^+$ 354.1.

E) (5Z)-5-({1-[2,4-bis(trifluoromethyl)benzyl] azepan-4-yl}methylidene)-4-(prop-2-yn-1-ylamino)-1,3-thiazol-2(5H)-one To a solution of 1-[2,4-bis(trifluoromethyl)benzyl] azepane-4-carbaldehyde (156.5 mg) in 2-propanol (2.22 mL) were added 4-(prop-2-yn-1-ylamino)-1,3-thiazol-2(5H)-one (137 mg) and piperidinium acetate (64.3 mg). The reaction mixture was stirred at 60° C. overnight, allowed to cool to room temperature, poured into saturated aqueous sodium hydrogen carbonate solution, and the mixture was extracted with ethyl acetate. The extract was washed with saturated brine, and dried over anhydrous magnesium sulfate, and the solvent was evaporated under reduced pressure. The residue was purified by silica gel column chromatography (NH, ethyl acetate/hexane) and recrystallized from ethyl acetate/hexane to give the title compound (63.0 mg).
$^1$H NMR (300 MHz, DMSO-$d_6$) δ 1.49-1.69 (3H, m), 1.69-1.89 (3H, m), 2.27-2.43 (1H, m), 2.56-2.76 (4H, m), 3.32-3.35 (1H, m), 3.86 (2H, s), 4.23 (2H, s), 6.97 (1H, d, J=9.0 Hz), 7.98 (1H, s), 8.06-8.11 (2H, m), 9.55 (1H, brs).

Example 63

4-[(4-{(Z)-[2-oxo-4-(prop-2-yn-1-ylamino)-1,3-thiazol-5(2H)-ylidene]methyl}piperidin-1-yl)methyl] naphthalene-1-carbonitrile To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added potassium carbonate (345 mg) and 4-(bromomethyl)naphthalene-1-carbonitrile (153 mg). The reaction mixture was stirred at room temperature overnight, water was added, and the mixture was extracted with ethyl is acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (134 mg).
$^1$H NMR (300 MHz, DMSO-$d_6$) δ 1.33-1.50 (2H, m), 1.64-1.78 (2H, m), 2.01-2.26 (3H, m), 2.79-2.91 (2H, m), 3.30-3.36 (1H, m), 3.98 (2H, s), 4.22 (2H, d, J=2.5 Hz), 6.87 (1H, d, J=8.9 Hz), 7.65 (1H, d, J=7.4 Hz), 7.70-7.86 (2H, m), 8.09-8.17 (2H, m), 8.44 (1H, d, J=8.1 Hz), 9.56 (1H, s).

Example 64

(5Z)-5-({1-[2-fluoro-6-(trifluoromethyl)benzyl]piperidin-4-yl}methylidene)-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added triethylamine (0.35 mL) and 2-fluoro-6-(trifluoromethyl)benzaldehyde (123 mg). The reaction mixture was stirred at room temperature for 1 hr, and sodium triacetoxyborohydride (554 mg) was added. The reaction mixture was stirred at room temperature overnight, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (83 mg).
$^1$H NMR (300 MHz, DMSO-$d_6$) δ 1.26-1.43 (2H, m), 1.62-1.75 (2H, m), 1.98-2.22 (3H, m), 2.66-2.77 (2H, m), 3.30-3.34 (1H, m), 3.61 (2H, s), 4.21 (2H, d, J=2.5 Hz), 6.85 (1H, d, J=9.1 Hz), 7.49-7.65 (3H, m), 9.54 (1H, s).

Example 65

(5Z)-5-{[1-(2-tert-butylbenzyl)piperidin-4-yl]methylidene}-4-(prop-2-yn-1-ylamino)-1,3-thiazol-2(5H)-one A) (2-tert-butylphenyl)methanol To a solution of 2-tert-butylbenzoic acid (1.00 g) in THF (20 mL) was added 1.0M borane THF complex THF solution (16.8 mL) under ice-cooling. The reaction mixture was stirred at room temperature overnight under a nitrogen atmosphere, 1N aqueous sodium hydroxide solution was added, and the mixture was extracted with ethyl acetate. The extract was dried over anhydrous magnesium sulfate, and the solvent was evaporated under reduced pressure. The residue was purified by silica gel column chromatography (ethyl acetate/hexane) to give the title compound (942 mg).
$^1$H NMR (300 MHz, DMSO-$d_6$) δ 1.35 (9H, s), 4.70 (2H, d, J=5.4 Hz), 5.10 (1H, t, J=5.4 Hz), 7.12-7.22 (2H, m), 7.27-7.34 (1H, m), 7.48-7.55 (1H, m).

B) 2-tert-butylbenzaldehyde

To a solution of (2-tert-butylphenyl)methanol (935 mg) in DMSO (20 mL) were added triethylamine (4.81 mL) and sulfur trioxide pyridine complex (3.02 g). The reaction mixture was stirred at room temperature for 1 hr, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (780 mg).
$^1$H NMR (300 MHz, DMSO-$d_6$) δ 1.46 (9H, s), 7.36-7.44 (1H, m), 7.49-7.62 (2H, m), 7.80 (1H, dd, J=7.6, 1.6 Hz), 10.74 (1H, s).

C) (5Z)-5-{[1-(2-tert-butylbenzyl)piperidin-4-yl]methylidene}-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (2 mL) was added a solution of triethylamine (0.35 mL) and 2-tert-butylbenzaldehyde (101 mg) in DMF (1 mL). The reaction mixture was stirred at room temperature for 1 hr, and sodium triacetoxyborohydride (554 mg) was added. The reaction mixture was stirred at room temperature overnight, saturated aqueous sodium hydrogen carbonate solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (92 mg).
$^1$H NMR (300 MHz, DMSO-$d_6$) δ 1.34-1.50 (2H, m), 1.39 (9H, s), 1.66-1.78 (2H, m), 2.02-2.17 (3H, m), 2.71-2.83 (2H, m), 3.32 (1H, t, J=2.5 Hz), 3.68 (2H, s), 4.23 (2H, d, J=2.5 Hz), 6.90 (1H, d, J=8.9 Hz), 7.12-7.21 (2H, m), 7.32-7.39 (1H, m), 7.54-7.61 (1H, m), 9.55 (1H, s).

Example 66

(5Z)-5-[(1-{[3,5-bis(trifluoromethyl)benzyl}piperidin-4-yl)methylidene]-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) were added potassium carbonate (345 mg) and 1-(bromomethyl)-3,5-bis(trifluoromethyl)benzene (198 mg). The reaction mixture was stirred at room temperature overnight, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (164 mg).
$^1$H NMR (300 MHz, DMSO-d) δ 1.36-1.54 (2H, m), 1.67-1.80 (2H, m), 1.99-2.19 (3H, m), 2.73-2.83 (2H, m), 3.30-3.34 (1H, m), 3.68 (2H, s), 4.23 (2H, d, J=2.5 Hz), 6.89 (1H, d, J=8.9 Hz), 8.00 (3H, s), 9.56 (1H, s).

Example 67

(5Z)-5-[(1-{[2,4-bis(trifluoromethyl)phenyl]acetyl}piperidin-4-yl)methylidene]-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (420 mg) in DMF (10 mL) were added [2,4-bis(trifluoromethyl)phenyl]acetic acid (426 mg), N-ethyl-N-(1-methylethyl)propan-2-amine (1.17 mL) and N-[(dimethylamino) (3H-[1,2,3]triazolo[4,5-b]pyridin-3-yloxy)methylidene]-N-methylmethanaminium hexafluorophosphate (595 mg). The reaction mixture was stirred at room temperature overnight under a nitrogen atmosphere, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (498 mg).

$^1$H NMR (300 MHz, DMSO-d$_6$) δ 1.16-1.31 (1H, m), 1.33-1.49 (1H, m), 1.68-1.89 (2H, m), 2.31-2.47 (1H, m), 2.76-2.89 (1H, m), 3.19-3.31 (1H, m), 3.34 (1H, t, J=2.5 Hz), 3.89-4.13 (3H, m), 4.18-4.28 (1H, m), 4.24 (2H, d, J=2.5 Hz), 6.88 (1H, d, J=8.9 Hz), 7.67 (1H, d, J=7.9 Hz), 7.98 (1H, s), 8.03 (1H, d, J=7.9 Hz), 9.58 (1H, s).

Example 68

(5Z)-5-({1-[2,4-bis(trifluoromethyl)benzyl]pyrrolidin-3-yl}methylidene)-4-(prop-2-yn-1-ylamino)-1,3-thiazol-2(5H)-one A) {1-[2,4-bis(trifluoromethyl)benzyl]pyrrolidin-3-yl}methanol To a solution of 1-(bromomethyl)-2,4-bis(trifluoromethyl)benzene (7.29 g) in N,N-dimethylformamide (10 mL) were added pyrrolidin-3-ylmethanol hydrochloride (4.9 g) and potassium carbonate (9.84 g), and the mixture was stirred at room temperature for 3 hr. Water/ethyl acetate were added to the reaction mixture, and the organic layer was separated, washed with water and saturated brine, and dried over anhydrous magnesium sulfate, and the solvent was evaporated under reduced pressure. The residue was purified by silica gel column chromatography (ethyl acetate/hexane) to give the title compound (5.00 g).

$^1$H NMR (300 MHz, CDCl$_3$) δ 1.64-1.75 (1H, m), 1.94-2.13 (1H, m), 2.33-2.62 (4H, m), 2.62-2.70 (1H, m), 2.84 (1H, td, J=8.7, 4.2 Hz), 3.52-3.61 (1H, m), 3.64-3.71 (1H, m), 3.83 (2H, s), 7.74-7.82 (1H, m), 7.85-7.93 (2H, m).

MS (ESI+): [M+H]$^+$ 328.1.

B) 1-[2,4-bis(trifluoromethyl)benzyl]pyrrolidine-3-carbaldehyde

To a solution of {1-[2,4-bis(trifluoromethyl)benzyl]pyrrolidin-3-yl}methanol (4.69 g) and triethylamine (5.99 mL) in dimethyl sulfoxide (50 mL) was added sulfur trioxide pyridine complex (6.84 g), and the mixture was stirred at room temperature for 4 hr. Water/ethyl acetate were added to the reaction mixture, and the organic layer was separated, washed with saturated aqueous sodium hydrogen carbonate solution and saturated brine, and dried over anhydrous magnesium sulfate, and the solvent was evaporated under reduced pressure. The residue was purified by silica gel column chromatography (ethyl acetate/hexane) to give the title compound (3.50 g).

$^1$H NMR (300 MHz, CDCl$_3$) δ 2.04-2.23 (2H, m), 2.44-2.55 (1H, m), 2.64 (1H, dd, J=9.4, 7.7 Hz), 2.81 (1H, td, J=8.4, 4.8 Hz), 2.88-3.01 (1H, m), 3.05 (1H, dd, J=9.4, 4.0 Hz), 3.86 (2H, s), 7.78 (1H, d, J=8.1 Hz), 7.87 (1H, s), 7.93 (1H, d, J=8.1 Hz), 9.68 (1H, d, J=1.9 Hz).

MS (ESI+): [M+H]$^+$ 326.1.

C) (5Z)-5-({1-[2,4-bis(trifluoromethyl)benzyl]pyrrolidin-3-yl}methylidene)-4-(prop-2-yn-1-ylamino)-1,3-thiazol-2(5H)-one To a solution of 1-[2,4-bis(trifluoromethyl)benzyl]pyrrolidine-3-carbaldehyde (1.1 g) in 2-propanol (10 mL) were added 4-(prop-2-yn-1-ylamino)-1,3-thiazol-2(5H)-one (0.782 g) and piperidinium acetate (0.491 g). The reaction mixture was stirred at 80° C. for 2 hr, and the solvent was evaporated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) and silica gel column chromatography (NH, ethyl acetate/hexane) to give the title compound (0.760 g).

$^1$H NMR (300 MHz, DMSO-d$_6$) δ 1.59-1.72 (1H, m), 2.10-2.31 (1H, m), 2.50-2.55 (1H, m), 2.54-2.75 (2H, m), 2.76-2.91 (2H, m), 3.28-3.38 (1H, m), 3.88 (2H, s), 4.23 (2H, d, J=2.5 Hz), 7.05 (1H, d, J=8.3 Hz), 7.99 (1H, s), 8.07 (2H, s), 9.60 (1H, s).

Example 69

(5Z)-5-({1-[2,4-bis(trifluoromethyl)benzyl]pyrrolidin-3-yl}methylidene)-4-(prop-2-yn-1-ylamino)-1,3-thiazol-2(5H)-one maleate To a solution of (5Z)-5-({1-[2,4-bis(trifluoromethyl)benzyl]pyrrolidin-3-yl}methylidene)-4-(prop-2-yn-1-ylamino)-1,3-thiazol-2(5H)-one (740 mg) in ethanol (10 mL) was added maleic acid (186 mg). The reaction mixture was stirred at 80° C. for 20 min, the solvent was evaporated under reduced pressure, and the residue was recrystallized from ethanol/heptane to give the title compound (800 mg).

$^1$H NMR (300 MHz, DMSO-d$_6$) δ 1.65-1.81 (1H, m), 2.17-2.33 (1H, m), 2.64-2.77 (1H, m), 2.79-3.01 (3H, m), 3.01-3.16 (1H, m), 3.33 (1H, t, J=2.5 Hz), 4.11 (2H, brs), 4.23 (2H, dd, J=5.3, 2.5 Hz), 6.20 (2H, s), 7.00 (1H, d, J=8.9 Hz), 8.01-8.20 (3H, m), 9.62 (1H, t, J=5.2 Hz).

Example 70

(5Z)-5-({1-[2,4-bis(trifluoromethyl)benzyl]piperidin-4-yl}methylidene)-4-{[(2Z)-4-(diethylamino)but-2-en-1-yl]amino}-1,3-thiazol-2(5H)-one To a solution of 4-{[(2Z)-4-(diethylamino)but-2-en-1-yl]amino}-1,3-thiazol-2(5H)-one (440 mg) in 2-propanol (5 mL) were added 1-[2,4-bis(trifluoromethyl)benzyl]piperidine-4-carbaldehyde (617 mg) and piperidinium acetate (264 mg) at room temperature, and the reaction mixture was stirred at 60° C. for 4 hr. The solvent was evaporated under reduced pressure, and the residue was purified by silica gel column chromatography (NH, ethyl acetate/hexane) to give the title compound (164 mg).

$^1$H NMR (300 MHz, DMSO-d$_6$) δ 0.95 (6H, t, J=7.2 Hz), 1.36-1.57 (2H, m), 1.64-1.81 (2H, m), 2.02-2.25 (3H, m), 2.44 (4H, q, J=7.2 Hz), 2.66-2.84 (2H, m), 3.11 (2H, d, J=4.9 Hz), 3.71 (2H, s), 4.09 (2H, d, J=4.9 Hz), 5.47-5.73 (2H, m), 6.85 (1H, d, J=8.7 Hz), 7.85-8.19 (3H, m), 9.34 (1H, brs).

Example 71

(5Z)-5-({1-[2,4-bis(trifluoromethyl)benzyl]piperidin-4-yl}methylidene)-4-{[(2Z)-4-(diethylamino)but-2-en-1-yl]amino}-1,3-thiazol-2(5H)-one tosylate To a solution of (5Z)-5-({1-[2,4-bis(trifluoromethyl)benzyl]piperidin-4-yl}methylidene)-4-{[(2Z)-4-(diethylamino)but-2-en-1-yl]amino}-1,3-thiazol-2(5H)-one (162 mg) in ethyl acetate (3 mL) was added tosylic acid monohydrate (55 mg) at room temperature. The reaction mixture was stirred at 60° C. for 5 min. The solvent was evaporated under reduced pressure, and the residue was recrystallized from ethyl acetate/heptane to give the title compound (179 mg).

$^1$H NMR (300 MHz, DMSO-d$_6$) δ 1.22 (6H, t, J=7.3 Hz), 1.36-1.56 (2H, m), 1.63-1.80 (2H, m), 2.00-2.23 (3H, m), 2.29 (3H, s), 2.68-2.84 (2H, m), 3.06-3.24 (4H, m), 3.71 (2H, s), 3.84-3.96 (2H, m), 4.13 (2H, dd, J=5.5, 5.5 Hz), 5.64-5.77 (1H, m), 5.83-5.96 (1H, m), 6.86 (1H, d, J=8.9 Hz), 7.12 (2H, d, J=8.1 Hz), 7.49 (2H, d, J=8.1 Hz), 7.99 (1H, s), 8.01-8.12 (2H, m), 9.24 (1H, brs), 9.50 (1H, t, J=5.5 Hz).

Example 72

(5Z)-4-amino-5-({1-[2,4-bis(trifluoromethyl)benzyl]piperidin-4-yl}methylidene)-1-methyl-1,5-dihydro-2H-imidazol-2-one A) 4-imino-1-methyl-3-(phenylcarbonyl)imidazolidin-2-one To a solution of N-methylaminoacetonitrile (6.19 g) in anhydrous THF (100 mL) was added benzoyl isocyanate (13.0 g) under ice-cooling. The reaction mixture was stirred at room temperature for 5 hr. The solvent was evaporated under reduced pressure, and the residue was purified by silica gel column chromatography (ethyl acetate/hexane) to give the title compound (18.6 g).

$^1$H NMR (300 MHz, DMSO-d$_6$) δ 3.03 (3H, s), 4.49 (2H, s), 7.42-7.56 (2H, m), 7.56-7.67 (1H, m), 7.83-7.91 (2H, m), 10.42 (1H, s).

B) (5Z)-4-amino-5-({1-[2,4-bis(trifluoromethyl)benzyl]piperidin-4-yl}methylidene)-1-methyl-1,5-dihydro-2H-imidazol-2-one To a solution of 1-[2,4-bis(trifluoromethyl)benzyl]piperidine-4-carbaldehyde (26.0 g) in ethanol (100 mL) were added 4-imino-1-methyl-3-(phenylcarbonyl)imidazolidin-2-one (16.7 g) and potassium tert-butoxide (8.60 g) under ice-cooling. The reaction mixture was stirred at 80° C. for 2 hr. To the reaction mixture was added saturated aqueous ammonium chloride solution at room temperature, and the solvent was evaporated under reduced pressure. Water and ethyl acetate were added to the residue, and the insoluble material was removed by filtration. The filtrate was extracted with ethyl acetate. The extract was washed with saturated brine, dried over anhydrous magnesium sulfate under reduced pressure, and the solvent was evaporated. The residue was purified by silica gel column chromatography (methanol/ethyl acetate) and recrystallized from ethanol/water to give the title compound (270 mg).

$^1$H NMR (300 MHz, DMSO-d$_6$) δ 1.29-1.53 (2H, m), 1.64-1.79 (2H, m), 2.07-2.25 (2H, m), 2.66-2.88 (3H, m), 3.15 (3H, s), 3.70 (2H, s), 5.56 (1H, d, J=10.2 Hz), 7.71-8.19 (5H, m).

Example 73

(5Z)-5-({1-[2,4-bis(trifluoromethyl)benzyl]piperidin-4-yl}methylidene)-1-methyl-4-(prop-2-yn-1-ylamino)-1,5-dihydro-2H-imidazol-2-one To a solution of (5Z)-4-amino-5-({1-[2,4-bis(trifluoromethyl)benzyl]piperidin-4-yl}methylidene)-1-methyl-1,5-dihydro-2H-imidazol-2-one (1.50 g) in toluene (10 mL) was added propargylamine (1.90 g) at room temperature. The reaction mixture was stirred at 100° C. overnight. The residue was purified by silica gel column chromatography (ethyl acetate/hexane) and recrystallized from ethyl acetate/heptane to give the title compound (870 mg).

$^1$H NMR (300 MHz, DMSO-d$_6$) δ 1.32-1.51 (2H, m), 1.64-1.79 (2H, m), 2.08-2.24 (2H, m), 2.69-2.89 (3H, m), 3.17 (3H, s), 3.25 (1H, t, J=2.3 Hz), 3.71 (2H, s), 4.11 (2H, d, J=2.1 Hz), 5.59 (1H, d, J=10.2 Hz), 7.98 (1H, s), 8.01-8.14 (2H, m), 8.79 (1H, brs).

Example 74

(5E)-4-amino-5-({1-[2,4-bis(trifluoromethyl)benzyl]piperidin-4-yl}methylidene)-1-methyl-1,5-dihydro-2H-imidazol-2-one To a solution of 1-[2,4-bis(trifluoromethyl)benzyl]piperidine-4-carbaldehyde (26.0 g) in ethanol (100 mL) were added 4-imino-1-methyl-3-(phenylcarbonyl)imidazolidin-2-one (16.7 g) and potassium tert-butoxide (8.60 g) under ice-cooling, and the reaction mixture was stirred at 80° C. for 2 hr. To the reaction mixture was added saturated aqueous ammonium chloride solution at room temperature, and the solvent was evaporated under reduced pressure. Water and ethyl acetate were added to the residue, and the insoluble material was removed by filtration. The filtrate was extracted with ethyl acetate. The extract was washed with saturated brine, dried over anhydrous magnesium sulfate under reduced pressure, and the solvent was evaporated. The residue was purified by silica gel column chromatography (ethyl acetate/methanol) and recrystallized from ethanol/water to give the title compound (220 mg).

$^1$H NMR (300 MHz, DMSO-d$_6$) δ 1.36-1.55 (2H, m), 1.57-1.74 (2H, m), 2.12-2.32 (2H, m), 2.66-2.92 (6H, m), 3.69 (2H, s), 5.12 (1H, d, J=10.4 Hz), 7.92-8.16 (3H, m).

Example 75

(5E)-5-({1-[2,4-bis(trifluoromethyl)benzyl]piperidin-4-yl}methylidene)-1-methyl-4-(prop-2-yn-1-ylamino)-1,5-dihydro-2H-imidazol-2-one To a solution of (5E)-4-amino-5-({1-[2,4-bis(trifluoromethyl)benzyl]piperidin-4-yl}methylidene)-1-methyl-1,5-dihydro-2H-imidazol-2-one (133 mg) in toluene (1 mL) was added propargylamine (843 mg) at room temperature. The reaction mixture was stirred at 100° C. overnight. The residue was purified by silica gel column chromatography (ethyl acetate/hexane) and recrystallized from ethyl acetate/heptane to give the title compound (87 mg).

$^1$H NMR (300 MHz, DMSO-d$_6$) δ 1.25-1.52 (2H, m), 1.56-1.77 (2H, m), 2.12 (2H, brs), 2.69-2.91 (6H, m), 3.11 (1H, brs), 3.69 (2H, s), 4.02 (2H, brs), 5.06 (1H, brs), 7.98 (1H, s), 8.01-8.13 (2H, m), 10.53 (1H, brs).

Example 76

(5Z)-5-({1-[2,4-bis(trifluoromethyl)benzyl]azepan-4-yl}methylidene)-4-[(2-hydroxy-2-methylpropyl)amino]-1,3-thiazol-2(5H)-one To a solution of 1-[2,4-bis(trifluoromethyl)benzyl]azepane-4-carbaldehyde (133.2 mg) in 2-propanol (1.89 mL) were added 4-[(2-hydroxy-2-methylpropyl)amino]-1,3-thiazol-2(5H)-one (142 mg) and piperidinium acetate (54.7 mg). The reaction mixture was stirred at 60° C. overnight, cooled to room temperature, and diluted with ethyl acetate. The mixed solution was washed with water and saturated brine, and dried over anhydrous magnesium sulfate, and the solvent was evaporated under reduced pressure. The residue was purified by silica gel column chromatography (NH, ethyl acetate/hexane) to give the title compound (86.3 mg).

$^1$H NMR (300 MHz, CDCl$_3$) δ 1.32 (6H, s), 1.60-1.75 (4H, m), 1.79-1.95 (3H, m), 2.39-2.57 (1H, m), 2.60-2.79 (4H, m), 3.63 (2H, d, J=5.7 Hz), 3.85 (2H, s), 6.27 (1H, d, J=9.0 Hz), 6.35-6.45 (1H, m), 7.80 (1H, d, J=8.7 Hz), 7.88 (1H, s), 8.02 (1H, d, J=8.7 Hz).

Example 77

(5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one A) 4-[(3-hydroxy-2,2-dimethylpropyl)amino]-1,3-thiazol-2(5H)-one To a solution of 3-amino-2,2-dimethylpropan-1-ol (4.05 g) in ethanol (100 mL) was added 4-thioxo-1,3-thiazolidin-2-one (5.07 g). The reaction mixture was stirred at room temperature overnight, and the solvent was evaporated under reduced pressure. The residue was purified by silica gel column chromatography (NH, ethyl acetate) to give the title compound (4.52 g).

$^1$H NMR (300 MHz, DMSO-d$_6$) δ 0.83 (6H, s), 3.13 (2H, d, J=4.7 Hz), 3.24 (2H, d, J=6.0 Hz), 4.28 (2H, s), 4.61-4.70 (1H, m), 8.86-8.97 (1H, m).

MS (ESI+): [M+H]$^+$ 203.0.

B) (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one To a solution of 1-[2,4-bis(trifluoromethyl)benzyl]piperidine-4-carbaldehyde (1.00 g) in 2-propanol (15 mL) were added 4-[(3-hydroxy-2,2-dimethylpropyl)amino]-1,3-thiazol-2(5H)-one (1.19 g) and piperidinium acetate (0.44 g). The reaction mixture was stirred at 60° C. overnight and concentrated. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (885 mg).

$^1$H NMR (300 MHz, DMSO-d$_6$) δ 0.84 (6H, s), 1.40-1.57 (2H, m), 1.69-1.81 (2H, m), 2.04-2.22 (3H, m), 2.71-2.84 (2H, m), 3.14 (2H, s), 3.34 (2H, s), 3.71 (2H, s), 4.70 (1H, brs), 6.95 (1H, d, J=8.7 Hz), 7.98 (1H, s), 8.01-8.12 (2H, m), 8.97 (1H, brs).

powder X-ray diffraction interplanar spacing (d): 16.66, 10.49, 8.31, 7.06, 6.21, 5.21, 5.11, 4.44, 4.26, 3.35 and 3.31 Å.

Example 78

(5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one fumarate To a solution of (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one (800 mg) in ethanol (5 mL) was added a solution of fumaric acid (181 mg) in ethanol (20 mL). The reaction mixture was stirred at room temperature for 1 hr, and the solvent was evaporated under reduced pressure. The residue was recrystallized from ethanol/heptane to give the title compound (800 mg).

$^1$H NMR (300 MHz, DMSO-d$_6$) δ 0.84 (6H, s), 1.41-1.57 (2H, m), 1.69-1.81 (2H, m), 2.04-2.24 (3H, m), 2.72-2.83 (2H, m), 3.14 (2H, s), 3.35 (2H, d, J=6.0 Hz), 3.71 (2H, s), 4.69 (1H, brs), 6.63 (2H, s), 6.95 (1H, d, J=8.9 Hz), 7.98 (1H, s), 8.01-8.11 (2H, m), 8.95 (1H, t, J=6.0 Hz), 13.13 (2H, brs).

Example 79

(5E)-5-({1-[2,4-bis(trifluoromethyl)benzyl]piperidin-4-yl}methylidene)-1-methyl-4-(methylamino)-1,5-dihydro-2H-imidazol-2-one To a solution of 1-[2,4-bis(trifluoromethyl)benzyl]piperidine-4-carbaldehyde (26.0 g) in ethanol (100 mL) were added 4-imino-1-methyl-3-(phenylcarbonyl)imidazolidin-2-one (16.7 g) and potassium tert-butoxide (8.60 g) under ice-cooling. The reaction mixture was stirred at 80° C. for 2 hr. To the reaction mixture was added saturated aqueous ammonium chloride solution at room temperature, and ethanol was evaporated under reduced pressure. Water and ethyl acetate were added to the residue, and the insoluble material was collected by filtration. The obtained solid was recrystallized from water/ethanol and further recrystallized from water/acetone for purification. To a solution of the obtained solid (2.03 g) in toluene (10 mL) was added a solution (4.8 mL) of methylamine in 40% methanol at room temperature. The reaction mixture was stirred at 70° C. overnight, a solution (4.8 mL) of methylamine in 40% methanol was added at room temperature, and the mixture was stirred at 70° C. overnight. The solvent was evaporated under reduced pressure, and the residue was purified by silica gel column chromatography (NH, methanol/ethyl acetate) and recrystallized from heptane to give the title compound (223 mg).

$^1$H NMR (300 MHz, CDCl$_3$) δ 1.55-1.87 (4H, m), 2.12-2.29 (2H, m), 2.30-2.49 (1H, m), 2.75-2.94 (2H, m), 2.97-3.03 (3H, m), 3.05-3.21 (3H, m), 3.72 (2H, s), 4.84-5.04 (1H, m), 5.59-5.74 (1H, m), 7.60-7.83 (1H, m), 7.88 (1H, s), 7.96-8.08 (1H, m).

Example 80

(5Z)-5-({1-[2,4-bis(trifluoromethyl)benzyl]piperidin-4-yl}methylidene)-1-methyl-4-(methylamino)-1,5-dihydro-2H-imidazol-2-one To a solution of 1-[2,4-bis(trifluoromethyl)benzyl]piperidine-4-carbaldehyde (26.0 g) in ethanol (100 mL) were added 4-imino-1-methyl-3-(phenylcarbonyl)imidazolidin-2-one (16.7 g) and potassium tert-butoxide (8.60 g) under ice-cooling. The reaction mixture was stirred at 80° C. for 2 hr. To the reaction mixture was added saturated aqueous ammonium chloride solution at room temperature, and ethanol was evaporated under reduced pressure. Water and ethyl acetate were added to the residue, and the insoluble material was collected by filtration, recrystallized from ethanol/water, and further recrystallized from acetone/water. To a solution of the obtained solid (2.03 g) in toluene (10 mL) was added a solution (4.8 mL) of methylamine in 40% methanol at room temperature. The reaction mixture was stirred at 70° C. overnight, 40% methanol solution (4.8 mL) was added at room temperature, and the mixture was stirred at 70° C. overnight. The solvent was evaporated under reduced pressure, and the residue was purified by silica gel column chromatography (NH, methanol/ethyl acetate) and recrystallized from ethyl acetate/heptane to give the title compound (1.10 g).

$^1$H NMR (300 MHz, DMSO-$d_6$) δ 1.28-1.54 (2H, m), 1.61-1.80 (2H, m), 2.05-2.26 (2H, m), 2.65-2.93 (6H, m), 3.15 (3H, s), 3.70 (2H, s), 5.46 (1H, d, J=10.2 Hz), 7.98 (1H, s), 8.01-8.13 (2H, m), 8.36 (1H, brs).

Example 81

(5Z)-5-({1-[2,4-bis(trifluoromethyl)benzyl]piperidin-4-yl}methylidene)-4-(cyclopentylamino)-1-methyl-1,5-dihydro-2H-imidazol-2-one To a solution of 1-[2,4-bis(trifluoromethyl)benzyl]piperidine-4-carbaldehyde (26.0 g) in ethanol (100 mL) were added 4-imino-1-methyl-3-(phenylcarbonyl)imidazolidin-2-one (16.7 g) and potassium tert-butoxide (8.60 g) under ice-cooling. The reaction mixture was stirred at 80° C. for 2 hr. To the reaction mixture was added saturated aqueous ammonium chloride solution at room temperature, and ethanol was evaporated under reduced pressure.

Water and ethyl acetate were added to the residue, and the insoluble material was collected by filtration, recrystallized from ethanol/water, and further recrystallized from acetone/water. To a solution of the obtained solid (1.23 g) in toluene (10 mL) was added cyclopentylamine (2.41 g) at room temperature. The reaction mixture was stirred at 80° C. overnight, the solvent was evaporated under reduced pressure, and the residue was purified by silica gel column chromatography (NH, methanol/ethyl acetate) and recrystallized from ethyl acetate/heptane to give the title compound (230 mg).

$^1$H NMR (300 MHz, DMSO-$d_6$) δ 1.28-1.79 (10H, m), 1.81-1.98 (2H, m), 2.06-2.22 (2H, m), 2.68-2.86 (3H, m), 3.14 (3H, s), 3.71 (2H, s), 4.05-4.21 (1H, m), 5.61 (1H, d, J=10.0 Hz), 7.95-8.19 (4H, m).

Example 82

(5Z)-5-({1-[2,4-bis(trifluoromethyl)phenyl]piperidin-4-yl}methylidene)-4-(prop-2-yn-1-ylamino)-1,3-thiazol-2(5H)-one A) {1-[2,4-bis(trifluoromethyl)phenyl]piperidin-4-yl}methanol To a solution of 1-fluoro-2,4-bis(trifluoromethyl)benzene (1.5 g) in N,N-dimethylformamide (10 mL) were added 4-piperidinemethanol (1.49 g) and potassium carbonate (1.79 g), and the mixture was stirred at 80° C. overnight. Water/ethyl acetate were added to the reaction mixture, and the organic layer was separated, washed with water and saturated brine, dried over anhydrous magnesium sulfate, and the solvent was evaporated under reduced pressure to give the title compound (1.84 g).

$^1$H NMR (300 MHz, CDCl$_3$) δ 1.38-1.75 (3H, m), 1.83 (2H, dd, J=12.6, 2.2 Hz), 2.69-2.83 (2H, m), 3.21 (2H, d, J=11.7 Hz), 3.58 (2H, d, J=6.4 Hz), 7.38 (1H, d, J=8.3 Hz), 7.73 (1H, d, J=8.5 Hz), 7.86 (1H, s).

MS (ESI+): [M+H]$^+$ 328.1.

B) 1-[2,4-bis(trifluoromethyl)phenyl]piperidine-4-carbaldehyde

To a solution of {1-[2,4-bis(trifluoromethyl)phenyl]piperidin-4-yl}methanol (2.41 g) and triethylamine (3.08 mL) in dimethyl sulfoxide (30 mL) was added sulfur trioxide pyridine complex (3.52 g), and the mixture was stirred at room temperature for 1 hr. To the reaction mixture were added saturated aqueous sodium hydrogen carbonate solution and ethyl acetate, and the organic layer was separated, washed with water and saturated brine, and dried over anhydrous magnesium sulfate, and the solvent was evaporated under reduced pressure. The residue was purified by silica gel column chromatography (ethyl acetate/hexane) to give the title compound (1.60 g).

$^1$H NMR (300 MHz, CDCl$_3$) δ 1.81-1.95 (2H, m), 1.98-2.09 (2H, m), 2.37-2.48 (1H, m), 2.79-2.90 (2H, m), 3.11-3.23 (2H, m), 7.38 (1H, d, J=8.3 Hz), 7.75 (1H, d, J=8.5 Hz), 7.87 (1H, s), 9.73 (1H, d, J=0.6 Hz).

MS (ESI+): [M+H]$^+$ 326.1.

C) (5Z)-5-({1-[2,4-bis(trifluoromethyl)phenyl]piperidin-4-yl}methylidene)-4-(prop-2-yn-1-ylamino)-1,3-thiazol-2(5H)-one To a solution of 1-[2,4-bis(trifluoromethyl)phenyl]piperidine-4-carbaldehyde (1.61 g) in 2-propanol (20 mL) were added 4-(prop-2-yn-1-ylamino)-1,3-thiazol-2(5H)-one (1.15 g) and piperidinium acetate (0.72 g). The reaction mixture was stirred at 80° C. for 1 hr, and the solvent was evaporated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane), and recrystallized from ethyl acetate/heptane to give the title compound (1.45 g).

$^1$H NMR (300 MHz, DMSO-$d_6$) δ 1.47-1.68 (2H, m), 1.86 (2H, d, J=10.4 Hz), 2.17-2.35 (1H, m), 2.85-2.98 (2H, m), 3.11 (2H, d, J=11.7 Hz), 3.35 (1H, t, J=2.5 Hz), 4.25 (2H, d, J=2.6 Hz), 6.96 (1H, d, J=9.1 Hz), 7.69 (1H, d, J=8.5 Hz), 7.94 (1H, s), 8.03 (1H, d, J=8.5 Hz), 9.57 (1H, brs).

Example 83

(5Z)-5-({1-[2,4-bis(trifluoromethyl)benzyl]piperidin-4-yl}methylidene)-4-[(3-cyclopropylprop-2-yn-1-yl)amino]-1,3-thiazol-2(5H)-one A) 4-[(3-cyclopropylprop-2-yn-1-yl)amino]-1,3-thiazol-2(5H)-one To a solution of 3-cyclopropylprop-2-yn-1-amine (4.61 g) in ethanol (50 mL) was added 4-thioxo-1,3-thiazolidin-2-one (3.24 g), and the mixture was stirred at room temperature for 2 hr. The reaction mixture was concentrated, and the residue was purified by silica gel column chromatography (NH, ethyl acetate/hexane) to give the title compound (4.20 g).

$^1$H NMR (300 MHz, DMSO-$d_6$) δ 0.55-0.64 (2H, m), 0.73-0.82 (2H, m), 1.25-1.42 (1H, m), 4.09 (2H, d, J=1.9 Hz), 4.24 (2H, s), 9.38 (1H, brs).

MS (ESI+): [M+H]$^+$ 195.0.

B) (5Z)-5-({1-[2,4-bis(trifluoromethyl)benzyl]piperidin-4-yl}methylidene)-4-[(3-cyclopropylprop-2-yn-1-yl)amino]-1,3-thiazol-2(5H)-one To a solution of 1-[2,4-bis(trifluoromethyl)benzyl]piperidine-4-carbaldehyde (1.5 g) in 2-propanol (20 mL) were added 4-[(3-cyclopropylprop-2-yn-1-yl)amino]-1,3-thiazol-2(5H)-one (1.29 g) and piperidinium acetate (0.64 g). The reaction mixture was stirred at 80° C. for 1 hr, and the solvent was evaporated under reduced pressure. Water was added to the residue, and the mixture was extracted with ethyl acetate.

The extract was washed with saturated brine, and dried over anhydrous magnesium sulfate, and the solvent was evaporated under reduced pressure. The residue was purified by silica gel column chromatography (ethyl acetate/hexane) to give the title compound (1.56 g).

$^1$H NMR (300 MHz, DMSO-$d_6$) δ 0.56-0.64 (2H, m), 0.73-0.83 (2H, m), 1.26-1.39 (1H, m), 1.39-1.59 (2H, m), 1.74 (2H, d, J=10.8 Hz), 2.02-2.25 (3H, m), 2.76 (2H, d, J=11.5 Hz), 3.71 (2H, s), 4.19 (2H, d, J=1.9 Hz), 6.91 (1H, d, J=8.9 Hz), 7.98 (1H, s), 8.01-8.12 (2H, m), 9.49 (1H, s).

Example 84

(5Z)-5-({1-[2,4-bis(trifluoromethyl)benzyl]piperidin-4-yl}methylidene)-4-[(3-cyclopropylprop-2-yn-1-yl)amino]-1,3-thiazol-2(5H)-one maleate To a solution of (5Z)-5-({1-[2,4-bis(trifluoromethyl)benzyl]piperidin-4-yl}methylidene)-4-[(3-cyclopropylprop-2-yn-1-yl)amino]-1,3-thiazol-2(5H)-one (1.11 g) in ethanol (15 mL) was added maleic acid (0.25 g). The reaction mixture was stirred at 80° C. for 20 min, the solvent was evaporated under reduced pressure, and the residue was recrystallized from ethanol/heptane to give the title compound (1.10 g).

$^1$H NMR (300 MHz, DMSO-$d_6$) δ 0.54-0.64 (2H, m), 0.73-0.81 (2H, m), 1.28-1.40 (1H, m), 1.55 (2H, q, J=10.6 Hz), 1.81 (2H, d, J=11.3 Hz), 2.10-2.32 (1H, m), 2.55-2.72 (2H, m), 2.80-3.12 (2H, m), 3.81-4.10 (2H, m), 4.20 (2H, dd, J=5.1, 1.9 Hz), 6.19 (2H, s), 6.87 (1H, d, J=8.7 Hz), 8.01-8.22 (3H, m), 9.50 (1H, t, J=5.1 Hz).

Example 85

(5Z)-5-({(1R,5S,6s)-3-[2,4-bis(trifluoromethyl)benzyl]-3-azabicyclo[3.1.0]hex-6-yl}ethyl idene)-4-(prop-2-yn-1-ylamino)-1,3-thiazol-2(5H)-one To a solution of (1R,5S,6r)-3-[2,4-bis(trifluoromethyl)benzyl]-3-azabicyclo[3.1.0]hexane-6-carbaldehyde (1.19 g) in 2-propanol (20 mL) were added 4-(prop-2-yn-1-ylamino)-1,3-thiazol-2(5H)-one (0.87 g) and piperidinium acetate (0.51 g). The reaction mixture was stirred at 80° C. for 2 hr, and the solvent was evaporated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (1.49 g).

$^1$H NMR (300 MHz, DMSO-$d_6$) δ 1.76 (1H, dt, J=10.2, 2.4 Hz), 1.89 (2H, s), 2.51-2.56 (2H, m), 3.01 (2H, d, J=9.1 Hz), 3.28-3.32 (1H, m), 3.86 (2H, s), 4.19 (2H, d, J=2.5 Hz), 6.53 (1H, d, J=10.4 Hz), 7.89 (1H, d, J=7.9 Hz), 7.98 (1H, s), 8.10 (1H, d, J=7.9 Hz), 9.37 (1H, brs).

Example 86

(5Z)-5-({(1R,5S,6s)-3-[2,4-bis(trifluoromethyl)benzyl]-3-azabicyclo[3.1.0]hex-6-yl}methylidene)-4-(prop-2-yn-1-ylamino)-1,3-thiazol-2(5H)-one maleate To a solution of (5Z)-5-({(1R,5S,6s)-3-[2,4-bis(trifluoromethyl)benzyl]-3-azabicyclo[3.1.0]hex-6-yl}methylidene)-4-(prop-2-yn-1-ylamino)-1,3-thiazol-2(5H)-one (1.36 g) in ethanol (15 mL) was added maleic acid (0.33 g). The reaction mixture was stirred at 80° C. for 20 min, the solvent was evaporated under reduced pressure, and the residue was recrystallized from ethanol/heptane to give the title compound (1.31 g).

$^1$H NMR (300 MHz, DMSO-$d_6$) δ 1.79 (1H, d, J=10.4 Hz), 1.93 (2H, brs), 2.65 (2H, brs), 3.09 (2H, d, J=7.6 Hz), 3.31 (1H, t, J=2.5 Hz), 3.95 (2H, brs), 4.20 (2H, dd, J=5.1, 2.5 Hz), 6.24 (2H, s), 6.52 (1H, d, J=10.4 Hz), 7.92 (1H, d, J=8.1 Hz), 8.00 (1H, s), 8.12 (1H, d, J=8.3 Hz), 9.36 (1H, t, J=5.3 Hz).

Example 87

(5Z)-5-({1-[2,4-bis(trifluoromethyl)benzyl]piperidin-4-yl}methylidene)-4-[(4-hydroxy-4-methylpent-2-yn-1-yl)amino]-1,3-thiazol-2(5H)-one A) 4-hydroxy-4-methylpent-2-yn-1-yl methanesulfonate To a solution of 4-methylpent-2-yne-1,4-diol (Synthesis 2001. 1013.) (1.00 g) in THF (40 mL) were added triethylamine (1.85 mL) and methanesulfonyl chloride (0.69 mL). The reaction mixture was stirred at room temperature overnight under a nitrogen atmosphere, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (1.57 g).

$^1$H NMR (300 MHz, DMSO-$d_6$) δ 1.38 (6H, s), 3.25 (3H, s), 4.96 (2H, s), 5.48 (1H, s).

B) 4-[(4-hydroxy-4-methylpent-2-yn-1-yl)amino]-1,3-thiazol-2(5H)-one

To a solution (40 mL) of 4-hydroxy-4-methylpent-2-yn-1-yl methanesulfonate (1.57 g) in THF was added 8M ammonia-methanol solution (10.2 mL) under ice-cooling. The reaction mixture was stirred at room temperature for 3 days, and the solvent was evaporated under reduced pressure. The residue was purified by silica gel column chromatography (methanol/ethyl acetate). To the obtained oil in ethanol (40 mL) was added 4-thioxo-1,3-thiazolidin-2-one (1.09 g). The reaction mixture was stirred at room temperature overnight, and the solvent was evaporated under reduced pressure. The residue was purified by silica gel column chromatography (NH, ethyl acetate/hexane) to give the title compound (370 mg).

$^1$H NMR (300 MHz, DMSO-$d_6$) δ 1.32-1.39 (6H, m), 3.30-3.36 (1H, m), 4.12-4.28 (3H, m), 5.20-5.38 (1H, m), 9.45 (1H, brs).

MS (ESI+): [M+H]$^+$ 213.0.

C) (5Z)-5-({1-[2,4-bis(trifluoromethyl)benzyl]piperidin-4-yl}methylidene)-4-[(4-hydroxy-4-methylpent-2-yn-1-yl)amino]-1,3-thiazol-2(5H)-one To a solution of 1-[2,4-bis(trifluoromethyl)benzyl]piperidine-4-carbaldehyde (400 mg) in 2-propanol (10 mL) were added a solution of 4-[(4-hydroxy-4-methylpent-2-yn-1-yl)amino]-1,3-thiazol-2(5H)-one (365 mg) in 2-propanol (5 mL) and piperidinium acetate (175 mg). The reaction mixture was stirred at 60° C. overnight and concentrated. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (540 mg).
$^1$H NMR (300 MHz, DMSO-d$_6$) δ 1.37 (6H, s), 1.40-1.57 (2H, m), 1.68-1.81 (2H, m), 2.04-2.24 (3H, m), 2.70-2.82 (2H, m), 3.71 (2H, s), 4.28 (2H, s), 5.34 (1H, s), 6.91 (1H, d, J=8.9 Hz), 7.98 (1H, s), 8.02-8.12 (2H, m), 9.54 (1H, brs).

Example 88

4-(4-{(Z)-[2-oxo-4-(prop-2-yn-1-ylamino)-1,3-thiazol-5(2H)-ylidene]methyl}piperidin-1-yl)-3-(trifluoromethyl)benzonitrile A) 4-[4-(hydroxymethyl)piperidin-1-yl]-3-(trifluoromethyl)benzonitrile To a solution of piperidin-4-ylmethanol (2.19 g) in DMSO (40 mL) were added 4-fluoro-3-(trifluoromethyl)benzonitrile (3.00 g) and potassium carbonate (3.21 g). The reaction mixture was stirred at 100° C. for 4 hr, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (3.59 g).
$^1$H NMR (300 MHz, DMSO-d$_6$) δ 1.20-1.36 (2H, m), 1.44-1.61 (1H, m), 1.68-1.81 (2H, m), 2.74-2.87 (2H, m), 3.14-3.24 (2H, m), 3.28-3.33 (2H, m), 4.51 (1H, t, J=5.3 Hz), 7.52 (1H, d, J=8.5 Hz), 8.03 (1H, dd, J=8.6, 2.0 Hz), 8.13 (1H, d, J=1.9 Hz).
MS (ESI+): [M+H]$^+$ 285.1.

B) 4-(4-formylpiperidin-1-yl)-3-(trifluoromethyl)benzonitrile

To a solution of 4-[4-(hydroxymethyl)piperidin-1-yl]-3-(trifluoromethyl)benzonitrile (3.55 g) in DMSO (50 mL) were added triethylamine (10.6 mL) and sulfur trioxide pyridine complex (6.63 g). The reaction mixture was stirred at room temperature for 1 hr, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (3.06 g).
$^1$H NMR (300 MHz, DMSO-d$_6$) δ 1.54-1.72 (2H, m), 1.91-2.03 (2H, m), 2.46-2.59 (1H, m), 2.84-2.97 (2H, m), 3.10-3.20 (2H, m), 7.56 (1H, d, J=8.5 Hz), 8.06 (1H, dd, J=8.5, 1.9 Hz), 8.16 (1H, d, J=1.9 Hz), 9.66 (1H, s).
MS (ESI+): [M+H]$^+$ 283.1.

C) 4-(4-{(Z)-[2-oxo-4-(prop-2-yn-1-ylamino)-1,3-thiazol-5(2H)-ylidene]methyl}piperidin-1-yl)-3-(trifluoromethyl)benzonitrile To a solution of 4-(4-formylpiperidin-1-yl)-3-(trifluoromethyl)benzonitrile (800 mg) in 2-propanol (15 mL) were added 4-(prop-2-yn-1-ylamino)-1,3-thiazol-2(5H)-one (874 mg) and piperidinium acetate (420 mg). The reaction mixture was stirred at 60° C. overnight and concentrated. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (849 mg).
$^1$H NMR (300 MHz, DMSO-d$_6$) δ 1.47-1.65 (2H, m), 1.80-1.92 (2H, m), 2.20-2.36 (1H, m), 2.87-3.00 (2H, m), 3.12-3.24 (2H, m), 3.35 (1H, t, J=2.5 Hz), 4.25 (2H, d, J=2.5 Hz), 6.95 (1H, d, J=8.9 Hz), 7.57 (1H, d, J=8.5 Hz), 8.08 (1H, dd, J=8.5, 1.9 Hz), 8.17 (1H, d, J=1.9 Hz), 9.56 (1H, s).

Example 89

(5Z)-5-({1-[2,4-bis(trifluoromethyl)benzyl]piperidin-4-yl}methylidene)-4-(but-3-yn-1-ylamino)-1,3-thiazol-2(5H)-one A) 4-(but-3-yn-1-ylamino)-1,3-thiazol-2(5H)-one To a solution of but-3-yn-1-amine hydrochloride (4.88 g) and triethylamine (6.44 mL) in ethanol (60 mL) was added 4-thioxo-1,3-thiazolidin-2-one (3.08 g), and the mixture was stirred at room temperature for 5 hr. The reaction mixture was concentrated, water was added to the residue, and the mixture was extracted with ethyl acetate. The extract was washed with saturated brine, and dried over anhydrous magnesium sulfate, and the solvent was evaporated under reduced pressure. The residue was washed with ethyl acetate to give the title compound (1.95 g).
$^1$H NMR (300 MHz, DMSO-d$_6$) δ 2.44 (2H, td, J=7.0, 2.7 Hz), 2.91 (1H, t, J=2.6 Hz), 3.39-3.48 (2H, m), 4.24 (2H, s), 9.23 (1H, brs).
MS (ESI+): [M+H]$^+$ 169.1.

B) (5Z)-5-({-[2,4-bis(trifluoromethyl)benzyl]piperidin-4-yl}methylidene)-4-(but-3-yn-1-ylamino)-1,3-thiazol-2(5H)-one To a solution of 1-[2,4-bis(trifluoromethyl)benzyl]piperidine-4-carbaldehyde (1.35 g) and 4-(but-3-yn-1-ylamino)-1,3-thiazol-2(5H)-one (1 g) in 2-propanol (20 mL) was added piperidinium acetate (0.58 g). The reaction mixture was stirred at 80° C. for 6 hr and concentrated. The residue was purified by silica gel column chromatography (ethyl acetate/hexane) and recrystallized from ethyl acetate/heptane to give the title compound (0.73 g).
$^1$H NMR (300 MHz, DMSO-d$_6$) δ 1.34-1.58 (2H, m), 1.65-1.85 (2H, m), 2.02-2.30 (3H, m), 2.53-2.55 (2H, m), 2.66-2.83 (2H, m), 2.92 (1H, t, J=2.6 Hz), 3.46-3.58 (2H, m), 3.71 (2H, s), 6.85 (1H, d, J=8.8 Hz), 7.98 (1H, s), 8.01-8.13 (2H, m), 9.33 (1H, t, J=5.4 Hz).
MS (ESI+): [M+H]$^+$ 490.1.

Example 90

1-[2,4-bis(trifluoromethyl)benzyl]-4-{(Z)-[2-oxo-4-(prop-2-yn-1-ylamino)-1,3-thiazol-5(2H)-ylidene]methyl}piperidin-2-one A) 2-oxopiperidine-4-carboxylic acid A solution of 2-hydroxypyridine-4-carboxylic acid (40.0 g) and 10% palladium hydroxide/carbon (8.0 g) in methanol (500 mL) was stirred at 30° C. for 24 hr under a hydrogen atmosphere (50 psi). The reaction mixture was filtered, the catalyst was removed, and the filtrate was concentrated under reduced pressure to give the title compound (38.0 g).
$^1$H NMR (400 MHz, CDCl$_3$) δ 1.64-1.73 (1H, m), 1.92-1.99 (1H, m), 2.20-2.32 (2H, m), 2.71-2.78 (1H, m), 3.11-3.17 (2H, m), 7.50 (1H, s), 12.49 (1H, brs).
MS (ESI+): [M−1]$^+$ 142.

B) 1-[2,4-bis(trifluoromethyl)benzyl]-2-oxopiperidine-4-carboxylic acid

To a solution of 2-oxopiperidine-4-carboxylic acid (21.3 g) in tetrahydrofuran (300 mL) was added 60% sodium hydride (18 g, containing mineral oil) under cooling to 0° C. The reaction mixture was stirred for 30 min under cooling to 0° C. To the reaction mixture was added dropwise 1-(bromomethyl)-2,4-bis(trifluoromethyl)benzene (46 g) under cooling to 0° C., and the mixture was further stirred at 80° C. for 2 days. Water was added to the reaction mixture under cooling to 0° C., and the mixture was extracted with ethyl acetate. To the aqueous layer was further added 10% hydrochloric acid, and the mixture was extracted with ethyl acetate. The extract was dried over sodium sulfate, and the solvent was evaporated under reduced pressure to give the title compound (32 g).

$^1$H NMR (400 MHz, CDCl$_3$) δ 2.03-2.09 (1H, m), 2.18-2.24 (1H, m), 2.81-2.82 (2H, m), 2.97-3.01 (1H, m), 3.28-3.31 (2H, m), 4.66 (1H, d, J=16.0 Hz), 5.10 (1H, d, J=16.0 Hz), 7.50 (1H, d, J=8.0 Hz), 7.78 (1H, d, J=8.0 Hz), 7.91 (1H, s).

MS (ESI+): [M+H]$^+$ 370.

C) 1-[2,4-bis(trifluoromethyl)benzyl]-4-(hydroxymethyl)piperidin-2-one

To a solution of 1-[2,4-bis(trifluoromethyl)benzyl]-2-oxopiperidine-4-carboxylic acid (16.8 g) and triethylamine (9.8 mL) in tetrahydrofuran (200 mL) was added ethyl chloroformate (8.0 mL) under cooling to 0° C. under a nitrogen atmosphere. The reaction mixture was stirred for 1 hr under cooling to 0° C., sodium borohydride (5.18 g) was added, and the mixture was further stirred at 30° C. overnight. Water was added to the reaction mixture, and the mixture was extracted with ethyl acetate. The extract was washed with saturated brine, dried over sodium sulfate, and the solvent was evaporated under reduced pressure. The residue was purified by silica gel column chromatography (ethyl acetate/petroleum ether) to give the title compound (10.9 g).

$^1$H NMR (400 MHz, CDCl$_3$) δ 1.59-1.63 (1H, m), 1.99-2.03 (1H, m), 2.12-2.15 (1H, m), 2.26-2.33 (1H, m), 2.62-2.68 (1H, m), 3.26-3.30 (2H, m), 3.53-3.63 (2H, m), 4.70 (1H, d, J=8.0 Hz), 5.02 (1H, d, J=8.0 Hz), 7.46 (1H, d, J=8.0 Hz), 7.77 (1H, d, J=8.0 Hz), 7.91 (1H, s).

MS (ESI+): [M+H]$^+$ 356.

D) 1-[2,4-bis(trifluoromethyl)benzyl]-2-oxopiperidine-4-carbaldehyde

To a solution of oxalyl chloride (4.5 mL) in dichloromethane (80 mL) was added a solution of dimethyl sulfoxide (7.3 mL) in dichloromethane (50 mL) under cooling to −78° C. The reaction mixture was stirred for 30 min under cooling to −78° C., and to the reaction mixture was added dropwise a solution of 1-[2,4-bis(trifluoromethyl)benzyl]-4-(hydroxymethyl)piperidin-2-one (10 g) in dichloromethane (50 mL). The reaction mixture was stirred for 40 min under cooling to −78° C., triethylamine (19.7 mL) was added, and the mixture was further stirred at room temperature for 30 min. To the reaction mixture was added saturated aqueous ammonium chloride solution, and the mixture was extracted with dichloromethane. The extract was washed with saturated brine, dried over sodium sulfate, and the solvent was evaporated under reduced pressure. The residue was purified by silica gel column chromatography (ethyl acetate/petroleum ether) to give the title compound (3.7 g).

$^1$H NMR (400 MHz, CDCl$_3$) δ 1.98-2.01 (1H, m), 2.19-2.22 (1H, m), 2.75-2.77 (2H, m), 2.94-2.97 (1H, m), 3.24-3.30 (2H, m), 4.67 (1H, d, J=8.2 Hz), 5.07 (1H, d, J=8.2 Hz), 7.46-7.48 (1H, m), 7.78-7.80 (1H, m), 7.91 (1H, s), 9.75 (1H, s).

MS (ESI+): [M+H]$^+$ 354.

E) 1-[2,4-bis(trifluoromethyl)benzyl]-4-{(Z)-[2-oxo-4-(prop-2-yn-1-ylamino)-1,3-thiazol-5(2H)-ylidene]methyl}piperidin-2-one To a solution of 1-[2,4-bis(trifluoromethyl)benzyl]-2-oxopiperidine-4-carbaldehyde (1.00 g) and 4-(prop-2-yn-1-ylamino)-1,3-thiazol-2(5H)-one (0.66 g) in 2-propanol (10 mL) was added piperidinium acetate (0.41 g). The reaction mixture was stirred at 80° C. for 4 hr and concentrated. Ethyl acetate was added to the residue, and the precipitate was removed. Water was added to the filtrate, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) and recrystallized from ethanol/heptane to give the title compound (0.48 g).

$^1$H NMR (300 MHz, DMSO-d$_6$) δ 1.75-1.94 (1H, m), 1.94-2.08 (1H, m), 2.26-2.42 (1H, m), 2.54-2.66 (1H, m), 2.69-2.87 (1H, m), 3.26-3.46 (3H, m), 4.25 (2H, d, J=2.5 Hz), 4.76 (2H, s), 6.91 (1H, d, J=8.7 Hz), 7.63 (1H, d, J=8.7 Hz), 8.00-8.08 (2H, m), 9.65 (1H, s).

MS (ESI+): [M+H]$^+$ 490.1.

Example 91

(5Z)-5-({1-[2,5-bis(trifluoromethyl)benzyl]piperidin-4-yl}methylidene)-4-(prop-2-yn-1-ylamino)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) was added a solution of potassium carbonate (345 mg) and 2-(bromomethyl)-1,4-bis(trifluoromethyl)benzene (0.129 mL) in DMF (2 mL). The reaction mixture was stirred at room temperature overnight, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (156 mg).

$^1$H NMR (300 MHz, DMSO-d$_6$) δ 1.38-1.54 (2H, m), 1.69-1.81 (2H, m), 2.05-2.26 (3H, m), 2.69-2.81 (2H, m), 3.33 (1H, t, J=2.5 Hz), 3.71 (2H, s), 4.23 (2H, d, J=2.5 Hz), 6.92 (1H, d, J=8.9 Hz), 7.86 (1H, d, J=8.0 Hz), 7.96 (1H, d, J=8.0 Hz), 8.12 (1H, s), 9.54 (1H, s).

MS (ESI+): [M+H]$^+$ 476.0.

Example 92

N-[(5Z)-5-({1-[2,4-bis(trifluoromethyl)benzyl]piperidin-4-yl}methylidene)-2-oxo-2,5-dihydro-1,3-thiazol-4-yl]glycine A reaction mixture of tert-butyl N-[(5Z)-5-({1-[2,4-bis(trifluoromethyl)benzyl]piperidin-4-yl}methylidene)-2-oxo-2,5-dihydro-1,3-thiazol-4-yl]glycinate (4.8 g) and 4N hydrogen chloride/ethyl acetate (20 mL) was stirred at room temperature for 2 hr. To the reaction mixture were added saturated aqueous sodium hydrogen carbonate solution and saturated aqueous ammonium chloride solution, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/methanol) and recrystallized from methanol/ethyl acetate to give the title compound (3.00 g).

$^1$H NMR (300 MHz, DMSO-$d_6$) δ 1.35-1.65 (2H, m), 1.67-1.89 (2H, m), 2.00-2.40 (3H, m), 2.63-2.96 (2H, m), 3.56-3.90 (2H, m), 4.11 (2H, d, J=5.8 Hz), 6.92 (1H, d, J=8.7 Hz), 7.81-8.33 (3H, m), 9.58 (1H, brs), 12.93 (1H, brs).

MS (ESI+): [M+H]$^+$ 496.1.

Example 93 tert-butyl N-[(5Z)-5-({1-[2,4-bis(trifluoromethyl)benzyl]piperidin-4-yl}methylidene)-2-oxo-2,5-dihydro-1,3-thiazol-4-yl]glycinate A) tert-butyl N-(2-oxo-2,5-dihydro-1,3-thiazol-4-yl)glycinate To a solution of tert-butyl glycinate hydrochloride (4.00 g) and triethylamine (3.33 mL) in ethanol (20 mL) was added 4-thioxo-1,3-thiazolidin-2-one (2.65 g), and the mixture was stirred at room temperature for 4 hr. The reaction mixture was concentrated under reduced pressure, water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (2.70 g).

$^1$H NMR (300 MHz, DMSO-$d_6$) δ 1.42 (9H, s), 4.01-4.08 (2H, m), 4.30 (2H, s), 9.35 (1H, t, J=5.3 Hz).

MS (ESI+): [M−$C_4H_9$+H]$^+$ 174.9.

B) tert-butyl N-[(5Z)-5-({1-[2,4-bis(trifluoromethyl)benzyl]piperidin-4-yl}methylidene)-2-oxo-2,5-dihydro-1,3-thiazol-4-yl]glycinate To a solution of tert-butyl N-(2-oxo-2,5-dihydro-1,3-thiazol-4-yl)glycinate (4.41 g) and 1-[2,4-bis(trifluoromethyl)benzyl]piperidine-4-carbaldehyde (5.00 g) in 2-propanol (50 mL) was added piperidinium acetate (2.14 g). The reaction mixture was stirred at 70° C. for 3 hr and concentrated under reduced pressure. The residue was purified by silica gel column chromatography (ethyl acetate/hexane) and recrystallized from ethyl acetate/heptane to give the title compound (5.25 g).

$^1$H NMR (300 MHz, DMSO-$d_6$) δ 1.42 (9H, s), 1.45-1.58 (2H, m), 1.69-1.81 (2H, m), 2.04-2.25 (3H, m), 2.69-2.87 (2H, m), 3.71 (2H, s), 4.10 (2H, s), 6.90 (1H, d, J=8.9 Hz), 7.98 (1H, s), 8.01-8.16 (2H, m), 9.51 (1H, s).

MS (ESI+): [M+H]$^+$ 552.0.

Example 94

(5Z)-4-(prop-2-yn-1-ylamino)-5-({-[4-(trifluoromethoxy)benzyl]piperidin-4-yl}methylidene)-1,3-thiazol-2(5H)-one To a solution of (5Z)-5-(piperidin-4-ylmethylidene)-4-(prop-2-yn-1-ylamino)-1,3-thiazol-2(5H)-one dihydrochloride (200 mg) in DMF (3 mL) was added a solution of potassium carbonate (345 mg) and 4-(trifluoromethoxy)benzyl bromide (0.113 mL) in DMF (2 mL). The reaction mixture was stirred at room temperature overnight, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (48.5 mg).

$^1$H NMR (300 MHz, DMSO-$d_6$) δ 1.35-1.51 (2H, m), 1.65-1.77 (2H, m), 1.97-2.12 (3H, m), 2.70-2.82 (2H, m), 3.29-3.33 (1H, m), 3.49 (2H, s), 4.22 (2H, d, J=2.5 Hz), 6.87 (1H, d, J=8.9 Hz), 7.31 (2H, d, J=8.0 Hz), 7.38-7.46 (2H, m), 9.57 (1H, s).

MS (ESI+): [M+H]$^+$ 423.9.

Example 95

$N^2$-[(5Z)-5-({1-[2,4-bis(trifluoromethyl)benzyl]piperidin-4-yl}methylidene)-2-oxo-2,5-dihydro-1,3-thiazol-4-yl]glycinamide A) $N^2$-(2-oxo-2,5-dihydro-1,3-thiazol-4-yl)glycinamide To a solution of glycinamide hydrochloride (5.00 g) and triethylamine (6.30 mL) in ethanol (60 mL) was added 4-thioxo-1,3-thiazolidin-2-one (5.02 g), and the mixture was stirred at room temperature overnight. The precipitate was collected by filtration and washed with ethanol to give the title compound (6.50 g).

$^1$H NMR (300 MHz, DMSO-$d_6$) δ 3.92 (2H, s), 4.28 (2H, s), 7.19 (1H, brs), 7.51 (1H, brs), 9.25 (1H, brs).

MS (ESI+): [M+H]$^+$ 174.1.

B) $N^2$-[(5Z)-5-({1-[2,4-bis(trifluoromethyl)benzyl]piperidin-4-yl}methylidene)-2-oxo-2,5-dihydro-1,3-thiazol-4-yl]glycinamide To a solution of 1-[2,4-bis(trifluoromethyl)benzyl]piperidine-4-carbaldehyde (1.5 g) in 2-propanol (15 mL) were added $N^2$-(2-oxo-2,5-dihydro-1,3-thiazol-4-yl)glycinamide (0.65 g) and piperidinium acetate (0.64 g). The reaction mixture was stirred at 80° C. for 3 hr and concentrated. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/methanol) and recrystallized from ethyl acetate/heptane/ethanol/water to give the title compound (0.60 g).

$^1$H NMR (300 MHz, DMSO-$d_6$) δ 1.41-1.57 (2H, m), 1.75 (2H, d, J=10.6 Hz), 2.05-2.26 (3H, m), 2.77 (2H, d, J=11.5 Hz), 3.71 (2H, s), 3.99 (2H, s), 6.90 (1H, d, J=8.9 Hz), 7.17 (1H, s), 7.54 (1H, s), 7.98 (1H, s), 8.04-8.10 (2H, m), 9.37 (1H, s).

MS (ESI+): [M+H]$^+$ 495.2.

Example 96

4-[(4-{(Z)-[2-oxo-4-(prop-2-yn-1-ylamino)-1,3-thiazol-5(2H)-ylidene]methyl}piperidin-1-yl)methyl]-2-(trifluoromethyl)benzonitrile To a solution of triethylamine (1.38 mL) and 4-formyl-2-(trifluoromethyl)benzonitrile (593 mg) in DMF (10 mL) was added (5Z)-5-(piperidin-4-ylmethylidene)-4-(prop-2-yn-1-ylamino)-1,3-thiazol-2(5H)-one dihydrochloride (800 mg). The reaction mixture was stirred at room temperature for 1 hr, and sodium triacetoxyborohydride (2.1 g) was added. The reaction mixture was stirred at room temperature for 3 hr, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (250 mg).

$^1$H NMR (300 MHz, DMSO-$d_6$) δ 1.34-1.55 (2H, m), 1.66-1.79 (2H, m), 1.98-2.17 (3H, m), 2.76 (2H, d, J=11.7 Hz), 3.33 (1H, brs), 3.67 (2H, s), 4.22 (2H, d, J=2.5 Hz), 6.88 (1H, d, J=8.9 Hz), 7.84 (1H, d, J=8.1 Hz), 7.92 (1H, s), 8.14 (1H, d, J=7.9 Hz), 9.56 (1H, s).

MS (ESI+): [M+H]$^+$ 433.1.

Example 97

(5Z)-5-({1-[2,4-bis(trifluoromethyl)benzyl]piperidin-4-yl}methylidene)-4-[(isoxazol-3-ylmethyl)amino]-1,3-thiazol-2(5H)-one A) 4-[(isoxazol-3-ylmethyl)amino]thiazol-2(5H)-one To a solution of 4-thioxo-1,3-thiazolidin-2-one (700 mg) in ethanol (20 mL) were added (isoxazol-3-ylmethyl)amine hydrochloride (707 mg) and N-ethyl-N-(1-methylethyl)propan-2-amine (1.42 mL), and the mixture was heated under reflux overnight. The reaction mixture was concentrated, the residue was purified by silica gel column chromatography (methanol/ethyl acetate), and the obtained powder was washed with ethyl acetate to give the title compound (513 mg).

$^1$H NMR (300 MHz, DMSO-$d_6$) δ 4.31 (2H, s), 4.65 (2H, s), 6.58 (1H, d, J=1.6 Hz), 8.90 (1H, d, J=1.6 Hz), 9.58 (1H, brs).

MS (ESI+): [M+H]$^+$ 198.0.

B) (5Z)-5-({1-[2,4-bis(trifluoromethyl)benzyl]piperidin-4-yl}methylidene)-4-[(isoxazol-3-ylmethyl)amino]-1,3-thiazol-2(5H)-one To a solution of 1-[2,4-bis(trifluoromethyl)benzyl]piperidine-4-carbaldehyde (413 mg) in 2-propanol (5 mL) were added 4-[(isoxazol-3-ylmethyl)amino]thiazol-2(5H)-one (480 mg) and piperidinium acetate (90 mg). The reaction mixture was stirred at 80° C. overnight, and the solvent was evaporated under reduced pressure. The residue was purified by silica gel column chromatography (ethyl acetate/hexane) and recrystallized from ethyl acetate/heptane to give the title compound (454 mg).

$^1$H NMR (300 MHz, DMSO-$d_6$) δ 1.38-1.57 (2H, m), 1.67-1.81 (2H, m), 2.06-2.25 (3M, m), 2.69-2.82 (2H, m), 3.71 (2H, s), 4.73 (2H, s), 6.59 (1H, d, J=1.7 Hz), 6.91 (1H, d, J=8.9 Hz), 7.98 (1H, s), 8.01-8.11 (2H, m), 8.90 (1H, d, J=1.7 Hz), 9.70 (1H, s).

MS (ESI+): [M+H]$^+$ 519.0.

Example 98

(5Z)-5-({1-[2,4-bis(trifluoromethyl)benzyl]piperidin-4-yl}methylidene)-4-{[3-(2-oxopyrrolidin-1-yl)propyl]amino}-1,3-thiazol-2(5H)-one A) 4-{[3-(2-oxopyrrolidin-1-yl)propyl]amino}thiazol-2(5H)-one To a solution of 1-(3-aminopropyl)-2-pyrrolidone (1.12 mL) in ethanol (40 mL) was added 4-thioxo-1,3-thiazolidin-2-one (1.00 g), and the mixture was stirred at room temperature overnight. The precipitate was collected by filtration and washed with ethyl acetate to give the title compound (1.56 g).

$^1$H NMR (300 MHz, DMSO-$d_6$) δ 1.65-1.79 (2H, m), 1.84-2.00 (2H, m), 2.14-2.27 (2H, m), 3.15-3.39 (6H, m), 4.23 (2H, s), 9.03 (1H, brs).

MS (ESI+): [M+H]$^+$ 242.0.

B) (5Z)-5-({1-[2,4-bis(trifluoromethyl)benzyl]piperidin-4-yl}methylidene)-4-{[3-(2-oxopyrrolidin-1-yl)propyl]amino}-1,3-thiazol-2(5H)-one To a solution of 1-[2,4-bis(trifluoromethyl)benzyl]piperidine-4-carbaldehyde (500 mg) in 2-propanol (10 mL) were added 4-([3-(2-oxopyrrolidin-1-yl)propyl]amino)thiazol-2(5H)-one (866 mg) and piperidinium acetate (107 mg). The reaction mixture was stirred at 60° C. overnight, and the solvent was evaporated under reduced pressure. The residue was purified by silica gel column chromatography (ethyl acetate/hexane) and recrystallized from ethyl acetate/heptane to give the title compound (439 mg).

$^1$H NMR (300 MHz, DMSO-$d_6$) δ 1.39-1.56 (2H, m), 1.68-1.84 (4H, m), 1.85-1.98 (2H, m), 2.03-2.27 (5H, m), 2.70-2.82 (2H, m), 3.23 (2H, t, J=6.9 Hz), 3.29-3.44 (4H, m), 3.71 (2H, s), 6.81 (1H, d, J=8.9 Hz), 7.98 (1H, s), 8.01-8.12 (2H, m), 9.12 (1H, s).

MS (ESI+): [M+H]$^+$ 563.0.

Example 99

(5Z)-5-({1-[2-(pentafluorosulfanyl)benzyl]piperidin-4-yl}methylidene)-4-(prop-2-yn-1-ylamino)-1,3-thiazol-2(5H)-one maleate A) (5Z)-5-({1-[2-(pentafluorosulfanyl)benzyl]piperidin-4-yl}methylidene)-4-(prop-2-yn-1-ylamino)-1,3-thiazol-2(5H)-one To a solution of 2-(bromomethyl)-1-(pentafluorosulfanyl)benzene (213 mg) in DMF (5 mL) were added (5Z)-5-(piperidin-4-ylmethylidene)-4-(prop-2-yn-1-ylamino)-1,3-thiazol-2(5H)-one dihydrochloride (210 mg) and potassium carbonate (362 mg). The reaction mixture was stirred at room temperature overnight, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (164 mg).

$^1$H NMR (300 MHz, DMSO-$d_6$) δ 1.35-1.52 (2H, m), 1.66-1.78 (2H, m), 2.08 (3H, t, J=10.4 Hz), 2.70-2.83 (2H, m), 3.31-3.34 (1H, m), 3.59 (2H, s), 4.22 (2H, d, J=2.4 Hz), 6.88 (1H, d, J=9.0 Hz), 7.54-7.64 (2H, m), 7.75-7.84 (2H, m), 9.56 (1H, brs).

MS (ESI+): [M+H]$^+$ 466.0.

B) (5Z)-5-({1-[2-(pentafluorosulfanyl)benzyl]piperidin-4-yl}methylidene)-4-(prop-2-yn-1-ylamino)-1,3-thiazol-2 (H)-one maleate To a solution of (5Z)-5-({1-[2-(pentafluorosulfanyl)benzyl]piperidin-4-yl}methylidene)-4-(prop-2-yn-1-ylamino)-1,3-thiazol-2(5H)-one (155 mg) in ethanol (3 mL) was added a solution of maleic acid (39 mg) in ethanol (2 mL). The reaction mixture was stirred at room temperature for 1 hr, and the solvent was evaporated under reduced pressure. The residue was recrystallized from ethanol/heptane to give the title compound (99 mg).

$^1$H NMR (300 MHz, DMSO-$d_6$) δ 1.48-1.71 (2H, m), 1.84-1.98 (2H, m), 2.27 (1H, brs), 2.87 (2H, brs), 3.26 (2H, brs), 3.34 (1H, t, J=2.5 Hz), 4.11-4.37 (2H, m), 4.24 (2H, dd, J=5.2, 2.5 Hz), 6.08 (2H, s), 6.81 (1H, d, J=5.7 Hz), 7.64-7.81 (2H, m), 7.91-8.11 (2H, m), 9.58 (1H, t, J=5.3 Hz).

Example 100

(5Z)-5-({1-[4-methoxy-2-(trifluoromethyl)benzyl]piperidin-4-yl}methylidene)-4-(prop-2-yn-1-ylamino)-1,3-thiazol-2(5H)-one maleate A) (5Z)-5-({1-[4-methoxy-2-(trifluoromethyl)benzyl]piperidin-4-yl}methylidene)-4-(prop-2-yn-1-ylamino)-1,3-thiazol-2(5H)-one To a solution of 4-methoxy-2-(trifluoromethyl)benzyl bromide (516 mg) in DMF (5 mL) were added (5Z)-5-(piperidin-4-ylmethylidene)-4-(prop-2-yn-1-ylamino)-1,3-thiazol-2(5H)-one dihydrochloride (500 mg) and potassium carbonate (862 mg). The reaction mixture was stirred at room temperature overnight, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (468 mg).

$^1$H NMR (300 MHz, DMSO-$d_6$) δ 1.35-1.51 (2H, m), 1.66-1.77 (2H, m), 2.02-2.16 (3H, m), 2.68-2.78 (2H, m), 3.32 (1H, t, J=2.5 Hz), 3.53 (2H, s), 3.82 (3H, s), 4.23 (2H, d, J=2.3 Hz), 6.90 (1H, d, J=8.9 Hz), 7.17 (1H, d, J=2.6 Hz), 7.23 (1H, dd, J=8.6, 2.5 Hz), 7.64 (1H, d, J=8.5 Hz), 9.56 (1H, s).

B) (5Z)-5-({1-[4-methoxy-2-(trifluoromethyl)benzyl]piperidin-4-yl}methylidene)-4-(prop-2-yn-1-ylamino)-1,3-thiazol-2(5H)-one maleate To a solution of (5Z)-5-({1-[4-methoxy-2-(trifluoromethyl)benzyl]piperidin-4-yl}methylidene)-4-(prop-2-yn-1-ylamino)-1,3-thiazol-2(5H)-one (460 mg) in ethanol (2 mL) was added a solution of maleic acid (123 mg) in ethanol (5 mL). The reaction mixture was stirred at room temperature for 2 hr, and the solvent was evaporated under reduced pressure. The residue was recrystallized from ethanol/heptane to give the title compound (393 mg).

$^1$H NMR (300 MHz, DMSO-$d_6$) δ 1.49-1.70 (2H, m), 1.80-1.94 (2H, m), 2.30 (1H, brs), 2.87 (2H, brs), 3.14 (3H, brs), 3.34 (1H, t, J=2.5 Hz), 3.86 (3H, s), 4.10 (1H, brs), 4.24 (2H, dd, J=5.2, 2.5 Hz), 6.11 (2H, s), 6.83 (1H, d, J=7.9 Hz), 7.28 (1H, s), 7.35 (1H, d, J=8.7 Hz), 7.75 (1H, d, J=8.7 Hz), 9.58 (1H, t, J=5.3 Hz).

Example 101

(5Z)-5-({1-[2,4-bis(trifluoromethyl)benzyl]piperidin-4-yl}methylidene)-4-({[4-(hydroxymethyl)tetrahydro-2H-pyran-4-yl]methyl}amino)-1,3-thiazol-2(5H)-one A) 4-{[(4-(hydroxymethyl)tetrahydro-2H-pyran-4-ylmethyl]amino}thiazol-2(5H)-one To a solution of 4-thioxo-1,3-thiazolidin-2-one (898 mg) in ethanol (15 mL) was added a solution (5 mL) of [4-(aminomethyl)tetrahydro-2H-pyran-4-yl]methanol (1.00 g) in ethanol, and the mixture was heated under reflux overnight. The reaction mixture was cooled to room temperature, the precipitate was collected by filtration, and the obtained powder was washed with ethyl acetate to give the title compound (1.44 g).

$^1$H NMR (300 MHz, DMSO-$d_6$) δ 1.28-1.45 (4H, m), 3.28-3.35 (2H, m), 3.42 (2H, d, J=6.1 Hz), 3.47-3.64 (4H, m), 4.28 (2H, s), 4.68 (1H, t, J=5.8 Hz), 8.93 (1H, t, J=5.7 Hz).

B) (5Z)-5-({1-[2,4-bis(trifluoromethyl)benzyl]piperidin-4-yl}methylidene)-4-({[4-(hydroxymethyl)tetrahydro-2H-pyran-4-yl]methyl}amino)-1,3-thiazol-2(5H)-one To a solution of 1-[2,4-bis(trifluoromethyl)benzyl]piperidine-4-carbaldehyde (972 mg) in 2-propanol (20 mL) were added 4-({[4-(hydroxymethyl)tetrahydro-2H-pyran-4-yl]methyl}amino)thiazol-2(5H)-one (1.05 g) and piperidinium acetate (425 mg). The reaction mixture was stirred at 80° C. overnight and concentrated under reduced pressure. The residue was purified by silica gel column chromatography (ethyl acetate/hexane) and recrystallized from ethyl acetate/heptane to give the title compound (774 mg).

$^1$H NMR (300 MHz, DMSO-$d_6$) δ 1.29-1.57 (6H, m), 1.68-1.81 (2H, m), 2.02-2.23 (3H, m), 2.72-2.83 (2H, m), 3.33 (2H, brs), 3.51 (2H, s), 3.52-3.66 (4H, m), 3.71 (2H, s), 4.73 (1H, brs), 6.94 (1H, d, J=8.8 Hz), 7.98 (1H, s), 8.01-8.13 (2H, m), 8.93 (1H, brs).

MS (ESI+): [M+H]$^+$ 566.1.

Example 102

(5Z)-5-({(3aR,5r,6aS)-2-[2,4-bis(trifluoromethyl)benzyl]octahydrocyclopenta[c]pyrrol-5-yl}methylidene)-4-(prop-2-yn-1-ylamino)-1,3-thiazol-2(5H)-one A) (3aR,6aS)-octahydrocyclopenta[c]pyrrol-5-ylmethanol hydrochloride A solution of tert-butyl(3aR,6aS)-5-(hydroxymethyl)hexahydrocyclopenta[c]pyrrole-2(1H)-carboxylate (2.24 g) (WO 2006/14325 A2, 2006) in 4N hydrogen chloride/ethyl acetate (10 mL) was stirred at room temperature for 1 hr. The reaction mixture was concentrated to give the title compound (1.65 g).

$^1$H NMR (300 MHz, DMSO-$d_6$) δ 0.87-1.27 (2H, m), 1.37-1.66 (1H, m), 1.80-2.09 (2H, m), 2.61-2.82 (2H, m), 2.90-3.02 (2H, m), 3.03-3.16 (2H, m), 3.25-3.44 (2H, m), 8.89-9.35 (2H, m).

B) {(3aR,6aS)-2-[2,4-bis(trifluoromethyl)benzyl]octahydrocyclopenta[c]pyrrol-5-yl}methanol To a solution of (3aR,6aS)-octahydrocyclopenta[c]pyrrol-5-ylmethanol hydrochloride (0.79 g) and potassium carbonate (1.53 g) in DMF (15 ml) was added 1-(bromomethyl)-2,4-bis(trifluoromethyl)benzene (1.5 g). The reaction mixture was stirred at room temperature for 3 hr, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (1.4 g).

¹H NMR (300 MHz, CDCl₃) δ 1.04-1.21 (2H, m), 1.41-1.68 (2H, m), 1.91-2.13 (2H, m), 2.28 (2H, dd, J=9.0, 6.4 Hz), 2.46-2.74 (4H, m), 3.54-3.68 (2H, m), 3.72-3.80 (2H, m), 7.78 (1H, d, J=8.2 Hz), 7.86 (1H, s), 7.98 (1H, d, J=8.2 Hz).
MS (ESI+): [M+H]⁺ 368.2.

C) (3aR,6aS)-2-[2,4-bis(trifluoromethyl)benzyl]octahydrocyclopenta[c]pyrrole-5-carbaldehyde To a solution of {(3aR,6aS)-2-[2,4-bis(trifluoromethyl)benzyl]octahydrocyclopenta[c]pyrrol-5-yl}methanol (1.4 g) and triethylamine (3.19 mL) in DMSO (7 mL) and ethyl acetate (7 mL) was added sulfur trioxide pyridine complex (1.82 g) under cooling to 0° C. The reaction mixture was stirred at room temperature for 1 hr. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (900 mg).
¹H NMR (300 MHz, CDCl₃) δ1.61-1.81 (2H, m), 1.94-2.18 (2H, m), 2.24-2.47 (2H, m), 2.52-3.08 (5H, m), 3.75 (2H, brs), 7.68-7.85 (1H, m), 7.87 (1H, s), 7.89-8.01 (1H, m), 9.53-9.71 (1H, m).
MS (ESI+): [M+H]⁺ 366.0.

D) (5Z)-5-({(3aR,5r,6aS)-2-[2,4-bis(trifluoromethyl)benzyl]octahydrocyclopenta[c]pyrrol-5-yl}methylidene)-4-(prop-2-yn-1-ylamino)-1,3-thiazol-2(5H)-one To a solution of (3aR,6aS)-2-[2,4-bis(trifluoromethyl)benzyl]octahydrocyclopenta[c]pyrrole-5-carbaldehyde (1.04 g) and 4-(prop-2-yn-1-ylamino)-1,3-thiazol-2(5H)-one (0.57 g) in 2-propanol (10 mL) was added piperidinium acetate (0.41 g). The reaction mixture was stirred at 70° C. for 3 hr and concentrated. The residue was subjected to silica gel column chromatography (ethyl acetate/hexane) to give the title crude product and (5Z)-5-({(3aR,5s,6aS)-2-[2,4-bis(trifluoromethyl)benzyl]octahydrocyclopenta[c]pyrrol-5-yl}methylidene)-4-(prop-2-yn-1-ylamino)-1,3-thiazol-2(5H)-one (716 mg). The title crude product was recrystallized from ethyl acetate/isopropyl ether/heptane to give the title compound (452 mg).
¹H NMR (300 MHz, CDCl₃) δ1.17-1.33 (2H, m), 2.04-2.43 (5H, m), 2.54-2.66 (4H, m), 3.32-3.34 (1H, m), 3.80 (2H, s), 4.22 (2H, d, J=2.5 Hz), 6.94 (1H, d, J=8.9 Hz), 7.96-8.03 (2H, m), 8.04-8.11 (1H, m), 9.55 (1H, s).
MS (ESI+): [M+H]⁺ 502.0.

Example 103

(5Z)-5-({(3aR,5s,6aS)-2-[2,4-bis(trifluoromethyl)benzyl]octahydrocyclopenta[c]pyrrol-5-yl}methylidene)-4-(prop-2-yn-1-ylamino)-1,3-thiazol-2(5H)-one maleate

A) (5Z)-5-({(3aR,5s,6aS)-2-[2,4-bis(trifluoromethyl)benzyl]octahydrocyclopenta[c]pyrrol-5-yl}methylidene)-4-(prop-2-yn-1-ylamino)-1,3-thiazol-2(5H)-one To a solution of (3aR,6aS)-2-[2,4-bis(trifluoromethyl)benzyl]octahydrocyclopenta[c]pyrrole-5-carbaldehyde (1.04 g) and 4-(prop-2-yn-1-ylamino)-1,3-thiazol-2(5H)-one (0.57 g) in 2-propanol (10 mL) was added piperidinium acetate (0.41 g). The reaction mixture was stirred at 70° C. for 3 hr and concentrated. The residue was subjected to silica gel column chromatography (ethyl acetate/hexane) to give (5Z)-5-({(3aR,5r,6aS)-2-[2,4-bis(trifluoromethyl)benzyl]octahydrocyclopenta[c]pyrrol-5-yl}methylidene)-4-(prop-2-yn-1-ylamino)-1,3-thiazol-2(5H)-one and the title compound (716 mg).
¹H NMR (300 MHz, CDCl₃) δ 1.58-1.71 (2H, m), 1.78-1.88 (2H, m), 2.40 (1H, t, J=2.5 Hz), 2.46 (2H, dd, J=9.2, 2.2 Hz), 2.55-2.65 (2H, m), 2.71-2.83 (2H, m), 2.92-3.07 (1H, m), 3.75 (2H, s), 4.39 (2H, dd, J=4.2, 2.5 Hz), 5.88 (1H, brs), 6.14 (1H, d, J=9.0 Hz), 7.82 (1H, d, J=8.5 Hz), 7.88 (1H, s), 7.97 (1H, d, J=8.1 Hz).
MS (ESI+): [M+H]⁺ 502.0.

B) (5Z)-5-({(3aR,5s,6aS)-2-[2,4-bis(trifluoromethyl)benzyl]octahydrocyclopenta[c]pyrrol-5-yl}methylidene)-4-(prop-2-yn-1-ylamino)-1,3-thiazol-2(5H)-one maleate To a solution of (5Z)-5-({(3aR,5s,6aS)-2-[2,4-bis(trifluoromethyl)benzyl]octahydrocyclopenta[c]pyrrol-5-yl}methylidene)-4-(prop-2-yn-1-ylamino)-1,3-thiazol-2(5H)-one (716 mg) in ethanol (10 mL) was added maleic acid (166 mg). The reaction mixture was concentrated, and the residue was recrystallized from heptane/ethanol to give the title compound (0.68 g).
¹H NMR (300 MHz, DMSO-d₆) δ 1.30-1.91 (4H, m), 2.56-2.99 (7H, m), 3.33 (1H, t, J=2.5 Hz), 3.83-4.90 (4H, m), 6.17 (2H, s), 6.87 (1H, d, J=8.8 Hz), 7.99-8.10 (2H, m), 8.10-8.23 (1H, m), 9.54 (1H, t, J=5.3 Hz).
MS (ESI+): [M−C₄H₄O₄+H]⁺ 502.0.

Example 104 ethyl N-[(5Z)-5-({1-[2,4-bis(trifluoromethyl)benzyl]piperidin-4-yl}methylidene)-2-oxo-2,5-dihydro-1,3-thiazol-4-yl]glycinate

A) ethyl N-(2-oxo-2,5-dihydro-1,3-thiazol-4-yl)glycinate

To a solution of ethyl glycinate hydrochloride (5.00 g) and triethylamine (4.99 mL) in ethanol (60 mL) was added 4-thioxo-1,3-thiazolidin-2-one (3.98 g), and the mixture was stirred at room temperature for 4 hr. The reaction mixture was concentrated, water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (3.84 g).
¹H NMR (300 MHz, DMSO-d₆) δ 1.21 (3H, t, J=7.1 Hz), 4.09-4.21 (4H, m), 4.32 (2H, s), 9.43 (1H, t, J=5.2 Hz).
MS (ESI+): [M+H]⁺ 203.0.

B) ethyl N-[(5Z)-5-({1-[2,4-bis(trifluoromethyl)benzyl]piperidin-4-yl}methylidene)-2-oxo-2,5-dihydro-1,3-thiazol-4-yl]glycinate To a solution of 1-[2,4-bis(trifluoromethyl)benzyl]piperidine-4-carbaldehyde (2.0 g) and ethyl N-(2-oxo-2,5-dihydro-1,3-thiazol-4-yl)glycinate (1.55 g) in 2-propanol (20 mL) was added piperidinium acetate (0.86 g). The reaction mixture was stirred at 70° C. for 2 hr and concentrated. The residue was purified by silica gel column chromatography (ethyl acetate/hexane) and recrystallized from ethyl acetate/heptane to give the title compound (2.62 g).

$^1$H NMR (300 MHz, DMSO-d$_6$) δ 1.21 (3H, t, J=7.1 Hz), 1.38-1.59 (2H, m), 1.76 (2H, d, J=11.0 Hz), 2.07-2.24 (3H, m), 2.77 (2H, d, J=11.5 Hz), 3.71 (2H, s), 4.07-4.26 (4H, m), 6.92 (1H, d, J=8.9 Hz), 7.98 (1H, s), 8.06-8.21 (2H, m), 9.58 (1H, s).

MS (ESI+): [M+H]$^+$ 524.0.

Example 105

(5Z)-5-({1-[2,4-bis(trifluoromethyl)benzyl]piperidin-4-yl}methylidene)-4-[(trans-2-hydroxycyclohexyl)amino]-1,3-thiazol-2(5H)-one A) 4-[(trans-2-hydroxycyclohexyl)amino]thiazol-2(5H)-one To a solution of trans-2-aminocyclohexanol (1.00 g) in ethanol (50 mL) was added 4-thioxo-1,3-thiazolidin-2-one (1.19 g), and the mixture was heated under reflux overnight. The reaction mixture was cooled to room temperature, the precipitate was removed, and the solvent of the filtrate was evaporated under reduced pressure. The residue was purified by silica gel column chromatography (NH, tetrahydrofuran). The obtained powder was washed with ethyl acetate to give the title compound (554 mg).

$^1$H NMR (300 MHz, DMSO-d$_6$) δ 1.10-1.31 (4H, m), 1.54-1.71 (2H, m), 1.79-1.95 (2H, m), 3.27-3.40 (1H, m), 3.49-3.63 (1H, m), 4.20 (2H, s), 4.76 (1H, d, J=4.9 Hz), 9.00 (1H, d, J=7.1 Hz).

B) (5Z)-5-({1-[2,4-bis(trifluoromethyl)benzyl]piperidin-4-yl}methylidene)-4-{[trans-2-hydroxycyclohexyl]amino}-1,3-thiazol-2(5H)-one To a solution of 1-[2,4-bis(trifluoromethyl)benzyl]piperidine-4-carbaldehyde (549 mg) in 2-propanol (5 mL) were added a solution of 4-[(trans-2-hydroxycyclohexyl)amino]thiazol-2(5H)-one (520 mg) in 2-propanol (5 mL) and piperidinium acetate (240 mg). The reaction mixture was stirred at 80° C. overnight, and the solvent was evaporated under reduced pressure. The residue was purified by silica gel column chromatography (ethyl acetate/hexane) and recrystallized from ethyl acetate/heptane to give the title compound (557 mg).

$^1$H NMR (300 MHz, DMSO-d$_6$) δ 1.12-1.35 (4H, m), 1.40-1.57 (2H, m), 1.66 (2H, brs), 1.70-1.81 (2H, m), 1.82-1.98 (2H, m), 2.02-2.25 (3H, m), 2.71-2.84 (2H, m), 3.39-3.54 (1H, m), 3.63-3.78 (3H, m), 4.81 (1H, d, J=5.6 Hz), 6.90 (1H, d, J=8.8 Hz), 7.98 (1H, s), 8.01-8.12 (2H, m), 8.87 (1H, d, J=5.9 Hz).

MS (ESI+): [M+H]$^+$ 536.1.

Example 106

1-[2,4-bis(trifluoromethyl)benzyl]-5-{(Z)-[2-oxo-4-(prop-2-yn-1-ylamino)-1,3-thiazol-5(2H)-ylidene]methyl}azepan-2-one A) ethyl 4-(hydroxyimino)cyclohexanecarboxylate To a solution of hydroxyamine hydrochloride (15.3 g) and sodium acetate (24.1 g) in water (60 mL) was added ethyl 4-oxocyclohexanecarboxylate (25.0 g) over 20 min. The reaction mixture was stirred at room temperature overnight, and extracted with tert-butyl methyl ether. The extract was washed with saturated brine, and dried over magnesium sulfate to give the title compound (27.2 g).

$^1$H NMR (400 MHz, CDCl$_3$) δ 1.26 (3H, t, J=7.2 Hz), 1.70-1.79 (2H, m), 2.04-2.21 (4H, m), 2.40-2.45 (1H, m), 2.54-2.59 (1H, m), 3.13-3.17 (1H, m), 4.16 (2H, q, J=7.2 Hz), 8.18 (1H, brs).

B) ethyl 4-({[(4-methylphenyl)sulfonyl]oxy}imino)cyclohexanecarboxylate

To a solution of ethyl 4-(hydroxyimino)cyclohexanecarboxylate (1.85 g) in pyridine (10 mL) was added 4-methylbenzenesulfonyl chloride (2.28 g) over 5-10 min at −20° C. The reaction mixture was stirred for several hours while allowing to gradually warm to 0° C. The reaction mixture was added to ice water, and the precipitate was collected by filtration, and washed with ice water to give the title compound (2.54 g).

$^1$H NMR (400 MHz, CDCl$_3$) δ 1.25 (3H, t, J=6.8 Hz), 1.60-2.53 (11H, m), 3.00-3.03 (1H, m), 4.15 (2H, q, J=6.8 Hz), 7.33-7.35 (2H, m), 7.84-7.86 (2H, m).

C) ethyl 7-oxoazepane-4-carboxylate

A solution of ethyl 4-({[(4-methylphenyl)sulfonyl]oxy}imino)cyclohexanecarboxylate (22.0 g) in acetic acid (150 mL) was stirred at room temperature for 1 hr, and the reaction mixture was concentrated under reduced pressure. Saturated aqueous sodium hydrogen carbonate solution was added, and the mixture was extracted with ethyl acetate. The extract was dried over anhydrous sodium sulfate, and the solvent was evaporated under reduced pressure to give the title compound (8.62 g).

$^1$H NMR (400 MHz, CDCl$_3$) δ 1.26 (3H, t, J=7.2 Hz), 1.76-1.89 (2H, m), 2.01-2.11 (2H, m), 2.42-2.64 (3H, m), 3.18-3.38 (2H, m), 4.15 (2H, q, J=7.2 Hz), 6.86 (1H, brs).

D) ethyl 1-[2,4-bis(trifluoromethyl)benzyl]-7-oxoazepane-4-carboxylate

To a solution of ethyl 7-oxoazepane-4-carboxylate (9.78 g) in THF (250 mL) was added 60% sodium hydride (2.33 g, containing mineral oil) under ice-cooling. The reaction mixture was stirred for 5 min under ice-cooling, and 1-(bromomethyl)-2,4-bis(trifluoromethyl)benzene (17.9 g) was added. The reaction mixture was stirred at room temperature overnight, water was added, and the mixture was extracted with ethyl acetate. The extract was dried over anhydrous sodium sulfate, and the solvent was evaporated under reduced pressure. The residue was purified by silica gel column chromatography (ethyl acetate/petroleum ether) to give the title compound (14.9 g).

$^1$H NMR (400 MHz, CDCl$_3$) δ 1.19 (3H, t, J=7.2 Hz), 1.68-1.94 (3H, m), 2.05-2.10 (1H, m), 2.55-2.62 (2H, m), 2.70-2.76 (1H, m), 3.28-3.32 (2H, m), 4.08 (2H, q, J=7.2 Hz), 4.67 (1H, d, J=16.4 Hz), 4.88 (1H, d, J=16.0 Hz), 7.43 (1H, d, J=8.0 Hz), 7.70 (1H, d, J=8.4 Hz), 7.83 (1H, s).

E) 1-[2,4-bis(trifluoromethyl)benzyl]-5-(hydroxymethyl)azepan-2-one

To a solution of ethyl 1-[2,4-bis(trifluoromethyl)benzyl]-7-oxoazepane-4-carboxylate (14.8 g) in THF (400 mL) was added lithium borohydride (4.5 g). The reaction mixture was stirred at 50° C. for 1 hr, water was added, and the mixture was extracted with ethyl acetate. The extract was dried over anhydrous sodium sulfate, and the solvent was evaporated under reduced pressure to give the title compound (12.0 g).

$^1$H NMR (400 MHz, CDCl$_3$) δ 1.21-1.30 (1H, m), 1.33-1.43 (1H, m), 1.75-1.82 (1H, m), 1.89-1.95 (1H, m), 2.00-2.04 (1H, m), 2.65-2.77 (2H, m), 3.16-3.21 (1H, m), 3.46-3.55 (3H, m), 4.58 (1H, d, J=16.8 Hz), 5.12 (1H, d, J=16.8 Hz), 7.51 (1H, d, J=8.0 Hz), 7.77 (1H, d, J=8.0 Hz), 7.90 (1H, s).

F) 1-[2,4-bis(trifluoromethyl)benzyl]-7-oxoazepane-4-carbaldehyde

To a solution of DMSO (1.40 g) in dichloromethane (100 mL) was slowly added a solution of oxalyl chloride (2.48 g) in dichloromethane (200 mL) at −78° C. The reaction mixture was stirred for 5 min, a solution of 1-[2,4-bis(trifluoromethyl)benzyl]-5-(hydroxymethyl)azepan-2-one (6.0 g) in dichloromethane (100 mL) was added dropwise, and the mixture was stirred for 15 min. Triethylamine (8.2 g) was added and the mixture was allowed to warm to room temperature. Saturated aqueous ammonium chloride solution was added, and the mixture was extracted with ethyl acetate. The extract was dried over anhydrous sodium sulfate, and the solvent was evaporated under reduced pressure. The residue was purified by silica gel column chromatography (ethyl acetate/petroleum ether) to give the title compound (2.76 g).

$^1$H NMR (400 MHz, CDCl$_3$) δ 1.72-1.80 (1H, m), 1.84-1.93 (1H, m), 2.00-2.04 (1H, m), 2.19-2.24 (1H, m), 2.57-2.63 (1H, m), 2.67-2.81 (2H, m), 3.32-3.44 (2H, m), 4.78 (1H, d, J=16.4 Hz), 4.91 (1H, d, J=16.0 Hz), 7.49 (1H, d, J=8.0 Hz), 7.77 (1H, d, J=8.4 Hz), 7.91 (1H, s), 9.68 (1H, s).

MS (ESI+): [M+H]$^+$ 368.1.

G) 1-[2,4-bis(trifluoromethyl)benzyl]-5-{(Z)-[2-oxo-4-(prop-2-yn-1-ylamino)-1,3-thiazol-5(2H)-ylidene]methyl}azepan-2-one To a solution of 1-[2,4-bis(trifluoromethyl)benzyl]-7-oxoazepane-4-carbaldehyde (1.00 g) and 4-(prop-2-yn-1-ylamino)-1,3-thiazol-2(5H)-one (0.63 g) in 2-propanol (10 mL) was added piperidinium acetate (0.40 g). The reaction mixture was stirred at 80° C. for 2 hr and concentrated. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane) to give the title compound (0.48 g).

$^1$H NMR (300 MHz, CDCl$_3$) δ 1.34-1.70 (2H, m), 1.87-2.15 (2H, m), 2.31-2.37 (1H, m), 2.38-2.53 (1H, m), 2.70-2.89 (2H, m), 3.23 (1H, dd, J=15.3, 5.9 Hz), 3.59 (1H, dd, J=15.6, 10.8 Hz), 4.36 (2H, dd, J=5.0, 2.5 Hz), 4.57 (1H, d, J=16.3 Hz), 5.15 (1H, d, J=16.3 Hz), 6.21 (1H, d, J=9.1 Hz), 6.67 (1H, t, J=4.9 Hz), 7.51 (1H, d, J=8.2 Hz), 7.79 (1H, d, J=8.1 Hz), 7.92 (1H, s).

MS (ESI+): [M+H]$^+$ 504.2.

Example 107

N$^2$-[(5Z)-5-({1-[2,4-bis(trifluoromethyl)benzyl]piperidin-4-yl}methylidene)-2-oxo-2,5-dihydro-1,3-thiazol-4-yl]-N-methylglycinamide A) N-methyl-N$^2$-(2-oxo-2,5-dihydro-1,3-thiazol-4-yl)glycinamide To a solution of N-methylglycinamide (4.06 g) in ethanol (22 mL) was added 4-thioxo-1,3-thiazolidin-2-one (5.11 g), and the mixture was stirred at room temperature for 4 hr. The precipitate was collected by filtration and washed with ethanol to give the title compound (6.26 g).

$^1$H NMR (300 MHz, DMSO-d$_6$) δ 2.61 (3H, d, J=4.5 Hz), 3.94 (2H, d, J=5.5 Hz), 4.28 (2H, s), 7.84-8.07 (1H, m), 9.29 (1H, brs).

B) N$^2$-[(5Z)-5-({1-[2,4-bis(trifluoromethyl)benzyl]piperidin-4-yl}methylidene)-2-oxo-2,5-dihydro-1,3-thiazol-4-yl]-N-methylglycinamide To a solution of 1-[2,4-bis(trifluoromethyl)benzyl]piperidine-4-carbaldehyde (9.45 g) and N-methyl-N$^2$-(2-oxo-2,5-dihydro-1,3-thiazol-4-yl)glycinamide (6.26 g) in 2-propanol (80 mL) was added piperidinium acetate (4.05 g). The reaction mixture was stirred at 80° C. for 3.5 hr and concentrated. Water and THF were added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/methanol) and recrystallized from ethyl acetate/heptane to give the title compound (6.50 g).

$^1$H NMR (300 MHz, DMSO-d$_6$) δ 1.32-1.64 (2H, m), 1.67-1.86 (2H, m), 2.02-2.30 (3H, m), 2.61 (3H, d, J=4.5 Hz), 2.68-2.86 (2H, m), 3.71 (2H, s), 4.00 (2H, s), 6.91 (1H, d, J=8.9 Hz), 7.92-8.15 (4H, m), 9.43 (1H, s).

MS (ESI+): [M+H]$^+$ 509.2.

Example 108

N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethylglycinamide A) N,N-dimethyl-N$^2$-(2-oxo-2,5-dihydro-1,3-thiazol-4-yl)glycinamide To a solution of N,N-dimethylglycinamide hydrochloride (5 g) and triethylamine (5.03 mL) in ethanol (20 mL) was added 4-thioxo-1,3-thiazolidin-2-one (4.81 g), and the mixture was stirred at room temperature for 4 hr. The reaction mixture was concentrated, and the residue was purified by silica gel column chromatography (NH, ethyl acetate/THF) to give the title compound (4.68 g).

$^1$H NMR (300 MHz, DMSO-d$_6$) δ 2.86 (3H, s), 2.96 (3H, s), 4.24 (2H, d, J=5.2 Hz), 4.29 (2H, s), 9.17 (1H, brs).

MS (ESI+): [M+H]$^+$ 202.1.

B) N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethylglycinamide To a solution of 1-[2,4-bis(trifluoromethyl)benzyl]piperidine-4-carbaldehyde (6.57 g) and N,N-dimethyl-N$^2$-(2-oxo-2,5-dihydro-1,3-thiazol-4-yl)glycinamide (4.68 g) in 2-propanol (60 mL) was added piperidinium acetate (2.81 g). The reaction mixture was stirred at 80° C. for 4 hr and concentrated. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (NH, ethyl acetate/hexane). The obtained solid was washed with diisopropyl ether and recrystallized from ethyl acetate/heptane to give the title compound (5.62 g).

¹H NMR (300 MHz, DMSO-d₆) δ 1.41-1.58 (2H, m), 1.64-1.85 (2H, m), 2.06-2.30 (3H, m), 2.70-2.81 (2H, m), 2.86 (3H, s), 3.00 (3H, s), 3.71 (2H, s), 4.29 (2H, s), 6.94 (1H, d, J=8.7 Hz), 7.98 (1H, s), 8.02-8.14 (2H, m), 9.32 (1H, s).
MS (ESI+): [M+H]⁺ 523.1.
powder X-ray diffraction interplanar spacing (d): 27.08, 13.55, 9.02, 6.76, 5.39, 4.98, 4.67, 4.34, 3.85, 3.56 and 3.37 Å

Example 109

N²-[(5Z)-5-({1-[2,4-bis(trifluoromethyl)benzyl]piperidin-4-yl}methylidene)-2-oxo-2,5-dihydro-1,3-thiazol-4-yl]-L-serinamide A) N²-(2-oxo-2,5-dihydro-1,3-thiazol-4-yl)-L-serinamide To a solution of L-serinamide hydrochloride (1.00 g) in ethanol (20 mL) were added 4-thioxo-1,3-thiazolidin-2-one (957 mg) and N-ethyl-N-(1-methylethyl)propan-2-amine (1.88 mL), and the mixture was heated under reflux overnight. The reaction mixture was concentrated under reduced pressure, the residue was purified by silica gel column chromatography (methanol/ethyl acetate), and the obtained powder was washed with ethyl acetate to give the title compound (1.09 g).
¹H NMR (300 MHz, DMSO-d₆) δ 3.59-3.78 (2H, m), 4.15-4.44 (3H, m), 5.03 (1H, t, J=5.5 Hz), 7.23 (1H, s), 7.52 (1H, s), 9.17 (1H, brs).

B) N²-[(5Z)-5-({1-[2,4-bis(trifluoromethyl)benzyl]piperidin-4-yl}methylidene)-2-oxo-2,5-dihydro-1,3-thiazol-4-yl]-L-serinamide To a solution of 1-[2,4-bis(trifluoromethyl)benzyl]piperidine-4-carbaldehyde (893 mg) in 2-propanol (20 mL) were added N²-(2-oxo-2,5-dihydro-1,3-thiazol-4-yl)-L-serinamide (1.07 g) and piperidinium acetate (195 mg). The reaction mixture was stirred at 60° C. overnight, and the solvent was evaporated under reduced pressure. The residue was purified by silica gel column chromatography (methanol/ethyl acetate) to give the title compound (217 mg).
¹H NMR (300 MHz, DMSO-d₆) δ 1.41-1.61 (2H, m), 1.69-1.83 (2H, m), 2.05-2.25 (3H, m), 2.71-2.85 (2H, m), 3.63-3.83 (4H, m), 4.47-4.60 (1H, m), 5.07 (1H, brs), 7.09 (1H, d, J=8.8 Hz), 7.23 (1H, brs), 7.59 (1H, brs), 7.98 (1H, s), 8.02-8.13 (2H, m), 9.01 (1H, brs).
MS (ESI+): [M+H]⁺ 525.2.

Example 110

(5Z)-5-({1-[2,4-bis(trifluoromethyl)benzyl]piperidin-4-yl}methylidene)-4-(prop-2-yn-1-ylamino)-1,3-oxazol-2(5H)-one A) 4-(prop-2-yn-1-ylamino)-1,3-oxazol-2(5H)-one To a solution of 4-thioxooxazolidin-2-one (180 mg) in ethanol (3 mL) was added prop-2-yn-1-amine (85 mg) at room temperature. The reaction mixture was stirred at room temperature for 2 hr. The precipitated white solid was collected by filtration, and washed with ethyl acetate/hexane to give the title compound (168 mg).
¹H NMR (300 MHz, DMSO-d₆) δ 3.32-3.34 (1H, m), 4.15 (2H, d, J=2.5 Hz), 4.75 (2H, s), 9.22 (1H, brs).

B) (5Z)-5-({1-[2,4-bis(trifluoromethyl)benzyl]piperidin-4-yl}methylidene)-4-(prop-2-yn-1-ylamino)-1,3-oxazol-2(5H)-one To a solution of 1-[2,4-bis(trifluoromethyl)benzyl]piperidine-4-carbaldehyde (339 mg) and 4-(prop-2-yn-1-ylamino)-1,3-oxazol-2(5H)-one (152 mg) in 2-propanol (3 mL) was added piperidinium acetate (160 mg) at room temperature. The reaction mixture was stirred at 90° C. for 2 hr. The reaction mixture was concentrated under reduced pressure, and the residue was purified by silica gel column chromatography (NH, ethyl acetate/hexane) and recrystallized from ethyl acetate/hexane to give the title compound (4.40 mg)
¹H NMR (300 MHz, CDCl₃) δ 1.35-1.89 (4H, m), 2.09-2.26 (2H, m), 2.39 (1H, d, J=1.5 Hz), 2.52-2.94 (3H, m), 3.69 (2H, brs), 4.37 (2H, brs), 5.42 (1H, d, J=9.1 Hz), 6.28 (1H, brs), 7.77 (1H, d, J=8.0 Hz), 7.88 (1H, s), 7.97 (1H, d, J=8.0 Hz).
MS (ESI+): [M+H]⁺ 460.2.

Example 111

(5Z)-5-({(3aR,5r,6aS)-2-[2,4-bis(trifluoromethyl)phenyl]octahydrocyclopenta[c]pyrrol-5-yl}methylidene)-4-(prop-2-yn-1-ylamino)-1,3-thiazol-2(5H)-one A) (3aR,6aS)-2-[2,4-bis(trifluoromethyl)phenyl]octahydrocyclopenta[c]pyrrole-5-carbaldehyde To a solution of (3aR,6aS)-octahydrocyclopenta[c]pyrrol-5-ylmethanol hydrochloride (862 mg) and potassium carbonate (1.68 g) in DMF (10 mL) was added 1-fluoro-2,4-bis(trifluoromethyl)benzene (1.24 g). The reaction mixture was stirred at 80° C. for 3 hr, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane). To a solution of the obtained oil (1.71 g) and triethylamine (2.03 mL) in DMSO (10 mL) and ethyl acetate (10 mL) was added sulfur trioxide pyridine complex (2.32 g) under cooling to 0° C. The reaction mixture was stirred at room temperature for 1 hr. To the reaction mixture was added saturated aqueous sodium hydrogen carbonate solution, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (215 mg).
¹H NMR (300 MHz, CDCl₃) δ 1.68-1.87 (2H, m), 2.10-2.30 (2H, m), 2.64-2.89 (3H, m), 2.98-3.40 (4H, m), 7.06-7.15 (1H, m), 7.64 (1H, dd, J=8.7, 1.7 Hz), 7.84 (1H, s), 9.54-9.76 (1H, m).

B) (5Z)-5-({(3aR,5r,6aS)-2-[2,4-bis(trifluoromethyl)phenyl]octahydrocyclopenta[c]pyrrol-5-yl}methylidene)-4-(prop-2-yn-1-ylamino)-1,3-thiazol-2(5H)-one To a solution of (3aR,6aS)-2-[2,4-bis(trifluoromethyl)phenyl]octahydrocyclopenta[c]pyrrole-5-carbaldehyde (215 mg) and 4-(prop-2-yn-1-ylamino)-1,3-thiazol-2(5H)-one (123 mg) in 2-propanol (3 mL) was added piperidinium acetate (89 mg). The reaction mixture was stirred at 70° C. for 3 hr and concentrated. The residue was purified by silica gel column chromatography (ethyl acetate/hexane) to give the title compound (30 mg) and (5Z)-5-({(3aR,5s,6aS)-2-[2,4-bis(trifluoromethyl)phenyl]octahydrocyclopenta[c]pyrrol-5-yl}methylidene)-4-(prop-2-yn-1-ylamino)-1,3-thiazol-2(5H)-one.

$^1$H NMR (300 MHz, DMSO-$d_6$) δ 1.22-1.40 (2H, m), 2.14-2.27 (2H, m), 2.47-2.50 (1H, m), 2.77 (2H, brs), 3.16-3.23 (4H, m), 3.31-3.35 (1H, m), 4.22 (2H, d, J=2.5 Hz), 6.93 (1H, d, J=8.9 Hz), 7.40 (1H, d, J=9.3 Hz), 7.85-7.90 (2H, m), 9.55 (1H, brs).

MS (ESI+): [M+H]$^+$ 488.1.

Example 112

(5Z)-5-({(3aR,5s,6aS)-2-[2,4-bis(trifluoromethyl) phenyl]octahydrocyclopenta[c]pyrrol-5-yl}methylidene)-4-(prop-2-yn-1-ylamino)-1,3-thiazol-2(5H)-one To a solution of (3aR,6aS)-2-[2,4-bis(trifluoromethyl)phenyl]octahydrocyclopenta[c]pyrrole-5-carbaldehyde (215 mg) and 4-(prop-2-yn-1-ylamino)-1,3-thiazol-2(5H)-one (123 mg) in 2-propanol (3 mL) was added piperidinium acetate (89 mg). The reaction mixture was stirred at 70° C. for 3 hr and concentrated. The residue was purified by silica gel column chromatography (ethyl acetate/hexane) to give (5Z)-5-({(3aR,5r,6aS)-2-[2,4-bis(trifluoromethyl)phenyl]octahydrocyclopenta[c]pyrrol-5-yl}methylidene)-4-(prop-2-yn-1-ylamino)-1,3-thiazol-2(5H)-one (30 mg) and the title crude product. The title crude product was recrystallized from ethyl acetate/diisopropyl ether/heptane to give the title compound (103 mg).

$^1$H NMR (300 MHz, DMSO-$d_6$) δ 1.63-1.89 (4H, m), 2.71-2.96 (3H, m), 3.13 (2H, d, J=9.7 Hz), 3.33-3.44 (3H, m), 4.22 (2H, d, J=2.5 Hz), 6.88 (1H, d, J=9.0 Hz), 7.37 (1H, d, J=9.4 Hz), 7.83-7.91 (2H, m), 9.53 (1H, s).

MS (ESI+): [M+H]$^+$ 488.2.

Example 113

(5Z)-5-({1-[(3-methyl-1-benzofuran-2-yl)carbonyl]piperidin-4-yl}methylidene)-4-(prop-2-yn-1-ylamino)-1,3-thiazol-2(5H)-one To a solution of (5Z)-4-(prop-2-yn-1-ylamino)-5-(piperidin-4-ylmethylidene)-1,3-thiazol-2(5H)-one dihydrochloride (500 mg) in DMF (10 mL) were added N-ethyl-N-(1-methylethyl)propan-2-amine (1.40 mL), O-(7-azabenzotriazol-1-yl)-N,N,N',N'-tetramethyluronium hexafluorophosphate (708 mg), and 3-methylbenzofuran-2-carboxylic acid (335 mg). The reaction mixture was stirred at room temperature overnight, water was added, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (625 mg).

$^1$H NMR (300 MHz, DMSO-$d_6$) δ 1.34-1.53 (2H, m), 1.75-1.92 (2H, m), 2.34 (3H, s), 2.38-2.48 (1H, m), 3.19 (2H, brs), 3.34 (1H, t, J=2.4 Hz), 4.14 (2H, brs), 4.24 (2H, d, J=2.4 Hz), 6.90 (1H, d, J=8.9 Hz), 7.29-7.38 (1H, m), 7.40-7.48 (1H, m), 7.60 (1H, d, J=8.2 Hz), 7.71 (1H, d, J=7.6 Hz), 9.57 (1H, brs).

MS (ESI+): [M+H]$^+$ 408.4.

Example 114

(5Z)-5-({1-[2,4-bis(trifluoromethyl)benzyl]piperidin-4-yl}methylidene)-4-{[(1R)-1-(hydroxymethyl)prop-2-yn-1-yl]amino}-1,3-thiazol-2(5H)-one

A) (R)-2-aminobut-3-yn-1-ol trifluoroacetate

To a solution of (R)-tert-butyl 4-ethynyl-2,2-dimethyloxazolidine-3-carboxylate (680 mg) (Tetrahedron 1996, 52, 11215.) in methanol (20 mL) was added trifluoroacetic acid (0.23 mL). The reaction mixture was stirred at room temperature for 4 hr and concentrated under reduced pressure to give the title compound (623 mg).

$^1$H NMR (300 MHz, DMSO-$d_6$) δ 3.57 (1H, dd, J=11.4, 7.1 Hz), 3.65-3.74 (2H, m), 4.07 (1H, brs), 8.43 (3H, brs).

B) (R)-4-[(1-hydroxybut-3-yn-2-yl)amino]thiazol-2(5H)-one

To a solution of (R)-2-aminobut-3-yn-1-ol trifluoroacetate (601 mg) in ethanol (15 mL) were added 4-thioxo-1,3-thiazolidin-2-one (402 mg) and N-ethyl-N-(1-methylethyl)propan-2-amine (1.63 mL), and the mixture was heated under reflux overnight. The reaction mixture was concentrated under reduced pressure, the residue was purified by silica gel column chromatography (NH, methanol/ethyl acetate), and the obtained powder was washed with ethyl acetate to give the title compound (112 mg).

$^1$H NMR (300 MHz, DMSO-$d_6$) δ 3.36 (1H, d, J=2.4 Hz), 3.45-3.68 (2H, m), 4.21 (1H, d, J=7.5 Hz), 4.29 (1H, d, J=7.5 Hz), 4.63-4.73 (1H, m), 5.25 (1H, t, J=6.1 Hz), 9.47 (1H, d, J=7.8 Hz).

C) (5Z)-5-({1-[2,4-bis(trifluoromethyl)benzyl]piperidin-4-yl}methylidene)-4-{[(1R)-1-(hydroxymethyl)prop-2-yn-1-yl]amino}-1,3-thiazol-2(5H)-one To a solution of 1-[2,4-bis(trifluoromethyl)benzyl]piperidine-4-carbaldehyde (135 mg) in 2-propanol (5 mL) were added (R)-4-[(1-hydroxybut-3-yn-2-yl)amino]thiazol-2(5H)-one (110 mg) and piperidinium acetate (59 mg). The reaction mixture was heated under reflux overnight, and the solvent was evaporated under reduced pressure. The residue was purified by silica gel column chromatography (NH, ethyl acetate/hexane) and recrystallized from ethyl acetate/heptane to give the title compound (83 mg).

$^1$H NMR (300 MHz, DMSO-$d_6$) δ 1.39-1.57 (2H, m), 1.69-1.82 (2H, m), 2.04-2.25 (3H, m), 2.70-2.82 (2H, m), 3.42 (1H, d, J=2.3 Hz), 3.60-3.68 (2H, m), 3.72 (2H, s), 4.78-4.87 (1H, m), 5.29 (1H, t, J=5.7 Hz), 7.02 (1H, d, J=8.7 Hz), 7.98 (1H, s), 8.01-8.12 (2H, m), 9.38 (1H, brs).

MS (ESI+): [M+H]$^+$ 506.0.

Example 115

N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide

A) (R)-benzyl([1-(dimethylamino)-3-hydroxy-1-oxopropan-2-yl]carbamate

To a solution of N-carbobenzoxy-D-serine (2.00 g) in ethanol (30 mL) were added dimethylamine (1.04 mL) and 4-(4,6-dimethoxy-1,3,5-triazin-2-yl)-4-methylmorpholinium chloride n-hydrate (2.57 g), and the mixture was stirred at room temperature overnight. The reaction mixture was concentrated under reduced pressure, and the residue was dissolved in ethyl acetate and water. The organic layer was separated, washed with water and saturated brine, dried over anhydrous magnesium sulfate, and the solvent was evaporated under reduced pressure to give the title compound (1.33 g).

$^1$H NMR (300 MHz, DMSO-$d_6$) δ 2.83 (3H, s), 3.05 (3H, s), 3.39-3.50 (1H, m), 3.51-3.63 (1H, m), 4.49-4.59 (1H, m), 4.84 (1H, t, J=5.9 Hz), 5.01 (2H, s), 7.25-7.41 (6H, m).

MS (ESI+): [M+H]$^+$ 267.3.

B) N,N-dimethyl-D-serinamide

A solution of (R)-benzyl[1-(dimethylamino)-3-hydroxy-1-oxopropan-2-yl]carbamate (1.30 g) and 10% palladium carbon (130 mg) in methanol (30 mL) was stirred at room temperature for 7 hr under a hydrogen atmosphere. The reaction mixture was filtered, and the filtrate was concentrated under reduced pressure to give the title compound (673 mg).

$^1$H NMR (300 MHz, DMSO-$d_6$) δ 2.83 (3H, s), 3.02 (3H, s), 3.20-3.29 (1H, m), 3.37-3.45 (1H, m), 3.68 (1H, t, J=6.5 Hz).

C) $N^2$-(2-oxo-2,5-dihydro-1,3-thiazol-4-yl)-N,N-dimethyl-D-serinamide

To a solution of N,N-dimethyl-D-serinamide (645 mg) in ethanol (20 mL) was added 4-thioxo-1,3-thiazolidin-2-one (650 mg), and the mixture was heated under reflux overnight. The reaction mixture was concentrated under reduced pressure, the residue was purified by silica gel column chromatography (NH, methanol/ethyl acetate), and the obtained powder was washed with ethyl acetate to give the title compound (799 mg).

$^1$H NMR (300 MHz, DMSO-$d_6$) δ 2.86 (3H, s), 3.08 (3H, s), 3.50-3.71 (2H, m), 4.24 (2H, s), 4.91-5.02 (1H, m), 5.10 (1H, t, J=5.5 Hz), 9.30 (1H, d, J=7.6 Hz).

D) $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide To a solution of 1-[2,4-bis(trifluoromethyl)benzyl]piperidine-4-carbaldehyde (753 mg) in 2-propanol (10 mL) were added $N^2$-(2-oxo-2,5-dihydro-1,3-thiazol-4-yl)-N,N-dimethyl-D-serinamide (770 mg) and piperidinium acetate (329 mg). The reaction mixture was stirred at 80° C. overnight, and the solvent was evaporated under reduced pressure. The residue was purified by silica gel column chromatography (methanol/ethyl acetate) and silica gel column chromatography (NH, methanol/ethyl acetate) to give the title compound (371 mg).

$^1$H NMR (300 MHz, DMSO-$d_6$) δ 1.41-1.58 (2H, m), 1.68-1.82 (2H, m), 2.04-2.25 (3H, m), 2.72-2.82 (2H, m), 2.86 (3H, s), 3.11 (3H, s), 3.60-3.80 (4H, m), 5.04 (1H, t, J=6.2 Hz), 5.10 (1H, t, J=5.9 Hz), 7.13 (1H, d, J=8.8 Hz), 7.98 (1H, s), 8.02-8.12 (2H, m), 9.22 (1H, brs).

Example 116

(5Z)-5-({1-[2,4-bis(trifluoromethyl)benzyl]piperidin-4-yl}methylidene)-4-[(cis-2-hydroxycyclohexyl)amino]-1,3-thiazol-2(5H)-one A) 4-[(cis-2-hydroxycyclohexyl)amino]thiazol-2(5H)-one To a solution of 4-thioxo-1,3-thiazolidin-2-one (870 mg) in ethanol (30 mL) were added cis-2-aminocyclohexanol hydrochloride (1.00 g) and N-ethyl-N-(1-methylethyl)propan-2-amine (2.32 mL), and the mixture was heated under reflux overnight. The reaction mixture was concentrated under reduced pressure, the residue was purified by silica gel column chromatography (methanol/ethyl acetate), and the obtained powder was washed with ethyl acetate to give the title compound (504 mg).

$^1$H NMR (300 MHz, DMSO-$d_6$) δ 1.20-1.37 (2H, m), 1.38-1.80 (6H, m), 3.70-3.82 (1H, m), 3.87 (1H, brs), 4.19 (2H, s), 4.77 (1H, d, J=4.2 Hz), 8.86 (1H, d, J=7.4 Hz).

MS (ESI+): [M+H]$^+$ 215.0.

B) (5Z)-5-({1-[2,4-bis(trifluoromethyl)benzyl]piperidin-4-yl}methylidene)-4-[(cis-2-hydroxycyclohexyl)amino]-1,3-thiazol-2(5H)-one To a solution of 1-[2,4-bis(trifluoromethyl)benzyl]piperidine-4-carbaldehyde (528 mg) in 2-propanol (10 mL) were added 4-[(cis-2-hydroxycyclohexyl)amino]thiazol-2(5H)-one (500 mg) and piperidinium acetate (230 mg). The reaction mixture was stirred at 80° C. overnight, and the solvent was evaporated under reduced pressure. The residue was purified by silica gel column chromatography (ethyl acetate/hexane) and silica gel column chromatography (NH, ethyl acetate/hexane) to give the title compound (153 mg).

$^1$H NMR (300 MHz, DMSO-$d_6$) δ 1.19-1.61 (7H, m), 1.62-1.93 (5H, m), 2.01-2.25 (3H, m), 2.70-2.83 (2H, m), 3.71 (2H, s), 3.87 (1H, d, J=10.5 Hz), 3.96 (1H, brs), 4.85 (1H, brs), 7.09 (1H, d, J=8.8 Hz), 7.98 (1H, s), 8.01-8.12 (2H, m), 8.68 (1H, brs).

MS (ESI+): [M+H]-536.1.

Example 117

(5Z)-5-({1-[2,4-bis(trifluoromethyl)benzyl]piperidin-4-yl}methylidene)-4-[trans-(4-hydroxytetrahydrofuran-3-yl)amino]-1,3-thiazol-2(5H)-one A) 4-[trans-(4-hydroxytetrahydrofuran-3-yl)amino]-1,3-thiazol-2(5H)-one To a solution of trans-4-aminotetrahydrofuran-3-ol hydrochloride (1.00 g) in ethanol (30 mL) were added 4-thioxo-1,3-thiazolidin-2-one (954 mg) and N-ethyl-N-(1-methylethyl)propan-2-amine (3.87 mL), and the mixture was heated under reflux overnight. The reaction mixture was concentrated under reduced pressure, and the residue was purified by silica gel column chromatography (methanol/ethyl acetate) to give the title compound (591 mg).

$^1$H NMR (300 MHz, DMSO-$d_6$) δ 3.53 (1H, dd, J=9.3, 2.0 Hz), 3.66 (1H, dd, J=9.3, 2.0 Hz), 3.85-3.98 (2H, m), 4.08-4.15 (1H, m), 4.15-4.21 (1H, m), 4.22 (2H, s), 5.43 (1H, d, J=3.9 Hz), 9.23 (1H, d, J=6.4 Hz).

MS (ESI+): [M+H]$^+$ 203.0.

B) (5Z)-5-({1-[2,4-bis(trifluoromethyl)benzyl]piperidin-4-yl}methylidene)-4-[trans-(4-hydroxytetrahydrofuran-3-yl)amino]-1,3-thiazol-2(5H)-one To a solution of 1-[2,4-bis(trifluoromethyl)benzyl]piperidine-4-carbaldehyde (649 mg) in 2-propanol (10 mL) were added 4-[trans-(4-hydroxytetrahydrofuran-3-yl)amino]-1,3-thiazol-2(5H)-one (580 mg) and piperidinium acetate (283 mg). The reaction mixture was stirred at 80° C. overnight, and the solvent was evaporated under reduced pressure. The residue was purified by silica gel column chromatography (ethyl acetate/hexane) and recrystallized from ethyl acetate/heptane to give the title compound (469 mg).

¹H NMR (300 MHz, DMSO-$d_6$) δ 1.39-1.56 (2H, m), 1.67-1.80 (2H, m), 2.02-2.23 (3H, m), 2.71-2.83 (2H, m), 3.32 (2H, s), 3.54 (1H, dd, J=9.4, 2.4 Hz), 3.67-3.78 (1H, m), 3.90-4.04 (2H, m), 4.21-4.31 (2H, m), 5.45 (1H, d, J=3.9 Hz), 7.01 (1H, d, J=8.8 Hz), 7.98 (1H, s), 8.01-8.12 (2H, m), 9.06 (1H, brs).

MS (ESI+): [M+H]⁺ 524.1.

Example 118

$N^2$-[(5Z)-5-({1-[2,4-bis(trifluoromethyl)benzyl]piperidin-4-yl}methylidene)-2-oxo-2,5-dihydro-1,3-thiazol-4-yl]-N,N-bis(2-methoxyethyl)glycinamide A) N-[(5Z)-5-({1-[2,4-bis(trifluoromethyl)benzyl]piperidin-4-yl}methylidene)-2-oxo-2,5-dihydro-1,3-thiazol-4-yl]glycine hydrochloride A reaction mixture of tert-butyl N-[(5Z)-5-({1-[2,4-bis(trifluoromethyl)benzyl]piperidin-4-yl}methylidene)-2-oxo-2,5-dihydro-1,3-thiazol-4-yl]glycinate (13.3 g) and 4N hydrogen chloride/ethyl acetate (80 mL) was stirred at room temperature for 2 hr. The reaction mixture was concentrated to give the title compound (12.8 g).

¹H NMR (300 MHz, DMSO-$d_6$) δ 1.81-1.90 (2H, m), 2.01-2.19 (2H, m), 2.34-2.48 (1H, m), 3.07-3.28 (2H, m), 3.31-3.55 (2H, m), 4.09 (2H, d, J=5.0 Hz), 4.54 (2H, brs), 6.93 (1H, d, J=8.9 Hz), 8.13 (1H, s), 8.26 (1H, d, J=8.1 Hz), 8.79 (1H, d, J=8.3 Hz), 9.79 (1H, brs), 11.56 (1H, brs).

B) $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-bis(2-methoxyethyl)glycinamide To a solution of N-[(5Z)-5-({1-[2,4-bis(trifluoromethyl)benzyl]piperidin-4-yl}methylidene)-2-oxo-2,5-dihydro-1,3-thiazol-4-yl]glycine hydrochloride (500 mg), N-ethyl-N-(1-methylethyl)propan-2-amine (0.49 mL) and 2-methoxy-N-(2-methoxyethyl)ethanamine (376 mg) in DMF (5 mL) was added (1-cyano-2-ethoxy-2-oxoethylideneaminooxy)dimethylamino-morpholino-carbenium hexafluorophosphate (403 mg), and the mixture was stirred at room temperature overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, methanol/ethyl acetate) to give the title compound (10 mg).

¹H NMR (300 MHz, CDCl₃) δ 1.42-1.62 (2H, m), 1.79 (2H, d, J=10.7 Hz), 2.10-2.26 (3H, m), 2.84 (2H, d, J=11.7 Hz), 3.31 (3H, s), 3.34 (3H, s), 3.47-3.73 (10H, m), 4.42 (2H, d, J=3.7 Hz), 6.28 (1H, d, J=9.0 Hz), 7.40 (1H, brs), 7.80 (1H, d, J=8.1 Hz), 7.88 (1H, s), 8.00 (1H, d, J=8.1 Hz).

MS (ESI+): [M+H]⁺ 611.1.

Example 119

(5Z)-5-({1-[4-hydroxy-2-(trifluoromethyl)benzyl]piperidin-4-yl}methylidene)-4-(prop-2-yn-1-ylamino)-1,3-thiazol-2(5H)-one A) 4-methyl-3-(trifluoromethyl)phenyl acetate To a solution of 4-methyl-3-(trifluoromethyl)phenol (5 g) and triethylamine (4.75 mL) in THF (40 mL) was added acetic anhydride (3.48 g), and the mixture was stirred at room temperature overnight. The reaction mixture was concentrated, saturated aqueous sodium hydrogen carbonate solution was added to the residue, and the mixture was extracted with ethyl acetate. The extract was washed with water and saturated brine, dried over anhydrous magnesium sulfate, and the solvent was evaporated under reduced pressure to give the title compound (6.04 g).

¹H NMR (300 MHz, CDCl₃) δ 2.30 (3H, s), 2.47 (3H, d, J=1.5 Hz), 7.16 (1H, dd, J=9.0 Hz, 3.0 Hz), 7.29 (1H, d, J=9.0 Hz), 7.33 (1H, d, J=2.4 Hz).

B) 4-(bromomethyl)-3-(trifluoromethyl)phenyl acetate

To a solution of 4-methyl-3-(trifluoromethyl)phenyl acetate (6.04 g) and 75% benzoyl peroxide (0.45 g) in (trifluoromethyl)benzene (60 mL) was added N-bromosuccinimide (5.42 g), and the mixture was stirred at 80° C. overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (5.6 g).

¹H NMR (300 MHz, CDCl₃) δ 2.32 (3H, s), 4.62 (2H, s), 7.31 (1H, dd, J=8.5, 2.3 Hz), 7.39 (1H, d, J=2.4 Hz), 7.61 (1H, d, J=8.4 Hz).

C) (5Z)-5-({1-[4-hydroxy-2-(trifluoromethyl)benzyl]piperidin-4-yl}methylidene)-4-(prop-2-yn-1-ylamino)-1,3-thiazol-2(5H)-one To a solution of (5Z)-4-(prop-2-yn-1-ylamino)-5-(piperidin-4-ylmethylidene)-1,3-thiazol-2(5H)-one dihydrochloride (2 g) in DMF (20 mL) were added potassium carbonate (3.45 g) and 4-(bromomethyl)-3-(trifluoromethyl)phenyl acetate (1.84 g). The reaction mixture was stirred at room temperature for 2 hr. Water was added to the reaction mixture, and the mixture was extracted with ethyl acetate. The extract was washed with water and saturated brine, and dried over anhydrous magnesium sulfate, and the solvent was evaporated under reduced pressure. To a solution of the residue in methanol (20 mL) was added potassium carbonate (858 mg), and the mixture was stirred at room temperature for 2 hr. To the reaction mixture was added saturated aqueous ammonium chloride solution, and the mixture was extracted with ethyl acetate. The extract was washed with saturated brine, and dried over anhydrous magnesium sulfate, and the solvent was evaporated under reduced pressure. The residue was purified by silica gel column chromatography (hexane/ethyl acetate), and the solid was recrystallized from ethyl acetate/heptane to give the title compound (0.75 g).

¹H NMR (300 MHz, DMSO-$d_6$) δ 1.31-1.53 (2H, m), 1.61-1.80 (2H, m), 2.01-2.14 (3H, m), 2.71-2.75 (2H, m), 3.32 (1H, s) 3.48 (2H, s), 4.22 (2H, d, J=2.2 Hz), 6.89 (1H, d, J=8.9 Hz), 6.96-7.07 (2H, m), 7.51 (1H, d, J=8.0 Hz), 9.56 (1H, brs), 9.94 (1H, s).

MS (ESI+): [M+H]⁺ 424.1.

Example 120

$N^2$-[(5Z)-5-({1-[2,4-bis(trifluoromethyl)benzyl]piperidin-4-yl}methylidene)-2-oxo-2,5-dihydro-1,3-thiazol-4-yl]-N-cyclopropylglycinamide A) N-cyclopropyl-$N^2$-(2-oxo-2,5-dihydro-1,3-thiazol-4-yl)glycinamide To a solution of N-cyclopropylglycinamide (1.22 g) (J. Med. Chem. 2005, 48, 7808-7820) in ethanol (12 mL) was added 4-thioxo-1,3-thiazolidin-2-one (1.42 g), and the mixture was stirred at room temperature for 5 hr. The precipitate was collected by filtration, and the solid was washed with ethanol to give the title compound (2.0 g).
$^1$H NMR (300 MHz, DMSO-$d_6$) δ 0.35-0.45 (2H, m), 0.56-0.74 (2H, m), 2.56-2.70 (1H, m), 3.92 (2H, d, J=5.6 Hz), 4.19-4.41 (2H, m), 8.12 (1H, d, J=3.7 Hz), 9.25 (1H, t, J=5.1 Hz).

B) $N^2$-[(5Z)-5-({1-[2,4-bis(trifluoromethyl)benzyl] piperidin-4-yl}methylidene)-2-oxo-2,5-dihydro-1,3-thiazol-4-yl]-N-cyclopropylglycinamide To a solution of 1-[2,4-bis(trifluoromethyl)benzyl]piperidine-4-carbaldehyde (2.65 g) and N-cyclopropyl-$N^2$-(2-oxo-2,5-dihydro-1,3-thiazol-4-yl)glycinamide (2 g) in 2-propanol (20 mL) was added piperidinium acetate (1.14 g). The reaction mixture was stirred at 80° C. for 3.5 hr and concentrated. Water and THF were added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (methanol/ethyl acetate) and recrystallized from ethyl acetate/water/heptane to give the title compound (2.64 g).
$^1$H NMR (300 MHz, DMSO-$d_6$) δ 0.33-0.50 (2H, m), 0.53-0.76 (2H, m), 1.36-1.59 (2H, m), 1.64-1.87 (2H, m), 2.03-2.29 (3H, m), 2.58-2.70 (1H, m), 2.71-2.86 (2H, m), 3.71 (2H, s), 3.97 (2H, s), 6.91 (1H, d, J=8.9 Hz), 7.98 (1H, s), 8.03-8.12 (2H, m), 8.18 (1H, d, J=4.0 Hz), 9.40 (1H, s).
MS (ESI+): [M+H]$^+$ 535.1.

Example 121

(5Z)-5-({1-[2,4-bis(trifluoromethyl)benzyl]piperidin-4-yl}methylidene)-4-[(2-oxo-2-pyrrolidin-1-ylethyl)amino]-1,3-thiazol-2(5H)-one To a solution of N-[(5Z)-5-({1-[2,4-bis(trifluoromethyl)benzyl]piperidin-4-yl}methylidene)-2-oxo-2,5-dihydro-1,3-thiazol-4-yl]glycine hydrochloride (500 mg), N-ethyl-N-(1-methylethyl)propan-2-amine (0.49 mL) and pyrrolidine (0.24 mL) in DMF (5 mL) was added (1-cyano-2-ethoxy-2-oxoethylideneaminooxy)dimethylamino-morpholino-carbenium hexafluorophosphate (403 mg), and the mixture was stirred at room temperature overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, methanol/ethyl acetate), and the solid was recrystallized from ethyl acetate/heptane to give the title compound (90 mg).
$^1$H NMR (300 MHz, DMSO-$d_6$) δ 1.40-1.60 (2H, m), 1.68-1.98 (6H, m), 2.04-2.27 (3H, m), 2.77 (2H, d, J=11.3 Hz), 3.25-3.35 (2H, m), 3.45 (2H, t, J=6.5 Hz), 3.71 (2H, brs), 4.21 (2H, s), 6.95 (1H, d, J=8.6 Hz), 7.98 (1H, s), 8.02-8.13 (2H, m), 9.36 (1H, brs).
MS (ESI+): [M+H]$^+$ 549.2.

Example 122

(5Z)-5-({1-[2,4-bis(trifluoromethyl)benzyl]piperidin-4-yl}methylidene)-4-[(2-morpholin-4-yl-2-oxoethyl)amino]-1,3-thiazol-2(5H)-one To a solution of N-[(5Z)-5-({1-[2,4-bis(trifluoromethyl)benzyl]piperidin-4-yl}methylidene)-2-oxo-2,5-dihydro-1,3-thiazol-4-yl]glycine hydrochloride (500 mg), N-ethyl-N-(1-methylethyl)propan-2-amine (0.49 mL) and morpholine (0.25 mL) in DMF (5 mL) was added (1-cyano-2-ethoxy-2-oxoethylideneaminooxy)dimethylamino-morpholino-carbenium hexafluorophosphate (403 mg), and the mixture was stirred at room temperature overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, methanol/ethyl acetate), and the solid was recrystallized from diisopropyl ether/heptane to give the title compound (160 mg).
$^1$H NMR (300 MHz, DMSO-$d_6$) δ 1.34-1.60 (2H, m), 1.66-1.86 (2H, m), 2.04-2.28 (3H, m), 2.70-2.84 (2H, m), 3.43-3.66 (8H, m), 3.71 (2H, s), 4.33 (2H, s), 6.94 (1H, d, J=8.9 Hz), 7.98 (1H, s), 8.02-8.12 (2H, m), 9.33 (1H, brs).
MS (ESI+): [M+H]$^+$ 565.1.

Example 123

(5Z)-5-({1-[2,4-bis(trifluoromethyl)benzyl]piperidin-4-yl}methylidene)-4-{[2-(4-methylpiperazin-1-yl)-2-oxoethyl]amino}-1,3-thiazol-2(5H)-one To a solution of N-[(5Z)-5-({1-[2,4-bis(trifluoromethyl)benzyl]piperidin-4-yl}methylidene)-2-oxo-2,5-dihydro-1,3-thiazol-4-yl]glycine hydrochloride (500 mg), N-ethyl-N-(1-methylethyl)propan-2-amine (0.33 mL) and 1-methylpiperazine (0.11 mL) in DMF (5 mL) was added O-(7-azabenzotriazol-1-yl)-N,N,N',N'-tetramethyluronium hexafluorophosphate (429 mg), and the mixture was stirred at room temperature for 2 hr. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, hexane/ethyl acetate), and the solid was recrystallized from diisopropyl ether/heptane to give the title compound (85 mg).
$^1$H NMR (300 MHz, DMSO-$d_6$) δ 1.37-1.59 (2H, m), 1.66-1.85 (2H, m), 2.04-2.38 (10H, m), 2.66-2.88 (2H, m), 3.45 (4H, brs), 3.71 (2H, s), 4.32 (2H, s), 6.93 (1H, d, J=9.0 Hz), 7.98 (1H, s), 8.01-8.15 (2H, m), 9.31 (1H, brs).
MS (ESI+): [M+H]$^+$ 578.1.

Example 124

(5Z)-5-({1-[2,4-bis(trifluoromethyl)benzyl]piperidin-4-yl}methylidene)-4-({[1-(hydroxymethyl)cyclobutyl]methyl}amino)-1,3-thiazol-2(5H)-one A) 4-({[1-(hydroxymethyl)cyclobutyl]methyl}amino)thiazol-2(5H)-one To a solution of [1-(aminomethyl)cyclobutyl]methanol (1.00 g) in ethanol (30 mL) was added 4-thioxo-1,3-thiazolidin-2-one (1.16 g), and the mixture was heated under reflux overnight. The reaction mixture was concentrated under reduced pressure, and the obtained powder was washed with ethyl acetate to give the title compound (795 mg).
$^1$H NMR (300 MHz, DMSO-$d_6$) δ 1.68-1.86 (6H, m), 3.37 (2H, d, J=5.2 Hz), 3.44 (2H, d, J=5.9 Hz), 4.27 (2H, s), 4.67 (1H, t, J=5.9 Hz), 8.95 (1H, brs).
MS (ESI+): [M+H]$^+$ 215.0.

B) (5Z)-5-({1-[2,4-bis(trifluoromethyl)benzyl]piperidin-4-yl}methylidene)-4-({[1-(hydroxymethyl)cyclobutyl]methyl}amino)-1,3-thiazol-2(5H)-one To a solution of 1-[2,4-bis(trifluoromethyl)benzyl]piperidine-4-carbaldehyde (500 mg) in 2-propanol (10 mL) were added 4-({[1-(hydroxymethyl)cyclobutyl]methyl}amino)thiazol-2(5H)-one (474 mg) and piperidinium acetate (218 mg). The reaction mixture was stirred at 80° C. overnight, and the solvent was evaporated under reduced pressure. The residue was purified by silica gel column chromatography (ethyl acetate/hexane) and recrystallized from ethyl acetate/heptane to give the title compound (258 mg).

$^1$H NMR (300 MHz, DMSO-$d_6$) δ 1.40-1.56 (2H, m), 1.67-1.86 (8H, m), 2.03-2.22 (3H, m), 2.71-2.83 (2H, m), 3.38 (2H, s), 3.54 (2H, s), 3.71 (2H, s), 4.73 (1H, brs), 6.93 (1H, d, J=8.8 Hz), 7.98 (1H, s), 8.01-8.11 (2H, m), 9.00 (1H, brs).

MS (ESI+): [M+H]$^+$ 536.1.

Example 125

(+)-(5Z)-5-({1-[2,4-bis(trifluoromethyl)benzyl]piperidin-4-yl}methylidene)-4-{[(1S,2S)-2-hydroxycyclohexyl]amino}-1,3-thiazol-2(5H)-one A) 4-{[(1S,2S)-2-hydroxycyclohexyl]amino}thiazol-2(5H)-one To a solution of (1S,2S)-2-aminocyclohexanol (1.00 g) in ethanol (30 mL) was added 4-thioxo-1,3-thiazolidin-2-one (1.17 g), and the mixture was heated under reflux overnight. The reaction mixture was concentrated under reduced pressure, and the residue was purified by silica gel column chromatography (ethyl acetate/hexane) to give the title compound (786 mg).

$^1$H NMR (300 MHz, DMSO-$d_6$) δ 1.09-1.31 (4H, m), 1.55-1.71 (2H, m), 1.78-1.95 (2H, m), 3.28-3.39 (1H, m), 3.49-3.63 (1H, m), 4.20 (2H, s), 4.76 (1H, d, J=4.8 Hz), 8.99 (1H, d, J=7.8 Hz).

MS (ESI+): [M+H]$^+$ 215.0.

B) (+)-(5Z)-5-({1-[2,4-bis(trifluoromethyl)benzyl]piperidin-4-yl}methylidene)-4-{[(1S,2S)-2-hydroxycyclohexyl]amino}-1,3-thiazol-2(5H)-one To a solution of 1-[2,4-bis(trifluoromethyl)benzyl]piperidine-4-carbaldehyde (823 mg) in 2-propanol (15 mL) were added 4-{[(1S,2S)-2-hydroxycyclohexyl]amino}thiazol-2(5H)-one (780 mg) and piperidinium acetate (360 mg). The reaction mixture was stirred at 80° C. overnight, and the solvent was evaporated under reduced pressure. The residue was purified by silica gel column chromatography (ethyl acetate/hexane) and silica gel column chromatography (NH, methanol/ethyl acetate), and recrystallized from ethyl acetate/heptane to give the title compound (645 mg).

$^1$H NMR (300 MHz, DMSO-$d_6$) δ 1.12-1.35 (4H, m), 1.40-1.57 (2H, m), 1.58-1.81 (4H, m), 1.82-1.97 (2H, m), 2.02-2.24 (3H, m), 2.72-2.84 (2H, m), 3.40-3.54 (1H, m), 3.64-3.78 (3H, m), 4.81 (1H, d, J=5.5 Hz), 6.90 (1H, d, J=8.8 Hz), 7.98 (1H, s), 8.01-8.12 (2H, m), 8.88 (1H, brs).

MS (ESI+): [M+H]$^+$ 536.1.

$[α]_D^{25}$+30.4 (c 0.50, DMSO)

Example 126

(−)-(5Z)-5-({1-[2,4-bis(trifluoromethyl)benzyl]piperidin-4-yl}methylidene)-4-{[(1R,2R)-2-hydroxycyclohexyl]amino}-1,3-thiazol-2(5H)-one A) 4-{[(1R,2R)-2-hydroxycyclohexyl]amino}thiazol-2(5H)-one To a solution of (1R,2R)-2-aminocyclohexanol (1.00 g) in ethanol (30 mL) was added 4-thioxo-1,3-thiazolidin-2-one (1.17 g), and the mixture was heated under reflux overnight. The reaction mixture was concentrated under reduced pressure, and the residue was purified by silica gel column chromatography (ethyl acetate/hexane) to give the title compound (971 mg).

$^1$H NMR (300 MHz, DMSO-$d_6$) δ 1.09-1.32 (4H, m), 1.53-1.73 (2H, m), 1.78-1.96 (2H, m), 3.27-3.42 (1H, m), 3.48-3.63 (1H, m), 4.20 (2H, s), 4.76 (1H, d, J=4.9 Hz), 8.99 (1H, d, J=7.9 Hz).

MS (ESI+): [M+H]$^+$ 215.0.

B) (−)-(5Z)-5-({1-[2,4-bis(trifluoromethyl)benzyl]piperidin-4-yl}methylidene)-4-{[(1R,2R)-2-hydroxycyclohexyl]amino}-1,3-thiazol-2(5H)-one To a solution of 1-[2,4-bis(trifluoromethyl)benzyl]piperidine-4-carbaldehyde (1.01 g) in 2-propanol (15 mL) were added 4-{[(1R,2R)-2-hydroxycyclohexyl]amino}thiazol-2(5H)-one (960 mg) and piperidinium acetate (443 mg). The reaction mixture was stirred at 80° C. overnight, and the solvent was evaporated under reduced pressure. The residue was purified by silica gel column chromatography (ethyl acetate/hexane) and silica gel column chromatography (NH, methanol/ethyl acetate), and recrystallized from ethyl acetate/heptane to give the title compound (712 mg).

$^1$H NMR (300 MHz, DMSO-$d_6$) δ 1.13-1.37 (4H, m), 1.38-1.57 (2H, m), 1.59-1.81 (4H, m), 1.88 (2H, d, J=17.9 Hz), 2.02-2.24 (3H, m), 2.71-2.84 (2H, m), 3.40-3.54 (1H, m), 3.64-3.78 (3H, m), 4.81 (1H, d, J=5.5 Hz), 6.90 (1H, d, J=8.8 Hz), 7.98 (1H, s), 8.01-8.12 (2H, m), 8.88 (1H, brs).

MS (ESI+): [M+H]$^+$ 536.1.

$[α]_D^{25}$−31.7 (c 0.50, DMSO)

Example 127

$N^2$-[(5Z)-5-({1-[2,4-bis(trifluoromethyl)benzyl]piperidin-4-yl}methylidene)-2-oxo-2,5-dihydro-1,3-thiazol-4-yl]-N-(2-hydroxyethyl)glycinamide To a solution of N-[(5Z)-5-({1-[2,4-bis(trifluoromethyl)benzyl]piperidin-4-yl}methylidene)-2-oxo-2,5-dihydro-1,3-thiazol-4-yl]glycine hydrochloride (500 mg), N-ethyl-N-(1-methylethyl)propan-2-amine (0.49 mL) and 2-aminoethanol (172 mg) in DMF (5 mL) was added (1-cyano-2-ethoxy-2-oxoethylideneaminooxy)dimethylamino-morpholino-carbenium hexafluorophosphate (403 mg), and the mixture was stirred at room temperature overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, methanol/ethyl acetate), and the solid was recrystallized from diisopropyl ether/heptane to give the title compound (20 mg).

$^1$H NMR (300 MHz, DMSO-$d_6$) δ 1.39-1.57 (2H, m), 1.69-1.83 (2H, m), 2.02-2.32 (3H, m), 2.77 (2H, d, J=11.1

Hz), 3.15 (2H, dt, J=5.9, 5.9 Hz), 3.41 (2H, dt, J=5.9, 5.9 Hz), 3.71 (2H, s), 4.04 (2H, s), 4.68 (1H, t, J=5.4 Hz), 6.91 (1H, d, J=8.7 Hz), 7.98 (1H, s), 8.02-8.15 (3H, m), 9.38 (1H, brs).

MS (ESI+): [M+H]$^+$ 539.1.

Example 128

$N^2$-[(5Z)-5-({1-[2,4-bis(trifluoromethyl)benzyl]piperidin-4-yl}methylidene)-2-oxo-2,5-dihydro-1,3-thiazol-4-yl]-N-(2-methoxyethyl)glycinamide To a solution of N-[(5Z)-5-({1-[2,4-bis(trifluoromethyl)benzyl]piperidin-4-yl}methylidene)-2-oxo-2,5-dihydro-1,3-thiazol-4-yl]glycine hydrochloride (500 mg), N-ethyl-N-(1-methylethyl)propan-2-amine (0.49 mL) and 2-methoxyethanamine (212 mg) in DMF (5 mL) was added (1-cyano-2-ethoxy-2-oxoethylideneaminooxy)dimethylamino-morpholino-carbenium hexafluorophosphate (403 mg), and the mixture was stirred at room temperature overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (methanol/ethyl acetate), and the solid was recrystallized from diisopropyl ether/heptane to give the title compound (31 mg).

$^1$H NMR (300 MHz, DMSO-d$_6$) δ 1.38-1.59 (2H, m), 1.64-1.85 (2H, m), 1.99-2.28 (3H, m), 2.67-2.86 (2H, m), 3.18-3.29 (5H, m), 3.29-3.39 (2H, m), 3.71 (2H, s), 4.03 (2H, s), 6.91 (1H, d, J=8.8 Hz), 7.98 (1H, s), 8.02-8.11 (2H, m), 8.18 (1H, t, J=5.4 Hz), 9.40 (1H, brs).

MS (ESI+): [M+H]$^+$ 553.1.

Example 129

$N^2$-[(5Z)-5-({1-[2,4-bis(trifluoromethyl)benzyl]piperidin-4-yl}methylidene)-2-oxo-2,5-dihydro-1,3-thiazol-4-yl]-N-(2-hydroxyethyl)-N-methylglycinamide To a solution of N-[(5Z)-5-({1-[2,4-bis(trifluoromethyl)benzyl]piperidin-4-yl}methylidene)-2-oxo-2,5-dihydro-1,3-thiazol-4-yl]glycine hydrochloride (500 mg), N-ethyl-N-(1-methylethyl)propan-2-amine (0.49 mL) and 2-(methylamino)ethanol (0.23 mL) in DMF (5 mL) was added (1-cyano-2-ethoxy-2-oxoethylideneaminooxy)dimethylamino-morpholino-carbenium hexafluorophosphate (403 mg), and the mixture was stirred at room temperature overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, methanol/ethyl acetate) to give the title compound (35 mg).

$^1$H NMR (300 MHz, DMSO-d$_6$) δ 1.38-1.59 (2H, m), 1.63-1.85 (2H, m), 2.03-2.29 (3H, m), 2.70-2.81 (2H, m), 2.82-3.08 (3H, m), 3.34-3.60 (4H, m), 3.71 (2H, s), 4.25-4.47 (2H, m), 4.68 (0.5H, t, J=5.4 Hz), 4.93 (0.5H, t, J=5.1 Hz), 6.95 (1H, dd, J=8.8, 3.9 Hz), 7.98 (1H, s), 8.02-8.13 (2H, m), 9.29 (1H, brs).

MS (ESI+): [M+H]$^+$ 553.1.

Example 130

(5Z)-5-({1-[2,4-bis(trifluoromethyl)benzyl]piperidin-4-yl}methylidene)-4-{[2-(3-hydroxypyrrolidin-1-yl)-2-oxoethyl]amino}-1,3-thiazol-2(5H)-one To a solution of N-[(5Z)-5-({1-[2,4-bis(trifluoromethyl)benzyl]piperidin-4-yl}methylidene)-2-oxo-2,5-dihydro-1,3-thiazol-4-yl]glycine hydrochloride (500 mg), N-ethyl-N-(1-methylethyl)propan-2-amine (0.49 mL) and pyrrolidin-3-ol (0.23 mL) in DMF (5 mL) was added (1-cyano-2-ethoxy-2-oxoethylideneaminooxy)dimethylamino-morpholino-carbenium hexafluorophosphate (403 mg), and the mixture was stirred at room temperature overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, methanol/ethyl acetate) to give the title compound (90 mg).

$^1$NMR (300 MHz, CDCl$_3$) δ 1.59-1.64 (2H, m), 1.72-1.87 (2H, m), 1.99-2.26 (5H, m), 2.78-2.92 (2H, m), 3.37-3.79 (6H, m), 4.18-4.31 (2H, m), 4.47-4.73 (1H, m), 6.30 (1H, d, J=9.2 Hz), 6.72 (1H, s), 7.80 (1H, d, J=8.3 Hz), 7.88 (1H, s), 8.00 (1H, d, J=8.1 Hz).

MS (ESI+): [M+H]$^+$ 565.1.

Example 131

(5Z)-5-({1-[2,4-bis(trifluoromethyl)benzyl]piperidin-4-yl}methylidene)-4-(cyclohexylamino)-1,3-thiazol-2(5H)-one A) 4-(cyclohexylamino)thiazol-2(5H)-one To a solution of 4-thioxo-1,3-thiazolidin-2-one (1.00 g) in ethanol (30 mL) was added cyclohexylamine (0.88 mL), and the mixture was heated under reflux overnight. The reaction mixture was concentrated under reduced pressure, the residue was purified by silica gel column chromatography (ethyl acetate/hexane), and the obtained powder was washed with ethyl acetate to give the title compound (599 mg).

$^1$H NMR (300 MHz, DMSO-d$_6$) δ 1.05-1.39 (5H, m), 1.50-1.95 (5H, m), 3.58-3.77 (1H, m), 4.20 (2H, s), 8.98 (1H, d, J=6.9 Hz).

B) (5Z)-5-({1-[2,4-bis(trifluoromethyl)benzyl]piperidin-4-yl}methylidene)-4-(cyclohexylamino)-1,3-thiazol-2(5H)-one To a solution of 1-[2,4-bis(trifluoromethyl)benzyl]piperidine-4-carbaldehyde (673 mg) in 2-propanol (15 mL) were added 4-(cyclohexylamino)thiazol-2(5H)-one (590 mg) and piperidinium acetate (294 mg). The reaction mixture was stirred at 80° C. overnight, and the solvent was evaporated under reduced pressure. The residue was purified by silica gel column chromatography (ethyl acetate/hexane) and silica gel column chromatography (NH, methanol/ethyl acetate) to give the title compound (582 mg).

$^1$H NMR (300 MHz, DMSO-d$_6$) δ 1.06-1.56 (7H, m), 1.57-1.80 (5H, m), 1.84-1.97 (2H, m), 2.01-2.23 (3H, m), 2.71-2.83 (2H, m), 3.71 (2H, s), 3.80 (1H, brs), 6.91 (1H, d, J=8.8 Hz), 7.98 (1H, s), 8.01-8.12 (2H, m), 8.84 (1H, brs).

Example 132

N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-serinamide

A) (S)-benzyl[1-(dimethylamino)-3-hydroxy-1-oxopropan-2-yl]carbamate

To a solution of N-carbobenzoxy-L-serine (5.00 g) in ethanol (70 mL) were added dimethylamine (2.51 mL) and 4-(4,6-dimethoxy-1,3,5-triazin-2-yl)-4-methylmorpholinium chloride n-hydrate (6.23 g), and the mixture was stirred at room temperature overnight. The reaction mixture was concentrated under reduced pressure, and the residue was dissolved in ethyl acetate/tetrahydrofuran and water. The organic layer was separated, washed with water and saturated brine, dried over anhydrous magnesium sulfate, and the solvent was evaporated under reduced pressure to give the title compound (3.23 g).

$^1$H NMR (300 MHz, DMSO-$d_6$) δ 2.83 (3H, s), 3.05 (3H, s), 3.40-3.50 (1H, m), 3.51-3.63 (1H, m), 4.49-4.60 (1H, m), 4.85 (1H, t, J=5.8 Hz), 5.02 (2H, s), 7.24-7.44 (6H, m).
MS (ESI+): [M+H]$^+$ 267.0.

B) N,N-dimethyl-L-serinamide

A solution of (S)-benzyl[1-(dimethylamino)-3-hydroxy-1-oxopropan-2-yl]carbamate (3.20 g) and 10% palladium carbon (320 mg) in methanol (30 mL) was stirred at room temperature for 5 hr under a hydrogen atmosphere. The reaction mixture was filtered, and the filtrate was concentrated under reduced pressure to give the title compound (1.61 g).

$^1$H NMR (300 MHz, DMSO-$d_6$) δ 2.83 (3H, s), 3.02 (3H, s), 3.20-3.30 (1H, m), 3.36-3.46 (1H, m), 3.64-3.72 (1H, m).

C) N²-(2-oxo-2,5-dihydro-1,3-thiazol-4-yl)-N,N-dimethyl-L-serinamide

To a solution of N,N-dimethyl-L-serinamide (1.61 g) in ethanol (50 mL) was added 4-thioxo-1,3-thiazolidin-2-one (1.63 g), and the mixture was stirred at 70° C. overnight. The reaction mixture was concentrated under reduced pressure, and the residue was purified by silica gel column chromatography (NH, methanol/ethyl acetate) to give the title compound (1.53 g).

$^1$H NMR (300 MHz, DMSO-$d_6$) δ 2.86 (3H, s), 3.08 (3H, s), 3.51-3.70 (2H, m), 4.24 (2H, s), 4.97 (1H, t, J=5.6 Hz), 5.11 (1H, brs), 9.31 (1H, brs).

D) N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-serinamide To a solution of 1-[2,4-bis(trifluoromethyl)benzyl]piperidine-4-carbaldehyde (1.47 g) in 2-propanol (10 mL) were added N²-(2-oxo-2,5-dihydro-1,3-thiazol-4-yl)-N,N-dimethyl-L-serinamide (1.50 g) and piperidinium acetate (641 mg). The reaction mixture was stirred at 80° C. overnight, and the solvent was evaporated under reduced pressure. The residue was purified by silica gel column chromatography (methanol/ethyl acetate) and silica gel column chromatography (NH, methanol/ethyl acetate) to give the title compound (1.24 g).

$^1$H NMR (300 MHz, DMSO-$d_6$) δ 1.40-1.59 (2H, m), 1.67-1.82 (2H, m), 2.04-2.26 (3H, m), 2.72-2.82 (2H, m), 2.86 (3H, s), 3.11 (3H, s), 3.59-3.81 (4H, m), 5.07 (2H, dt, J=18.3, 6.2 Hz), 7.13 (1H, d, J=8.8 Hz), 7.98 (1H, s), 8.02-8.13 (2H, m), 9.22 (1H, brs).
MS (ESI+): [M+H]$^+$ 553.1.

Example 133

N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-alaninamide

A) N,N-dimethyl-N²-(2-oxo-2,5-dihydro-1,3-thiazol-4-yl)-L-alaninamide

50% Aqueous dimethylamine solution (2.86 g) was added to a solution of N-(tert-butoxycarbonyl)-L-alanine (5 g), N-(3-dimethylaminopropyl)-N'-ethylcarbodiimide hydrochloride (6.08 g) and 1-hydroxybenzotriazole anhydride (4.28 g) in DMF (15 mL). The reaction mixture was stirred at room temperature overnight. Water was added to the reaction mixture, and the mixture was extracted with ethyl acetate. The organic layer was separated, washed with water and saturated brine, dried over anhydrous magnesium sulfate, and concentrated under reduced pressure. 4N hydrogen chloride/ethyl acetate solution (13.2 mL) was added to the residue, and the mixture was stirred at room temperature for 3 hr. The reaction mixture was concentrated under reduced pressure. To a solution of the residue and triethylamine (11 mL) in ethanol (40 mL) was added 4-thioxothiazolidin-2-one (3.52 g), and the reaction mixture was stirred at room temperature for 4 hr. The reaction mixture was concentrated under reduced pressure, the reaction mixture was added to water at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (210 mg).

$^1$H NMR (300 MHz, CDCl$_3$) δ 1.44 (3H, d, J=6.8 Hz), 3.01 (3H, s), 3.11 (3H, s), 4.18 (2H, d, J=2.1 Hz), 4.99-5.35 (1H, m), 8.08 (1H, brs).

B) N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-alaninamide To a solution of 1-[2,4-bis(trifluoromethyl)benzyl]piperidine-4-carbaldehyde (305 mg) and N,N-dimethyl-N²-(2-oxo-2,5-dihydro-1,3-thiazol-4-yl)-L-alaninamide (213 mg) in 2-propanol (2 mL) was added piperidinium acetate (144 mg) at room temperature. The reaction mixture was stirred at 60° C. overnight. The solvent was evaporated, and the residue was purified by silica gel column chromatography (ethyl acetate/hexane) to give the title compound (180 mg).

$^1$H NMR (300 MHz, DMSO-$d_6$) δ 1.35 (3H, d, J=7.0 Hz), 1.41-1.59 (2H, m), 1.67-1.83 (2H, m), 2.02-2.26 (3H, m), 2.68-2.82 (2H, m), 2.85 (3H, s), 3.05 (3H, s), 3.72 (2H, s), 4.90-5.02 (1H, m), 7.09 (1H, d, J=8.9 Hz), 7.98 (1H, s), 8.02-8.13 (2H, m), 9.23 (1H, brs).
MS (ESI+): [M+H]$^+$ 537.2.

Example 134

N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-phenylalaninamide

A) N,N-dimethyl-L-phenylalaninamide hydrochloride

To a solution of N-(tert-butoxycarbonyl)-L-phenylalanine (5.31 g) and 50% aqueous dimethylamine solution (1.80 g)

and N-ethyl-N-(1-methylethyl)propan-2-amine (6.99 mL) in DMF (100 mL) was added O-(7-azabenzotriazol-1-yl)-N,N,N',N'-tetramethyluronium hexafluorophosphate (9.13 g) at room temperature. The reaction mixture was stirred at room temperature for 3 hr. Water was added to the reaction mixture at room temperature, and the mixture was extracted with ethyl acetate. The organic layer was separated, washed with water and saturated brine, dried over anhydrous magnesium sulfate, and concentrated under reduced pressure. To a solution of the residue in ethyl acetate (20 mL) was added 4N hydrogen chloride/ethyl acetate solution (20 mL) under ice-cooling. The reaction mixture was stirred at room temperature overnight, and the precipitated white solid was collected by filtration to give the title compound (4.05 g).

$^1$H NMR (300 MHz, DMSO-$d_6$) δ 2.60 (3H, s), 2.78 (3H, s), 2.94 (1H, dd, J=13.1, 8.1 Hz), 3.08 (1H, dd, J=13.1, 6.0 Hz), 4.48-4.59 (1H, m), 7.16-7.25 (2H, m), 7.25-7.40 (3H, m), 8.29 (3H, brs).

B) N,N-dimethyl-$N^2$-(2-oxo-2,5-dihydro-1,3-thiazol-4-yl)-L-phenylalaninamide

To a solution of N,N-dimethyl-L-phenylalaninamide hydrochloride (3.50 g) and triethylamine (6.39 mL) in ethanol (50 mL) was added 4-thioxothiazolidin-2-one (2.04 g) at room temperature. The reaction mixture was stirred at room temperature overnight. The obtained solid was suspended in THF, and the suspension was filtered through celite pad and silica gel pad. The filtrate was concentrated, and the residue was purified by silica gel column chromatography (NH, ethyl acetate/hexane) to give the title compound (1.55 g).

$^1$H NMR (300 MHz, DMSO-$d_6$) δ 2.76-3.08 (8H, m), 4.14 (1H, d, J=17.6 Hz), 4.25 (1H, d, J=17.6 Hz), 4.98-5.11 (1H, m), 7.17-7.39 (5H, m), 9.54 (1H, brs).

C) $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-phenylalaninamide To a solution of 1-[2,4-bis(trifluoromethyl)benzyl]piperidine-4-carbaldehyde (1360 mg) and N,N-dimethyl-$N^2$-(2-oxo-2,5-dihydro-1,3-thiazol-4-yl)-L-phenylalaninamide (1170 mg) in 2-propanol (20 mL) was added piperidinium acetate (581 mg) at room temperature. The reaction mixture was stirred at 60° C. for 3 hr. The solvent was evaporated, and the residue was purified by silica gel column chromatography (ethyl acetate/hexane) and recrystallized from ethyl acetate/heptane to give the title compound (860 mg).

$^1$H NMR (300 MHz, DMSO-$d_6$) δ 1.35-1.60 (2H, m), 1.64-1.84 (2H, m), 2.00-2.28 (3H, m), 2.68-2.84 (5H, m), 2.89 (3H, s), 2.97-3.17 (2H, m), 3.72 (2H, s), 5.09 (1H, brs), 7.12 (1H, d, J=8.9 Hz), 7.17-7.36 (5H, m), 7.99 (1H, s), 8.03-8.15 (2H, m), 9.44 (1H, brs).

MS (ESI+): [M+H]$^+$ 613.1.

Example 135

$N^2$-[(5Z)-5-({1-[2,4-bis(trifluoromethyl)benzyl]piperidin-4-yl}methylidene)-2-oxo-2,5-dihydro-1,3-thiazol-4-yl]-N,N,3-trimethyl-L-valinamide A) benzyl[(2S)-1-(dimethylamino)-3,3-dimethyl-1-oxobutan-2-yl]carbamate To a solution of 50% aqueous dimethylamine solution (0.816 g) and N-[(benzyloxy)carbonyl]-3-methyl-L-valine (2.00 g) and N-ethyl-N-(1-methylethyl)propan-2-amine (1.95 g) in DMF (20 mL) was added O-(7-azabenzotriazol-1-yl)-N,N,N',N'-tetramethyluronium hexafluorophosphate (3.15 g) at room temperature. The reaction mixture was stirred at room temperature overnight. Water was added to the reaction mixture at room temperature, and the mixture was extracted with ethyl acetate. The organic layer was separated, washed with water and saturated brine, dried over anhydrous magnesium sulfate, and concentrated under reduced pressure. The residue was purified by short silica gel column chromatography (NH, ethyl acetate) to give a crude product containing the title compound.

$^1$H NMR (300 MHz, DMSO-$d_6$) δ 0.92 (9H, s), 2.83 (3H, s), 3.08 (3H, s), 4.45 (1H, d, J=9.2 Hz), 4.94-5.11 (2H, m), 7.17 (1H, d, J=9.3 Hz), 7.25-7.43 (5H, m).

B) $N^2$-[(5Z)-5-({1-[2,4-bis(trifluoromethyl)benzyl]piperidin-4-yl}methylidene)-2-oxo-2,5-dihydro-1,3-thiazol-4-yl]-N,N,3-trimethyl-L-valinamide To a solution of the crude product containing benzyl[(2S)-1-(dimethylamino)-3,3-dimethyl-1-oxobutan-2-yl]carbamate obtained in A) in ethanol (10 mL) was added 10% palladium carbon (1.06 g) at room temperature. The reaction mixture was stirred at room temperature for 4 hr under a hydrogen atmosphere. The solid was removed by filtration, and the filtrate was concentrated under reduced pressure. To a solution of the residue in ethanol (10 mL) was added 4-thioxothiazolidin-2-one (1.00 g) at room temperature. The reaction mixture was stirred at room temperature overnight. The solvent was evaporated under reduced pressure, and the residue was purified by silica gel column chromatography (NH, ethyl acetate/hexane). To a solution of the residue and 1-[2,4-bis(trifluoromethyl)benzyl]piperidine-4-carbaldehyde (817 mg) in 2-propanol (5 mL) was added piperidinium acetate (350 mg) at room temperature. The reaction mixture was stirred at 60° C. for 3 hr. The solvent was evaporated, and the residue was purified by silica gel column chromatography (NH, ethyl acetate/hexane) to give the title compound (40 mg).

$^1$H NMR (300 MHz, CDCl$_3$) δ 1.06 (9H, s), 1.48-1.88 (4H, m), 2.09-2.27 (3H, m), 2.79-2.91 (2H, m), 3.00 (3H, s), 3.17 (3H, s), 3.70 (2H, s), 5.23 (1H, d, J=9.2 Hz), 6.23 (1H, d, J=8.8 Hz), 6.82 (1H, d, J=9.2 Hz), 7.79 (1H, d, J=8.3 Hz), 7.88 (1H, s), 8.00 (1H, d, J=8.3 Hz).

MS (ESI+): [M+H]$^+$ 579.2.

Example 136

(5Z)-5-({-[2,4-bis(trifluoromethyl)benzyl]piperidin-4-yl}methylidene)-4-(prop-2-yn-1-ylamino)-1,3-thiazol-2(5H)-one tartrate To a solution of (5Z)-5-({1-[2,4-bis(trifluoromethyl)benzyl]piperidin-4-yl}methylidene)-4-(prop-2-yn-1-ylamino)-1,3-thiazol-2(5H)-one (1 g) in ethanol (15 mL) was added L-(+)-tartaric acid (0.32 g). The reaction mixture was stirred at 60° C. for 20 min, the solvent was evaporated under reduced pressure, and the residue was recrystallized from 2-propanol/heptane to give the title compound (1.14 g).

$^1$H NMR (300 MHz, DMSO-$d_6$) δ 1.35-1.60 (2H, m), 1.65-1.88 (2H, m), 2.00-2.30 (3H, m), 2.63-2.86 (2H, m), 3.33 (1H, t, J=2.3 Hz), 3.72 (2H, s), 4.23 (2H, dd, J=5.1, 2.4 Hz), 4.31 (2H, s), 6.91 (1H, d, J=9.0 Hz), 7.98 (1H, s), 8.01-8.16 (2H, m), 9.57 (1H, t, J=5.1 Hz), 12.61 (1H, brs).

MS (ESI+): [M−C$_4$H$_6$O$_6$+H]$^+$ 476.2.

Example 137

(5Z)-5-({1-[2,4-bis(trifluoromethyl)benzyl]piperidin-4-yl}methylidene)-4-(prop-2-yn-1-ylamino)-1,3-thiazol-2(5H)-one citrate To a solution of (5Z)-5-({1-[2,4-bis(trifluoromethyl)benzyl]piperidin-4-yl}methylidene)-4-(prop-2-yn-1-ylamino)-1,3-thiazol-2(5H)-one (1 g) in ethanol (15 mL) was added citric acid (0.40 g). The reaction mixture was stirred at 80° C. for 20 min, the solvent was evaporated under reduced pressure, and the residue was recrystallized from 2-propanol/heptane to give the title compound (1.21 g).
$^1$H NMR (300 MHz, DMSO-$d_6$) δ 1.36-1.58 (2H, m), 1.62-1.85 (2H, m), 2.03-2.30 (3H, m), 2.58-2.86 (6H, m), 3.33 (1H, t, J=2.2 Hz), 3.73 (2H, s), 4.23 (2H, dd, J=5.1, 2.3 Hz), 6.91 (1H, d, J=8.8 Hz), 7.99 (1H, s), 8.02-8.17 (2H, m), 9.57 (1H, t, J=5.2 Hz), 12.31 (2H, brs).
MS (ESI+): [M−$C_6H_8O_7$+H]$^+$ 476.2.

Example 138

(5Z)-5-({1-[2,4-bis(trifluoromethyl)benzyl]piperidin-4-yl}methylidene)-4-(prop-2-yn-1-ylamino)-1,3-thiazol-2(5H)-one phosphate To a solution of (5Z)-5-({1-[2,4-bis(trifluoromethyl)benzyl]piperidin-4-yl}methylidene)-4-(prop-2-yn-1-ylamino)-1,3-thiazol-2(5H)-one (1 g) in ethanol (15 mL) was added phosphoric acid (0.14 mL). The reaction mixture was stirred at 60° C. for 1 hr, the solvent was evaporated under reduced pressure, and the residue was recrystallized from ethanol/heptane. The crystals were suspended in ethyl acetate at 65° C., and the precipitate was is collected by filtration to give the title compound (0.95 g).
$^1$H NMR (300 MHz, DMSO-$d_6$) δ 1.34-1.58 (2H, m), 1.65-1.84 (2H, m), 2.01-2.28 (3H, m), 2.62-2.85 (2H, m), 3.33 (1H, t, J=2.4 Hz), 3.71 (2H, s), 4.23 (2H, dd, J=5.4, 2.5 Hz), 6.91 (1H, d, J=8.9 Hz), 7.98 (1H, s), 8.01-8.17 (2H, m), 9.57 (1H, t, J=5.4 Hz).
MS (ESI+): [M−$H_3PO_4$+H]$^+$ 476.2.

Example 139

(5Z)-5-[(1-{[2,4-bis(trifluoromethyl)phenyl]carbonyl}piperidin-4-yl)methylidene]-4-(prop-2-yn-1-ylamino)-1,3-thiazol-2(5H)-one 2,4-Bis(trifluoromethyl)benzoic acid (1.20 g) was added to a solution of 1-hydroxybenzotriazole (0.76 g), 1-ethyl-3-(3-dimethylaminopropyl)carbodiimide hydrochloride (1.07 g), (5Z)-4-(methylamino)-5-(piperidin-4-ylmethylidene)-1,3-thiazol-2(5H)-one dihydrochloride (1.5 g), triethylamine (1.3 mL) in DMF (50 mL), and the mixture was stirred at room temperature overnight. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and recrystallized from ethyl acetate/heptane to give the title compound (1.7 g).
$^1$H NMR (300 MHz, DMSO-$d_6$) δ 1.11-1.73 (3H, m), 1.76-1.95 (1H, m), 2.39-2.45 (1H, m), 2.94-3.30 (3H, m), 3.33-3.36 (1H, m), 4.23 (2H, s), 4.29-4.55 (1H, m), 6.85-6.90 (1H, m), 7.73-7.83 (1H, m), 8.07-8.31 (2H, m), 9.57 (1H, brs).
MS (ESI+): [M+H]$^+$ 490.1.

Example 140

$N^3$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-β-alaninamide A) N,N-dimethyl-$N^3$-(2-oxo-2,5-dihydro-1,3-thiazol-4-yl)-β-alaninamide To a solution of N,N-dimethyl-R-alaninamide (2.12 g) in ethanol (25 mL) was added 4-thioxo-1,3-thiazolidin-2-one (2.43 g), which N,N-dimethyl-β-alaninamide hydrochloride was treated with AMBERLYST (registered trademark) A21, and the mixture was stirred at room temperature overnight. The reaction mixture was concentrated, and the residue was purified by silica gel column chromatography (NH, ethyl acetate/methanol) to give the title compound (0.33 g).
$^1$H NMR (300 MHz, DMSO-$d_6$) δ 2.59 (2H, t, J=6.6 Hz), 2.83 (3H, s), 2.94 (3H, s), 3.51 (2H, t, J=6.7 Hz), 4.19 (2H, s), 9.08 (1H, brs).

B) $N^3$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-β-alaninamide To a solution of 1-[2,4-bis(trifluoromethyl)benzyl]piperidine-4-carbaldehyde (520 mg) and N,N-dimethyl-$N^3$-(2-oxo-2,5-dihydro-1,3-thiazol-4-yl)-β-alaninamide (330 mg) in 2-propanol (60 mL) was added piperidinium acetate (223 mg). The reaction mixture was stirred at 80° C. for 4 hr and concentrated. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/methanol). The obtained solid was recrystallized from ethyl acetate/heptane to give the title compound (356 mg).
$^1$H NMR (300 MHz, DMSO-$d_6$) δ 1.33-1.58 (2H, m), 1.64-1.84 (2H, m), 1.94-2.34 (3H, m), 2.66 (2H, t, J=7.0 Hz), 2.71-2.80 (2H, m), 2.83 (3H, s), 2.95 (3H, s), 3.58 (2H, t, J=7.0 Hz), 3.71 (2H, s), 6.85 (1H, d, J=8.8 Hz), 7.98 (1H, s), 8.01-8.12 (2H, m), 9.18 (1H, s).
MS (ESI+): [M+H]$^+$ 537.2.
powder X-ray diffraction interplanar spacing (d): 11.56, 7.25, 5.96, 5.77, 5.01, 4.61, 4.50, 4.14, 4.02, 3.90, 3.83, 3.43 and 3.31 Å.

Example 141

(2S)-2-{[(5Z)-5-({1-[2,4-bis(trifluoromethyl)benzyl]piperidin-4-yl}methylidene)-2-oxo-2,5-dihydro-1,3-thiazol-4-yl]amino}-N,N-dimethylbutanamide To a solution of (2S)-2-[(tert-butoxycarbonyl)amino]butanoic acid (374 mg) and 50% aqueous dimethylamine solution (199 mg) and N-ethyl-N-(1-methylethyl)propan-2-amine (476 mg) in DMF (3 mL) was added O-(7-azabenzotriazol-1-yl)-N,N,N',N'-tetramethyluronium hexafluorophosphate (700 mg) at room temperature. The reaction mixture was stirred at room temperature overnight. Water was added to the reaction mixture at room temperature, and the mixture was extracted with ethyl acetate. The organic layer was separated, washed with water and saturated brine, dried over anhydrous magnesium sulfate, and concentrated under reduced pressure. To a solution of the residue in ethyl acetate (3 mL) was added 4N hydrogen chloride/ethyl acetate solution (3 mL) under ice-cooling. The reaction mixture was stirred at room temperature overnight, and the solvent was evaporated. To a solution of the residue and triethylamine (1012 mg) in ethanol (3 mL) was added 4-thioxothiazolidin-2-one (666 mg) at room temperature. The reaction mixture was stirred at room temperature overnight. The reaction mixture was purified by short silica gel column chromatography (ethyl acetate) and purified by silica gel column chromatography (NH, ethyl acetate/hexane). To a solution of the residue and 1-[2,4-bis(trifluoromethyl)benzyl]piperidine-4-carbaldehyde (533 mg) in 2-propanol (5 mL) was added piperidinium acetate (228 mg) at room temperature. The reaction mixture was stirred at 60° C. for 3 hr. The solvent was evaporated, and the residue was purified by silica gel column chromatography (NH, ethyl acetate/hexane) and recrystallized from ethyl acetate/heptane to give the title compound (83 mg).

$^1$H NMR (300 MHz, CDCl$_3$) δ 0.95 (3H, t, J=7.5 Hz), 1.41-1.60 (2H, m), 1.67-1.88 (3H, m), 1.93-2.28 (4H, m), 2.76-2.91 (2H, m), 3.03 (3H, s), 3.12 (3H, s), 3.70 (2H, s), 5.06-5.19 (1H, m), 6.30 (1H, d, J=8.9 Hz), 7.49 (1H, d, J=7.2 Hz), 7.80 (1H, d, J=8.1 Hz), 7.88 (1H, s), 7.99 (1H, d, J=8.2 Hz).

MS (ESI+): [M+H]$^+$ 551.1.

Example 142

N$^2$-[(5Z)-5-({1-[2,4-bis(trifluoromethyl)benzyl]piperidin-4-yl}methylidene)-2-oxo-2,5-dihydro-1,3-thiazol-4-yl]-N$^1$,N$^1$,N$^4$,N$^4$-tetramethyl-L-aspartamide A) benzyl[(2S)-1,4-bis(dimethylamino)-1,4-dioxobutan-2-yl]carbamate To a solution of 50% aqueous dimethylamine solution (2.16 g) and N-[(benzyloxy)carbonyl]-L-aspartic acid (2.13 g) and N-ethyl-N-(1-methylethyl)propan-2-amine (4.12 g) in DMF (20 mL) was added O-(7-azabenzotriazol-1-yl)-N,N,N',N'-tetramethyluronium hexafluorophosphate (6.06 g) at room temperature. The reaction mixture was stirred at room temperature overnight. Water was added to the reaction mixture at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (NH, methanol/ethyl acetate) to give the title compound (550 mg).

$^1$H NMR (300 MHz, DMSO-d$_6$) δ 2.41-2.49 (1H, m), 2.72-2.84 (7H, m), 2.93 (3H, s), 3.04 (3H, s), 4.74-4.91 (1H, m), 5.01 (2H, s), 7.26-7.43 (5H, m), 7.62 (1H, d, J=8.7 Hz).

B) N$^1$,N$^1$,N$^4$,N$^4$-tetramethyl-L-aspartamide

To a solution of benzyl[(2S)-1,4-bis(dimethylamino)-1,4-dioxobutan-2-yl]carbamate (550 mg) in ethanol (5 mL) was added 10% palladium carbon (182 mg) at room temperature. The reaction mixture was stirred at room temperature for 5 hr under a hydrogen atmosphere. The solid was removed by filtration, and the filtrate was concentrated under reduced pressure to give the title compound (350 mg).

$^1$H NMR (300 MHz, DMSO-d$_6$) δ 2.37 (1H, dd, J=16.1, 6.6 Hz), 2.64 (1H, dd, J=16.1, 6.6 Hz), 2.79 (3H, s), 2.81 (3H, s), 2.94 (3H, s), 3.03 (3H, s), 4.02 (1H, dd, J=6.6, 6.6 Hz).

C) N$^2$-[(5Z)-5-({1-[2,4-bis(trifluoromethyl)benzyl]piperidin-4-yl}methylidene)-2-oxo-2,5-dihydro-1,3-thiazol-4-yl]-N$^1$,N$^1$,N$^4$,N$^4$-tetramethyl-L-aspartamide To a solution of N$^1$,N$^1$,N$^4$,N$^4$-tetramethyl-L-aspartamide (350 mg) in ethanol (5 mL) was added 4-thioxothiazolidin-2-one (249 mg) at room temperature. The reaction mixture was stirred at room temperature overnight. The solvent was evaporated under reduced pressure, and the residue was purified by silica gel column chromatography (NH, methanol/ethyl acetate). To a solution of the obtained solid and 1-[2,4-bis(trifluoromethyl)benzyl]piperidine-4-carbaldehyde (687 mg) in 2-propanol (5 mL) was added piperidinium acetate (294 mg) at room temperature. The reaction mixture was stirred at 80° C. overnight. Water was added to the reaction mixture at room temperature, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane) and recrystallized from ethyl acetate/heptane to give the title compound (156 mg).

$^1$H NMR (300 MHz, CDCl$_3$) δ 1.43-1.63 (2H, m), 1.70-1.84 (2H, m), 2.06-2.25 (3H, m), 2.77-2.96 (7H, m), 2.98-3.06 (6H, m), 3.20 (3H, s), 3.69 (2H, s), 5.38-5.50 (1H, m), 6.28 (1H, dd, J=8.9, 1.5 Hz), 7.73-7.91 (3H, m), 7.99 (1H, d, J=8.1 Hz).

MS (ESI+): [M+H]$^+$ 608.1.

Example 143

(8Z)-8-({1-[2,4-bis(trifluoromethyl)benzyl]piperidin-4-yl}methylidene)-4,8-dihydro[1,3]thiazolo[3,4-a]pyrimidin-6-one A) 4,8-dihydro[1,3]thiazolo[3,4-a]pyrimidin-6-one A solution of 4-(prop-2-yn-1-ylamino)-1,3-thiazol-2(5H)-one (120 mg) in methanol (2 mL) was stirred at 140° C. for 1 hr under microwave irradiation, and the solvent was evaporated. The residue was purified by silica gel column chromatography (ethyl acetate/hexane) to give the title compound (38 mg).

$^1$H NMR (300 MHz, CDCl$_3$) δ 3.98 (2H, t, J=1.8 Hz), 4.30-4.37 (2H, m), 5.03 (1H, dt, J=8.4, 2.9 Hz), 6.68 (1H, dt, J=8.4, 1.8 Hz).

B) (8Z)-8-({1-[2,4-bis(trifluoromethyl)benzyl]piperidin-4-yl}methylidene)-4,8-dihydro[1,3]thiazolo[3,4-a]pyrimidin-6-one To a solution of 4,8-dihydro[1,3]thiazolo[3,4-a]pyrimidin-6-one (38 mg) and 1-[2,4-bis(trifluoromethyl)benzyl]piperidine-4-carbaldehyde (125 mg) in 2-propanol (2 mL) was added piperidinium acetate (54 mg) at room temperature. The reaction mixture was stirred at 60° C. overnight. The reaction mixture was added to water at room temperature, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (38 mg).

$^1$H NMR (300 MHz, CDCl$_3$) δ 1.47-1.66 (2H, m), 1.68-1.82 (2H, m), 2.05-2.25 (3H, m), 2.77-2.89 (2H, m), 3.69 (2H, s), 4.40-4.44 (2H, m), 5.08 (1H, dt, J=8.4, 2.9 Hz), 6.68 (1H, d, J=9.4 Hz), 6.75 (1H, dt, J=8.4, 1.8 Hz), 7.78 (1H, d, J=8.3 Hz), 7.87 (1H, s), 8.00 (1H, d, J=8.1 Hz).
MS (ESI+): [M+H]$^+$ 476.2.

Example 144

(5Z)-5-({1-[2,4-bis(trifluoromethyl)benzyl]piperidin-4-yl}methylidene)-4-{[(3R)-1-methyl-2-oxopyrrolidin-3-yl]amino}-1,3-thiazol-2(5H)-one A) tert-butyl[(3R)-2-oxopyrrolidin-3-yl]carbamate To a solution of (R)-aminopyrrolidin-2-one (1.7 g) and triethylamine (4.73 mL) in methanol (20 mL) was added di-tert-butyl bicarbonate (5.91 mL). The reaction mixture was stirred at room temperature overnight and further heated under reflux for 2 hr. The reaction mixture was concentrated, and the residue was purified by silica gel column chromatography (ethyl acetate).
$^1$H NMR (300 MHz, DMSO-d$_6$) δ 1.38 (9H, s), 1.70-1.93 (1H, m), 2.11-2.35 (1H, m), 3.12 (2H, dd, J=9.3, 5.0 Hz), 3.88-4.11 (1H, m), 7.00 (1H, d, J=8.7 Hz), 7.69 (1H, s).

B) (5Z)-5-({1-[2,4-bis(trifluoromethyl)benzyl]piperidin-4-yl}methylidene)-4-{[(3R)-1-methyl-2-oxopyrrolidin-3-yl]amino}-1,3-thiazol-2(5H)-one A solution of tert-butyl[(3R)-2-oxopyrrolidin-3-yl]carbamate (1.87 g) and iodomethane (0.70 mL) in THF (5 mL) and DMF (5 mL) was added to a solution of 60% sodium hydride (0.53 g, containing mineral oil) in THF (10 mL). The reaction mixture was stirred at room temperature overnight, saturated aqueous ammonium chloride solution was added, and the mixture was extracted with ethyl acetate. The extract was washed with water and saturated brine, and dried over anhydrous magnesium sulfate, and the solvent was evaporated under reduced pressure. The residue was purified by silica gel column chromatography is (ethyl acetate/methanol). To a solution of the obtained solid in ethyl acetate (20 mL) was added 4N hydrogen chloride/ethyl acetate solution (20 mL), the mixture was stirred at room temperature for 2 hr, and the reaction mixture was concentrated. To a solution of the obtained residue in methanol (20 mL) was added AMBERLYST (registered trademark) A21, and the mixture was stirred for 15 min. The reaction solution was filtered, AMBERLYST (registered trademark) A21 was removed, and the filtrate was concentrated under reduced pressure. To a solution of the obtained residue in ethanol (10 mL) was added 4-thioxo-1,3-thiazolidin-2-one (889 mg), and the mixture was stirred at room temperature for 5 hr. The reaction mixture was concentrated under reduced pressure, and the residue was purified by silica gel column chromatography (NH, ethyl acetate/methanol) to give a mixture (0.32 g) of 4-{[(3R)-1-methyl-2-oxopyrrolidin-3-yl]amino}-1,3-thiazol-2(5H)-one and 4-{[(3R)-2-oxopyrrolidin-3-yl]amino}-1,3-thiazol-2(5H)-one, and 4-{[(3R)-2-oxopyrrolidin-3-yl]amino}-1,3-thiazol-2(5H)-one (0.14 g). To a solution of the mixture (0.32 g) of 4-{[(3R)-1-methyl-2-oxopyrrolidin-3-yl]amino}-1,3-thiazol-2(5H)-one and 4-{[(3R)-2-oxopyrrolidin-3-yl]amino}-1,3-thiazol-2(5H)-one, and 1-[2,4-bis(trifluoromethyl)benzyl]piperidine-4-carbaldehyde (761 mg) in 2-propanol (5 mL) was added piperidinium acetate (217 mg). The reaction mixture was stirred at 80° C. for 6 hr and concentrated under reduced pressure. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/methanol). The obtained solid was recrystallized from ethyl acetate/heptane to give the title compound (200 mg).
$^1$H NMR (300 MHz, DMSO-d$_6$) δ 1.32-1.62 (2H, m), 1.63-1.85 (2H, m), 1.90-2.26 (4H, m), 2.29-2.46 (1H, m), 2.67-2.84 (5H, m), 3.33-3.41 (2H, m), 3.71 (2H, s), 4.73 (1H, t, J=9.3 Hz), 6.89 (1H, d, J=8.9 Hz), 7.98 (1H, s), 8.01-8.13 (2H, m), 9.37 (1H, s).
MS (ESI+): [M+H]$^+$ 535.0.

Example 145

(5Z)-5-({1-[2,4-bis(trifluoromethyl)benzyl]piperidin-4-yl}methylidene)-4-{[(3R)-2-oxopyrrolidin-3-yl]amino}-1,3-thiazol-2(5H)-one To a solution of 4-{[(3R)-2-oxopyrrolidin-3-yl]amino}-1,3-thiazol-2(5H)-one (140 mg) and 1-[2,4-bis(trifluoromethyl)benzyl]piperidine-4-carbaldehyde (358 mg) in 2-propanol (5 mL) was added piperidinium acetate (102 mg). The reaction mixture was stirred at 80° C. for 6 hr and concentrated under reduced pressure. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/methanol). The obtained solid was recrystallized from ethyl acetate/heptane to give the title compound (80 mg).
$^1$H NMR (300 MHz, DMSO-d$_6$) δ 1.29-1.61 (2H, m), 1.65-1.84 (2H, m), 1.93-2.30 (4H, m), 2.34-2.47 (1H, m), 2.66-2.93 (2H, m), 3.17-3.29 (2H, m), 3.71 (2H, s), 4.68 (1H, t, J=9.5 Hz), 6.91 (1H, d, J=8.8 Hz), 7.98 (1H, s), 8.00-8.13 (3H, m), 9.32 (1H, brs).
MS (ESI+): [M+H]$^+$ 521.0.

Example 146

(5Z)-5-({1-[2,4-bis(trifluoromethyl)benzyl]piperidin-4-yl}methylidene)-4-{[2-(methylsulfonyl)ethyl]amino}-1,3-thiazol-2(5H)-one A) 4-{[2-(methylsulfonyl)ethyl]amino}-1,3-thiazol-2(5H)-one To a solution of 4-thioxo-1,3-thiazolidin-2-one (865 mg) in ethanol (10 mL) was added 2-(methylsulfonyl)ethanamine (1 g), and the mixture was stirred at room temperature for 3 hr. The precipitate was collected by filtration to give the title compound (1.39 g).
$^1$H NMR (300 MHz, DMSO-d$_6$) δ 3.05 (3H, s), 3.41 (2H, t, J=6.1 Hz), 3.72 (2H, q, J=6.1 Hz), 4.24 (2H, s), 9.30 (1H, brs).

B) (5Z)-5-({1-[2,4-bis(trifluoromethyl)benzyl]piperidin-4-yl}methylidene)-4-{[2-(methylsulfonyl)ethyl]amino}-1,3-thiazol-2(5H)-one To a solution of 4-{[2-(methylsulfonyl)ethyl]amino}-1,3-thiazol-2(5H)-one (1.39 g) and 1-[2,4-bis(trifluoromethyl)benzyl]piperidine-4-carbaldehyde (1.77 g) in 2-propanol (20 mL) was added piperidinium acetate (757 mg). The reaction mixture was stirred at 80° C. for 3 hr and concentrated under reduced pressure. Water was added to the residue, and the mixture was extracted with ethyl acetate. The extract was washed with water and saturated brine, and dried over anhy-

Example 147

(5Z)-5-({1-[(1-methyl-1H-indol-2-yl)carbonyl]piperidin-4-yl}methylidene)-4-(prop-2-yn-1-ylamino)-1,3-thiazol-2(5H)-one To a solution of (5Z)-4-(prop-2-yn-1-ylamino)-5-(piperidin-4-ylmethylidene)-1,3-thiazol-2(5H)-one dihydrochloride (200 mg) in DMF (3 mL) were added N-ethyl-N-(1-methylethyl)propan-2-amine (0.56 mL), O-(7-azabenzotriazol-1-yl)-N,N,N',N'-tetramethyluronium hexafluorophosphate (283 mg) and 1-methyl-1H-indole-2-carboxylic acid (135 mg). The reaction mixture was stirred at room temperature overnight, water was added, and the mixture was extracted with ethyl acetate/tetrahydrofuran. The extract was washed with water and saturated brine, and dried over anhydrous magnesium sulfate, and the solvent was evaporated under reduced pressure. The residue was recrystallized from ethyl acetate/heptane to give the title compound (111 mg).

$^1$H NMR (300 MHz, DMSO-$d_6$) δ 1.35-1.53 (2H, m), 1.71-1.92 (2H, m), 2.36-2.47 (1H, m), 3.19 (2H, brs), 3.30-3.34 (1H, m), 3.75 (3H, s), 3.95-4.48 (2H, m), 4.23 (2H, s), 6.64 (1H, s), 6.90 (1H, d, J=8.8 Hz), 7.05-7.14 (1H, m), 7.20-7.30 (1H, m), 7.51 (1H, d, J=8.3 Hz), 7.60 (1H, d, J=7.9 Hz), 9.59 (1H, brs).

MS (ESI+): [M+H]$^+$ 407.0.

Example 148

(5Z)-5-({1-[(1-methyl-1H-benzimidazol-2-yl)carbonyl]piperidin-4-yl}methylidene)-4-(prop-2-yn-1-ylamino)-1,3-thiazol-2 (H)-one To a solution of (5Z)-4-(prop-2-yn-1-ylamino)-5-(piperidin-4-ylmethylidene)-1,3-thiazol-2(5H)-one dihydrochloride (200 mg) in DMF (3 mL) were added N-ethyl-N-(1-methylethyl)propan-2-amine (0.56 mL), O-(7-azabenzotriazol-1-yl)-N,N,N',N'-tetramethyluronium hexafluorophosphate (283 mg) and 1-methyl-1H-benzo[d]imidazole-2-carboxylic acid (135 mg). The reaction mixture was stirred at room temperature overnight, water was added, and the mixture was extracted with ethyl acetate/tetrahydrofuran. The extract was washed with water and saturated brine, and dried over anhydrous magnesium sulfate, and the solvent was evaporated under reduced pressure. The residue was recrystallized from ethyl acetate/heptane to is give the title compound (97 mg).

$^1$H NMR (300 MHz, DMSO-$d_6$) δ 1.36-1.60 (2H, m), 1.72-1.96 (2H, m), 2.39-2.49 (1H, m), 3.05-3.18 (1H, m), 3.24-3.38 (2H, m), 3.85 (3H, s), 4.02-4.14 (1H, m), 4.23 (2H, s), 4.39-4.50 (1H, m), 6.90 (1H, d, J=9.1 Hz), 7.25-7.33 (1H, m), 7.33-7.41 (1H, m), 7.65 (1H, d, J=8.0 Hz), 7.71 (1H, d, J=7.9 Hz), 9.59 (1H, brs).

MS (ESI+): [M+H]$^+$ 408.0.

The title compound from previous example continues (above Example 147):

drous magnesium sulfate, and the solvent was evaporated under reduced pressure. The residue was purified by silica gel column chromatography (ethyl acetate/hexane), and the obtained solid was recrystallized from ethyl acetate/heptane to give the title compound (1.6 g).

$^1$H NMR (300 MHz, DMSO-$d_6$) δ 1.30-1.57 (2H, m), 1.64-1.86 (2H, m), 1.90-2.30 (3H, m), 2.64-2.84 (2H, m), 3.06 (3H, s), 3.47 (2H, t, J=6.8 Hz), 3.71 (2H, s), 3.76-3.89 (2H, m), 6.83 (1H, d, J=8.6 Hz), 7.98 (1H, s), 8.01-8.15 (2H, m), 9.39 (1H, s).

MS (ESI+): [M+H]$^+$ 544.0.

Example 149

$N^2$-[(5Z)-5-({1-[2,4-bis(trifluoromethyl)benzyl]piperidin-4-yl}methylidene)-2-oxo-2,5-dihydro-1,3-thiazol-4-yl]-N,N,O-trimethyl-L-serinamide A) $N^2$-(tert-butoxycarbonyl)-N,N,O-trimethyl-L-serinamide To a solution of N-(tert-butoxycarbonyl)-O-methyl-L-serine (2.00 g), 50% aqueous dimethylamine solution (0.987 g) and N-ethyl-N-(1-methylethyl)propan-2-amine (2.36 g) in DMF (20 mL) was added O-(7-azabenzotriazol-1-yl)-N,N,N',N'-tetramethyluronium hexafluorophosphate (3.82 g) under ice-cooling. The reaction mixture was stirred at room temperature overnight. The reaction mixture was added to water, and the mixture was extracted with ethyl acetate. The organic layer was separated, washed with water and saturated brine, dried over anhydrous magnesium sulfate, concentrated under reduced pressure. The residue was purified by silica gel column chromatography (NH, ethyl acetate/hexane) to give the title compound (2.08 g).

$^1$H NMR (300 MHz, DMSO-$d_6$) δ 1.37 (9H, s), 2.82 (3H, s), 3.02 (3H, s), 3.22 (3H, s), 3.32-3.51 (2H, m), 4.50-4.65 (1H, m), 6.92 (1H, d, J=8.3 Hz).

B) N,N,O-trimethyl-L-serinamide

To a solution of $N^2$-(tert-butoxycarbonyl)-N,N,O-trimethyl-L-serinamide (2.08 g) in ethyl acetate (10 mL) was is added 4N hydrogen chloride/ethyl acetate solution (10 mL) under ice-cooling. The reaction mixture was stirred at room temperature overnight, and the solvent was evaporated under reduced pressure. To a solution of the residue in methanol (20 mL) was added AMBERLYST (registered trademark) A21 (2.0 g) at room temperature. The reaction mixture was stirred at room temperature for 1 hr. The insoluble material was removed by filtration, and the filtrate was concentrated under reduced pressure to give the title compound (1.82 g).

$^1$H NMR (300 MHz, DMSO-$d_6$) δ 2.86 (3H, s), 3.03 (3H, s), 3.26 (3H, s), 3.43 (1H, dd, J=10.0, 5.6 Hz), 3.52 (1H, dd, J=10.0, 5.6 Hz), 4.23 (1H, dd, J=5.8, 5.6 Hz).

C) N,N,O-trimethyl-$N^2$-(2-oxo-2,5-dihydro-1,3-thiazol-4-yl)-L-serinamide

To a solution of 4-thioxothiazolidin-2-one (1.00 g) in ethanol (20 mL) was added N,N,O-trimethyl-L-serinamide (1.82 g) at room temperature. The reaction mixture was stirred at room temperature overnight, and the solvent was evaporated under reduced pressure. The residue was purified by silica gel column chromatography (ethyl acetate/hexane) to give the title compound (434 mg).

$^1$H NMR (300 MHz, DMSO-$d_6$) δ 2.86 (3H, s), 3.08 (3H, s), 3.27 (3H, s), 3.49-3.63 (2H, m), 4.25 (2H, s), 5.01-5.13 (1H, m), 9.42 (1H, d, J=7.6 Hz).

D) $N^2$-[(5Z)-5-({1-[2,4-bis(trifluoromethyl)benzyl]piperidin-4-yl}methylidene)-2-oxo-2,5-dihydro-1,3-thiazol-4-yl]-N,N,O-trimethyl-L-serinamide To a solution of N,N,O-trimethyl-$N^2$-(2-oxo-2,5-dihydro-1,3-thiazol-4-yl)-L-serinamide (434 mg) and 1-[2,4-bis(trifluoromethyl)benzyl]piperidine-4-carbaldehyde (780 mg) in 2-propanol (10 mL) was added piperidinium acetate (334 mg)

at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (409 mg).

$^1$H NMR (300 MHz, DMSO-$d_6$) δ 1.40-1.58 (2H, m), 1.67-1.82 (2H, m), 2.03-2.26 (3H, m), 2.70-2.82 (2H, m), 2.86 (3H, s), 3.09 (3H, s), 3.29 (3H, s), 3.65 (2H, d, J=6.6 Hz), 3.71 (2H, s), 5.16 (1H, t, J=6.5 Hz), 7.11 (1H, d, J=8.8 Hz), 7.98 (1H, s), 8.01-8.13 (2H, m), 9.34 (1H, brs).

MS (ESI+): [M+H]$^+$ 567.2.

Example 150

N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-leucinamide A) N$^2$-(tert-butoxycarbonyl)-N,N-dimethyl-L-leucinamide To a solution of N-(tert-butoxycarbonyl)-L-leucine (23.1 g), dimethylamine hydrochloride (16.3 g) and N-ethyl-N-(1-methylethyl)propan-2-amine (51.6 g) in DMF (400 mL) was added O-(7-azabenzotriazol-1-yl)-N,N,N',N'-tetramethyluronium hexafluorophosphate (76.0 g) at room temperature. The reaction mixture was stirred at room temperature overnight, water was added to the reaction mixture, and the mixture was extracted with ethyl acetate. The organic layer was separated, washed with water and saturated brine, dried over sodium sulfate, and concentrated under reduced pressure to give a crude product containing the title compound.

$^1$H NMR (400 MHz, CDCl$_3$) δ 0.93 (3H, d, J=6.8 Hz), 0.99 (3H, d, J=6.8 Hz), 1.28-1.32 (2H, m), 1.43 (9H, s), 1.69-1.74 (1H, m), 2.96 (3H, s), 3.10 (3H, s), 4.63-4.69 (1H, m), 5.37 (1H, d, J=8.8 Hz).

B) N,N-dimethyl-L-leucinamide hydrochloride

To a solution of the crude product containing N$^2$-(tert-butoxycarbonyl)-N,N-dimethyl-L-leucinamide obtained in A) in ethyl acetate (100 mL) was added 4N hydrogen chloride/ethyl acetate solution (100 mL) under ice-cooling. The reaction mixture was stirred at room temperature overnight, and the solvent was evaporated under reduced pressure to give a crude product (22.0 g) containing the title compound.

$^1$H NMR (400 MHz, DMSO-$d_6$) δ 0.88 (3H, d, J=6.4 Hz), 0.92 (3H, d, J=6.4 Hz), 1.28-1.35 (2H, m), 1.77-1.82 (1H, m), 2.88 (3H, s), 3.03 (3H, s), 4.25-4.26 (1H, m), 8.36 (3H, brs).

C) N,N-dimethyl-N$^2$—(2-oxo-2,5-dihydro-1,3-thiazol-4-yl)-L-leucinamide

To a solution of the crude product containing N,N-dimethyl-L-leucinamide hydrochloride (11.7 g) obtained in B) and triethylamine (18.2 g) in ethanol (150 mL) was added 4-thioxothiazolidin-2-one (8.00 g) at room temperature. The reaction mixture was stirred at room temperature for 3 hr. The solvent was evaporated under reduced pressure, and the obtained solid was suspended in THF. The suspension was filtered through celite pad and silica gel pad, and the filtrate was concentrated under reduced pressure. The residue was purified by silica gel column chromatography (NH, ethyl acetate/petroleum ether) to give the title compound (8.1 g).

$^1$H NMR (400 MHz, DMSO-$d_6$) δ 0.90 (6H, d, J=6.0 Hz), 1.42-1.48 (1H, m), 1.55-1.65 (2H, m), 2.84 (3H, s), 3.05 (3H, s), 4.20-4.29 (2H, m), 4.86-4.91 (1H, m), 9.37 (1H, d, J=8.0 Hz).

MS (ESI+): [M+H]$^+$ 258.

D) N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-leucinamide To a solution of N,N-dimethyl-N$^2$-(2-oxo-2,5-dihydro-1,3-thiazol-4-yl)-L-leucinamide (772 mg) and 1-[2,4-bis(trifluoromethyl)benzyl]piperidine-4-carbaldehyde (1221 mg) in 2-propanol (10 mL) was added piperidinium acetate (523 mg) at room temperature. The reaction mixture was stirred at 60° C. overnight. After evaporation of the solvent, the residue was purified by silica gel column chromatography (NH, ethyl acetate/hexane) and recrystallized from ethyl acetate/heptane to give the title compound (888 mg).

$^1$H NMR (300 MHz, DMSO-$d_6$) δ 0.90 (3H, d, J=6.9 Hz), 0.93 (3H, d, J=6.9 Hz), 1.38-1.86 (7H, m), 2.02-2.25 (3H, m), 2.70-2.82 (2H, m), 2.85 (3H, s), 3.07 (3H, s), 3.72 (2H, s), 4.96 (1H, d, J=7.4 Hz), 7.12 (1H, d, J=8.5 Hz), 7.98 (1H, s), 8.02-8.12 (2H, m), 9.25 (1H, brs).

MS (ESI+): [M+H]$^+$ 579.1.

Example 151

N$^2$-[(5Z)-5-({1-[2,4-bis(trifluoromethyl)benzyl]piperidin-4-yl}methylene)-2-oxo-2,5-dihydro-1,3-thiazol-4-yl]-N,N-dimethyl-L-isoleucinamide A) N$^2$-(tert-butoxycarbonyl)-N,N-dimethyl-L-isoleucinamide To a solution of N-(tert-butoxycarbonyl)-L-isoleucine (15.0 g), dimethylamine hydrochloride (11.3 g) and N-ethyl-N-(1-methylethyl)propan-2-amine (26.7 g) in DMF (150 mL) was added O-(7-azabenzotriazol-1-yl)-N,N,N',N'-tetramethyluronium hexafluorophosphate (31.5 g) at room temperature. The reaction mixture was stirred at room temperature overnight, water was added to the reaction mixture, and the mixture was extracted with ethyl acetate. The organic layer was separated, washed with water and saturated brine, dried over sodium sulfate, and concentrated under reduced pressure to give a crude product (19.7 g) containing the title compound.

$^1$H NMR (400 MHz, DMSO-$d_6$) δ 0.77-0.83 (6H, m), 1.00-1.11 (1H, m), 1.37 (9H, s), 1.40-1.48 (1H, m), 1.66-1.70 (1H, m), 2.69 (3H, s), 3.06 (3H, s), 4.23 (1H, t, J=8.8 Hz), 6.75 (1H, d, J=8.8 Hz).

B) N,N-dimethyl-L-isoleucinamide hydrochloride

To a solution of the crude product containing N$^2$-(tert-butoxycarbonyl)-N,N-dimethyl-L-isoleucinamide obtained in A) in ethyl acetate (100 mL) was added 4N hydrogen chloride/ethyl acetate solution (100 mL) under ice-cooling. The reaction mixture was stirred at room temperature overnight. The solvent was evaporated under reduced pressure to give a crude product (19.4 g) containing the title compound.

$^1$H NMR (400 MHz, DMSO-$d_6$) δ 0.85 (3H, d, J=7.2 Hz), 0.94 (3H, d, J=6.8 Hz), 1.08-1.14 (1H, m), 1.46-1.52 (1H, m), 1.78-1.85 (1H, m), 2.89 (3H, s), 3.04 (3H, s), 4.16-4.20 (1H, m), 8.25 (3H, brs).

C) N,N-dimethyl-N²-(2-oxo-2,5-dihydro-1,3-thiazol-4-yl)-L-isoleucinamide

To a solution of the crude product (19.4 g) containing N,N-dimethyl-L-isoleucinamide hydrochloride obtained in B) and triethylamine (49.5 g) in ethanol (150 mL) was added 4-thioxothiazolidin-2-one (16.3 g) at room temperature. The reaction mixture was stirred at room temperature for 3 hr. The solvent was evaporated under reduced pressure, the obtained solid was suspended in THF, and the suspension was filtered through celite pad and silica gel pad. The filtrate was concentrated under reduced pressure. The residue was purified by silica gel column chromatography (NH, ethyl acetate/petroleum ether) to give the title compound (6.2 g).

$^1$H NMR (300 MHz, DMSO-$d_6$) δ 0.83-0.86 (6H, m), 1.11-1.18 (1H, m), 1.47-1.53 (1H, m), 1.82-1.85 (1H, m), 2.86 (3H, s), 3.12 (3H, s), 4.20-4.30 (2H, m), 4.75 (1H, d, J=8.4 Hz), 9.37 (1H, d, J=8.4 Hz).

MS (ESI+): [M+H]$^+$ 258.

D) N²-[(5Z)-5-({1-[2,4-bis(trifluoromethyl)benzyl]piperidin-4-yl}methylene)-2-oxo-2,5-dihydro-1,3-thiazol-4-yl]-N,N-dimethyl-L-isoleucinamide To a solution of N,N-dimethyl-N²-(2-oxo-2,5-dihydro-1,3-thiazol-4-yl)-L-isoleucinamide (772 mg) and 1-[2,4-bis(trifluoromethyl)benzyl]piperidine-4-carbaldehyde (1221 mg) in 2-propanol (10 mL) was added piperidinium acetate (523 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (770 mg).

$^1$H NMR (300 MHz, DMSO-$d_6$) δ 0.77-0.92 (6H, m), 1.22-1.31 (1H, m), 1.38-1.60 (3H, m), 1.64-1.82 (2H, m), 2.01-2.24 (4H, m), 2.68-2.82 (2H, m), 2.87 (3H, s), 3.17 (3H, s), 3.71 (2H, s), 4.79 (1H, d, J=9.7 Hz), 7.20 (1H, d, J=8.7 Hz), 7.98 (1H, s), 8.01-8.13 (2H, m), 9.28 (1H, brs).

MS (ESI+): [M+H]$^+$ 579.1.

Example 152

N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-valinamide

A) N²-(tert-butoxycarbonyl)-N,N-dimethyl-L-valinamide

To a solution of N-(tert-butoxycarbonyl)-L-valine (15.0 g), dimethylamine hydrochloride (11.3 g) and N-ethyl-N-(1-methylethyl)propan-2-amine (26.7 g) in DMF (150 mL) was added O-(7-azabenzotriazol-1-yl)-N,N,N',N'-tetramethyluronium hexafluorophosphate (31.5 g) at room temperature. The reaction mixture was stirred at room temperature overnight, water was added to the reaction mixture, and the mixture was extracted with ethyl acetate. The organic layer was separated, washed with water and saturated brine, dried over sodium sulfate, and concentrated under reduced pressure to give a crude product (20.6 g) containing the title compound.

$^1$H NMR (400 MHz, DMSO-$d_6$) δ 0.82-0.84 (6H, m), 1.37 (9H, s), 1.86-1.93 (1H, m), 2.69 (3H, s), 3.04 (3H, s), 4.19 (1H, t, J=8.0 Hz), 6.69 (1H, d, J=8.8 Hz).

B) N,N-dimethyl-L-valinamide hydrochloride

To a solution of the crude product containing N²-(tert-butoxycarbonyl)-N,N-dimethyl-L-valinamide obtained in A) in ethyl acetate (100 mL) was added 4N hydrogen chloride/ethyl acetate solution (100 mL) under ice-cooling. The reaction mixture was stirred at room temperature overnight. The solvent was evaporated under reduced pressure to give a crude product (19.6 g) containing the title compound.

$^1$H NMR (400 MHz, DMSO-$d_6$) δ 0.92 (3H, d, J=6.8 Hz), 0.97 (3H, d, J=7.2 Hz), 2.05-2.09 (1H, m), 2.89 (3H, s), 3.05 (3H, s), 4.17 (1H, t, J=5.2 Hz), 8.25 (3H, brs).

C) N,N-dimethyl-N²-(2-oxo-2,5-dihydro-1,3-thiazol-4-yl)-L-valinamide

To a solution of the crude product (19.6 g) containing N,N-dimethyl-L-valinamide hydrochloride obtained in B) and triethylamine (44.0 g) in ethanol (150 mL) was added 4-thioxothiazolidin-2-one (14.4 g) at room temperature, and the reaction mixture was stirred at room temperature for 3 hr. The solvent was evaporated under reduced pressure, the obtained solid was suspended in THF, and the suspension was filtered through celite pad and silica gel pad. The filtrate was concentrated under reduced pressure, and the residue was purified by silica gel column chromatography (NH, ethyl acetate/petroleum ether) to give the title compound (4.2 g).

$^1$H NMR (400 MHz, DMSO-$d_6$) δ 0.88 (3H, d, J=6.8 Hz), 0.92 (3H, d, J=6.8 Hz), 2.02-2.07 (1H, m), 2.86 (3H, s), 3.11 (3H, s), 4.21-4.31 (2H, m), 4.73 (1H, t, J=8.4 Hz), 9.33 (1H, d, J=8.0 Hz).

MS (ESI+): [M+H]$^+$ 244.

D) N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-valinamide To a solution of N,N-dimethyl-N²-(2-oxo-2,5-dihydro-1,3-thiazol-4-yl)-L-valinamide (973 mg) and 1-[2,4-bis(trifluoromethyl)benzyl]piperidine-4-carbaldehyde (1764 mg) in 2-propanol (10 mL) was added piperidinium acetate (755 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (960 mg)

$^1$H NMR (300 MHz, DMSO-$d_6$) δ 0.90 (3H, d, J=6.8 Hz), 0.95 (3H, d, J=6.6 Hz), 1.38-1.59 (2H, m), 1.65-1.82 (2H, m), 2.02-2.31 (4H, m), 2.68-2.82 (2H, m), 2.87 (3H, s), 3.16 (3H, s), 3.71 (2H, s), 4.73 (1H, d, J=9.3 Hz), 7.21 (1H, d, J=8.8 Hz), 7.98 (1H, s), 8.01-8.13 (2H, m), 9.25 (1H, brs).

MS (ESI+): [M+H]$^+$ 565.1.

Example 153

N²-[(5Z)-5-({1-[2,4-bis(trifluoromethyl)benzyl]piperidin-4-yl}methylene)-2-oxo-2,5-dihydro-1,3-thiazol-4-yl]-N,N-dimethyl-L-threoninamide

A) N²-(tert-butoxycarbonyl)-N,N-dimethyl-L-threoninamide

To a solution of N-(tert-butoxycarbonyl)-L-threonine (15.8 g) and dimethylamine hydrochloride (11.7 g) and N-ethyl-N-(1-methylethyl)propan-2-amine (27.9 g) in DMF (250 mL) was added O-(7-azabenzotriazol-1-yl)-N,N,N',N'-tetramethyluronium hexafluorophosphate (32.7 g) at room temperature. The reaction mixture was stirred at room temperature overnight. Water was added to the reaction mixture at room temperature, and the mixture was extracted with ethyl acetate. The organic layer was separated, washed with water and saturated brine, dried over sodium sulfate, and concentrated under reduced pressure to give a crude product (12.0 g) containing the title compound.

$^1$H NMR (400 MHz, CDCl$_3$) δ 1.17 (3H, d, J=6.0 Hz), 1.45 (9H, s), 2.90 (1H, s), 2.97 (3H, s), 3.15 (3H, s), 4.09-4.11 (1H, m), 4.72 (1H, d, J=10.0 Hz), 5.46 (1H, d, J=9.2 Hz).

B) N,N-dimethyl-L-threoninamide hydrochloride

To a solution of the crude product (12.0 g) containing N$^2$-(tert-butoxycarbonyl)-N,N-dimethyl-L-threoninamide obtained in A) in ethyl acetate (80 mL) was added 4N hydrogen chloride/ethyl acetate solution (80 mL) under ice-cooling. The reaction mixture was stirred at room temperature for 4 hr. The solvent was evaporated under reduced pressure to give a crude product (12.0 g) containing the title compound.

$^1$H NMR (400 MHz, DMSO-d$_6$) δ 1.13 (3H, d, J=6.0 Hz), 2.78 (3H, s), 2.99 (3H, s), 3.89-3.96 (2H, m), 4.15 (1H, d, J=4.8 Hz).

C) N,N-dimethyl-N$^2$-(2-oxo-2,5-dihydro-1,3-thiazol-4-yl)-L-threoninamide

To a solution of the crude product (12.0 g) containing N,N-dimethyl-L-threoninamide hydrochloride obtained in B) and triethylamine (20.0 g) in ethanol (150 mL) was added 4-thioxothiazolidin-2-one (8.8 g) at room temperature. The reaction mixture was stirred at room temperature for 4 hr. The solvent was evaporated under reduced pressure, the obtained solid was suspended in THF, and the suspension was filtered through celite pad and silica gel pad. The filtrate was concentrated under reduced pressure. The residue was purified by silica gel column chromatography (NH, ethyl acetate/petroleum ether) to give the title compound (3.0 g).

$^1$H NMR (400 MHz, DMSO-d$_6$) δ 1.07 (3H, d, J=6.0 Hz), 2.86 (3H, s), 3.11 (3H, s), 3.91-3.95 (1H, m), 4.25 (2H, s), 4.85-4.89 (1H, m), 5.06 (1H, d, J=5.2 Hz), 9.29 (1H, d, J=8.8 Hz).

MS (ESI+): [M+H]$^+$ 246.

D) N$^2$-[(5Z)-5-({1-[2,4-bis(trifluoromethyl)benzyl]piperidin-4-yl}methylene)-2-oxo-2,5-dihydro-1,3-thiazol-4-yl]-N,N-dimethyl-L-threoninamide To a solution of N,N-dimethyl-N$^2$-(2-oxo-2,5-dihydro-1,3-thiazol-4-yl)-L-threoninamide (981 mg) and 1-[2,4-bis(trifluoromethyl)benzyl]piperidine-4-carbaldehyde (1764 mg) in 2-propanol (10 mL) was added piperidinium acetate (755 mg) at room temperature. The reaction mixture was stirred at 60° C. overnight, and the solvent was evaporated under reduced pressure. The residue was purified by silica gel column chromatography (NH, ethyl acetate/hexane) to give the title compound (560 mg).

$^1$H NMR (300 MHz, DMSO-d$_6$) δ 1.10 (3H, d, J=6.2 Hz), 1.40-1.59 (2H, m), 1.75 (2H, d, J=11.2 Hz), 2.01-2.26 (3H, m), 2.68-2.82 (2H, m), 2.86 (3H, s), 3.16 (3H, s), 3.72 (2H, s), 4.02 (1H, brs), 4.89 (1H, d, J=7.3 Hz), 4.99 (1H, brs), 7.19 (1H, d, J=8.8 Hz), 7.98 (1H, s), 8.01-8.13 (2H, m), 9.20 (1H, brs).

MS (ESI+): [M+H]$^+$ 567.2.

Example 154

N$^2$-[(5Z)-5-({1-[2,4-bis(trifluoromethyl)benzyl]piperidin-4-yl}methylene)-2-oxo-2,5-dihydro-1,3-thiazol-4-yl]-N,N,O-trimethyl-L-threoninamide A) N$^2$-(tert-butoxycarbonyl)-N,N,O-trimethyl-L-threoninamide To a solution of N-(tert-butoxycarbonyl)-O-methyl-L-threonine (2.33 g), 50% aqueous dimethylamine solution (1.08 g) and N-ethyl-N-(1-methylethyl)propan-2-amine (2.58 g) in DMF (30 mL) was added O-(7-azabenzotriazol-1-yl)-N,N,N',N'-tetramethyluronium hexafluorophosphate (4.18 g) under ice-cooling. The reaction mixture was stirred at room temperature overnight, the reaction mixture was added to water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (2.02 g).

$^1$H NMR (300 MHz, DMSO-d$_6$) δ 1.01 (3H, d, J=6.1 Hz), 1.37 (9H, s), 2.83 (3H, s), 3.06 (3H, s), 3.23 (3H, s), 3.49 (1H, qd, J=6.1, 6.1 Hz), 4.42 (1H, dd, J=8.4, 6.1 Hz), 6.56 (1H, d, J=8.4 Hz).

B) N,N,O-trimethyl-L-threoninamide

To a solution of N$^2$-(tert-butoxycarbonyl)-N,N,O-trimethyl-L-threoninamide (2.02 g) in ethyl acetate (10 mL) was added 4N hydrogen chloride/ethyl acetate solution (10 mL) at room temperature. The reaction mixture was stirred at room temperature for 3 hr, and the reaction mixture was concentrated under reduced pressure. To the reaction mixture was added methanol (10 mL). To the reaction mixture was added AMBERLYST (registered trademark) A21 (1.00 g) at room temperature. The reaction mixture was stirred at room temperature for 1 hr, the insoluble material was removed by filtration, and the filtrate was concentrated under reduced pressure to give the title compound (1.20 g).

$^1$H NMR (300 MHz, DMSO-d$_6$) δ 1.10 (3H, d, J=6.2 Hz), 2.88 (3H, s), 3.05 (3H, s), 3.27 (3H, s), 3.51 (1H, qd, J=6.2, 6.2 Hz), 4.08 (1H, d, J=5.8 Hz).

C) N,N,O-trimethyl-N$^2$-(2-oxo-2,5-dihydro-1,3-thiazol-4-yl)-L-threoninamide

To a solution of N,N,O-trimethyl-L-threoninamide (1198 mg) in ethanol (10 mL) was added 4-thioxothiazolidin-2-one (996 mg) at room temperature. The reaction mixture was stirred at room temperature overnight, the solvent was evaporated under reduced pressure, and the residue was purified by silica gel column chromatography (NH, ethyl acetate/hexane) to give the title compound (680 mg).

$^1$H NMR (300 MHz, DMSO-d$_6$) δ 1.09 (3H, d, J=6.1 Hz), 2.86 (3H, s), 3.11 (3H, s), 3.27 (3H, s), 3.65 (1H, qd, J=6.1, 5.9 Hz), 4.26 (2H, s), 4.94 (1H, d, J=5.9 Hz), 9.40 (1H, brs).

D) N$^2$-[(5Z)-5-({1-[2,4-bis(trifluoromethyl)benzyl]piperidin-4-yl}methylene)-2-oxo-2,5-dihydro-1,3-thiazol-4-yl]-N,N,O-trimethyl-L-threoninamide To a solution of N,N,O-trimethyl-N$^2$-(2-oxo-2,5-dihydro-1,3-thiazol-4-yl)-L-threoninamide (670 mg) and 1-[2,4-bis(trifluoromethyl)benzyl]piperidine-4-carbaldehyde (1140 mg) in 2-propanol (10 mL) was added piperidinium acetate (488 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (890 mg).

$^1$H NMR (300 MHz, DMSO-d$_6$) δ 1.10 (3H, d, J=6.1 Hz), 1.40-1.61 (2H, m), 1.66-1.82 (2H, m), 2.02-2.24 (3H, m), 2.70-2.82 (2H, m), 2.86 (3H, s), 3.17 (3H, s), 3.28 (3H, s), 3.72 (2H, s), 3.73-3.84 (1H, m), 4.96 (1H, d, J=7.6 Hz), 7.20 (1H, d, J=8.7 Hz), 7.99 (1H, s), 8.02-8.13 (2H, m), 9.33 (1H, brs).

MS (ESI+): [M+H]$^+$ 581.1.

Example 155

(5Z)-5-{[1-(1-benzofuran-2-ylcarbonyl)piperidin-4-yl]methylidene}-4-(prop-2-yn-1-ylamino)-1,3-thiazol-2(5H)-one To a solution of (5Z)-4-(prop-2-yn-1-ylamino)-5-(piperidin-4-ylmethylidene)-1,3-thiazol-2(5H)-one dihydrochloride (200 mg) in DMF (3 mL) were added N-ethyl-N-(1-methylethyl)propan-2-amine (0.56 mL), O-(7-azabenzotriazol-1-yl)-N,N,N',N'-tetramethyluronium hexafluorophosphate (283 mg), and benzofuran-2-carboxylic acid (124 mg). The reaction mixture was stirred at room temperature overnight, water was added, and the mixture was extracted with ethyl acetate/tetrahydrofuran. The extract was washed with water and saturated brine, and dried over anhydrous magnesium sulfate, and the solvent was evaporated under reduced pressure. The residue was recrystallized from ethyl acetate/heptane to give the title compound (167 mg).

$^1$H NMR (300 MHz, DMSO-d$_6$) δ 1.36-1.55 (2H, m), 1.85 (2H, d, J=11.8 Hz), 2.37-2.50 (1H, m), 2.96-3.48 (3H, m), 4.16-4.37 (4H, m), 6.89 (1H, d, J=8.8 Hz), 7.29-7.37 (1H, m), 7.39 (1H, s), 7.41-7.48 (1H, m), 7.66 (1H, d, J=8.2 Hz), 7.75 (1H, d, J=7.7 Hz), 9.60 (1H, brs).

MS (ESI+): [M+H]$^+$ 394.0.

Example 156

(5Z)-5-({1-[(5-chloro-1-benzofuran-2-yl)carbonyl]piperidin-4-yl}methylidene)-4-(prop-2-yn-1-ylamino)-1,3-thiazol-2(5H)-one To a solution of (5Z)-4-(prop-2-yn-1-ylamino)-5-(piperidin-4-ylmethylidene)-1,3-thiazol-2(5H)-one dihydrochloride (200 mg) in DMF (3 mL) were added N-ethyl-N-(1-methylethyl)propan-2-amine (0.56 mL), O-(7-azabenzotriazol-1-yl)-N,N,N',N'-tetramethyluronium hexafluorophosphate (283 mg), and 5-chlorobenzofuran-2-carboxylic acid (151 mg). The reaction mixture was stirred at room temperature overnight, water was added, the mixture was extracted with ethyl acetate. The extract was washed with water and saturated brine, and dried over anhydrous magnesium sulfate, and the solvent was evaporated under reduced pressure. The residue was recrystallized from ethyl acetate/heptane to give the title compound (57 mg).

$^1$H NMR (300 MHz, DMSO-d$_6$) δ 1.36-1.55 (2H, m), 1.77-1.93 (2H, m), 2.37-2.48 (1H, m), 2.98-3.45 (3H, m), 4.10-4.41 (4H, m), 6.89 (1H, d, J=8.8 Hz), 7.36 (1H, s), 7.47 (1H, d, J=8.9 Hz), 7.72 (1H, d, J=8.9 Hz), 7.83 (1H, s), 9.62 (1H, brs).

MS (ESI+): [M+H]$^+$ 427.9.

Example 157

N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-alaninamide A) benzyl[(2R)-1-(dimethylamino)-1-oxopropan-2-yl]carbamate To a solution of N-[(benzyloxy)carbonyl]-D-alanine (4.46 g), 11% dimethylamine methanol solution (11.0 mL) and N-ethyl-N-(1-methylethyl)propan-2-amine (5.17 g) in DMF (30 mL) was added O-(7-azabenzotriazol-1-yl)-N,N,N',N'-tetramethyluronium hexafluorophosphate (8.37 g) under ice-cooling. The reaction mixture was stirred at room temperature overnight, the reaction mixture was added to water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (3.73 g).

$^1$H NMR (300 MHz, DMSO-d$_6$) δ 1.15 (3H, d, J=7.0 Hz), 2.82 (3H, s), 3.01 (3H, s), 4.49 (1H, qd, J=7.1, 7.1 Hz), 5.01 (2H, s), 7.21-7.52 (6H, m).

B) N,N-dimethyl-N$^2$-(2-oxo-2,5-dihydro-1,3-thiazol-4-yl)-D-alaninamide

To a solution of benzyl[(2R)-1-(dimethylamino)-1-oxopropan-2-yl]carbamate (3.73 g) in ethanol (20 mL) was added 10% palladium carbon (1.59 g) at room temperature. The reaction mixture was stirred at room temperature for 3 hr under a hydrogen atmosphere. The solid was removed by filtration, and the filtrate was concentrated under reduced pressure. To a solution of the residue in ethanol (20 mL) was added 4-thioxothiazolidin-2-one (2.00 g) at room temperature. The reaction mixture was stirred at room temperature overnight, the solvent was evaporated under reduced pressure, and the residue was purified by silica gel column chromatography (NH, ethyl acetate/hexane) to give the title compound (1.42 g).

$^1$H NMR (300 MHz, DMSO-d$_6$) δ 1.28 (3H, d, J=6.8 Hz), 2.86 (3H, s), 3.04 (3H, s), 4.24 (2H, s), 4.88 (1H, qd, J=6.9, 6.9 Hz), 9.33 (1H, d, J=7.1 Hz).

C) N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-alaninamide To a solution of N,N-dimethyl-N$^2$-(2-oxo-2,5-dihydro-1,3-thiazol-4-yl)-D-alaninamide (1.02 g) and 1-[2,4-bis(trifluoromethyl)benzyl]piperidine-4-carbaldehyde (1.93 g) in 2-propanol (10 mL) was added piperidinium acetate (826 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (1.30 g)

$^1$H NMR (300 MHz, DMSO-d$_6$) δ 1.36 (3H, d, J=7.0 Hz), 1.41-1.59 (2H, m), 1.65-1.84 (2H, m), 2.02-2.25 (3H, m), 2.69-2.82 (2H, m), 2.85 (3H, s), 3.06 (3H, s), 3.71 (2H, s), 4.96 (1H, q, J=6.9 Hz), 7.10 (1H, d, J=8.8 Hz), 7.98 (1H, s), 8.02-8.13 (2H, m), 9.24 (1H, brs).

MS (ESI+): [M+H]$^+$ 537.2.

Example 158

(5Z)-5-({1-[2,4-bis(trifluoromethyl)benzyl]piperidin-4-yl}methylidene)-4-[(3-hydroxypropyl)amino]-1,3-thiazol-2(5H)-one

A) 4-[(3-hydroxypropyl)amino]-1,3-thiazol-2(5H)-one

To a solution of 4-thioxothiazolidin-2-one (2.66 g) in ethanol (50 mL) was added 3-aminopropan-1-ol (1.50 g) at room temperature. The reaction mixture was stirred at room temperature for 4 hr, the solvent was evaporated under reduced pressure, and the residue was purified by silica gel column chromatography (NH, methanol/ethyl acetate) to give the title compound (2.70 g).

$^1$H NMR (300 MHz, DMSO-$d_6$) δ 1.61-1.74 (2H, m), 3.33-3.40 (2H, m), 3.45 (2H, td, J=5.6, 5.6 Hz), 4.22 (2H, s), 4.52 (1H, t, J=5.1 Hz), 9.04 (1H, brs).

B) (5Z)-5-({1-[2,4-bis(trifluoromethyl)benzyl]piperidin-4-yl}methylidene)-4-[(3-hydroxypropyl)amino]-1,3-thiazol-2(5H)-one To a solution of 4-[(3-hydroxypropyl)amino]-1,3-thiazol-2(5H)-one (900 mg) and 1-[2,4-bis(trifluoromethyl)benzyl]piperidine-4-carbaldehyde (1.75 g) in 2-propanol (20 mL) was added piperidinium acetate (750 mg) at room temperature. The reaction mixture was stirred at 60° C. overnight. After evaporation of the solvent, the residue was purified by silica gel column chromatography (NH, methanol/ethyl acetate) and recrystallized from ethyl acetate/heptane to give the title compound (1.17 g).

$^1$H NMR (300 MHz, DMSO-$d_6$) δ 1.35-1.59 (2H, m), 1.65-1.84 (4H, m), 2.01-2.27 (3H, m), 2.68-2.86 (2H, m), 3.39-3.56 (4H, m), 3.61-3.79 (2H, m), 4.55 (1H, brs), 6.85 (1H, d, J=8.7 Hz), 7.98 (1H, s), 8.02-8.13 (2H, m), 9.15 (1H, brs).

MS (ESI+): [M+H]$^+$ 496.0.

Example 159

(5Z)-5-({1-[2,4-bis(trifluoromethyl)benzyl]piperidin-4-yl}methylidene)-4-[(2-hydroxyethyl)amino]-1,3-thiazol-2(5H)-one

A) 4-[(2-hydroxyethyl)amino]-1,3-thiazol-2(5H)-one

To a solution of 4-thioxothiazolidin-2-one (2.66 g) in ethanol (50 mL) was added 2-aminoethanol (1.22 g) at room temperature. The reaction mixture was stirred at room temperature for 4 hr, and the precipitate was collected by filtration and washed with ethanol to give the title compound (2.24 g).

$^1$H NMR (300 MHz, DMSO-$d_6$) δ 3.38 (2H, td, J=5.5, 5.5 Hz), 3.53 (2H, td, J=5.5, 5.5 Hz), 4.22 (2H, s), 4.85 (1H, t, J=5.3 Hz), 9.12 (1H, brs).

B) (5Z)-5-({1-[2,4-bis(trifluoromethyl)benzyl]piperidin-4-yl}methylidene)-4-[(2-hydroxyethyl)amino]-1,3-thiazol-2(5H)-one To a solution of 4-[(2-hydroxyethyl)amino]-1,3-thiazol-2(5H)-one (1.20 g) and 1-[2,4-bis(trifluoromethyl)benzyl]piperidine-4-carbaldehyde (2.54 g) in 2-propanol (20 mL) was added piperidinium acetate (1.09 g) at room temperature. The reaction mixture was stirred at 60° C. overnight, and the solvent was evaporated under reduced pressure. The residue was purified by silica gel column chromatography (NH, methanol/ethyl acetate) and recrystallized from ethyl acetate/heptane to give the title compound (1.12 g)

$^1$H NMR (300 MHz, DMSO-$d_6$) δ 1.38-1.56 (2H, m), 1.66-1.82 (2H, m), 2.02-2.25 (3H, m), 2.69-2.85 (2H, m), 3.40-3.51 (2H, m), 3.52-3.63 (2H, m), 3.71 (2H, s), 4.90 (1H, brs), 6.90 (1H, d, J=8.8 Hz), 7.98 (1H, s), 8.01-8.14 (2H, m), 9.21 (1H, brs).

MS (ESI+): [M+H]$^+$ 482.2.

Example 160

1,5-anhydro-3-{[(5Z)-5-({1-[2,4-bis(trifluoromethyl)benzyl]piperidin-4-yl}methylidene)-2-oxo-2,5-dihydro-1,3-thiazol-4-yl]amino}-2,3-dideoxy-threo-pentitol

A) tetrahydro-2H-pyran-4-yl methanesulfonate

To a solution of tetrahydro-2H-pyran-4-ol (10.0 g) and triethylamine (19.1 mL) in dichloromethane (100 mL) was added dropwise methanesulfonyl chloride (10.7 mL) under ice-cooling. The reaction mixture was stirred at room temperature for 1 hr, and dichloromethane was added. The organic layer was washed with saturated aqueous sodium hydrogen carbonate and saturated brine, dried over anhydrous sodium sulfate, and the solvent was evaporated under reduced pressure to give the title compound (16.2 g).

$^1$H NMR (400 MHz, CDCl$_3$) δ 1.84-1.93 (2H, m), 2.03-2.08 (2H, m), 3.04 (3H, s), 3.52-3.58 (2H, m), 3.92-3.98 (2H, m), 4.88-4.94 (1H, m).

B) 3,6-dihydro-2H-pyran

A solution of tetrahydro-2H-pyran-4-yl methanesulfonate (45.0 g) in 1,8-diazabicyclo[5.4.0]undec-7-ene (100 mL) was stirred at 80° C. overnight. The reaction solution was allowed to cool to room temperature and evaporated under reduced pressure (10 mmHg) to give the title compound (13.0 g).

$^1$H NMR (400 MHz, CDCl$_3$) δ 2.11-2.17 (2H, m), 3.80 (2H, t, J=6.0 Hz), 4.12-4.14 (2H, m), 5.70-5.74 (1H, m), 5.82-5.87 (1H, m).

C) 1,5:3,4-dianhydro-2-deoxypentitol

To a solution of 3,6-dihydro-2H-pyran (13.0 g) in dichloromethane (150 mL) was added 3-chlorobenzenecarboperoxoic acid (32.0 g) under ice-cooling. The reaction mixture was stirred at room temperature overnight, and the precipitate was removed by filtration, and washed with dichloromethane. The filtrate was washed with 4N aqueous sodium hydroxide solution and saturated brine, dried over anhydrous sodium sulfate, and the solvent was evaporated under reduced pressure to give the title compound (10.1 g).

$^1$H NMR (400 MHz, CDCl$_3$) δ 1.99-2.02 (2H, m), 3.18 (1H, t, J=3.6 Hz), 3.35 (1H, t, J=2.0 Hz), 3.41-3.47 (1H, m), 3.50-3.56 (1H, m), 3.94-4.04 (2H, m).

D) 3-amino-1,5-anhydro-2,3-dideoxy-threo-pentitol hydrochloride

To a solution of 1,5:3,4-dianhydro-2-deoxypentitol (7.00 g) in methanol (120 mL) were added ammonium chloride (3.36 g) and sodium azide (9.75 g). The reaction solution was stirred at 78° C. for 3 hr and allowed to cool to room temperature, and the precipitate was removed by filtration, and washed with methanol. The filtrate was concentrated under reduced pressure, dichloromethane was added, the mixture was washed with saturated aqueous sodium hydrogen carbonate and saturated brine, dried over anhydrous sodium sulfate, and the solvent was evaporated under reduced pressure. The residue was dissolved in methanol (100 mL), palladium carbon (570 mg) was added, and the mixture was stirred at room temperature overnight under a hydrogen atmosphere. The reaction solution was filtered, the filtrate was concentrated under reduced pressure, and 4M hydrogen chloride/ethyl acetate solution (50 mL) and diethyl ether (150 mL) were added under ice-cooling. The precipitate was collected by filtration, and washed with diethyl ether. The obtained powder was recrystallized from methanol/ethyl acetate to give the title compound (1.20 g).

$^1$H NMR (400 MHz, CDCl$_3$) δ 1.57-1.67 (1H, m), 1.92-1.96 (1H, m), 2.91-3.01 (2H, m), 3.25-3.31 (1H, m), 3.45-3.52 (1H, m), 3.78-3.82 (2H, m), 5.65 (1H, d, J=5.2 Hz), 8.23 (3H, s).

MS (ESI+): [M−Cl]$^+$ 118.

E) 1,5-anhydro-2,3-dideoxy-3-[(2-oxo-2,5-dihydro-1,3-thiazol-4-yl)amino]-threo-pentitol To a solution of 3-amino-1,5-anhydro-2,3-dideoxy-threo-pentitol (3.20 g) in ethanol (100 mL) was added 4-thioxo-1,3-thiazolidin-2-one (3.63 g), and the mixture was heated under reflux overnight. The reaction mixture was filtered, the filtrate was concentrated under reduced pressure, and the residue was purified by silica gel column chromatography (ethyl acetate/petroleum ether) to give the title compound (2.36 g).

$^1$H NMR (400 MHz, CDCl$_3$) δ 1.43-1.48 (1H, m), 1.88-1.92 (1H, m), 2.49-2.51 (1H, m), 2.99-3.45 (2H, m), 3.76-3.82 (3H, m), 4.38 (2H, s), 9.13 (1H, d, J=8.0 Hz).

MS (ESI+): [M+H]$^+$ 217.

F) 1,5-anhydro-3-{[(5Z)-5-({1-[2,4-bis(trifluoromethyl)benzyl]piperidin-4-yl}methylidene)-2-oxo-2,5-dihydro-1,3-thiazol-4-yl]amino}-2,3-dideoxy-threo-pentitol To a solution of 1-[2,4-bis(trifluoromethyl)benzyl]piperidine-4-carbaldehyde (1.05 g) in 2-propanol (20 mL) were added 1,5-anhydro-2,3-dideoxy-3-[(2-oxo-2,5-dihydro-1,3-thiazol-4-yl)amino]-threo-pentitol (1.00 g) and piperidinium acetate (457 mg). The reaction mixture was stirred at 75° C. overnight, and the solvent was evaporated under reduced pressure. The residue was purified by silica gel column chromatography (ethyl acetate/hexane) and silica gel column chromatography (NH, methanol/ethyl acetate), and the obtained powder was washed with diisopropyl ether to give the title compound (571 mg).

$^1$H NMR (300 MHz, DMSO-d$_6$) δ 1.40-1.65 (3H, m), 1.70-1.81 (2H, m), 1.83-1.94 (1H, m), 2.03-2.24 (3H, m), 2.72-2.84 (2H, m), 2.95-3.08 (1H, m), 3.25-3.38 (1H, m), 3.51-3.66 (1H, m), 3.72 (2H, s), 3.77-4.00 (3H, m), 5.15 (1H, d, J=5.6 Hz), 6.90 (1H, d, J=8.8 Hz), 7.99 (1H, s), 8.04 (1H, d, J=8.4 Hz), 8.09 (1H, d, J=8.4 Hz), 8.98 (1H, brs).

MS (ESI+): [M+H]$^+$ 538.1.

Example 161

(2S)-1-[(5Z)-5-({1-[2,4-bis(trifluoromethyl)benzyl]piperidin-4-yl}methylidene)-2-oxo-2,5-dihydro-1,3-thiazol-4-yl]-N,N-dimethylazetidine-2-carboxamide A) tert-butyl(2S)-2-(dimethylcarbamoyl)azetidine-1-carboxylate To a solution of (2S)-1-(tert-butoxycarbonyl)azetidine-2-carboxylic acid (10.9 g) and dimethylamine hydrochloride (8.8 g) and N-ethyl-N-(1-methylethyl)propan-2-amine (21.0 g) in DMF (200 mL) was added O-(7-azabenzotriazol-1-yl)-N,N,N',N'-tetramethyluronium hexafluorophosphate (24.7 g) at room temperature. The reaction mixture was stirred at room temperature overnight, water was added to the reaction mixture, and the mixture was extracted with ethyl acetate. The organic layer was separated, washed with water and saturated brine, dried over sodium sulfate, and concentrated under reduced pressure to give a crude product (9.5 g) containing the title compound.

$^1$H NMR (400 MHz, CDCl$_3$) δ 1.43 (9H, s), 2.16-2.22 (1H, m), 2.38-2.47 (1H, m), 2.96-3.00 (6H, m), 3.83-3.89 (1H, m), 4.02-4.06 (1H, m), 4.94-4.97 (1H, m).

B) (2S)—N,N-dimethyl-1-(2-oxo-2,5-dihydro-1,3-thiazol-4-yl)azetidine-2-carboxamide To a solution of the crude product containing tert-butyl (2S)-2-(dimethylcarbamoyl)azetidine-1-carboxylate obtained in A) in ethyl acetate (50 mL) was added 4N hydrogen chloride/ethyl acetate solution (150 mL) under ice-cooling. The reaction mixture was stirred at room temperature overnight, and the solvent was evaporated under reduced pressure. To a solution of the residue and triethylamine (10.7 g) in ethanol (100 mL) was added 4-thioxothiazolidin-2-one (4.7 g) at room temperature. The reaction mixture was stirred at room temperature for 3 hr, and the solvent was evaporated under reduced pressure. The obtained solid was suspended in THF, and the suspension was filtered through celite pad and silica gel pad. The filtrate was concentrated under reduced pressure, and the residue was purified by silica gel column chromatography (NH, ethyl acetate) to give the title compound (3.64 g).

$^1$H NMR (400 MHz, CDCl$_3$) δ 2.37-2.49 (1H, m), 2.79-2.88 (1H, m), 2.91-3.04 (6H, m), 3.81-3.85 (0.55H, m), 3.96-4.05 (1H, m), 4.12-4.18 (0.45H, m), 4.24-4.29 (1.55H, m), 4.36-4.40 (0.45H, m), 5.19-5.23 (0.55H, m), 5.32-5.35 (0.45H, m).

MS (ESI+): [M+H]$^+$ 228.

C) (2S)-1-[(5Z)-5-({1-[2,4-bis(trifluoromethyl)benzyl]piperidin-4-yl}methylidene)-2-oxo-2,5-dihydro-1,3-thiazol-4-yl]-N,N-dimethylazetidine-2-carboxamide To a solution of (2S)—N,N-dimethyl-1-(2-oxo-2,5-dihydro-1,3-thiazol-4-yl)azetidine-2-carboxamide (682 mg) and 1-[2,4-bis(trifluoromethyl)benzyl]piperidine-4-carbaldehyde (1018 mg) is in 2-propanol (10 mL) was added piperidinium acetate (436 mg) at room temperature. The reaction mixture was stirred at 60° C. overnight, and the solvent was evaporated. The residue was purified by silica gel column chromatography (NH, ethyl acetate/hexane) and recrystallized from ethyl acetate/heptane to give the title compound (590 mg).

$^1$H NMR (300 MHz, DMSO-d$_6$) δ 1.29-1.79 (4H, m), 1.94-2.34 (4H, m), 2.55-3.03 (9H, m), 3.61-3.76 (2H, m), 4.16 (0.62H, t, J=7.5 Hz), 4.41-4.56 (0.69H, m), 4.56-4.71 (0.69H, m), 5.43 (0.69H, dd, J=9.0, 5.2 Hz), 5.95 (0.31H, d, J=8.5 Hz), 6.03 (0.31H, dd, J=9.0, 4.5 Hz), 6.35 (0.69H, d, J=8.9 Hz), 7.92-8.17 (3H, m).

MS (ESI+): [M+H]$^+$ 549.5.

Example 162

N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethylalaninamide

A) N²-(tert-butoxycarbonyl)-N,N-dimethylalaninamide

To a solution of N-(tert-butoxycarbonyl)alanine (3.78 g), 2M dimethylamine methanol solution (11 mL) and 1H-benzotriazol-1-ol (2.70 g) in DMA (50 mL) was added N-[3-(dimethylamino)propyl]-N'-ethylcarbodiimide hydrochloride (3.83 g) under ice-cooling. The reaction mixture was stirred at room temperature overnight, the reaction mixture was added to water, and the mixture was extracted with ethyl acetate. The organic layer was separated, washed with water and saturated brine, dried over magnesium sulfate, and concentrated under reduced pressure. The residue was purified by silica gel column chromatography (NH, ethyl acetate/hexane) to give a crude product containing the title compound.

$^1$H NMR (300 MHz, DMSO-$d_6$) δ 1.11 (3H, d, J=6.9 Hz), 1.36 (9H, s), 2.81 (3H, s), 2.99 (3H, s), 4.40 (1H, dq, J=7.6, 7.4 Hz), 6.87 (1H, d, J=7.6 Hz).

B) N,N-dimethylalaninamide hydrochloride

To a solution of the crude product containing N²-(tert-butoxycarbonyl)-N,N-dimethylalaninamide obtained in A) in ethyl acetate (5 mL) was added 4N hydrogen chloride/ethyl acetate solution (5 mL) at room temperature. The reaction mixture was stirred at room temperature for 3 hr, and the precipitate was collected by filtration to give a crude product containing the title compound.

$^1$H NMR (300 MHz, DMSO-$d_6$) δ 1.32 (3H, d, J=6.8 Hz), 2.88 (3H, s), 3.02 (3H, s), 4.14-4.43 (1H, m), 8.32 (3H, brs).

C) N,N-dimethylalaninamide

To a solution of the crude product containing N,N-dimethylalaninamide hydrochloride obtained in B) in methanol (10 mL) was added AMBERLYST (registered trademark) A21 (2.0 g) at room temperature, and the reaction mixture was stirred overnight. The insoluble material was removed through celite pad, and the filtrate was concentrated under reduced pressure to give a crude product containing the title compound.

$^1$H NMR (300 MHz, DMSO-$d_6$) δ 1.26 (3H, d, J=6.8 Hz), 2.87 (3H, s), 3.01 (3H, s), 4.18 (1H, q, J=6.8 Hz), 7.15 (2H, brs).

D) N,N-dimethyl-N²-(2-oxo-2,5-dihydro-1,3-thiazol-4-yl)alaninamide

To a solution of the crude product containing N,N-dimethylalaninamide obtained in C) and triethylamine (2 mL) in ethanol (20 mL) was added 4-thioxothiazolidin-2-one (1998 mg) at room temperature. The reaction mixture was stirred at room temperature overnight, and the solvent was evaporated under reduced pressure. The residue was purified by silica gel column chromatography (NH, ethyl acetate/hexane) to give the title compound (960 mg).

$^1$H NMR (300 MHz, DMSO-$d_6$) δ 1.28 (3H, d, J=6.9 Hz), 2.85 (3H, s), 3.04 (3H, s), 4.24 (2H, s), 4.87 (1H, qd, J=7.0, 7.0 Hz), is 9.33 (1H, d, J=6.9 Hz).

E) N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethylalaninamide To a solution of N,N-dimethyl-N²-(2-oxo-2,5-dihydro-1,3-thiazol-4-yl)alaninamide (646 mg) and 1-[2,4-bis(trifluoromethyl)benzyl]piperidine-4-carbaldehyde (1018 mg) in 2-propanol (10 mL) was added piperidinium acetate (436 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (1.08 g).

$^1$H NMR (300 MHz, DMSO-$d_6$) δ 1.35 (3H, d, J=7.0 Hz), 1.39-1.61 (2H, m), 1.65-1.83 (2H, m), 2.02-2.26 (3H, m), 2.68-2.82 (2H, m), 2.85 (3H, s), 3.05 (3H, s), 3.71 (2H, s), 4.96 (1H, q, J=6.9 Hz), 7.09 (1H, d, J=8.6 Hz), 7.90-8.21 (3H, m), 9.25 (1H, brs).

MS (ESI+): [M+H]$^+$ 537.1.

Example 163

1-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-prolinamide

A) tert-butyl(2S)-2-(dimethylcarbamoyl)pyrrolidine-1-carboxylate

To a solution of 1-(tert-butoxycarbonyl)-L-proline (10.7 g), dimethylamine hydrochloride (8.2 g) and N-ethyl-N-(1-methylethyl)propan-2-amine (19.3 g) in DMF (200 mL) was added O-(7-azabenzotriazol-1-yl)-N,N,N',N'-tetramethyluronium hexafluorophosphate (22.8 g) at room temperature. The reaction mixture was stirred at room temperature overnight, water was added to the reaction mixture, and the mixture was extracted with ethyl acetate. The organic layer was separated, washed with water and saturated brine, dried over sodium sulfate, and concentrated under reduced pressure to give a crude product containing the title compound.

$^1$H NMR (400 MHz, CDCl$_3$) δ 1.40-1.46 (9H, m), 1.79-1.89 (2H, m), 2.00-2.18 (2H, m), 2.95-2.97 (3H, m), 2.96-3.09 (3H, m), 3.39-3.63 (2H, m), 4.53-4.69 (1H, m).

B) N,N-dimethyl-L-prolinamide hydrochloride

To a solution of the crude product containing tert-butyl (2S)-2-(dimethylcarbamoyl)pyrrolidine-1-carboxylate obtained in A) in ethyl acetate (50 mL) was added 4N hydrogen chloride/ethyl acetate solution (150 mL) under ice-cooling. The reaction mixture was stirred at room temperature overnight, and the solvent was evaporated under reduced pressure to give a crude product (10.3 g) containing the title compound.

$^1$H NMR (400 MHz, CDCl$_3$) δ 1.90-2.08 (2H, m), 2.16-2.23 (1H, m), 2.52-2.61 (1H, m), 2.95-3.01 (6H, m), 3.49-3.70 (2H, m), 4.76-4.83 (1H, m).

C) N,N-dimethyl-1-(2-oxo-2,5-dihydro-1,3-thiazol-4-yl)-L-prolinamide

To a solution of the crude product containing N,N-dimethyl-L-prolinamide hydrochloride obtained in B) (10.5 g) and triethylamine (13.6 g) in ethanol (100 mL) was added 4-thioxothiazolidin-2-one (6.0 g) at room temperature. The reaction mixture was stirred at room temperature for 3 hr, and the solvent was evaporated under reduced pressure. The obtained solid was suspended in THF, and the suspension was filtered through celite pad and silica gel pad. The filtrate was concentrated under reduced pressure, and the residue was purified by silica gel column chromatography (NH, ethyl acetate) to give the title compound (4.3 g).

$^1$H NMR (400 MHz, CDCl$_3$) δ 2.02-2.14 (2H, m), 2.24-2.34 (2H, m), 2.96-3.02 (3H, m), 3.11-3.13 (3H, m), 3.54-3.60 (1H, m), 3.75-3.81 (1H, m), 3.86-4.22 (2H, m), 5.07-5.09 (1H, m).

MS (ESI+): [M+H]$^+$ 242.

D) 1-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-prolinamide To a solution of N,N-dimethyl-1-(2-oxo-2,5-dihydro-1,3-thiazol-4-yl)-L-prolinamide (724 mg) and 1-[2,4-bis(trifluoromethyl)benzyl]piperidine-4-carbaldehyde (1018 mg) in 2-propanol (10 mL) was added piperidinium acetate (436 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (389 mg).

$^1$H NMR (300 MHz, DMSO-d$_6$) δ 1.48-2.34 (11H, m), 2.64-2.90 (5H, m), 3.07 (2.49H, s), 3.12 (0.51H, s), 3.71 (2H, brs), 3.73-3.82 (0.34H, m), 3.92 (1.66H, t, J=6.7 Hz), 5.15 (0.83H, dd, J=8.3, 4.2 Hz), 5.50 (0.17H, d, J=5.9 Hz), 6.10 (0.17H, d, J=9.0 Hz), 6.73 (0.83H, d, J=8.8 Hz), 7.92-8.15 (3H, m).

MS (ESI+): [M+H]$^+$ 563.1.

Example 164

3-{[(5Z)-5-({1-[2,4-bis(trifluoromethyl)benzyl]piperidin-4-yl}methylidene)-2-oxo-2,5-dihydro-1,3-thiazol-4-yl]amino}piperidin-2-one To a solution of 3-aminopiperidin-2-one hydrochloride (1.50 g) in methanol (10 mL) was added AMBERLYST (registered trademark) A21 (750 mg) at room temperature. The reaction mixture was stirred at room temperature overnight, the insoluble material was removed by filtration, and the filtrate was concentrated under reduced pressure. To a solution of the residue in ethanol (20 mL) was added 4-thioxothiazolidin-2-one (1.330 g) at room temperature. The reaction mixture was stirred at room temperature overnight, and the solvent was evaporated under reduced pressure. The residue was purified by silica gel column chromatography (NH, methanol/ethyl acetate). To a solution of the residue and 1-[2,4-bis(trifluoromethyl)benzyl]piperidine-4-carbaldehyde (1018 mg) in 2-propanol (10 mL) was added piperidinium acetate (436 mg) at room temperature. The reaction mixture was stirred at 60° C. overnight, and the solvent was evaporated under reduced pressure. The residue was purified by silica gel column chromatography (NH, methanol/ethyl acetate) and recrystallized from ethyl acetate/diisopropyl ether to give the title compound (530 mg).

$^1$H NMR (300 MHz, DMSO-d$_6$) δ 1.38-1.59 (2H, m), 1.68-1.91 (5H, m), 2.01-2.27 (4H, m), 2.69-2.84 (2H, m), 3.17 (2H, brs), 3.71 (2H, s), 4.43-4.55 (1H, m), 6.89 (1H, d, J=8.8 Hz), 7.83 (1H, brs), 7.98 (1H, s), 8.02-8.12 (2H, m), 9.34 (1H, brs).

MS (ESI+): [M+H]$^+$ 535.1.

Example 165

(5Z)-5-({1-[2,4-bis(trifluoromethyl)benzyl]piperidin-4-yl}methylidene)-4-[(1-methylprop-2-yn-1-yl)amino]-1,3-thiazol-2(5H)-one A) 4-(but-3-yn-2-ylamino)-1,3-thiazol-2(5H)-one To a solution of 4-thioxo-1,3-thiazolidin-2-one (2 g) in ethanol (35 mL) were added but-3-yn-2-amine hydrochloride (2.38 g) and triethylamine (3.14 mL), and the mixture was stirred at room temperature for 4 hr. The reaction mixture was concentrated, water was added to the residue, and the mixture was extracted with ethyl acetate. The extract was washed with water and saturated brine, and dried over anhydrous magnesium sulfate, and the solvent was evaporated under reduced pressure. The residue was washed with ethyl acetate to give the title compound (1.42 g).

$^1$H NMR (300 MHz, DMSO-d$_6$) δ 1.39 (3H, d, J=6.9 Hz), 3.33 (1H, s), 4.14-4.35 (2H, m), 4.66-4.76 (1H, m), 9.52 (1H, d, J=7.2 Hz).

MS (ESI+): [M+H]$^+$ 169.1.

B) (5Z)-5-({1-[2,4-bis(trifluoromethyl)benzyl]piperidin-4-yl}methylidene)-4-[(1-methylprop-2-yn-1-yl)amino]-1,3-thiazol-2(5H)-one To a solution of 1-[2,4-bis(trifluoromethyl)benzyl]piperidine-4-carbaldehyde (1.91 g) in 2-propanol (20 mL) were added 4-(but-3-yn-2-ylamino)-1,3-thiazol-2(5H)-one (1.42 g) and piperidinium acetate (834 mg). The reaction mixture was stirred at 75° C. for 6 hr and concentrated under reduced pressure. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) to give the title compound (1.0 g).

$^1$H NMR (300 MHz, DMSO-d$_6$) δ 1.33-1.58 (5H, m), 1.63-1.85 (2H, m), 1.96-2.31 (3H, m), 2.68-2.87 (2H, m), 3.41 (1H, s), 3.71 (2H, s), 4.66-4.99 (1H, m), 6.98 (1H, d, J=8.8 Hz), 7.99 (1H, s), 8.01-8.15 (2H, m), 9.44 (1H, brs).

MS (ESI+): [M+H]$^+$ 490.0.

Example 166

(5Z)-5-({1-[2,4-bis(trifluoromethyl)benzyl]piperidin-4-yl}methylidene)-4-[(1-methylprop-2-yn-1-yl)amino]-1,3-thiazol-2(5H)-one hydrochloride To a solution of (5Z)-5-({1-[2,4-bis(trifluoromethyl)benzyl]piperidin-4-yl}methylidene)-4-[(1-methylprop-2-yn-1-yl)amino]-1,3-thiazol-2(5H)-one (980 mg) in ethyl acetate (10 mL) was added 4N hydrogen chloride/ethyl acetate (0.50 mL) solution, and the precipitate was collected by filtration to give the title compound (635 mg).

$^1$H NMR (300 MHz, DMSO-d$_6$) δ 1.45 (3H, d, J=7.0 Hz), 1.71-2.19 (4H, m), 2.32-2.46 (1H, m), 3.02-3.30 (2H, m), 3.37-3.66 (3H, m), 4.53 (2H, brs), 4.74-5.01 (1H, m), 6.97 (1H, d, J=8.9 Hz), 8.14 (1H, brs), 8.27 (1H, d, J=7.8 Hz), 8.70 (1H, d, J=7.7 Hz), 9.59 (1H, d, J=7.3 Hz), 11.24 (1H, brs).

MS (ESI+): [M−Cl]$^+$ 490.0.

Example 167

N²-[(5Z)-5-({1-[2,4-bis(trifluoromethyl)benzyl]piperidin-4-yl}methylidene)-2-oxo-2,5-dihydro-1,3-thiazol-4-yl]-N-cyclopropylglycinamide hydrochloride To a solution of N²-[(5Z)-5-({1-[2,4-bis(trifluoromethyl)benzyl]piperidin-4-yl}methylidene)-2-oxo-2,5-dihydro-1,3-thiazol-4-yl]-N-cyclopropylglycinamide (700 mg) in THF (10 mL) was added a solution of 4N hydrogen chloride/ethyl acetate (0.33 mL), and the precipitate was so collected by filtration to give the title compound (301 mg).

¹H NMR (300 MHz, DMSO-$d_6$) δ 0.41 (2H, brs), 0.52-0.79 (2H, m), 1.81-2.12 (4H, m), 2.33-2.47 (1H, m), 2.57-2.71 (1H, m), 3.10-3.50 (4H, m), 3.96 (2H, d, J=5.7 Hz), 4.55 (2H, brs), 6.87 (1H, d, J=9.0 Hz), 8.10-8.22 (2H, m), 8.28 (1H, d, J=7.8 Hz), 8.57-8.72 (1H, m), 9.36-9.69 (1H, m), 10.99 (1H, brs).

MS (ESI+): [M−Cl]⁺ 535.1.

Example 168

(5Z)-5-({1-[2,4-bis(trifluoromethyl)benzyl]piperidin-4-yl}methylidene)-4-(prop-2-yn-1-ylamino)-1,3-thiazol-2(5H)-one To a suspension of 1-[2,4-bis(trifluoromethyl)benzyl]piperidine-4-carbaldehyde (35.0 g) and 4-(prop-2-yn-1-ylamino)-1,3-thiazol-2(5H)-one (23.9 g) in 2-propanol (400 mL) was added piperidinium acetate (15.0 g) at room temperature. The reaction mixture was stirred at 80° C. for 4 hr and concentrated under reduced pressure. Ethyl acetate was added to the residue, and the precipitate was removed by filtration. Water and ethyl acetate were added to the filtrate, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane), and the obtained solid was washed with diisopropyl ether to give a solid. The obtained solid was recrystallized from ethyl acetate/heptane/diisopropyl ether to give the title compound (28.9 g).

¹H NMR (300 MHz, DMSO-$d_6$) δ 1.34-1.59 (2H, m), 1.63-1.85 (2H, m), 2.03-2.25 (3H, m), 2.61-2.88 (2H, m), 3.33-3.35 (1H, m), 3.71 (2H, s), 4.24 (2H, d, J=2.5 Hz), 6.91 (1H, d, J=8.8 Hz), 7.98 (1H, s), 8.01-8.12 (2H, m), 9.57 (1H, s).

MS (ESI+): [M+H]⁺ 476.2.

powder X-ray diffraction interplanar spacing (d): 17.31, 11.75, 8.65, 7.61, 7.27, 5.76, 5.24, 4.71, 4.54, 4.10, 4.03, 3.92, 3.80 and 3.73 Å.

Example 169

(−)-1,5-anhydro-3-{[(5Z)-5-({1-[2,4-bis(trifluoromethyl)benzyl]piperidin-4-yl}methylidene)-2-oxo-2,5-dihydro-1,3-thiazol-4-yl]amino}-2,3-dideoxy-threo-pentitol A racemate (200 mg) of 1,5-anhydro-3-{[(5Z)-5-({1-[2,4-bis(trifluoromethyl)benzyl]piperidin-4-yl}methylidene)-2-oxo-2,5-dihydro-1,3-thiazol-4-yl]amino}-2,3-dideoxy-threo-pentitol was separated by HPLC (column: CHIRALPAK AD, 50 mmID×500 mL, manufactured by DAICEL CHEMICAL INDUSTRIES, LTD., mobile phase: hexane/ethanol=90/10), and the title compound (83 mg) having a shorter retention time was obtained. Absolute configuration undetermined.

¹H NMR (300 MHz, DMSO-$d_6$) δ 1.38-1.66 (3H, m), 1.69-1.95 (3H, m), 2.04-2.25 (3H, m), 2.70-2.86 (2H, m), 2.96-3.09 (1H, m), 3.25-3.34 (1H, m), 3.51-3.64 (1H, m), 3.72 (2H, brs), 3.77-4.00 (3H, m), 5.14 (1H, d, J=5.6 Hz), 6.91 (1H, d, J=8.7 Hz), 7.99 (1H, s), 8.02-8.14 (2H, m), 8.98 (1H, d, J=7.8 Hz).

MS (ESI+): [M+H]⁺ 538.1.

$[\alpha]_D^{25}$ −30.8 (c 0.50, DMSO)

Example 170

(+)-1,5-anhydro-3-{[(5Z)-5-({1-[2,4-bis(trifluoromethyl)benzyl]piperidin-4-yl}methylidene)-2-oxo-2,5-dihydro-1,3-thiazol-4-yl]amino}-2,3-dideoxy-threo-pentitol A racemate (200 mg) of 1,5-anhydro-3-{[(5Z)-5-({1-[2,4-bis(trifluoromethyl)benzyl]piperidin-4-yl}methylidene)-2-oxo-2,5-dihydro-1,3-thiazol-4-yl]amino}-2,3-dideoxy-threo-pentitol was separated by HPLC (column: CHIRALPAK AD, 50 mmID×500 mL, manufactured by DAICEL CHEMICAL INDUSTRIES, LTD., mobile phase: hexane/ethanol=90/10), and the title compound (80 mg) having a longer retention time was obtained. Absolute configuration undetermined.

¹H NMR (300 MHz, DMSO-$d_6$) δ 1.39-1.66 (3H, m), 1.69-1.95 (3H, m), 2.03-2.25 (3H, m), 2.70-2.86 (2H, m), 2.96-3.09 (1H, m), 3.24-3.34 (1H, m), 3.52-3.64 (1H, m), 3.72 (2H, brs), 3.77-4.01 (3H, m), 5.14 (1H, d, J=5.6 Hz), 6.91 (1H, d, J=8.7 Hz), 7.99 (1H, s), 8.02-8.13 (2H, m), 8.98 (1H, d, J=7.8 Hz).

MS (ESI+): [M+H]⁺ 538.1.

$[\alpha]_D^{25}$ +28.6 (c 0.50, DMSO)

Example 171

(7Z)-7-({1-[2,4-bis(trifluoromethyl)benzyl]piperidin-4-yl}methylidene)-2,7-dihydro-3H-imidazo[1,2-c][1,3]thiazol-5-one A) 2,7-dihydro-3H-imidazo[1,2-c][1,3]thiazol-5-one To a solution of 4-[(2-hydroxyethyl)amino]-1,3-thiazol-2(5H)-one (641 mg) and triphenylphosphine (1570 mg) in THF (10 mL) was added 1.9M diisopropyl azodicarboxylate toluene solution (3.16 mL) at room temperature. The reaction mixture was stirred overnight at 40° C. The solvent was evaporated, and the residue was purified by silica gel column chromatography (ethyl acetate/hexane) to give the title compound (260 mg).

¹H NMR (300 MHz, DMSO-$d_6$) δ 3.63 (2H, t, J=8.5 Hz), 4.14-4.27 (4H, m).

B) (7Z)-7-({1-[2,4-bis(trifluoromethyl)benzyl]piperidin-4-yl}methylidene)-2,7-dihydro-3H-imidazo[1,2-c][1,3]thiazol-5-one To a solution of 2,7-dihydro-3H-imidazo[1,2-c][1,3]thiazol-5-one (260 mg) and 1-[2,4-bis(trifluoromethyl)benzyl]piperidine-4-carbaldehyde (620 mg) in 2-propanol (5 mL) was added piperidinium acetate (292 mg) at room temperature. The reaction mixture was stirred at 60° C. overnight, and the solvent was evaporated under reduced pressure. The residue was purified by silica gel column chromatography (NH, ethyl acetate/hexane) and recrystallized from heptane to give the title compound (140 mg).

$^1$H NMR (300 MHz, DMSO-$d_6$) δ 1.43-1.73 (4H, m), 1.95-2.20 (3H, m), 2.71-2.84 (2H, m), 3.65-3.80 (4H, m), 4.29 (2H, t, J=8.7 Hz), 6.63 (1H, d, J=9.3 Hz), 7.98 (1H, s), 8.01-8.13 (2H, m).

MS (ESI+): [M+H]$^+$ 464.0.

Example 172

$N^2$-[(5Z)-5-({1-[2,4-bis(trifluoromethyl)benzyl]piperidin-4-yl}methylidene)-2-oxo-2,5-dihydro-1,3-thiazol-4-yl]-3-hydroxy-N,N-dimethyl-L-valinamide A) $N^2$-(tert-butoxycarbonyl)-3-hydroxy-N,N-dimethyl-L-valinamide To a solution of N-(tert-butoxycarbonyl)-3-hydroxy-L-valine (1.00 g), 2M dimethylamine methanol solution (2.14 mL) and N-ethyl-N-(1-methylethyl)propan-2-amine (1.11 g) in DMF (10 mL) was added O-(7-azabenzotriazol-1-yl)-N,N,N',N'-tetramethyluronium hexafluorophosphate (1.63 g) at room temperature. The reaction mixture was stirred at room temperature overnight. Water was added to the reaction mixture at room temperature, and the mixture was extracted with ethyl acetate. The organic layer was separated, washed with water and saturated brine, dried over magnesium sulfate, and concentrated under reduced pressure. The residue was purified by silica gel column chromatography (ethyl acetate/hexane) to give the title compound (670 mg).

$^1$H NMR (300 MHz, DMSO-$d_6$) δ 1.06 (3H, s), 1.12 (3H, s), 1.37 (9H, s), 2.84 (3H, s), 3.07 (3H, s), 4.44 (1H, d, J=9.3 Hz), 4.72 (1H, s), 6.46 (1H, d, J=9.2 Hz).

B) 3-hydroxy-N,N-dimethyl-L-valinamide hydrochloride

To a solution of $N^2$-(tert-butoxycarbonyl)-3-hydroxy-N,N-dimethyl-L-valinamide (670 mg) in ethyl acetate (10 mL) was added 4N hydrogen chloride/ethyl acetate solution (10 mL) at room temperature. The reaction mixture was stirred at room temperature overnight and concentrated under reduced pressure to give a crude product containing the title compound.

$^1$H NMR (300 MHz, DMSO-$d_6$) δ 1.17 (3H, s), 1.20 (3H, s), 2.90 (3H, s), 3.09 (3H, s), 4.23 (1H, s), 5.28 (1H, s), 8.21 (3H, brs).

C) 3-hydroxy-N,N-dimethyl-L-valinamide

To a solution of the crude product containing 3-hydroxy-N,N-dimethyl-L-valinamide hydrochloride obtained in B) methanol (10 mL) was added AMBERLYST (registered trademark) A21 (1.0 g) at room temperature. The reaction mixture was stirred at room temperature overnight, the insoluble material was removed by filtration, and the filtrate was concentrated to give a crude product containing the title compound.

$^1$H NMR (300 MHz, DMSO-$d_6$) δ1.09 (3H, s), 1.12 (3H, s), 2.86 (3H, s), 3.06 (3H, s), 3.17 (1H, s), 3.74 (1H, s), 4.90 (2H, brs).

D) 3-hydroxy-N,N-dimethyl-$N^2$-(2-oxo-2,5-dihydro-1,3-thiazol-4-yl)-L-valinamide To a solution of the crude product containing 3-hydroxy-N,N-dimethyl-L-valinamide obtained in C) in ethanol (5 mL) was added 4-thioxothiazolidin-2-one (380 mg) at room temperature. The reaction mixture was stirred at room temperature overnight, The solvent was evaporated under reduced pressure. The residue was purified by silica gel column chromatography (NH, ethyl acetate/hexane) to give the title compound (300 mg).

$^1$H NMR (300 MHz, CDCl$_3$) δ 1.25 (6H, s), 3.01 (3H, s), 3.28 (3H, s), 4.14-4.34 (2H, m), 4.81 (1H, brs), 5.05 (1H, d, J=8.7 Hz), 8.52 (1H, d, J=8.4 Hz).

E) $N^2$-[(5Z)-5-({1-[2,4-bis(trifluoromethyl)benzyl]piperidin-4-yl}methylidene)-2-oxo-2,5-dihydro-1,3-thiazol-4-yl]-3-hydroxy-N,N-dimethyl-L-valinamide To a solution of 3-hydroxy-N,N-dimethyl-$N^2$-(2-oxo-2,5-dihydro-1,3-thiazol-4-yl)-L-valinamide (300 mg) and 1-[2,4-bis(trifluoromethyl)benzyl]piperidine-4-carbaldehyde (392 mg) in 2-propanol (5 mL) was added piperidinium acetate (168 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (170 mg).

$^1$H NMR (300 MHz, DMSO-$d_6$) δ 1.18 (3H, s), 1.21 (3H, s), 1.42-1.60 (2H, m), 1.67-1.79 (2H, m), 2.01-2.23 (3H, m), 2.70-2.84 (2H, m), 2.88 (3H, s), 3.14 (3H, s), 3.71 (2H, s), 4.99 (1H, s), 5.16 (1H, brs), 7.34 (1H, d, J=8.6 Hz), 7.98 (1H, s), 8.01-8.13 (2H, m), 8.80 (1H, brs).

MS (ESI+): [M+H]$^+$ 581.1.

Example 173

(8Z)-8-({1-[2,4-bis(trifluoromethyl)benzyl]piperidin-4-yl}methylidene)-2,3,4,8-tetrahydro[1,3]thiazolo[3,4-a]pyrimidin-6-one A) 2,3,4,8-tetrahydro[1,3]thiazolo[3,4-a]pyrimidin-6-one To a solution of 4-[(3-hydroxypropyl)amino]-1,3-thiazol-2(5H)-one (1.36 g) and triphenylphosphine (2.66 g) in THF (15 mL) was added 1.9M diisopropyl azodicarboxylate toluene solution (5.34 mL) at room temperature. The reaction mixture was stirred at room temperature overnight. The solvent was evaporated, and the residue was purified by silica gel column chromatography (ethyl acetate/hexane) to give the title compound (872 mg).

$^1$H NMR (300 MHz, DMSO-$d_6$) δ 1.65-1.75 (2H, m), 3.34-3.41 (2H, m), 3.56 (2H, t, J=6.0 Hz), 4.08 (2H, s).

B) (8Z)-8-({1-[2,4-bis(trifluoromethyl)benzyl]piperidin-4-yl}methylidene)-2,3,4,8-tetrahydro[1,3]thiazolo[3,4-a]pyrimidin-6-one To a solution of 2,3,4,8-tetrahydro[1,3]thiazolo[3,4-a]pyrimidin-6-one (0.469 g) and 1-[2,4-bis(trifluoromethyl)benzyl]piperidine-4-carbaldehyde (1.12 g) in 2-propanol (10 mL) was added piperidinium acetate (0.479 g) at room temperature. The reaction mixture was stirred at 60° C. overnight, and the solvent was evaporated under reduced pressure. The residue was purified by silica gel column chromatography (NH, ethyl acetate/hexane) and recrystallized from heptane to give the title compound (1.08 g).

$^1$H NMR (300 MHz, DMSO-$d_6$) δ 1.40-1.82 (6H, m), 2.00-2.22 (3H, m), 2.71-2.83 (2H, m), 3.50 (2H, t, J=5.3 Hz), 3.63 (2H, t, J=5.8 Hz), 3.70 (2H, s), 6.62 (1H, d, J=9.3 Hz), 7.98 (1H, s), 8.01-8.13 (2H, m).
MS (ESI+): [M+H]$^+$ 478.0.

Example 174

N$^2$-[(5Z)-5-({1-[2,4-bis(trifluoromethyl)benzyl]piperidin-4-yl}methylidene)-2-oxo-2,5-dihydro-1,3-thiazol-4-yl]-N-(2-hydroxy-2-methylpropyl)glycinamide To a solution of N-[(5Z)-5-({1-[2,4-bis(trifluoromethyl)benzyl]piperidin-4-yl}methylidene)-2-oxo-2,5-dihydro-1,3-thiazol-4-yl]glycine hydrochloride (1.2 g), N-ethyl-N-(1-methylethyl)propan-2-amine (0.79 mL) and 1-amino-2-methylpropan-2-ol (0.40 g) in DMF (10 mL) was added O-(7-azabenzotriazol-1-yl)-N,N,N',N'-tetramethyluronium hexafluorophosphate (1.03 g), and the mixture was stirred at room temperature for 2 hr. Water was added to the reaction mixture, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, methanol/ethyl acetate), and the obtained solid was recrystallized from ethyl acetate/heptane to give the title compound (294 mg).
$^1$H NMR (300 MHz, DMSO-d$_6$) δ 1.05 (6H, s), 1.39-1.58 (2H, m), 1.63-1.85 (2H, m), 2.02-2.31 (3H, m), 2.59-2.90 (2H, m), 3.05 (2H, d, J=5.9 Hz), 3.71 (1H, s), 4.08 (2H, brs), 4.45 (1H, s), 6.91 (1H, d, J=8.9 Hz), 7.90-8.00 (2H, m), 8.02-8.20 (2H, m), 9.40 (1H, brs).
MS (ESI+): [M+H]$^+$ 567.2.

Example 175

(−)-1,5-anhydro-2-{[(5Z)-5-({-[2,4-bis(trifluoromethyl)benzyl]piperidin-4-yl}methylidene)-2-oxo-2,5-dihydro-1,3-thiazol-4-yl]amino}-2,4-dideoxy-threo-pentitol A) 2-amino-1,5-anhydro-2,4-dideoxy-threo-pentitol To a solution of 1,5:3,4-dianhydro-2-deoxypentitol (3.60 g) in 2-propanol (150 mL) was added (R)-1-phenethylamine (4.30 g) over 40 min, and 2-propanol (150 mL) was added. The reaction mixture was stirred at 65° C. for 72 hr, and the solvent was evaporated under reduced pressure. tert-Butyl methyl ether (150 mL) was added to the residue, and the mixture was stirred at room temperature overnight. The precipitate was collected by filtration, and washed with tert-butyl methyl ether to give a powder (2.20 g). A solution of the obtained powder (2.20 g) and 10% palladium carbon (1.0 g) in ethanol (100 mL) was stirred at 50° C. overnight under a hydrogen atmosphere. The palladium carbon was removed, and washed with ethanol, and the filtrate was concentrated under reduced pressure to give the title compound (1.10 g).
$^1$H NMR (400 MHz, CDCl$_3$) δ 1.59-1.69 (4H, m), 1.94-1.99 (1H, m), 2.60-2.66 (1H, m), 2.96-3.02 (1H, m), 3.30-3.45 (2H, m), 3.88-3.98 (2H, m).

B) 1,5-anhydro-2,4-dideoxy-2-[(2-oxo-2,5-dihydro-1,3-thiazol-4-yl)amino]-threo-pentitol To a solution of 2-amino-1,5-anhydro-2,4-dideoxy-threo-pentitol (1.09 g) in ethanol (100 mL) was added 4-thioxo-1,3-thiazolidin-2-one (1.28 g), and the mixture was heated under reflux for 15 hr. The reaction mixture was concentrated under reduced pressure, and the residue was purified by silica gel column chromatography (NH, ethyl acetate) to give the title compound (1.00 g).
$^1$H NMR (400 MHz, CDCl$_3$) δ 1.44-1.48 (1H, m), 1.87-1.93 (1H, m), 3.07-3.16 (1H, m), 3.33-3.40 (1H, m), 3.58-3.64 (2H, m), 3.77-3.86 (2H, m), 4.23 (2H, s), 5.10-5.12 (1H, m), 9.10-9.12 (1H, m).
MS (ESI+): [M+H]$^+$ 217.

C) (−)-1,5-anhydro-2-{[(5Z)-5-({1-[2,4-bis(trifluoromethyl)benzyl]piperidin-4-yl}methylidene)-2-oxo-2,5-dihydro-1,3-thiazol-4-yl]amino}-2,4-dideoxy-threo-pentitol To a solution of 1-[2,4-bis(trifluoromethyl)benzyl]piperidine-4-carbaldehyde (941 mg) in 2-propanol (20 mL) were added 1,5-anhydro-2,4-dideoxy-2-[(2-oxo-2,5-dihydro-1,3-thiazol-4-yl)amino]-threo-pentitol (900 mg) and piperidinium acetate (411 mg). The reaction mixture was stirred at 75° C. overnight, and the solvent was evaporated under reduced pressure. The residue was purified by silica gel column chromatography (ethyl acetate/hexane) and silica gel column chromatography (NH, methanol/ethyl acetate) to give the title compound (806 mg). Absolute configuration undetermined.
$^1$H NMR (300 MHz, DMSO-d$_6$) δ 1.40-1.59 (31H, m), 1.68-1.81 (2H, m), 1.86-1.98 (1H, m), 2.03-2.24 (3H, m), 2.71-2.84 (2H, m), 3.03-3.18 (1H, m), 3.26-3.41 (1H, m), 3.64-3.91 (6H, m), 5.12 (1H, d, J=5.2 Hz), 6.94 (1H, d, J=8.8 Hz), 7.99 (1H, s), 8.01-8.12 (2H, m), 8.87 (1H, brs).
MS (ESI+): [M+H]$^+$ 538.1.
[α]$_D^{25}$ −40.0 (c 0.50, DMSO)

Example 176

(−)-(5Z)-5-({1-[2,4-bis(trifluoromethyl)benzyl]piperidin-4-yl}methylidene)-4-[trans-(4-hydroxytetrahydrofuran-3-yl)amino]-1,3-thiazol-2(5H)-one A racemate (100 mg) of (5Z)-5-({1-[2,4-bis(trifluoromethyl)benzyl]piperidin-4-yl}methylidene)-4-[trans-(4-hydroxytetrahydrofuran-3-yl)amino]-1,3-thiazol-2(5H)-one was separated by SFC (column: CHIRALCEL ODH, 20 mmID×250 mL, manufactured by DAICEL CHEMICAL INDUSTRIES, LTD., mobile phase: carbon dioxide/2-propanol=840/160), and the title compound (45 mg) having a shorter retention time was obtained. Absolute configuration undetermined.
$^1$H NMR (300 MHz, DMSO-d$_6$) δ 1.38-1.58 (2H, m), 1.65-1.82 (2H, m), 2.02-2.24 (3H, m), 2.67-2.85 (2H, m), 3.54 (1H, d, J=8.4 Hz), 3.64-3.81 (3H, m), 3.88-4.08 (2H, m), 4.18-4.34 (2H, m), 5.46 (1H, brs), 7.02 (1H, d, J=8.3 Hz), 7.98 (1H, brs), 8.01-8.13 (2H, m), 9.07 (1H, brs).
MS (ESI+): [M+H]$^+$ 524.1.
[α]$_D^{25}$ −44.4 (c 0.50, DMSO)

Example 177

(+)-(5Z)-5-({1-[2,4-bis(trifluoromethyl)benzyl]piperidin-4-yl}methylidene)-4-[trans-(4-hydroxytetrahydrofuran-3-yl)amino]-1,3-thiazol-2(5H)-one A racemate (100 mg) of (5Z)-5-({1-[2,4-bis(trifluoromethyl)benzyl]piperidin-4-yl}methylidene)-4-[trans-(4-hydroxytetrahydrofuran-3-yl)amino]-1,3-thiazol-2(5H)-one was separated by SFC (column: CHIRALCEL ODH, 20 mmID×250 mL, manufactured by DAICEL CHEMICAL INDUSTRIES, LTD., mobile phase: carbon dioxide/2-propanol=840/160), and the title compound (44 mg) having a longer retention time was obtained. Absolute configuration undetermined.

$^1$H NMR (300 MHz, DMSO-$d_6$) δ 1.39-1.57 (2H, m), 1.66-1.81 (2H, m), 2.02-2.24 (3H, m), 2.70-2.85 (2H, m), 3.55 (1H, dd, J=9.4, 2.3 Hz), 3.76 (3H, d, J=2.6 Hz), 3.90-4.08 (2H, m), 4.20-4.33 (2H, m), 5.47 (1H, brs), 7.02 (1H, d, J=8.8 Hz), 7.98 (1H, s), 8.01-8.13 (2H, m), 9.08 (1H, brs).

MS (ESI+): [M+H]$^+$ 524.1.

$[α]_D^{25}$ +43.8 (c 0.50, DMSO)

Example 178

(5Z)-5-({1-[2,4-bis(trifluoromethyl)benzyl]piperidin-4-yl}methylidene)-4-[(1,3-oxazol-2-ylmethyl)amino]-1,3-thiazol-2(5H)-one A) 4-[(1,3-oxazol-2-ylmethyl)amino]-1,3-thiazol-2(5H)-one To a solution of 1-(1,3-oxazol-2-yl)methanamine hydrochloride (500 mg) in ethanol (10 mL) were added triethylamine (0.99 mL) and 4-thioxothiazolidin-2-one (495 mg) at room temperature. The reaction mixture was stirred at room temperature overnight, and the solvent was evaporated under reduced pressure. The residue was purified by silica gel column chromatography (NH, methanol/ethyl acetate) to give the title compound (357 mg).

$^1$H NMR (300 MHz, DMSO-$d_6$) δ 4.32 (2H, s), 4.69 (2H, s), 7.21 (1H, s), 8.11 (1H, s), 9.70 (1H, brs).

B) (5Z)-5-({-[2,4-bis(trifluoromethyl)benzyl]piperidin-4-yl}methylidene)-4-[(1,3-oxazol-2-ylmethyl)amino]-1,3-thiazol-2(5H)-one To a solution of 4-[(1,3-oxazol-2-ylmethyl)amino]-1,3-thiazol-2(5H)-one (357 mg) and 1-[2,4-bis(trifluoromethyl)benzyl]piperidine-4-carbaldehyde (676 mg) in 2-propanol (5 mL) was added piperidinium acetate (289 mg) at room temperature. The reaction mixture was stirred at 60° C. for 5 hr, and the solvent was evaporated under reduced pressure. The residue was purified by silica gel column chromatography (methanol/ethyl acetate) and recrystallized from ethyl acetate/heptane to give the title compound (751 mg).

$^1$H NMR (300 MHz, DMSO-$d_6$) δ 1.38-1.58 (2H, m), 1.68-1.83 (2H, m), 2.04-2.26 (3H, m), 2.68-2.86 (2H, m), 3.71 (2H, s), 4.77 (2H, s), 6.95 (1H, d, J=8.9 Hz), 7.21 (1H, d, J=0.8 Hz), 7.98 (1H, s), 8.02-8.15 (3H, m), 9.80 (1H, brs).

MS (ESI+): [M+H]$^+$ 519.0.

Example 179

$N^2$-[(5Z)-5-({1-[2,4-bis(trifluoromethyl)benzyl]piperidin-4-yl}methylidene)-2-oxo-2,5-dihydro-1,3-thiazol-4-yl]-3-methoxy-N,N-dimethyl-L-valinamide A) $N^2$-(tert-butoxycarbonyl)-3-methoxy-N,N-dimethyl-L-valinamide To a solution of N-(tert-butoxycarbonyl)-3-hydroxy-L-valine (2.00 g) in THF (50 mL) was added 1.6M n-butyllithium hexane solution (12.9 mL) under ice-cooling. The reaction mixture was stirred for under ice-cooling, and to the reaction mixture was added dimethyl sulfate (1.41 g). The reaction mixture was stirred at room temperature overnight, water was added, and the solution was adjusted with 8N aqueous sodium hydroxide solution to about pH 13 at room temperature. The organic solvent was evaporated under reduced pressure, and the remaining aqueous layer was washed with toluene. The aqueous layer was adjusted with saturated aqueous citric acid solution to pH 3, and the mixture was extracted with ethyl acetate. The organic layer was separated, washed with saturated brine, dried over magnesium sulfate, and the solvent was concentrated under reduced pressure. To a solution of the residue, 50% aqueous dimethylamine solution (1.06 g) and N-ethyl-N-(1-methylethyl)propan-2-amine (2.53 g) in DMF (20 mL) was added O-(7-azabenzotriazol-1-yl)-N,N,N',N'-tetramethyluronium hexafluorophosphate (4.47 g) at room temperature. The reaction mixture was stirred at room temperature overnight, water was added to the reaction mixture, and the mixture was extracted with ethyl acetate. The organic layer was separated, washed with water and saturated brine, dried over magnesium sulfate, and the solvent was concentrated under reduced pressure to give the title compound (1.28 g).

$^1$H NMR (300 MHz, DMSO-$d_6$) δ 1.09 (3H, s), 1.13 (3H, s), 1.37 (9H, s), 2.82 (3H, s), 3.05 (3H, s), 3.10 (3H, s), 4.59 (1H, d, J=9.3 Hz), 6.47 (1H, d, J=9.3 Hz).

B) 3-methoxy-N,N-dimethyl-L-valinamide hydrochloride

To a solution of the crude product containing $N^2$-(tert-butoxycarbonyl)-3-methoxy-N,N-dimethyl-L-valinamide obtained in A) in ethyl acetate (10 mL) was added 4N hydrogen chloride/ethyl acetate solution (10 mL) at room temperature. The reaction mixture was stirred at room temperature overnight, and the solvent was evaporated under reduced pressure. To a solution of the residue in methanol (10 mL) was added AMBERLYST (registered trademark) A21 (300 mg) at room temperature. The reaction mixture was stirred at room temperature overnight, the insoluble material was removed, and the filtrate was concentrated under reduced pressure to give a crude product containing the title compound.

$^1$H NMR (300 MHz, DMSO-$d_6$) δ 1.11 (3H, s), 1.17 (3H, s), 2.86 (3H, s), 3.05 (3H, s), 3.13 (3H, s), 3.98 (1H, s), 6.87 (3H, brs).

C) 3-methoxy-N,N-dimethyl-$N^2$-(2-oxo-2,5-dihydro-1,3-thiazol-4-yl)-L-valinamide To a solution of the crude product containing 3-methoxy-N,N-dimethyl-L-valinamide hydrochloride obtained in B) (697 mg) and triethylamine (810 mg) in ethanol (10 mL) was added 4-thioxothiazolidin-2-one (533 mg) at room temperature. The reaction mixture was stirred at room temperature overnight, the solvent was evaporated under reduced pressure, and the residue was purified by silica gel column chromatography (NH, ethyl acetate/hexane) to give the title compound (560 mg).

$^1$H NMR (300 MHz, DMSO-$d_6$) δ 1.19 (6H, s), 2.85 (3H, s), 3.11 (3H, s), 3.13 (3H, s), 4.26 (2H, s), 5.15 (1H, s), 9.29 (1H, brs).

D) $N^2$-[(5Z)-5-({1-[2,4-bis(trifluoromethyl)benzyl]piperidin-4-yl}methylidene)-2-oxo-2,5-dihydro-1,3-thiazol-4-yl]-3-methoxy-N,N-dimethyl-L-valinamide To a solution of 3-methoxy-N,N-dimethyl-$N^2$-(2-oxo-2,5-dihydro-1,3-thiazol-4-yl)-L-valinamide (460 mg) and 1-[2,4-bis(trifluoromethyl)benzyl]piperidine-4-carbaldehyde (628 mg) in 2-propanol (15 mL) was added piperidinium acetate (269 mg) at room temperature. The reaction mixture was stirred at 60° C. for 3 hr, and the solvent was evaporated under reduced pressure. The residue was purified by silica gel column chromatography (ethyl acetate/hexane) and recrystallized from ethyl acetate/heptane to give the title compound (380 mg).

$^1$H NMR (300 MHz, DMSO-d$_6$) δ 1.23 (3H, s), 1.25 (3H, s), 1.41-1.59 (2H, m), 1.66-1.82 (2H, m), 2.00-2.22 (3H, m), 2.70-2.83 (2H, m), 2.86 (3H, s), 3.13 (3H, s), 3.14 (3H, s), 3.71 (2H, s), 5.31 (1H, brs), 7.39 (1H, d, J=8.1 Hz), 7.92-8.16 (3H, m), 8.75 (1H, brs).

MS (ESI+): [M+H]$^+$ 595.3.

Example 180

(2S)-2-{[(5Z)-5-({1-[2,4-bis(trifluoromethyl)benzyl] piperidin-4-yl}methylidene)-2-oxo-2,5-dihydro-1,3-thiazol-4-yl]amino}-2-cyclopropyl-N,N-dimethyl-ethanamide A) tert-butyl[(1S)-1-cyclopropyl-2-(dimethylamino)-2-oxoethyl]carbamate To a solution of (2S)-[(tert-butoxycarbonyl)amino](cyclopropyl)ethanoic acid (5.0 g), dimethylamine hydrochloride (3.8 g) and N-ethyl-N-(1-methylethyl)propan-2-amine (9.0 g) in DMF (150 mL) was added O-(7-azabenzotriazol-1-yl)-N,N,N',N'-tetramethyluronium hexafluorophosphate (10.6 g) at room temperature. The reaction mixture was stirred at room temperature overnight, water was added, and the mixture was extracted with ethyl acetate. The organic layer was separated, washed with water and saturated brine, dried over sodium sulfate, and concentrated under reduced pressure to give a crude product containing the title compound.

$^1$H NMR (400 MHz, CDCl$_3$) δ 0.36-0.41 (2H, m), 0.46-0.52 (2H, m), 1.10-1.15 (1H, m), 1.48 (9H, s), 2.81 (3H, s), 2.96 (3H, s), 4.49-4.53 (1H, m), 5.42 (1H, d, J=8.0 Hz).

B) (2S)-2-cyclopropyl-N,N-dimethyl-2-[(2-oxo-2,5-dihydro-1,3-thiazol-4-yl)amino]ethanamide To a solution of the crude product containing tert-butyl [(1S)-1-cyclopropyl-2-(dimethylamino)-2-oxoethyl]carbamate obtained in A) in ethyl acetate (100 mL) was added 4N hydrogen chloride/ethyl acetate solution (100 mL) under ice-cooling. The reaction mixture was stirred at room temperature overnight, and the solvent was evaporated under reduced pressure. To a solution of the obtained residue (6 g) and triethylamine (8.5 g) in ethanol (150 mL) was added 4-thioxothiazolidin-2-one (3.75 g) at room temperature. The reaction mixture was stirred at room temperature for 5 hr, and the solvent was evaporated under reduced pressure. The obtained solid was suspended in THF, the suspension was filtered through celite pad and silica gel pad, and the filtrate was concentrated under reduced pressure. The residue was purified by silica gel column chromatography (NH, ethyl acetate/petroleum ether) to give the title compound (3.8 g).

$^1$H NMR (400 MHz, DMSO-d$_6$) δ 0.33-0.53 (4H, m), 1.20-1.25 (1H, m), 2.86 (3H, s), 3.06 (3H, s), 4.19-4.29 (2H, m), 4.58 (1H, t, J=8.0 Hz), 9.39 (1H, d, J=7.2 Hz).

MS (ESI+): [M+H]$^+$ 242.

C) (2S)-2-{[(5Z)-5-({1-[2,4-bis(trifluoromethyl) benzyl]piperidin-4-yl}methylidene)-2-oxo-2,5-dihydro-1,3-thiazol-4-yl]amino}-2-cyclopropyl-N,N-dimethylethanamide To a solution of (2S)-2-cyclopropyl-N,N-dimethyl-2-[(2-oxo-2,5-dihydro-1,3-thiazol-4-yl)amino]ethanamide (796 mg) and 1-[2,4-bis(trifluoromethyl)benzyl]piperidine-4-carbaldehyde (1018 mg) in 2-propanol (10 mL) was added piperidinium acetate (479 mg) at room temperature. The reaction mixture was stirred at 60° C. overnight, and the solvent was evaporated under reduced pressure. The residue was purified by silica gel column chromatography (ethyl acetate/hexane) and recrystallized from ethyl acetate/heptane to give the title compound (1111 mg).

$^1$H NMR (300 MHz, DMSO-d$_6$) δ 0.31-0.61 (4H, m), 1.28-1.37 (1H, m), 1.40-1.58 (2H, m), 1.68-1.81 (2H, m), 2.02-2.23 (3H, m), 2.71-2.82 (2H, m), 2.86 (3H, s), 3.07 (3H, s), 3.72 (2H, s), 4.41 (1H, d, J=9.3 Hz), 7.18 (1H, d, J=8.6 Hz), 7.99 (1H, s), 8.02-8.12 (2H, m), 9.48 (1H, brs).

MS (ESI+): [M+H]$^+$ 563.1.

Example 181

3-{[(5Z)-5-({1-[2,4-bis(trifluoromethyl)benzyl]piperidin-4-yl}methylidene)-2-oxo-2,5-dihydro-1,3-thiazol-4-yl]amino}-1-methylpiperidin-2-one A) tert-butyl(2-oxopiperidin-3-yl)carbamate To a solution of 3-aminopiperidin-2-one hydrochloride (3.49 g) and triethylamine (6.20 mL) in THF (50 mL) was added di-tert-butyl bicarbonate (6.07 g) at room temperature. The reaction mixture was stirred at room temperature overnight, water was added, and the mixture was extracted with ethyl acetate. The organic layer was separated, washed with water, dried over magnesium sulfate, and concentrated under reduced pressure. The residue was purified by silica gel column chromatography (ethyl acetate/hexane) to give the title compound (3.41 g).

$^1$H NMR (300 MHz, DMSO-d$_6$) δ 1.38 (9H, s), 1.53-2.03 (4H, m), 3.09 (2H, brs), 3.68-3.91 (1H, m), 6.83 (1H, d, J=8.1 Hz), 7.48 (1H, brs).

B) tert-butyl(1-methyl-2-oxopiperidin-3-yl)carbamate

To a solution of tert-butyl(2-oxopiperidin-3-yl)carbamate (1714 mg) in DMF (20 mL) was added 60% sodium hydride (480 mg, containing mineral oil) under ice-cooling. The reaction mixture was stirred at room temperature for 30 min, and iodomethane (1703 mg) was added. The reaction mixture was stirred at room temperature overnight, water was added, and the mixture was extracted with ethyl acetate. The organic layer was separated, washed with water and saturated brine, dried over magnesium sulfate, and concentrated under reduced pressure. The residue was purified by silica gel column chromatography (ethyl acetate/hexane) to give the title compound (530 mg).

$^1$H NMR (300 MHz, DMSO-d$_6$) δ 1.37 (9H, s), 1.56-1.97 (4H, m), 2.79 (3H, s), 3.22 (2H, t, J=5.8 Hz), 3.78-3.93 (1H, m), 6.86 (1H, d, J=7.8 Hz).

C) 3-amino-1-methylpiperidin-2-one hydrochloride

To a solution of tert-butyl(1-methyl-2-oxopiperidin-3-yl) carbamate (960 mg) in ethyl acetate (10 mL) was added 4N hydrogen chloride/ethyl acetate (5 mL) at room temperature. The reaction mixture was stirred at room temperature overnight, and the solvent was evaporated under reduced pressure to give the title compound as a crude product.

$^1$H NMR (300 MHz, DMSO-d$_6$) δ 1.66-1.90 (3H, m), 2.08-2.28 (1H, m), 2.86 (3H, s), 3.21-3.40 (2H, m), 3.67-3.92 (1H, m), 8.41 (3H, brs).

D) 1-methyl-3-[(2-oxo-2,5-dihydro-1,3-thiazol-4-yl) amino]piperidin-2-one

To a solution of the crude product containing 3-amino-1-methylpiperidin-2-one hydrochloride obtained in C) and triethylamine (3 mL) in ethanol (15 mL) was added 4-thioxothiazolidin-2-one (666 mg) at room temperature. The reaction mixture was stirred at room temperature overnight, and the solvent was evaporated under reduced pressure. The residue was purified by silica gel column chromatography (NH, ethyl acetate/hexane) to give the title compound (220 mg).

$^1$H NMR (300 MHz, DMSO-d$_6$) δ 1.60-1.95 (3H, m), 2.06-2.21 (1H, m), 2.81-2.87 (3H, m), 3.25-3.31 (2H, m), 4.17-4.33 (2H, m), 4.36-4.47 (1H, m), 9.35 (1H, brs).

E) 3-{[(5Z)-5-({-[2,4-bis(trifluoromethyl)benzyl] piperidin-4-yl}methylidene)-2-oxo-2,5-dihydro-1,3-thiazol-4-yl]amino}-1-methylpiperidin-2-one To a solution of 1-methyl-3-[(2-oxo-2,5-dihydro-1,3-thiazol-4-yl)amino]piperidin-2-one (220 mg) and 1-[2,4-bis(trifluoromethyl)benzyl]piperidine-4-carbaldehyde (339 mg) in 2-propanol (5 mL) was added piperidinium acetate (141 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (158 mg).

$^1$H NMR (300 MHz, DMSO-d$_6$) δ 1.34-2.31 (11H, m), 2.67-2.83 (2H, m), 2.86 (3H, s), 3.27-3.31 (2H, m), 3.71 (2H, s), 4.44-4.65 (1H, m), 6.87 (1H, d, J=8.8 Hz), 7.98 (1H, s), 8.02-8.11 (2H, m), 9.33 (1H, brs).

MS (ESI+): [M+H]$^+$ 549.1.

Example 182

N$^2$-[(5Z)-5-({1-[2,4-bis(trifluoromethyl)benzyl]piperidin-4-yl}methylidene)-2-oxo-2,5-dihydro-1,3-thiazol-4-yl]-3-(dimethylamino)-N,N-dimethyl-L-alaninamide A) benzyl[(2S)-2-[(tert-butoxycarbonyl)amino]-3-(dimethylamino)-3-oxopropyl]carbamate To a solution of 3-{[(benzyloxy)carbonyl]amino}-N-(tert-butoxycarbonyl)-L-alanine (5.0 g), dimethylamine hydrochloride (2.4 g) and N-ethyl-N-(1-methylethyl)propan-2-amine (5.7 g) in DMF (100 mL) was added O-(7-azabenzotriazol-1-yl)-N,N,N',N'-tetramethyluronium hexafluorophosphate (6.7 g) at room temperature. The reaction mixture was stirred at room temperature overnight, water was added, and the mixture was extracted with ethyl acetate. The organic layer was separated, washed with water and saturated brine, dried over sodium sulfate, and concentrated under reduced pressure to give a crude product (9.9 g) containing the title compound.

$^1$H NMR (400 MHz, DMSO-d$_6$) δ 1.37 (9H, s), 2.80 (3H, s), 3.02 (3H, s), 3.06-3.14 (1H, m), 3.19-3.25 (1H, m), 4.58 (1H, q, J=7.6 Hz), 5.02 (2H, s), 6.83 (2H, d, J=8.4 Hz), 7.28-7.38 (5H, m)

B) N$^2$-(tert-butoxycarbonyl)-3-(dimethylamino)-N,N-dimethyl-L-alaninamide

A solution of the crude product (6.80 g) containing benzyl [(2S)-2-[(tert-butoxycarbonyl)amino]-3-(dimethylamino)-3-oxopropyl]carbamate obtained in A) and 10% palladium carbon (1.36 g) in methanol (50 mL) was stirred at room temperature for 3 hr under a hydrogen atmosphere. The reaction mixture was filtered through celite, and the filtrate was concentrated to give a residue (4.3 g). A solution of the residue (3.80 g), formalin solution (6 mL) and 10% palladium carbon (760 mg) in methanol (30 mL) was stirred at 50° C. overnight under a hydrogen atmosphere (50 Psi). The reaction mixture was filtered through celite, and the filtrate was concentrated to give the title compound as a crude product (3.825 g).

$^1$H NMR (400 MHz, CDCl$_3$) δ 1.43 (9H, s), 2.28 (6H, s), 2.51 (2H, d, J=9.2 Hz), 2.98 (3H, s), 3.14 (3H, s), 4.70-4.75 (1H, m), 5.37 (1H, d, J=9.2 Hz).

C) 3-(dimethylamino)-N,N-dimethyl-N$^2$-(2-oxo-2,5-dihydro-1,3-thiazol-4-yl)-L-alaninamide To a solution of the crude product (4.45 g) containing N$^2$-(tert-butoxycarbonyl)-3-(dimethylamino)-N,N-dimethyl-L-alaninamide obtained in B) in methanol (10 mL) was added 4N hydrogen chloride/ethyl acetate solution (50 mL) at room temperature. The reaction mixture was stirred at room temperature for 4 hr, and the solvent was evaporated under reduced pressure. To a solution of the residue and triethylamine (10.6 mL) in ethanol (30 mL) was added 4-thioxothiazolidin-2-one (2.28 g), and the reaction mixture was stirred at 40° C. overnight. After evaporation of the solvent, the residue was purified by silica gel column chromatography (NH, ethyl acetate/petroleum ether) to give the title compound (1.95 g).

$^1$H NMR (400 MHz, CDCl$_3$) δ 2.28 (6H, s), 2.57-2.61 (1H, m), 2.66-2.71 (1H, m), 3.00 (3H, s), 3.18 (3H, s), 4.09-4.21 (2H, m), 5.19-5.23 (1H, m).

MS (ESI+): [M+H]$^+$ 259.

D) N$^2$-[(5Z)-5-({1-[2,4-bis(trifluoromethyl)benzyl] piperidin-4-yl}methylidene)-2-oxo-2,5-dihydro-1,3-thiazol-4-yl]-3-(dimethylamino)-N,N-dimethyl-L-alaninamide To a solution of 3-(dimethylamino)-N,N-dimethyl-N$^2$-(2-oxo-2,5-dihydro-1,3-thiazol-4-yl)-L-alaninamide (775 mg) and 1-[2,4-bis(trifluoromethyl)benzyl]piperidine-4-carbaldehyde (1018 mg) in 2-propanol (10 mL) was added piperidinium acetate (436 mg) at room temperature. The reaction mixture was stirred at 60° C. overnight, the solvent was evaporated under reduced pressure, and the residue was purified by silica gel column chromatography (NH, ethyl acetate/hexane) and recrystallized from ethyl acetate/heptane to give the title compound (593 mg)

$^1$H NMR (300 MHz, DMSO-d$_6$) δ 1.37-1.61 (2H, m), 1.69-1.84 (2H, m), 2.02-2.30 (9H, m), 2.52-2.55 (1H, m), 2.65-2.83 (3H, m), 2.86 (3H, s), 3.10 (3H, s), 3.72 (2H, s), 5.07 (1H, dd, J=9.0, 4.9 Hz), 7.10 (1H, d, J=8.9 Hz), 7.99 (1H, s), 8.02-8.14 (2H, m), 9.29 (1H, brs).

MS (ESI+): [M+H]$^+$ 580.5.

Example 183

(5Z)-5-({1-[2,4-bis(trifluoromethyl)benzyl]piperidin-4-yl}methylidene)-4-[(1,4-dioxan-2-ylmethyl) amino]-1,3-thiazol-2(5H)-one To a solution of 4-thioxothiazolidin-2-one (568 mg) in ethanol (5 mL) was added 1-(1,4-dioxan-2-yl)methanamine (500 mg), and the reaction mixture was stirred at room temperature overnight. The precipitate was collected by filtration and washed with ethanol to give powder (560 mg). To a solution of the obtained solid (433 mg) and 1-[2,4-bis(trifluoromethyl)benzyl]piperidine-4-carbaldehyde (679 mg) in 2-propanol (5 mL) was added piperidinium acetate (290 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (512 mg)

$^1$H NMR (300 MHz, DMSO-$d_6$) δ 1.38-1.57 (2H, m), 1.67-1.81 (2H, m), 2.01-2.24 (3H, m), 2.69-2.82 (2H, m), 3.23 (1H, dd, J=11.9, 10.2 Hz), 3.38-3.82 (10H, m), 6.89 (1H, d, J=8.9 Hz), to 7.99 (1H, s), 8.01-8.13 (2H, m), 9.27 (1H, brs).

MS (ESI+): [M+H]$^+$ 538.1.

Example 184

(+)-1,5-anhydro-2-{[(5Z)-5-({1-[2,4-bis(trifluoromethyl)benzyl]piperidin-4-yl}methylidene)-2-oxo-2,5-dihydro-1,3-thiazol-4-yl]amino}-2,4-dideoxy-threo-pentitol A) 1,5-anhydro-2,4-dideoxy-2-{[(1S)-1-phenylethyl]amino}-threo-pentitol To a solution of 1,5:3,4-dianhydro-2-deoxypentitol (3.00 g) in 2-propanol (100 mL) was added (S)-1-phenethylamine (3.60 g) over 40 min, and 2-propanol (150 mL) was added. The reaction mixture was stirred at 65° C. for 72 hr, and the solvent was evaporated under reduced pressure. tert-Butyl methyl ether (150 mL) was added to the residue, and the mixture was stirred at room temperature overnight. The precipitate was collected by filtration, and washed with tert-butyl methyl ether to give the title compound (1.80 g).

$^1$H NMR (400 MHz, DMSO-$d_6$) δ 1.22-1.24 (3H, m), 1.32-1.41 (1H, m), 1.73-1.79 (1H, m), 2.22-2.27 (1H, m), 2.66-2.72 (1H, m), 3.16-3.22 (1H, m), 3.30-3.34 (2H, m), 3.65-3.69 (1H, m), 3.86-3.90 (1H, m), 4.91 (1H, d, J=5.2 Hz), 7.17-7.34 (5H, m).

B) 2-amino-1,5-anhydro-2,4-dideoxy-threo-pentitol

A solution of 1,5-anhydro-2,4-dideoxy-2-{[(1S)-1-phenylethyl]amino}-threo-pentitol (1.8 g) and 10% palladium carbon (1.0 g) in ethanol (100 mL) was stirred at 50° C. overnight under a hydrogen atmosphere. The palladium carbon was removed, and washed with ethanol, and the filtrate was concentrated under reduced pressure to give the title compound (950 mg).

$^1$H NMR (400 MHz, CDCl$_3$) δ 1.59-1.70 (4H, m), 1.94-1.99 (1H, m), 2.60-2.66 (1H, m), 2.93-3.02 (1H, m), 3.30-3.45 (2H, m), 3.88-3.98 (2H, m).

C) 1,5-anhydro-2,4-dideoxy-2-[(2-oxo-2,5-dihydro-1,3-thiazol-4-yl)amino]-threo-pentitol To a solution of 2-amino-1,5-anhydro-2,4-dideoxy-threo-pentitol (527 mg) in ethanol (100 mL) was added 4-thioxo-1,3-thiazolidin-2-one (590 mg), and the mixture was heated under reflux for 15 hr. The reaction mixture was concentrated under reduced pressure, and the residue was purified by silica gel column chromatography (NH, ethyl acetate) to give the title compound (700 mg).

$^1$H NMR (400 MHz, CDCl$_3$) δ 1.44-1.47 (1H, m), 1.87-1.93 (1H, m), 3.07-3.14 (1H, m), 3.25-3.41 (2H, m), 3.58-3.86 (3H, m), 4.23 (2H, s), 5.10-5.12 (1H, m), 9.10-9.12 (1H, m).

MS (ESI+): [M+H]$^+$ 217.

D) (+)-1,5-anhydro-2-{[(5Z)-5-({1-[2,4-bis(trifluoromethyl)benzyl]piperidin-4-yl}methylidene)-2-oxo-2,5-dihydro-1,3-thiazol-4-yl]amino}-2,4-dideoxy-threo-pentitol To a solution of 1-[2,4-bis(trifluoromethyl)benzyl]piperidine-4-carbaldehyde (1.03 g) in 2-propanol (20 mL) were added 1,5-anhydro-2,4-dideoxy-2-[(2-oxo-2,5-dihydro-1,3-thiazol-4-yl)amino]-threo-pentitol (980 mg) and piperidinium acetate (448 mg). The reaction mixture was stirred at 75° C. overnight, and the solvent was evaporated under reduced pressure. The residue was purified by silica gel column chromatography (ethyl acetate/hexane) and silica gel column chromatography (NH, methanol/ethyl acetate) to give the title compound (260 mg). Absolute configuration undetermined.

$^1$H NMR (300 MHz, DMSO-$d_6$) δ 1.39-1.58 (3H, m), 1.69-1.82 (2H, m), 1.87-1.97 (1H, m), 2.04-2.23 (3H, m), 2.70-2.84 (2H, m), 3.03-3.15 (1H, m), 3.27-3.39 (1H, m), 3.64-3.90 (6H, m), 5.12 (1H, d, J=5.4 Hz), 6.94 (1H, d, J=8.8 Hz), 7.99 (1H, s), 8.04 (1H, d, J=8.4 Hz), 8.08 (1H, d, J=8.4 Hz), 8.87 (1H, d, J=6.0 Hz).

MS (ESI+): [M+H]$^+$ 538.1.

$[α]_D^{25}$+35.9 (c 0.50, DMSO)

Example 185

(−)-(5Z)-5-({1-[2,4-bis(trifluoromethyl)benzyl]piperidin-4-yl}methylidene)-4-[trans-(5,5-difluoro-2-hydroxycyclohexyl)amino]-1,3-thiazol-2(5H)-one A racemate (200 mg) of (5Z)-5-({1-[2,4-bis(trifluoromethyl)benzyl]piperidin-4-yl}methylidene)-4-[trans-(5,5-difluoro-2-hydroxycyclohexyl)amino]-1,3-thiazol-2(5H)-one was separated by HPLC (column: CHIRALPAK IC, 50 mmID×500 mL, manufactured by DAICEL CHEMICAL INDUSTRIES, LTD., mobile phase: hexane/2-propanol=90/10), and the title compound (76 mg) having a longer retention time was obtained. Absolute configuration undetermined.

$^1$H NMR (300 MHz, DMSO-$d_6$) δ 1.37-1.59 (3H, m), 1.67-2.39 (9H, m), 2.70-2.84 (2H, m), 3.60-3.75 (3H, m), 3.88-4.03 (1H, m), 4.31-4.38 (1H, m), 5.13 (1H, d, J=5.6 Hz), 6.88 (1H, d, J=8.8 Hz), 7.99 (1H, s), 8.01-8.12 (2H, m), 8.99 (1H, brs).

MS (ESI+): [M+H]$^+$ 572.1.

$[α]_D^{25}$−34.1 (c 0.50, DMSO)

Example 186

(+)-(5Z)-5-({1-[2,4-bis(trifluoromethyl)benzyl]piperidin-4-yl}methylidene)-4-[trans-(5,5-difluoro-2-hydroxycyclohexyl)amino]-1,3-thiazol-2(5H)-one A racemate (200 mg) of (5Z)-5-({1-[2,4-bis(trifluoromethyl)benzyl]piperidin-4-yl}methylidene)-4-[trans-(5,5-difluoro-2-hydroxycyclohexyl)amino]-1,3-thiazol-2(5H)-one was separated by HPLC (column: CHIRALPAK IC, 50 mmID×500 mL, manufactured by DAICEL CHEMICAL INDUSTRIES, LTD., mobile phase: hexane/2-propanol=90/10), and the title compound (80 mg) having a shorter retention time was obtained. Absolute configuration undetermined.

¹H NMR (300 MHz, DMSO-d₆) δ 1.35-1.60 (3H, m), 1.68-2.40 (9H, m), 2.71-2.84 (2H, m), 3.59-3.84 (3H, m), 3.89-4.03 (1H, m), 4.31-4.38 (1H, m), 5.13 (1H, d, J=5.7 Hz), 6.88 (1H, d, J=8.8 Hz), 7.99 (1H, s), 8.01-8.12 (2H, m), 8.99 (1H, brs).

MS (ESI+): [M+H]⁺ 572.1.

$[\alpha]_D^{25}$+36.4 (c 0.50, DMSO)

Example 187

N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-valinamide A) N²-(tert-butoxycarbonyl)-N,N-dimethyl-D-valinamide To a solution of N-(tert-butoxycarbonyl)-D-valine (15.0 g), dimethylamine hydrochloride (11.3 g) and N-ethyl-N-(1-methylethyl)propan-2-amine (26.7 g) in DMF (150 mL) was added O-(7-azabenzotriazol-1-yl)-N,N,N',N'-tetramethyluronium hexafluorophosphate (31.5 g) at room temperature. The reaction mixture was stirred at room temperature overnight, water was added to the reaction mixture, and the mixture was extracted with ethyl acetate. The organic layer was separated, washed with water and saturated brine, dried over sodium sulfate, and concentrated under reduced pressure to give a crude product (20.6 g) containing the title compound.

¹H NMR (400 MHz, DMSO-d₆) δ 0.82-0.84 (6H, m), 1.37 (9H, s), 1.86-1.93 (1H, m), 2.69 (3H, s), 3.04 (3H, s), 4.19 (1H, t, J=8.0 Hz), 6.69 (1H, d, J=8.8 Hz).

B) N,N-dimethyl-D-valinamide hydrochloride

To a solution of the crude product containing N²-(tert-butoxycarbonyl)-N,N-dimethyl-D-valinamide obtained in A) in ethyl acetate (100 mL) was added 4N hydrogen chloride/ethyl acetate solution (100 mL) under ice-cooling. The reaction mixture was stirred at room temperature overnight, and the solvent was evaporated under reduced pressure to give a crude product (19.6 g) containing the title compound.

¹H NMR (400 MHz, DMSO-d₆) δ 0.92 (3H, d, J=6.8 Hz), 0.97 (3H, d, J=7.2 Hz), 2.05-2.09 (1H, m), 2.89 (3H, s), 3.05 (3H, s), 4.17 (1H, t, J=5.2 Hz), 8.25 (3H, brs).

C) N,N-dimethyl-N²-(2-oxo-2,5-dihydro-1,3-thiazol-4-yl)-D-valinamide

To a solution of the crude product (19.6 g) containing N,N-dimethyl-D-valinamide hydrochloride obtained in B) and triethylamine (44.0 g) in ethanol (150 mL) was added 4-thioxothiazolidin-2-one (14.4 g) at room temperature. The reaction mixture was stirred at room temperature for 3 hr, and the solvent was evaporated under reduced pressure. The obtained solid was suspended in THF, and the suspension was filtered through celite pad and silica gel pad. The filtrate was concentrated under reduced pressure, and the residue was purified by silica gel column chromatography (NH, ethyl acetate) to give the title compound (4.2 g).

¹H NMR (400 MHz, DMSO-d₆) δ 0.88 (3H, d, J=6.8 Hz), 0.92 (3H, d, J=6.8 Hz), 2.02-2.07 (1H, m), 2.86 (3H, s), 3.11 (3H, s), 4.21-4.31 (2H, m), 4.73 (1H, t, J=8.4 Hz), 9.33 (1H, d, J=8.0 Hz).

MS (ESI+): [M+H]⁺ 244.

D) N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-valinamide To a solution of N,N-dimethyl-N²-(2-oxo-2,5-dihydro-1,3-thiazol-4-yl)-D-valinamide (0.730 g) and 1-[2,4-bis(trifluoromethyl)benzyl]piperidine-4-carbaldehyde (1.018 g) in 2-propanol (10 mL) was added piperidinium acetate (0.436 g) under ice-cooling. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (1.050 g).

¹H NMR (300 MHz, DMSO-d₆) δ 0.89 (3H, d, J=6.8 Hz), 0.94 (3H, d, J=6.6 Hz), 1.38-1.57 (2H, m), 1.66-1.83 (2H, m), 2.01-2.28 (4H, m), 2.69-2.82 (2H, m), 2.86 (3H, s), 3.15 (3H, s), 3.71 (2H, s), 4.71 (1H, d, J=10.2 Hz), 7.19 (1H, brs), 7.99 (1H, s), 8.01-8.12 (2H, m), 9.25 (1H, brs).

MS (ESI+): [M+H]⁺ 565.1.

Example 188

N²-[(5Z)-5-({1-[2,4-bis(trifluoromethyl)benzyl]piperidin-4-yl}methylidene)-2-oxo-2,5-dihydro-1,3-thiazol-4-yl]-N,N,O-trimethyl-D-serinamide A) N,N,O-trimethyl-N²-(2-oxo-2,5-dihydro-1,3-thiazol-4-yl)-D-serinamide To a solution of N-(tert-butoxycarbonyl)-O-methyl-D-serine N-cyclohexylcyclohexanamine salt (10 g), dimethylamine hydrochloride (4.1 g) and N-ethyl-N-(1-methylethyl)propan-2-amine (74.9 g) in DMF (150 mL) was added O-(7-azabenzotriazol-1-yl)-N,N,N',N'-tetramethyluronium hexafluorophosphate (11.4 g) at room temperature. The reaction mixture was stirred at room temperature overnight, water was added to the reaction mixture, and the mixture was extracted with ethyl acetate. The organic layer was separated, washed with water and saturated brine, dried over sodium sulfate, and concentrated under reduced pressure. To a solution of the residue in ethyl acetate (100 mL) was added 4N hydrogen chloride/ethyl acetate solution (100 mL) under ice-cooling. The reaction mixture was stirred at room temperature overnight, and the solvent was evaporated under reduced pressure. To a solution of the residue and triethylamine (9.9 g) in ethanol (100 mL) was added 4-thioxothiazolidin-2-one (3.6 g) at room temperature. The reaction mixture was stirred at room temperature overnight, and the solvent was evaporated under reduced pressure. The obtained solid was suspended in THF, the suspension was filtered through celite pad and silica gel pad, and the filtrate was concentrated under reduced pressure. The residue was purified by silica gel column chromatography (NH, ethyl acetate/petroleum ether) to give the title compound (2.56 g).

¹H NMR (400 MHz, DMSO-d₆) δ 3.03 (3H, s), 3.13 (3H, s), 3.34 (3H, s), 3.64-3.73 (2H, m), 4.17 (2H, s), 5.26-5.31 (1H, m), 7.72 (1H, d, J=6.4 Hz).

MS (ESI+): [M+H]⁺ 246.

B) N²-[(5Z)-5-({1-[2,4-bis(trifluoromethyl)benzyl]
piperidin-4-yl}methylidene)-2-oxo-2,5-dihydro-1,3-
thiazol-4-yl]-N,N,O-trimethyl-D-serinamide To a solution of N,N,O-trimethyl-N²-(2-oxo-2,5-dihydro-1,3-thiazol-4-yl)-D-serinamide (736 mg) and 1-[2,4-bis(trifluoromethyl)benzyl]piperidine-4-carbaldehyde (1018 mg) in 2-propanol (10 mL) was added piperidinium acetate (436 mg). The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (766 mg).
¹H NMR (300 MHz, DMSO-d₆) δ 1.39-1.58 (2H, m), 1.67-1.82 (2H, m), 2.03-2.24 (3H, m), 2.69-2.82 (2H, m), 2.85 (3H, s), 3.09 (3H, s), 3.28 (3H, s), 3.64 (2H, d, J=6.6 Hz), 3.71 (2H, s), 5.16 (1H, t, J=6.7 Hz), 7.10 (1H, d, J=8.5 Hz), 7.99 (1H, s), 8.01-8.13 (2H, m), 9.36 (1H, brs).
MS (ESI+): [M+H]⁺ 567.2.

Example 189

(5Z)-5-({1-[2,4-bis(trifluoromethyl)benzyl]piperi-
din-4-yl}methylidene)-4-[(1-methyl-5-oxopyrroli-
din-3-yl)amino]-1,3-thiazol-2(5H)-one To a solution of 4-amino-1-methylpyrrolidin-2-one hydrochloride (5.0 g) and triethylamine (3.86 mL) in ethanol (50 mL) was added 4-thioxo-1,3-thiazolidin-2-one (3.68 g), and the mixture was stirred at room temperature for 3 hr. The reaction mixture was concentrated, and the residue was purified by silica gel column chromatography (methanol/ethyl acetate). To a solution of the obtained solid and 1-[2,4-bis(trifluoromethyl)benzyl]piperidine-4-carbaldehyde (7.82 g) in 2-propanol (80 mL) was added piperidinium acetate (3.35 g). The reaction mixture was stirred at 80° C. for 3.5 hr and concentrated under reduced pressure. Water and THF were added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/methanol), and the obtained solid was recrystallized from ethyl acetate/heptane to give the title compound (7.3 g).
¹H NMR (300 MHz, DMSO-d₆) δ 1.36-1.59 (2H, m), 1.65-1.84 (2H, m), 2.01-2.23 (3H, m), 2.32-2.44 (1H, m), 2.62-2.84 (6H, m), 3.29-3.37 (1H, m), 3.60-3.82 (3H, m), 4.46-4.47 (1H, m), 6.92 (1H, d, J=8.8 Hz), 7.98 (1H, s), 8.00-8.12 (2H, m), 9.28 (1H, s).
MS (ESI+): [M+H]⁺ 535.1.

Example 190

(2S)-2-{[(5Z)-5-({1-[2,4-bis(trifluoromethyl)benzyl]
piperidin-4-yl}methylidene)-2-oxo-2,5-dihydro-1,3-
thiazol-4-yl]amino}-2-(1-hydroxycyclopropyl)-N,N-
dimethylethanamide A) methyl N-[(benzyloxy)carbonyl]-D-serinate To a solution of D-serine (10.5 g) in methanol (100 mL) was added thionyl chloride (8.76 mL) under ice-cooling. The reaction mixture was stirred at room temperature for 4 hr, and to the reaction mixture were added sodium hydrogen carbonate (25.2 g) and benzyl chloroformate (17.1 mL). The reaction mixture was stirred at room temperature overnight, the reaction mixture was added to water, and the mixture was extracted with ethyl acetate. The organic layer was separated, washed with saturated brine, dried over magnesium sulfate, and concentrated under reduced pressure. The residue was purified by silica gel column chromatography (ethyl acetate/hexane) to give the title compound (10.3 g).
¹H NMR (300 MHz, DMSO-d₆) δ 3.51-3.72 (5H, m), 4.09-4.21 (1H, m), 4.96 (1H, t, J=5.9 Hz), 5.04 (2H, s), 7.23-7.43 (5H, m), 7.53 (1H, d, J=7.9 Hz)

B) 3-benzyl 4-methyl(4R)-2,2-dimethyl-1,3-oxazoli-
dine-3,4-dicarboxylate

To a solution of methyl N-[(benzyloxy)carbonyl]-D-serinate (1013 mg) and 2,2-dimethoxypropane (4166 mg) in acetone (20 mL) was added pyridin-1-ium 4-methylbenzenesulfonate (201 mg) at room temperature, and the reaction mixture was stirred at 60° C. overnight. The solvent was evaporated, and the residue was purified by silica gel column chromatography (ethyl acetate/hexane) to give the title compound (860 mg).
¹H NMR (300 MHz, DMSO-d₆) δ 1.40-1.49 (3H, m), 1.52-1.60 (3H, m), 3.59-3.70 (3H, m), 3.97-4.08 (1H, m), 4.14-4.24 (1H, m), 4.47-4.61 (1H, m), 4.95-5.16 (2H, m), 7.24-7.44 (5H, m).

C) benzyl(4R)-4-(1-hydroxycyclopropyl)-2,2-dim-
ethyl-1,3-oxazolidine-3-carboxylate To a solution of 3-benzyl 4-methyl(4R)-2,2-dimethyl-1,3-oxazolidine-3,4-dicarboxylate (6.66 g) and titanium tetraisopropoxide (3.33 mL) in diethyl ether (200 mL) was added dropwise 3M ethyl magnesium bromide diethyl ether solution (18.9 mL) over 20 min under ice-cooling. The reaction mixture was stirred at room temperature overnight, and to the reaction mixture was added saturated aqueous ammonium chloride solution. The precipitated solid was removed by filtration. The filtrate was extracted with ethyl acetate, and the organic layer was separated, washed with saturated brine, dried over magnesium sulfate, and concentrated. The residue was purified by silica gel column chromatography (ethyl acetate/hexane) to give the title compound (2.52 g).
¹H NMR (300 MHz, DMSO-d) δ 0.22-0.83 (4H, m), 1.31-1.59 (6H, m), 3.60-3.87 (1H, m), 3.96-4.13 (2H, m), 5.07 (2H, brs), 5.40 is (1H, s), 7.23-7.46 (5H, m).

D) benzyl[(1R)-2-hydroxy-1-(1-hydroxycyclopro-
pyl)ethyl]carbamate

To a solution of benzyl(4R)-4-(1-hydroxycyclopropyl)-2,2-dimethyl-1,3-oxazolidine-3-carboxylate (2.45 g) in methanol (100 mL) was added pyridin-1-ium 4-methylbenzenesulfonate (2.33 g) at room temperature. The reaction mixture was stirred at room temperature overnight, to the reaction mixture was added saturated aqueous sodium hydrogen carbonate solution, and the mixture was extracted with ethyl acetate. The organic layer was separated, washed with saturated brine, dried over magnesium sulfate, and concentrated under reduced pressure. The residue was purified by silica gel column chromatography (ethyl acetate/hexane) to give the title compound (1.68 g).
¹H NMR (300 MHz, CDCl₃) δ 0.53-0.95 (4H, m), 2.61 (1H, brs), 3.06-3.19 (1H, m), 3.43 (1H, brs), 3.85-4.06 (2H, m), 5.11 (2H, s), 5.78 (1H, d, J=7.2 Hz), 7.29-7.40 (5H, m).

E) benzyl[(1S)-2-(dimethylamino)-1-(1-hydroxycy-
clopropyl)-2-oxoethyl]carbamate To a mixed solution consisting of benzyl[(1R)-2-hydroxy-1-(1-hydroxycyclopropyl)ethyl]carbamate (900 mg) and 2,2, 6,6-tetramethylpiperidine 1-oxyl (39.2 mg) in acetonitrile (5 mL) and phosphate buffer (pH 6.8, 5 mL) were simultaneously added dropwise 0.033M aqueous sodium hypochlorite solution (2.17 mL) and 2M aqueous sodium chlorite solution (3.58 mL) over 30 min. The reaction mixture was stirred at 35° C. for 2 days, and to the reaction mixture was added saturated aqueous sodium thiosulfate solution at room temperature. The mixture was adjusted with 8N aqueous sodium hydroxide solution to about pH at room temperature, and to the reaction mixture was added a small amount of diisopropyl ether. The reaction mixture was vigorously stirred at room temperature for 30 min, and the aqueous layer was separated and adjusted with 6N hydrochloric acid to about pH 2 at room temperature. The reaction mixture was added to water, and the mixture was extracted with ethyl acetate. The organic layer was separated, washed with saturated brine, dried over magnesium sulfate, and concentrated under reduced pressure. To a solution of the residue, 50% aqueous dimethylamine solution (323 mg) and N-ethyl-N-(1-methylethyl)propan-2-amine (925 mg) in DMF (5 mL) was added O-(7-azabenzotriazol-1-yl)-N,N,N',N'-tetramethyluronium hexafluorophosphate (1361 mg) at room temperature. The reaction mixture was stirred at room temperature for 4 hr, water was added to the reaction mixture, and the mixture was extracted with ethyl acetate. The organic layer was separated, washed with water and saturated brine, dried over magnesium sulfate, and concentrated under reduced pressure. The residue was purified by silica gel column chromatography (NH, ethyl acetate/hexane) to give the title compound (190 mg).

$^1$H NMR (300 MHz, CDCl$_3$) δ 0.49-0.68 (2H, m), 0.74-0.94 (2H, m), 2.96 (3H, s), 3.11 (3H, s), 4.35 (1H, d, J=8.6 Hz), 4.82 (1H, brs), 5.11 (2H, s), 6.21 (1H, d, J=8.6 Hz), 7.25-7.40 (5H, m).

MS (ESI+): [M+H]$^+$ 293.3.

F) (2S)-2-amino-2-(1-hydroxycyclopropyl)-N,N-dimethylethanamide

To a solution of benzyl[(1S)-2-(dimethylamino)-1-(1-hydroxycyclopropyl)-2-oxoethyl]carbamate (190 mg) in ethanol (5 mL) was added 10% palladium carbon (69 mg) at room temperature. The reaction mixture was stirred at room temperature for 5 hr under a hydrogen atmosphere. The reaction mixture was filtered, and the filtrate was concentrated under reduced pressure to give the title compound (60 mg).

$^1$H NMR (300 MHz, CDCl$_3$) δ 0.41-0.61 (2H, m), 0.77-0.93 (2H, m), 2.98 (3H, s), 3.12 (3H, s), 3.19-3.63 (3H, m).

G) (2S)-2-(1-hydroxycyclopropyl)-N,N-dimethyl-2-[(2-oxo-2,5-dihydro-1,3-thiazol-4-yl)amino]ethanamide To a solution of (2S)-2-amino-2-(1-hydroxycyclopropyl)-N,N-dimethylethanamide (60 mg) in ethanol (1 mL) was added 4-thioxothiazolidin-2-one (51 mg) at room temperature. The reaction mixture was stirred at room temperature overnight, and concentrated under reduced pressure. The residue was purified by silica gel column chromatography (NH, ethyl acetate/hexane) to give the title compound (13 mg).

$^1$H NMR (300 MHz, CDCl$_3$) δ 0.56-0.74 (2H, m), 0.80-1.04 (2H, m), 3.02 (3H, s), 3.20 (3H, s), 4.20 (1H, d, J=17.1 Hz), 4.28 (1H, d, J=17.1 Hz), 4.97 (1H, s), 7.90 (1H, brs).

H) (2S)-2-{[(5Z)-5-({1-[2,4-bis(trifluoromethyl)benzyl]piperidin-4-yl}methylidene)-2-oxo-2,5-dihydro-1,3-thiazol-4-yl]amino}-2-(1-hydroxycyclopropyl)-N,N-dimethylethanamide To a solution of (2S)-2-(1-hydroxycyclopropyl)-N,N-dimethyl-2-[(2-oxo-2,5-dihydro-1,3-thiazol-4-yl)amino]ethanamide (13 mg) and 1-[2,4-bis(trifluoromethyl)benzyl]piperidine-4-carbaldehyde (17 mg) in 2-propanol (1 mL) was added piperidinium acetate (7 mg) at room temperature. The reaction mixture was stirred at 60° C. overnight, and the solvent was evaporated under reduced pressure. The residue was purified by silica gel column chromatography (NH, methanol/ethyl acetate) to give the title compound (10 mg).

$^1$H NMR (300 MHz, CDCl$_3$) δ 0.51-0.72 (2H, m), 0.80-0.92 (1H, m), 0.98-1.14 (1H, m), 1.46-1.90 (4H, m), 2.09-2.27 (3H, m), 2.78-2.93 (2H, m), 3.05 (3H, s), 3.21 (3H, s), 3.70 (2H, s), 4.97 (1H, d, J=6.2 Hz), 5.27 (1H, brs), 6.33 (1H, d, J=8.9 Hz), 7.62 (1H, d, J=6.2 Hz), 7.80 (1H, d, J=8.1 Hz), 7.88 (1H, s), 7.99 (1H, d, J=8.3 Hz).

MS (ESI+): [M+H]$^+$ 579.1.

Example 191

(5Z)-5-({1-[2,4-bis(trifluoromethyl)benzyl]piperidin-4-yl}methylidene)-4-{[(1S)-2-methyl-1-(morpholin-4-ylcarbonyl)propyl]amino}-1,3-thiazol-2(5H)-one A) benzyl[(2S)-3-methyl-1-(morpholin-4-yl)-1-oxobutan-2-yl]carbamate To a solution of N-[(benzyloxy)carbonyl]-L-valine (1.26 g) and morpholine (0.479 g) and N-ethyl-N-(1-methylethyl)propan-2-amine (0.711 g) in DMF (20 mL) was added O-(7-azabenzotriazol-1-yl)-N,N,N',N'-tetramethyluronium hexafluorophosphate (1.90 g) at room temperature. The reaction mixture was stirred at room temperature overnight, the reaction mixture was added to water, and the mixture was extracted with ethyl acetate. The organic layer was separated, washed with water and saturated brine, dried over magnesium sulfate, and concentrated under reduced pressure. The residue was dissolved in ethyl acetate/hexane, and the insoluble material was removed by filtration. The filtrate was concentrated under reduced pressure to give the title compound (1.53 g).

$^1$H NMR (300 MHz, DMSO-d$_6$) δ 0.77-0.93 (6H, m), 1.87-1.98 (1H, m), 3.33-3.64 (8H, m), 4.24 (1H, t, J=8.3 Hz), 5.02 (2H, s), 7.25-7.41 (5H, m), 7.46 (1H, d, J=8.5 Hz).

B) (2S)-2-amino-3-methyl-1-(morpholin-4-yl)butan-1-one

A solution of benzyl[(2S)-3-methyl-1-(morpholin-4-yl)-1-oxobutan-2-yl]carbamate (1.83 g) and 10% palladium carbon (0.608 g) in ethanol (30 mL) was stirred at room temperature overnight under a hydrogen atmosphere. The reaction mixture was filtered, and the filtrate was concentrated under reduced pressure to give the title compound (850 mg).

$^1$H NMR (300 MHz, CDCl$_3$) δ 0.92 (3H, d, J=6.8 Hz), 1.00 (3H, d, J=6.8 Hz), 1.77-1.97 (1H, m), 2.55 (2H, brs), 3.41-3.81 (9H, m).

C) 4-{[(2S)-3-methyl-1-(morpholin-4-yl)-1-oxobutan-2-yl]amino}-1,3-thiazol-2(5H)-one To a solution of (2S)-2-amino-3-methyl-1-(morpholin-4-yl)butan-1-one (850 mg) in ethanol (10 mL) was added 4-thioxothiazolidin-2-one (608 mg) at room temperature. The reaction mixture was stirred at room temperature overnight, and the solvent was evaporated under reduced pressure. The residue was purified by silica gel column chromatography (NH, ethyl acetate/hexane) to give the title compound (583 mg).

¹H NMR (300 MHz, DMSO-d₆) δ 0.90 (3H, d, J=6.7 Hz), 0.93 (3H, d, J=6.8 Hz), 1.93-2.14 (1H, m), 3.39-3.76 (8H, m), 4.24 (1H, d, J=17.7 Hz), 4.31 (1H, d, J=17.7 Hz), 4.74 (1H, d, J=5.5 Hz), 9.38 (1H, brs).

D) (5Z)-5-({1-[2,4-bis(trifluoromethyl)benzyl]piperidin-4-yl}methylidene)-4-{[(1S)-2-methyl-1-(morpholin-4-ylcarbonyl)propyl]amino}-1,3-thiazol-2(5H)-one To a solution of 4-{[(2S)-3-methyl-1-(morpholin-4-yl)-1-oxobutan-2-yl]amino}-1,3-thiazol-2(5H)-one (371 mg) and 1-[2,4-bis(trifluoromethyl)benzyl]piperidine-4-carbaldehyde (441 mg) in 2-propanol (10 mL) was added piperidinium acetate (189 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (416 mg).

¹H NMR (300 MHz, DMSO-d₆) δ 0.91 (3H, d, J=6.8 Hz), 0.98 (3H, d, J=6.6 Hz), 1.41-1.59 (2H, m), 1.68-1.83 (2H, m), 2.02-2.29 (4H, m), 2.69-2.86 (2H, m), 3.36-3.83 (10H, m), 4.72 (1H, d, J=8.5 Hz), 7.21 (1H, d, J=8.9 Hz), 7.98 (1H, s), 8.02-8.12 (2H, m), 9.28 (1H, d, J=4.5 Hz).

MS (ESI+): [M+H]⁺ 607.1.

Example 192

2-{[(5Z)-5-({1-[2,4-bis(trifluoromethyl)benzyl]piperidin-4-yl}methylidene)-2-oxo-2,5-dihydro-1,3-thiazol-4-yl]amino}-4,4,4-trifluoro-N,N-dimethylbutanamide

A) tert-butyl[1-(dimethylamino)-4,4,4-trifluoro-1-oxobutan-2-yl]carbamate

To a solution of 2-[(tert-butoxycarbonyl)amino]-4,4,4-trifluorobutanoic acid (1.0 g), dimethylamine hydrochloride (634 mg) and N-ethyl-N-(1-methylethyl)propan-2-amine (1.5 g) in DMF (20 mL) was added O-(7-azabenzotriazol-1-yl)-N,N,N',N'-tetramethyluronium hexafluorophosphate (1.8 g) at room temperature. The reaction mixture was stirred at room temperature overnight, water was added to the reaction mixture, and the mixture was extracted with ethyl acetate. The organic layer was separated, washed with water and saturated brine, dried over sodium sulfate, concentrated under reduced pressure to give a crude product (2 g) containing the title compound.

¹H NMR (400 MHz, CDCl₃) δ 1.44 (9H, s), 2.39-2.50 (1H, m), 2.52-2.61 (1H, m), 2.98 (3H, s), 3.13 (3H, s), 5.00 (1H, q, J=6.8 Hz), 5.26 (1H, d, J=8.8 Hz).

B) 2-amino-4,4,4-trifluoro-N,N-dimethylbutanamide hydrochloride

To a solution of the crude product (2.0 g) containing tert-butyl[1-(dimethylamino)-4,4,4-trifluoro-1-oxobutan-2-yl]carbamate obtained in A) in ethyl acetate (25 mL) was added 4N hydrogen chloride/ethyl acetate solution (25 mL) under ice-cooling. The reaction mixture was stirred at room temperature overnight, and the solvent was evaporated under reduced pressure to give a crude product (1.3 g) containing the title compound.

¹H NMR (400 MHz, DMSO-d₆) δ 2.69 (2H, s), 2.88 (3H, s), 3.06 (3H, s), 4.66 (1H, brs), 8.63 (3H, brs).

MS (ESI+): [M+H]⁺ 185.

C) 2-{[(5Z)-5-({1-[2,4-bis(trifluoromethyl)benzyl]piperidin-4-yl}methylidene)-2-oxo-2,5-dihydro-1,3-thiazol-4-yl]amino}-4,4,4-trifluoro-N,N-dimethylbutanamide To a solution of 2-amino-4,4,4-trifluoro-N,N-dimethylbutanamide hydrochloride (408 mg) and triethylamine (0.74 mL) in ethanol (5 mL) was added 4-thioxothiazolidin-2-one (246 mg) at room temperature. The reaction mixture was stirred at room temperature overnight, and the solvent was evaporated under reduced pressure. The residue was purified by silica gel column chromatography (NH, ethyl acetate/hexane).

To a solution of the obtained solid and 1-[2,4-bis(trifluoromethyl)benzyl]piperidine-4-carbaldehyde (170 mg) in 2-propanol (2 mL) was added piperidinium acetate (73 mg) at room temperature. The reaction mixture was stirred at 60° C. overnight, and the solvent was evaporated under reduced pressure. The residue was purified by silica gel column chromatography (NH, ethyl acetate/hexane) to give the title compound (15 mg).

¹H NMR (300 MHz, DMSO-d₆) δ 1.38-1.58 (2H, m), 1.66-1.84 (2H, m), 2.03-2.25 (3H, m), 2.70-2.93 (7H, m), 3.08 (3H, s), 3.71 (2H, s), 5.26 (1H, dd, J=7.8, 4.8 Hz), 7.02 (1H, d, J=7.7 Hz), 7.92-8.13 (3H, m), 9.58 (1H, brs).

MS (ESI+): [M+H]⁺ 605.1.

Example 193

(−)-(5Z)-5-({1-[2,4-bis(trifluoromethyl)benzyl]piperidin-4-yl}methylidene)-4-[(1,4-dioxan-2-ylmethyl)amino]-1,3-thiazol-2(5H)-one A racemate (150 mg) of (5Z)-5-({1-[2,4-bis(trifluoromethyl)benzyl]piperidin-4-yl}methylidene)-4-[(1,4-dioxan-2-ylmethyl)amino]-1,3-thiazol-2(5H)-one was separated by HPLC (column: CHIRALPAK AD (NF001), 50 mmID×500 mL, manufactured by DAICEL CHEMICAL INDUSTRIES, LTD., mobile phase: hexane/ethanol=900/100), and the title compound (75 mg) having a shorter retention time was obtained. Absolute configuration undetermined.

¹H NMR (300 MHz, DMSO-d₆) δ 1.35-1.58 (2H, m), 1.66-1.84 (2H, m), 2.00-2.25 (3H, m), 2.69-2.84 (2H, m), 3.23 (1H, dd, J=11.9, 10.0 Hz), 3.38-3.80 (10H, m), 6.90 (1H, d, J=8.9 Hz), 7.99 (1H, s), 8.01-8.12 (2H, m), 9.26 (1H, brs).

MS (ESI+): [M+H]⁺ 538.1.

$[\alpha]_D^{25}$ −8.3 (c 0.25, DMSO)

Example 194

(+)-(5Z)-5-({1-[2,4-bis(trifluoromethyl)benzyl]piperidin-4-yl}methylidene)-4-[(1,4-dioxan-2-ylmethyl)amino]-1,3-thiazol-2(5H)-one A racemate (150 mg) of (5Z)-5-({1-[2,4-bis(trifluoromethyl)benzyl]piperidin-4-yl}methylidene)-4-[(1,4-dioxan-2-ylmethyl)amino]-1,3-thiazol-2(5H)-one was separated by HPLC (column: CHIRALPAK AD (NF001), 50 mmID×500 mL, manufactured by DAICEL CHEMICAL INDUSTRIES, LTD., mobile phase: hexane/ethanol=900/100), and the title compound (69 mg) having a longer retention time was obtained. Absolute configuration undetermined.

¹H NMR (300 MHz, DMSO-d₆) δ 1.36-1.59 (2H, m), 1.67-1.82 (2H, m), 2.00-2.27 (3H, m), 2.68-2.84 (2H, m), 3.15-

3.28 (1H, min), 3.38-3.84 (10H, m), 6.90 (1H, d, J=8.7 Hz), 7.99 (1H, s), 8.01-8.14 (2H, m), 9.26 (1H, brs).
MS (ESI+): [M+H]$^+$ 538.1.
[α]$_D^{25}$+7.4 (c 0.25, DMSO)

Example 195

(5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one hydrochloride To a solution of (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one (7.86 g) in tert-butyl methyl ether (70 mL) was added dropwise a solution of 4N hydrogen chloride/ethyl acetate (3.74 mL), and the mixture was stirred at room temperature for 1 hr. The precipitate was collected by filtration, and the obtained solid was recrystallized from ethanol/heptane to give the title compound (5.63 g).
$^1$H NMR (300 MHz, DMSO-d$_6$) δ 1.75-2.10 (4H, m), 2.31-2.47 (1H, m), 3.08-3.30 (2H, m), 3.34-3.72 (11H, m), 4.54 (2H, brs), 6.89 (1H, d, J=9.0 Hz), 8.14 (1H, s), 8.27 (1H, d, J=7.7 Hz), 8.68 (1H, d, J=8.7 Hz), 9.42 (1H, brs), 11.18 (1H, brs).
MS (ESI+): [M−Cl]$^+$ 526.0.
powder X-ray diffraction interplanar spacing (d): 22.87, 12.87, 11.38, 9.19, 7.58, 6.15, 5.68, 4.54, 4.37, 3.88, 3.79 and 3.67 Å.

Example 196

N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-3-(methylsulfonyl)-L-alaninamide A) N$^2$-(tert-butoxycarbonyl)-N,N,S-trimethyl-L-cysteinamide To a solution of N-(tert-butoxycarbonyl)-S-methyl-L-cysteine (2.0 g), dimethylamine hydrochloride (1.4 g) and N-ethyl-N-(1-methylethyl)propan-2-amine (3.3 g) in DMF (50 mL) was added O-(7-azabenzotriazol-1-yl)-N,N,N',N'-tetramethyluronium hexafluorophosphate (3.8 g) at room temperature. The reaction mixture was stirred at room temperature overnight, water was added to the reaction mixture, and the mixture was extracted with ethyl acetate. The organic layer was separated, washed with water and saturated brine, dried over sodium sulfate, and concentrated under reduced pressure to give a crude product (4.0 g) containing the title compound.
$^1$H NMR (400 MHz, CDCl$_3$) δ 1.43 (9H, s), 2.15 (3H, s), 2.70-2.75 (1H, m), 2.80-2.89 (1H, m), 2.98 (3H, s), 3.16 (3H, s), 4.81-4.84 (1H, m), 5.47 (1H, d, J=8.4 Hz).

B) N$^2$-(tert-butoxycarbonyl)-N,N-dimethyl-3-(methylsulfonyl)-L-alaninamide

To a solution of the crude product (4.0 g) containing N$^2$-(tert-butoxycarbonyl)-N,N,S-trimethyl-L-cysteinamide obtained in A) in acetic acid (20 mL) was added 30% aqueous hydrogen peroxide (8 mL) under ice-cooling. The reaction mixture was stirred at room temperature 24 hr, water was added to the reaction mixture, and the mixture was extracted with ethyl acetate. The organic layer was washed with water and saturated brine, dried over sodium sulfate, and concentrated under reduced pressure to give a crude product (3.6 g) containing the title compound.
$^1$H NMR (400 MHz, CDCl$_3$) δ 1.48 (9H, s), 3.00 (6H, s), 3.18 (3H, s), 3.30-3.36 (1H, m), 5.21 (1H, d, J=6.0 Hz), 5.63 (1H, d, J=8.8 Hz)

C) N,N-dimethyl-3-(methylsulfonyl)-L-alaninamide hydrochloride

To a solution of the crude product (3.6 g) containing N$^2$-(tert-butoxycarbonyl)-N,N-dimethyl-3-(methylsulfonyl)-L-alaninamide obtained in B) in ethyl acetate (25 mL) was added 4N hydrogen chloride/ethyl acetate solution (25 mL) under ice-cooling. The reaction mixture was stirred at room temperature overnight, and the solvent was evaporated under reduced pressure to give a crude product (1.5 g) containing the title compound.
$^1$H NMR (400 MHz, DMSO-d$_6$) δ 2.90 (3H, s), 3.09 (3H, s), 3.18 (3H, s), 3.57-3.62 (1H, m), 3.76-3.81 (1H, m), 4.82 (1H, brs), 8.54 (3H, brs).
MS (ESI+): [M+H]$^+$ 195.

D) N,N-dimethyl-3-(methylsulfonyl)-N$^2$-(2-oxo-2,5-dihydro-1,3-thiazol-4-yl)-L-alaninamide To a solution of N,N-dimethyl-3-(methylsulfonyl)-L-alaninamide hydrochloride (923 mg) and triethylamine (1.07 mL) in ethanol (10 mL) was added 4-thioxothiazolidin-2-one (533 mg) at room temperature. The reaction mixture was stirred at room temperature overnight, and the solvent was evaporated under reduced pressure. The residue was purified by silica gel column chromatography (NH, methanol/ethyl acetate) to give the title compound (150 mg).
$^1$H NMR (300 MHz, DMSO-d$_6$) δ 2.87 (3H, s), 3.07 (3H, s), 3.08 (3H, s), 3.45 (1H, dd, J=14.7, 7.3 Hz), 3.71 (1H, dd, J=14.7, 5.3 Hz), 4.20 (1H, d, J=17.4 Hz), 4.34 (1H, d, J=17.4 Hz), 5.33 (1H, dd, J=7.3, 5.3 Hz), 9.70 (1H, brs).

E) N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-3-(methylsulfonyl)-L-alaninamide To a solution of N,N-dimethyl-3-(methylsulfonyl)-N$^2$-(2-oxo-2,5-dihydro-1,3-thiazol-4-yl)-L-alaninamide (150 mg) and 1-[2,4-bis(trifluoromethyl)benzyl]piperidine-4-carbaldehyde (173 mg) in 2-propanol (5 mL) was added piperidinium acetate (74 mg) at room temperature. The reaction mixture was stirred at 60° C. overnight, and the solvent was evaporated under reduced pressure. The residue was purified by silica gel column chromatography (NH, ethyl acetate/hexane) and recrystallized from ethyl acetate/heptane to give the title compound (55 mg).
$^1$H NMR (300 MHz, DMSO-d$_6$) δ 1.35-1.58 (2H, m), 1.65-1.85 (2H, m), 2.03-2.25 (3H, m), 2.68-2.83 (2H, m), 2.87 (3H, s), 3.07 (3H, s), 3.09 (3H, s), 3.50-3.85 (4H, m), 5.41 (1H, dd, J=7.1, 4.6 Hz), 7.00 (1H, d, J=7.7 Hz), 7.99 (1H, s), 8.02-8.13 (2H, m), 9.60 (1H, brs).
MS (ESI+): [M+H]$^+$ 615.0.

Example 197

N$^2$-[(5Z)-5-({1-[2,4-bis(trifluoromethyl)benzyl]piperidin-4-yl}methylidene)-2-oxo-2,5-dihydro-1,3-thiazol-4-yl]-N-oxetan-3-ylglycinamide A)
benzyl[2-(oxetan-3-ylamino)-2-oxoethyl]carbamate To a solution of N-[(benzyloxy)carbonyl]glycine (5.9 g), N-ethyl-N-(1-methylethyl)propan-2-amine (7.3 g) and oxetane-3-amine (2.5 g) in DMF (100 mL) was added O-(7-azabenzotriazol-1-yl)-N,N,N',N'-tetramethyluronium hexafluorophosphate (13 g), and the mixture was stirred at room temperature for 4 hr. Water was added to the reaction mixture, and the mixture was extracted with ethyl acetate. The extract was washed with water and saturated brine, dried over sodium sulfate, and the solvent was evaporated under reduced pressure to give a crude product (10.5 g) containing the title compound.

$^1$H NMR (400 MHz, CDCl$_3$) δ 3.71 (2H, d, J=4.0 Hz), 4.49-4.52 (2H, m), 4.89-4.90 (2H, m), 5.01-5.06 (1H, m), 5.14 (2H, s), 5.62 (1H, brs), 7.06 (1H, brs), 7.33-7.39 (5H, m).

B) N-oxetan-3-ylglycinamide

To a solution of the crude resultant product (10.5 g) containing benzyl[2-(oxetan-3-ylamino)-2-oxoethyl]carbamate obtained in A) in methanol (100 mL) was added palladium carbon (10% w/t, 2.1 g), and the mixture was stirred at room temperature overnight under a hydrogen atmosphere. The reaction mixture was filtered, the palladium carbon was removed, and the filtrate was concentrated under reduced pressure to give a crude product (5.7 g) containing the title compound.

$^1$H NMR (400 MHz, CDCl$_3$) δ 3.49 (2H, s), 4.55 (2H, t, J=6.4 Hz), 4.94 (2H, t, J=6.4 Hz), 5.08-5.12 (1H, m).

C) N-oxetan-3-yl-N$^2$-(2-oxo-2,5-dihydro-1,3-thiazol-4-yl)glycinamide

To a solution of the crude product (5.7 g) containing N-oxetan-3-ylglycinamide obtained in B) and triethylamine (13.3 g) in ethanol (100 mL) was added 4-thioxo-1,3-thiazolidin-2-one (5.8 g), and the mixture was stirred at room temperature is for 4 hr. The reaction mixture was concentrated under reduced pressure, and the residue was purified by silica gel column chromatography (NH, ethyl acetate/methanol/dichloromethane) to give the title compound (2.03 g).

$^1$H NMR (400 MHz, DMSO-d$_6$) δ 4.00 (2H, d, J=5.6 Hz), 4.28 (2H, s), 4.43 (2H, t, J=6.4 Hz), 4.72 (2H, t, J=6.4 Hz), 4.80-4.85 (1H, m), 8.80 (1H, d, J=6.4 Hz), 9.30 (1H, t, J=5.2 Hz).

MS (ESI+): [M+H]$^+$ 230.

D) N$^2$-[(5Z)-5-({1-[2,4-bis(trifluoromethyl)benzyl]piperidin-4-yl}methylidene)-2-oxo-2,5-dihydro-1,3-thiazol-4-yl]-N-oxetan-3-ylglycinamide To a solution of N-oxetan-3-yl-N$^2$-(2-oxo-2,5-dihydro-1,3-thiazol-4-yl)glycinamide (2 g) and 1-[2,4-bis(trifluoromethyl)benzyl]piperidine-4-carbaldehyde (2.47 g) in 2-propanol (20 mL) was added piperidinium acetate (1.06 g). The reaction mixture was stirred at 80° C. for 3.5 hr and concentrated under reduced pressure. Water and THF were added to the residue, and the mixture was extracted with ethyl acetate. The extract was washed with water and saturated brine, and dried over anhydrous magnesium sulfate, and the solvent was evaporated under reduced pressure. The residue was recrystallized from ethyl acetate/heptane/water to give the title compound (2.1 g).

$^1$H NMR (300 MHz, DMSO-d$_6$) δ 1.33-1.59 (2H, m), 1.64-1.84 (2H, m), 2.02-2.28 (3H, m), 2.70-2.85 (2H, m), 3.71 (2H, s), 4.06 (2H, d), 4.45 (2H, t, J=6.2 Hz), 4.66-4.89 (3H, m), 6.91 (1H, d, J=8.9 Hz), 7.98 (1H, s), 8.02-8.14 (2H, m), 8.89 (1H, d, J=6.4 Hz), 9.44 (1H, brs).

MS (ESI+): [M+H]$^+$ 551.1.

Example 198

(5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one To a solution of 1-[2,4-bis(trifluoromethyl)benzyl]piperidine-4-carbaldehyde (23.5 g) and 4-[(3-hydroxy-2,2-dimethylpropyl)amino]-1,3-thiazol-2(5H)-one (7.00 g) in 2-propanol (200 mL) was added piperidinium acetate (10.1 g). The reaction mixture was stirred at 60° C. overnight, and the solvent was evaporated under reduced pressure. The residue was purified by silica gel column chromatography (NH, ethyl acetate/hexane), and the obtained solid was washed with diisopropyl ether to give a solid. The obtained solid was recrystallized from ethyl acetate/heptane to give the title compound (8.83 g).

$^1$H NMR (300 MHz, DMSO-d$_6$) δ 0.84 (6H, s), 1.37-1.59 (2H, m), 1.65-1.82 (2H, m), 2.00-2.24 (3H, m), 2.70-2.84 (2H, m), 3.14 (2H, s), 3.35 (2H, s), 3.71 (2H, s), 4.71 (1H, brs), 6.95 (1H, d, J=8.7 Hz), 7.98 (1H, s), 8.01-8.12 (2H, m), 8.96 (1H, brs).

MS (ESI+): [M+H]$^+$ 524.1.

Example 199

(5Z)-5-({1-[2,4-bis(trifluoromethyl)benzyl]piperidin-4-yl}methylidene)-4-(ethylamino)-1,3-thiazol-2(H)-one A) 4-(ethylamino)-1,3-thiazol-2(5H)-one To a solution of 4-thioxo-1,3-thiazolidin-2-one (640 mg) in ethanol (6 mL) was added 30% ethanamine ethanol solution (722 mg), and the mixture was stirred at room temperature for 3 hr. The reaction mixture was concentrated under reduced pressure, and the residue was washed with 2-propanol to give the title compound (320 mg).

$^1$H NMR (300 MHz, DMSO-d$_6$) δ 1.13 (3H, t, J=7.3 Hz), 3.26-3.42 (2H, m), 4.21 (2H, d, J=0.7 Hz), 9.05 (1H, brs).

MS (ESI+): [M+H]$^+$ 145.1.

B) (5Z)-5-({1-[2,4-bis(trifluoromethyl)benzyl]piperidin-4-yl}methylidene)-4-(ethylamino)-1,3-thiazol-2(5H)-one To a solution of 4-(ethylamino)-1,3-thiazol-2(5H)-one (310 mg) and 1-[2,4-bis(trifluoromethyl)benzyl]piperidine-4-carbaldehyde (802 mg) in 2-propanol (10 mL) was added piperidinium acetate (312 mg). The reaction mixture was stirred at 75° C. for 4 hr and concentrated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane), and the obtained solid was washed with diisopropyl ether to give the title compound (110 mg).

$^1$H NMR (300 MHz, DMSO-d$_6$) δ 1.17 (3H, t, J=7.2 Hz), 1.36-1.57 (2H, m), 1.64-1.83 (2H, m), 2.01-2.24 (3H, m), 2.67-2.85 (2H, m), 3.43 (2H, q, J=7.1 Hz), 3.71 (2H, s), 6.82 (1H, d, J=8.8 Hz), 7.98 (1H, s), 8.01-8.13 (2H, m), 9.15 (1H, brs).

MS (ESI+): [M+H]$^+$ 466.1.

Example 200

(5Z)-5-({1-[2,4-bis(trifluoromethyl)benzyl]piperidin-4-yl}methylidene)-4-(propylamino)-1,3-thiazol-2(5H)-one A) 4-(propylamino)-1,3-thiazol-2(5H)-one To a solution of 4-thioxo-1,3-thiazolidin-2-one (640 mg) in ethanol (6 mL) was added propan-1-amine (0.397 mL), and the mixture was stirred at room temperature for 3 hr. The reaction mixture was concentrated under reduced pressure, and the residue was purified by silica gel column chromatography (ethyl acetate/hexane) to give the title compound (450 mg).

$^1$H NMR (300 MHz, DMSO-$d_6$) δ 0.89 (3H, t, J=7.4 Hz), 1.54 (2H, tq, J=7.3, 7.3 Hz), 3.22-3.32 (2H, m), 4.23 (2H, d, J=0.6 Hz), 9.05 (1H, brs).

MS (ESI+): [M+H]$^+$ 159.2.

B) (5Z)-5-({1-[2,4-bis(trifluoromethyl)benzyl]piperidin-4-yl}methylidene)-4-(propylamino)-1,3-thiazol-2(5H)-one To a solution of 4-(propylamino)-1,3-thiazol-2(5H)-one (450 mg) and 1-[2,4-bis(trifluoromethyl)benzyl]piperidine-4-carbaldehyde (1.06 g) in 2-propanol (10 mL) was added piperidinium acetate (413 mg). The reaction mixture was stirred at 75° C. for 4 hr and concentrated under reduced pressure. Water was added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/hexane), and the obtained solid was washed with diisopropyl ether to give the title compound (350 mg).

$^1$H NMR (300 MHz, DMSO-$d_6$) δ 0.89 (3H, t, J=7.4 Hz), 1.34-1.84 (6H, m), 2.01-2.32 (3H, m), 2.68-2.83 (2H, m), 3.36 (2H, t, J=7.2 Hz), 3.71 (2H, s), 6.84 (1H, d, J=8.8 Hz), 7.98 (1H, s), 8.01-8.11 (2H, m), 9.14 (1H, s).

MS (ESI+): [M+H]$^+$ 480.2.

Example 201

(5Z)-5-({1-[2,4-bis(trifluoromethyl)benzyl]piperidin-4-yl}methylidene)-4-[(2-hydroxy-2-methylpropyl)amino]-1,3-thiazol-2(5H)-one To a solution of 1-[2,4-bis(trifluoromethyl)benzyl]piperidine-4-carbaldehyde (25.2 g) and 4-[(2-hydroxy-2-methylpropyl)amino]-1,3-thiazol-2(5H)-one (7.00 g) in 2-propanol (200 mL) was added piperidinium acetate (10.8 g). The reaction mixture was stirred at 60° C. overnight, and the solvent was evaporated under reduced pressure. The residue was purified by silica gel column chromatography (NH, ethyl acetate/hexane), and the obtained solid was washed with diisopropyl ether to give a solid. The obtained solid was recrystallized from ethyl acetate/heptane to give the title compound (11.5 g).

$^1$H NMR (300 MHz, DMSO-$d_6$) δ 1.12 (6H, s), 1.40-1.58 (2H, m), 1.68-1.81 (2H, m), 2.03-2.24 (3H, m), 2.70-2.84 (2H, m), 3.43 (2H, s), 3.71 (2H, s), 4.70 (1H, s), 7.03 (1H, d, J=8.9 Hz), 7.98 (1H, s), 8.02-8.13 (2H, m), 8.96 (1H, brs).

MS (ESI+): [M+H]$^+$ 510.1.

powder X-ray diffraction interplanar spacing (d): 16.35, 8.17, 7.70, 6.40, 6.27, 5.23, 5.07, 4.44, 4.26, 4.17, 4.02, 3.96 and 3.88 Å.

Example 202

$N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide To a solution of 1-[2,4-bis(trifluoromethyl)benzyl]piperidine-4-carbaldehyde (5.57 g) and $N^2$-[2-oxo-2,5-dihydro-1,3-thiazol-4-yl]-N,N-dimethyl-D-serinamide (5.70 g) in ethanol (80 mL) was added piperidinium acetate (2.39 g). The reaction mixture was stirred at 80° C. overnight, and the solvent was evaporated under reduced pressure. Water was added to the residue, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/hexane) and silica gel column chromatography (methanol/ethyl acetate), and the obtained solid was washed with diisopropyl ether to give a solid. The obtained solid was recrystallized from ethyl acetate/heptane to give the title compound (3.45 g).

$^1$H NMR (300 MHz, DMSO-$d_6$) δ 1.39-1.58 (2H, m), 1.67-1.83 (2H, m), 2.03-2.26 (3H, m), 2.70-2.82 (2H, m), 2.85 (3H, s), 3.10 (3H, s), 3.58-3.80 (4H, m), 5.04 (1H, t, J=6.5 Hz), 5.11 (1H, t, J=5.9 Hz), 7.13 (1H, d, J=8.9 Hz), 7.99 (1H, s), 8.01-8.13 (2H, m), 9.24 (1H, brs).

MS (ESI+): [M+H]$^+$ 553.1.

powder X-ray diffraction interplanar spacing (d): 11.84, 10.47, 8.19, 7.88, 5.90, 5.49, 5.00, 4.92, 4.71, 4.36, 4.05 and 3.91 Å.

Example 203

(5Z)-5-({-[2,4-bis(trifluoromethyl)benzyl]piperidin-4-yl}methylidene)-4-[trans-(5,5-difluoro-2-hydroxycyclohexyl)amino]-1,3-thiazol-2(5H)-one A) (1,4-dioxaspiro[4.5]dec-7-en-8-yloxy)[tri(propan-2-yl)]silane To a solution of 1,4-dioxaspiro[4.5]decan-8-one (11.6 g) in dichloromethane (200 mL) were added dropwise triethylamine (20.7 mL) and trifluoromethyl tri(propan-2-yl)silyl sulfate (25.0 g). The reaction mixture was stirred at room temperature so for 1 hr, and ice-cooled water was added. The organic layer was separated, washed with water and saturated brine, dried over anhydrous sodium sulfate, and the solvent was evaporated under reduced pressure. The residue was purified by silica gel column chromatography (ethyl acetate/petroleum ether) to give the title compound (22.0 g).

$^1$H NMR (400 MHz, CDCl$_3$) δ 1.08-1.11 (21H, m), 1.84 (2H, t, J=6.8 Hz), 2.28-2.31 (4H, m), 3.97-4.01 (4H, m), 4.77 (1H, t, J=3.6 Hz).

B) 7-azido-1,4-dioxaspiro[4.5]decan-8-one

To a solution of (1,4-dioxaspiro[4.5]dec-7-en-8-yloxy)[tri(propan-2-yl)]silane (22.9 g) in acetonitrile (180 mL) were added dropwise sodium azide (21.4 g) and ammonium hexanitratocerate (IV) (121 g) at −20° C. The reaction mixture was stirred at −20° C. for 4 hr, ice-cooled water was added, and the mixture was extracted with diethyl ether. The extract was washed with water and saturated brine, dried over anhydrous sodium sulfate, and the solvent was evaporated under reduced pressure. The residue was purified by silica gel column chromatography (ethyl acetate/petroleum ether) to give the title compound (11.5 g).

$^1$H NMR (400 MHz, CDCl$_3$) δ 1.98-2.10 (3H, m), 2.31-2.36 (1H, m), 2.50-2.55 (1H, m), 2.67-2.76 (1H, m), 4.01-4.13 (4H, m), 4.24-4.29 (1H, m).

C) trans-3-benzyltetrahydro-1,3-benzoxazole-2,5(3H,4H)-dione

To a solution of ice-cooled lithium aluminum hydride (4.42 g) in tetrahydrofuran (100 mL) was added dropwise a solution of 7-azido-1,4-dioxaspiro[4.5]decan-8-one (11.5 g) in tetrahydrofuran (100 mL) under a nitrogen atmosphere. To the reaction solution was added sodium sulfate (10 hydrate), the precipitate was removed by filtration, and washed with dichloromethane, and the filtrate was concentrated under reduced pressure. The residue was dissolved in 1,4-dioxane (200 mL), and saturated aqueous sodium hydrogen carbonate (200 mL) and benzyl chloroformate (14.9 g) were added. The reaction mixture was stirred at room temperature overnight, and the mixture was extracted with dichloromethane. The extract was washed with water and saturated brine, dried over anhydrous sodium sulfate, and the solvent was evaporated under reduced pressure to give a powder (13.3 g). To a solution of the obtained powder (13.3 g) in DMF (80 mL) was added 60% sodium hydride (4.15 g, containing mineral oil). The reaction mixture was stirred at room temperature for 30 min, (bromomethyl)benzene (22.2 g) was added, and the mixture was stirred at room temperature overnight. To the reaction solution was added methanol (10 mL), the mixture was stirred at room temperature for 10 min, and the solvent was evaporated under reduced pressure. The residue was washed with dichloromethane, and the washing was concentrated. To a solution of the residue (11.4 g) in acetone (600 mL) was added 1N hydrochloric acid (200 mL). The reaction mixture was stirred at 60° C. for 2 days, and the solvent was evaporated under reduced pressure. To the residue was added sodium bicarbonate to pH>9, and the mixture was extracted with dichloromethane. The extraction solution was dried over anhydrous sodium sulfate, and the solvent was evaporated under reduced pressure. The residue was purified by silica gel column chromatography (ethyl acetate/petroleum ether) to give the title compound (9.67 g).

$^1$H NMR (400 MHz, CDCl$_3$) δ 1.93-2.02 (1H, m), 2.33-2.49 (3H, m), 2.63-2.71 (2H, m), 3.31-3.38 (1H, m), 4.27-4.34 (2H, m), 4.56 (1H, d, J=14.8 Hz), 7.31-7.40 (5H, m).

D) trans-3-benzyl-5,5-difluorohexahydro-1,3-benzoxazol-2(3H)-one

To a solution of trans-3-benzyltetrahydro-1,3-benzoxazole-2,5(3H,4H)-dione (1.37 g) in dichloromethane (100 mL) was added dropwise N-ethyl-N-(trifluorosulfanyl)ethanamine (1.80 g) under ice-cooling. The reaction mixture was stirred at room temperature overnight, and dichloromethane was added. The mixture was washed with water and saturated brine, dried over anhydrous sodium sulfate, and the solvent was evaporated under reduced pressure. The residue was purified by silica gel column chromatography (ethyl acetate/petroleum ether) to give the title compound (980 mg).

$^1$H NMR (400 MHz, CDCl$_3$) δ 1.65-1.93 (3H, m), 2.22-2.34 (3H, m), 3.23-3.29 (1H, m), 3.89-3.95 (1H, m), 4.36-4.46 (2H, m), 7.27-7.38 (5H, m).

E) trans-2-(benzylamino)-4,4-difluorocyclohexanol

To a solution of trans-3-benzyl-5,5-difluorohexahydro-1,3-benzoxazol-2(3H)-one (980 mg) in ethanol (60 mL)/water (6 mL) was added potassium hydroxide (411 mg). The reaction mixture was stirred at 80° C. overnight, and the solvent was evaporated under reduced pressure. The residue was purified by silica gel column chromatography (methanol/dichloromethane) to give the title compound (540 mg).

$^1$H NMR (400 MHz, CDCl$_3$) δ 1.47-1.64 (6H, m), 1.72-1.88 (1H, m), 2.04-2.19 (2H, m), 3.30-3.36 (1H, m), 3.73 (1H, d, J=12.8 Hz), 3.94 (1H, d, J=12.8 Hz), 7.28-7.39 (5H, m).

F) trans-2-amino-4,4-difluorocyclohexanol hydrochloride

To a solution (100 mL) of trans-2-(benzylamino)-4,4-difluorocyclohexanol (3.00 g) in methanol was added palladium carbon (300 mg), and the mixture was stirred at room temperature overnight under a hydrogen atmosphere. The reaction solution was filtered, and the filtrate was concentrated under reduced pressure. 4M Hydrogen chloride/ethyl acetate (100 mL) was added to the residue, and the reaction solution was concentrated under reduced pressure to give the title compound (2.26 g).

$^1$H NMR (400 MHz, CDCl$_3$) δ 1.39-1.48 (1H, m), 1.86-2.11 (4H, m), 2.38-2.45 (1H, m), 2.90-2.96 (1H, m), 3.55-3.62 (1H, m), 5.66 (1H, d, J=5.6 Hz), 8.20 (3H, brs).

MS (ESI+): [M−Cl]$^+$ 152.

G) 4-[trans-(5,5-difluoro-2-hydroxycyclohexyl)amino]-1,3-thiazol-2(5H)-one

To a solution of trans-2-amino-4,4-difluorocyclohexanol (1.08 g) in ethanol (100 mL) was added 4-thioxo-1,3-thiazolidin-2-one (950 mg), and the mixture was heated under reflux for 15 hr. The reaction mixture was concentrated under reduced pressure, and the residue was purified by silica gel column chromatography (NH, ethyl acetate) to give the title compound (1000 mg).

$^1$H NMR (400 MHz, CDCl$_3$) δ 1.41-1.50 (1H, m), 1.80-2.02 (4H, m), 2.30-2.37 (1H, m), 3.55-3.60 (1H, m), 3.78-3.86 (1H, m), 4.19-4.54 (2H, m), 5.09 (0.89H, d, J=5.2 Hz), 5.40 (0.11H, d, J=5.2 Hz), 9.12 (0.89H, d, J=7.6 Hz), 9.39 (0.11H, d, J=9.6 Hz).

MS (ESI+): [M+H]$^+$ 251.

H) (5Z)-5-({1-[2,4-bis(trifluoromethyl)benzyl]piperidin-4-yl}methylidene)-4-[trans-(5,5-difluoro-2-hydroxycyclohexyl)amino]-1,3-thiazol-2(5H)-one To a solution of 1-[2,4-bis(trifluoromethyl)benzyl]piperidine-4-carbaldehyde (777 mg) in 2-propanol (5 mL) were added 4-[trans-(5,5-difluoro-2-hydroxycyclohexyl)amino]-1,3-thiazol-2(5H)-one (860 mg) and piperidinium acetate (339 mg). The reaction mixture was stirred at 75° C. overnight, and the solvent was evaporated under reduced pressure. The residue was purified by silica gel column chromatography (ethyl acetate/hexane) and silica gel column chromatography (NH, methanol/ethyl acetate) to give the title compound (941 mg).

$^1$H NMR (300 MHz, DMSO-d$_6$) δ 1.38-1.58 (3H, m), 1.69-1.82 (2H, m), 1.82-2.24 (7H, m), 2.25-2.41 (1H, m), 2.71-2.84 (2H, m), 3.61-3.75 (3H, m), 3.89-4.04 (1H, m), 5.12 (1H, d, J=5.9 Hz), 6.88 (1H, d, J=8.8 Hz), 7.99 (1H, s), 8.01-8.12 (2H, m), 8.98 (1H, brs).

MS (ESI+): [M+H]$^+$ 572.1.

Example 204

(5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one

A) 4-{[2-(2-hydroxyethoxy)ethyl]amino}-1,3-thiazol-2(5H)-one

To a suspension of 4-thioxo-1,3-thiazolidin-2-one (10 g) in 2-propanol (25 mL) and ethyl acetate (75 mL) was added 2-(2-aminoethoxy)ethanol (7.50 mL), and the mixture was stirred at room temperature for 2 hr and further stirred for 2 hr under ice-cooling. The precipitate was collected by filtration, and the obtained solid was washed with ethyl acetate to give the title compound (12.5 g).

$^1$H NMR (300 MHz, DMSO-$d_6$) δ 3.42-3.63 (8H, m), 4.23 (2H, s), 4.60 (1H, brs), 9.14 (1H, brs).

MS (ESI+): [M+H]$^+$ 205.2.

B) (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one To a suspension of 4-{[2-(2-hydroxyethoxy)ethyl]amino}-1,3-thiazol-2(5H)-one (1.58 g) and 1-[2,4-bis(trifluoromethyl)benzyl]piperidine-4-carbaldehyde (2.89 g) in 2-propanol (30 mL) was added piperidinium acetate (1.12 g). The reaction mixture was stirred at 80° C. for 8 hr and concentrated. Water and ethyl acetate were added to the residue, and the mixture was extracted with ethyl acetate. The extract was washed with saturated brine, and dried over anhydrous magnesium sulfate, and the solvent was evaporated under reduced pressure. The residue was purified by silica gel column chromatography (ethyl acetate/methanol) to give an oil. The oil was diluted with ethyl acetate (9 mL) and heptane (45 mL). The mixture was gradually cooled from 50° C. to 0° C., and the mixture was stirred for 6 hr. The precipitate was collected by filtration, and the obtained solid was washed with a mixed solution of ethyl acetate and heptane to give a white solid. The obtained white solid was recrystallized from ethyl acetate/heptane to give the title compound (2.53 g).

$^1$H NMR (300 MHz, DMSO-$d_6$) δ 1.32-1.59 (2H, m), 1.64-1.86 (2H, m), 2.00-2.30 (3H, m), 2.64-2.86 (2H, m), 3.41-3.64 (8H, m), 3.71 (2H, s), 4.62 (1H, brs), 6.88 (1H, d, J=9.1 Hz), 7.98 (1H, s), 8.02-8.13 (2H, m), 9.22 (1H, brs).

MS (ESI+): [M+H]$^+$ 526.3.

powder X-ray diffraction interplanar spacing (d): 27.08, 13.59, 9.05, 6.78, 5.43, 5.28, 4.52, 4.27, 4.14, 3.98, 3.87, 3.75 and 3.39 Å.

The Example compounds produced by the above-mentioned methods or methods analogous thereto are shown in the following Tables. MS in the Tables shows actually measured value.

TABLE 1-1

| Example Number | Compound Name | Molstructure | Salt | MS |
|---|---|---|---|---|
| 1 | (5Z)-5-[(1-{[2,4-bis(trifluoromethyl)phenyl]carbonyl}piperidin-4-yl)methylidene]-4-(methylamino)-1,3-thiazol-2(5H)-one | | | 466.1 |
| 2 | 4-(4-{(Z)-[4-(methylamino)-2-oxo-1,3-thiazol-5(2H)-ylidene]methyl}piperidin-1-yl)-3-(trifluoromethyl)benzonitrile | | | 395.0 |

TABLE 1-1-continued

| Example Number | Compound Name | Molstructure | Salt | MS |
|---|---|---|---|---|
| 3 | (5Z)-5-({1-[2,4-bis(trifluoromethyl)benzyl]piperidin-4-yl}methylidene)-4-(methylamino)-1,3-thiazol-2(5H)-one | | | 452.2 |
| 4 | (5Z)-5-({1-[2,4-bis(trifluoromethyl)benzyl]piperidin-4-yl}methylidene)-4-(3-hydroxypyrrolidin-1-yl)-1,3-thiazol-2(5H)-one | | | 508.2 |
| 5 | (5Z)-5-({1-[2,4-bis(trifluoromethyl)benzyl]piperidin-4-yl}methylidene)-4-(3-hydroxypyrrolidin-1-yl)-1,3-thiazol-2(5H)-one | | fumarate | 508.2 |

TABLE 1-2

| | | | | |
|---|---|---|---|---|
| 6 | (5Z)-5-({1-[2,4-bis(trifluoromethyl)benzyl]piperidin-4-yl}methylidene)-4-{[2-(diethylamino)ethyl]amino}-1,3-thiazol-2(5H)-one | | | 537.2 |
| 7 | (5Z)-5-({1-[2,4-bis(trifluoromethyl)benzyl]piperidin-4-yl}methylidene)-4-(prop-2-yn-1-ylamino)-1,3-thiazol-2(5H)-one | | | 476.1 |

TABLE 1-2-continued

| # | Name | Structure | Salt | MS |
|---|------|-----------|------|-----|
| 8 | (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one | 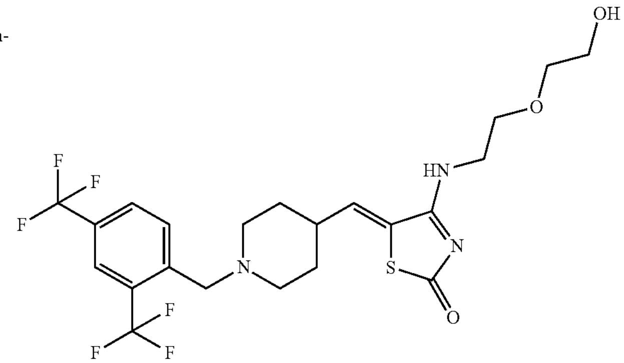 | | 526.2 |
| 9 | (5Z)-5-({1-[2,4-bis(trifluoromethyl)benzyl]piperidin-4-yl}methylidene)-4-{[2-(diethylamino)ethyl]amino}-1,3-thiazol-2(5H)-one | 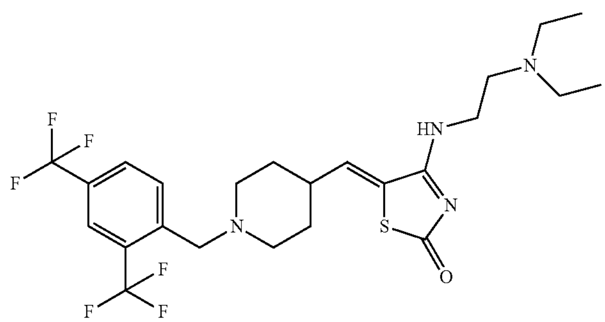 [SMILES: CCN(CC)CCNC1=NC(=O)S/C1=C\C1CCN(Cc2ccc(C(F)(F)F)cc2C(F)(F)F)CC1] | 2HCl | 537.3 |
| 10 | (5Z)-5-({1-[2,4-bis(trifluoromethyl)benzyl]piperidin-4-yl}methylidene)-4-(prop-2-yn-1-ylamino)-1,3-thiazol-2(5H)-one | 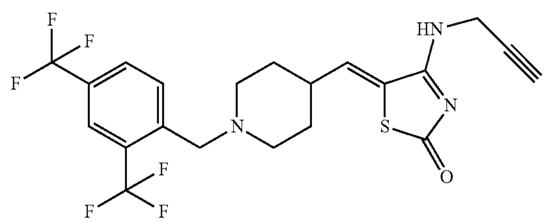 [SMILES: C#CCNC1=NC(=O)S/C1=C\C1CCN(Cc2ccc(C(F)(F)F)cc2C(F)(F)F)CC1] | fumarate | 476.1 |

TABLE 1-3

| # | Name | Structure | MS |
|---|------|-----------|-----|
| 11 | (5Z)-5-({1-[2,4-bis(trifluoromethyl)benzyl]azetidin-3-yl}methylidene)-4-(methylamino)-1,3-thiazol-2(5H)-one | 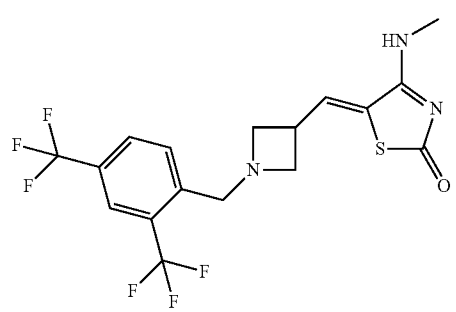 [SMILES: CNC1=NC(=O)S/C1=C\C1CN(Cc2ccc(C(F)(F)F)cc2C(F)(F)F)C1] | 424.1 |
| 12 | (5Z)-5-({1-[2,4-bis(trifluoromethyl)benzyl]-4-methylpiperidin-4-yl}methylidene)-4-(methylamino)-1,3-thiazol-2(5H)-one | 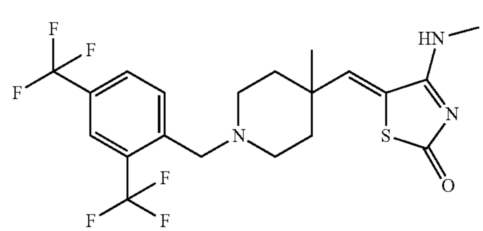 [SMILES: CNC1=NC(=O)S/C1=C\C1(C)CCN(Cc2ccc(C(F)(F)F)cc2C(F)(F)F)CC1] | 466.2 |

TABLE 1-3-continued

| | | | | |
|---|---|---|---|---|
| 13 | (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one | | 2TsOH | 526.2 |
| 14 | (5Z)-5-({(1R,5S,6s)-3-[2,4-bis(trifluoromethyl)benzyl]-3-azabicyclo[3.1.0]hex-6-yl}methylidene)-4-(methylamino)-1,3-thiazol-2(5H)-one | | | 450.2 |
| 15 | (5Z)-5-({(3-exo)-8-[2,4-bis(trifluoromethyl)benzyl]-8-azabicyclo[3.2.1]oct-3-yl}methylidene)-4-(methylamino)-1,3-thiazol-2(5H)-one | | | 478.2 |

TABLE 1-4

| | | | | |
|---|---|---|---|---|
| 16 | (5Z)-5-({1-[2,4-bis(trifluoromethyl)benzyl]piperidin-4-yl}methylidene)-4-(prop-2-yn-1-ylamino)-1,3-thiazol-2(5H)-one | | HCl | 476.2 |
| 17 | (5Z)-5-({1-[2,4-bis(trifluoromethyl)benzyl]piperidin-4-yl}methylidene)-4-[(2-hydroxy-2-methylpropyl)amino]-1,3-thiazol-2(5H)-one | | fumarate | 510.2 |
| 18 | (5Z)-5-({1-[2,4-bis(trifluoromethyl)benzyl]piperidin-4-yl}methylidene)-4-[(2-ethoxyethyl)amino]-1,3-thiazol-2(5H)-one | | | 510.2 |

TABLE 1-4-continued

| | | | |
|---|---|---|---|
| 19 | (5Z)-5-({1-[2,4-bis(trifluoromethyl)benzyl]piperidin-4-yl}methylidene)-4-(prop-2-en-1-ylamino)-1,3-thiazol-2(5H)-one | 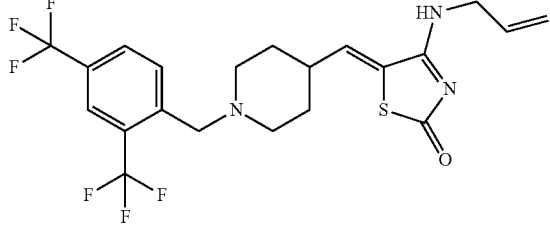 | 478.2 |
| 20 | (5Z)-5-({1-[2,4-bis(trifluoromethyl)benzyl]piperidin-4-yl}methylidene)-4-(oxetan-3-ylamino)-1,3-thiazol-2(5H)-one | 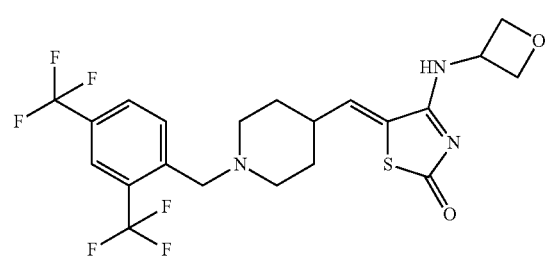 [SMILES: O=C1N=C(NC2COC2)/C(=C/C2CCN(Cc3ccc(C(F)(F)F)cc3C(F)(F)F)CC2)S1] | 494.2 |

TABLE 1-5

| | | | |
|---|---|---|---|
| 21 | (5Z)-5-({1-[2,4-bis(trifluoromethyl)benzyl]piperidin-4-yl}methylidene)-4-[(cyclopropylmethyl)amino]-1,3-thiazol-2(5H)-one | 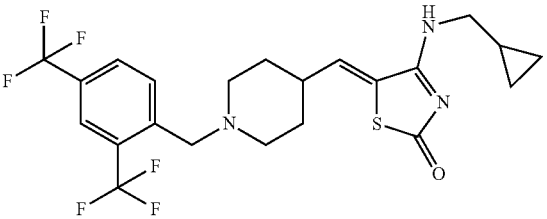 [SMILES: O=C1N=C(NCC2CC2)/C(=C/C2CCN(Cc3ccc(C(F)(F)F)cc3C(F)(F)F)CC2)S1] | 492.2 |
| 22 | (5Z)-5-{[1-(cyclohexylmethyl)piperidin-4-yl]methylidene}-4-(prop-2-yn-1-ylamino)-1,3-thiazol-2(5H)-one | 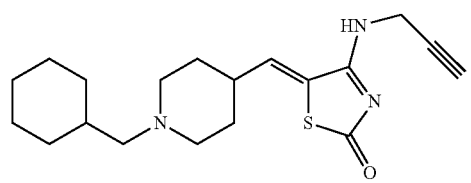 [SMILES: C#CCNC1=NC(=O)S/C1=C\C1CCN(CC2CCCCC2)CC1] | 346.2 |
| 23 | (5Z)-5-[(1-benzylpiperidin-4-yl)methylidene]-4-(prop-2-yn-1-ylamino)-1,3-thiazol-2(5H)-one | 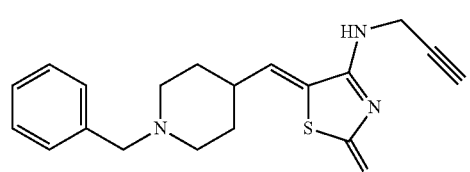 | fumarate 340.2 |
| 24 | (5Z)-5-({1-[4-chloro-2-(trifluoromethyl)benzyl]piperidin-4-yl}methylidene)-4-(prop-2-yn-1-ylamino)-1,3-thiazol-2(5H)-one | 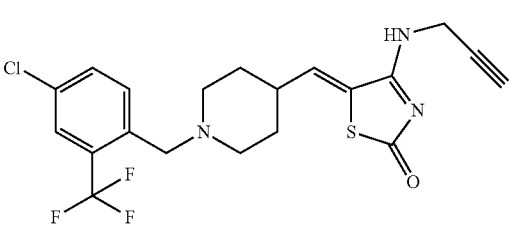 [SMILES: C#CCNC1=NC(=O)S/C1=C\C1CCN(Cc2ccc(Cl)cc2C(F)(F)F)CC1] | fumarate 442.1 |
| 25 | (5Z)-5-({1-[4-bromo-2-(trifluoromethyl)benzyl]piperidin-4-yl}methylidene)-4-(prop-2-yn-1-ylamino)-1,3-thiazol-2(5H)-one | 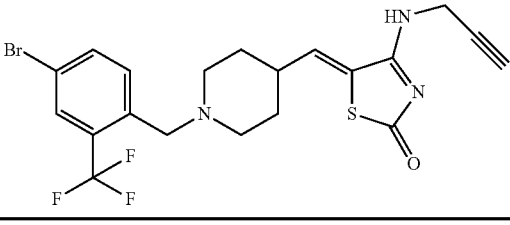 | 486.1 |

TABLE 1-6

| 26 | (5Z)-4-(prop-2-yn-1-ylamino)-5-({1-[2-(trifluoromethoxy)benzyl]piperidin-4-yl}methylidene)-1,3-thiazol-2(5H)-one | 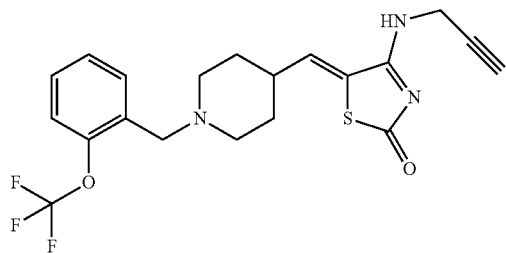 [SMILES: C#CCNC1=NC(=O)S/C1=C\C1CCN(Cc2ccccc2OC(F)(F)F)CC1] | 424.2 |
| --- | --- | --- | --- |
| 27 | (5Z)-5-{[1-(naphthalen-1-ylmethyl)piperidin-4-yl]methylidene}-4-(prop-2-yn-1-ylamino)-1,3-thiazol-2(5H)-one | 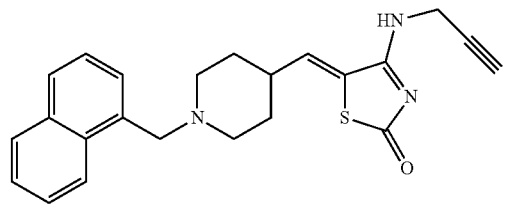 [SMILES: C#CCNC1=NC(=O)S/C1=C\C1CCN(Cc2cccc3ccccc23)CC1] | 390.2 |
| 28 | (5Z)-4-(methylamino)-5-({1-[(3-methyl-1-benzofuran-2-yl)carbonyl]piperidin-4-yl}methylidene)-1,3-thiazol-2(5H)-one | 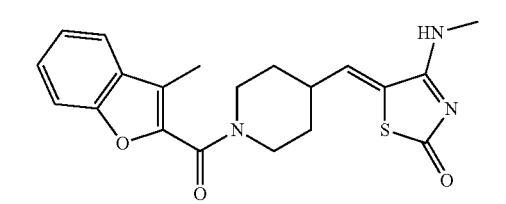 [SMILES: CNC1=NC(=O)S/C1=C\C1CCN(C(=O)c2oc3ccccc3c2C)CC1] | 384.0 |
| 29 | 4-[(4-{(Z)-[2-oxo-4-(prop-2-yn-1-ylamino)-1,3-thiazol-5(2H)-ylidene]methyl}piperidin-1-yl)methyl]benzonitrile | 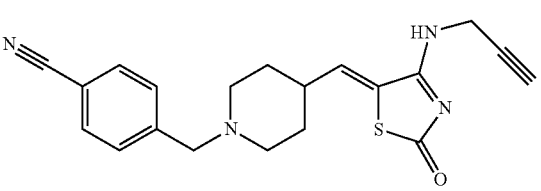 [SMILES: C#CCNC1=NC(=O)S/C1=C\C1CCN(Cc2ccc(C#N)cc2)CC1] | 1/2fumarate 365.1 |
| 30 | (5Z)-5-({3-[2,4-bis(trifluoromethyl)benzyl]-3-azabicyclo[3.3.1]non-7-yl}methylidene)-4-(prop-2-yn-1-ylamino)-1,3-thiazol-2(5H)-one | 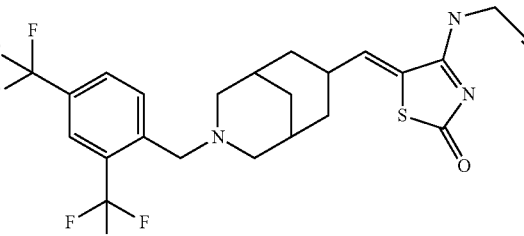 | 516.2 |

TABLE 1-7

| 31 | (5Z)-5-({1-[2,4-bis(trifluoromethyl)benzyl]piperidin-4-yl}methylidene)-4-[(2-hydroxy-2-methylpropyl)amino]-1,3-thiazol-2(5H)-one | 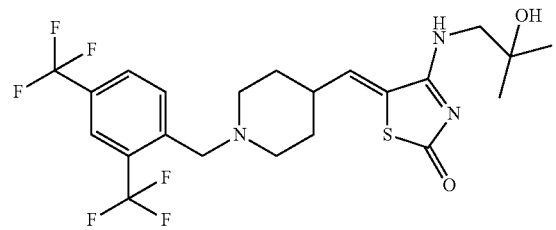 [SMILES: CC(C)(O)CNC1=NC(=O)S/C1=C\C1CCN(Cc2ccc(C(F)(F)F)cc2C(F)(F)F)CC1] | 510.2 |
| --- | --- | --- | --- |
| 32 | (5Z)-5-[(1-benzylpiperidin-4-yl)methylidene]-4-(prop-2-yn-1-ylamino)-1,3-thiazol-2(5H)-one | 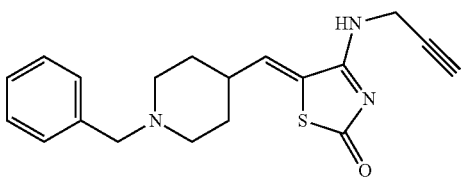 [SMILES: C#CCNC1=NC(=O)S/C1=C\C1CCN(Cc2ccccc2)CC1] | 340.2 |

TABLE 1-7-continued

| | | | |
|---|---|---|---|
| 33 | (5Z)-5-({1-[4-chloro-2-(trifluoromethyl)benzyl]piperidin-4-yl}methylidene)-4-(prop-2-yn-1-ylamino)-1,3-thiazol-2(5H)-one | | 442.1 |
| 34 | (5Z)-4-(prop-2-yn-1-ylamino)-5-({1-[4-(trifluoromethyl)benzyl]piperidin-4-yl}methylidene)-1,3-thiazol-2(5H)-one | | fumarate 408.1 |
| 35 | (5Z)-5-{[1-(2-methoxybenzyl)piperidin-4-yl]methylidene}-4-(prop-2-yn-1-ylamino)-1,3-thiazol-2(5H)-one | | 370.2 |

TABLE 1-8

| | | | |
|---|---|---|---|
| 36 | (5Z)-4-(prop-2-yn-1-ylamino)-5-({1-[3-(trifluoromethyl)benzyl]piperidin-4-yl}methylidene)-1,3-thiazol-2(5H)-one | | 408.1 |
| 37 | (5Z)-5-({1-[2,4-bis(trifluoromethyl)benzyl]piperidin-4-yl}methylidene)-4-(methylamino)-1,3-thiazol-2(5H)-one | | fumarate 452.1 |
| 38 | (5Z)-4-(prop-2-yn-1-ylamino)-5-({1-[4-(trifluoromethyl)benzyl]piperidin-4-yl}methylidene)-1,3-thiazol-2(5H)-one | | 408.1 |
| 39 | (5Z)-5-({1-[2,4-bis(trifluoromethyl)benzyl]piperidin-4-yl}methylidene)-4-{[2-(2-methoxyethoxy)ethyl]amino}-1,3-thiazol-2(5H)-one | | 540.2 |

TABLE 1-8-continued

| 40 | 4-[(4-{(Z)-[2-oxo-4-(prop-2-yn-1-ylamino)-1,3-thiazol-5(2H)-ylidene]methyl}piperidin-1-yl)methyl]-3-(trifluoromethyl)benzonitrile | 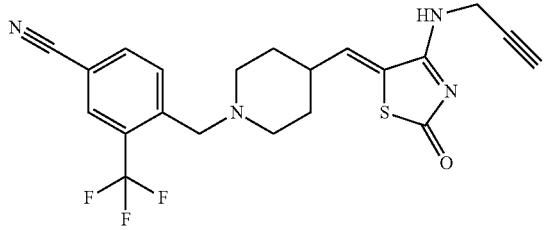 [SMILES: C#CCNC1=NC(=O)S/C1=C\C1CCN(Cc2ccc(C#N)cc2C(F)(F)F)CC1] | | 433.2 |
|---|---|---|---|---|

TABLE 1-9

| 41 | (5Z)-4-(prop-2-yn-1-ylamino)-5-({1-[2-(trifluoromethyl)benzyl]piperidin-4-yl}methylidene)-1,3-thiazol-2(5H)-one | 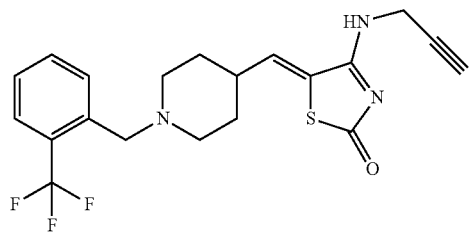 [SMILES: C#CCNC1=NC(=O)S/C1=C\C1CCN(Cc2ccccc2C(F)(F)F)CC1] | | 408.2 |
|---|---|---|---|---|
| 42 | (5Z)-5-({1-[2,4-bis(trifluoromethyl)benzyl]piperidin-4-yl}methylidene)-4-(tetrahydrofuran-3-ylamino)-1,3-thiazol-2(5H)-one | 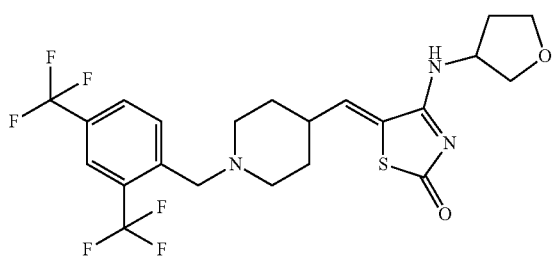 [SMILES: O=C1N=C(NC2CCOC2)/C(=C/C2CCN(Cc3ccc(C(F)(F)F)cc3C(F)(F)F)CC2)S1] | | 508.2 |
| 43 | (5Z)-5-({1-[2,4-bis(trifluoromethyl)benzyl]piperidin-4-yl}methylidene)-4-(tetrahydrofuran-3-ylamino)-1,3-thiazol-2(5H)-one | 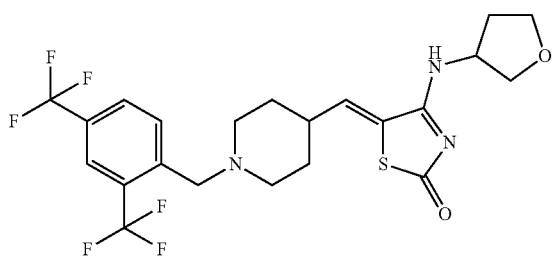 [SMILES: O=C1N=C(NC2CCOC2)/C(=C/C2CCN(Cc3ccc(C(F)(F)F)cc3C(F)(F)F)CC2)S1] | 1/2fumarate | 508.2 |
| 44 | (5Z)-5-({1-[2,4-bis(trifluoromethyl)benzyl]piperidin-4-yl}methylidene)-4-(oxetan-3-ylamino)-1,3-thiazol-2(5H)-one | 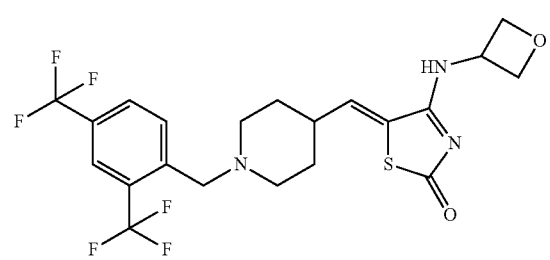 [SMILES: O=C1N=C(NC2COC2)/C(=C/C2CCN(Cc3ccc(C(F)(F)F)cc3C(F)(F)F)CC2)S1] | fumarate | 494.2 |
| 45 | (5Z)-5-({1-[2-chloro-4-(trifluoromethyl)benzyl]piperidin-4-yl}methylidene)-4-(prop-2-yn-1-ylamino)-1,3-thiazol-2(5H)-one | 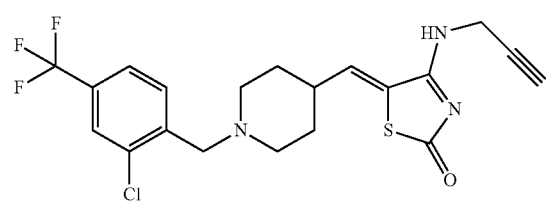 [SMILES: C#CCNC1=NC(=O)S/C1=C\C1CCN(Cc2ccc(C(F)(F)F)cc2Cl)CC1] | | 442.1 |

TABLE 1-10

| | | | |
|---|---|---|---|
| 46 | (5Z)-5-({1-[2,4-bis(trifluoromethyl)benzyl]piperidin-4-yl}methylidene)-4-({2-[2-(diethylamino)ethoxy]ethyl}amino)-1,3-thiazol-2(5H)-one | | 581.3 |
| 47 | (5Z)-5-({1-[2,4-bis(trifluoromethyl)benzyl]piperidin-4-yl}methylidene)-4-({2-[2-(diethylamino)ethoxy]ethyl}amino)-1,3-thiazol-2(5H)-one | | 2TsOH 581.3 |
| 48 | (5Z)-5-{[1-(4-chlorobenzyl)piperidin-4-yl]methylidene}-4-(prop-2-yn-1-ylamino)-1,3-thiazol-2(5H)-one | | 374.2 |
| 49 | 4-[(4-{(Z)-[2-oxo-4-(prop-2-yn-1-ylamino)-1,3-thiazol-5(2H)-ylidene]methyl}piperidin-1-yl)methyl]benzonitrile | | 365.2 |
| 50 | (5Z)-5-{[1-(naphthalen-2-ylmethyl)piperidin-4-yl]methylidene}-4-(prop-2-yn-1-ylamino)-1,3-thiazol-2(5H)-one | | 390.2 |

TABLE 1-11

| | | | |
|---|---|---|---|
| 51 | (5Z)-5-({1-[2-chloro-4-(trifluoromethyl)benzyl]piperidin-4-yl}methylidene)-4-[(2-hydroxy-2-methylpropyl)amino]-1,3-thiazol-2(5H)-one | | 476.2 |
| 52 | (5Z)-5-({1-[4-chloro-2-(trifluoromethyl)benzyl]piperidin-4-yl}methylidene)-4-[(2-hydroxy-2-methylpropyl)amino]-1,3-thiazol-2(5H)-one | | 476.2 |

TABLE 1-11-continued

| # | Name | Salt | MS |
|---|---|---|---|
| 53 | 4-({4-[(Z)-{4-[(2-hydroxy-2-methylpropyl)amino]-2-oxo-1,3-thiazol-5(2H)-ylidene}methyl]piperidin-1-yl}methyl)-3-(trifluoromethyl)benzonitrile | | 467.2 |
| 54 | (5Z)-5-({1-[2,4-bis(trifluoromethyl)benzyl]piperidin-4-yl}methylidene)-4-{[4-(diethylamino)but-2-yn-1-yl]amino}-1,3-thiazol-2(5H)-one | | 561.3 |
| 55 | (5Z)-5-({1-[2,4-bis(trifluoromethyl)benzyl]piperidin-4-yl}methylidene)-4-{[4-(diethylamino)but-2-yn-1-yl]amino}-1,3-thiazol-2(5H)-one | TsOH | 561.3 |

TABLE 1-12

| # | Name | Salt | MS |
|---|---|---|---|
| 56 | (5Z)-5-({1-[2,4-bis(trifluoromethyl)benzyl]piperidin-4-yl}methylidene)-4-[(2,3-dihydroxypropyl)amino]-1,3-thiazol-2(5H)-one | | 512.2 |
| 57 | (5Z)-5-({1-[2,4-bis(trifluoromethyl)benzyl]piperidin-4-yl}methylidene)-4-({2-[(2-hydroxyethyl)(methyl)amino]ethyl}amino)-1,3-thiazol-2(5H)-one | | 539.3 |
| 58 | (5Z)-5-({1-[2,4-bis(trifluoromethyl)benzyl]piperidin-4-yl}methylidene)-4-({2-[(2-hydroxyethyl)(methyl)amino]ethyl}amino)-1,3-thiazol-2(5H)-one | 1/2fumarate | 539.2 |

TABLE 1-12-continued

| | | | | |
|---|---|---|---|---|
| 59 | (5Z)-5-({1-[2-chloro-4-(trifluoromethyl)benzyl]piperidin-4-yl}methylidene)-4-(prop-2-yn-1-ylamino)-1,3-thiazol-2(5H)-one | | fumarate | 442.1 |
| 60 | (5Z)-5-[(1-{1-[2,4-bis(trifluoromethyl)phenyl]ethyl}piperidin-4-yl)methylidene]-4-(prop-2-yn-1-ylamino)-1,3-thiazol-2(5H)-one | | | 490.2 |

TABLE 1-13

| | | | | |
|---|---|---|---|---|
| 61 | (5Z)-5-({1-[2,4-bis(trifluoromethyl)benzyl]piperidin-4-yl}methylidene)-4-[(cyclopropylmethyl)amino]-1,3-thiazol-2(5H)-one | | fumarate | 492.2 |
| 62 | (5Z)-5-({1-[2,4-bis(trifluoromethyl)benzyl]azepan-4-yl}methylidene)-4-(prop-2-yn-1-ylamino)-1,3-thiazol-2(5H)-one | | | 490.2 |
| 63 | 4-[(4-{(Z)-[2-oxo-4-(prop-2-yn-1-ylamino)-1,3-thiazol-5(2H)-ylidene]methyl}piperidin-1-yl)methyl]naphthalene-1-carbonitrile | | | 415.2 |
| 64 | (5Z)-5-({1-[2-fluoro-6-(trifluoromethyl)benzyl]piperidin-4-yl}methylidene)-4-(prop-2-yn-1-ylamino)-1,3-thiazol-2(5H)-one | | | 426.1 |

TABLE 1-13-continued

| | | | |
|---|---|---|---|
| 65 | (5Z)-5-{[1-(2-tert-buty[benzyl)piperidin-4-yl]methylidene}-4-(prop-2-yn-1-ylamino)-1,3-thiazol-2(5H)-one | | 396.2 |

TABLE 1-14

| | | | |
|---|---|---|---|
| 66 | (5Z)-5-({1-[3,5-bis(trifluoromethyl)benzyl]piperidin-4-yl}methylidene)-4-(prop-2-yn-1-ylamino)-1,3-thiazol-2(5H)-one | | 476.2 |
| 67 | (5Z)-5-[(1-{[2,4-bis(trifluoromethyl)phenyl]acetyl}piperidin-4-yl)methylidene]-4-(prop-2-yn-1-ylamino)-1,3-thiazol-2(5H)-one | | 504.1 |
| 68 | (5Z)-5-({1-[2,4-bis(trifluoromethyl)benzyl]pyrrolidin-3-yl}methylidene)-4-(prop-2-yn-1-ylamino)-1,3-thiazol-2(5H)-one | | 462.1 |
| 69 | (5Z)-5-({1-[2,4-bis(trifluoromethyl)benzyl]pyrrolidin-3-yl}methylidene)-4-(prop-2-yn-1-ylamino)-1,3-thiazol-2(5H)-one | | maleate 462.1 |
| 70 | (5Z)-5-({1-[2,4-bis(trifluoromethyl)benzyl]piperidin-4-yl}methylidene)-4-{[(2Z)-4-(diethylamino)but-2-en-1-yl]amino}-1,3-thiazol-2(5H)-one | | 563.3 |

TABLE 1-15

| # | Name | | |
|---|---|---|---|
| 71 | (5Z)-5-({1-[2,4-bis(trifluoromethyl)benzyl]piperidin-4-yl}methylidene)-4-{[(2Z)-4-(diethylamino)but-2-en-1-yl]amino}-1,3-thiazol-2(5H)-one | TsOH | 563.3 |
| 72 | (5Z)-4-amino-5-({1-[2,4-bis(trifluoromethyl)benzyl]piperidin-4-yl}methylidene)-1-methyl-1,5-dihydro-2H-imidazol-2-one | | 435.2 |
| 73 | (5Z)-5-({1-[2,4-bis(trifluoromethyl)benzyl]piperidin-4-yl}methylidene)-1-methyl-4-(prop-2-yn-1-ylamino)-1,5-dihydro-2H-imidazol-2-one | | 473.2 |
| 74 | (5E)-4-amino-5-({1-[2,4-bis(trifluoromethyl)benzyl]piperidin-4-yl}methylidene)-1-methyl-1,5-dihydro-2H-imidazol-2-one | | 435.2 |
| 75 | (5E)-5-({1-[2,4-bis(trifluoromethyl)benzyl]piperidin-4-yl}methylidene)-1-methyl-4-(prop-2-yn-1-ylamino)-1,5-dihydro-2H-imidazol-2-one | | 473.2 |

TABLE 1-16

| 76 | (5Z)-5-({1-[2,4-bis(trifluoromethyl)benzyl]azepan-4-yl}methylidene)-4-[(2-hydroxy-2-methylpropyl)amino]-1,3-thiazol-2(5H)-one | | 524.2 |
|---|---|---|---|
| 77 | (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)one | | 524.2 |
| 78 | (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one | | fumarate 524.2 |
| 79 | (5E)-5-({1-[2,4-bis(trifluoromethyl)benzyl]piperidin-4-yl}methylidene)-1-methyl-4-(methylamino)-1,5-dihydro-2H-imidazol-2-one | | 435.2 |
| 80 | (5Z)-5-({1-[2,4-bis(trifluoromethyl)benzyl]piperidin-4-yl}methylidene)-1-methyl-4-(methylamino)-1,5-dihydro-2H-imidazol-2-one | | 435.2 |

TABLE 1-17

| 81 | (5Z)-5-({1-[2,4-bis(trifluoromethyl)benzyl]piperidin-4-yl}methylidene)-4-(cyclopentylamino)-1-methyl-1,5-dihydro-2H-imidazol-2-one | | 503.2 |
|---|---|---|---|
| 82 | (5Z)-5-({1-[2,4-bis(trifluoromethyl)phenyl]piperidin-4-yl}methylidene)-4-(prop-2-yn-1-ylamino)-1,3-thiazol-2(5H)-one | | 462.1 |
| 83 | (5Z)-5-({1-[2,4-bis(trifluoromethyl)benzyl]piperidin-4-yl}methylidene)-4-[(3-cyclopropylprop-2-yn-1-yl)amino]-1,3-thiazol-2(5H)-one | | 516.2 |
| 84 | (5Z)-5-({1-[2,4-bis(trifluoromethyl)benzyl]piperidin-4-yl}methylidene)-4-[(3-cyclopropylprop-2-yn-1-yl)amino]-1,3-thiazol-2(5H)-one | maleate | 516.2 |
| 85 | (5Z)-5-({(1R,5S,6s)-3-[2,4-bis(trifluoromethyl)benzyl]-3-azabicyclo[3.1.0]hex-6-yl}methylidene)-4-(prop-2-yn-1-ylamino)-1,3-thiazol-2(5H)-one | | 474.1 |

TABLE 1-18

| | | | | |
|---|---|---|---|---|
| 86 | (5Z)-5-({(1R,5S,6s)-3-[2,4-bis(trifluoromethyl)benzyl]-3-azabicyclo[3.1.0]hex-6-yl}methylidene)-4-(prop-2-yn-1-ylamino)-1,3-thiazol-2(5H)-one | | maleate | 474.1 |
| 87 | (5Z)-5-({1-[2,4-bis(trifluoromethyl)benzyl]piperidin-4-yl}methylidene)-4-[(4-hydroxy-4-methylpent-2-yn-1-yl)amino]-1,3-thiazol-2(5H)-one | | | 534.2 |
| 88 | 4-(4-{(Z)-[2-oxo-4-(prop-2-yn-1-ylamino)-1,3-thiazol-5(2H)-ylidene]methyl}piperidin-1-yl)-3-(trifluoromethyl)benzonitrile | | | 419.1 |
| 89 | (5Z)-5-({1-[2,4-bis(trifluoromethyl)benzyl]piperidin-4-yl}methylidene)-4-(but-3-yn-1-ylamino)-1,3-thiazol-2(5H)-one | | | 490.1 |
| 90 | 1-[2,4-bis(trifluoromethyl)benzyl]-4-{(Z)-[2-oxo-4-(prop-2-yn-1-ylamino)-1,3-thiazol-5(2H)-ylidene]methyl}piperidin-2-one | | | 490.1 |

TABLE 1-19

| 91 | (5Z)-5-({1-[2,5-bis(trifluoromethyl)benzyl]piperidin-4-yl}methylidene)-4-(prop-2-yn-1-ylamino)-1,3-thiazol-2(5H)-one | 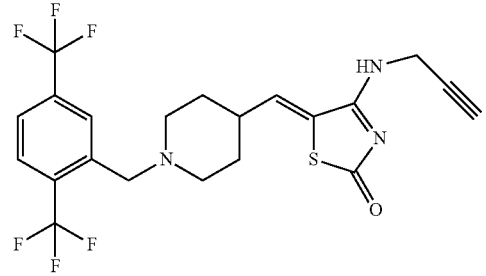 [SMILES: C#CCNC1=NC(=O)S/C1=C\C1CCN(Cc2cc(C(F)(F)F)ccc2C(F)(F)F)CC1] | 476.0 |
| 92 | N-[(5Z)-5-({1-[2,4-bis(trifluoromethyl)benzyl]piperidin-4-yl}methylidene)-2-oxo-2,5-dihydro-1,3-thiazol-4-yl]glycine | 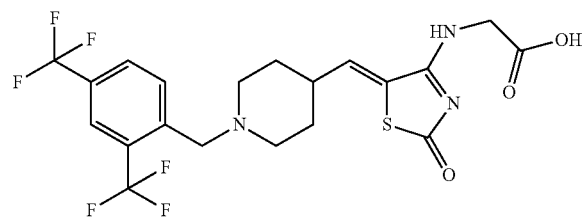 [SMILES: O=C(O)CNC1=NC(=O)S/C1=C\C1CCN(Cc2ccc(C(F)(F)F)cc2C(F)(F)F)CC1] | 496.1 |
| 93 | tert-butyl N-[(5Z)-5-({1-[2,4-bis(trifluoromethyl)benzyl]piperidin-4-yl}methylidene)-2-oxo-2,5-dihydro-1,3-thiazol-4-yl]glycinate | 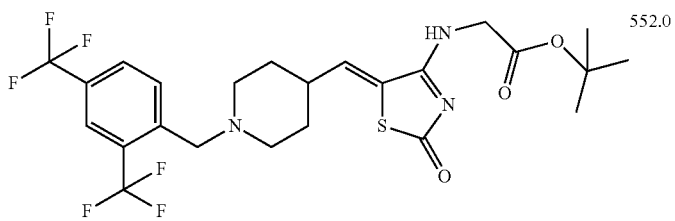 | 552.0 |
| 94 | (5Z)-4-(prop-2-yn-1-ylamino)-5-({1-[4-(trifluoromethoxy)benzyl]piperidin-4-yl}methylidene)-1,3-thiazol-2(5H)-one | 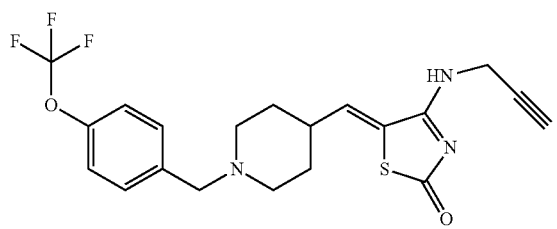 [SMILES: C#CCNC1=NC(=O)S/C1=C\C1CCN(Cc2ccc(OC(F)(F)F)cc2)CC1] | 423.9 |
| 95 | $N^2$-[(5Z)-5-({1-[2,4-bis(trifluoromethyl)benzyl]piperidin-4-yl}methylidene)-2-oxo-2,5-dihydro-1,3-thiazol-4-yl]glycinamide | 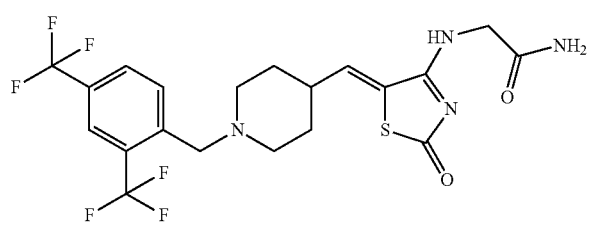 [SMILES: NC(=O)CNC1=NC(=O)S/C1=C\C1CCN(Cc2ccc(C(F)(F)F)cc2C(F)(F)F)CC1] | 495.2 |

TABLE 1-20

| 96 | 4-[(4-{(Z)-[2-oxo-4-(prop-2-yn-1-ylamino)-1,3-thiazol-5(2H)-ylidene]methyl}piperidin-1-yl)methyl]-2-(trifluoromethyl)benzonitrile | 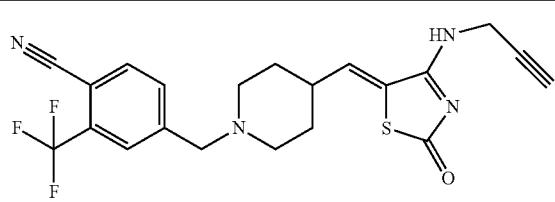 | 433.1 |

TABLE 1-20-continued

| # | Name | Structure | MS |
|---|---|---|---|
| 97 | (5Z)-5-({1-[2,4-bis(trifluoromethyl)benzyl]piperidin-4-yl}methylidene)-4-[(isoxazol-3-ylmethyl)amino]-1,3-thiazol-2(5H)-one | | 519.0 |
| 98 | (5Z)-5-({1-[2,4-bis(trifluoromethyl)benzyl]piperidin-4-yl}methylidene)-4-{[3-(2-oxopyrrolidin-1-yl)propyl]amino}-1,3-thiazol-2(5H)-one | | 563.0 |
| 99 | (5Z)-5-{{1-[2-(pentafluorosulfanyl)benzyl]piperidin-4-yl}methylidene}-4-(prop-2-yn-1-ylamino)-1,3-thiazol-2(5H)-one | | maleate no data |
| 100 | (5Z)-5-({1-[4-methoxy-2-(trifluoromethyl)benzyl]piperidin-4-yl}methylidene)-4-(prop-2-yn-1-ylamino)-1,3-thiazol-2(5H)-one | | maleate no data |

TABLE 1-21

| # | Name | Structure | MS |
|---|---|---|---|
| 101 | (5Z)-5-({1-[2,4-bis(trifluoromethyl)benzyl]piperidin-4-yl}methylidene)-4-({[4-(hydroxymethyl)tetrahydro-2H-pyran-4-yl]methyl}amino)-1,3-thiazol-2(5H)-one | 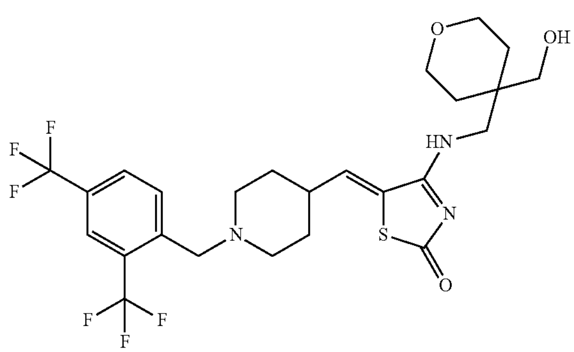 [SMILES: O=C1N=C(NCC2(CO)CCOCC2)/C(=C/C2CCN(Cc3ccc(C(F)(F)F)cc3C(F)(F)F)CC2)S1] | 566.1 |

TABLE 1-21-continued

| | | | |
|---|---|---|---|
| 102 | (5Z)-5-({(3aR,5r,6aS)-2-[2,4-bis(trifluoromethyl)benzyl]octahydrocyclopenta[c]pyrrol-5-yl}methylidene)-4-(prop-2-yn-1-ylamino)-1,3-thiazol-2(5H)-one | 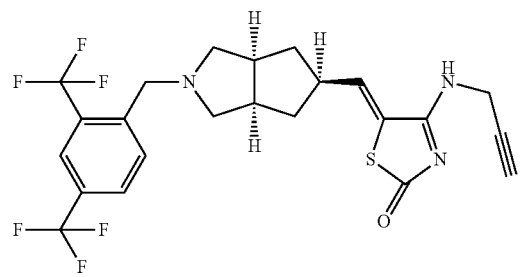 [SMILES: C#CCNC1=NC(=O)S/C1=C\[C@@H]1C[C@@H]2CN(Cc3ccc(C(F)(F)F)cc3C(F)(F)F)C[C@@H]2C1] | 502.0 |
| 103 | (5Z)-5-({(3aR,5s,6aS)-2-[2,4-bis(trifluoromethyl)benzyl]octahydrocyclopenta[c]pyrrol-5-yl}methylidene)-4-(prop-2-yn-1-ylamino)-1,3-thiazol-2(5H)-one | 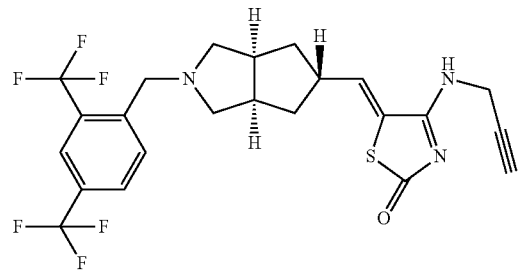 [SMILES: C#CCNC1=NC(=O)S/C1=C\[C@H]1C[C@@H]2CN(Cc3ccc(C(F)(F)F)cc3C(F)(F)F)C[C@@H]2C1] | maleate 502.0 |
| 104 | ethyl N-[(5Z)-5-({1-{2,4-bis(trifluoromethyl)benzyl]piperidin-4-yl}methylidene)-2-oxo-2,5-dihydro-1,3-thiazol-4-yl]glycinate | 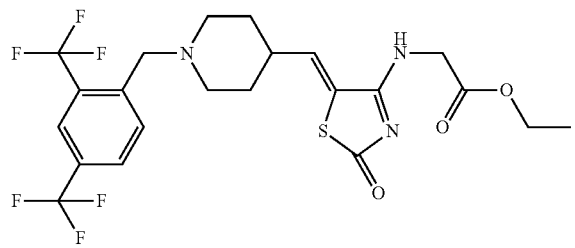 [SMILES: CCOC(=O)CNC1=NC(=O)S/C1=C\C1CCN(Cc2ccc(C(F)(F)F)cc2C(F)(F)F)CC1] | 524.0 |
| 105 | (5Z)-5-({1-[2,4-bis(trifluoromethyl)benzyl]piperidin-4-yl}methylidene)-4-[(trans-2-hydroxycyclohexyl)amino]-1,3-thiazol-2(5H)-one | 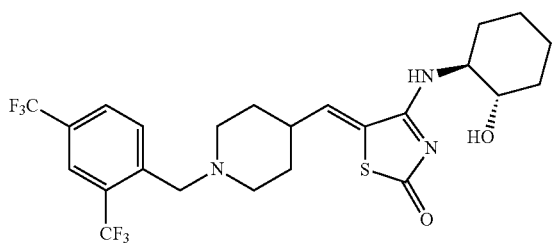 [SMILES: O=C1N=C(N[C@H]2CCCC[C@@H]2O)/C(=C/C2CCN(Cc3ccc(C(F)(F)F)cc3C(F)(F)F)CC2)S1] | 536.1 |

TABLE 1-22

| | | | |
|---|---|---|---|
| 106 | 1-[2,4-bis(trifluoromethyl)benzyl]-5-{(Z)-[2-oxo-4-(prop-2-yn-1-ylamino)-1,3-thiazol-5(2H)-ylidene]methyl}azepan-2-one | 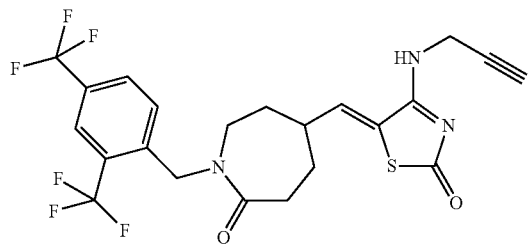 [SMILES: C#CCNC1=NC(=O)S/C1=C\C1CCC(=O)N(Cc2ccc(C(F)(F)F)cc2C(F)(F)F)CC1] | 504.2 |
| 107 | N²-[(5Z)-5-({1-[2,4-bis(trifluoromethyl)benzyl]piperidin-4-yl}methylidene)-2-oxo-2,5-dihydro-1,3-thiazol-4-yl]-N-methylglycinamide | 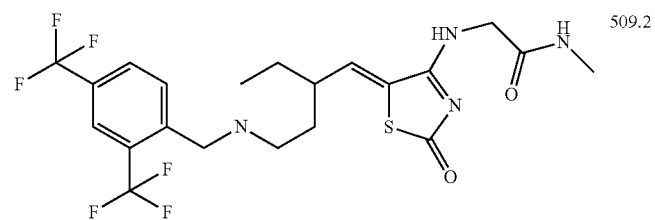 | 509.2 |

TABLE 1-22-continued

| 108 | N²-[(5Z)-5-({[2,4-bis(trifluoromethyl)benzyl]piperidin-4-yl}methylidene)-2-oxo-2,5-dihydro-1,3-thiazol-4-yl]-N,N-dimethylglycinamide | | 523.1 |
|---|---|---|---|
| 109 | N²-[(5Z)-5-({1-[2,4-bis(trifluoromethyl)benzyl]piperidin-4-yl}methylidene)-2-oxo-2,5-dihydro-1,3-thiazol-4-yl]-L-serinamide | | 525.2 |
| 110 | (5Z)-5-({1-[2,4-bis(trifluoromethyl)benzyl]piperidin-4-yl}methylidene)-4-(prop-2-yn-1-ylamino)-1,3-oxazol-2(5H)-one | | 460.2 |

TABLE 1-23

| 111 | (5Z)-5-({{(3aR,5r,6aS)-2-[2,4-bis(trifluoromethyl)phenyl]octahydrocyclopenta[c]pyrrol-5-yl}methylidene)-4-(prop-2-yn-1-ylamino)-1,3-thiazol-2(5H)-one | | 488.1 |
|---|---|---|---|
| 112 | (5Z)-5-({{(3aR,5s,6aS)-2-[2,4-bis(trifluoromethyl)phenyl]octahydrocyclopenta[c]pyrrol-5-yl}methylidene)-4-(prop-2-yn-1-ylamino)-1,3-thiazol-2(5H)-one | | 488.2 |
| 113 | (5Z)-5-({1-[(3-methyl-1-benzofuran-2-yl)carbonyl]piperidin-4-yl}methylidene)-4-(prop-2-yn-1-ylamino)-1,3-thiazol-2(5H)-one | | 408.4 |

TABLE 1-23-continued

| 114 | (5Z)-5-({1-[2,4-bis(trifluoromethyl)benzyl]piperidin-4-yl}methylidene)-4-{[(1R)-1-(hydroxymethyl)prop-2-yn-1-yl]amino}-1,3-thiazol-2(5H)-one | 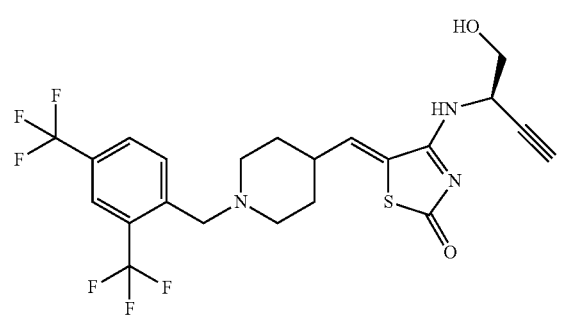 [SMILES: C#C[C@H](CO)NC1=NC(=O)S/C1=C\C1CCN(Cc2ccc(C(F)(F)F)cc2C(F)(F)F)CC1] | 506.0 |
|---|---|---|---|
| 115 | N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide | 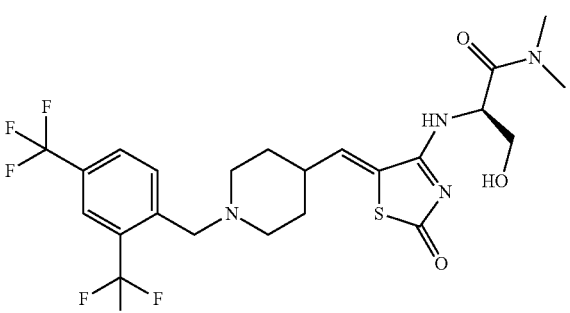 | no data |

TABLE 1-24

| 116 | (5Z)-5-({1-[2,4-bis(trifluoromethyl)benzyl]piperidin-4-yl}methylidene)-4-[(cis-2-hydroxycyclohexyl)amino]-1,3-thiazol-2(5H)-one | 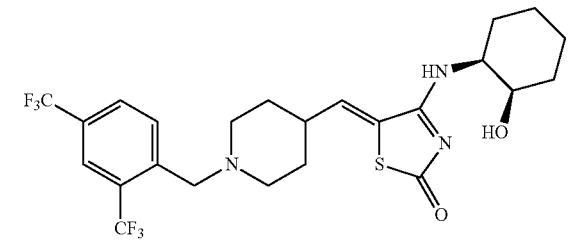 [SMILES: O=C1N=C(N[C@H]2CCCC[C@H]2O)/C(=C/C2CCN(Cc3ccc(C(F)(F)F)cc3C(F)(F)F)CC2)S1] | 536.1 |
|---|---|---|---|
| 117 | (5Z)-5-({1-[2,4-bis(trifluoromethyl)benzyl]piperidin-4-yl}methylidene)-4-[trans-(4-hydroxytetrahydrofuran-3-yl)amino]-1,3-thiazol-2(5H)-one | 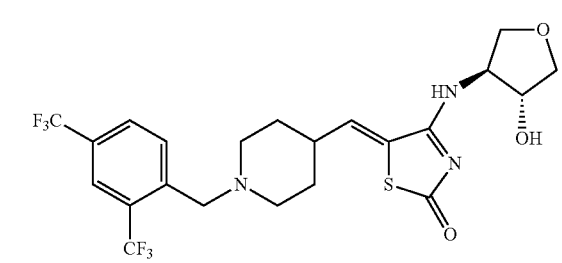 [SMILES: O=C1N=C(N[C@H]2COC[C@@H]2O)/C(=C/C2CCN(Cc3ccc(C(F)(F)F)cc3C(F)(F)F)CC2)S1] | 524.1 |
| 118 | N²-[(5Z)-5-({1-[2,4-bis(trifluoromethyl)benzyl]piperidin-4-yl}methylidene)-2-oxo-2,5-dihydro-1,3-thiazol-4-yl]-N,N-bis(2-methoxyethyl)glycinamide | 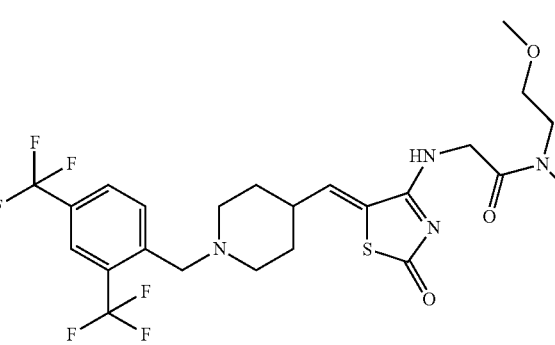 | 611.1 |

TABLE 1-24-continued

| 119 | (5Z)-5-({1-[4-hydroxy-2-(trifluoromethyl)benzyl]piperidin-4-yl}methylidene)-4-(prop-2-yn-1-ylamino)-1,3-thiazol-2(5H)-one | 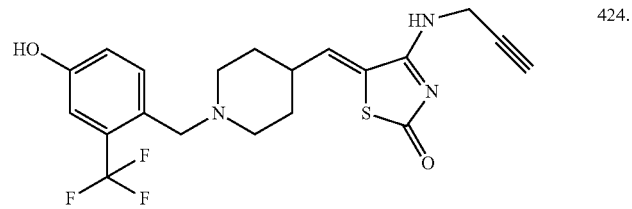 | 424.1 |
|---|---|---|---|
| 120 | N²-[(5Z)-5-({1-[2,4-bis(trifluoromethyl)benzyl]piperidin-4-yl}methylidene)-2-oxo-2,5-dihydro-1,3-thiazol-4-yl]-N-cyclopropylglycinamide | 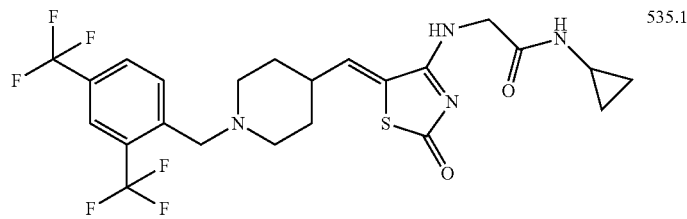 | 535.1 |

TABLE 1-25

| 121 | (5Z)-5-({1-[2,4-bis(trifluoromethyl)benzyl]piperidin-4-yl}methylidene)-4-[(2-oxo-2-pyrrolidin-1-ylethyl)amino]-1,3-thiazol-2(5H)-one | 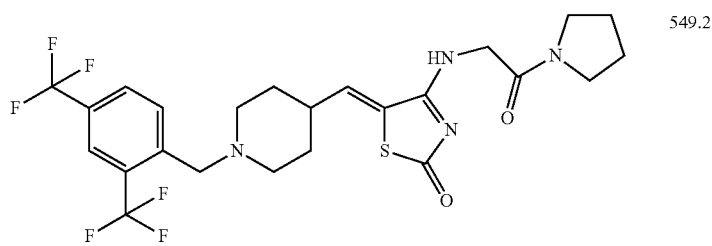 | 549.2 |
|---|---|---|---|
| 122 | (5Z)-5-({1-[2,4-bis(trifluoromethyl)benzyl]piperidin-4-yl}methylidene)-4-[(2-morpholin-4-yl-2-oxoethyl)amino]-1,3-thiazol-2(5H)-one | 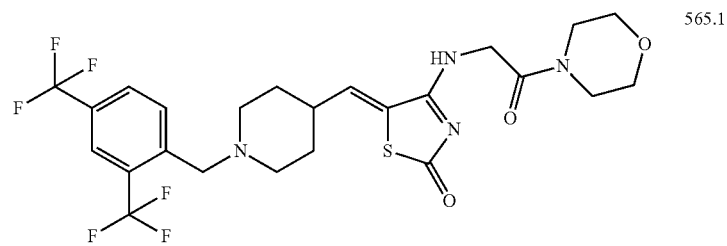 | 565.1 |
| 123 | (5Z)-5-({1-[2,4-bis(trifluoromethyl)benzyl]piperidin-4-yl}methylidene)-4-{[2-(4-methylpiperazin-1-yl)-2-oxoethyl]amino}-1,3-thiazol-2(5H)-one | 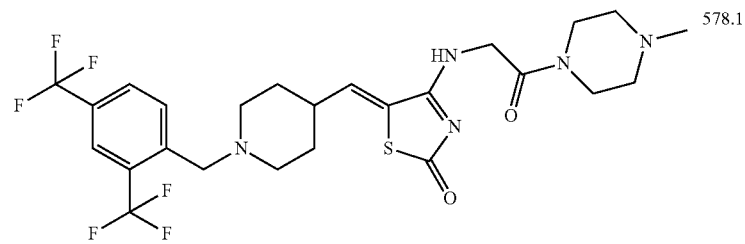 | 578.1 |
| 124 | (5Z)-5-({1-[2,4-bis(trifluoromethyl)benzyl]piperidin-4-yl}methylidene)-4-({[1-(hydroxymethyl)cyclobutyl]methyl}amino)-1,3-thiazol-2(5H)-one | 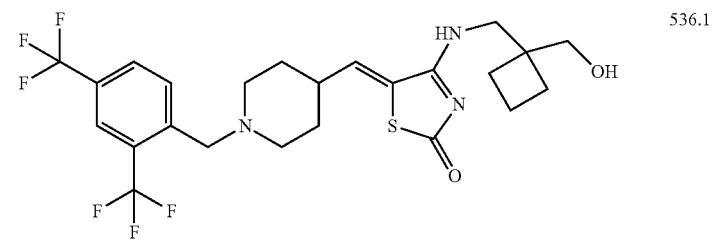 | 536.1 |

TABLE 1-25-continued

| 125 | (+)-(5Z)-5-({1-[2,4-bis(trifluoromethyl)benzyl]piperidin-4-yl}methylidene)-4-{[(1S,2S)-2-hydroxycyclohexyl]amino}-1,3-thiazol-2(5H)-one | 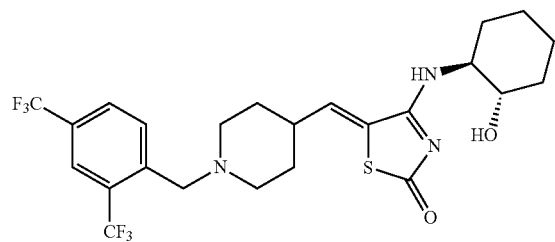 [SMILES: O=C1N=C(N[C@H]2CCCC[C@@H]2O)/C(=C/C2CCN(Cc3ccc(C(F)(F)F)cc3C(F)(F)F)CC2)S1] | 536.1 |
|---|---|---|---|

TABLE 1-26

| 126 | (−)-(5Z)-5-({1-[2,4-bis(trifluoromethyl)benzyl]piperidin-4-yl}methylidene)-4-{[(1R,2R)-2-hydroxycyclohexyl]amino}-1,3-thiazol-2(5H)-one | 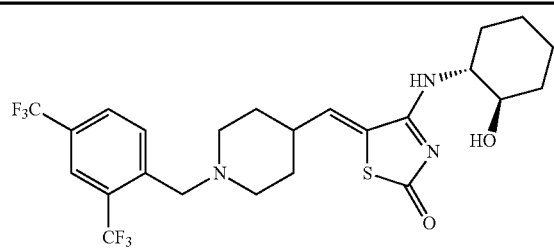 | 536.1 |
|---|---|---|---|
| 127 | $N^2$-[(5Z)-5-({1-[2,4-bis(trifluoromethyl)benzyl]piperidin-4-yl}methylidene)-2-oxo-2,5-dihydro-1,3-thiazol-4-yl]-N-(2-hydroxyethyl)glycinamide | 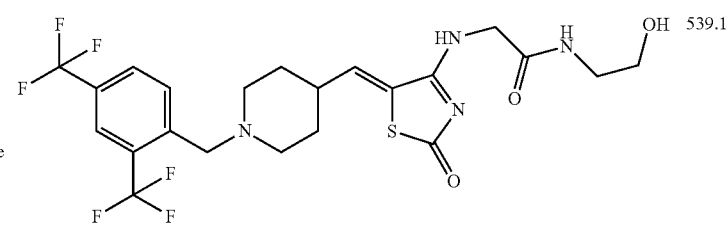 | 539.1 |
| 128 | $N^2$-[(5Z)-5-({1-[2,4-bis(trifluoromethyl)benzyl]piperidin-4-yl}methylidene)-2-oxo-2,5-dihydro-1,3-thiazol-4-yl]-N-(2-methoxyethyl)glycinamide | 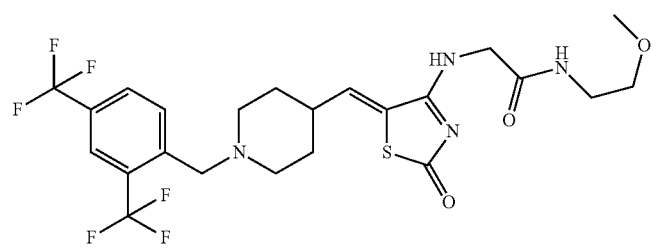 [SMILES: COCCNC(=O)CNC1=NC(=O)S/C1=C\C1CCN(Cc2ccc(C(F)(F)F)cc2C(F)(F)F)CC1] | 553.1 |
| 129 | $N^2$-[(5Z)-5-({1-[2,4-bis(trifluoromethyl)benzyl]piperidin-4-yl}methylidene)-2-oxo-2,5-dihydro-1,3-thiazol-4-yl]-N-(2-hydroxyethyl)-N-methylglycinamide | 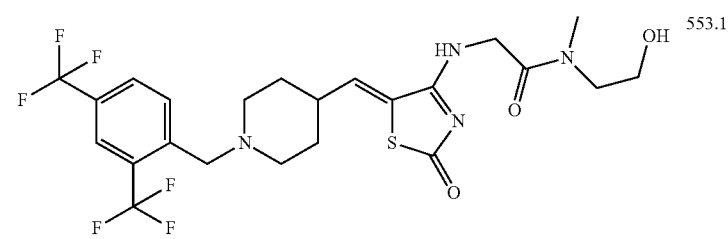 | 553.1 |
| 130 | (5Z)-5-({1-[2,4-bis(trifluoromethyl)benzyl]piperidin-4-yl}methylidene)-4-{[2-(3-hydroxypyrrolidin-1-yl)-2-oxoethyl]amino}-1,3-thiazol-2(5H)-one | 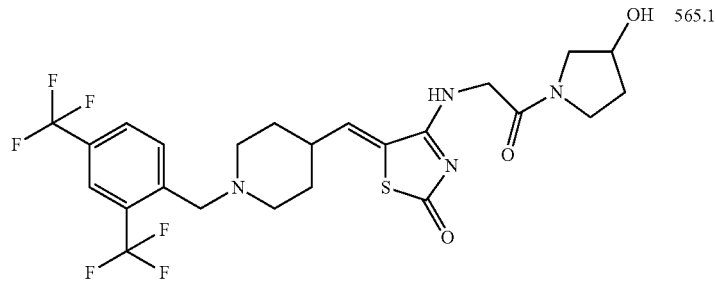 | 565.1 |

TABLE 1-27

| # | Name | Structure | MS |
|---|---|---|---|
| 131 | (5Z)-5-({1-[2,4-bis(trifluoromethyl)benzyl]piperidin-4-yl}methylidene)-4-cyclohexylamino)-1,3-thiazol-2(5H)-one | 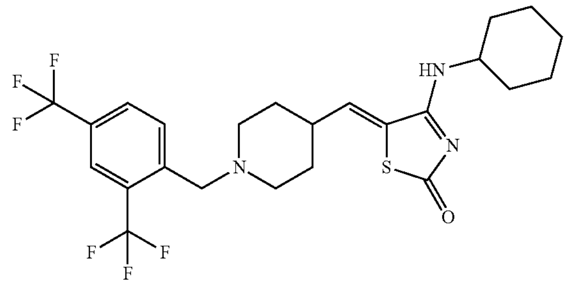 [SMILES: O=C1N=C(NC2CCCCC2)/C(=C/C2CCN(Cc3ccc(C(F)(F)F)cc3C(F)(F)F)CC2)S1] | no data |
| 132 | $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-serinamide | 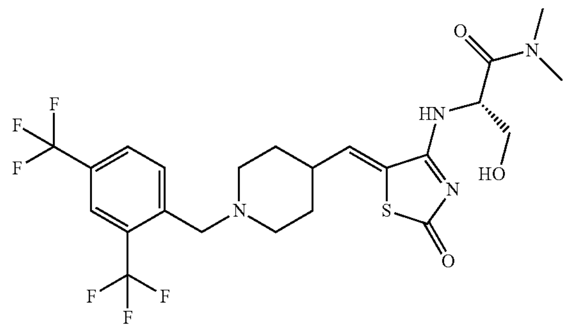 [SMILES: CN(C)C(=O)[C@H](CO)NC1=NC(=O)S/C1=C\C1CCN(Cc2ccc(C(F)(F)F)cc2C(F)(F)F)CC1] | 553.1 |
| 133 | $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-alaninamide | 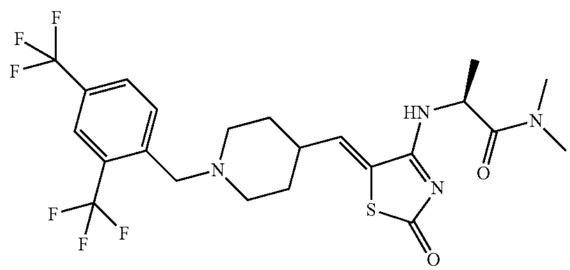 [SMILES: C[C@H](NC1=NC(=O)S/C1=C\C1CCN(Cc2ccc(C(F)(F)F)cc2C(F)(F)F)CC1)C(=O)N(C)C] | 537.2 |
| 134 | $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-phenylalaninamide | 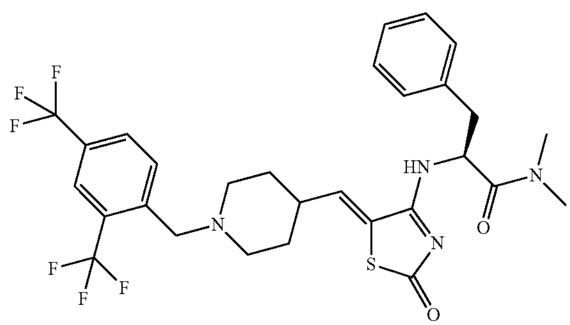 [SMILES: CN(C)C(=O)[C@H](Cc1ccccc1)NC1=NC(=O)S/C1=C\C1CCN(Cc2ccc(C(F)(F)F)cc2C(F)(F)F)CC1] | 613.1 |
| 135 | $N^2$-[(5Z)-5-({1-[2,4-bis(trifluoromethyl)benzyl]piperidin-4-yl}methylidene)-2-oxo-2,5-dihydro-1,3-thiazol-4-yl]-N,N,3-trimethyl-L-valinamide | 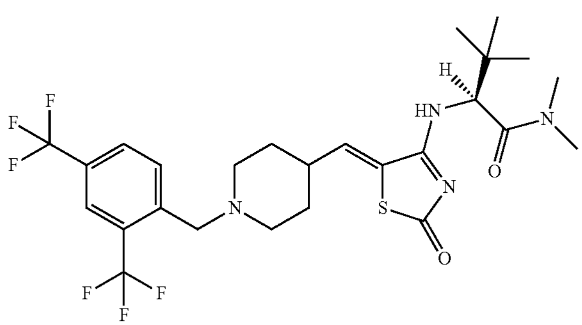 [SMILES: CN(C)C(=O)[C@@H](NC1=NC(=O)S/C1=C\C1CCN(Cc2ccc(C(F)(F)F)cc2C(F)(F)F)CC1)C(C)(C)C] | 579.2 |

TABLE 1-28

| 136 | (5Z)-5-({1-[2,4-bis(trifluoromethyl)benzyl]piperidin-4-yl}methylidene)-4-(prop-2-yn-1-ylamino)-1,3-thiazol-2(5H)-one | | tartarate | 476.2 |
|---|---|---|---|---|
| 137 | (5Z)-5-({1-[2,4-bis(trifluoromethyl)benzyl]piperidin-4-yl}methylidene)-4-(prop-2-yn-1-ylamino)-1,3-thiazol-2(5H)-one | | citrate | 476.2 |
| 138 | (5Z)-5-({1-[2,4-bis(trifluoromethyl)benzyl]piperidin-4-yl}methylidene)-4-(prop-2-yn-1-ylamino)-1,3-thiazol-2(5H)-one | | $H_3PO_4$ | 476.2 |
| 139 | (5Z)-5-[(1-{[2,4-bis(trifluoromethyl)phenyl]carbonyl}piperidin-4-yl)methylidene]-4-(prop-2-yn-1-ylamino)-1,3-thiazol-2(5H)-one | | | 490.1 |
| 140 | $N^3$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-β-alaninamide | | | 537.2 |

TABLE 1-29

| 141 | (2S)-2-{[(5Z)-5-({1-[2,4-bis(trifluoromethyl)benzyl]piperidin-4-yl}methylidene)-2-oxo-2,5-dihydro-1,3-thiazol-4-yl]amino}-N,N-dimethylbutanamide | | | 551.1 |
|---|---|---|---|---|

TABLE 1-29-continued

| | | | |
|---|---|---|---|
| 142 | N²-[(5Z)-5-({1-[2,4-bis(trifluoromethyl)benzyl]piperidin-4-yl}methylidene)-2-oxo-2,5-dihydro-1,3-thiazol-4-yl]-N¹,N¹,N⁴,N⁴-tetramethyl-L-aspartamide | | 608.1 |
| 143 | (8Z)-8-({1-[2,4-bis(trifluoromethyl)benzyl]piperidin-4-yl}methylidene)-4,8-dihydro[1,3]thiazolo[3,4-a]pyrimidin-6-one | | 476.2 |
| 144 | (5Z)-5-({1-[2,4-bis(trifluoromethyl)benzyl]piperidin-4-yl}methylidene)-4-{[(3R)-1-methyl-2-oxopyrrolidin-3-yl]amino}-1,3-thiazol-2(5H)-one | | 535.0 |
| 145 | (5Z)-5-({1-[2,4-bis(trifluoromethyl)benzyl]piperidin-4-yl}methylidene)-4-{[(3R)-2-oxopyrrolidin-3-yl]amino}-1,3-thiazol-2(5H)-one | | 521.0 |

TABLE 1-30

| | | | |
|---|---|---|---|
| 146 | (5Z)-5-({1-[2,4-bis(trifluoromethyl)benzyl]piperidin-4-yl}methylidene)-4-{[2-(methylsulfonyl)ethyl]amino}-1,3-thiazol-2(5H)-one | | 544.0 |

TABLE 1-30-continued

| 147 | (5Z)-5-({1-[(1-methyl-1H-indol-2-yl)carbonyl]piperidin-4-yl}methylidene)-4-(prop-2-yn-1-ylamino)-1,3-thiazol-2(5H)-one | | 407.0 |
| --- | --- | --- | --- |
| 148 | (5Z)-5-({1-[(1-methyl-1H-benzimidazol-2-yl)carbonyl]piperidin-4-yl}methylidene)-4-(prop-2-yn-1-ylamino)-1,3-thiazol-2(5H)-one | | 408.0 |
| 149 | $N^2$-[(5Z)-5-({1-[2,4-bis(trifluoromethyl)benzyl]piperidin-4-yl}methylidene)-2-oxo-2,5-dihydro-1,3-thiazol-4-yl]-N,N,O-trimethyl-L-serinamide | | 567.2 |
| 150 | $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-leucinamide | | 579.1 |

TABLE 1-31

| 151 | $N^2$-[(5Z)-5-({1-[2,4-bis(trifluoromethyl)benzyl]piperidin-4-yl}methylene)-2-oxo-2,5-dihydro-1,3-thiazol-4-yl]-N,N-dimethyl-L-isoleucinamide | | 579.1 |
| --- | --- | --- | --- |

TABLE 1-31-continued

| | | | |
|---|---|---|---|
| 152 | N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-valinamide | | 565.1 |
| 153 | N²-[(5Z)-5-({1-[2,4-bis(trifluoromethyl)benzyl]piperidin-4-yl}methylene)-2-oxo-2,5-dihydro-1,3-thiazol-4-yl]-N,N-dimethyl-L-threoninamide | | 567.2 |
| 154 | N²-[(5Z)-5-({1-[2,4-bis(trifluoromethyl)benzyl]piperidin-4-yl}methylene)-2-oxo-2,5-dihydro-1,3-thiazol-4-yl]-N,N,O-trimethyl-L-threoninamide | | 581.1 |
| 155 | (5Z)-5-{[1-(1-benzofuran-2-ylcarbonyl)piperidin-4-yl]methylidene}-4-(prop-2-yn-1-ylamino)-1,3-thiazol-2(5H)-one | | 394.0 |

TABLE 1-32

| | | | |
|---|---|---|---|
| 156 | (5Z)-5-({1-[(5-chloro-1-benzofuran-2-yl)carbonyl]piperidin-4-yl}methylidene)-4-(prop-2-yn-1-ylamino)-1,3-thiazol-2(5H)-one | | 427.9 |

TABLE 1-32-continued

| 157 | N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-alaninamide | 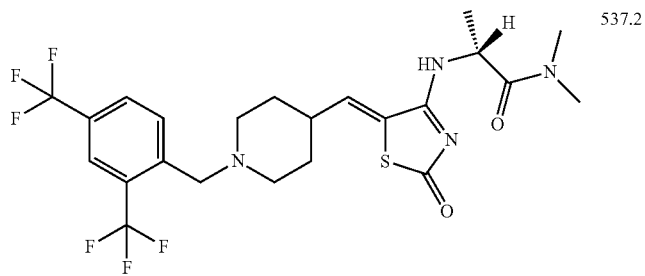 | 537.2 |
| --- | --- | --- | --- |
| 158 | (5Z)-5-({1-[2,4-bis(trifluoromethyl)benzyl]piperidin-4-yl}methylidene)-4-[(3-hydroxypropyl)amino]-1,3-thiazol-2(5H)-one | 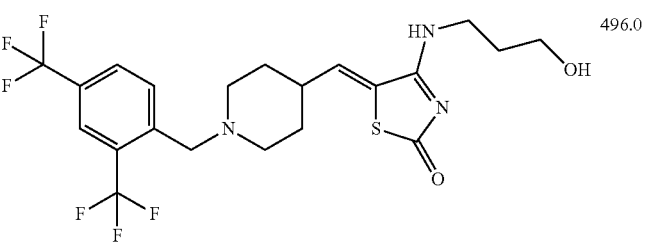 | 496.0 |
| 159 | (5Z)-5-({1-[2,4-bis(trifluoromethyl)benzyl]piperidin-4-yl}methylidene)-4-[(2-hydroxyethyl)amino]-1,3-thiazol-2(5H)-one | 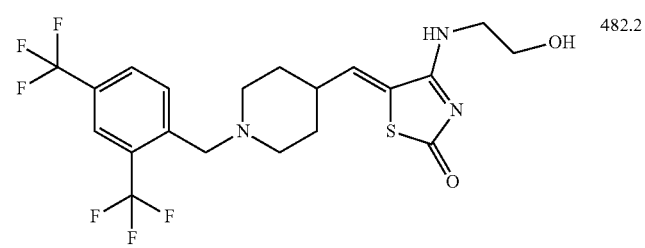 | 482.2 |
| 160 | 1,5-anhydro-3-{[(5Z)-5-({1-[2,4-bis(trifluoromethyl)benzyl]piperidin-4-yl}methylidene)-2-oxo-2,5-dihydro-1,3-thiazol-4-yl]amino}-2,3-dideoxy-threo-pentitol | 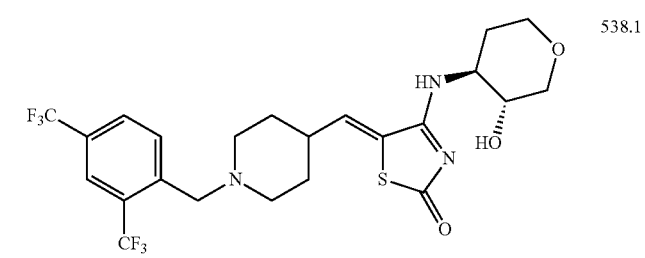 | 538.1 |

TABLE 1-33

| 161 | (2S)-1-[(5Z)-5-({1-[2,4-bis(trifluoromethyl)benzyl]piperidin-4-yl}methylidene)-2-oxo-2,5-dihydro-1,3-thiazol-4-yl]-N,N-dimethylazetidine-2-carboxamide | 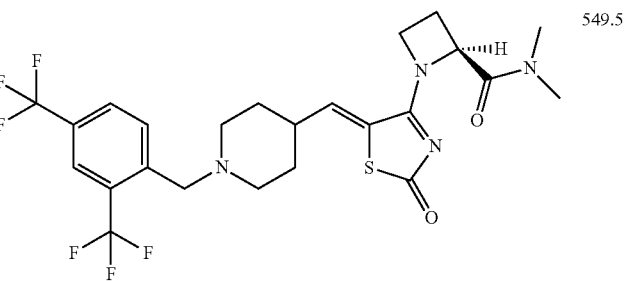 | 549.5 |

TABLE 1-33-continued

| | | | |
|---|---|---|---|
| 162 | N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethylalaninamide | | 537.1 |
| 163 | 1-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-L-prolinamide | | 563.1 |
| 164 | 3-{[(5Z)-5-({1-[2,4-bis(trifluoromethyl)benzyl]piperidin-4-yl}methylidene)-2-oxo-2,5-dihydro-1,3-thiazol-4-yl]amino}piperidin-2-one | | 535.1 |
| 165 | (5Z)-5-({1-[2,4-bis(trifluoromethyl)benzyl]piperidin-4-yl}methylidene)-4-[(1-methylprop-2-yn-1-yl)amino]-1,3-thiazol-2(5H)-one | | 490.0 |

TABLE 1-34

| | | | |
|---|---|---|---|
| 166 | (5Z)-5-({1-[2,4-bis(trifluoromethyl)benzyl]piperidin-4-yl}methylidene)-4-[(1-methylprop-2-yn-1-yl)amino]-1,3-thiazol-2(5H)-one | | HCl 490.0 |

TABLE 1-34-continued

| 167 | N²-[(5Z)-5-({1-[2,4-bis(trifluoromethyl)benzyl]piperidin-4-yl}methylidene)-2-oxo-2,5-dihydro-1,3-thiazol-4-yl]-N-cyclopropylglycinamide | | HCl | 535.1 |
| 168 | (5Z)-5-({1-[2,4-bis(trifluoromethyl)benzyl]piperidin-4-yl}methylidene)-4-(prop-2-yn-1-ylamino)-1,3-thiazol-2(5H)-one | | | 476.2 |
| 169 | (−)-1,5-anhydro-3-{[(5Z)-5-({1-[2,4-bis(trifluoromethyl)benzyl]piperidin-4-yl}methylidene)-2-oxo-2,5-dihydro-1,3-thiazol-4-yl]amino}-2,3-dideoxy-threo-pentitol | | | 538.1 |
| 170 | (+)-1,5-anhydro-3-{[(5Z)-5-({1-[2,4-bis(trifluoromethyl)benzyl]piperidin-4-yl}methylidene)-2-oxo-2,5-dihydro-1,3-thiazol-4-yl]amino}-2,3-dideoxy-threo-pentitol | | | 538.1 |

TABLE 1-35

| 171 | (7Z)-7-({1-[2,4-bis(trifluoromethyl)benzyl]piperidin-4-yl}methylidene)-2,7-dihydro-3H-imidazo[1,2-c][1,3]thiazol-5-one | | 464.0 |
| 172 | N²-[(5Z)-5-({1-[2,4-bis(trifluoromethyl)benzyl]piperidin-4-yl}methylidene)-2-oxo-2,5-dihydro-1,3-thiazol-4-yl]-3-hydroxy-N,N-dimethyl-L-valinamide | | 581.1 |

TABLE 1-35-continued

| | | | |
|---|---|---|---|
| 173 | (8Z)-8-({1-[2,4-bis(trifluoromethyl)benzyl]piperidin-4-yl}methylidene)-2,3,4,8-tetrahydro[1,3]thiazolo[3,4-a]pyrimidin-6-one | 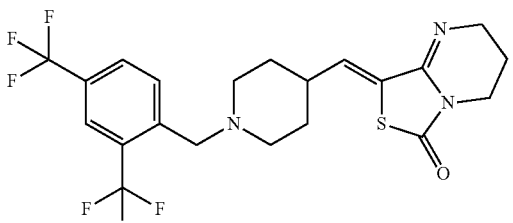 | 478.0 |
| 174 | $N^2$-[(5Z)-5-({1-[2,4-bis(trifluoromethyl)benzyl]piperidin-4-yl}methylidene)-2-oxo-2,5-dihydro-1,3-thiazol-4-yl]-N-(2-hydroxy-2-methylpropyl)glycinamide | 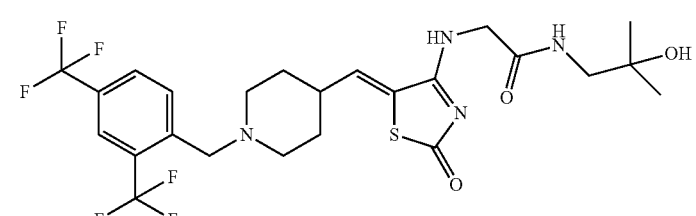 | 567.2 |
| 175 | (−)-1,5-anhydro-2-{[(5Z)-5-({1-[2,4-bis(trifluoromethyl)benzyl]piperidin-4-yl}methylidene)-2-oxo-2,5-dihydro-1,3-thiazol-4-yl]amino}-2,4-dideoxy-threo-pentitol | 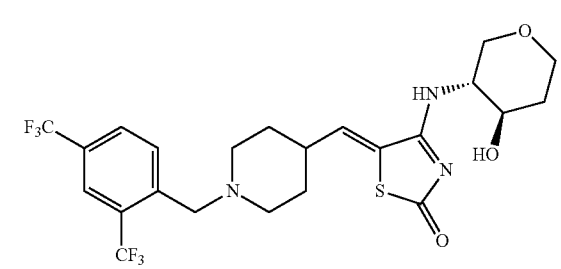 [SMILES: O=C1N=C(N[C@@H]2COCC[C@H]2O)/C(=C/C2CCN(Cc3ccc(C(F)(F)F)cc3C(F)(F)F)CC2)S1] | 538.1 |

TABLE 1-36

| | | | |
|---|---|---|---|
| 176 | (−)-(5Z)-5-({1-[2,4-bis(trifluoromethyl)benzyl]piperidin-4-yl}methylidene)-4-[trans-(4-hydroxytetrahydrofuran-3-yl)amino]-1,3-thiazol-2(5H)-one | 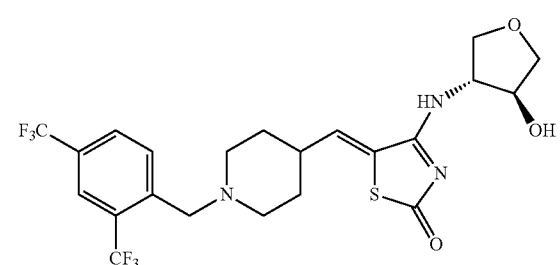 | 524.1 |
| 177 | (+)-(5Z)-5-({1-[2,4-bis(trifluoromethyl)benzyl]piperidin-4-yl}methylidene)-4-[trans-(4-hydroxytetrahydrofuran-3-yl)amino]-1,3-thiazol-2(5H)-one | 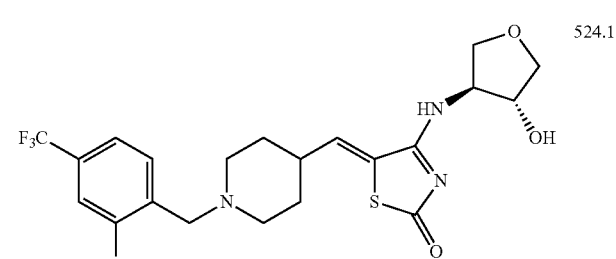 | 524.1 |

TABLE 1-36-continued

| 178 | (5Z)-5-({1-[2,4-bis(trifluoromethyl)benzyl]piperidin-4-yl}methylidene)-4-[(1,3-oxazol-2-ylmethyl)amino]-1,3-thiazol-2(5H)-one | 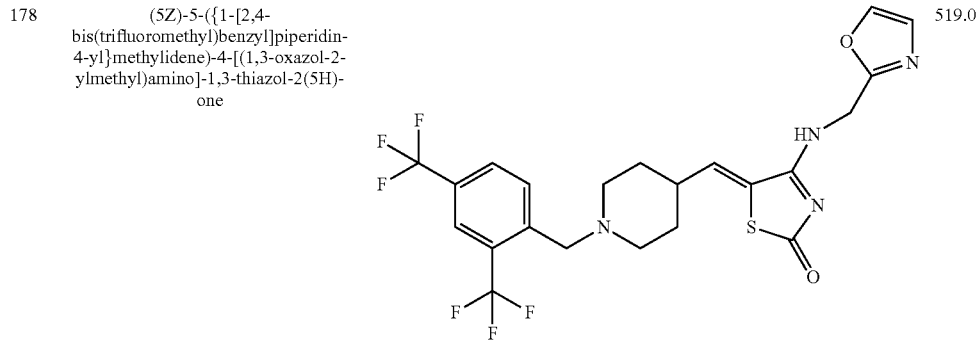 | 519.0 |

| 179 | N²-[(5Z)-5-({1-[2,4-bis(trifluoromethyl)benzyl]piperidin-4-yl}methylidene)-2-oxo-2,5-dihydro-1,3-thiazol-4-yl]-3-methoxy-N,N-dimethyl-L-valinamide | 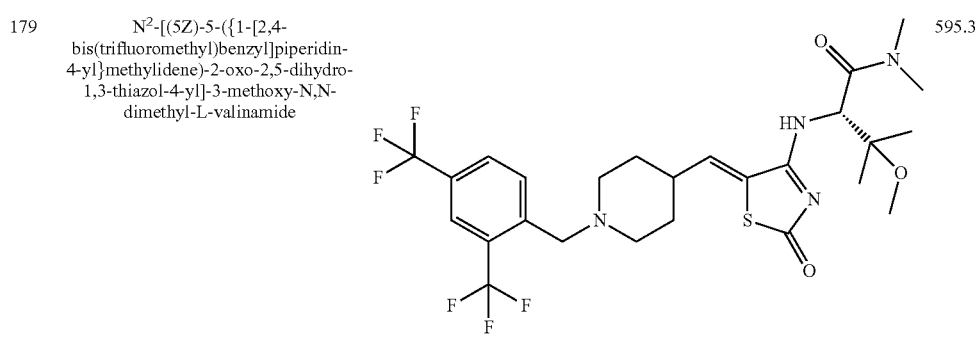 | 595.3 |

| 180 | (2S)-2-{[(5Z)-5-({1-[2,4-bis(trifluoromethyl)benzyl]piperidin-4-yl}methylidene)-2-oxo-2,5-dihydro-1,3-thiazol-4-yl]amino}-2-cyclopropyl-N,N-dimethylethanamide | 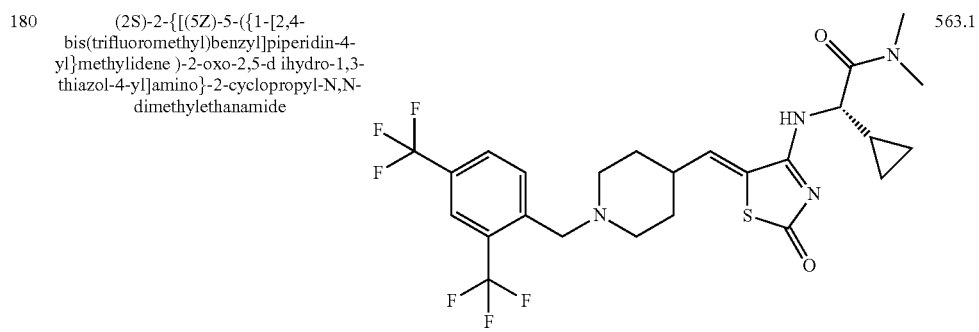 | 563.1 |

TABLE 1-37

| 181 | 3-{[(5Z)-5-({1-[2,4-bis(trifluoromethyl)benzyl]piperidin-4-yl}methylidene)-2-oxo-2,5-dihydro-1,3-thiazol-4-yl]amino}-1-methylpiperidin-2-one | 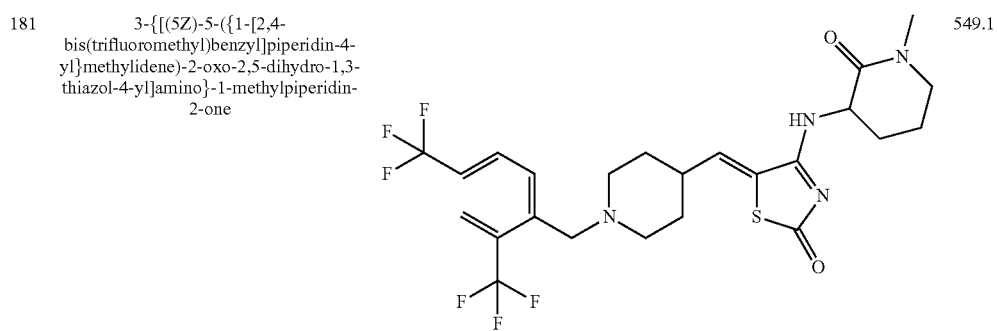 | 549.1 |

TABLE 1-37-continued

| 182 | N²-[(5Z)-5-({1-[2,4-bis(trifluoromethyl)benzyl]piperidin-4-yl}methylidene)-2-oxo-2,5-dihydro-1,3-thiazol-4-yl]-3-(dimethylamino)-N,N-dimethyl-L-alaninamide | | 580.5 |
|---|---|---|---|
| 183 | (5Z)-5-({1-[2,4-bis(trifluoromethyl)benzyl]piperidin-4-yl}methylidene)-4-[(1,4-dioxan-2-ylmethyl)amino]-1,3-thiazol-2(5H)-one | | 538.1 |
| 184 | (+)-1,5-anhydro-2-{[(5Z)-5-({1-[2,4-bis(trifluoromethyl)benzyl]piperidin-4-yl}methylidene)-2-oxo-2,5-dihydro-1,3-thiazol-4-yl]amino}-2,4-dideoxy-threo-pentitol | | 538.1 |
| 185 | (−)-(5Z)-5-({1-[2,4-bis(trifluoromethyl)benzyl]piperidin-4-yl}methylidene)-4-[trans-(5,5-difluoro-2-hydroxycyclohexyl)amino]-1,3-thiazol-2(5H)-one | | 572.1 |

TABLE 1-38

| 186 | (+)-(5Z)-5-({1-[2,4-bis(trifluoromethyl)benzyl]piperidin-4-yl}methylidene(-4-[trans-(5,5-difluoro-2-hydroxycyclohexyl)amino]-1,3-thiazol-2(5H)-one | | 572.1 |
|---|---|---|---|
| 187 | $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-valinamide | | 565.1 |
| 188 | $N^2$-[(5Z)-5-({1-[2,4-bis(trifluoromethyl)benzyl]piperidin-4-yl}methylidene)-2-oxo-2,5-dihydro-1,3-thiazol-4-yl]-N,N,O-trimethyl-D-serinamide | | 567.2 |
| 189 | (5Z)-5-({1-[2,4-bis(trifluoromethyl)benzyl]piperidin-4-yl}methylidene)-4-[(1-methyl-5-oxopyrrolidin-3-yl)amino]-1,3-thiazol-2(5H)-one | | 535.1 |
| 190 | (2S)-2-{[(5Z)-5-({1-[2,4-bis(trifluoromethyl)benzyl]piperidin-4-yl}methylidene)-2-oxo-2,5-dihydro-1,3-thiazol-4-yl]amino}-2-(1-hydroxycyclopropyl)-N,N-dimethylethanamide | | 579.1 |

TABLE 1-39

| | | | |
|---|---|---|---|
| 191 | (5Z)-5-({1-[2,4-bis(trifluoromethyl)benzyl]piperidin-4-yl}methylidene)-4-{[(1S)-2-methyl-1-(morpholin-4-ylcarbonyl)propyl]amino}-1,3-thiazol-2(5H)-one | 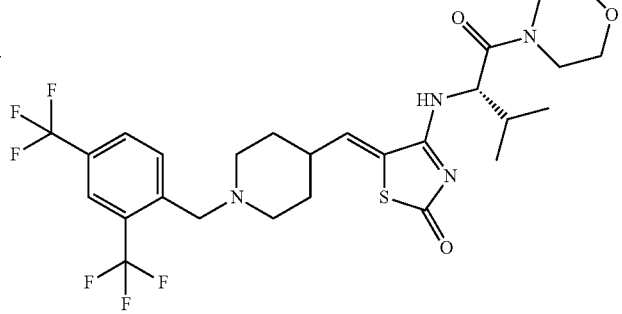 | 607.1 |
| 192 | 2-{[(5Z)-5-({1-{2,4-bis(trifluoromethyl)benzyl]piperidin-4-yl}methylidene)-2-oxo-2,5-dihydro-1,3-thiazol-4-yl]amino}-4,4,4-trifluoro-N,N-dimethylbutanamide | 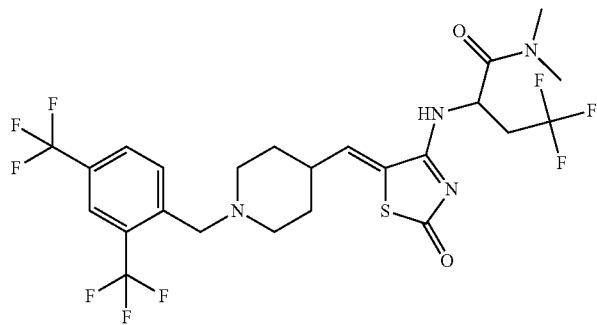 [SMILES: CN(C)C(=O)C(CC(F)(F)F)NC1=NC(=O)S/C1=C\C1CCN(Cc2ccc(C(F)(F)F)cc2C(F)(F)F)CC1] | 605.1 |
| 193 | (−)-(5Z)-5-({1-[2,4-bis(trifluoromethyl)benzyl]piperidin-4-yl}methylidene)-4-{[(1,4-dioxan-2-ylmethyl]amino}-1,3-thiazol-2(5H)-one | 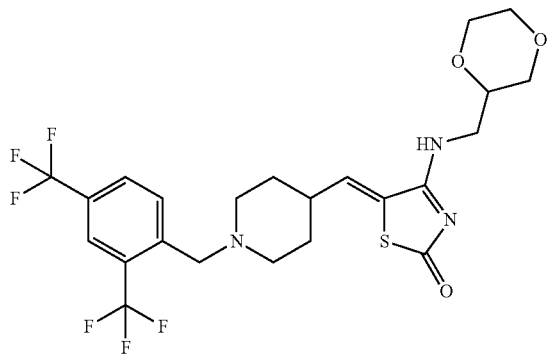 [SMILES: O=C1N=C(NCC2COCCO2)/C(=C/C2CCN(Cc3ccc(C(F)(F)F)cc3C(F)(F)F)CC2)S1] | 538.1 |
| 194 | (+)-(5Z)-5-({1-[2,4-bis(trifluoromethyl)benzyl]piperidin-4-yl}methylidene)-4-{[(1,4-dioxan-2-ylmethyl]amino}-1,3-thiazol-2(5H)-one | 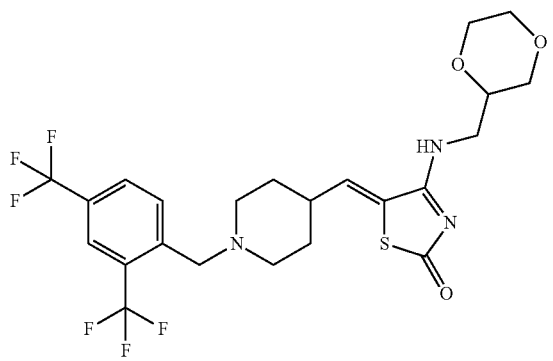 [SMILES: O=C1N=C(NCC2COCCO2)/C(=C/C2CCN(Cc3ccc(C(F)(F)F)cc3C(F)(F)F)CC2)S1] | 538.1 |

TABLE 1-39-continued

| | | | |
|---|---|---|---|
| 195 | (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one | 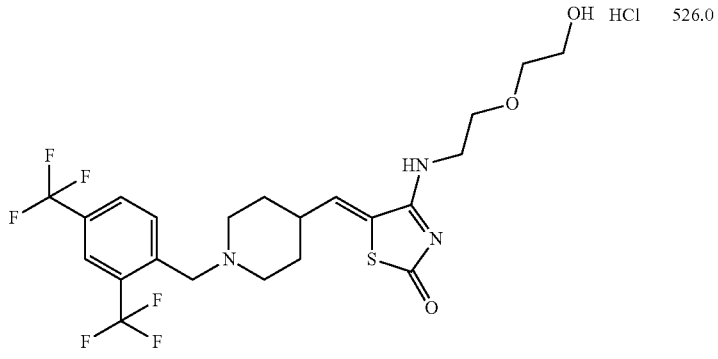 | HCl 526.0 |

TABLE 1-40

| | | | |
|---|---|---|---|
| 196 | $N^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-3-(methylsulfonyl)-L-alaninamide | 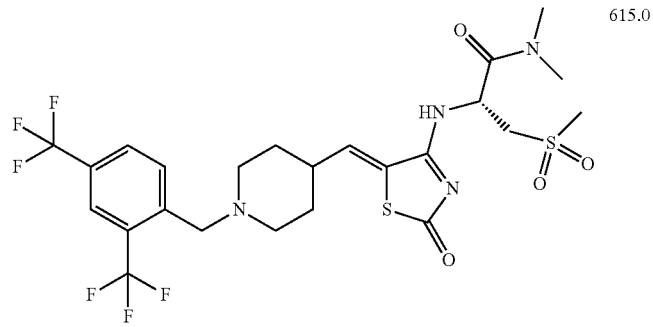 | 615.0 |
| 197 | $N^2$-[(5Z)-5-({1-[2,4-bis(trifluoromethyl)benzyl]piperidin-4-yl}methylidene)-2-oxo-2,5-dihydro-1,3-thiazol-4-yl]-N-oxetan-3-ylglycinamide | 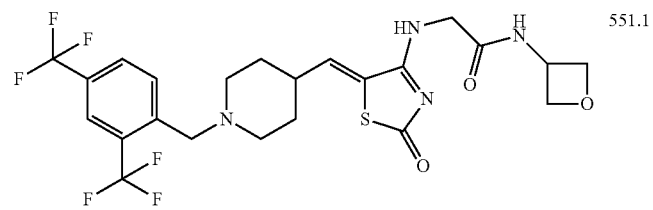 | 551.1 |
| 198 | (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one | 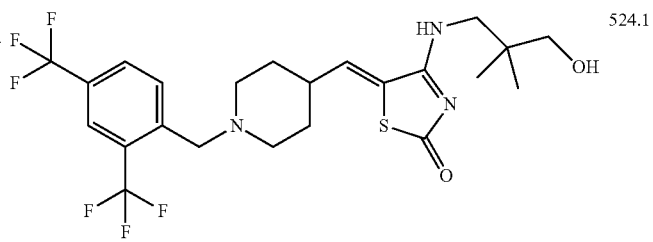 | 524.1 |
| 199 | (5Z)-5-({1-[2,4-bis(trifluoromethyl)benzyl]piperidin-4-yl}methylidene)-4-(ethylamino)-1,3-thiazol-2(5H)-one | 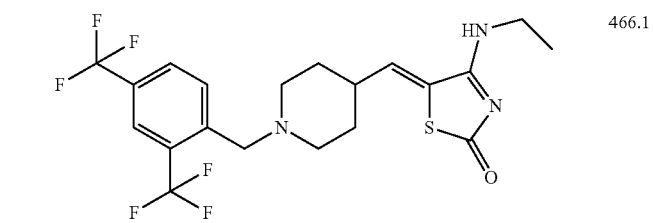 | 466.1 |

TABLE 1-40-continued

| 200 | (5Z)-5-({1-[2,4-bis(trifluoromethyl)benzyl]piperidin-4-yl}methylidene)-4-(propylamino)-1,3-thiazol-2(5H)-one | 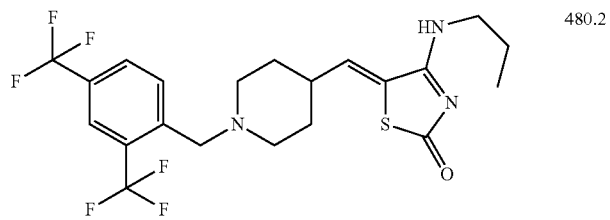 | 480.2 |

TABLE 1-41

| 201 | (5Z)-5-({1-[2,4-bis(trifluoromethyl)benzyl]piperidin-4-yl}methylidene)-4-[(2-hydroxy-2-methylpropyl)amino]-1,3-thiazol-2(5H)-one | 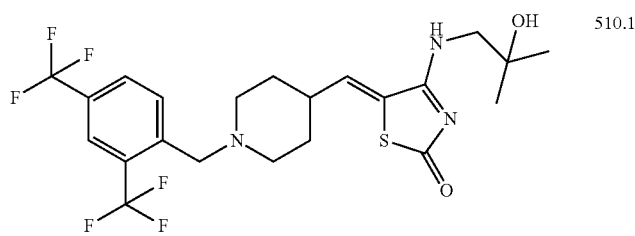 | 510.1 |
| 202 | N²-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide | 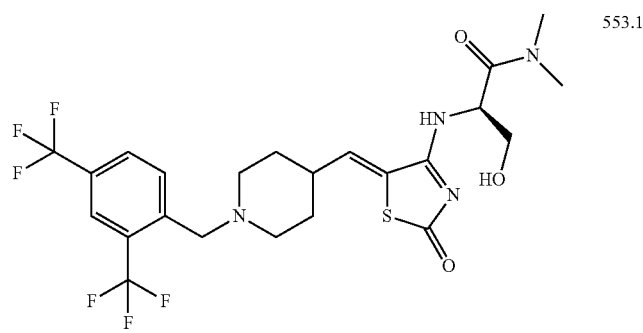 | 553.1 |
| 203 | (5Z)-5-({1-[2,4-bis(trifluoromethyl)benzyl]piperidin-4-yl}methylidene)-4-[trans-(5,5-difluoro-2-hydroxycyclohexyl)amino]-1,3-thiazol-2(5H)-one | 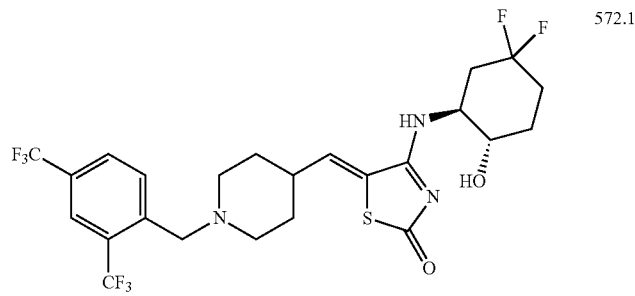 | 572.1 |
| 204 | (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one | 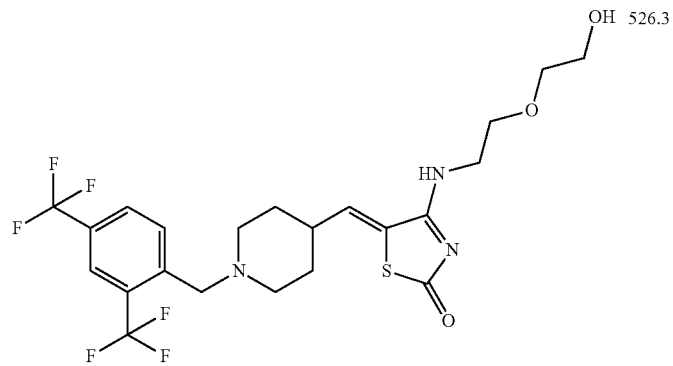 | 526.3 |

Experimental Example 1 Compound Evaluation in HTRF Assay System Using ERR-α Ligand-Binding Domain An assay buffer (25 mM HEPES, 100 mM NaCl, 1 mM DTT, 0.1% BSA) containing 5 nM GST-ERR-α ligand-binding domain (final concentration 1.25 nM) was added to a 384 well plate, then 40 μM N-[5-(trifluoromethyl)-1,3,4-thiadiazol-2-yl]-2-cyano-3-[3-methoxy-4-[2,4-di(trifluoromethyl)benzyloxy]phenyl]propenamide (XCT-790) (final concentration 10 μM), or 120 μM compound (final concentration 30 μM) was added. Furthermore, an assay buffer containing XL665 conjugated Streptavidin, $Eu^{3+}$ criptate conjugated GST antibody and 200 nM biotinylated SRC-1 (676-700) (final concentration 100 nM) was added, and the mixture was reacted at room temperature for 2 hr. Using Multiplate reader Envision (Perkin Elmer Inc.), after excitation at 320 nm, fluorescence values at 620 nm and 665 nm were measured. The inverse agonist activity of the compound was calculated in percentage with the 665/620 ratio value inhibited by no addition of compound as 0%, and with addition of final concentration 10 μM of XCT-790 as 100%. The results are shown in Table 2.

TABLE 2

| Example No. | inhibition rate (%) at 30 μM |
| --- | --- |
| 3 | 109 |
| 7 | 100 |
| 8 | 97 |
| 9 | 107 |
| 10 | 102 |
| 13 | 105 |
| 15 | 102 |
| 16 | 112 |
| 17 | 106 |
| 20 | 105 |
| 24 | 105 |
| 31 | 101 |
| 37 | 109 |
| 39 | 106 |
| 40 | 73 |
| 43 | 106 |
| 47 | 108 |
| 56 | 106 |
| 58 | 110 |
| 59 | 49 |
| 61 | 95 |
| 69 | 67 |
| 77 | 109 |
| 78 | 109 |
| 80 | 105 |
| 108 | 89 |
| 115 | 99 |
| 132 | 102 |
| 140 | 100 |
| 195 | 102 |
| 199 | 101 |
| 200 | 101 |

As is clear from the results in Table 2, the compound of the present invention has a superior ERR-α inverse agonist activity.

Experimental Example 2 Compound Evaluation in Reporter Assay System Using 293T Cells 293T cells derived from human kidney were seeded in a 150 $cm^2$ flask by 6,000,000 cells, and cultured in a medium (DMEM medium containing 10% inactivated Fetal Bovine Serum sterile filtered (FBS), 50 g/ml Gentamicin, 10 mM HEPES buffer (pH 7.4)) at 37° C. in the presence of 5% $CO_2$ for 1 day.

Then, vector DNA having a gene encoding a fusion protein, containing GAL4-DNA-binding domain and ERR full-length and a vector DNA wherein luciferase gene is fused at the downstream of GAL4-binding-sequence were cotransfected by a lipofection method, and the cells were cultured at 37° C. in the presence of 5% $CO_2$ for 1 day. The cells were recovered, sown in a 384 well plate by 15,000 cells, and cultured at 37° C. in the presence of 5% $CO_2$ for 3 hrs. Furthermore, 50 μM N-[5-(trifluoromethyl)-1,3,4-thiadiazol-2-yl]-2-cyano-3-[3-methoxy-4-[2,4-di(trifluoromethyl)benzyloxy]phenyl]propenamide (XCT-790) (final concentration 10 μM) or 15 μM compound (final concentration 3 μM) was added, and the cells were cultured at 37° C. in the presence of 5% $CO_2$ for 1 day. The luciferase activity was measured by using multiplate reader Envision (Perkin Elmer Inc.). The inverse agonist activity of the compound was calculated in percentage with the luciferase activity inhibited by no addition of compound as 0%, and with addition of final concentration 10 μM of XCT-790 as 100%. The results are shown in Table 3.

TABLE 3

| Example No. | inhibition rate (%) at 3 μM |
| --- | --- |
| 3 | 88 |
| 7 | 87 |
| 8 | 87 |
| 9 | 88 |
| 10 | 93 |
| 13 | 89 |
| 15 | 88 |
| 16 | 89 |
| 17 | 97 |
| 20 | 95 |
| 24 | 92 |
| 31 | 87 |
| 87 | 88 |
| 39 | 85 |
| 40 | 62 |
| 43 | 87 |
| 47 | 90 |
| 56 | 91 |
| 58 | 91 |
| 59 | 67 |
| 61 | 90 |
| 69 | 87 |
| 77 | 82 |
| 78 | 82 |
| 80 | 86 |
| 108 | 81 |
| 115 | 90 |
| 132 | 78 |
| 140 | 90 |
| 195 | 90 |
| 199 | 84 |
| 200 | 88 |

As is clear from the results in Table 3, the compound of the present invention has a superior ERR-α inverse agonist activity.

Experimental Example 3 Antitumor Test using MDA-MB-231-luc Cells

6-Week-old Balb/c nu/nu mice were transplanted subcutaneously with $5 \times 10^6$ cells/100 μL, and the mice were grouped according to the body weight and tumor volume after 1 to 2 weeks. Vehicle (0.5% MC) or a compound was administered orally to mice (6 mice per group). The administration was twice per day and performed continuously during the dosing period. Setting the change in tumor volume of the vehicle-treated group as 100%, the change rate in tumor volume of the compound-treated group (□/C %) was calculated. The results are shown in Table 4.

TABLE 4

| Example No. | T/C (%) | dose (mg/kg) | dosing period (days) |
|---|---|---|---|
| 7 | 24 | 50 | 14 |
| 10 | 15 | 60 | 15 |
| 13 | 20 | 100 | 15 |
| 17 | 40 | 50 | 15 |
| 78 | 11 | 50 | 14 |
| 108 | 45 | 50 | 14 |
| 115 | 55 | 50 | 14 |
| 195 | 56 | 50 | 17 |

As is clear from the results in Table 4, the compound of the present invention has a superior antitumor effect.

Formulation Example 1

A medicament containing the compound of the present invention as an active ingredient can be produced, for example, according to the following formulation.

1. Capsule

| (1) | compound obtained in Example 1 | 10 mg |
|---|---|---|
| (2) | lactose | 90 mg |
| (3) | crystalline cellulose | 70 mg |
| (4) | magnesium stearate | 10 mg |
| | 1 capsule | 180 mg |

The total amount of the above-mentioned (1), (2) and (3) and 5 mg of (4) are blended, and the mixture is granulated. Thereto is added the remaining 5 mg of (4), and the whole is sealed in a gelatin capsule.

2. Tablet

| (1) | compound obtained in Example 1 | 10 mg |
|---|---|---|
| (2) | lactose | 35 mg |
| (3) | cornstarch | 150 mg |
| (4) | crystalline cellulose | 30 mg |
| (5) | magnesium stearate | 5 mg |
| | 1 tablet | 230 mg |

The total amount of the above-mentioned (1), (2) and (3), mg of (4) and 2.5 mg of (5) are blended, and the mixture is granulated. Thereto are added the remaining 10 mg of (4) and 2.5 mg of (5), and the mixture is compression-molded to give a tablet.

INDUSTRIAL APPLICABILITY

Since the compound of the present invention has a superior activity as an ERR-α modulator (particularly, inverse agonist), it is useful as an agent for the prophylaxis or treatment of ERR-α associated diseases such as malignant tumor (e.g., breast cancer, malignant lymphoma, multiple myeloma, prostate cancer, colorectal cancer, lung cancer, ovarian cancer, endometrial carcinoma) and the like.

This application is based on patent application No. 2011-171387 filed in Japan, the contents of which are encompassed in full herein.

The invention claimed is:

1. A compound represented by the formula $$A-L^a-L^b-L^c-N\overset{G}{\underset{}{}}-E \quad (I)$$

wherein
A is a cyclic group optionally having substituent(s);
$L^a$ is a bond, —O—, —CO—, —S—, —SO—, —SO$_2$—, —NR$^{L1}$— or —NR$^{L1}$—CO—;
$L^b$ is a bond or a C$_{1-3}$ alkylene group optionally having substituent(s);
$L^c$ is a bond, —CO—, —O—CO—, —NR$^{L2}$—CO—, —SO$_2$— or —NR$^{L2}$—SO$_2$—;
$R^{L1}$ and $R^{L2}$ are each independently a hydrogen atom, a hydrocarbon group optionally having substituent(s), a heterocyclic group optionally having substituent(s), a hydroxy group optionally having a substituent, an amino group optionally having substituent(s), or an acyl group;
ring G is a 4- to 10-membered saturated heterocycle containing one nitrogen atom as a ring-constituting hetero atom, which is optionally bridged and optionally has substituent(s); and
E is a group represented by the formula $$\begin{array}{c}R^1\\R^2-N\\\Big\backslash\\\text{—CH—}\overset{}{\underset{X}{\bigcirc}}=O\end{array} \quad Ea$$

wherein
X is —S—, —O— or —NR$^X$—; and
$R^1$, $R^2$ and $R^X$ are each independently a hydrogen atom, a hydrocarbon group optionally having substituent(s), a heterocyclic group optionally having substituent(s), a hydroxy group optionally having a substituent, an amino group optionally having substituent(s), or an acyl group, or
$R^1$ and $R^2$ in combination optionally form, together with the adjacent nitrogen atom, a nitrogen-containing heterocycle optionally having substituent(s),
or a salt thereof.

2. A compound represented by the formula $$A-L^a-L^b-L^c-N\overset{G}{\underset{}{}}-E \quad (I)$$

wherein
A is a cyclic group optionally having substituent(s);
$L^a$ is a bond, —O—, —CO—, —S—, —SO—, —SO$_2$—, —NR$^{L1}$— or —NR$^{L1}$—CO—;
$L^b$ is a bond or a C$_{1-3}$ alkylene group optionally having substituent(s);

$L^c$ is a bond, —CO—, —O—CO—, —$NR^{L2}$—CO—, —$SO_2$— or —$NR^{L2}$—$SO_2$—;

$R^{L1}$ and $R^{L2}$ are each independently a hydrogen atom, a hydrocarbon group optionally having substituent(s), a heterocyclic group optionally having substituent(s), a hydroxy group optionally having a substituent, an amino group optionally having substituent(s), or an acyl group;

ring G is a 4- to 10-membered saturated heterocycle containing one nitrogen atom as a ring-constituting hetero atom, which is optionally bridged and optionally has substituent(s); and E is a group represented by the formula

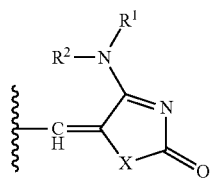

wherein

X is —S—, —O— or —$NR^X$—; and $R^1$, $R^2$ and $R^X$ are each independently a hydrogen atom, a hydrocarbon group optionally having substituent(s), a heterocyclic group optionally having substituent(s), a hydroxy group optionally having a substituent, an amino group optionally having substituent(s), or an acyl group, or $R^1$ and $R^2$ in combination optionally form, together with the adjacent nitrogen atom, a nitrogen-containing heterocycle optionally having substituent(s), or a salt thereof.

3. The compound or salt of claim 1, wherein A is a $C_{6-10}$ aryl group, an aromatic heterocyclic group or a $C_{3-10}$ cycloalkyl group, each optionally having substituent(s).

4. The compound or salt of claim 1, wherein the substituent of the cyclic group optionally having substituent(s) for A is selected from
   (a) a halogen atom,
   (b) a cyano group,
   (c) a $C_{1-6}$ alkyl group optionally substituted by 1 to 3 halogen atoms,
   (d) a $C_{1-6}$ alkoxy group optionally substituted by 1 to 3 halogen atoms,
   (e) a hydroxy group, and
   (f) a pentafluorosulfanyl group.

5. The compound or salt of claim 1, wherein
$L^a$ is a bond;
$L^b$ is a bond or a $C_{1-3}$ alkylene group optionally substituted by 1 to 3 $C_{1-6}$ alkyl groups; and
$L^c$ is a bond or —CO—.

6. The compound or salt of claim 1, wherein ring G is an azetidine ring, a pyrrolidine ring, a piperidine ring, an azepane ring, a 3-azabicyclo[3.1.0]hexane ring, a 8-azabicyclo[3.2.1]octane ring, a 3-azabicyclo[3.3.1]nonane ring or a 3-azabicyclo[3.3.0]octane ring, each optionally having substituent(s).

7. The compound or salt of claim 1, wherein E is a group represented by the formula

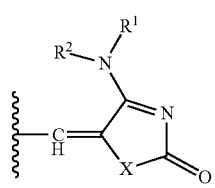

wherein

X is —S—, —O— or —$NR^X$—;

$R^X$ is a $C_{1-6}$ alkyl group;

$R^1$ is (1) a hydrogen atom;
(2) a $C_{1-6}$ alkyl group optionally substituted by 1 to 5 substituents selected from
   (a) an amino group optionally mono- or di-substituted by $C_{1-6}$ alkyl group(s) optionally substituted by 1 to 3 hydroxy groups,
   (b) a hydroxy group,
   (c) a $C_{1-6}$ alkoxy group optionally substituted by 1 to 3 substituents selected from a hydroxy group, a $C_{1-6}$ alkoxy group and a mono- or di-$C_{1-6}$ alkylamino group,
   (d) a carboxy group,
   (e) a halogen atom,
   (f) a $C_{1-6}$ alkoxy-carbonyl group,
   (g) a carbamoyl group optionally mono- or di-substituted by substituent(s) selected from
      (i) a $C_{1-6}$ alkyl group optionally substituted by 1 to 3 substituents selected from a hydroxy group and a $C_{1-6}$ alkoxy group,
      (ii) a $C_{3-10}$ cycloalkyl group, and
      (iii) a 4- to 6-membered non-aromatic heterocyclic group,
   (h) a $C_{1-6}$ alkylsulfonyl group,
   (i) a $C_{6-14}$ aryl group,
   (j) a 5- or 6-membered aromatic heterocyclic group,
   (k) a 4- to 6-membered non-aromatic heterocyclic group optionally substituted by 1 to 3 substituents selected from
      (i) an oxo group, and
      (ii) a $C_{1-6}$ alkyl group optionally substituted by 1 to 3 hydroxy groups, and
   (l) a 4- to 6-membered non-aromatic heterocyclylcarbonyl group optionally substituted by 1 to 3 substituents selected from
      (i) a hydroxy group, and
      (ii) a $C_{1-6}$ alkyl group;
(3) a $C_{2-6}$ alkenyl group optionally substituted by 1 to 3 mono- or di-$C_{1-6}$ alkylamino groups;
(4) a $C_{2-6}$ alkynyl group optionally substituted by 1 to 3 substituents selected from
   (a) a mono- or di-$C_{1-6}$ alkylamino group,
   (b) a $C_{3-10}$ cycloalkyl group, and
   (c) a hydroxy group;
(5) a $C_{3-10}$ cycloalkyl group optionally substituted by 1 to 3 substituents selected from
   (a) a halogen atom, and
   (b) a hydroxy group;

(6) a $C_{3-10}$ cycloalkyl-$C_{1-6}$ alkyl group optionally substituted by 1 to 3 substituents selected from
  (a) a hydroxy group,
  (b) a $C_{1-6}$ alkyl group optionally substituted by 1 to 3 hydroxy groups, and
  (c) a carbamoyl group optionally mono- or di-substituted by $C_{1-6}$ alkyl group(s); or
(7) a 4- to 6-membered non-aromatic heterocyclic group optionally substituted by 1 to 3 substituents selected from
  (a) a $C_{1-6}$ alkyl group,
  (b) a hydroxy group, and
  (c) an oxo group; and
$R^2$ is a hydrogen atom; or
$R^1$ and $R^2$ in combination form, together with the adjacent nitrogen atom, a 4- to 7-membered nitrogen-containing heterocycle optionally substituted by 1 to 3 substituents selected from
  (1) a hydroxy group, and
  (2) a carbamoyl group optionally mono- or di-substituted by $C_{1-6}$ alkyl group(s).

8. The compound or salt of claim 1, wherein
A is a phenyl group, a naphthyl group, a benzofuryl group, an indolyl group, a benzimidazolyl group or a $C_{3-10}$ cycloalkyl group, each optionally substituted by 1 to 3 substituents selected from
  (a) a halogen atom,
  (b) a cyano group,
  (c) a $C_{1-6}$ alkyl group optionally substituted by 1 to 3 halogen atoms,
  (d) a $C_{1-6}$ alkoxy group optionally substituted by 1 to 3 halogen atoms,
  (e) a hydroxy group, and
  (f) a pentafluorosulfanyl group;
$L^a$ is a bond;
$L^b$ is a bond or a $C_{1-3}$ alkylene group optionally substituted by 1 to 3 $C_{1-6}$ alkyl groups;
$L^c$ is a bond or —CO—;
ring G is an azetidine ring, a pyrrolidine ring, a piperidine ring, an azepane ring, a 3-azabicyclo[3.1.0]hexane ring, a 8-azabicyclo[3.2.1]octane ring, a 3-azabicyclo[3.3.1]nonane ring or a 3-azabicyclo[3.3.0]octane ring, each optionally substituted by 1 to 3 $C_{1-6}$ alkyl groups or one oxo group; and
E is a group represented by the formula

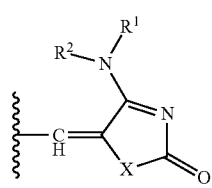

Ea wherein
X is —S—, —O— or —$NR^X$—;
$R^X$ is a $C_{1-6}$ alkyl group;
$R^1$ is
(1) a hydrogen atom;
(2) a $C_{1-6}$ alkyl group optionally substituted by 1 to 5 substituents selected from
  (a) a halogen atom,
  (b) an amino group optionally mono- or di-substituted by $C_{1-6}$ alkyl group(s) optionally substituted by 1 to 3 hydroxy groups,
  (c) a hydroxy group,
  (d) a $C_{1-6}$ alkoxy group optionally substituted by 1 to 3 substituents selected from a hydroxy group, a $C_{1-6}$ alkoxy group and a di-$C_{1-6}$ alkylamino group,
  (e) a carbamoyl group optionally mono- or di-substituted by substituent(s) selected from
    (i) a $C_{1-6}$ alkyl group optionally substituted by 1 to 3 substituents selected from a hydroxy group and a $C_{1-6}$ alkoxy group,
    (ii) a $C_{1-6}$ cycloalkyl group, and
    (iii) an oxetanyl group,
  (f) a carboxy group,
  (g) a $C_{1-6}$ alkoxy-carbonyl group,
  (h) a pyrrolidylcarbonyl group optionally substituted by hydroxy group(s),
  (i) a morpholinylcarbonyl group,
  (j) a piperazinylcarbonyl group substituted by $C_{1-6}$ alkyl group(s),
  (k) a dioxanyl group,
  (l) a tetrahydropyranyl group substituted by $C_{1-6}$ alkyl group(s) substituted by hydroxy group(s),
  (m) an oxopyrrolidinyl group,
  (n) an oxazolyl group,
  (o) an isoxazolyl group,
  (p) a phenyl group, and
  (q) a $C_{1-6}$ alkylsulfonyl group;
(3) a $C_{2-6}$ alkenyl group optionally substituted by 1 to 3 di-$C_{1-6}$ alkylamino groups;
(4) a $C_{2-6}$ alkynyl group optionally substituted by 1 to 3 substituents selected from
  (a) a di-$C_{1-6}$ alkylamino group,
  (b) a $C_{3-10}$ cycloalkyl group, and
  (c) a hydroxy group;
(5) a $C_{3-10}$ cycloalkyl group optionally substituted by 1 to 3 substituents selected from
  (a) a halogen atom, and
  (b) a hydroxy group;
(6) a $C_{3-10}$ cycloalkyl-$C_{1-6}$ alkyl group optionally substituted by 1 to 3 substituents selected from
  (a) a hydroxy group,
  (b) a $C_{1-6}$ alkyl group substituted by hydroxy group(s), and
  (c) a di-$C_{1-6}$ alkyl-carbamoyl group;
(7) an oxetanyl group;
(8) a tetrahydrofuryl group optionally substituted by hydroxy group(s);
(9) a tetrahydropyranyl group optionally substituted by hydroxy group(s);
(10) a pyrrolidinyl group optionally substituted by 1 to 3 substituents selected from a $C_{1-6}$ alkyl group and an oxo group; or
(11) a piperidyl group optionally substituted by 1 to 3 substituents selected from a $C_{1-6}$ alkyl group and an oxo group; and
$R^2$ is a hydrogen atom; or
$R^1$ and $R^2$ in combination form, together with the adjacent nitrogen atom,
(1) a pyrrolidine ring optionally substituted by 1 to 3 hydroxy groups or carbamoyl group(s) di-substituted by $C_{1-6}$ alkyl groups; or
(2) an azetidine ring substituted by carbamoyl group(s) di-substituted by $C_{1-6}$ alkyl groups.

9. The compound or salt of claim 1, wherein
A is a phenyl group optionally substituted by 1 to 3 substituents selected from
  (a) a halogen atom,
  (b) a cyano group, and (c) a $C_{1-6}$ alkyl group optionally substituted by 1 to 3 halogen atoms;
$L^a$ is a bond;
$L^b$ is a $C_{1-3}$ alkylene group;
$L^c$ is a bond;
ring G is pyrrolidine ring, a piperidine ring or a 8-azabicyclo[3.2.1]octane ring; and
E is a group represented by the formula

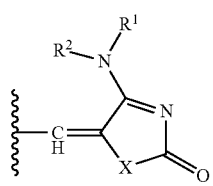

Ea wherein
X is —S— or —NR$^X$—;
$R^X$ is a $C_{1-6}$ alkyl group;
$R^1$ is
(1) a $C_{1-6}$ alkyl group optionally substituted by 1 to 3 substituents selected from
  (a) an amino group di-substituted by $C_{1-6}$ alkyl groups optionally substituted by 1 to 3 hydroxy groups,
  (b) a hydroxy group,
  (c) a $C_{1-6}$ alkoxy group substituted by 1 to 3 substituents selected from a hydroxy group, a $C_{1-6}$ alkoxy group and a di-$C_{1-6}$ alkylamino group, and
  (d) a carbamoyl group di-substituted by $C_{1-6}$ alkyl groups;
(2) a $C_{2-6}$ alkynyl group;
(3) a $C_{3-10}$ cycloalkyl-$C_{1-6}$ alkyl group;
(4) an oxetanyl group; or
(5) a tetrahydrofuryl group; and
$R^2$ is a hydrogen atom.

10. The compound or salt of claim 1, wherein
A is a phenyl group substituted by 1 to 3 substituents selected from a $C_{1-6}$ alkyl group optionally substituted by 1 to 3 halogen atoms;
$L^a$ is a bond;
$L^b$ is a $C_{1-3}$ alkylene group;
$L^c$ is a bond;
ring G is a piperidine ring; and
E is a group represented by the formula

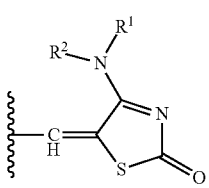

Eaa wherein
$R^1$ is
(1) a $C_{1-6}$ alkyl group optionally substituted by 1 to 3 substituents selected from
  (a) a hydroxy group,
  (b) a $C_{1-6}$ alkoxy group substituted by 1 to 3 hydroxy groups, and
  (c) a carbamoyl group di-substituted by $C_{1-6}$ alkyl groups; or
(2) a $C_{2-6}$ alkynyl group; and
$R^2$ is a hydrogen atom.

11. (5Z)-5-({1-[2,4-bis(trifluoromethyl)benzyl]piperidin-4-yl}methylidene)-4-(prop-2-yn-1-ylamino)-1,3-thiazol-2(5H)-one or a salt thereof.

12. (5Z)-5-({1-[2,4-bis(trifluoromethyl)benzyl]piperidin-4-yl}methylidene)-4-[(2-hydroxy-2-methylpropyl)amino]-1,3-thiazol-2(5H)-one or a salt thereof.

13. (5Z)-5-({1-[2,4-bis(trifluoromethyl)benzyl]piperidin-4-yl}methylidene)-4-[(3-hydroxy-2,2-dimethylpropyl)amino]-1,3-thiazol-2(5H)-one or a salt thereof.

14. N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethylglycinamide or a salt thereof.

15. N$^2$-[(5Z)-5-({1-[2,4-bis(trifluoromethyl)benzyl]piperidin-4-yl}methylidene)-2-oxo-2,5-dihydro-1,3-thiazol-4-yl]-N,N-dimethyl-D-serinamide or a salt thereof.

16. (5Z)-5-({1-[2,4-bis(trifluoromethyl)benzyl]piperidin-4-yl}methylidene)-4-{[2-(2-hydroxyethoxy)ethyl]amino}-1,3-thiazol-2(5H)-one or a salt thereof.

17. A medicament comprising the compound or salt of claim 1.

18. The medicament of claim 17, which is an ERR-α inverse agonist.

19. The medicament of claim 17, which is an agent for the treatment of cancer.

20. A method of inversing ERR-α in a mammal in need thereof, which comprises administering an effective amount of the compound or salt of claim 1 to the mammal.

21. A method for the treatment of cancer in a mammal in need thereof, which comprises administering an effective amount of the compound or salt of claim 1 to the mammal.

22. The medicament of claim 19, wherein the cancer is selected from the group consisting of breast cancer, malignant lymphoma, multiple myeloma, prostate cancer, colorectal cancer, lung cancer, ovarian cancer and endometrial carcinoma.

23. The method of claim 21, wherein the cancer is selected from the group consisting of breast cancer, malignant lymphoma, multiple myeloma, prostate cancer, colorectal cancer, lung cancer, ovarian cancer and endometrial carcinoma.

* * * * *